United States Patent
Tang et al.

(10) Patent No.: US 11,104,689 B2
(45) Date of Patent: Aug. 31, 2021

(54) INFLUENZA VIRUS REPLICATION INHIBITOR AND USE THEREOF

(71) Applicants: SUNSHINE LAKE PHARMA CO., LTD., Guangdong (CN); NORTH & SOUTH BROTHER PHARMACY INVESTMENT COMPANY LIMITED, Wanchai (HK)

(72) Inventors: Changhua Tang, Dongguan (CN); Qingyun Ren, Dongguan (CN); Huichao Luo, Dongguan (CN); Junjun Yin, Dongguan (CN); Kai Yi, Dongguan (CN); Yibo Lei, Dongguan (CN); Yejun Wang, Dongguan (CN); Yingjun Zhang, Dongguan (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 0 days.

(21) Appl. No.: 16/646,072

(22) PCT Filed: Sep. 18, 2018

(86) PCT No.: PCT/CN2018/106092
§ 371 (c)(1),
(2) Date: Mar. 10, 2020

(87) PCT Pub. No.: WO2019/052565
PCT Pub. Date: Mar. 21, 2019

(65) Prior Publication Data
US 2020/0283454 A1 Sep. 10, 2020

(30) Foreign Application Priority Data
Sep. 18, 2017 (CN) .......................... 201710841921.4

(51) Int. Cl.
| | | |
|---|---|---|
| *C07D 498/14* | (2006.01) | |
| *A61P 31/16* | (2006.01) | |
| *A61K 31/5383* | (2006.01) | |
| *A61K 31/554* | (2006.01) | |
| *A61K 45/06* | (2006.01) | |

(52) U.S. Cl.
CPC ........ *C07D 498/14* (2013.01); *A61K 31/5383* (2013.01); *A61K 31/554* (2013.01); *A61K 45/06* (2013.01); *A61P 31/16* (2018.01)

(58) Field of Classification Search
CPC .................................................. C07D 498/14
See application file for complete search history.

(56) References Cited

U.S. PATENT DOCUMENTS

| | | |
|---|---|---|
| 8,835,461 B2 | 9/2014 | Fujishita et al. |
| 8,865,907 B2 | 10/2014 | Sumino et al. |
| 8,927,710 B2 | 1/2015 | Akiyama et al. |
| 8,987,441 B2 | 3/2015 | Takahashi et al. |
| 9,260,453 B2 | 2/2016 | Sumino et al. |
| 9,469,638 B2 | 10/2016 | Akiyama et al. |
| 9,505,783 B2 | 11/2016 | Sumino et al. |
| 9,758,515 B2 | 9/2017 | Takahashi et al. |
| 9,815,835 B2 | 11/2017 | Akiyama et al. |
| 10,202,379 B2 | 2/2019 | Takahashi et al. |
| 10,392,406 B2 | 8/2019 | Kawai |
| 2019/0169206 A1 | 6/2019 | Kawai et al. |

FOREIGN PATENT DOCUMENTS

| | | | |
|---|---|---|---|
| CN | 103228653 | * | 7/2013 |
| CN | 108440564 A | | 8/2018 |
| JP | 2017-137291 A | | 8/2017 |
| JP | 2017137291 | * | 8/2017 |
| TW | 201702245 | * | 1/2017 |
| WO | 2012-039414 A1 | | 3/2012 |
| WO | 2017-104691 A1 | | 6/2017 |
| WO | WO2017104691 | * | 6/2017 |

OTHER PUBLICATIONS

Vippagunta et al. (2001).*
Dec. 27, 2018 International Search Report issued in International Patent Application No. PCT/CN2018/106092.
Dec. 27, 2018 Written Opinion of the International Searching Authority issued in International Patent Application No. PCT/CN2018/106092.

* cited by examiner

*Primary Examiner* — Paul V Ward
(74) *Attorney, Agent, or Firm* — Oliff PLC

(57) ABSTRACT

Disclosed are a compound as shown in formula (I) as an influenza virus replication inhibitor and a preparation method therefor, a pharmaceutical composition comprising the compound and the use of the compound and pharmaceutical composition thereof in the treatment of influenza.

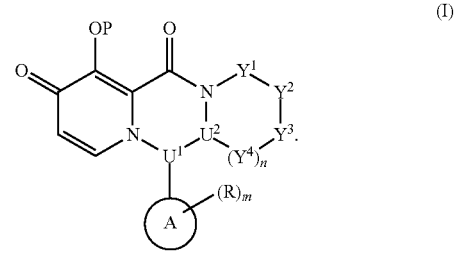

21 Claims, No Drawings

INFLUENZA VIRUS REPLICATION INHIBITOR AND USE THEREOF

CROSS-REFERENCE TO RELATED APPLICATION

The present application claims the priority and the benefit of the patent application No. 201710841921.4, filed with the State Intellectual Property Office of China on Sep. 18, 2017, the disclosure of which is hereby incorporated by reference.

FIELD OF THE INVENTION

The present invention belongs to the field of medicine, and in particular relates to a novel compound as an influenza virus replication inhibitor, a preparation method thereof, a pharmaceutical composition comprising the compound, and the use of the compound and a pharmaceutical composition thereof in treating influenza. More specifically, the compound of the present invention is useful as inhibitor of influenza virus RNA polymerase.

BACKGROUND OF THE INVENTION

Influenza (hereinafter referred to as flu) is an acute respiratory infection that is seriously harmful to human health. It is caused by influenza virus and has a high prevalence rate, widespread epidemics and rapid spread. Influenza virus can cause more serious symptoms in elderly and children with weak immunity and some patients with immune disorders, such as pneumonia or cardiopulmonary failure, etc. Influenza virus was found in 1993 by a Britishman Wilson Smith, called H1NI. H stands for hemagglutinin; N stands for neuraminidase. Numbers represent different types. Since the discovery of the flu virus, it has caused many pandemics on a global scale. An explosive epidemic occurs in a decade or so, causing huge losses on a global scale. Influenza viruses can cause 250,000 to 500,000 deaths each year, 3 to 5 million serious illness cases, and about 5% to 15% of people worldwide are infected. Each pandemic is caused by a new strain of virus that appears in humans. Typically, these new strains are caused by the spread of existing influenza viruses from other animal species to humans.

The influenza virus is an RNA virus of the Orthomyxoviridae family and belongs to the genus of influenza virus. According to the antigenic characteristics and gene characteristics of virion nucleoprotein (NP) and matrix protein (M), influenza viruses are mainly classified into three types: A, B, and C. These three types have similar biochemical and biological characteristics. Viral particles are 80-120 nm in diameter and are usually similar to spheres, but filamentous forms may appear. The virus consists of three layers, the inner layer is the viral nucleocapsid, containing nuclear protein (NP), P protein and RNA. NP is a soluble antigen (S antigen), which is type-specific and antigen-stable. P protein (P1, P2, P3) may be a polymerase required for RNA transcription and replication. The middle layer is a viral envelope composed of a layer of lipids and a membrane protein (MP). MP is antigenically stable and also has type specificity. The outer layer is a radial protrusion composed of two different glycoproteins, namely hemagglutinin H and neuraminidase N. H can cause red blood cell agglutination, which is a tool for the virus to suck on the surface of sensitive cells. N can hydrolyze mucus protein and hydrolyze cell surface receptor-specific glycoprotein-terminal N-acetylneuraminic acid, which is a tool for the virus to detach from the cell surface after viral replication is completed. H and N both have variation characteristics, and only have the strain specific antigen, the antibody of which has a protective effect.

Influenza A virus has one species. Wild waterbirds are the natural hosts of a large number of influenza A viruses. Sometimes, viruses spread to other species and can cause devastating outbreaks in poultry or human influenza pandemics. Among the three influenza types, type A virus is the most virulent human pathogen causing most serious diseases, which can be transmitted to other species and cause a large-scale epidemic of human influenza. According to the antibody response to these viruses, influenza A virus can be subdivided into different serotypes. In the order of the number of deaths caused by known human pandemic, we have confirmed that the human serotypes are: H1N1 (Spain influenza in 1918), H2N2 (Asian influenza in 1957), H3N2 (Hongkong influenza in 1968), H5N1 (the threat of influenza season's pandemic in 2007-08), H7N7 (rare animal infectious potential), H1N2 (endemic in humans and pigs), H9N2, H7N2, H7N3 and H10N7.

Influenza B virus has one species, influenza B virus, which often causes local influenza epidemic, does not cause a worldwide influenza pandemic, is only found in human and seals. This type of influenza mutates at a rate 2-3 times slower than type A, resulting in a low genetic diversity, with only one serotype of influenza B. Owing to the lack of diversity of these antigens, humans usually acquire a certain level of immunity to influenza B at an early age. However, the mutation of influenza B virus is enough to make it impossible to sustain immunity. But the rate of change of its antigen is low, combined with its restricted host change (inhibiting cross-species antigen transformation), which ensures that there will be no pandemic of influenza B.

Influenza C virus has one species. Influenza C virus exists mostly in the form of dispersal. It mainly infects infants and young children, and generally does not cause influenza pandemic. It can infect humans and pigs.

Unusual for viruses, the genome is not a single fragment of nucleic acid; instead, the genome contains seven or eight fragments of fragmented antisense RNA. Influenza A genome encodes 11 proteins: Hemagglutinin (H), Neuraminidase (N), nucleoprotein (NP), M1, M2, NS1, NS2 (NEP), PA, PB1, PB1-F2 and PB2. H and N are macromolecular glycoproteins outside viral particles. HA is an agglutinin that mediates viral binding to target cells and viral genomes entering into target cells, while NA involves releasing offspring from infected cells by splitting sugars bound to mature viral particles. Therefore, these proteins have become the target of antiviral drugs. Moreover, these proteins are antigens which can produce antibodies. Influenza A viruses are classified into subtypes based on their antibody responses to H and N, forming the basis for the distinction between H and N in H5N1, for example.

Vaccination and use of antiviral drugs are important means to cope with influenza pandemic. However, due to the strong mutation ability of influenza virus antigen, it is almost impossible to produce large-scale vaccine before the pandemic. Currently available antiviral therapeutic agents include M2 ion channel blockers such as amantadine and rimantadine, and neuraminidase inhibitors oseltamivir, Zanamivir, Peramivir and Lanimamivir. However, for all of these drugs, the influenza virus has developed resistance. Therefore, there is a continuing need for new anti-influenza therapeutics.

Favipiravir, a new anti-influenza agent with a new mechanism of action, has been marketed to achieve antiviral effects by inhibiting influenza virus RNA polymerase targeting viral gene replication, but its therapeutic effect and influenza virus for its drug resistance remain to be proved, so there is still a need to develop other compounds that inhibit influenza by this mechanism of action.

SUMMARY OF THE INVENTION

The present invention provides a novel class of compounds which are inhibitors of influenza virus RNA polymerase, and more particularly, the present invention provides a novel class of cap-dependent endonuclease inhibitors of influenza viruses, such compounds and the compositions thereof can be used for the preparation of a medicament for preventing, managing, treating or ameliorating a viral infection in a patient. Compared with the existing analogous compounds, the compounds of the present invention not only can inhibit influenza virus well, but also have lower cytotoxicity, more excellent pharmacokinetic properties and pharmacodynamic properties in vivo. Therefore, the compound provided by the present invention has more excellent druggability than the conventional compound of the same type.

In one aspect, the present invention relates to a compound having Formula (I) or a stereoisomer, a tautomer, an N-oxide, a solvate, a metabolite, a pharmaceutically acceptable salt or a prodrug thereof,

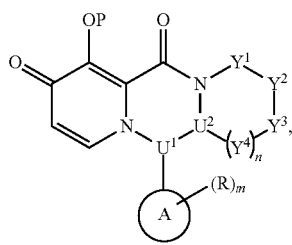

(I)

wherein, $U^1$ is N or CH;
$U^2$ is N or CH;
$Y^1$ is $CR^{1a}R^{1b}$, S or O;
$Y^2$ is $CR^{2a}R^{2b}$, S or O;
$Y^3$ is $CR^{3a}R^{3b}$, S or O;
each $Y^4$ is independently $CR^{4a}R^{4b}$, S or O;
each $R^{1a}$, $R^{1b}$, $R^{1b}$, $R^{2a}$, $R^{2a}$, $R^{2b}$, $R^{3a}$, $R^{3b}$, $R^{3a}$, $R^{3b}$, $R^{4a}$ and $R^{4b}$ is independently H, deuterium, F, Cl, Br, I, CN, $NO_2$, $OR^b$, $R^bO$—$C_{1-4}$ alkylene, $R^dR^cN$—$C_{1-4}$ alkylene, $C_{1-6}$ haloalkyl, $C_{1-6}$ alkyl, $C_{2-6}$ alkenyl, $C_{2-6}$ alkynyl, $C_{3-8}$ carbocyclyl, 3-8 membered heterocyclyl, $C_{6-10}$ aryl or 5-10 membered heteroaryl; wherein each $C_{1-6}$ haloalkyl, $C_{1-6}$ alkyl, $C_{2-6}$ alkenyl, $C_{2-6}$ alkynyl, $C_{3-8}$ carbocyclyl, 3-8 membered heterocyclyl, $C_{6-10}$ aryl and 5-10 membered heteroaryl is independently unsubstituted or substituted with 1, 2, 3 or 4 substituents independently selected from deuterium, F, Cl, Br, I, CN, OH, $NH_2$, $C_{1-6}$ alkyl, $C_{1-6}$ haloalkyl, $C_{1-6}$ alkoxy or $C_{1-6}$ alkylamino;

or optionally two $R^{1a}$, $R^{1b}$, $R^{2a}$, $R^{2b}$, $R^{3a}$, $R^{3b}$, $R^{4a}$, $R^{4b}$ together with the carbon atom to which they are attached form a $C_{3-8}$ carbocyclic ring or 3-8 membered heterocyclic ring; wherein each $C_{3-8}$ carbocyclic ring and 3-8 membered heterocyclic ring is independently unsubstituted or substituted with 1, 2, 3 or 4 substituent independently selected from deuterium, F, Cl, Br, I, CN, OH, $NH_2$, $C_{1-6}$ alkyl, $C_{1-6}$ haloalkyl, $C_{1-6}$ alkoxy or $C_{1-6}$ alkylamino;

ring A is a 10-30 membered monocyclic, bicyclic, tricyclic, tetracyclic, pentacyclic or hexacyclic ring system; wherein the 10-30 membered monocyclic, bicyclic, tricyclic, tetracyclic, pentacyclic or hexacyclic ring system is a carbocyclic, heterocyclic, aromatic or heteroaromatic ring.

Each R is independently H, deuterium, F, Cl, Br, I, CN, $NO_2$, OXO (=O), —C(=O)$R^a$, —C(=O)$OR^b$, —C(=O)$NR^cR^d$, —$OR^b$, —$NR^cR^d$, $R^bO$—$C_{1-4}$ alkylene, $R^dR^cN$—$C_{1-4}$ alkylene, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkyl-$C_{1-4}$ alkylene, 3-8 membered heterocyclyl, (3-8 membered heterocyclyl)-$C_{1-4}$ alkylene, $C_{6-10}$ aryl, $C_{6-10}$ aryl-$C_{1-4}$ alkylene, 5-10 membered heteroaryl or (5-10 membered heteroaryl)-$C_{1-4}$ alkylene; wherein each $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkyl-$C_{1-4}$ alkylene, 3-8 membered heterocyclyl, (3-8 membered heterocyclyl)-$C_{1-4}$ alkylene, $C_{6-10}$ aryl, $C_{6-10}$ aryl-$C_{1-4}$ alkylene, 5-10 membered heteroaryl and (5-10 membered heteroaryl)-$C_{1-4}$ alkylene is independently unsubstituted or substituted with 1, 2, 3 or 4 substituents independently selected from deuterium, F, Cl, Br, I, CN, $NO_2$, —$OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene;

or any two R together with carbon atom or nitrogen atom to which they are attached form a $C_{3-8}$ carbocyclic ring, 3-8 membered heterocyclic ring, $C_{6-10}$ aromatic ring or a 5-10 membered heteroaromatic ring; wherein each $C_{3-8}$ carbocyclic ring, 3-8 membered heterocyclic ring, $C_{6-10}$ aromatic ring and 5-10 membered heteroaromatic ring is independently unsubstituted or substituted with 1, 2, 3 or 4 substituents independently selected from deuterium, F, Cl, Br, I, CN, $NO_2$, —$OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene;

P is H, deuterium, $C_{1-6}$ alkyl, $C_{2-6}$ alkenyl, $C_{3-8}$ carbocyclyl, $C_{3-8}$ carbocyclyl-$C_{1-4}$ alkylene, 3-8 membered heterocyclyl, (3-8 membered heterocyclyl)-$C_{1-4}$ alkylene, $C_{6-10}$ aryl, $C_{6-10}$ aryl-$C_{1-4}$ alkylene, 5-10 membered heteroaryl, (5-10 membered heteroaryl)-$C_{1-4}$ alkylene, —C(=O)—$R^{Pa}$, —C(=O)-L-$R^{Pe}$, —C(=O)-L-O—$R^{Pb}$, —C(=O)-L-O-L-O—$R^{Pb}$, —C(=O)-L-O—C(=NO)—$R^{Pa}$, —C(=O)—$NR^{Pf}R^d$, —C(=O)—O—$R^{Pb}$, —S(=O)$_2$—$R^{Pk}$, —P(=O)—($R^{Pg}$)($R^{Ph}$), —C(=O)—O-L-O—$R^{Pb}$, —C(=N$^+R^{Pi}R^{Pj}$)(—$NR^{Pc}R^{Pd}$), $R^{Pb}$—O—$C_{1-4}$ alkylene, $R^{Pb}$—O-L-O—$C_{1-4}$ alkylene, $R^{Pa}$—(C=O)—O—$C_{1-4}$ alkylene, $R^{Pb}$—O—(C=O)—$C_{1-4}$ alkylene, $R^{Pb}$—O—(C=O)—NR$^f$—$C_{1-4}$ alkylene, $R^{Pb}$—O—(C=O)—O—$C_{1-4}$ alkylene, $NR^{Pf}R^{Pd}$—O—(C=)—O—$C_{1-4}$ alkylene, $R^{Pb}$—O-L-O—(C=O)—O—$C_{1-4}$ alkylene, $NR^{Pc}R^{Pd}$-L-O—(C=O)—O—$C_{1-4}$ alkylene, $R^{Pb}$—O-L-$NR^{Pf}$—(C=O)—O—$C_{1-4}$ alkylene, $NR^{Pc}R^{Pd}$-L-N($R^{Pf}$)—(C=O)—O—$C_{1-4}$ alkylene, $R^{Pb}$—O-L-O-L-O—(C=O)—O—$C_{1-4}$alkylene, $(HO)_2P(=O)$—$C_{1-4}$ alkylene, $(BnO)_2P(=O)$—$C_{1-4}$ alkylene or $R^{Pa}$—(C=O)—$NR^{Pf}$-L-O—(C=O)—O—$C_{1-4}$ alkylene, wherein each of $C_{1-6}$ alkyl, $C_{2-6}$ alkenyl, $C_{3-8}$ carbocyclyl, $C_{3-8}$ carbocyclyl-$C_{1-4}$ alkylene, 3-8 membered heterocyclyl, (3-8 membered heterocyclyl)-$C_{1-4}$ alkylene, $C_{6-10}$ aryl, $C_{6-10}$ aryl-$C_{1-4}$ alkylene, 5-10 membered heteroaryl and (5-10 membered heteroaryl)-$C_{1-4}$ alkylene is independently unsubstituted or substituted with 1, 2, 3, or 4 substituents independently selected from deuterium, F, Cl, Br, I, oxo (=O), CN, $NO_2$, —$OR^b$, —$NR^cR^d$, —C(=O)$R^a$, —O(C=O)$R^a$, —C(=O)$OR^b$, $C_{1-6}$ alkyl, $R^bO$—$C_{1-4}$ alkylene, —$NR^cR^cC(=O)R^a$ or $R^dR^cN$—$C_{1-4}$ alkylene;

each L is independently C$_{1-6}$ alkylene or C$_{2-6}$ alkenylene;

each R$^{Pf}$ is independently H or C$_{1-6}$ alkyl;

each R$^{Pa}$, R$^{Pb}$, R$^{Pc}$, R$^{Pd}$, R$^{Pe}$, R$^{Pi}$, R$^{Pj}$ and R$^{Pk}$ is independently C$_{1-6}$ alkyl, C$_{3-8}$ carbocyclyl, C$_{3-8}$ carbocyclyl-C$_{1-4}$ alkylene, 3-8 membered heterocyclyl, (3-8 membered heterocyclyl)-C$_{1-4}$ alkylene, C$_{6-10}$ aryl, C$_{6-10}$ aryl-C$_{1-4}$ alkylene, 5-10 membered heteroaryl, (5-10 membered heteroaryl)-C$_{1-4}$ alkylene, C$_{1-6}$ alkylamino, C$_{1-6}$ alkylthio or C$_{1-6}$ alkylsilyl, wherein each C$_{1-6}$ alkyl, C$_{3-8}$ carbocyclyl, C$_{3-8}$ carbocyclyl-C$_{1-4}$ alkylene, 3-8 membered heterocyclyl, (3-8 membered heterocyclyl)-C$_{1-4}$ alkylene, C$_{6-10}$ aryl, C$_{6-10}$ aryl-C$_{1-4}$ alkylene, 5-10 membered heteroaryl, (5-10 membered heteroaryl)-C$_{1-4}$ alkylene, C$_{1-6}$ alkylamino and C$_{1-6}$ alkylthio is independently unsubstituted or substituted with 1, 2, 3 or 4 substituents independently selected from deuterium, F, Cl, Br, I, OXO(=O), CN, NO$_2$, —OR$^b$, —NR$^c$R$^d$, —C(=O)R$^a$, —O(C=O)R$^a$, —C(=O)OR$^b$, C$_{1-6}$ alkyl, R$^b$O—C$_{1-4}$ alkylene, —NR$^d$R$^c$C(=O)R$^a$ or R$^d$R$^c$N—C$_{1-4}$ alkylene;

each R$^{Pg}$ and R$^{Ph}$ is independently C$_{1-6}$ alkoxy, C$_{1-6}$ alkylamino, C$_{3-8}$ carbocyclyloxy, C$_{3-8}$ carbocyclylamino, 3-8 membered heterocyclyloxy, 3-8 membered heterocyclylamino, C$_{6-10}$ aryloxy, C$_{6-10}$ arylamino, 5-10 membered heteroaryloxy and 5-10 membered heteroarylamino, wherein each C$_{1-6}$ alkoxy, C$_{1-6}$ alkylamino, C$_{3-8}$ carbocyclyloxy, C$_{3-8}$ carbocyclylamino, 3-8 membered heterocyclyloxy, 3-8 membered heterocyclylamino, C$_{6-10}$ aryloxy, C$_{6-10}$ arylamino, 5-10 membered heteroaryloxy or 5-10 membered heteroarylamino is independently unsubstituted or substituted with 1, 2, 3 or 4 substituent is independently selected from deuterium, F, Cl, Br, I, oxo(=O), CN, NO$_2$, —OR$^b$, —NR$^c$R$^d$, —C(=O)R$^a$, —O(C=O)R$^a$, —C(=O)OR$^b$, C$_{1-6}$ alkyl, R$^b$O—C$_{1-4}$ alkylene, —NR$^d$R$^c$C(=O)R$^a$ or R$^d$R$^c$N—C$_{1-4}$ alkylene;

or, R$^{Pg}$ and R$^{Ph}$ together with phosphorus atom to which they are attached form a 3-8 membered heterocyclic ring or a 5-10 membered heteroaromatic ring; wherein each of the 3-8 membered heterocyclic ring and 5-10 membered heteroaromatic ring is independently unsubstituted or substituted with 1, 2, 3 or 4 substituents independently selected from deuterium, F, Cl, Br, I, OXO(=O), CN, NO$_2$, —OR$^b$, —NR$^c$R$^d$, —C(=O)R$^a$, —O(C=O)R$^a$, —C(=O)OR$^b$, C$_{1-6}$ alkyl, C$_{1-6}$ haloalkyl, R$^b$O—C$_{1-4}$ alkylene, —NR$^d$R$^c$C(=O)R$^a$ or R$^d$R$^c$N—C$_{1-4}$ alkylene;

each R$^a$, R$^b$, R$^c$ and R$^d$ is independently H, deuterium, C$_{1-6}$ haloalkyl, C$_{1-6}$ alkyl, C$_{1-6}$ alkenyl, C$_{2-6}$ alkynyl, C$_{3-6}$ carbocyclyl, C$_{3-6}$ carbocyclyl-C$_{1-4}$ alkylene, C$_{6-10}$ aryl, C$_{6-10}$ aryl-C$_{1-4}$ alkylene, 5-10 membered heteroaryl or (5-10 membered heteroaryl)-C$_{1-4}$ alkylene, wherein each C$_{1-6}$ alkyl, C$_{2-6}$ alkenyl, C$_{2-6}$ alkynyl, C$_{3-6}$ carbocyclyl, C$_{3-6}$ carbocyclyl-C$_{1-4}$ alkylene, 3-6 membered heterocyclyl, (3-6 membered heterocyclyl)-C$_{1-4}$ alkylene, C$_{6-10}$ aryl, C$_{6-10}$ aryl—C$_{1-4}$ alkylene, 5-10 membered heteroaryl and (5-10 membered heteroaryl)-C$_{1-4}$ alkylene is independently unsubstituted or substituted with 1, 2, 3 or 4 substituents independently selected from deuterium, F, Cl, Br, I, CN, OH, NH$_2$, NO$_2$, C$_{1-6}$ alkyl, C$_{1-6}$ haloalkyl, C$_{1-6}$ alkoxy or C$_{1-6}$ alkylamino;

or, R$^c$ and R$^d$ together with the nitrogen atom to which they are attached form a 3-6 membered heterocyclic ring or a 5-8 membered heteroaromatic ring; wherein each of the 3-6 membered heterocyclic ring and 5-8 membered heteroaromatic ring is independently unsubstituted or substituted with 1, 2, 3 or 4 substituents independently selected from deuterium, F, Cl, Br, I, CN, OH, NH$_2$, NO$_2$, C$_{1-6}$ alkyl, C$_{1-6}$ haloalkyl, C$_{1-6}$ alkoxy or C$_{1-6}$ alkylamino;

m is 0, 1, 2, 3, 4, 5, 6, 7 or 8, with the proviso that ring A is not

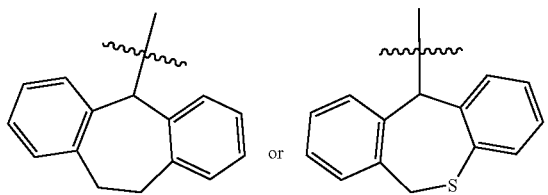 [SMILES: *C1c2ccccc2CCc2ccccc21 ; *C1c2ccccc2CSc2ccccc21]

when m is 0 or 1, and when m is 2 and ring A is

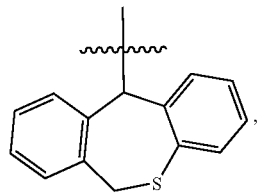 [SMILES: *C1c2ccccc2CSc2ccccc21]

optionally two R together with carbon atoms to which they are attached form a C$_{3-8}$ carbocyclic ring, 3-8 membered heterocyclic ring, C$_{6-10}$ aromatic ring or 5-10 membered heteroaromatic ring; wherein each of the C$_{3-8}$ carbocyclic ring, 3-8 membered heterocyclic ring, C$_{6-10}$ aromatic ring, and 5-10 membered heteroaromatic ring is independently unsubstituted or substituted with 1, 2, 3 or 4 substituents independently selected from deuterium, F, Cl, Br, I, CN, NO$_2$, —OR$^b$, —NR$^c$R$^d$, C$_{1-6}$ alkyl, C$_{1-6}$ haloalkyl, R$^b$O—C$_{1-4}$ alkylene or R$^d$R$^c$N—C$_{1-4}$ alkylene;

n is 0, 1, 2, or 3.

In some embodiments, ring A is a 12-20 membered monocyclic, bicyclic, tricyclic, tetracyclic, pentacyclic or hexacyclic ring system; wherein the 12-20 membered monocyclic, bicyclic, tricyclic, tetracyclic, pentacyclic or hexacyclic ring system is a carbocyclic, heterocyclic, aromatic or heteroaromatic ring.

In other embodiments, ring A is one of the following sub-formulae:

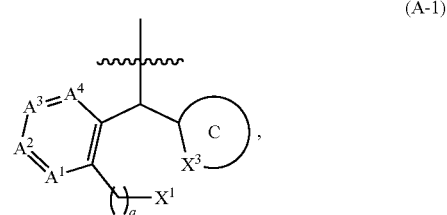

(A-1)

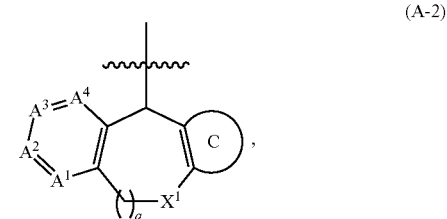

(A-2)

(A-3) 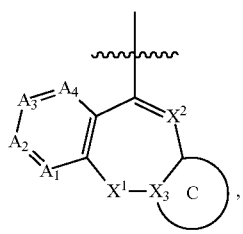

(A-4) 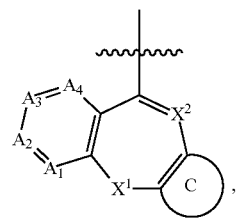

(A-5) 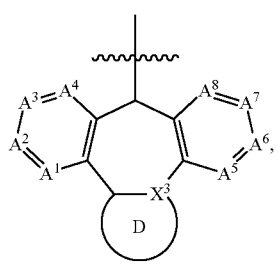

(A-6) 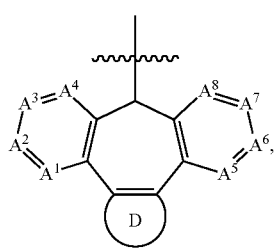

(A-7) 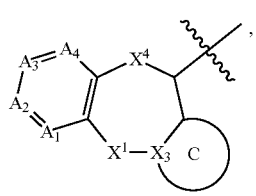

(A-8) 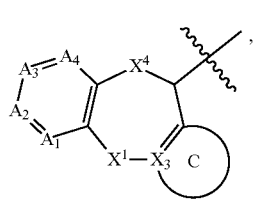

(A-9) 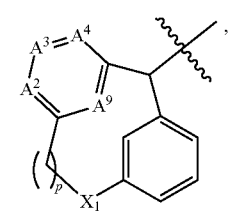

(A-10) 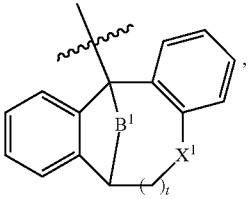

(A-11) 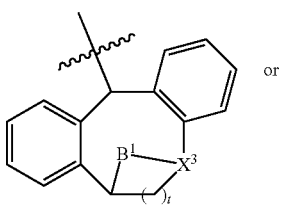

or (A-12) 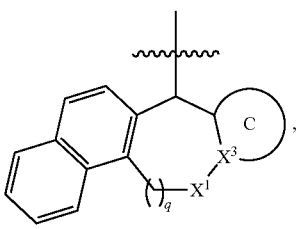

wherein,
each $X^1$ is independently S, S(=O), S(=O)$_2$, O, NH, CH$_2$ or absent;
each $X^2$ is independently CH or N;
each $X^3$ is independently CH or N;
each $X^4$ is independently S, O, NH or CH$_2$;
each of $A^1$, $A^2$, $A^3$, $A^4$, $A^5$, $A^6$, $A^7$, $A^8$ and $A^9$ is independently C or N;
$B^1$ is —CH$_2$—, —CH$_2$CH$_2$—, —CH$_2$CH$_2$CH$_2$— or O;
ring C is C$_{3-8}$ carbocyclic ring, 3-8 membered heterocyclic ring, C$_{6-10}$ aromatic ring, C$_{11}$ aromatic ring, C$_{12}$ aromatic ring or 5-10 membered heteroaromatic ring;
ring D is a C$_{3-8}$ carbocyclic ring, 3-8 membered heterocyclic ring, C$_{6-10}$ aromatic ring, C$_{11}$ aromatic ring, C$_{12}$ aromatic ring or 5-10 membered heteroaromatic ring;
each q is independently 0, 1, 2, 3, 4, 5 or 6;
p is 0, 1, 2, 3, 4, 5 or 6;
each t is independently 0, 1, 2 or 3.

In some embodiments, wherein ring D is C$_{3-6}$ carbocyclic ring, 5 membered heterocyclic ring, 6 membered heterocyclic ring, C$_{6-10}$ aromatic ring, 5 membered heteroaromatic ring or 6 membered heteroaromatic ring.

In other embodiments, wherein ring C is cyclopropane, cyclobutane, cyclopentane, cyclohexane, cycloheptane, benzocyclohexane, benzocyclopentane, azetidine, oxetane, pyrrolidine, piperidine, piperazine, tetrahydrofuran, tetrahydropyran, morpholine, benzene, naphthalene, furan, benzofuran, pyrrole, pyridine, pyrazole, imidazole, benzoimidazole, benzopyrazole, triazole, tetrazole, oxazole, oxadiazole, 1,3,5-triazine, thiazole, thiophene, benzothiophene, pyrazine, pyridazine, pyrimidine, benzopyrimidine, indole, purine, quinoline, isoquinoline, bicyclic [2.2.2]octane or benzobicyclic [2.2.2] octane;
and ring D is cyclopropane, cyclobutane, cyclopentane, cyclohexane, cycloheptane, cyclopentene, cyclopentadiene, cyclohexene, cyclohexadiene, benzocyclohexane, benzocyclopentane, cyclopropylethane, azetidine, oxetane, pyrrolidine, piperidine, piperazine, tetrahydrofuran, tetrahydropyran, morpholine, thiomorpholine, benzene, naphthalene, furan, benzofuran, pyrrole, pyridine, pyrazole, imidazole, benzimidazole, benzopyrazole, triazole, tetrazole, oxazole, isoxazole, oxadiazole, 1,3,5-triazine, thiazole, thiophene, benzothiophene, pyrazine, pyridazine, pyrimidine, benzopyrimidine, indole, purine, quinoline, isoquinoline, bicyclic [2.2.2] octane or benzobicyclic [2.2.2] octane.

In other embodiments, ring A is one of the following sub-formulae:

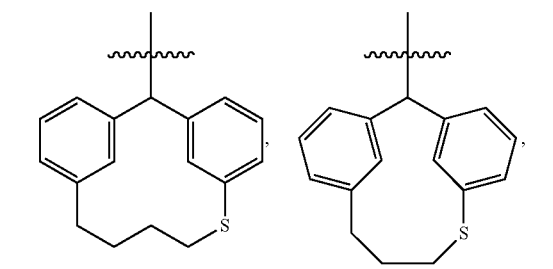

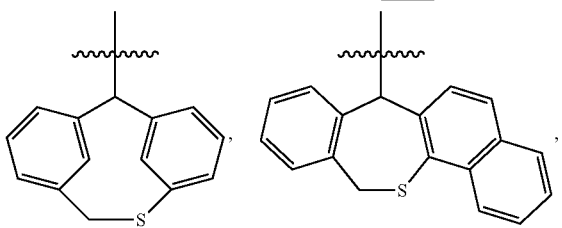

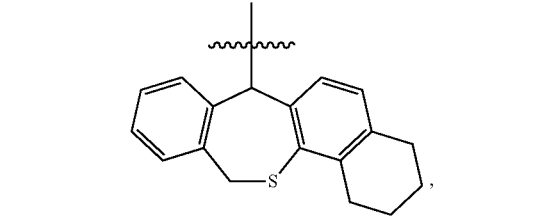

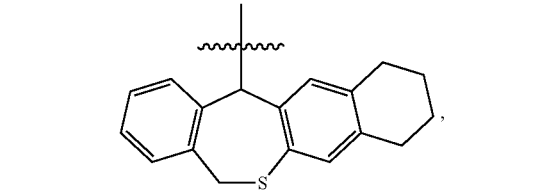

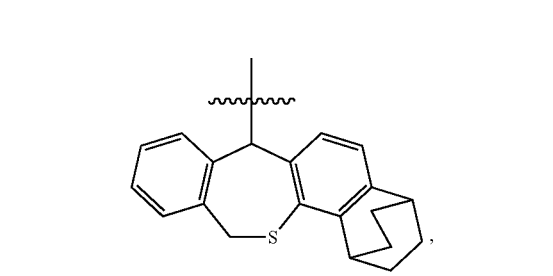

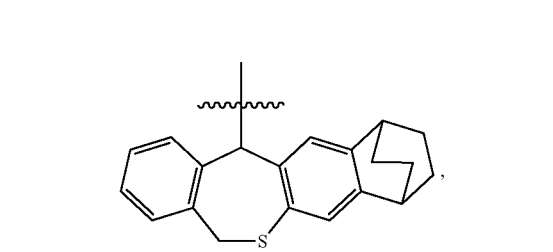

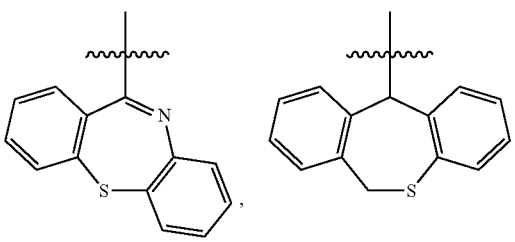

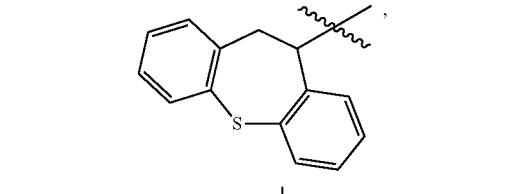

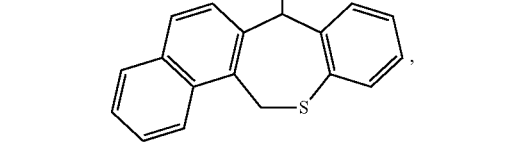

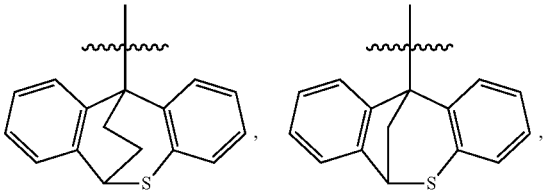

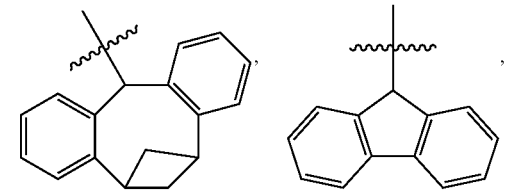

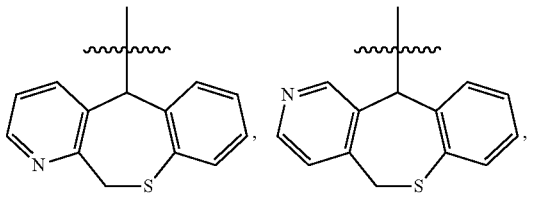

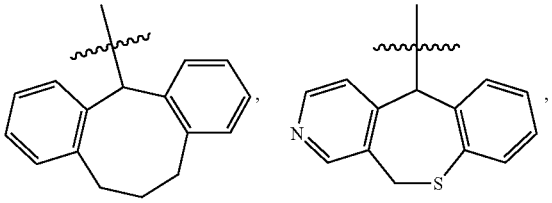

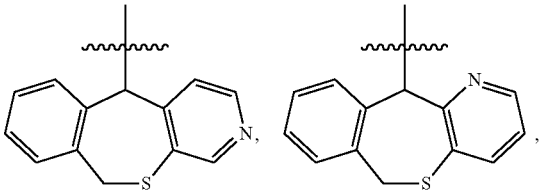

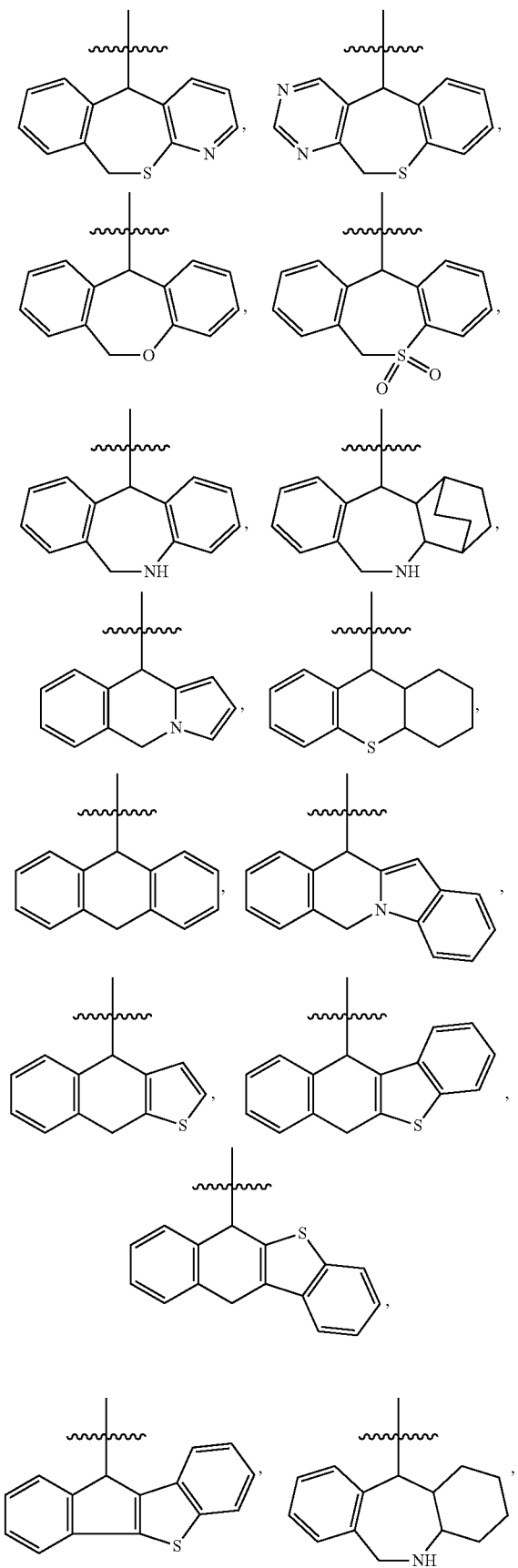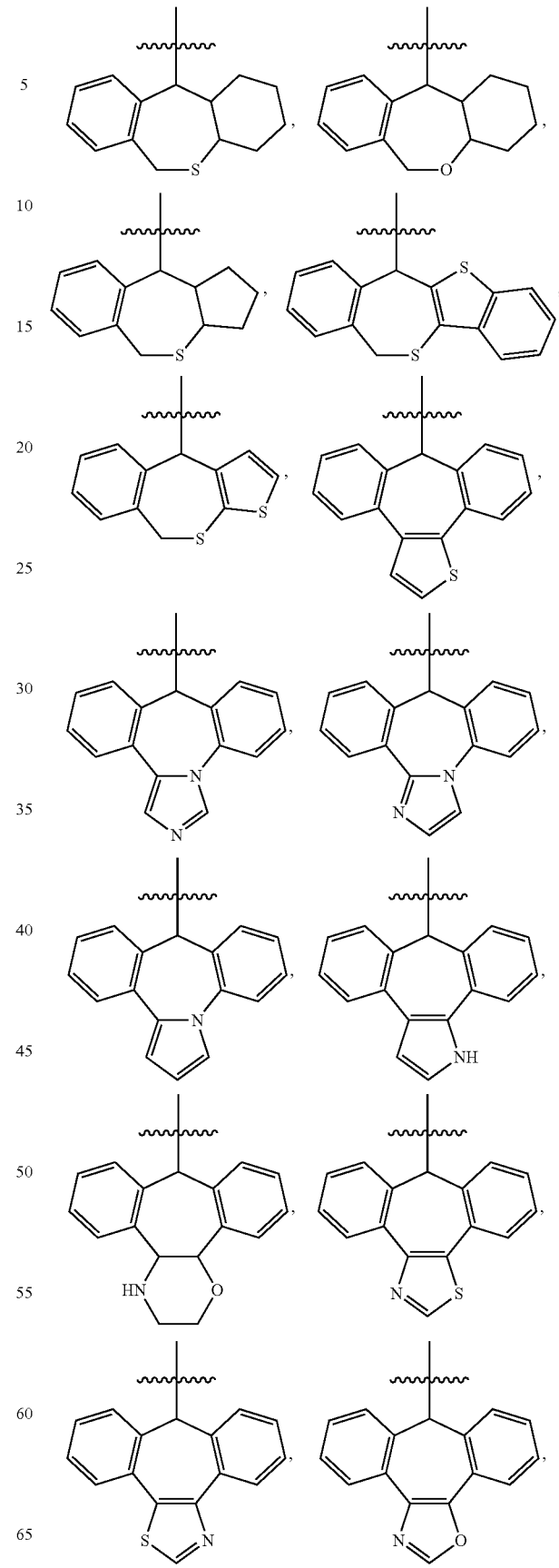

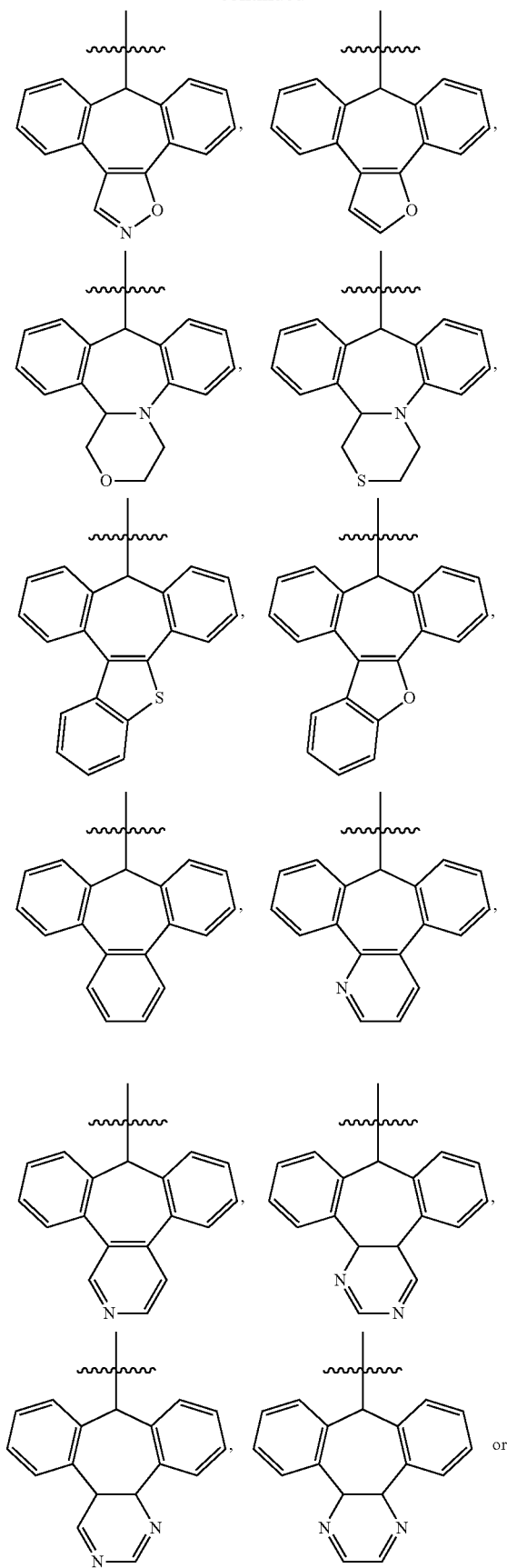

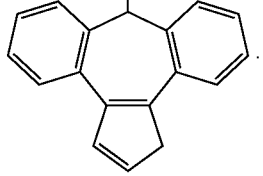

In other embodiments, each R is independently H, deuterium, F, Cl, Br, I, CN, $NO_2$, oxo (=O), —C(=O)$R^a$, —C(=O)O$R^b$, —C(=O)N$R^cR^d$, —O$R^b$, —N$R^cR^d$, $R^bO$—$C_{1-4}$ alkylene, $R^dR^cN$—$C_{1-4}$ alkylene, $C_{1-4}$ alkyl, $C_{1-4}$ haloalkyl, $C_{2-4}$ alkenyl, $C_{2-4}$ alkynyl, $C_{3-6}$ cycloalkyl, $C_{3-6}$ cycloalkyl-$C_{1-2}$ alkylene, 3-6 membered heterocyclyl, (3-6 membered heterocyclyl)-$C_{1-2}$ alkylene, $C_{6-10}$ aryl, $C_{6-10}$ aryl-$C_{1-2}$ alkylene, 5-10 membered heteroaryl or (5-10 membered heteroaryl)-$C_{1-2}$ alkylene; wherein each $C_{1-4}$ alkyl, $C_{1-4}$ haloalkyl, $C_{2-4}$ alkenyl, $C_{2-4}$ alkynyl, $C_{3-6}$ cycloalkyl, $C_{3-6}$ cycloalkyl-$C_{1-2}$ alkylene, 3-6 membered heterocyclyl, (3-6 membered heterocyclyl)-$C_{1-2}$ alkylene, $C_{6-10}$ aryl, $C_{6-10}$ aryl-$C_{1-2}$ alkylene, 5-10 membered heteroaryl, and (5-10 membered heteroaryl)-$C_{1-2}$ alkylene is independently unsubstituted or substituted with 1, 2, 3 or 4 substituents independently selected from deuterium, F, Cl, Br, I, CN, $NO_2$, —O$R^b$, —N$R^cR^d$, $C_{1-4}$ alkyl, $C_{1-4}$ haloalkyl, $R^bO$—$C_{1-4}$ alkylene or $R^dR^cN$—$C_{1-4}$ alkylene;

or optionally two R together with the carbon atom or nitrogen atom to which they are attached form a $C_{3-8}$ carbocyclic ring, $C_{6-10}$ aromatic ring or 5-10 membered heteroaromatic ring; wherein each $C_{3-8}$ carbocyclic ring, 3-8 membered heterocyclic ring, $C_{6-10}$ aromatic ring and 5-10 membered heteroaromatic ring is independently unsubstituted or substituted with 1, 2, 3 or 4 substituents independently selected from deuterium, F, Cl, Br, I, CN, $NO_2$, —O$R^b$, —N$R^cR^d$, $C_{1-4}$ alkyl, $C_{1-4}$ haloalkyl, $R^bO$—$C_{1-4}$ alkylene or $R^dR^cN$—$C_{1-4}$ alkylene.

In other embodiments, each R is independently H, deuterium, F, Cl, Br, I, CN, $NO_2$, OXO(=O), —C(=O)OH, —C(=O)OCH$_3$, —C(=O)NH$_2$, —OH, —OCH$_3$, —OCH$_2$CH$_3$, —OCF$_3$, —OCHF$_2$, —OCH$_2$CF$_3$, —NH$_2$, methyl, ethyl, n-propyl, isopropyl, trifluoromethyl, trifluoroethyl, cyclopropyl, cyclobutyl, cyclopentyl, cyclohexyl, cycloheptyl, oxiranyl, azetidinyl, oxetanyl, pyrrolidinyl, piperidinyl, piperazinyl, tetrahydrofuranyl, tetrahydropyranyl, morpholinyl, phenyl, naphthyl, furanyl, benzofuranyl, pyrrolidinyl, pyridyl, pyrazolyl, imidazolyl, benzimidazolyl, benzopyrazolyl, triazolyl, tetrazolyl, oxazolyl, oxadiazolyl, 1,3,5-triazinyl, thiazolyl, thiophenyl, benzothiophenyl, pyrazinyl, pyridazinyl, pyrimidinyl, indolyl, purinyl, quinolinyl or isoquinolinyl, wherein each methyl, ethyl, n-propyl, isopropyl, trifluoromethyl, trifluoroethyl, cyclopropyl, cyclobutyl, cyclopentyl, cyclohexyl, cycloheptyl, oxiranyl, azetidinyl, oxetanyl, pyrrolidinyl, piperidinyl, piperazinyl, tetrahydrofuranyl, tetrahydropyranyl, morpholinyl, phenyl, naphthyl, furanyl, benzofuranyl, pyrrolidinyl, pyridyl, pyrazolyl, imidazolyl, benzimidazolyl, benzopyrazolyl, triazolyl, tetrazolyl, oxazolyl, oxadiazolyl, 1,3,5-triazinyl, thiazolyl, thiophenyl, benzothiophenyl, pyrazinyl, pyridazinyl, pyrimidinyl, indolyl, purinyl, quinolinyl and isoquinolinyl is independently unsubstituted or substituted with 1, 2, 3 or 4 substituents is independently selected from deuterium, F, Cl, Br, CN, $NO_2$, OH, —NH$_2$, methyl, ethyl, n-propyl, isopropyl, trifluoromethyl or methoxy;

or optionally two R together with the carbon atom or nitrogen atom to which they are attached form cyclopropane, cyclobutane, cyclopentane, cyclohexane, cycloheptane, oxirane, azetidine, oxetane, pyrrolidine, piperidine, piperazine, tetrahydrofuran, tetrahydropyran, morpholine, thiomorpholine, benzene, furan, pyrrole, pyridine, pyrazole, imidazole, triazole, tetrazole, oxazole, oxadiazole, 1,3,5-triazine, thiazole, thiophene, pyrazine, pyridazine or pyrimidine, wherein each cyclopropane, cyclobutane, cyclopentane, cyclohexane, cycloheptane, oxirane, azetidine, oxetane, pyrrolidine, piperidine, piperazine, tetrahydrofuran, tetrahydropyran, morpholine, thiomorpholine, benzene, furan, pyrrole, pyridine, pyrazole, imidazole, triazole, tetrazole, oxazole, oxadiazole, 1,3,5-triazine, thiazole, thiophene, pyrazine, pyridazine and pyrimidine is independently unsubstituted or substituted with 1, 2, 3 or 4 substituents independently selected from deuterium, F, Cl, Br, CN, $NO_2$, OH, —$NH_2$, methyl, ethyl, n-propyl, isopropyl, trifluoromethyl or methoxy.

In other embodiments, each $R^{1a}$, $R^{1b}$, $R^{1b}$, $R^{2a}$, $R^{2a}$, $R^{2b}$, $R^{3a}$, $R^{3b}$, $R^{3a}$, $R^{3b}$, $R^{3b}$, $R^{4a}$ and $R^{4b}$ is independently H, deuterium, F, Cl, Br, I, CN, CN, $NO_2$, $OR^b$, $R^bO$—$C_{1-2}$ alkylene, $R^dR^cN$—$C_{1-2}$ alkylene, $C_{1-4}$ haloalkyl, $C_{1-4}$ alkyl, $C_{2-4}$ alkenyl, $C_{2-4}$ alkynyl, $C_{3-6}$ carbocyclyl, 3-6 membered heterocyclyl, $C_{6-10}$ aryl or 5-10 membered heteroaryl; wherein each $C_{1-4}$ haloalkyl, $C_{1-4}$ alkyl, $C_{2-4}$ alkenyl, $C_{2-4}$ alkynyl, $C_{3-6}$ carbocyclyl, 3-6 membered heterocyclyl, $C_{6-10}$ aryl and 5-10 membered heteroaryl is unsubstituted or substituted with 1, 2, 3 or 4 substituents independently selected from deuterium, F, Cl, Br, I, CN, OH, $NH_2$, $C_{1-4}$ alkyl, $C_{1-4}$ haloalkyl, $C_{1-6}$ alkoxy or $C_{1-4}$ alkylamino;

or optionally two $R^{1a}$, $R^{1b}$, $R^{2a}$, $R^{2b}$, $R^{3a}$, $R^{3b}$, $R^{4a}$, $R^{4b}$ together with the carbon atom to which they are attached form a $C_{3-8}$ carbocyclic ring or 3-8 membered heterocyclic ring; wherein each $C_{3-8}$ carbocyclic ring and 3-8 membered heterocyclyl is unsubstituted or substituted with 1, 2, 3 or 4 substituents independently selected from deuterium, F, Cl, Br, I, CN, OH, $NH_2$, $C_{1-4}$ alkyl, $C_{1-4}$ haloalkyl, $C_{1-4}$ alkoxy or $C_{1-4}$ alkylamino;

In other embodiments, each $R^{1a}$, $R^{1b}$, $R^{2a}$, $R^{2b}$, $R^{3a}$, $R^{3b}$, $R^{4a}$ and $R^{4b}$ is independently H, deuterium, F, Cl, Br, I, CN, $NO_2$, $OR^b$, $R^bO$—$C_{1-2}$ alkylene, $R^dR^cN$—$C_{1-2}$ alkylene, trifluoromethyl, trifluoroethyl, methyl, ethyl, n-propyl, isopropyl, cyclopropyl, cyclobutyl, cyclopentyl, oxiranyl, azetidinyl, oxetanyl, pyrrolidinyl, piperidinyl, piperazinyl, tetrahydrofuranyl, tetrahydropyranyl, morpholinyl, phenyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, wherein each trifluoroethyl, methyl, ethyl, n-propyl, isopropyl, cyclopropyl, cyclobutyl, cyclopentyl, oxiranyl, azetidinyl, oxetanyl, pyrrolidinyl, piperidinyl, piperazinyl, tetrahydrofuranyl, tetrahydropyranyl, morpholinyl, phenyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with 1, 2, 3 or 4 substituents independently selected from deuterium, F, Cl, Br, I, CN, OH, $NH_2$, methyl, ethyl, n-propyl, isopropyl, trifluoromethyl, methoxy or ethoxy;

or optionally two $R^{1a}$, $R^{1b}$, $R^{2a}$, $R^{2b}$, $R^{3a}$, $R^{3b}$, $R^{4a}$, $R^{4b}$ together with carbon atom to which they are attached form cyclopropane, cyclobutane, cyclopentane, cyclohexane, cycloheptane, oxirane, oxetane, azetidine, pyrrolidine, piperidine, piperazine, tetrahydrofuran, tetrahydropyran or morpholine, wherein each cyclopropane, cyclobutane, cyclopentane, cyclohexane, cycloheptane, oxirane, oxetane, azetidine, pyrrolidine, piperidine, piperazine, tetrahydrofuran, tetrahydropyran or morpholine is independently unsubstituted or substituted with 1, 2, 3 or 4 substituents independently selected from deuterium, F, Cl, Br, I, CN, OH, $NH_2$, methyl, ethyl, n-propyl, isopropyl, trifluoromethyl, methoxy or ethoxy.

In other embodiments, P is H, deuterium, $C_{1-4}$ alkyl, $C_{2-4}$ alkenyl, $C_{3-6}$ carbocyclyl, $C_{3-6}$ carbocyclyl-$C_{1-2}$ alkylene, 3-6 membered heterocyclyl, (3-6 membered heterocyclyl)-$C_{1-2}$ alkylene, $C_{6-10}$ aryl, $C_{6-10}$ aryl-$C_{1-2}$ alkylene, 5-10 membered heteroaryl, (5-10 membered heteroaryl)-$C_{1-2}$ alkylene, —C(=O)—$R^{Pa}$, —C(=O)—O—$R^{Pb}$, —C(=O)—$NR^{Pf}R^{Pd}$, —P(=O)—($R^{Pg}$)($R^{Ph}$), —C(=O)—O-L-O—$R^{Pb}$, $R^{Pa}$—(C=O)—O—$C_{1-4}$ alkylene, $R^{Pb}$—O—(C=O)—$C_{1-4}$ alkylene, $R^{Pb}$—O—(C=O)—$NR^{Pf}$—$C_{1-4}$ alkylene, $R^{Pb}$—O—(C=O)—O—$C_{1-4}$ alkylene or $R^{Pb}$—O-L-O—(C=O)—O—$C_{1-4}$ alkylene, wherein each $C_{1-4}$ alkyl, $C_{2-4}$ alkenyl, $C_{3-6}$ carbocyclyl, $C_{3-6}$ carbocyclyl-$C_{1-2}$ alkylene, 3-6 membered heterocyclyl, (3-6 membered heterocyclyl)-$C_{1-2}$ alkylene, $C_{6-10}$ aryl, $C_{6-10}$ aryl-$C_{12}$ alkylene, 5-10 membered heteroaryl, or (5-10 membered heteroaryl)-$C_{1-2}$ alkylene is independently unsubstituted or substituted with 1, 2, 3 or 4 substituents independently selected from deuterium, F, Cl, Br, I, OXO(=O), CN, $NO_2$, —$OR^b$, —$NR^cR^d$, —C(=O)$R^a$, —O(C=O)$R^a$, —C(=O)$OR^b$, $C_{1-6}$ alkyl, $R^bO$—$C_{1-4}$ alkylene, —$NR^dR^cC(=O)R^a$ or $R^dR^cN$—$C_{1-4}$ alkylene;

each L is independently $C_{1-6}$ alkylene;
each $R^{pf}$ is independently H or $C_{1-6}$ alkyl;
each $R^{pa}$, $R^{pb}$, and $R^{pd}$ is independently $C_{1-4}$ alkyl, $C_{3-6}$ carbocyclyl, $C_{3-6}$ carbocyclyl-$C_{1-2}$ alkylene, 3-6 membered heterocyclyl, (3-6 membered heterocyclyl)-$C_{1-2}$ alkylene, $C_{6-10}$ aryl, $C_{6-10}$ aryl-$C_{1-2}$ alkylene, 5-10 membered heteroaryl or (5-10 membered heteroaryl)-$C_{1-2}$ alkylene, wherein each $C_{1-4}$ alkyl, $C_{3-6}$ carbocyclyl, $C_{3-6}$ carbocyclyl-$C_{1-2}$ alkylene, 3-6 membered heterocyclyl, (3-6 membered heterocyclyl)-$C_{1-2}$ alkylene, $C_{6-10}$ aryl, $C_{6-10}$ aryl-$C_{1-2}$ alkylene, 5-10 membered heteroaryl and (5-10 membered heteroaryl)-$C_{1-2}$ alkylene is independently unsubstituted or substituted with 1, 2, 3 or 4 substituents independently selected from deuterium, F, Cl, Br, I, oxo(=O), CN, $NO_2$, —$OR^b$, —$NR^cR^d$, —C(=O)$R^a$, —O(C=O)$R^a$, —C(=O)$OR^b$, $C_{1-6}$ alkyl, $R^bO$—$C_{1-4}$ alkylene, —$NR^dR^cC(=O)R^a$ or $R^dR^cN$—$C_{1-4}$ alkylene;

each $R^{Pg}$ and $R^{Ph}$ is independently $C_{1-4}$ alkoxy, $C_{1-4}$ alkylamino, $C_{3-6}$ carbocyclyloxy, $C_{3-6}$ carbocyclylamino, 3-6 membered heterocyclyloxy, 3-6 membered heterocyclylamino, $C_{6-10}$ aryloxy, $C_{6-10}$ arylamino, 5-6 membered heteroaryloxy or 5-6 membered heteroarylamino, wherein each $C_{1-4}$ alkoxy, $C_{1-4}$ alkylamino, $C_{3-6}$ carbocyclyloxy, $C_{3-6}$ carbocyclylamino, 3-6 membered heterocyclyloxy, 3-6 membered heterocyclylamino, $C_{6-10}$ aryloxy, $C_{6-10}$ arylamino, 5-6 membered heterocyclyloxy and 5-6 membered heterocyclylamino is independently unsubstituted or substituted with 1, 2, 3 or 4 substituents independently selected from deuterium, F, Cl, Br, I, oxo(=O), CN, $NO_2$, —$OR^b$, —$NR^cR^d$, —C(=O)$R^a$, —O(C=O)$R^a$, —C(=O)$OR^b$, $C_{1-6}$ alkyl, $R^bO$—$C_{1-4}$ alkylene, —$NR^dR^cC(=O)R^a$ or $R^dR^cN$—$C_{1-4}$ alkylene;

or, $R^{Pg}R^{Ph}$ together with phosphorus atom to which they are attached form a 3-6 membered heterocyclic ring, or a 5-6 membered heteroaromatic ring; wherein each of the 3-6 membered heterocyclic ring and 5-6 membered heteroaromatic ring is independently unsubstituted or substituted with 1, 2, 3 or 4 substituents independently selected from deuterium, F, Cl, Br, I, oxo(=O), CN, $NO_2$, —$OR^b$, —$NR^cR^d$, —C(=O)R$^a$, —O(C=O)R$^a$, —C(=O)OR$^b$, C$_{1-6}$ alkyl, R$^b$O—C$_{1-4}$ alkylene, —NR$^d$R$^c$C(=O)R$^a$ or R$^d$R$^c$N—C$_{1-4}$ alkylene.

In other embodiments, P is H, deuterium,

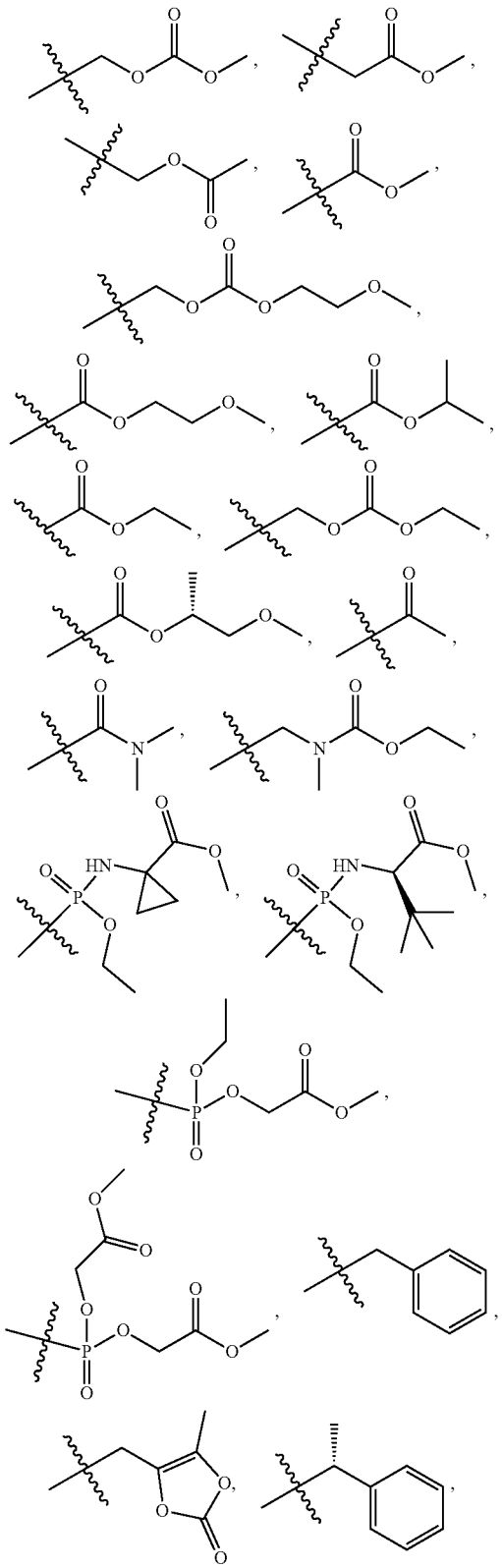

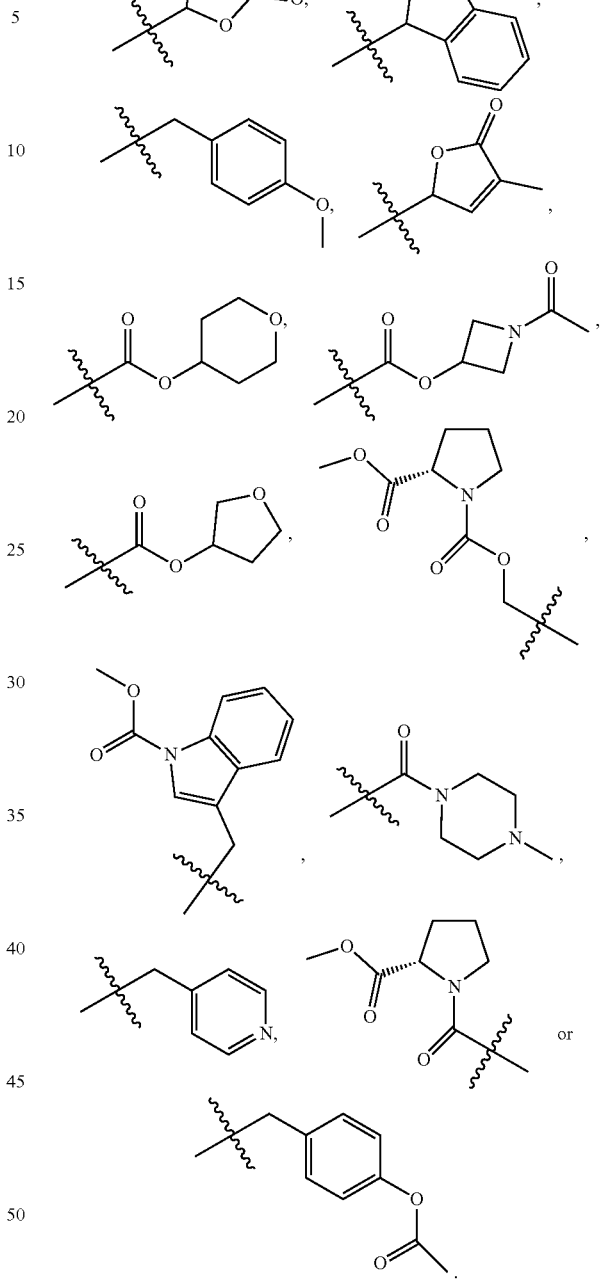

In other embodiments, each R$^a$, R$^b$, R$^c$ and R$^d$ is independently H, deuterium, trifluoromethyl, trifluoroethyl, methyl, ethyl, n-propyl, isopropyl, tert-butyl, cyclopropyl, cyclobutyl, 3-6 membered heterocyclyl, phenyl or 5-10 membered heteroaryl, wherein each methyl, ethyl, n-propyl, isopropyl, tert-butyl, cyclopropyl, cyclobutyl, 3-6 membered heterocyclyl, phenyl and 5-10 membered heteroaryl is unsubstituted or substituted with 1, 2, 3 or 4 substituents independently selected from deuterium, F, Cl, CN, OH, NH$_2$, NO$_2$, methyl, ethyl, n-propyl, isopropyl, trifluoromethyl or methoxy;

or R$^c$, R$^d$ together with nitrogen atom to which they are attached form a 3-6 membered heterocyclic ring or 5-6 membered heterocyclic ring; wherein each of the 3-6 membered heterocyclic ring and 5-6 membered heteroaromatic ring is independently unsubstituted or substituted with 1, 2, 3 or 4 substituents independently selected from deuterium, F, Cl, CN, OH, $NH_2$, $NO_2$, methyl, ethyl, n-propyl, isopropyl, trifluoromethyl or methoxy.

In other embodiments, the present invention provides a compound of Formula (II) or a stereoisomer, a tautomer, an N-oxide, a solvate, a metabolite, a pharmaceutically acceptable salt or a prodrug thereof,

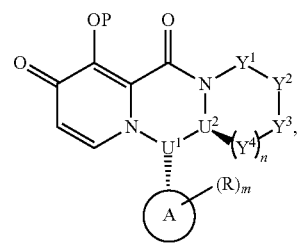
(II)

wherein P, $U^1$, $U^2$, $Y^1$, $Y^2$, $Y^3$, $Y^4$, R, ring A, n and m have definitions as described in the present invention, with the proviso that ring A is not

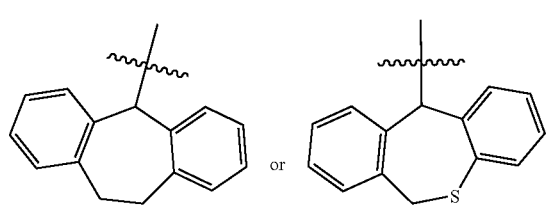 [SMILES: *C1c2ccccc2CCc2ccccc21 ; *C1c2ccccc2CSc2ccccc21]

when m is 0 or 1, and when m is 2 and ring A is

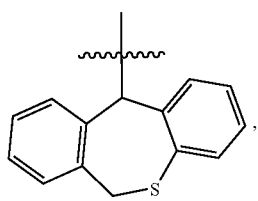 [SMILES: *C1c2ccccc2CSc2ccccc21]

optionally two R together with carbon atom to which they are attached form a $C_{3-8}$ carbocyclic ring, 3-8 membered heterocyclic ring, $C_{6-10}$ aromatic ring or 5-10 membered heteroaryl ring; wherein each $C_{3-8}$ carbocyclic ring, 3-8 membered heterocyclic ring, $C_{6-10}$ aromatic ring, and 5-10 membered heteroaryl ring is independently unsubstituted or substituted with 1, 2, 3 or 4 substituents independently selected from deuterium, F, Cl, Br, I, CN, $NO_2$, —$OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene.

In some embodiments, the present invention provides a compound having Formula (III), Formula (IV), Formula (V), Formula (VI), Formula (VII), or a stereoisomer, a tautomer, an N-oxide, a solvate, a metabolite, a pharmaceutically acceptable salt or a prodrug thereof,

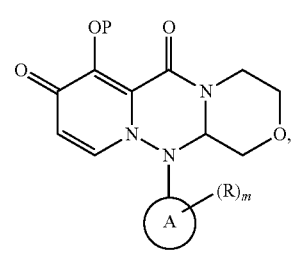
(III)

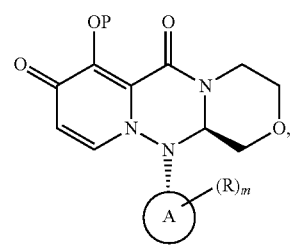
(IV)

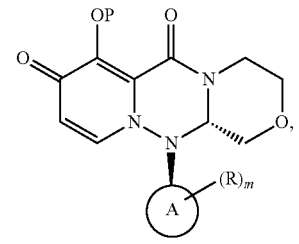
(V)

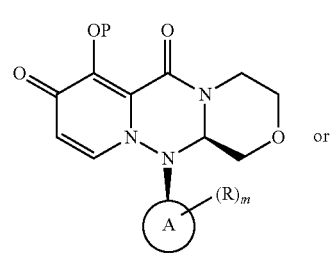
(VI)

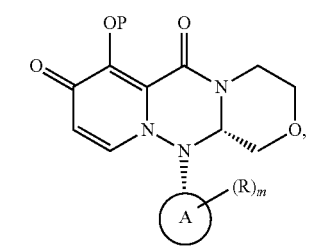
(VII)

Wherein P, R, ring A and m have the definitions as described in the present invention, with the proviso that ring A is not

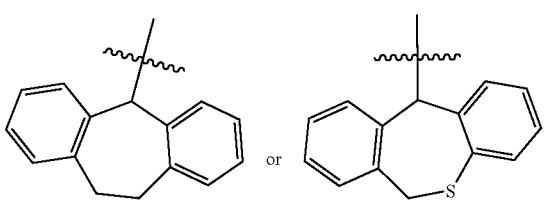 [SMILES: *C1c2ccccc2CCc2ccccc21 ; *C1c2ccccc2CSc2ccccc21]

when m is 0 or 1, and when m is 2 and ring A is

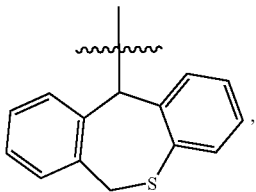 [SMILES: *C1c2ccccc2CSc2ccccc21]

optionally two R together with the carbon atom to which they are attached form a $C_{3-8}$ carbon ring, 3-8 membered heterocyclic ring, $C_{6-10}$ aromatic ring or 5-10 membered heteroaromatic ring; wherein each $C_{3-8}$ carbocyclic ring, 3-8 membered heterocyclic ring, $C_{6-10}$ aromatic ring, and 5-10 membered heteroaromatic ring is independently unsubstituted or substituted with 1, 2, 3 or 4 substituents independently selected from deuterium, F, Cl, Br, I, CN, $NO_2$, $-OR^b$, $-NR^cR^d$, $C_{1-6}$ alkyl, $C_{1-6}$ haloalkyl, $R^bO-C_{1-4}$ alkylene or $R^dR^cN-C_{1-4}$ alkylene.

In other embodiments, the compound of the present invention is a compound having Formula (VIII), Formula (IX), Formula (X), Formula (XI) or a stereoisomer, a tautomer, an N-oxide, a solvate, a metabolite, a pharmaceutically acceptable salt or a prodrug thereof,

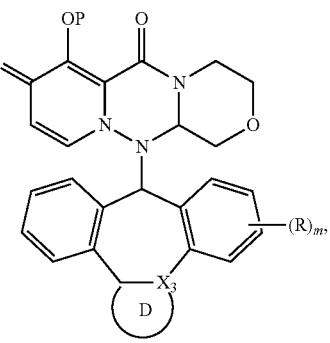
(VIII)

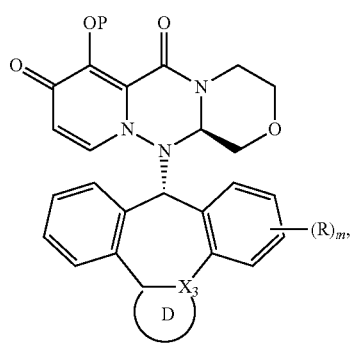
(IX)

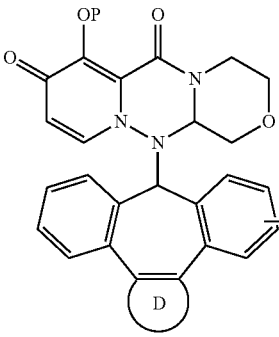
(X)

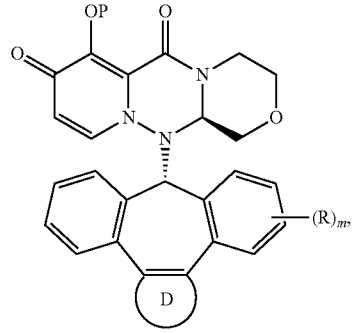
(XI)

wherein P, R, $X^3$, ring D and m have a definition as described in the present invention.

In other aspect, provided herein is a pharmaceutical composition comprising the compound disclosed herein.

In some embodiments, the compound further comprises at least one pharmaceutically acceptable carrier, adjuvant, vehicle or a combination thereof.

In some embodiments, the pharmaceutical compositions of the present invention further comprise one or more other therapeutic agents.

In other embodiments, the other therapeutic agent is selected from anti-influenza agents or vaccines.

In other embodiments, the other therapeutic agent of the pharmaceutical compositions relates to Amantadine, Rimantadine, Oseltamivir, Zanamivir, Peramivir, Lanimamivir, Lanimitine Laninamivir Octanoate Hydrate, Favipiravir, Arbidol, Ribavirin, Steffren, Ingavirin, Influenza Fludase), CAS No. 1422050-75-6, pimodivir, S-033188, Flu Vaccine (FluMist Quadrivalent®, Fluarix® Quadrivalent, Fluzone® Quadrivalent, Flucelvax® or FluBlok®), or their combination.

In other aspect, provided herein is use of the compound or the pharmaceutical composition disclosed herein in the manufacture a medicament for preventing, treating or reducing viral infectious diseases.

In some embodiments, the viral infection is an influenza virus infection.

In other embodiments, provided herein is use of the compound or the pharmaceutical composition disclosed herein in the manufacture a medicament for inhibiting RNA polymerase of influenza virus.

In some embodiments, the RNA polymerase is Cap-dependent endonuclease.

In other aspect, provided herein is the compound or the pharmaceutical composition for use in preventing, managing, treating or lessening disease of virus infection.

In some embodiments, the viral infection is an influenza virus infection.

In other embodiments, the compound or the pharmaceutical composition of the present invention can be used for inhibiting RNA polymerase of influenza virus.

In some embodiments, the RNA polymerase is Cap-dependent endonuclease.

In other aspect, provided herein is a method for preventing, managing, treating or lessening a virus infection disease comprising administering a therapeutically effective amount of a compound of the invention or the pharmaceutical composition to a patient in need thereof.

In some embodiments, the viral infection is an influenza virus infection.

In other embodiments, provided herein is a method for inhibiting RNA polymerase of flu virus comprising administering a therapeutically effective amount of a compound of the invention or the pharmaceutical composition to a patient in need thereof.

In some embodiments, the RNA polymerase is Cap-dependent endonuclease.

The foregoing merely summarizes certain aspects disclosed herein and is not intended to be limiting in nature. These aspects and other aspects and embodiments are described more fully below.

EXAMPLES

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application (including but not limited to defined terms, term usage, described techniques, or the like), this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The technical and scientific terms used in the present invention have the same meaning as understandings of the skilled in the art, unless otherwise indicated, all patent publications cited in the entire disclosure of the disclosure is incorporated in its entirety as a whole.

The present invention will apply the following definitions unless otherwise indicated. For the purposes of the present invention, chemical elements are defined in accordance with the Periodic Table of the Elements, CAS version and Handbook of Chemicals, 75, $^{th}$Ed, 1994.

Additionally, general principles of organic chemistry are described in "Organic Chemistry", Thomas Sorrell, University Science Books, Sausalito: 1999, and "March's Advanced Organic Chemistry", by Michael B. Smith and Jerry March, John Wiley & Sons, New York: 2007, therefore, all the contents of the present invention incorporate references.

As used herein, the term "subject" refers to an animal. Typically the animal is a mammal. A subject also refers to primates (eg., humans), cows, sheep, goats, horses, dogs, cats, rabbits, rats, mice, fish, birds and the like. In certain embodiments, the subject is a primate. In yet other embodiments, the subject is a human.

The terms "subject" and "patient" as used herein are used interchangeably. The terms "subject" and "patient" refer to animals (eg., birds or mammals such as chickens, quails, or turkeys), particularly "mammals" including non-primates (eg., cows, pigs), horses, sheep, rabbits, guinea pigs, rats, cats, dogs, and mice) and primates (eg., monkeys, chimpanzees, and humans), and more particularly humans. In one embodiment, subject is non-human animal, for example livestock (eg. horse, cow, pig or sheep) or Pets (eg. dogs, cats, guinea pigs or rabbits). In other embodiments, "patient" refers to a human.

The invention also includes isotopically-labeled compounds of the invention which are identical to those described herein except the fact that one or more atoms are replaced by an atom having an atomic mass or mass different from the natural common atomic mass or mass number. Exemplary isotopes that may also be incorporated into the compounds of the invention include isotopes of hydrogen, carbon, nitrogen, oxygen, phosphorus, sulfur, fluorine, and chlorine, for example $^{2}$H, $^{3}$H, $^{13}$C, $^{14}$C, $^{15}$N, $^{16}$O, $^{17}$O, $^{31}$P, $^{32}$P, $^{36}$S, $^{18}$F and $^{37}$Cl.

Compounds of the invention comprising the aforementioned isotopes and/or other isotopes of other atoms, as well as pharmaceutically acceptable salts of said compounds are included within the scope of the invention. Certain isotopically-labeled compounds of the present invention, for example those into which radioactive isotopes eg. $^{3}$H or $^{14}$C are incorporated, are useful in drug and/or substrate tissue distribution assays. Deuterated, i.e., $^{3}$H, and carbon-14, i.e., $^{14}$C isotope is particularly preferred because of its ease of preparation and detection. In addition, substitution with heavy isotopes such as deuterium, i.e., $^{2}$H, may provide some therapeutic advantages resulting from greater metabolic stability, such as increased in vivo half-life or reduced dosage requirements. Therefore, it may be preferable in some cases.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that these stereoisomers are mirror images of one another. A specific stereoisomer is referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

The compounds disclosed herein may contain asymmetric or chiral centers, and therefore exist in different stereoisomeric forms. It is contemplated that all stereoisomeric forms of the compounds of the invention include, but are not limited to, diastereomers, enantiomers, atropisomers and geometric (or conformational) isomers and mixtures thereof, such as racemic mixtures, which are all within the scope of the invention.

Unless otherwise indicated, structures depicted in the present invention are also meant to include all isomers (e.g., enantiomers, diastereomeric atropisomers, and geometric (or conformation)) forms of this structure; for example, R and S configurations of each asymmetric center, the (Z) and (E) double bond isomers, and the (Z) and (E) conformers. Thus, individual stereochemical isomers as well as mixtures of enantiomers, diastereomeric mixtures and geometric isomers (or conformational isomers) of the compounds of the invention are within the scope of the invention.

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by recombination of some of the bonding electrons. A specific example of keto-enol tautomerization is the interconversion of pentane-2,4-dione and 4-hydroxypent-3-en-2-one tautomers. Another example of tautomerization is phenol-keto tautomerization. The specific example of phenol-keto tautomerisms is pyridin-4-ol and pyridin-4(1H)-one tautomerism. Unless otherwise stated, all tautomeric forms of the compounds disclosed herein are within the scope of the invention.

An "N-oxide" refers to one or more than one nitrogen atoms oxidised to form an N-oxide, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g. peroxycarboxylic acid) (See, Advanced Organic Chemistry, by Jerry March, 4th Edition, Wiley Interscience, pages). More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine. The term "hydrate" refers to the complex where the solvent molecule is water.

A "metabolite" is a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in J. Pharmaceutical Sciences, 1977, 66: 1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "prodrug" refers to a compound that is transformed in vivo into a compound releasing active drug to exert a pharmacological effect via chemical modification. Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_{1-24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, Nature Reviews Drug Discovery, 2008, 7, 255-270, and Hecker et al., Prodrugs of Phosphates and Phosphonates, J. Med. Chem., 2008, 51, 2328-2345, all of which are incorporated herein by reference in their entireties.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. If possible, a substituent on an atom having an unsaturated double bond may exist in the form of cis-(Z)- or trans-(E)-.

Thus, as described herein, the compounds of the invention may exist in the form of one of the possible isomers, rotamers, atropisomers, tautomers, or mixtures thereof, for example, pure geometric (cis or trans) isomer, diastereomer, optical isomer (enantiomer), racemate or a mixture thereof.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); Principles of Asymmetric Synthesis (2nd Ed. Robert E. Gawley, Jeffrey Aubé, Elsevier, Oxford, U K, 2012); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972).

As described herein, compounds disclosed herein may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted". The term "optional" or "optionally" means that the subsequently described event or condition may, but does not necessarily, occur, and that the description includes the circumstances in which the event or condition occurred, and the circumstances in which the event or condition did not occur. In general, the term "substituted" refers to no replacement or replacement of one or more hydrogen radicals in a given structure with the radical of a specified substituent, no matter whether the term "optionally" is before the term "substituted". Unless otherwise indicated, an optionally substituted group may have a substituent at each substitutable position of the group. When more than one position in a given structure can be substituted with more than one substituent selected from a specified group, the substituent may be either the same or different at each position. The substituents described therein may be, but are not limited to, deuterium, F, Cl, Br, CN, $N_3$, OH, $NH_2$, $NO_2$, OXO (=O), —C(=O)$R^a$, —C(=O)O$R^b$, —O(C=O)$R^a$, —C(=O)NR$^c$R$^d$, —S(=O)$_2$NR$^e$C(=O)$R^a$, —S(=O)$_2$NR$^c$R$^d$, ($R^b$O)$_2$P(=O)—$C_{0-2}$ alkylene, O$R^b$, —NR$^c$R$^d$, $R^b$O-alkylene, $R^d$R$^c$N-alkylene, —C(=O)—$R^{Pa}$, —C(=O)-L-$R^{Pe}$, —C(=O)-L-O—$R^{Pb}$, —C(=O)-L-O-L-O—$R^{Pb}$, —C(=O)-L-O—C(=NO)—$R^{Pa}$, —C(=O)—NR$^{Pc}$R$^{Pd}$, —C(=O)—O—$R^{Pb}$, —S(=O)$_2$—$R^{Pk}$, P(=O)—($R^{Pg}$)($R^{Ph}$), —C(=O)—O-L-O—$R^{Pb}$, —C(=$N^+$R$^{Pi}$R$^{Pj}$)(NR$^{Pc}$R$^{Pd}$), $R^{Pb}$—O-alkylene, $R^{Pb}$—O-L-O-alkylene, $R^{Pa}$—(C=O)—O-alkylene, $R^{Pb}$—O—(C=O)-alkylene, $R^{Pb}$—O—(C=O)—NR$^{Pf}$-alkylene, $R^{Pb}$—O—(C=O)—O-alkylene, NR$^{Pf}$R$^{Pd}$—O—(C=O)—O-alkylene, $R^{Pb}$—O-L-O—(C=O)—O-alkylene, NR$^{Pc}$R$^{Pd}$-L-O—(C=O)—O-alkylene, $R^{Pb}$—O-L-NR$^{Pf}$—(C=O)—O-alkylene, NR$^{Pe}$R$^{Pd}$-L-N(R$^{Pf}$)—(C=O)—O-alkylene, $R^{Pb}$—O-L-O-L-O—(C=O)—O-alkylene, (HO)$_2$P(=O)-alkylene, (BnO)$_2$P(=O)-alkylene, $R^{Pa}$—(C=O)—NR$^{Pf}$-L-O—(C=O)—O-alkylene, alkyl, haloalkyl, alkoxy, alkylamino, carbocyclyloxy, carbocyclylamino, heterocyclyloxy, heterocyclylamino, aryloxy, arylamino, heteroaryloxy, heteroarylamino, alkenyl, alkynyl, carbocyclyl, carbocyclyl-alkylene, cycloalkyl, cycloalkyl-alkylene, heterocyclyl, heterocyclyl-$C_{1-4}$ alkylene, aryl, aryl-alkylene, heteroaryl or heteroaryl-alkylene, wherein, each $R^a$, $R^b$, $R^c$, $R^d$, $R^{Pa}$, $R^{Pb}$, $R^{Pc}$, $R^{Pd}$, $R^{Pe}$, $R^{Pf}$, $R^{Pg}$, $R^{Ph}$, $R^{Pe}$, $R^{Pj}$ and $R^{Pk}$ has the definition as described in the present invention.

Furthermore, what need to be explained is that the phrase "each . . . is independently" and "each of . . . and . . . is independently", unless otherwise stated, should be broadly understood. The specific options expressed by the same symbol are independent of each other in different groups; or the specific options expressed by the same symbol are independent of each other in same groups.

At various places in the present specification, substituents of compounds disclosed herein are disclosed in groups or in ranges. It is specifically intended that the invention include each and every individual subcombination of the members of such groups and ranges. The term "$C_{1-6}$ alkyl" specifically refers to $C_1$ (methyl), $C_2$ (ethyl), $C_3$ alkyl, $C_4$ alkyl, $C_5$ alkyl and $C_6$ alkyl independently disclosed; the term "5-10 membered heteroaromatic ring" specifically refers to a heteroaromatic ring composed of 5 atoms independently disclosed, a heteroaromatic ring composed of 6 atoms, a heteroaromatic ring composed of 7 atoms, a heteroaromatic ring composed of 8 atoms, a heteroaromatic ring composed of 9 atoms and a heteroaromatic ring composed of 10 atoms; the term "3-8 membered heterocyclic ring" particularly refers to a heterocyclic ring composed of 3 atoms, a heterocyclic ring composed of 4 atoms, and a heterocyclic ring composed of 5 atoms, a heterocyclic ring composed of 6 atoms, a heterocyclic ring composed of 7 atoms, and a heterocyclic ring composed of 8 atoms independently disclosed.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" as used herein, denotes a saturated straight or branched monovalent hydrocarbon radical containing 1 to 20 carbon atoms. Unless otherwise specified, the alkyl group contains 1-20 carbon atoms. In some embodiments, the alkyl group contains 1-12 carbon atoms. In some embodiments, the alkyl group contains 1-10 carbon atoms. In other embodiments, the alkyl group contains 1-9 carbon atoms. In other embodiments, the alkyl group contains 1-8 carbon atoms. In other embodiments, the alkyl group contains 1-6 carbon atoms. In still other embodiments, the alkyl group contains 1-4 carbon atoms. In yet other embodiments, the alkyl group contains 1-3 carbon atoms and in still yet other embodiments, the alkyl group contains 1-2 carbon atoms.

Examples of alkyl groups include, but are not limited to, methyl (Me, —CH$_3$), ethyl (Et, —CH$_2$CH$_3$), n-propyl (n-Pr, —CH$_2$CH$_2$CH$_3$), Isopropyl (i-Pr, —CH(CH$_3$)$_2$), n-butyl (n-Bu, —CH$_2$CH$_2$CH$_2$CH$_3$), Isobutyl (i-Bu, —CH$_2$CH(CH$_3$)$_2$), sec-butyl (s-Bu, —CH(CH$_3$)CH$_2$CH$_3$), tert-butyl (t-Bu, —C(CH$_3$)$_3$), n-pentyl (—CH$_2$CH$_2$CH$_2$CH$_2$CH$_3$), 2-pentyl (—CH(CH$_3$)CH$_2$CH$_2$CH$_3$) 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$) n-hexyl (—CH$_2$CH$_2$CH$_2$CH$_2$CH$_2$CH$_3$) 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 2-methyl-2-pentyl (—CH(CH$_3$)CH(CH$_3$)CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), n-heptyl, n-octyl, etc., wherein the alkyl group may be independently unsubstituted or substituted with one or more substituents described herein.

The term "alkyl" or the prefix "alk-" is inclusive of both straight chain and branched saturated carbon chain.

The term "alkylene" refers to a saturated divalent hydrocarbon group derived from a straight or branched chain saturated hydrocarbon by the removal of two hydrogen atoms. Unless otherwise specified, the alkylene group contains 1-10 carbon atoms. In other embodiments, the alkylene group contains 1-6 carbon atoms. In other embodiments, the alkylene group contains 1-4 carbon atoms. In still other embodiments, the alkylene group contains 1-2 carbon atoms. Such examples include methylene (—CH$_2$—), ethylene (—CH$_2$CH$_2$—), isopropylidene (—CH(CH$_3$)CH$_2$—), etc.

The alkylene group may be optionally unsubstituted or substituted with one or more substituents disclosed herein.

The term "alkenyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, sp2 double bond, wherein the alkenyl radical may be optionally substituted independently with one or more substituents described herein, and includes radicals having "cis" and "trans" orientations, or alternatively, "E" and "Z" orientations. Specific examples include, but are not limited to, vinyl (—CH=CH$_2$), allyl (—CH$_2$CH=CH$_2$), and the like.

The term "alkynyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, sp triple bond, wherein the alkynyl radical is independently unsubstituted or substituted with one or more substituents described herein. Specific examples include, but are not limited to, ethynyl (—C≡CH), propargyl (—CH$_2$C≡CH), 1-propynyl (—C≡C—CH$_3$), and the like.

The term "alkoxy" refers to an alkyl group, as previously defined, attached to the parent molecular moiety via an oxygen atom. In some embodiments, the alkoxy group contains 1-20 carbon atoms. In other embodiments, the alkoxy group contains 1-10 carbon atoms. In other embodiments, the alkoxy group contains 1-8 carbon atoms. In other embodiments, the alkoxy group contains 1-6 carbon atoms. In still other embodiments, the alkoxy group contains 1-4 carbon atoms.

In yet other embodiments, the alkoxy group contains 1-3 carbon atoms and in still yet other embodiments, the alkoxy group contains 1-2 carbon atoms.

Examples of alkoxy group include, but are not limited to, methoxy(MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentyloxy (n-pentyloxy, —OCH$_2$CH$_2$CH$_2$CH$_2$CH$_3$), 2-pentyloxy (—OCH(CH$_3$)CH$_2$CH$_2$CH$_3$), 3-pentyloxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), etc., wherein the alkoxy group may be independently unsubstituted or substituted with one or more substituents described herein.

The term "carbocyclyloxy" refers to an carbocyclic group, as previously defined, attached to the parent molecular moiety via an oxygen atom. Examples of carbocyclyloxy groups include, but are not limited to,

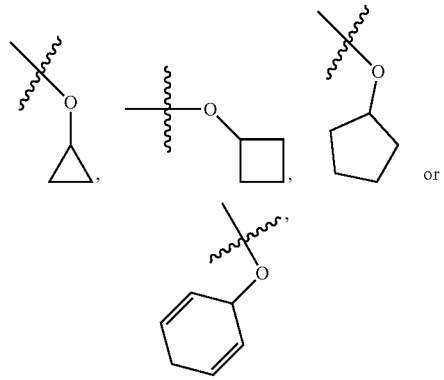

etc., wherein the carbocyclyloxy group may be optionally substituted with one or more substituents disclosed herein.

The term "heterocyclyloxy" refers to an heterocyclyl group, as previously defined, attached to the parent molecular moiety via an oxygen atom. Examples of heterocyclyloxy group include, but are not limited to,

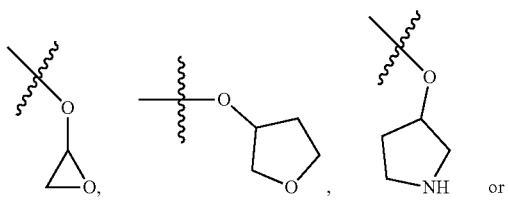

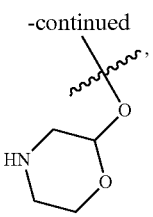

etc., wherein heterocyclyloxy group may be independently unsubstituted or substituted with one or more substituents disclosed herein.

The term "aryloxy" refers to an aryl group, as previously defined, attached to the parent molecular moiety via an oxygen atom, wherein the aryl group has the meaning as described in the present invention. Examples of aryloxy group include, but are not limited to,

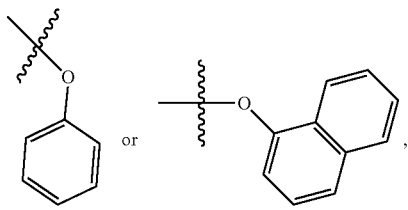 [SMILES: *Oc1ccccc1 ; *Oc1cccc2ccccc12]

etc., wherein aryloxy group may be independently unsubstituted or substituted with one or more substituents disclosed herein.

The term "heteroaryloxy" refers to an heteroaryl group, as previously defined, attached to the parent molecular moiety via an oxygen atom. Examples of heteroaryloxy group include, but are not limited to,

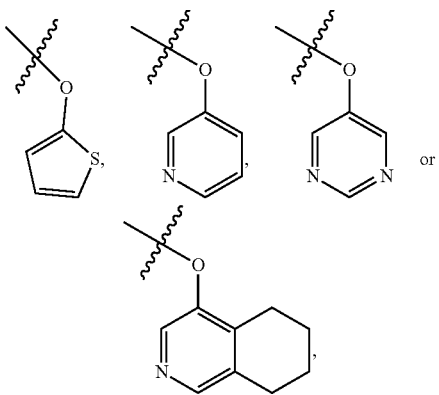

etc., wherein heteroaryloxy group may be optionally substituted with one or more substituents disclosed herein.

The term "haloalkyl" refers to an alkyl group substituted with one or more identical or different halogen atoms. In some embodiments, the haloalkyl group contains 1-10 carbon atoms. In other embodiments, the haloalkyl group contains 1-8 carbon atoms. In other embodiments, the haloalkyl group contains 1-6 carbon atoms. In still other embodiments, the haloalkyl group contains 1-4 carbon atoms. In yet other embodiments, the haloalkyl group contains 1-3 carbon atoms. Such examples include, but are not limited to, trifluoromethyl, trifluoroethyl (such as —CH$_2$CF$_3$, —CHFCHF$_2$, —CF$_2$CH$_2$F), etc.

The terms "haloalkoxy" refer to alkoxy, as the case may be, substituted with one or more halogen atoms. In some embodiments, the haloalkoxy group contains 1-10 carbon atoms. In other embodiments, the haloalkoxy group contains 1-8 carbon atoms. In other embodiments, the haloalkoxy group contains 1-6 carbon atoms. In still other embodiments, the haloalkoxy group contains 1-4 carbon atoms. In yet other embodiments, the haloalkoxy group contains 1-3 carbon atoms. Such examples include, but are not limited to, trifluoromethoxy (—OCF$_3$), difluoromethoxy (—OCHF$_2$), trifluoroethoxy (e.g., —OCH$_2$CF$_3$, —OCHFCHF$_2$, —OCF$_2$CH$_2$F) and the like.

The terms "carbocyclic ring", "carbocyclyl" or "carbocyclic" are used interchangeably herein, which all refer to a saturated non-aromatic carbocyclic ring system composed of 3-30 ring carbon atoms or a non-aromatic carbocyclic ring system composed of 3-30 ring carbon atoms containing one or more unsaturated units. In some embodiments, the number of carbon atoms is 10-30; in other embodiments, the number of carbon atoms is 10-25; in other embodiments, the number of carbon atoms is 12-20; in some embodiments, the number of carbon atoms is 3-12; in other embodiments, the number of carbon atoms is 3-10; in other embodiments, the number of carbon atoms is 3-8; in other embodiments, the number of carbon atoms is 3-6; in other embodiments, the number of carbon atoms is 5-6; in other embodiments, the number of carbon atoms is 5-8. In other embodiments, the number of carbon atoms is 6-8. In yet other embodiments, the number of carbon atoms is 3. In yet other embodiments, the number of carbon atoms is 4. In yet other embodiments, the number of carbon atoms is 5. In yet other embodiments, the number of carbon atoms is 6. This "carbocyclyl" includes monocyclic, bicyclic or polycyclic fused, spiro or bridged carbocyclic ring systems. Bicyclic carbocyclyl includes bridged bicyclic carbocyclyl, fused bicyclic carbocyclyl and spirobicyclic carbocyclyl, and "fused" bicyclic ring system comprises two rings sharing two adjacent ring atoms. A bridged bicyclic group includes two rings that share 3 or 4 adjacent ring atoms. The spiro bicyclic ring system shares one ring atom. Some non-limiting examples of the carbocyclyl include cycloalkyl, cycloalkenyl and cycloalkynyl. Examples of the carbocyclyl include, but are not limited to, cyclopropyl, cyclobutyl, cyclopentyl, cyclohexyl, cycloheptyl, cyclopentenyl (eg. 1-cyclopentyl-1-enyl, 1-cyclopentyl-2-enyl, 1-cyclopentyl-3-enyl), cyclopentadienyl, cyclohexyl, cyclohexenyl (eg. 1-cyclohexyl-1-enyl, 1-cyclohexyl-2-enyl, 1-cyclohexyl-3-enyl), cyclohexadienyl, cycloheptyl, cyclooctyl, cyclononyl, cyclodecyl, cycloundecyl, cyclododecyl, and the like. Bridged carbocyclyl groups include, but are not limited to, bicyclo [2.2.2] octyl, bicyclo [2.2.1] heptyl, bicyclo [3.3.1] nonyl, bicyclo [3.2.3] nonyl and the like.

The term "cycloalkyl" refers to a saturated monocyclic, bicyclic or polycyclic ring system composed of 3 to 30 carbon atoms having one or more attachment points attached to the remainder of the molecule. In some embodiments, cycloalkyl is a ring system containing 10-30 carbon atoms; In other embodiments, cycloalkyl is a ring system containing 10-25 carbon atoms; In other embodiments, cycloalkyl is a ring system containing 3-10 carbon atoms; In other embodiments, cycloalkyl is a ring system containing 3-8 carbon atoms; In other embodiments, cycloalkyl is a ring system containing 3-6 carbon atoms; In other embodiments, cycloalkyl is a ring system containing 5-6 carbon atoms; examples of cycloalkyl groups include, but are not limited to, cyclopropyl, cyclobutyl, cyclopentyl, cyclohexyl, cycloheptyl, and the like; and the cycloalkyl group may be independently unsubstituted or substituted with one or more substituents described herein.

The terms "heterocyclyl" and "heterocyclic ring" used interchangeably herein, all refer to a saturated or partially saturated non-aromatic system composed of 3-30 atoms in which at least one ring member is selected from nitrogen, sulfur and oxygen. The heterocyclyl is non-aromatic and does not contain any aromatic ring, and the ring system has one or more attachment points attached to the remainder of the molecule. The term "heterocyclyl" includes monocyclic, bicyclic or polycyclic fused, spiro or bridged heterocyclic ring systems. Bicyclic heterocyclyl include bridged bicyclic heterocyclyl, fused bicyclic heterocyclyl, and spirobicyclic heterocyclyl. Unless otherwise specified, the heterocyclyl may be carbon or nitrogen base, and a —$CH_2$— group can be optionally replaced by a —C(=O)— group. In which, the sulfur can be optionally oxygenized to S-oxide. And the nitrogen can be optionally oxygenized to N-oxide. In some embodiments, heterocyclyl is a ring system composed of 3 to 30 ring atoms; in other embodiments, heterocyclyl is a ring system composed of 10 to 30 ring atoms; in other embodiments, heterocyclyl group is a ring system composed of 10 to 25 ring atoms; in other embodiments, heterocyclyl is a ring system composed of 12 to 20 ring atoms; in other embodiments, heterocyclyl is a ring system composed of 3 to 8 ring atoms; in other embodiments, heterocyclyl is a ring system composed of 3 to 6 ring atoms; in other embodiments, heterocyclyl is a ring system composed of 5 to 7 ring atoms; in other embodiments, heterocyclyl is a ring system composed of 5 to 8 ring atoms; in other embodiments, heterocyclyl is a ring system composed of 6 to 8 ring atoms; in other embodiments, heterocyclyl is a ring system composed of 5 to 6 ring atoms; in other embodiments, heterocyclyl is a ring system composed of 4 ring atoms; in other embodiments, heterocyclyl is a ring system composed of 5 ring atoms; in other embodiments, heterocyclyl is a ring system composed of 6 ring atoms; in other embodiments, heterocyclyl is a ring system composed of 7 ring atoms; in other embodiments, heterocyclyl is a ring system composed of 8 ring atoms.

Examples of heterocyclyl include, but are not limited to, oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl and the like. Some non-limiting examples that —$CH_2$— group in heterocyclyl is replaced by —C(=O)— moiety include 2-oxopyrrolidinyl, oxo-1,3-thiazolidinyl, 2-piperidinonyl, 3,5-dioxopiperidinyl, and pyrimidinedionyl. Some non-limited examples of heterocyclyl wherein the ring sulfur atom is oxidized is sulfolanyl, 1,1-dioxo-thiomorpholinyl. Some non-limited examples of bridged heterocyclic group include 2-oxabicyclo[2.2.2]octyl, 1-azabicyclo[2.2.2]octyl, 3-azabicyclo[3.2.1]octyl, etc. The heterocyclyl group may be optionally substituted with one or more substituents disclosed herein.

The term "z membered", where z is an integer typically describes the number of ring-forming atoms in a moiety where the number of ring-forming atoms is z. For example, piperidinyl is an example of a 6 membered heterocyclyl and 1,2,3,4-tetrahydronaphthyl is an example of a 10 membered carbocyclyl group.

The term "heteroatom" refers to one or more of oxygen, sulfur, nitrogen, phosphorus and silicon, including any oxidized form of nitrogen, sulfur, or phosphorus; the quaternized form of any basic nitrogen; or a substitutable nitrogen of a heterocyclic ring, for example, N (as in 3-dihydro-2H-pyrrolyl), NH (as in pyrrolidinyl) or NR (as in N-substituted pyrrolidinyl).

The term "halogen" refers to fluoro (F), chloro (Cl), bromo (Br), or iodo (I).

The term "aryl" used alone or as a substantial part of "aralkyl", "aryloxy", "aralkyloxy", "arylamino" or "aryloxyalkyl" refers to monocyclic, bicyclic and tricyclic carbocyclic ring systems having a total of six to fourteen ring members, or six to twelve ring members, or six to ten ring members, or ten to thirty ring members, or ten to twenty five ring members, wherein at least one ring in the system is aromatic, wherein each ring in the system contains 3 to 15 ring members and that has a single point or multipoint of attachment to the rest of the molecule. The term "aryl" may be used interchangeably with the term "aromatic ring", as an aromatic ring may include phenyl, 2,3-dihydro-1H-indenyl, naphthyl, anthracenyl,

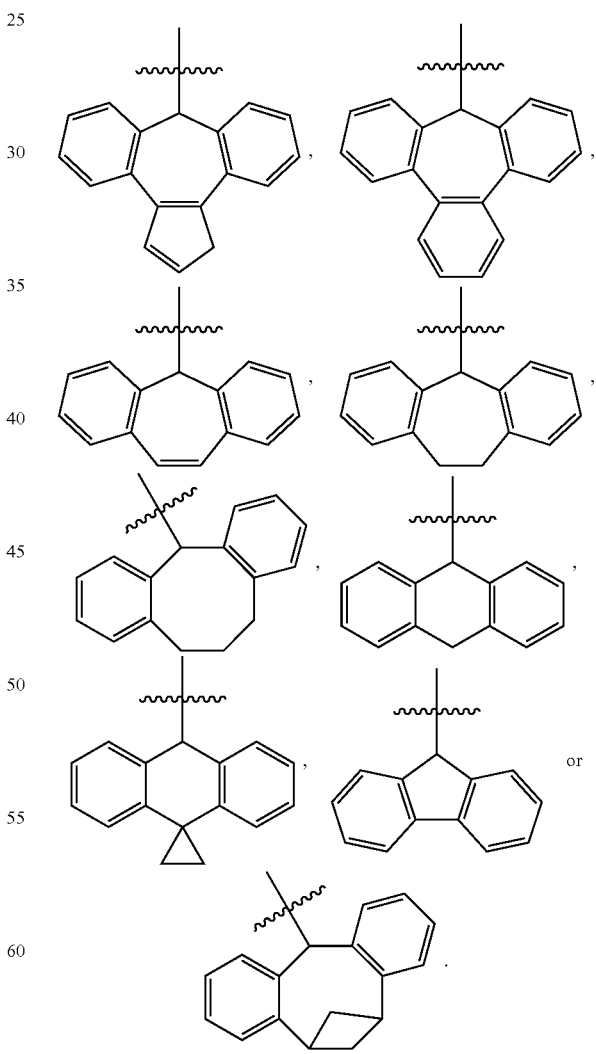

The aryl group may be optionally substituted with one or more substituents disclosed herein.

The term "heteroaryl" used alone or as a major part of "heteroarylalkyl", "heteroaryloxy", "heteroarylamino" or "heteroarylalkoxy" refers to monocyclic, bicyclic and tricyclic carbocyclic ring systems having a total of five to thirty ring atoms, wherein at least one ring is aromatic, and in which at least one ring contains one or more heteroatoms, and the aromatic system has a single point or multipoint of attachment to the rest of the molecule. When a —CH$_2$— group is present in a heteroaryl group, the —CH$_2$— group can be optionally replaced by —C(=O)—. The term "heteroaryl" and "heteroaromatic ring" or "heteroaromatic compound" can be used interchangeably herein. In some embodiments, a heteroaryl group is a heteroaryl group consisting of 10-30 atoms containing 1, 2, 3 or 4 heteroatoms independently selected from O, S and N. In some embodiments, a heteroaryl group is a heteroaryl group consisting of 10-25 atoms containing 1, 2, 3 or 4 heteroatoms independently selected from O, S and N. In some embodiments, a heteroaryl group is a heteroaryl group consisting of 12-20 atoms containing 1, 2, 3 or 4 heteroatoms independently selected from O, S and N. In some embodiments, a heteroaryl group is a heteroaryl group consisting of 5-14 atoms containing 1, 2, 3 or 4 heteroatoms independently selected from O, S and N. In other embodiments, a heteroaryl group is a heteroaryl group consisting of 5-12 atoms containing 1, 2, 3 or 4 heteroatoms independently selected from O, S and N. In other embodiments, a heteroaryl group is a heteroaryl group consisting of 5-10 atoms containing 1, 2, 3 or 4 heteroatoms independently selected from O, S and N. In other embodiments, a heteroaryl group is a heteroaryl group consisting of 5-8 atoms containing 1, 2, 3 or 4 heteroatoms independently selected from O, S and N. In other embodiments, a heteroaryl group is a heteroaryl group consisting of 5-7 atoms containing 1, 2, 3 or 4 heteroatoms independently selected from O, S and N. In other embodiments, a heteroaryl group is a heteroaryl group consisting of 5-6 atoms containing 1, 2, 3 or 4 heteroatoms independently selected from O, S and N. In other embodiments, a heteroaryl group is a heteroaryl group consisting of 5 atoms containing 1, 2, 3 or 4 heteroatoms independently selected from O, S and N. In other embodiments, a heteroaryl group is a heteroaryl group consisting of 6 atoms containing 1, 2, 3 or 4 heteroatoms independently selected from O, S and N.

In other embodiments, the heteroaryl group includes, but is not limited to the following monocyclic groups: 2-furyl, 3-furyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (eg. 3-pyridazinyl), 2-thiazolyl, 4-thiazolyl, 5-thiazolyl, tetrazolyl (eg. 5H-tetrazolyl, 2H-tetrazolyl), triazolyl (eg. 2-triazolyl, 5-triazolyl, 4H-1,2,4-triazolyl, 1H-1,2,4-triazolyl, 1,2,3-triazolyl), 2-thienyl, 3-thienyl, pyrazolyl (eg. 2-pyrazolyl and 3-pyrazolyl), isothiazolyl, 1,2,3-oxadiazolyl, 1,2,5-oxadiazolyl, 1,2,4-oxadiazolyl, 1,3,4-oxadiazolyl, 1,2,3-thiodiazolyl, 1,3,4-thiodiazolyl, 1,2,5-thiodiazolyl, pyrazinyl, 1,3,5-triazinyl; also included are the following bicyclic groups, but are not limited to these bicyclic groups: indolinyl, 1,2,3,4-tetrahydroisoquinolinyl, benzimidazolyl, benzofuranyl, benzothienyl, indolyl (eg. 2-indolyl), purinyl, quinolinyl (eg. 2-quinolyl, 3-quinolinyl, 4-quinolinyl), isoquinolinyl (eg. 1-isoquinolinyl, 3-isoquinolinyl or 4-isoquinolinyl), phenoxathiinyl,

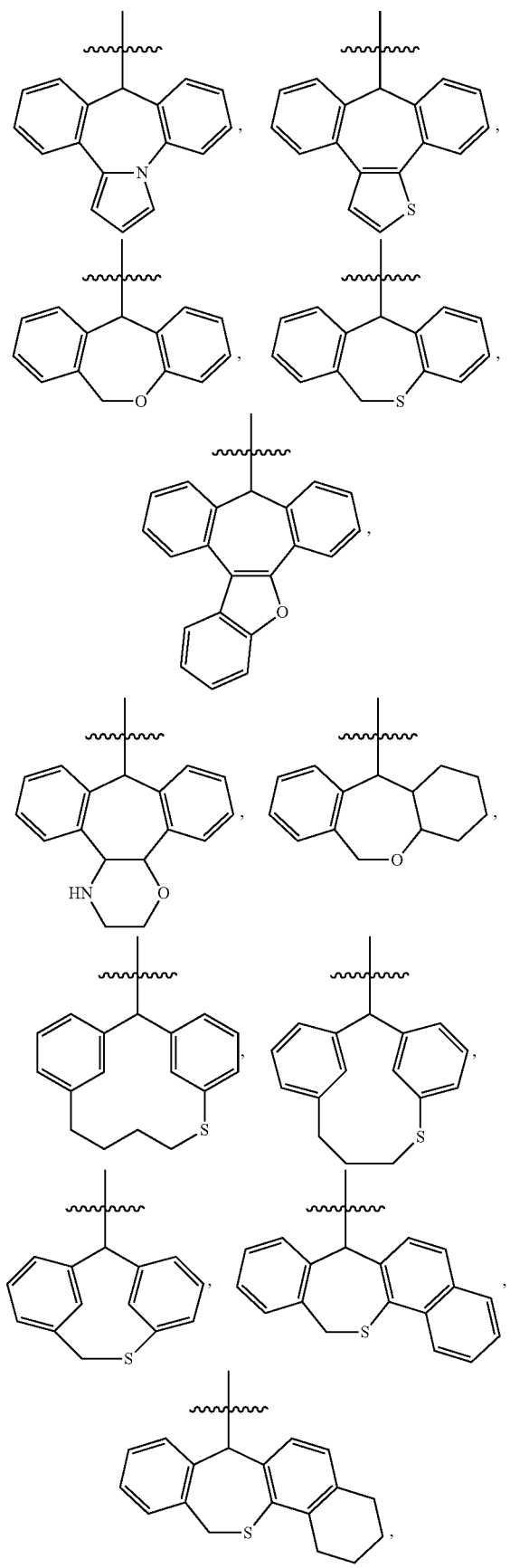

-continued
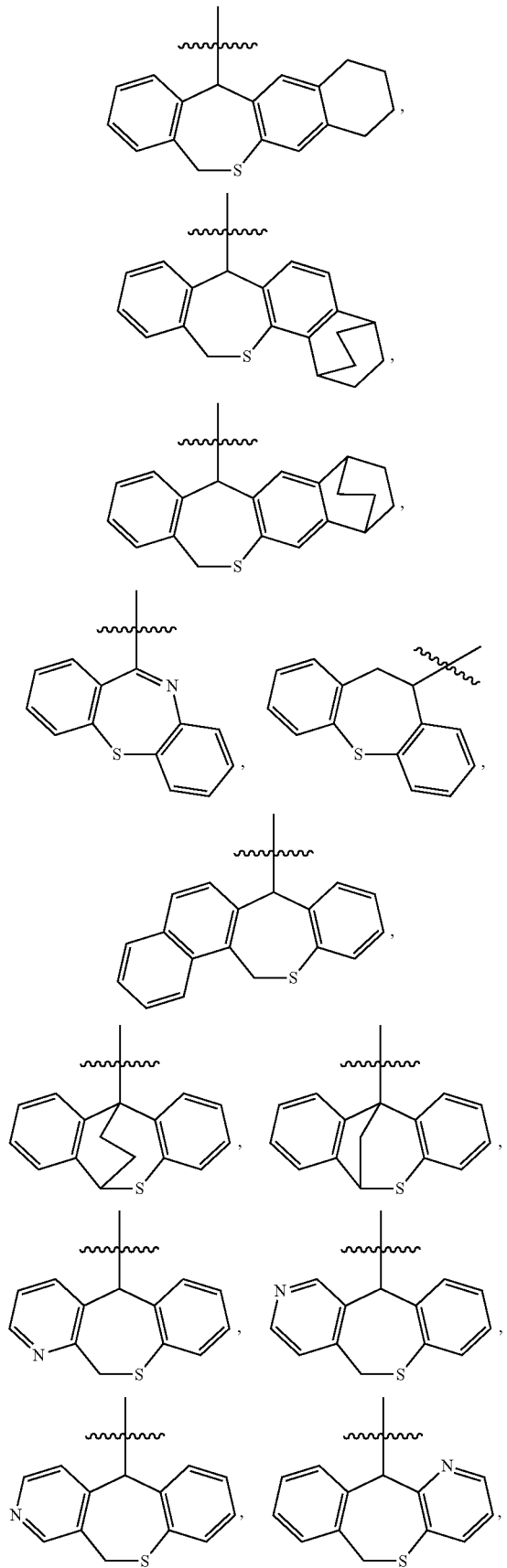
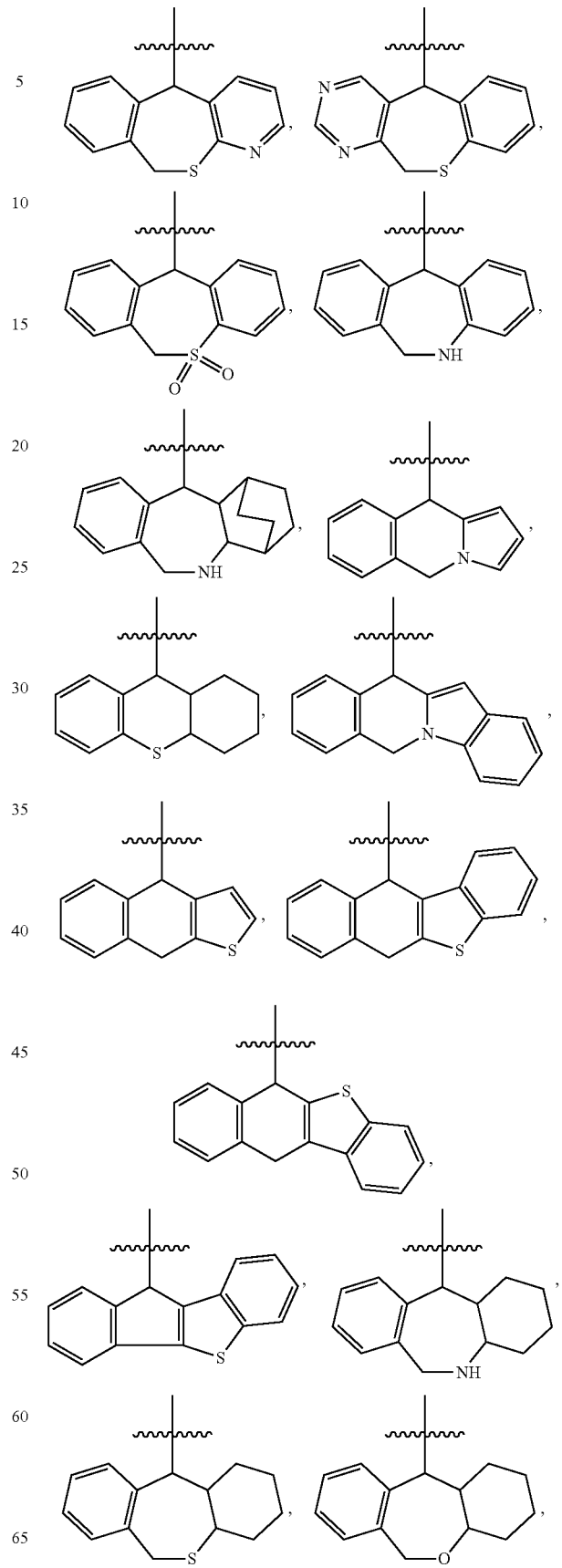

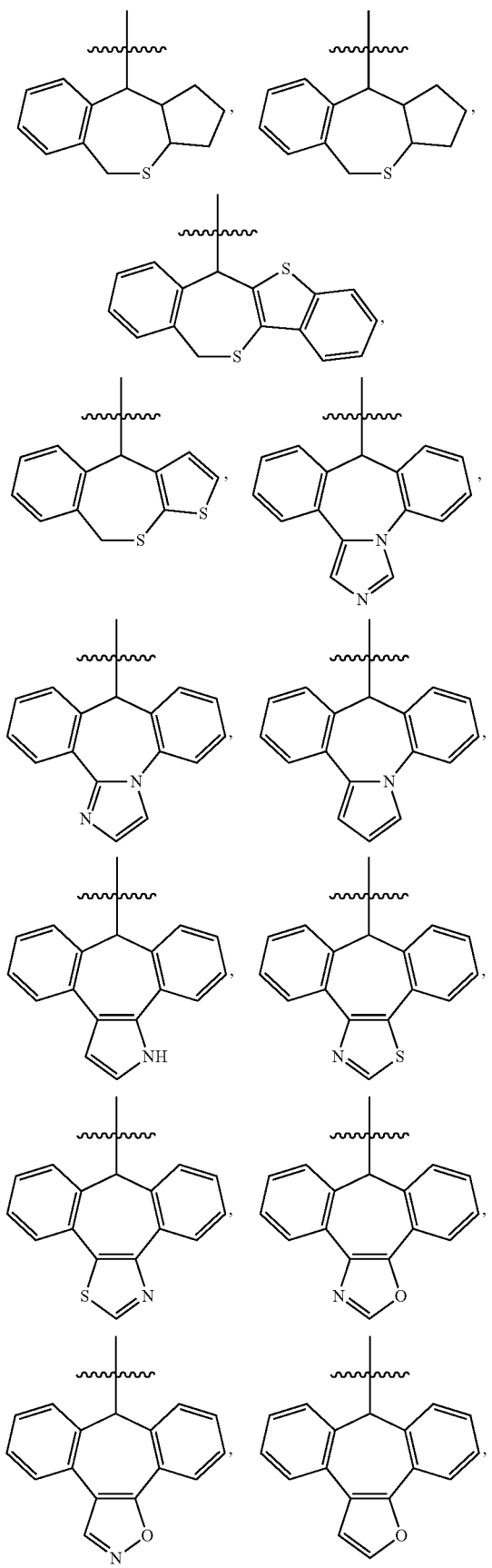
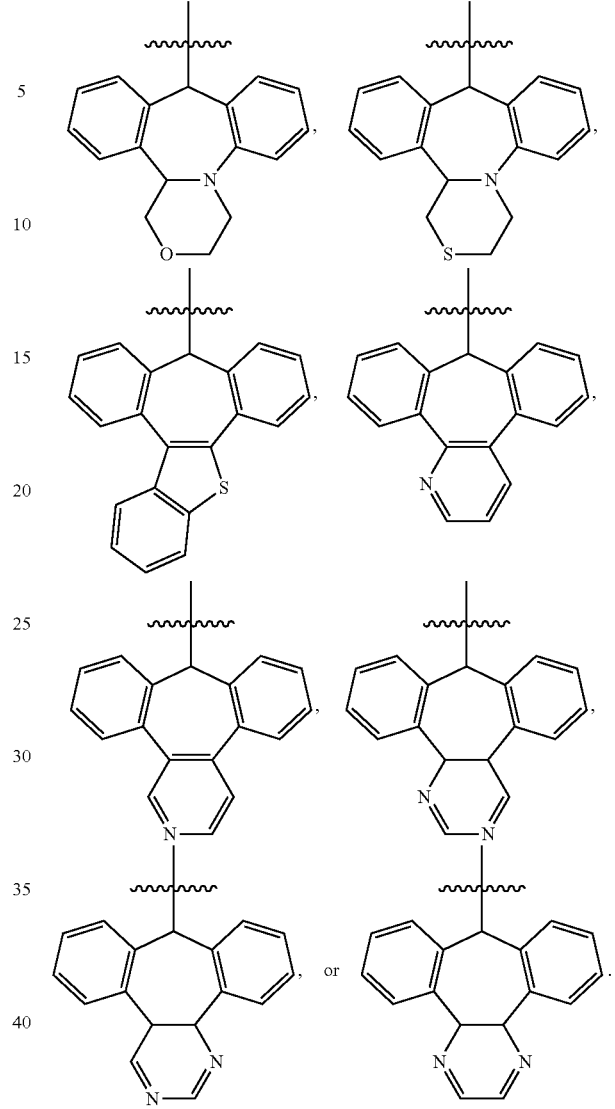

The heteroaryl group is optionally substituted with one or more substituents disclosed herein.

The term "carboxy", whether used alone or in conjunction with other terms, such as "carboxyalkyl", means —CO$_2$H.

The terms "carboxy" or "carboxyl", whether used alone or with other terms, such as "aminoacyl" or "acyloxy", refer to —(C=O)—.

The term "—OBn" refers to benzyloxy.

The term "alkylamino" refers to "N-alkylamino" and "N,N-dialkylamino" wherein amino groups are independently substituted with one alkyl radical or two alkyl radicals, respectively. In some embodiments, the alkylamino group is lower alkylamino group having one or two C$_{1-6}$ alkyl groups attached to nitrogen atom. In other embodiments, the alkylamino group is lower alkylamino group having 1 to 3 carbon atoms. Some non-limiting examples of the alkylamino group include monoalkylamino or dialkylamino such as N-methylamino, N-ethylamino, N,N-dimethylamino, N,N-diethylamino, N-tert-butylamino and the like. The alkylamino group may be optionally substituted with one or more substituents disclosed herein.

The term "carbocyclylamino" refers to an amino group substituted with one or two carbocyclyl groups. Some non-limiting examples of such group include N-cyclopropylamino. The carbocyclylamino group may be optionally substituted with one or more substituents disclosed herein.

The term "arylamino" refers to an amino group substituted with one or two aryl groups. Some non-limiting examples of such group include N-phenylamino. The arylamino group may be independently unsubstituted or substituted with one or more substituents disclosed herein.

The term "heteroarylamino" refers to an amino group substituted with one or two aryl groups. Some non-limiting examples of such group included N-pyrimidinylamino. The heteroaryloxy group may be independently unsubstituted or substituted with one or more substituents disclosed herein.

The term "heterocyclylamino" refers to an amino group substituted with one or two heterocyclyl groups. Some non-limiting examples of such group included N-pyrrolidinylamino. The heterocyclylamino group may be independently unsubstituted or substituted with one or more substituents disclosed herein.

The term "aminoalkyl" refers to a $C_{1-10}$ linear or branched-chain alkyl group substituted with one or more amino groups. In some embodiments, the aminoalkyl is a $C_{1-6}$ lower aminoalkyl substituted with one or more amino groups. Some non-limiting examples of the aminoalkyl group include aminomethyl, aminoethyl, aminopropyl, aminobutyl and aminohexyl.

As described herein, a bond drawn from a substituent to the center of one ring within a ring system represents substitution at any substitutable position on the rings. This ring system includes monocyclic, bicyclic or polycyclic systems. For example, the formula a represents that any position on the ring A which may be substituted may be optionally substituted by m R; for example, the formula b represents that the substituent R may be substituted at any position on the ring which may be substituted, as shown in formulae b-1 to b-12:

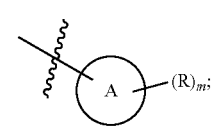

formula a

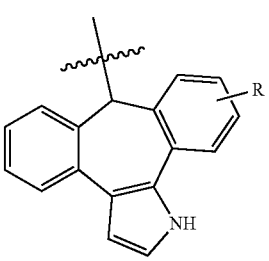

formula b

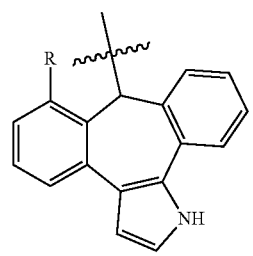

formula b-1

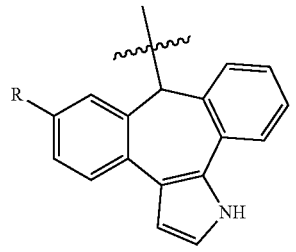

formula b-2

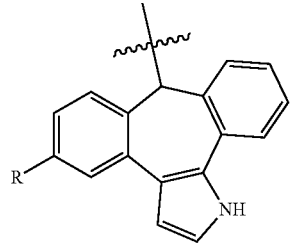

formula b-3

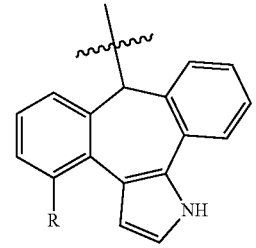

formula b-4

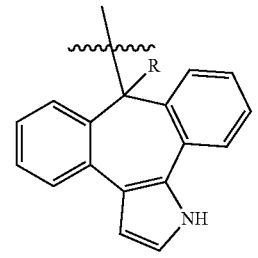

formula b-5

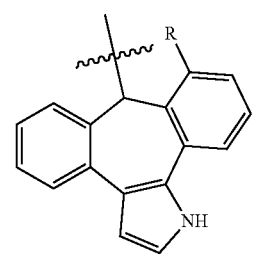

formula b-6

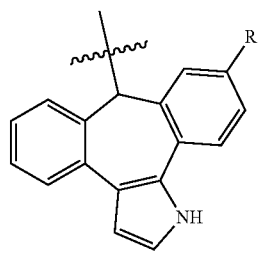

formula b-7 formula b-8

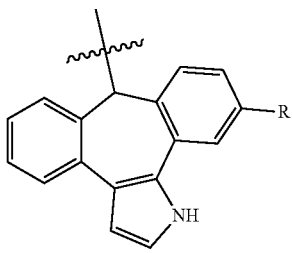

formula b-9

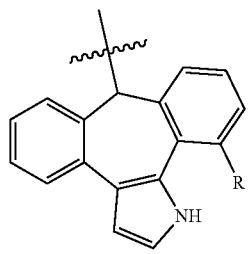

formula b-10

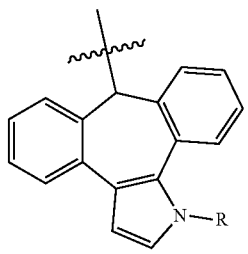

formula b-11

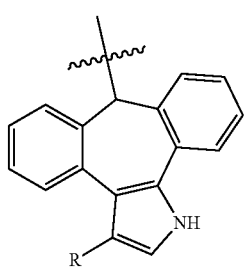

formula b-12

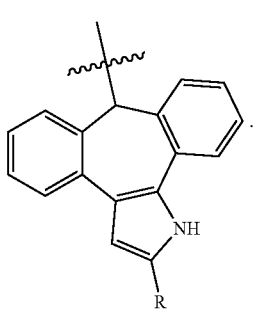

As described herein, a ring system formed by bonding a bond to the center of the ring means that the bond can be attached to the remainder of the molecule at any attachable position on the ring system. For example, formula c represents any position on the ring that may be attached to the rest of the molecule, as shown in formula c-1 and formula c-2.

formula c

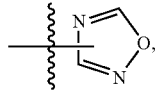

formula c-1

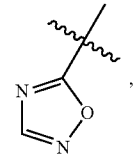

formula c-2

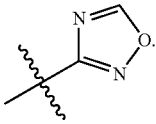

As described in the present invention, any two substituents together with the carbon or nitrogen atom to which they are attached form a carbocyclic, heterocyclic, aromatic ring or heteroaromatic ring, representing the substituents may be arbitrarily combined, and together with the carbon or nitrogen atom to which they are attached form a ring for example, "a compound of formula d, optionally two $R^{2a}$, $R^{2b}$, $R^{4a}$, $R^{4b}$ and the carbon atom to which they are attached, form a $C_{3-8}$ carbocyclic ring or 3-8 membered heterocyclic ring" represent "$R^{2a}R^{2b}$ together with the carbon atom to which they are attached form a $C_{3-8}$ carbocyclic ring or 3-8 membered heterocyclic ring, as shown in formula d-1", "$R^{4a}$ $R^{4b}$ together with the carbon atom to which they are attached form a $C_{3-8}$ carbocyclic ring or 3-8 membered heterocyclic ring, as shown in formula d-2", "$R^{2a}$ $R^{2b}$ together with the carbon atom to which they are attached form a $C_{3-8}$ carbocyclic ring or 3-8 membered heterocyclic ring, while $R^{4a}$ and $R^{4b}$ together with the carbon atom to which they are attached form a $C_{3-8}$ carbocyclic ring or 3-8 membered heterocyclic ring at the same time, as shown in formula d-3", "$R^{2a}$ and $R^{4a}$ together with the carbon atom to which they are attached form a $C_{3-8}$ carbocyclic ring or 3-8 membered heterocyclic ring, as shown in formula d-4", "$R^{2a}$ and $R^{4b}$ together with the carbon atom to which they are attached form a $C_{3-8}$ carbocyclic ring or 3-8 membered heterocyclic ring, as shown in formula d-5", "$R^{2b}$ and $R^{4a}$ together with the carbon atom to which they are attached form a $C_{3-8}$ carbocyclic ring or 3-8 membered heterocyclic ring, as shown in formula d-6", "$R^{2b}$ and $R^{4b}$ together with the carbon atom to which they are attached form a $C_{3-8}$ carbocyclic ring or 3-8 membered heterocyclic ring, as shown in formula d-7", "$R^{2a}$ and $R^{4a}$ together with the carbon atom to which they are attached form a $C_{3-8}$ carbocyclic ring or 3-8 membered heterocyclic ring, while $R^{2b}$ and $R^{4b}$ together with the carbon atom to which they are attached form a $C_{3-8}$ carbocyclic ring or 3-8 membered heterocyclic ring; or $R^{2a}$ and $R^{4b}$ together with the carbon atom to which they are attached form a $C_{3-8}$ carbocyclic ring or 3-8 membered heterocyclic ring while $R^{2b}$ and $R^{4a}$ together with the carbon atom to which they are attached form a $C_{3-8}$ carbocyclic ring or 3-8 membered heterocyclic ring at the same time, as shown in formula d-8", wherein

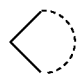

represents a $C_{3-8}$ carbocyclic ring or a 3-8 membered heterocyclic ring,

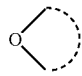

represents 3-8 membered heterocyclic rings containing oxygen:

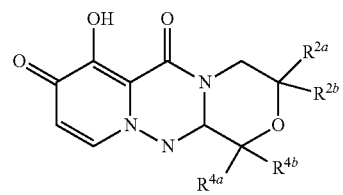

formula d

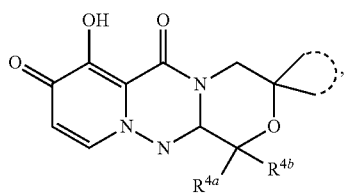

formula d-1

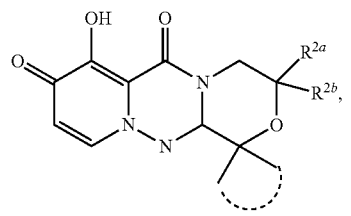

formula d-2

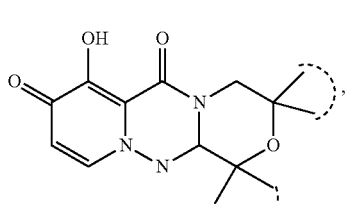

formula d-3

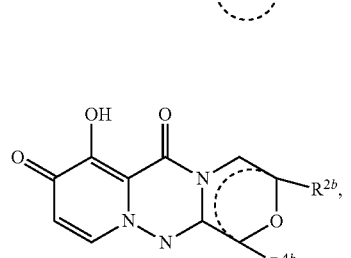

formula d-4

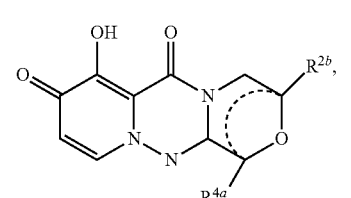

formula d-5

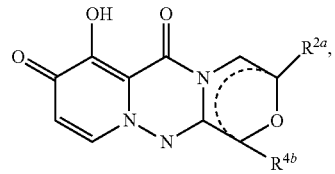

formula d-6

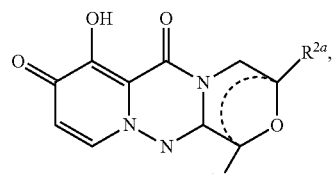

formula d-7

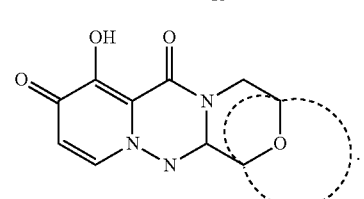

formula d-8

The term "unsaturated" refers to a moiety having one or more units of unsaturation.

The term "comprise" is an open expression, it means comprising the contents disclosed herein, but don't exclude other contents.

As disclosed herein, the term "pharmaceutically acceptable carrier" includes any solvent, dispersion medium, coating, surfactant, antioxidant, preservative (eg., antibacterial, antifungal), isotonic, salt, drug stabilizer, adhesive, excipient, dispersant, lubricant, sweetener, flavoring, coloring agent, or combination thereof, which are known to those skilled in the art (As described by Remington's Pharmaceutical Sciences, 18th Ed. Mack Printing Company, 1990, pp. 1289-1329).

The use thereof in a therapeutic or pharmaceutical composition is encompassed except where any conventional carrier is incompatible with the active ingredient.

As used herein, the term "inhibiting replication of an influenza virus" includes reducing the amount of viral replication (e.g., reducing at least 10%) and completely preventing viral replication (i.e., 100% reducing the amount of viral replication). In some embodiments, influenza virus replication is inhibited by at least 50%, at least 65%, at least 75%, at least 85%, at least 90%, or at least 95%.

The term "effective amount" of a compound of the invention refers to an amount that causes the desired biological response. In the present invention, it is expected that the biological reaction is to inhibit influenza virus replication, reduce the amount of influenza virus or reduce or improve the severity, duration, progression or onset of influenza virus infection, prevent the spread of influenza virus infection, and prevent recurrence, evolution, onset or progression of symptoms associated with influenza virus infection, or enhance the prophylactic or therapeutic effect of another anti-influenza infection therapy. The exact amount of compound administered to a subject will depend on the mode of administration, the type and severity of the infection, and the characteristics of the subject, such as health, age, sex, weight, and tolerance to the drug. The skilled person will be able to determine the appropriate dosage based on these and other factors. When administered in combination with other antiviral agents, such as in combination with an anti-influenza drug, the "effective amount" of the second agent will depend on the type of drug employed. Suitable dosages of the approved agents are known and can be adjusted by the skilled depending on the symptoms of the subject, the type of condition being treated and the amount of the compound of the invention employed. In cases where the amount is not explicitly stated, an effective amount should be taken. For example, a compound of the invention can be administered to a subject in a dosage range of about 0.01 to 100 mg per body weight per day for therapeutic or prophylactic treatment.

The term "treatment" as used herein refers to both therapeutic and prophylactic treatment. Therapeutic treatment includes alleviating or ameliorating the progression, severity and/or duration of an influenza virus-mediated condition, or ameliorating one or more symptoms of an influenza virus-mediated condition (in particular, one or more discernible symptoms), by administration of one or more therapies (for example, one or more therapeutic agents, e.g. compounds and compositions of the present invention). In a particular embodiment, the therapeutic treatment comprises ameliorating at least one measurable physical parameter of influenza virus-mediated condition. In other embodiments, therapeutic treatment includes physical suppression of influenza virus-mediated symptoms by, for example, stabilizing identifiable symptoms, or physiological suppression of influenza virus-mediated symptoms by, for example, stabilizing physical parameters. In other implementations, therapeutic treatment includes mitigation or stabilization of influenza virus-mediated infections. Antiviral drugs can be used in the community to treat people already suffering from influenza to reduce the severity of symptoms and reduce days of illness.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Non-limited suitable amino-protecting groups include acetyl, trifluoroacetyl, p-toluenesulfonyl (Ts), t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —CH2CH2SO2Ph, cyanoethyl, 2-(trimethylsilyl)ethyl, 2-(trimethylsilyl) ethoxy-methyl, 2-(p-toluenesulfonyl) ethyl, 2-(p-nitrophenylsulfonyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

Description of Compounds of the Invention

The present invention provides a novel class of compounds which are inhibitors of influenza virus RNA polymerase, and more particularly, the present invention provides a novel class of inhibitors of influenza virus cap-dependent endonuclease, such compounds and the composition thereof can be used to prevent, treat or ameliorate a viral infection in a patient. Compared with the existing analogous compounds, the compounds of the present invention not only have better pharmacological activities, but also have lower toxicity, more excellent pharmacokinetic properties and pharmacodynamic properties in vivo. Therefore, the compound provided by the present invention has more excellent druggabilitys than the conventional compound of the same type.

In one aspect, the present invention relates to a compound having Formula (I) or a stereoisomer, a tautomer, an N-oxide, a solvate, a metabolite, a pharmaceutically acceptable salt or a prodrug thereof,

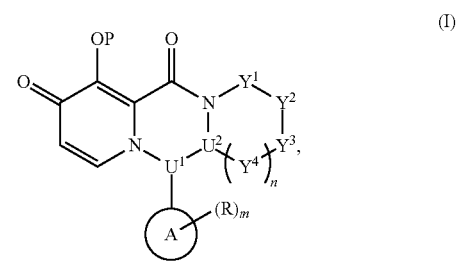

(I)

wherein ring A, P, R, $U^1$, $U^2$, $Y^1$, $Y^2$, $Y^3$, $Y^4$, n and m have the definition as described in the present invention, with the proviso that ring A is not

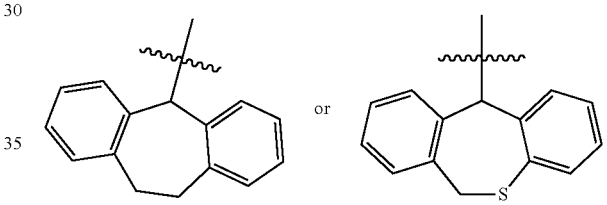

when m is 0 or 1, and when m is 2 and ring A is

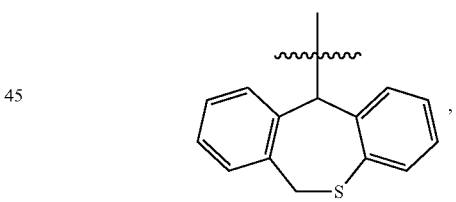

optionally two R together with carbon atom to which they are attached form a $C_{3-8}$ carbocyclic ring, 3-8 membered heterocyclic ring, $C_{6-10}$ aromatic ring or 5-10 membered heteroaromatic ring; wherein each $C_{3-8}$ carbocyclic ring, 3-8 membered heterocyclic rings, $C_{6-10}$ aromatic ring and 5-10 membered heteroaromatic ring is independently unsubstituted or substituted with 1, 2, 3 or 4 substituents independently selected from deuterium, F, Cl, Br, I, CN, $NO_2$, —$OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene.

In some embodiments, $U^1$ is N or CH.
In some embodiments, $U^2$ is N or CH.
In some embodiments, $Y^1$ is $CR^{1a}R^{1b}$, S or O.
In some embodiments, $Y^2$ is $CR^{2a}R^{2b}$, S or O.
In some embodiments, $Y^3$ is $CR^{3a}R^{3b}$, S or O.
In some embodiments, each $Y^4$ is independently $CR^{4a}R^{4b}$, S or O; n is 0, 1, 2 or 3.

In some embodiments, each $R^{1a}$, $R^{1b}$, $R^{1b}$, $R^{2a}$, $R^{2a}$, $R^{2b}$, $R^{3a}$, $R^{3b}$, $R^{3a}$, $R^{3b}$, $R^{3b}$, $R^{4a}$ and $R^{4b}$ is independently H, deuterium, F, Cl, Br, I, CN, NO$_2$, OR$^b$, R$^b$O—C$_{1-4}$ alkylene, R$^d$R$^c$N—C$_{1-4}$ alkylene, C$_{1-6}$ haloalkyl, C$_{1-6}$ alkyl, C$_{2-6}$ alkenyl, C$_{2-6}$ alkynyl, C$_{3-8}$ carbocyclyl, 3-8 membered heterocyclyl, C$_{6-10}$ aryl or 5-10 membered heteroaryl; wherein each C$_{1-6}$ haloalkyl, C$_{1-6}$ alkyl, C$_{2-6}$ alkenyl, C$_{2-6}$ alkynyl, C$_{3-8}$ carbocyclyl, 3-8 membered heterocyclyl, C$_{6-10}$ aryl and 5-10 membered heteroaryl is independently unsubstituted or substituted with 1, 2, 3 or 4 substituents independently selected from deuterium, F, Cl, Br, I, CN, OH, NH$_2$, C$_{1-6}$ alkyl, C$_{1-6}$ haloalkyl, C$_{1-6}$ alkoxy or C$_{1-6}$ alkylamino;

or any two $R^{1a}$, $R^{1b}$, $R^{2a}$, $R^{2b}$, $R^{3a}$, $R^{3b}$, $R^{4a}$, $R^{4b}$ together with the carbon atom to which they are attached form a C$_{3-8}$ carbocyclic ring or 3-8 membered heterocyclic ring; wherein each C$_{3-8}$ carbocyclic ring and 3-8 membered heterocyclic ring is independently unsubstituted or substituted with 1, 2, 3 or 4 substituents independently selected from deuterium, F, Cl, Br, I, CN, OH, NH$_2$, C$_{1-6}$ alkyl, C$_{1-6}$ haloalkyl, C$_{1-6}$ alkoxy or C$_{1-6}$ alkylamino.

In some embodiments, ring A is a 10-30 membered monocyclic, bicyclic, tricyclic, tetracyclic, pentacyclic or hexacyclic ring system; wherein the 10-30 membered monocyclic, bicyclic, tricyclic, tetracyclic, pentacyclic or hexacyclic ring system is a carbocyclic, heterocyclic, aromatic or heteroaromatic ring.

In some embodiments, each R is independently H, deuterium, F, Cl, Br, I, CN, NO$_2$, oxo (=O), —C(=O)R$^a$, —C(=O)OR$^b$, —C(=O)NR$^c$R$^d$, —OR$^b$, —NR$^c$R$^d$, R$^b$O—C$_{1-4}$ alkylene, R$^d$R$^c$N—C$_{1-4}$ alkylene, C$_{1-6}$ alkyl, C$_{1-6}$ haloalkyl, C$_{2-6}$ alkenyl, C$_{2-6}$ alkynyl, C$_{3-8}$ cycloalkyl, C$_{3-8}$ cycloalkyl-C$_{1-4}$ alkylene, 3-8 membered heterocyclyl, (3-8 membered heterocyclyl)-C$_{1-4}$ alkylene, C$_{6-10}$ aryl, C$_{6-10}$ aryl-C$_{1-4}$ alkylene, 5-10 membered heteroaryl, or (5-10 membered heteroaryl)-C$_{1-4}$ alkylene; wherein each C$_{1-6}$ alkyl, C$_{1-6}$ haloalkyl, C$_{2-6}$ alkenyl, C$_{2-6}$ alkynyl, C$_{3-8}$ cycloalkyl, C$_{3-8}$ cycloalkyl-C$_{1-4}$ alkylene, C$_{6-10}$ aryl, C$_{6-10}$ aryl-C$_{1-4}$ alkylene, 5-10 membered heteroaryl, and (5-10 membered heteroaryl)-C$_{1-4}$ alkylene is independently unsubstituted or substituted with 1, 2, 3 or 4 substituents independently selected from deuterium, F, Cl, Br, I, CN, NO$_2$, —OR$^b$, —NR$^c$R$^d$, C$_{1-6}$ alkyl, C$_{1-6}$ haloalkyl, R$^b$O—C$_{1-4}$ alkylene or R$^d$R$^c$N—C$_{1-4}$ alkylene;

or optionally two R together with carbon atom or nitrogen atom to which they are attached form a C$_{3-8}$ carbocyclic ring, 3-8 membered heterocyclic ring, C$_{6-10}$ aromatic ring or 5-10 membered heteroaromatic ring; wherein each C$_{3-8}$ carbocyclic ring, 3-8 membered heterocyclic ring, a C$_{6-10}$ aromatic ring, and 5-10 membered heteroaromatic ring is independently unsubstituted or substituted with 1, 2, 3 or 4 substituents independently selected from deuterium, F, Cl, Br, I, CN, NO$_2$, —OR$^b$, —NR$^c$R$^d$, C$_{1-6}$ alkyl, C$_{1-6}$ haloalkyl, R$^b$O—C$_{1-4}$ alkylene or R$^d$R$^c$N—C$_{1-4}$ alkylene;

m is 0, 1, 2, 3, 4, 5, 6, 7 or 8.

In some embodiments, P is H, deuterium, C$_{1-6}$ alkyl, C$_{2-6}$ alkenyl, C$_{3-8}$ carbocyclic group, C$_{3-8}$ carbocyclyl-C$_{1-4}$ alkylene, 3-8 membered heterocyclyl, (3-8 membered heterocyclyl)-C$_{1-4}$ alkylene, C$_{6-10}$ aryl, C$_{6-10}$ aryl-C$_{1-4}$ alkylene, 5-10 membered heteroaryl, (5-10 membered heteroaryl)-C$_{1-4}$ alkylene, —C(=O)—R$^{Pa}$, —C(=O)-L-R$^{Pe}$, —C(=O)-L-O—R$^{Pb}$, —C(=O)-L-O-L-O—R$^{Pb}$, —C(=O)-L-O—C(=O)—R$^a$, —C(=O)—NR$^{Pf}$R$^{Pd}$, —C(=O)—O—R$^{Pb}$, —S(=O)$_2$—R$^{Pk}$, —P(=O)—(R$^{Pg}$)(R$^{Ph}$), —C(=O)—O-L-O—R$^{Pb}$, —C(=N$^+$R$^{Pi}$R$^{Pj}$)(—NR$^{Pc}$R$^{Pd}$), R$^{Pb}$—O—C$_{1-4}$ alkylene, R$^{Pb}$—O-L-O—C$_{1-4}$alkylene, R$^{Pa}$—(C=O)—O—C$_{1-4}$ alkylene, R$^{Pb}$—O—(C=O)—C$_{1-4}$ alkylene, R$^{Pb}$—O—(C=O)—NR$^{Pf}$—C$_{1-4}$ alkylene, R$^{Pb}$—O—(C=O)—O—C$_{1-4}$ alkylene, NR$^{Pf}$R$^{Pd}$—O—(C=O)—O—C$_{1-4}$ alkylene, R$^{Pb}$—O-L-O—(C=O)—O—C$_{1-4}$ alkylene, NR$^{Pc}$R$^{Pd}$-L-O—(C=O)—O—C$_{1-4}$ alkylene, R$^{Pb}$—O-L-NR$^{Pf}$—(C=O)—O—C$_{1-4}$alkylene, NR$^{Pc}$R$^{Pd}$-L-N(R$^{Pf}$)—(C=O)—O—C$_{1-4}$ alkylene, R$^{Pb}$—O-L-O-L-O—(C=O)—O—C$_{1-4}$ alkylene, (HO)$_2$P(=O)—C$_{1-4}$ alkylene, (BnO)$_2$P(=O)—C$_{1-4}$alkylene or R$^{Pa}$—(C=O)—NR$^{Pf}$-L-O—(C=O)—O—C$_{1-4}$ alkylene, wherein each of C$_{1-6}$ alkyl, C$_{2-6}$ alkenyl, C$_{3-8}$ carbocyclyl, C$_{3-8}$ carbocyclyl-C$_{1-4}$ alkylene, 3-8 membered heterocyclyl, (3-8 membered heterocyclyl)-C$_{1-4}$ alkylene, C$_{6-10}$ aryl, C$_{6-10}$ aryl-C$_{1-4}$ alkylene, 5-10 membered heteroaryl, (5-10 membered heteroaryl)-C$_{1-4}$ alkylene is independently unsubstituted or substituted with 1, 2, 3 or 4 substituents independently selected from deuterium, F, Cl, Br, I, OXO(=O), CN, NO$_2$, —OR$^b$, —NR$^c$R$^d$, —C(=O)R$^a$—O(C=O)R$^a$, —C(=O)OR$^b$, C$_{1-6}$ alkyl, R$^b$O—C$_{1-4}$ alkylene, —NR$^d$R$^c$C(=O)R$^a$ or R$^d$R$^c$N—C$_{1-4}$ alkylene;

each L is independently C$_{1-6}$ alkylene or C$_{2-6}$ alkenylene;
each R$^{Pf}$ is independently H or C$_{1-6}$ alkyl;
each R$^{Pa}$, R$^{Pb}$, R$^{Pc}$, R$^{Pd}$, R$^{Pe}$, R$^{Pi}$, R$^{Pj}$ and R$^{Pk}$ is independently C$_{1-6}$ alkyl, C$_{3-8}$ carbocyclyl, C$_{3-8}$ carbocyclyl-C$_{1-4}$ alkylene, 3-8 membered heterocyclyl, (3-8 membered heterocyclyl)-C$_{1-4}$ alkylene, C$_{6-10}$ aryl, C$_{6-10}$ aryl-C$_{1-4}$ alkylene, 5-10 membered heteroaryl, (5-10 membered heteroaryl)-C$_{1-4}$ alkylene, C$_{1-6}$ alkylamino, C$_{1-6}$ alkylthio or C$_{1-6}$ alkylsilyl, wherein each C$_{1-6}$ alkyl, C$_{3-8}$ carbocyclyl, C$_{3-8}$ carbocyclyl-C$_{1-4}$ alkylene, 3-8 membered heterocyclyl, (3-8 membered heterocyclyl)-C$_{1-4}$ alkylene, C$_{6-10}$ aryl, C$_{6-10}$ aryl-C$_{1-4}$ alkylene, 5-10 membered heteroaryl, (5-10 membered heteroaryl)-C$_{1-4}$ alkylene, C$_{1-6}$ alkylamino and C$_{1-6}$ alkylthio is independently unsubstituted or substituted with 1, 2, 3 or 4 substituents independently selected from deuterium, F, Cl, Br, I, oxo(=O), CN, NO$_2$, —OR$^b$, —NR$^c$R$^d$, —C(=O)R$^a$, —O(C=O)R$^a$, —C(=O)OR$^b$, C$_{1-6}$ alkyl, R$^b$O—C$_{1-4}$ alkylene, —NR$^d$R$^c$C(=O)R$^a$ or R$^d$R$^c$N—C$_{1-4}$ alkylene;

each R$^{Pg}$ and R$^{Ph}$ is independently C$_{1-6}$ alkoxy, C$_{1-6}$ alkylamino, C$_{3-8}$ carbocyclyloxy, C$_{3-8}$ carbocyclylamino, 3-8 membered heterocyclyloxy, 3-8 membered heterocyclylamino, C$_{6-10}$ aryloxy, C$_{6-10}$ arylamino, 5-10 membered heteroaryloxy or 5-10 membered heterocyclylamino, wherein each C$_{1-6}$ alkoxy, C$_{1-6}$ alkylamino, C$_{3-8}$ carbocyclyloxy, C$_{3-8}$ carbocyclylamino, 3-8 membered heterocyclyloxy, 3-8 membered heterocyclylamino, C$_{6-10}$ aryloxy, C$_{6-10}$ arylamino, 5-10 membered heterocyclyloxy and 5-10 membered heterocyclylamino group is independently unsubstituted or substituted with 1, 2, 3 or 4 substituents independently selected from deuterium, F, Cl, Br, I, oxo(=O), CN, NO$_2$, —OR$^b$, —NR$^c$R$^d$, —C(=O)R$^a$, —O(C=O)R$^a$, —C(=O)OR$^b$, C$_{1-6}$ alkyl, R$^b$O—C$_{1-4}$ alkylene, —NR$^d$R$^c$C(=O)R$^a$ or R$^d$R$^c$N—C$_{1-4}$ alkylene;

or, R$^{Pg}$ R$^{Ph}$ together with phosphorus atom to which they are attached form a 3-8 membered heterocyclic ring, or 5-10 membered heteroaromatic ring; wherein each of the 3-8 membered heterocyclic ring and 5-10 membered heteroaryl ring is independently unsubstituted or substituted with 1, 2, 3 or 4 substituents independently selected from deuterium, F, Cl, Br, I, oxo(=O), CN, NO$_2$, —OR$^b$, —NR$^c$R$^d$, —C(=O)R$^a$, —O(C=O)R$^a$, —C(=O)OR$^b$, C$_{1-6}$ alkyl, R$^b$O—C$_{1-4}$ alkylene, —NR$^d$R$^c$C(=O)R$^a$ or R$^d$R$^c$N—C$_{1-4}$ alkylene.

In some embodiments, each R$^a$, R$^b$, R$^c$ and R$^d$ is independently H, deuterium, C$_{1-6}$ haloalkyl, C$_{1-6}$ alkyl, C$_{2-6}$ alkenyl, C$_{2-6}$ alkynyl, C$_{3-6}$ carbocyclyl, C$_{3-6}$ carbocyclyl-C$_{1-4}$ alkylene, 3-6 membered heterocyclyl, (3-6 membered heterocyclyl)-C$_{1-4}$ alkylene, C$_{6-10}$ aryl, C$_{6-10}$ aryl —C$_{1-4}$ alkylene, 5-10 membered heteroaryl or (5-10 membered heteroaryl)-$C_{1-4}$ alkylene, wherein each $C_{1-6}$ alkyl, $C_{2-6}$ alkenyl, $C_{2-6}$ alkynyl, $C_{3-6}$ carbocyclyl, $C_{3-6}$ carbocyclyl-$C_{1-4}$ alkylene, 3-6 membered heterocyclyl, (3-6 membered heterocyclyl)-$C_{1-4}$ alkylene, $C_{6-10}$ aryl, $C_{6-10}$ aryl —$C_{1-4}$ alkylene, 5-10 membered heteroaryl and (5-10 membered heteroaryl)-$C_{1-4}$ alkylene is independently unsubstituted or substituted with 1, 2, 3 or 4 substituents independently selected from deuterium, F, Cl, Br, I, CN, OH, $NH_2$, $NO_2$, $C_{1-6}$ alkyl, $C_{1-6}$ haloalkyl, $C_{1-6}$ alkoxy or $C_{1-6}$ alkylamino;

or, $R^c$ $R^d$ together with nitrogen atom to which they are attached form a 3-6 membered heterocyclic ring, or 5-8 membered heteroaromatic ring; wherein each of the 3-6 membered heterocyclic ring and 5-8 membered heteroaromatic ring is independently unsubstituted or substituted with 1, 2, 3 or 4 substituents independently selected from deuterium, F, Cl, Br, I, CN, OH, $NH_2$, $NO_2$, $C_{1-6}$ alkyl, $C_{1-6}$ haloalkyl, $C_{1-6}$ alkoxy or $C_{1-6}$ alkyl amino.

In other embodiments, ring A is a 12-20 membered monocyclic, bicyclic, tricyclic, tetracyclic, pentacyclic or hexacyclic ring system; wherein the 12-20 membered monocyclic, bicyclic, tricyclic, tetracyclic, pentacyclic or hexacyclic ring system is a carbocyclic, heterocyclic, aromatic or heteroaromatic ring.

In other embodiments, ring A is one of the following sub-formulae:

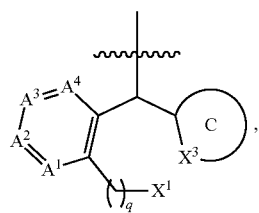
(A-1)

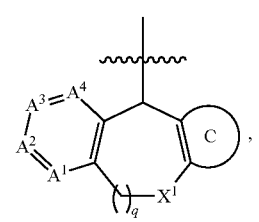
(A-2)

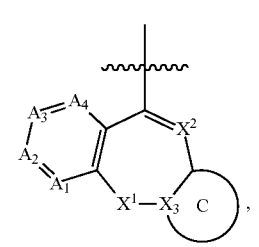
(A-3)

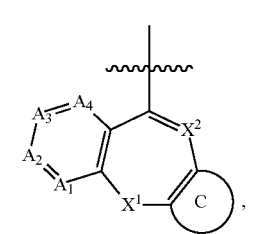
(A-4)

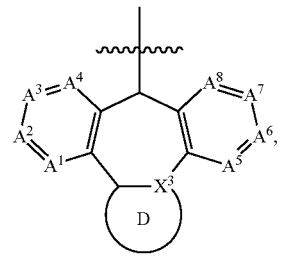
(A-5)

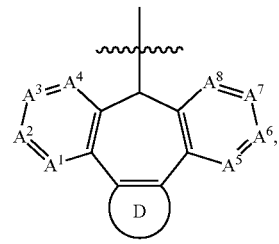
(A-6)

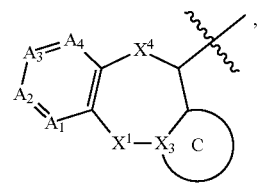
(A-7)

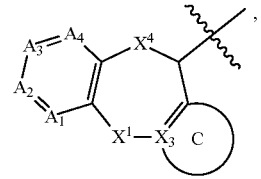
(A-8)

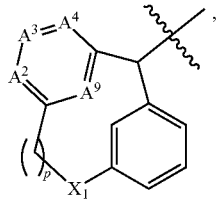
(A-9)

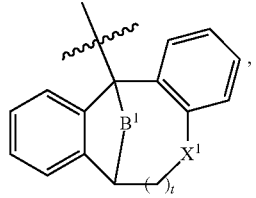
(A-10)

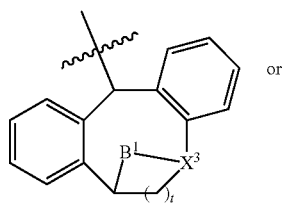
(A-11)

or

-continued

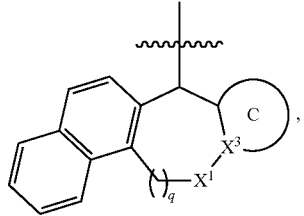
(A-12)

wherein, each $X^1$ is independently S, S(=O), S(=O)$_2$, O, NH, CH$_2$ or absent;

each $X^2$ is independently CH or N;

each $X^3$ is independently CH or N;

each $X^4$ is independently S, O, NH or CH$_2$;

each $A^1$, $A^2$, $A^3$, $A^4$, $A^5$, $A^6$, $A^7$, $A^8$ and $A^9$ is independently C or N;

B1 is —CH$_2$—, —CH$_2$CH$_2$—, —CH$_2$CH$_2$CH$_2$— or O;

ring C is C$_{3-8}$ carbon ring, 3-8 atomic heterocyclic ring, C$_{6-10}$ aromatic ring, C$_{11}$ aromatic ring, C$_{12}$ aromatic ring or 5-10 atomic heteroaromatic ring;

ring D is C$_{3-8}$ carbocyclic ring, 3-8 membered heterocyclic ring, C$_{6-10}$ aromatic ring, C$_{11}$ aromatic ring, C$_{12}$ aromatic ring or 5-10 membered heteroaromatic ring;

each q is 0, 1, 2, 3, 4, 5 or 6;

each p is 0, 1, 2, 3, 4, 5 or 6;

each t is 0, 1, 2, or 3.

In some embodiments, ring D is a C$_{3-6}$ carbocyclic ring, 5 membered heterocyclic ring, 6 membered heterocyclic ring, C$_{6-10}$ aromatic ring, 5 membered heteroaromatic ring or 6 membered heteroaromatic ring.

In other embodiments, ring C is cyclopropane, cyclobutane, cyclopentane, cyclohexane, cycloheptane, benzocyclohexane, benzocyclopentane, azetidine, oxetane, pyrrolidine, piperidine, piperazine, tetrahydrofuran, tetrahydropyran, morpholine, benzene, naphthalene, furan, benzofuran, pyrrole, pyridine, pyrazole, imidazole, benzoimidazole, benzopyrazole, triazole, tetrazole, oxazole, oxadiazole, 1,3,5-triazine, thiazole, thiophene, benzothiophene, pyrazine, pyridazine, pyrimidine, benzopyrimidine, indole, purine, quinoline, isoquinoline, bicyclic [2.2.2] octane or benzobicyclic [2.2.2] octane.

In other embodiments, ring D is cyclopropane, cyclobutane, cyclopentane, cyclohexane, cycloheptane, cyclopentene, cyclopentadiene, cyclohexene, cyclohexadiene, benzocyclohexane, benzocyclopentane, cyclopropane, azetidine, oxetane, pyrrolidine, piperidine, piperazine, tetrahydrofuran, tetrahydropyran, morpholine, thiomorpholine, benzene, naphthalene, furan, benzofuran, pyrrole, pyridine, pyrazole, imidazole, benzoimidazole, benzopyrazole, triazole, tetrazole, oxazole, isoxazole, oxadiazole, 1,3,5-triazine, thiazole, thiophene, benzothiophene, pyrazine, pyridazine, pyrimidine, benzopyrimidine, indole, purine, quinoline, isoquinoline, bicyclic [2.2.2] octane or benzobicyclic [2.2.2] octane.

In other embodiments, ring A is one of the following sub-formulae:

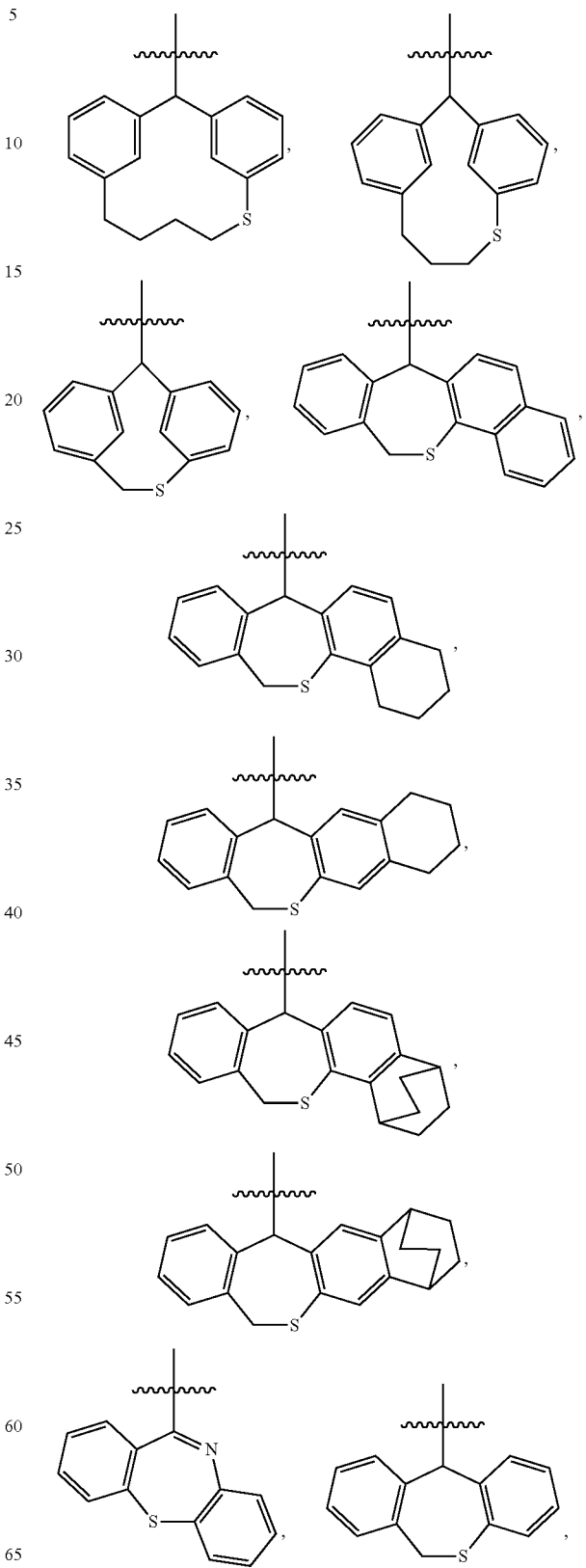

-continued
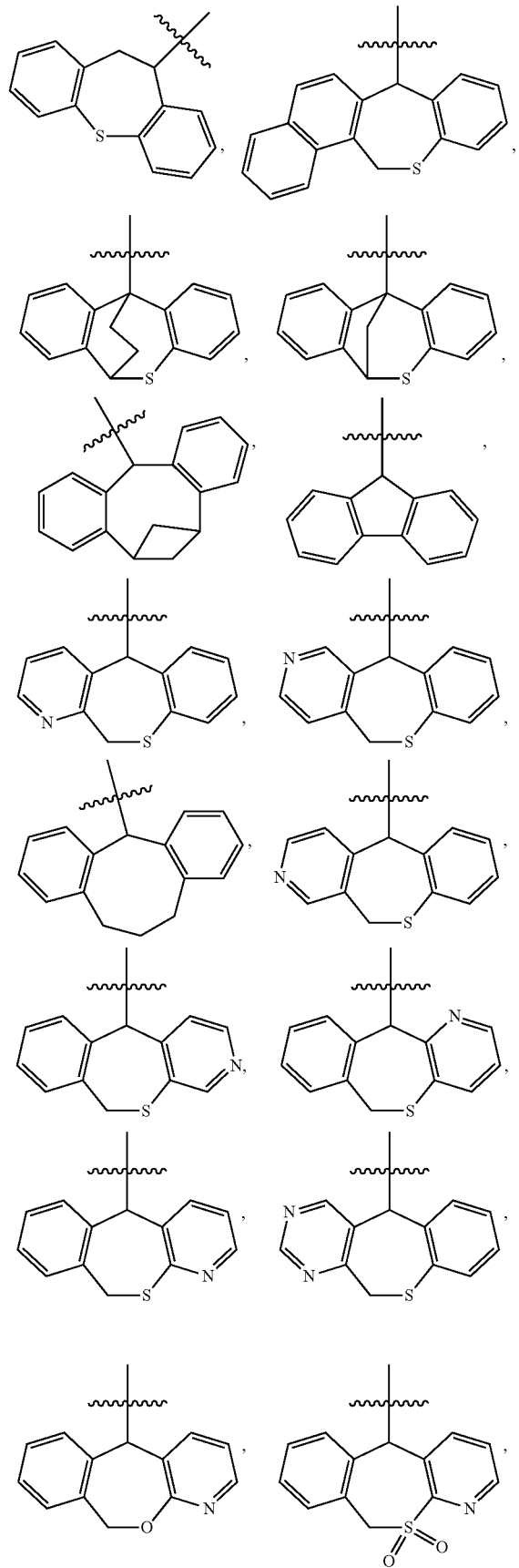
-continued
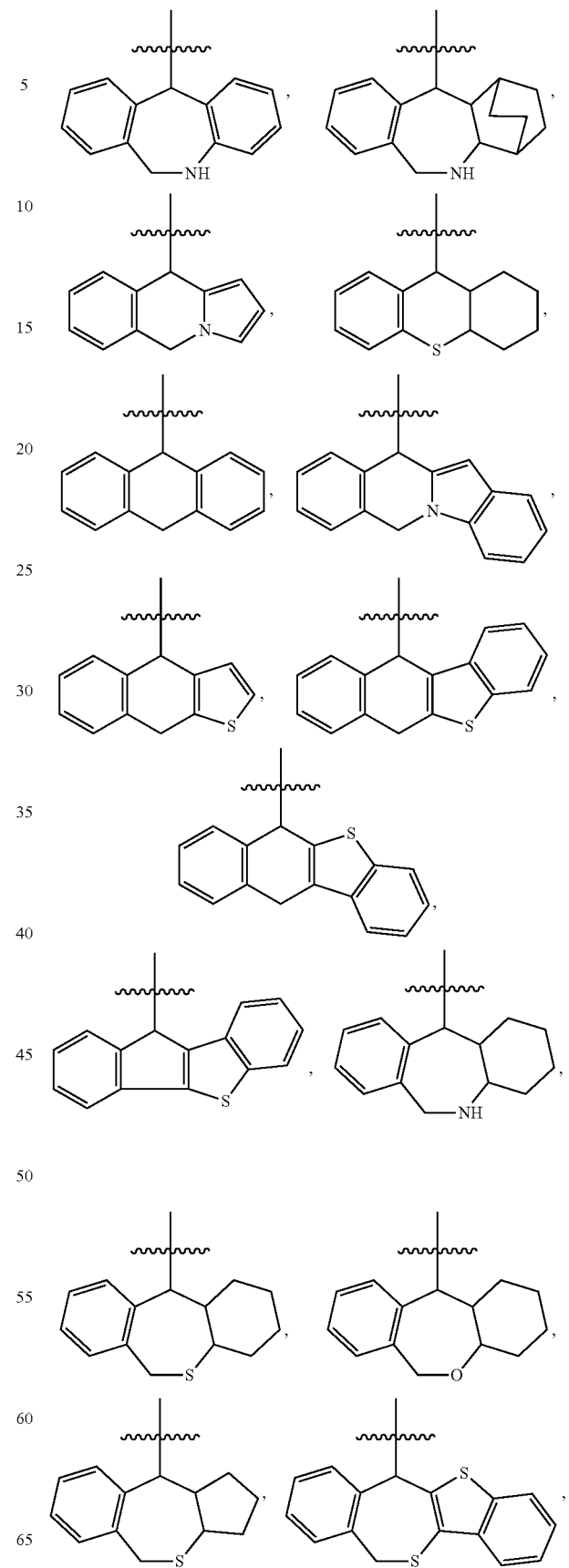

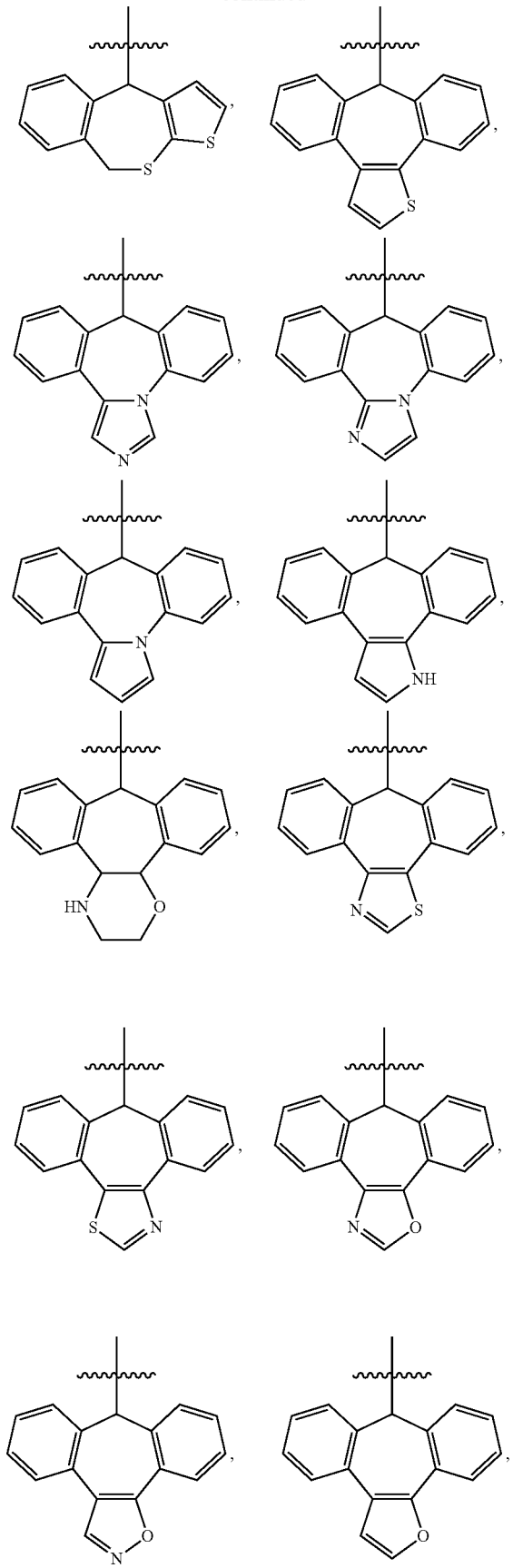
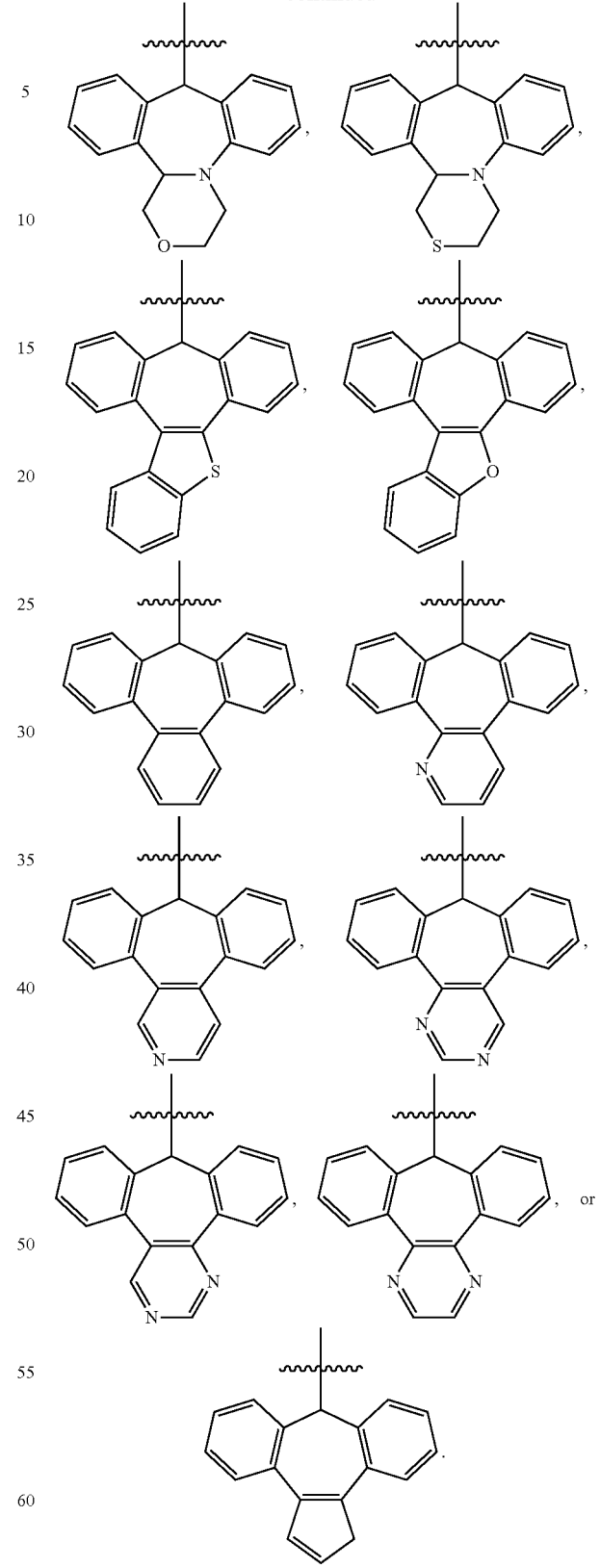
In some embodiments, each R is independently H, deuterium, F, Cl, Br, I, CN, $NO_2$, oxo (=O), —C(=O)$R^a$, —C(=O)O$R^b$, —C(=O)N$R^c R^d$, —O$R^b$, —N$R^c R^d$, $R^b$O—

$C_{1-4}$ alkylene, $R^dR^cN—C_{1-4}$ alkylene, $C_{1-4}$ alkyl, $C_{1-4}$ haloalkyl, $C_{2-4}$ alkenyl, $C_{2-4}$ alkynyl, $C_{3-6}$ cycloalkyl, $C_{3-6}$ cycloalkyl-$C_{1-2}$ alkylene, 3-6 membered heterocyclyl, (3-6 membered heterocyclyl)-$C_{1-2}$ alkylene, $C_{6-10}$ aryl, $C_{6-10}$ aryl-$C_{1-2}$ alkylene, 5-10 membered heteroaryl, or (5-10 membered heteroaryl)-$C_{1-2}$ alkylene; wherein each $C_{1-4}$ alkyl, $C_{1-4}$ haloalkyl, $C_{2-4}$ alkenyl, $C_{2-4}$ alkynyl, $C_{3-6}$ cycloalkyl, $C_{3-6}$ cycloalkyl-$C_{1-2}$ alkylene, 3-6 membered heterocyclyl, (3-6 membered heterocyclyl)-$C_{1-2}$ alkylene, $C_{6-10}$ aryl, $C_{6-10}$ aryl-$C_{1-2}$ alkylene, 5-10 membered heteroaryl, and (5-10 membered heteroaryl)-$C_{1-2}$ alkylene is independently unsubstituted or substituted with 1, 2, 3 or 4 substituents independently selected from deuterium, F, Cl, Br, I, CN, $NO_2$, —$OR^b$, —$NR^cR^d$, $C_{1-4}$ alkyl, $C_{1-4}$ haloalkyl, $R^bO—C_{1-4}$ alkylene or $R^dR^cN—C_{1-4}$ alkylene;

or optionally two R together with carbon atom or nitrogen atom to which they are attached form a $C_{3-8}$ carboncyclic ring, 3-8 membered heterocyclic ring, $C_{6-10}$ membered aromatic ring or 5-10 membered heteroaryl ring; wherein each $C_{3-8}$ carbocyclic ring, 3-8 membered heterocyclic ring, a $C_{6-10}$ aromatic ring and 5-10 membered heteroaryl ring is independently unsubstituted or substituted with 1, 2, 3 or 4 substituents independently selected from deuterium, F, Cl, Br, I, CN, $NO_2$, —$OR^b$, —$NR^cR^d$, $C_{1-4}$ alkyl, $C_{1-4}$ haloalkyl, $R^bO—C_{1-4}$ alkylene or $R^dR^cN—C_{1-4}$ alkylene.

In other embodiments, each R is H, deuterium, F, Cl, Br, I, CN, $NO_2$, oxo(=O), —C(=O)OH, —C(=O)OCH$_3$, —C(=O)NH$_2$, —OH, —OCH$_3$, —OCH$_2$CH$_3$, —OCF$_3$, —OCHF$_2$, —OCH$_2$CF$_3$, —NH$_2$, methyl, ethyl, n-propyl, isopropyl, trifluoromethyl, trifluoroethyl, cyclopropyl, cyclobutyl, cyclopentyl, cyclohexyl, cycloheptyl, oxiranyl, azetidinyl, oxetanyl, pyrrolidinyl, piperidinyl, piperazinyl, tetrahydrofuranyl, tetrahydropyranyl, morpholinyl, phenyl, naphthyl, furanyl, benzofuranyl, pyrrolidinyl, pyridyl, imidazole, benzimidazolyl, benzopyrazolyl, triazolyl, tetrazolyl, oxazolyl, oxadiazolyl, 1,3,5-triazinyl, thiazolyl, thiophenyl, benzothiophenyl, pyrazinyl, pyridazinyl, pyrimidinyl, indolyl, purinyl, quinolinyl or isoquinolinyl, wherein each methyl, ethyl, n-propyl, isopropyl, trifluoromethyl, trifluoroethyl, cyclopropyl, cyclobutyl, cyclopentyl, cyclohexyl, cycloheptyl, oxiranyl, azetidinyl, oxetanyl, pyrrolidinyl, piperidinyl, piperazinyl, tetrahydrofuranyl, tetrahydropyranyl, morpholinyl, phenyl, naphthyl, furanyl, benzofuranyl, pyrrolidinyl, pyridyl, pyrazolyl, imidazolyl, benzimidazolyl, benzopyrazolyl, triazolyl, tetrazolyl, oxazolyl, oxadiazolyl, 1,3,5-triazinyl, thiazolyl, thiophenyl, benzothiophenyl, pyrazinyl, pyrimidinyl, indolyl, purinyl, quinolinyl and isoquinolinyl is independently unsubstituted or substituted by 1, 2, 3 or 4 substituents independently selected from deuterium, F, Cl, Br, CN, $NO_2$, OH, —NH$_2$, methyl, ethyl, n-propyl, isopropyl, trifluoromethyl or methoxy;

or optionally two R together with carbon atom or nitrogen atom to which they are attached form cyclopropane, cyclobutane, cyclopentane, cyclohexane, cycloheptane, oxirane, azetidine, oxetane, pyrrolidine, piperidine, piperazine, tetrahydrofuran, tetrahydropyran, morpholine, thiomorpholine, benzene, furan, pyrrole, pyridine, pyrazole, imidazole, triazole, tetrazole, oxazole, oxadiazole, 1,3,5-triazine, thiazole, thiophene, pyrazine, pyridazine or pyrimidine, wherein each of the cyclopropane, cyclobutane, cyclopentane, cyclohexane, cycloheptane, oxirane, azetidine, oxetane, pyrrolidine, piperidine, piperazine, tetrahydrofuran, tetrahydropyran, morpholine, thiomorpholine, benzene, furan, pyrrole, pyridine, pyrazole, imidazole, triazole, tetrazole, oxazole, oxadiazole, 1,3,5-triazine, thiazole, thiophene, pyrazine, pyridazine and pyrimidine is independently unsubstituted or substituted with 1, 2, 3 or 4 substituents independently selected from deuterium, F, Cl, Br, CN, $NO_2$, OH, NH$_2$, methyl, ethyl, n-propyl, isopropyl, trifluoromethyl, or methoxy.

In some embodiments,

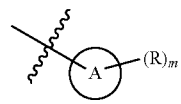

is one of the following sub-formulae:

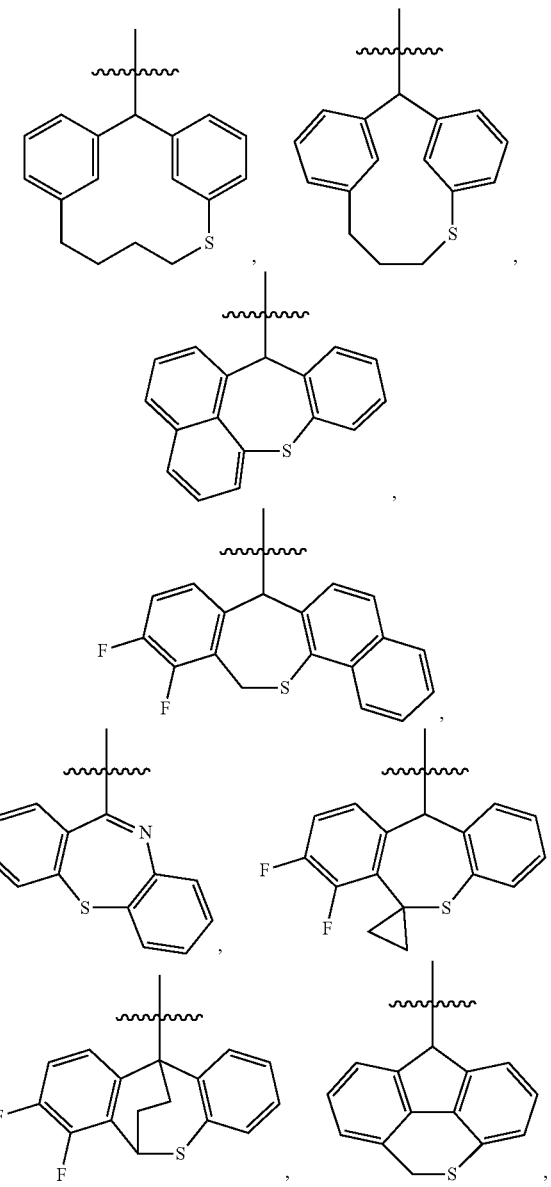

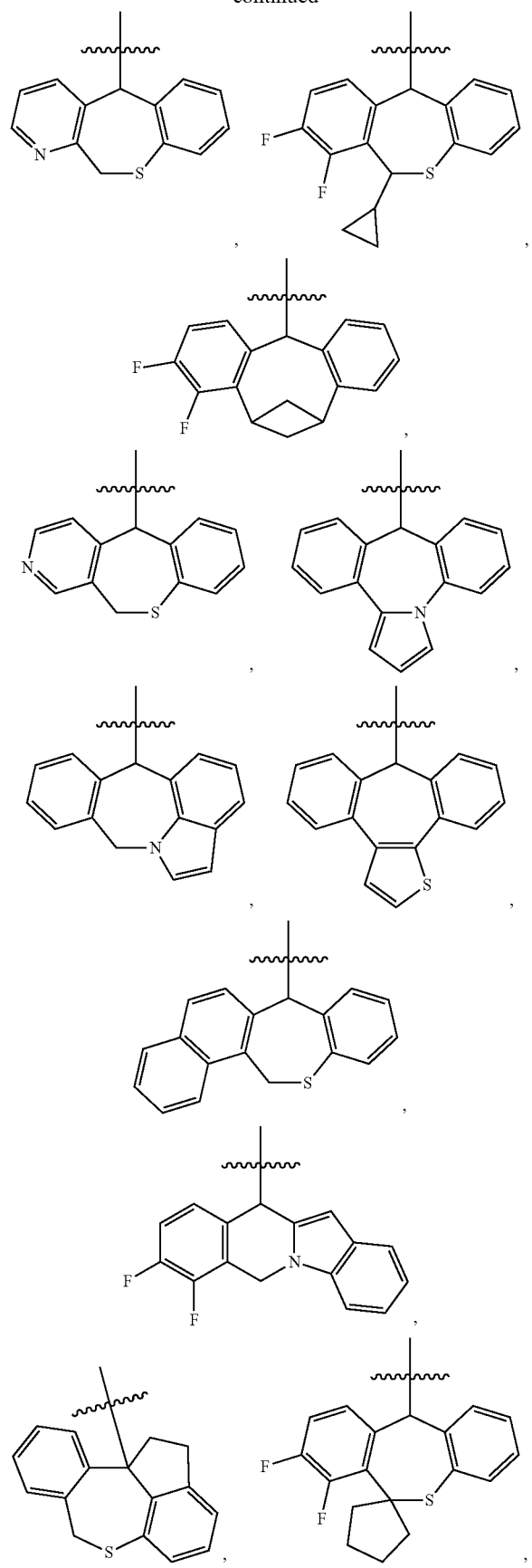
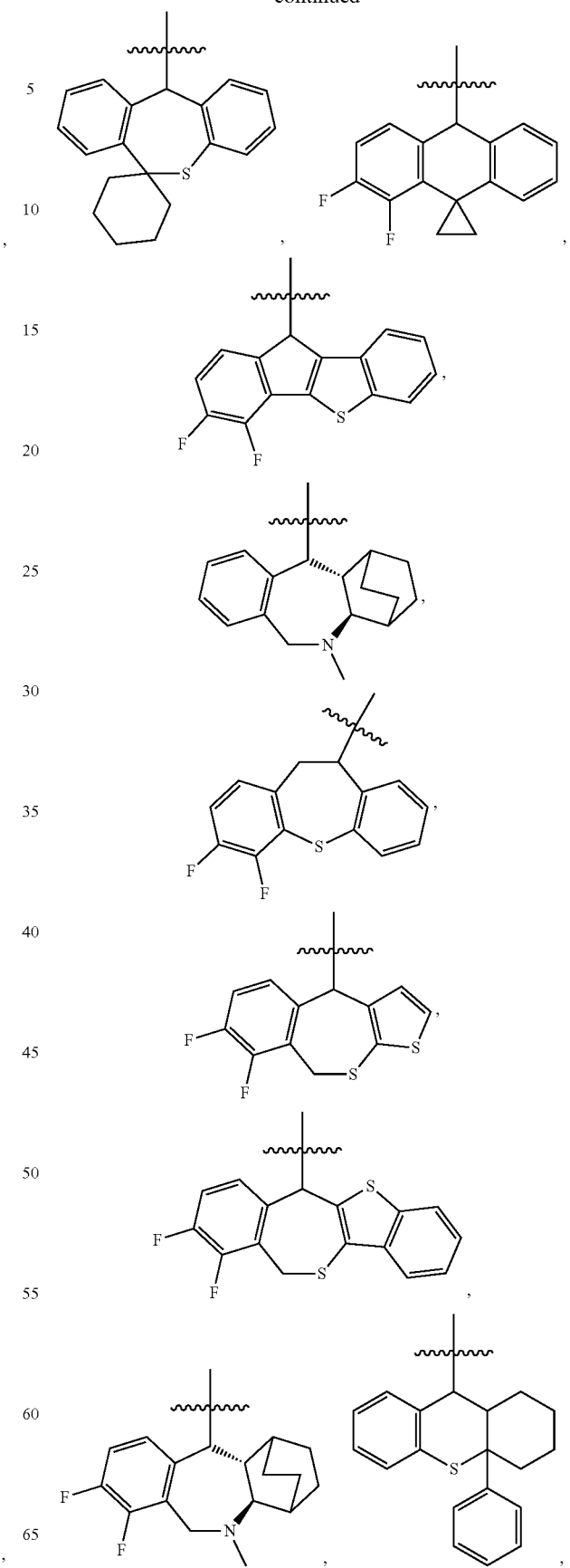

63
-continued
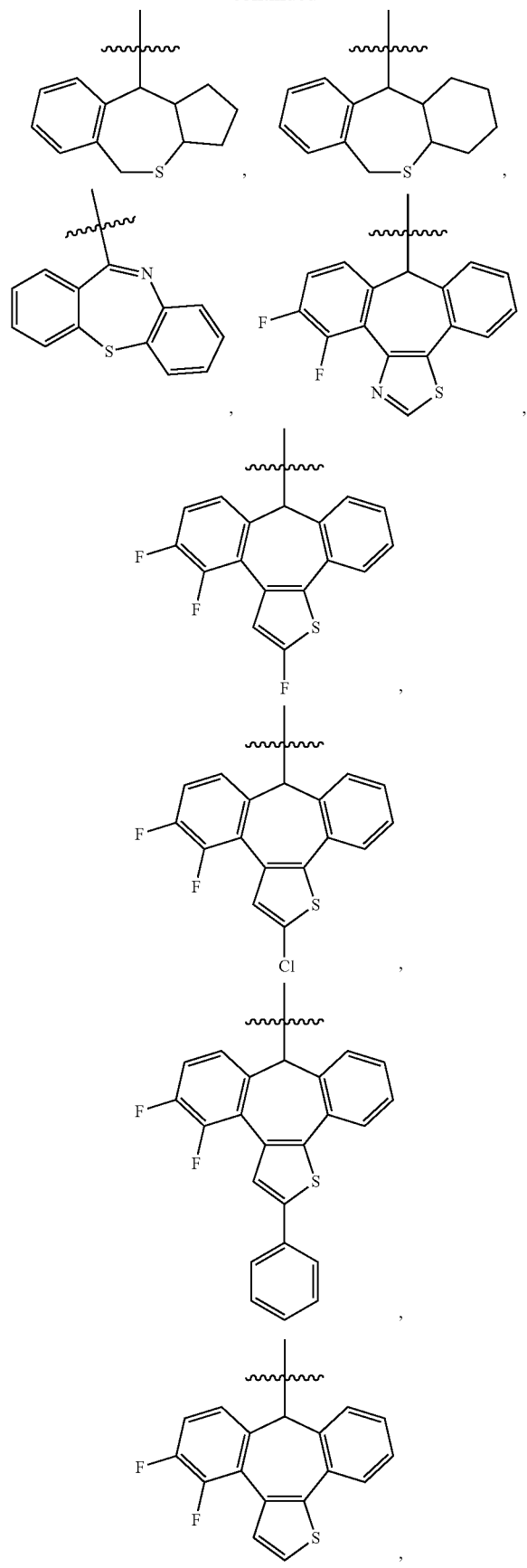
64
-continued
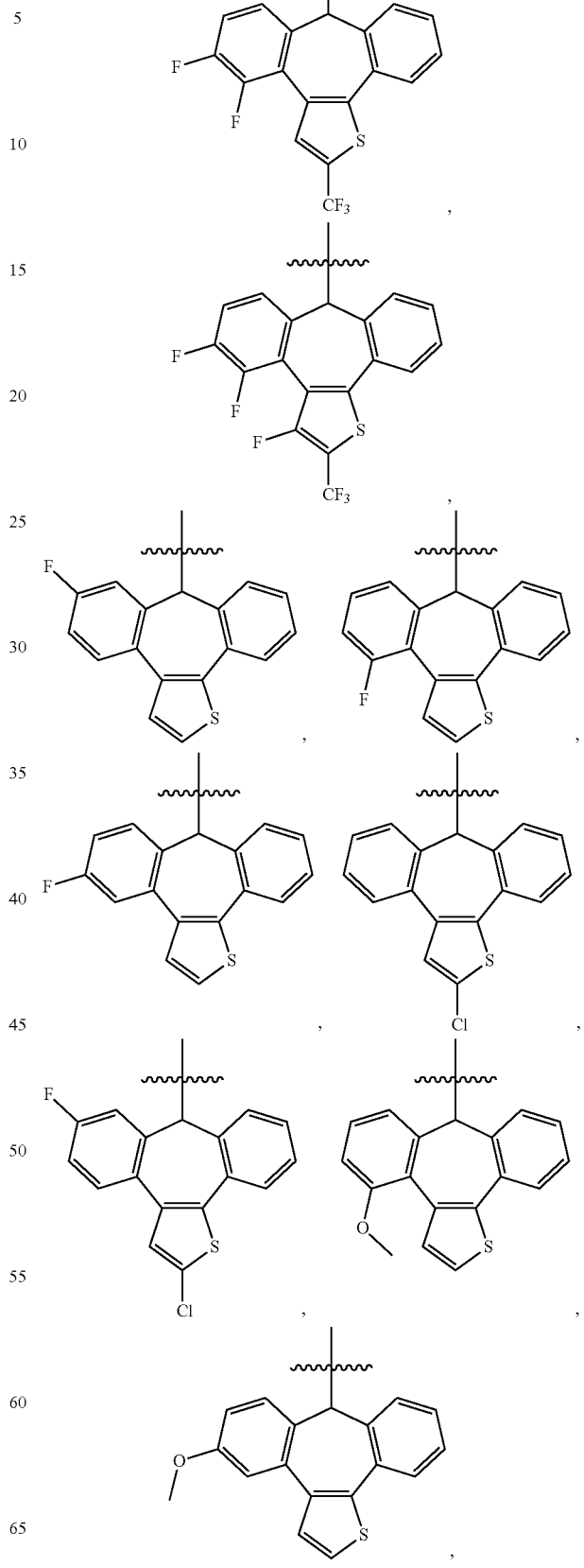

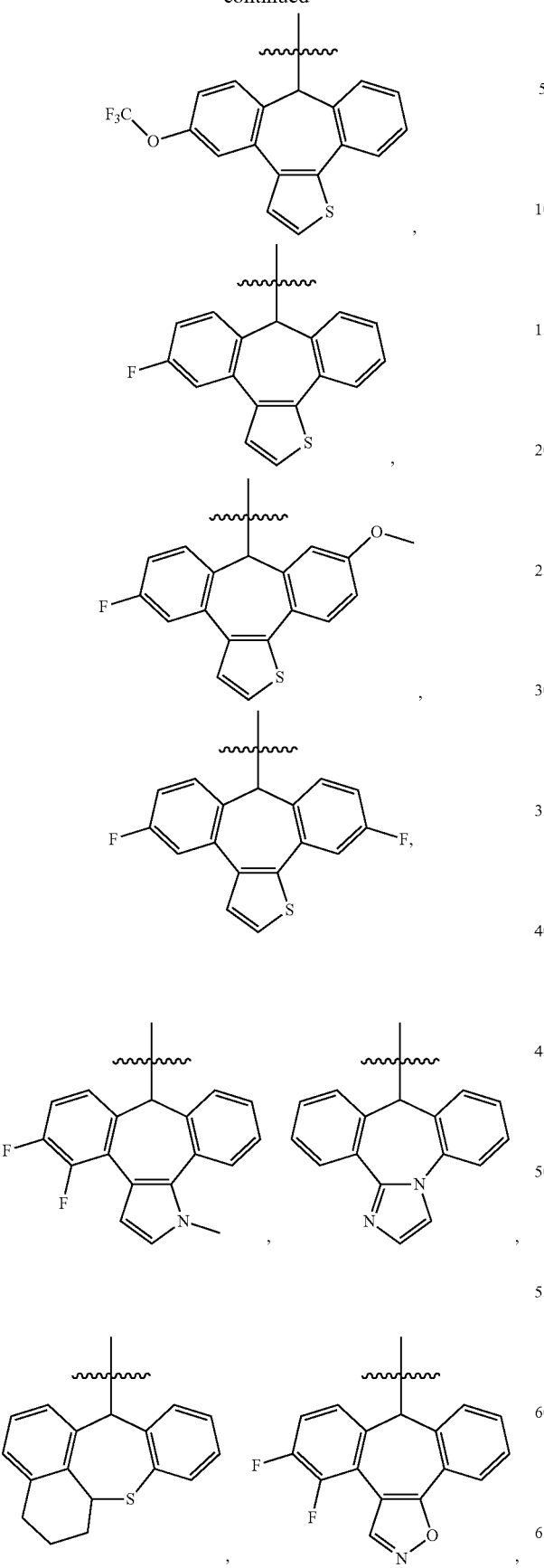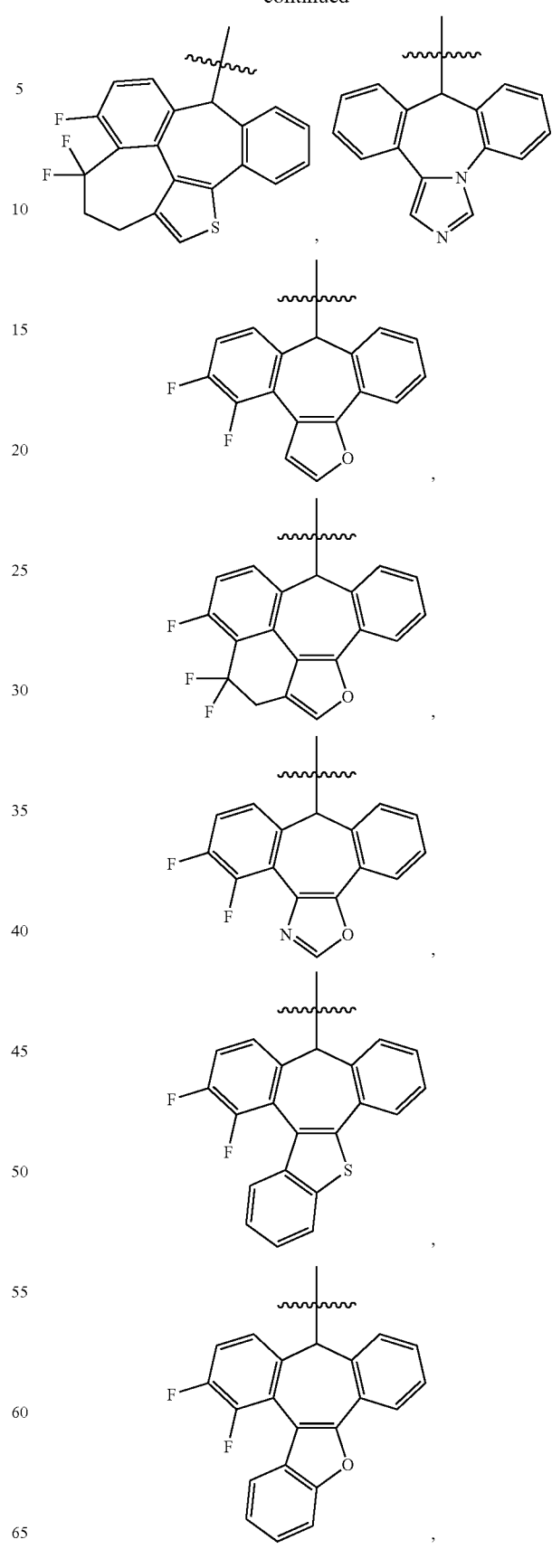

-continued
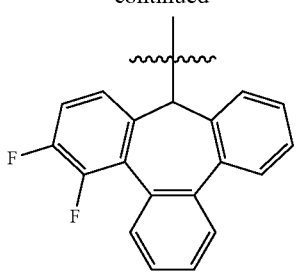,
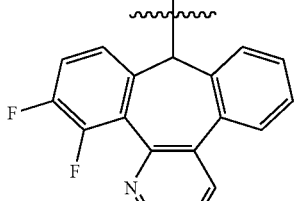,
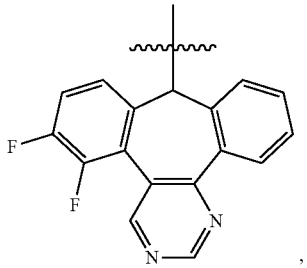,
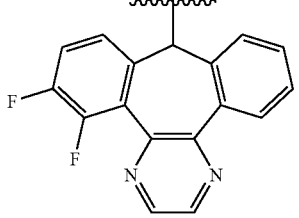,
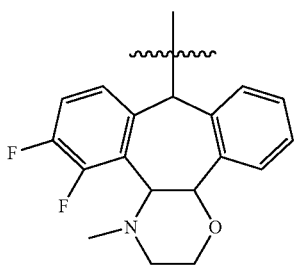,
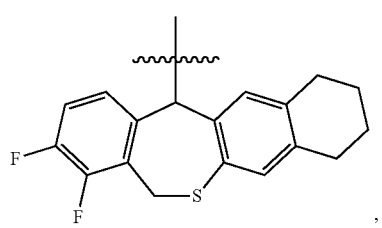,
-continued
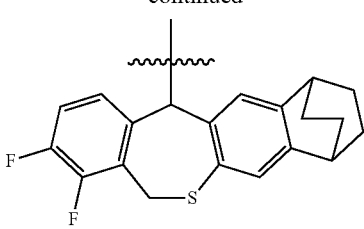,
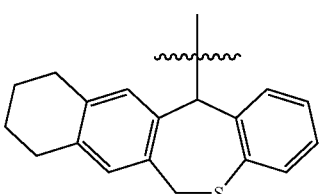,
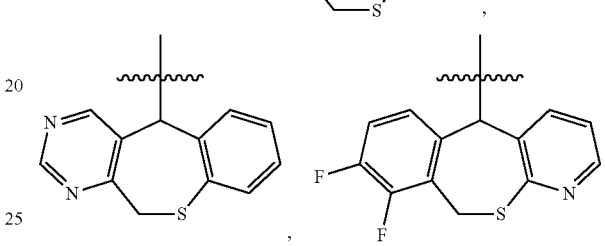,
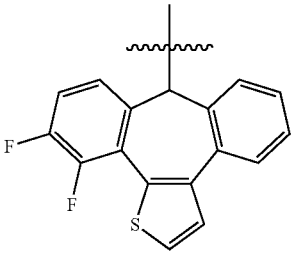,
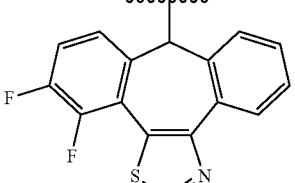,
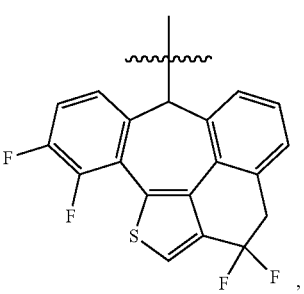,
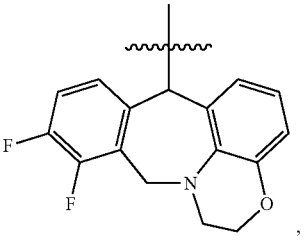,

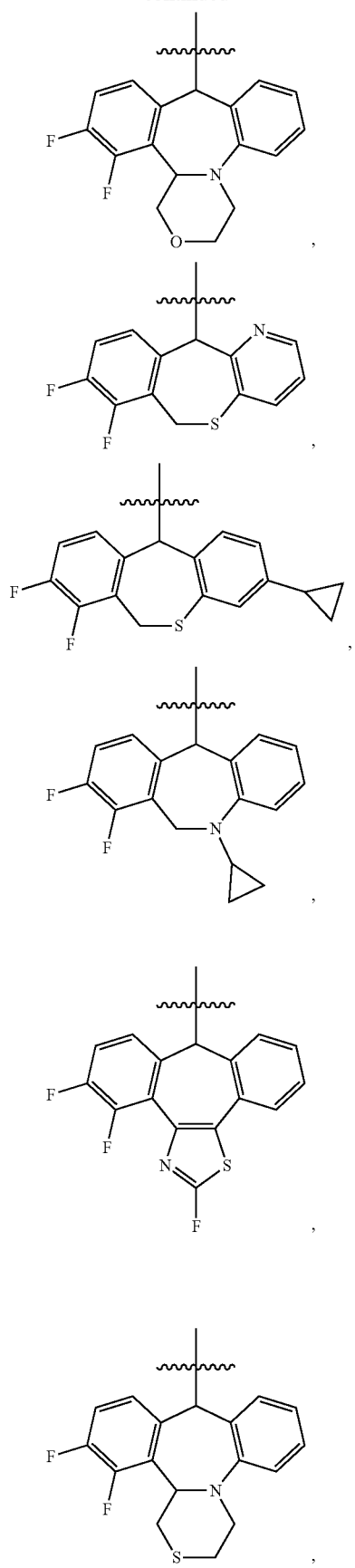
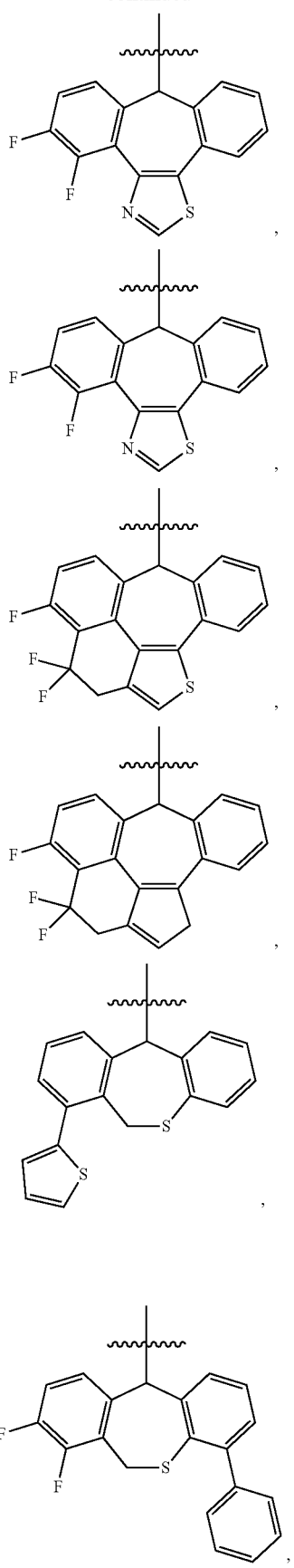

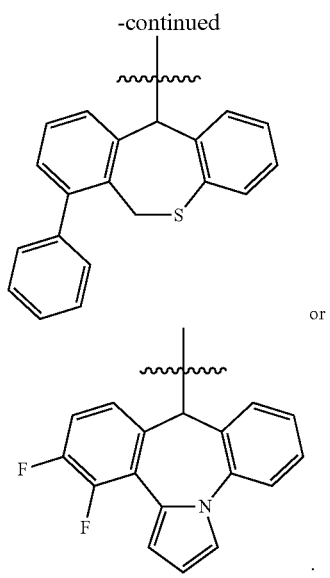

In other embodiments, each $R^{1a}$, $R^{1b}$, $R^{1b}$, $R^{2a}$, $R^{2a}$, $R^{2b}$, $R^{3a}$, $R^{3b}$, $R^{3a}$, $R^{3b}$, $R^{3b}$, $R^{4a}$ and $R^{4b}$ is independently H, deuterium, F, Cl, Br, I, CN, $NO_2$, $OR^b$, $R^bO-C_{1-2}$ alkylene, $R^dR^cN-C_{1-2}$ alkylene, $C_{1-4}$ haloalkyl, $C_{1-4}$ alkyl, $C_{2-4}$ alkenyl, $C_{2-4}$ alkynyl, $C_{3-6}$ carbocyclyl, 3-6 membered heterocyclyl, $C_{6-10}$ aryl or 5-10 membered heteroaryl; wherein each $C_{1-4}$ haloalkyl, $C_{1-4}$ alkyl, $C_{2-4}$ alkenyl, $C_{2-4}$ alkynyl, $C_{3-6}$ carbocyclyl, 3-6 membered heterocyclyl consisting of 3-6 atoms, $C_{6-10}$ aryl and 5-10 membered heteroaryl group is unsubstituted or substituted with 1, 2, 3 or 4 substituents independently selected from deuterium, F, Cl, Br, I, CN, OH, $NH_2$, $C_{1-4}$ alkyl, $C_{1-4}$ haloalkyl, $C_{1-4}$ alkoxy or $C_{1-4}$ alkylamino;

or optionally two $R^{1a}$, $R^{1b}$, $R^{2a}$, $R^{2b}$, $R^{3a}$, $R^{3b}$, $R^{4a}$, $R^{4b}$ together with the carbon atom to which they are attached form a $C_{3-8}$ carbocyclic ring or 3-8 membered heterocyclic ring; wherein each of $C_{3-8}$ carbocyclic ring and 3-8 membered heterocyclic ring is independently unsubstituted or substituted with 1, 2, 3 or 4 substituents independently selected from deuterium, F, Cl, Br, I, CN, OH, $NH_2$, $C_{1-4}$ alkyl, $C_{1-4}$ haloalkyl, $C_{1-4}$ alkoxy or $C_{1-4}$ alkylamino.

In other embodiments, each $R^{1a}$, $R^{1b}$, $R^{2a}$, $R^{2b}$, $R^{3a}$, $R^{3b}$, $R^{4a}$ and $R^{4b}$ is independently H, deuterium, F, Cl, Br, I, CN, $NO_2$, $OR^b$, $R^bO-C_{12}$ alkylene, $R^dR^cN-C_{12}$ alkylene, trifluoromethyl, trifluoroethyl, methyl, ethyl, n-propyl, isopropyl, cyclopropyl, cyclobutyl, cyclopentyl, oxiranyl, azetidinyl, oxetanyl, pyrrolidinyl, piperidinyl, piperazinyl, tetrahydrofuranyl, tetrahydropyranyl, morpholinyl, phenyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, wherein each trifluoroethyl, methyl, ethyl, n-propyl, isopropyl, cyclopropyl, cyclobutyl, cyclopentyl, oxiranyl, azetidinyl, oxetanyl, pyrrolidinyl, piperidinyl, piperazinyl, tetrahydrofuranyl, tetrahydropyranyl, morpholinyl, phenyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with 1, 2, 3 or 4 substituents independently selected from deuterium, F, Cl, Br, I, CN, OH, $NH_2$, methyl, ethyl, n-propyl, isopropyl, trifluoromethyl, methoxy or ethoxy;

or optionally two $R^{1a}$, $R^{1b}$, $R^{2a}$, $R^{2b}$, $R^{3a}$, $R^{3b}$, $R^{4a}$, $R^{4b}$ together with carbon atom to which they are attached form cyclopropane, cyclobutane, cyclopentane, cyclohexane, cycloheptane, oxirane, oxetane, azetidine, pyrrolidine, piperidine, piperazine, tetrahydrofuran, tetrahydropyan or morpholine, wherein each cyclopropane, cyclobutane, cyclopentane, cyclohexane, cycloheptane, oxirane, oxetane, azetidine, pyrrolidine, piperidine, piperazine, tetrahydrofuran, tetrahydropyran and morpholine is independently unsubstituted or substituted with 1, 2, 3 or 4 substituents independently selected from deuterium, F, Cl, Br, I, CN, OH, $NH_2$, methyl, ethyl, n-propyl, isopropyl, trifluoromethyl, methoxy or ethoxy;

In other embodiments, P is H, deuterium, $C_{1-4}$ alkyl, $C_{2-4}$ alkenyl, $C_{3-6}$ carbocyclyl, $C_{3-6}$ carbocyclyl-$C_{1-2}$ alkylene, $C_{3-6}$ heterocyclyl, ($C_{3-6}$ heterocyclyl)-$C_{1-2}$ alkylene, $C_{6-10}$ aryl, $C_{6-10}$ aryl-$C_{1-2}$ alkylene, 5-10 membered heteroaryl, (5-10 membered heteroaryl)-$C_{1-2}$ alkylene, $-C(=O)-R^{Pa}$, $-C(=O)-O-R^{Pb}$, $-C(=O)-NR^{Pf}R^{Pd}$, $P(=O)-(R^{Pg})(R^{Ph})$, $-C(=O)-O-L-O-R^{Pb}$, $R^{Pa}-(C=O)-O-C_{1-4}$ alkylene, $R^{Pb}-O-(C=O)-C_{1-4}$ alkylene, $R^{Pb}-O-(C=O)-NR^{Pf}-C_{1-4}$ alkylene, $R^{Pb}-O-(C=O)-O-C_{1-4}$alkylene or $R^{Pb}-O-L-O-(C=O)-O-C_{1-4}$ alkylene, wherein each $C_{1-4}$ alkyl, $C_{2-4}$ alkenyl, $C_{3-6}$ carbocyclyl, $C_{3-6}$ carbocyclyl-$C_{1-2}$ alkylene, $C_{3-6}$ heterocyclyl, ($C_{3-6}$ heterocyclyl)-$C_{1-2}$ alkylene, $C_{6-10}$ aryl, $C_{6-10}$ aryl-$C_{1-2}$ alkylene, 5-10 membered heteroaryl, (5-10 membered heteroaryl)-$C_{1-2}$ alkylene is independently unsubstituted or substituted with 1, 2, 3 or 4 substituents independently selected from deuterium, F, Cl, Br, I, oxo(=O), CN, $NO_2$, $-OR^b$, $-NR^cR^d$, $-C(=O)R^a$, $-O(C=O)R^a$, $-C(=O)OR^b$, $C_{1-6}$ alkyl, $R^bO-C_{1-4}$ alkylene, $-NR^dR^cC(=O)R^a$ or $R^dR^cN-C_{1-4}$ alkylene;

each L is independently $C_{1-6}$ alkylene;

each $R^{pf}$ is independently H or $C_{1-6}$ alkyl groups;

each $R^{pa}$, $R^{pb}$, and $R^{pd}$ is independently $C_{1-4}$ alkyl, $C_{3-6}$ carbocyclyl, $C_{3-6}$ carbocyclyl-$C_{1-2}$ alkylene, 3-6 membered heterocyclyl, (3-6 membered heterocyclyl)-$C_{1-2}$ alkylene, $C_{6-10}$ aryl, $C_{6-10}$ aryl $-C_{1-2}$ alkylene, 5-10 membered heteroaryl or (5-10 membered heteroaryl)-$C_{1-2}$ alkylene, wherein each $C_{1-4}$ alkyl, $C_{3-6}$ carbocyclyl, $C_{3-6}$ carbocyclyl-$C_{1-2}$ alkylene, 3-6 membered heterocyclyl, (3-6 membered heterocyclyl)-$C_{1-2}$ alkylene, $C_{6-10}$ aryl, $C_{6-10}$ aryl $-C_{1-2}$ alkylene, 5-10 membered heteroaryl and (5-10 membered heteroaryl)-$C_{1-2}$ alkylene is independently unsubstituted or substituted with 1, 2, 3 or 4 substituents independently selected from deuterium, F, Cl, Br, I, oxo(=O), CN, $NO_2$, $-OR^b$, $-NR^cR^d$, $-C(=O)R^a$, $-O(C=O)R^a$, $-C(=O)OR^b$, $C_{1-6}$ alkyl, $R^bO-C_{1-4}$ alkylene, $-NR^dR^cC(=O)R^a$ or $R^dR^cN-C_{1-4}$ alkylene;

each $R^{Pg}$ and $R^{Ph}$ is independently $C_{1-4}$ alkoxy, $C_{1-4}$ alkylamino, $C_{3-6}$ carbocyclyloxy, $C_{3-6}$ carbocyclylamino, 3-6 membered heterocyclyloxy, 3-6 membered heterocyclylamino, $C_{6-10}$ aryloxy, $C_{6-10}$ arylamino, 5-6 membered heterocyclyloxy or 5-6 membered heterocyclylamino, wherein $C_{1-4}$ alkoxy, $C_{1-4}$ alkylamino, $C_{3-6}$ carbocyclyloxy, $C_{3-6}$ carbocyclylamino, 3-6 atomic heterocyclyloxy, 3-6 atomic heterocyclylamino, $C_{6-10}$ aryloxy group, $C_{6-10}$ arylamino, 5-6 membered heterocyclyloxy and 5-6 membered heterocyclylamino group is independently unsubstituted or substituted with 1, 2, 3 or 4 substituents independently selected from deuterium, F, Cl, Br, I, oxo(=O), CN, $NO_2$, $-OR^b$, $-NR^cR^d$, $-C(=O)R^a$, $-O(C=O)R^a$, $-C(=O)OR^b$, $C_{1-6}$ alkyl, $R^bO-C_{1-4}$ alkylene, $-NR^dR^cC(=O)R^a$ or $R^dR^cN-C_{1-4}$ alkylene;

or $R^{Pg}$, $R^{Ph}$ together with phosphorus atom to which they are attached form a 3-6 membered heterocyclic ring, or 5-6 membered heteroaromatic ring; wherein each of 3-6 membered heterocyclic ring and 5-6 membered heteroaromatic ring is independently unsubstituted or substituted with 1, 2, 3 or 4 substituents independently selected from deuterium, F, Cl, Br, I, oxo(=O), CN, NO$_2$, —OR$^b$, —NR$^c$R$^d$, —C(=O)R$^a$, —O(C=O)R$^a$, —C(=O)OR$^b$, C$_{1-6}$ alkyl, R$^b$O—C$_{1-4}$ alkylene, —NR$^d$R$^c$C(=O)R$^a$ or R$^d$R$^c$N—C$_{1-4}$ alkylene.

In other embodiments, H, deuterium,

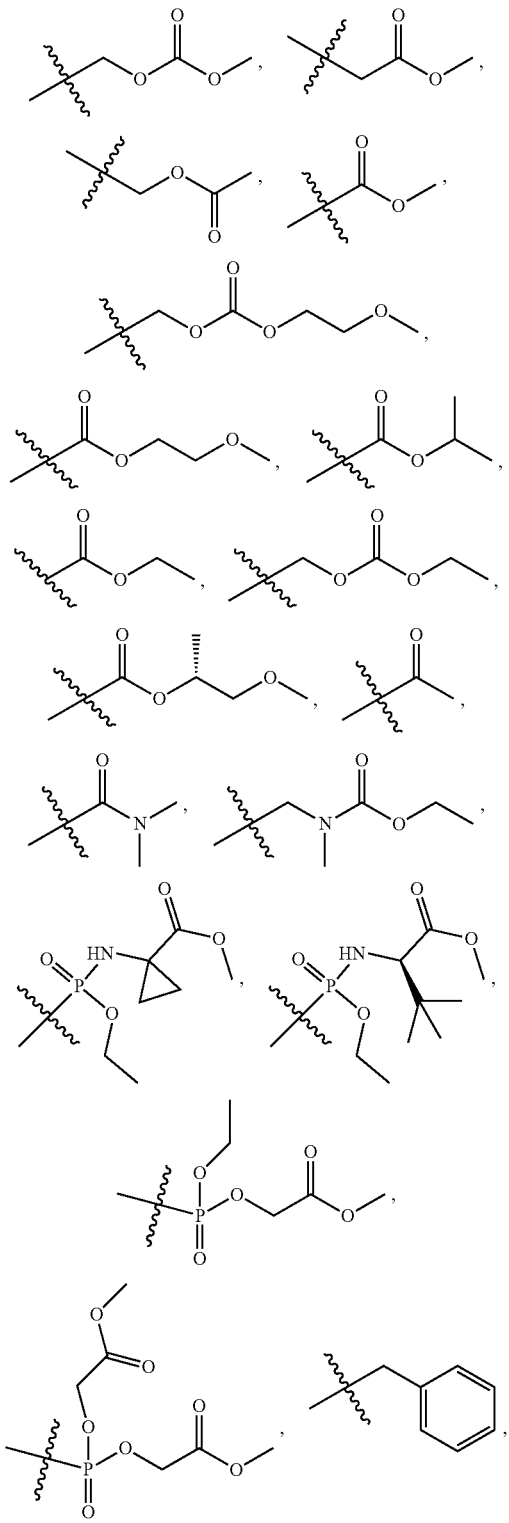
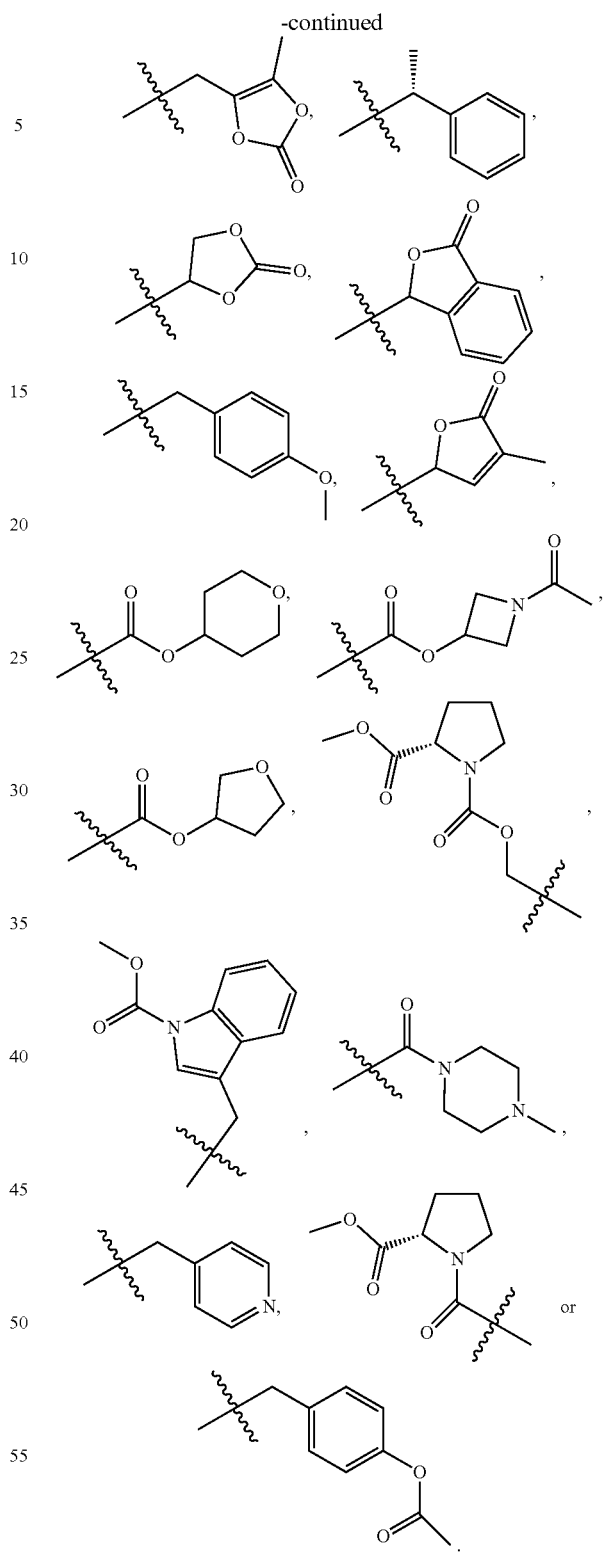

In other embodiments, each R$^a$, R$^b$, R$^c$ and R$^d$ is independently H, deuterium, trifluoromethyl, trifluoroethyl, methyl, ethyl, n-propyl, isopropyl, tert-butyl, cyclopropyl, cyclobutyl, 3-6 membered heterocyclyl, phenyl or 5-10 membered heteroaryl group, wherein each methyl, ethyl, n-propyl, isopropyl, tert-butyl, cyclopropyl, cyclobutyl, 3-6 membered heterocyclyl, phenyl and 5-10 membered heteroaryl is independently unsubstituted or substituted with 1, 2, 3 or 4 substituents independently selected from deuterium, F, Cl, CN, OH, $NH_2$, $NO_2$, methyl, ethyl, n-propyl, isopropyl, trifluoromethyl or methoxy;

or, $R^c$ $R^d$ together with nitrogen atom to which they are attached form a 3-6 membered heterocyclic ring or 5-6 membered heteroaryl ring; wherein each 3-6 membered heterocyclic ring and 5-6 membered heteroaryl ring is independently unsubstituted or substituted with 1, 2, 3 or 4 substituents independently selected from deuterium, F, Cl, CN, OH, $NH_2$, $NO_2$, methyl, ethyl, n-propyl, isopropyl, trifluoromethyl or methoxy.

In other embodiments, the compound of the present invention is a compound having Formula (II), or a stereoisomer, a tautomer, an N-oxide, a solvate, a metabolite, a pharmaceutically acceptable salt or a prodrug thereof,

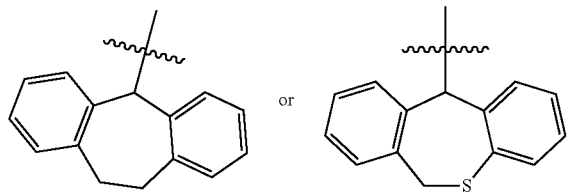 [SMILES: *C1c2ccccc2CCc2ccccc21 ; *C1c2ccccc2CSc2ccccc21]

(II)

wherein ring A, P, R, $U^1$, $U^2$, $Y^1$, $Y^2$, $Y^3$, $Y^4$, n and m have the definition as described in the present invention, with the proviso that ring A is not

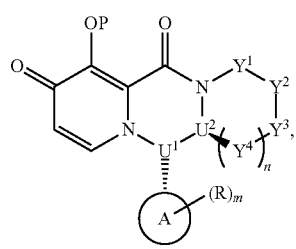

or s when m is 0 or 1, and when m is 2 and ring A is

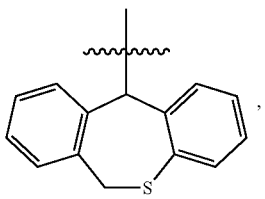 [SMILES: *C1c2ccccc2CSc2ccccc21]

optionally two R together with the carbon atom to which they are attached form a $C_{3-8}$ carbocyclic ring, 3-8 membered heterocyclic ring, $C_{6-10}$ aromatic ring or 5-10 membered heteroaryl ring; wherein each a $C_{3-8}$ carbocyclic ring, 3-8 membered heterocyclic ring, $C_{6-10}$ aromatic ring and 5-10 membered heteroaromatic ring is independently unsubstituted or substituted with 1, 2, 3 or 4 substituents independently selected from deuterium, F, Cl, Br, I, CN, $NO_2$, —$OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene.

In other embodiments, the present invention provides a compound having Formula (III) or a stereoisomer, a tautomer, an N-oxide, a hydrate, a solvate, a metabolite, a pharmaceutically acceptable salt or a prodrug thereof,

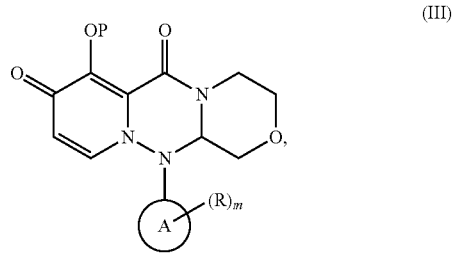

(III)

wherein ring A, P, R, and m have the definition as described in the present invention, provided that ring A is not

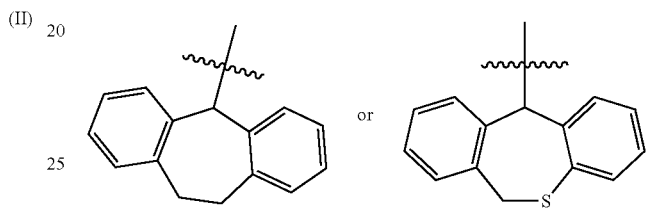

when m is 0 or 1, and when m is 2 and ring A is

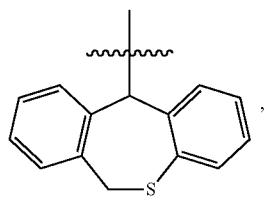

optionally two R together with carbon atom to which they are attached form a $C_{3-8}$ carbocyclic ring, 3-8 membered heterocyclic ring, $C_{6-10}$ aromatic ring or 5-10 membered heteroaromatic ring; wherein each $C_{3-8}$ carbocyclic ring, 3-8 membered heterocyclic ring, $C_{6-10}$ aromatic ring, and 5-10 membered heteroaromatic ring is independently unsubstituted or substituted with 1, 2, 3 or 4 substituents independently selected from deuterium, F, Cl, Br, I, CN, $NO_2$, —$OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene.

In other embodiments, the compound of the present invention is a compound having Formula (IV), or a stereoisomer, a tautomer, an N-oxide, a solvate, a metabolite, a pharmaceutically acceptable salt or a prodrug thereof,

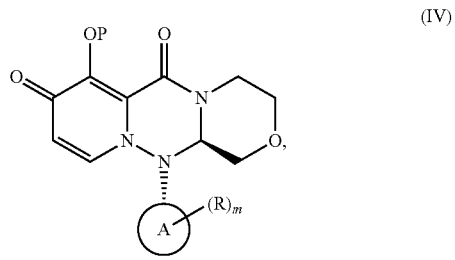

(IV)

wherein ring A, P, R, and m have the definition as described in the present invention, with the proviso that ring A is not

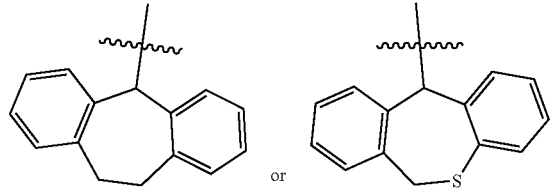 [SMILES: *C1c2ccccc2CCc2ccccc21 ; *C1c2ccccc2CSc2ccccc21]

or when m is 0 or 1, and when m is 2 and ring A is

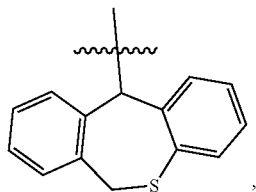 [SMILES: *C1c2ccccc2CSc2ccccc21]

, optionally two R together with carbon atom to which they are attached form a $C_{3-8}$ carbocyclic ring, 3-8 membered heterocyclic ring, $C_{6-10}$ aromatic ring or 5-10 membered heteroaromatic ring; wherein each $C_{3-8}$ carbocyclic ring, 3-8 membered heterocyclic ring, $C_{6-10}$ aromatic ring and 5-10 membered heteroaromatic ring is independently unsubstituted or substituted with 1, 2, 3 or 4 substituents independently selected from deuterium, F, Cl, Br, I, CN, $NO_2$, —$OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene.

In other embodiments, the compound of the present invention is a compound having Formula (V), or a stereoisomer, a tautomer, an N-oxide, a solvate, a metabolite, a pharmaceutically acceptable salt or a prodrug thereof, (V)

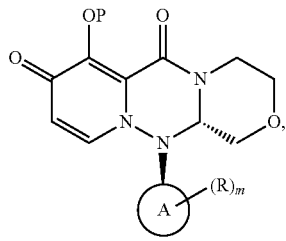

wherein ring A, P, R and m have the definition as described in the present invention, with the proviso that ring A is not

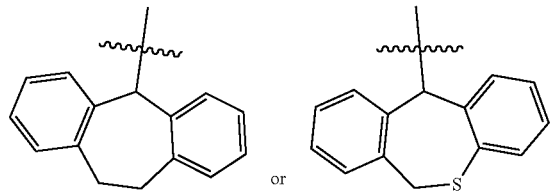 [SMILES: *C1c2ccccc2CCc2ccccc21 ; *C1c2ccccc2CSc2ccccc21]

or when m is 0 or 1, and when m is 2 and ring A is

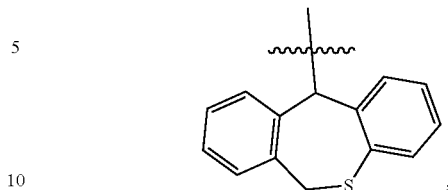

, optionally two R together with carbon atom to which they are attached form a $C_{3-8}$ carbocyclic ring, 3-8 membered heterocyclic ring, $C_{6-10}$ aromatic ring or 5-10 membered heteroaryl ring; wherein each $C_{3-8}$ carbocylic ring, 3-8 membered heterocyclic ring, $C_{6-10}$ aromatic ring, and 5-10 membered heteroaromatic ring is independently unsubstituted or substituted with 1, 2, 3 or 4 substituents independently selected from deuterium, F, Cl, Br, I, CN, $NO_2$, —$OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene.

In other embodiments, the compound of the present invention is a compound having Formula (VI), or a stereoisomer, a tautomer, an N-oxide, a solvate, a metabolite, a pharmaceutically acceptable salt or a prodrug thereof, (VI)

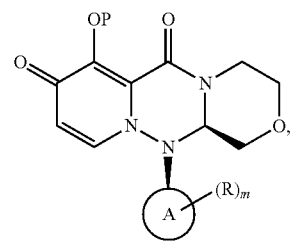

wherein ring A, P, R, and m have the definition as described in the present invention, with the proviso that ring A is not

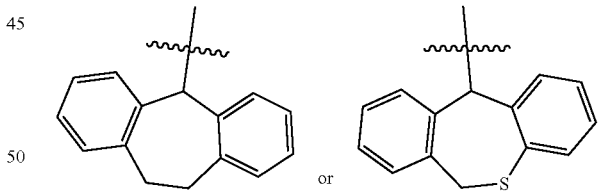

when m is 0 or 1, and when m is 2 and ring A is

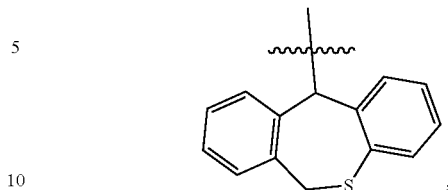

, optionally two R together with carbon atom to which they are attached form a $C_{3-8}$ carbocyclic ring, 3-8 membered heterocyclic ring, $C_{6-10}$ aromatic ring or 5-10 membered heteroaromatic ring; wherein each $C_{3-8}$ carbon ring, 3-8 membered heterocyclic ring, $C_{6-10}$ aromatic ring and 5-10 membered heteroaromatic ring is independently unsubstituted or substituted with 1, 2, 3 or 4 substituents independently selected from deuterium, F, Cl, Br, I, CN, $NO_2$, $-OR^b$, $-NR^cR^d$, $C_{1-6}$ alkyl, $C_{1-6}$ haloalkyl, $R^bO-C_{1-4}$ alkylene or $R^dR^cN-C_{1-4}$ alkylene.

In other embodiments, the compound of the present invention is a compound having Formula (VII), or a stereoisomer, a tautomer, an N-oxide, a solvate, a metabolite, a pharmaceutically acceptable salt or a prodrug thereof,

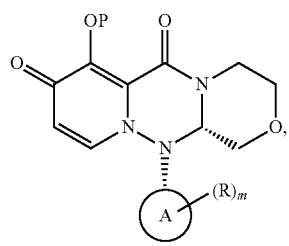
(VII)

Wherein ring A, P, R and m have the definition as described in the present invention, with the proviso that ring A is not

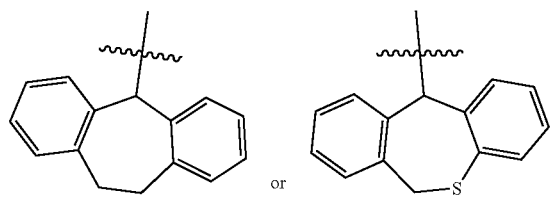 [SMILES: *C1c2ccccc2CCc2ccccc21 ; *C1c2ccccc2CSc2ccccc21]

when m is 0 or 1, and when m is 2 and ring A is

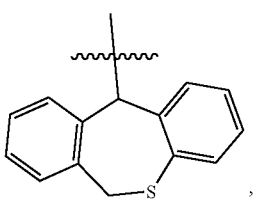 [SMILES: *C1c2ccccc2CSc2ccccc21]

optionally two R together with the carbon atom to which they are attached form a $C_{3-8}$ carbocyclic ring, 5-8 membered heterocyclic ring, $C_{6-10}$ aromatic ring or 5-10 membered heteroaromatic ring; wherein each $C_{3-8}$ carbocyclic ring, 3-8 membered heterocyclic ring, $C_{6-10}$ aromatic ring, and 5-10 membered heteroaromatic ring is independently unsubstituted or substituted with 1, 2, 3 or 4 substituents independently selected from deuterium, F, Cl, Br, I, CN, $NO_2$, $-OR^b$, $-NR^cR^d$, $C_{1-6}$ alkyl, $C_{1-6}$ haloalkyl, $R^bO-C_{1-4}$ alkylene or $R^dR^cN-C_{1-4}$ alkylene.

In other embodiments, the compound of the present invention is a compound having Formula (VIII), or a stereoisomer, a tautomer, an N-oxide, a solvate, a metabolite, a pharmaceutically acceptable salt or a prodrug thereof,

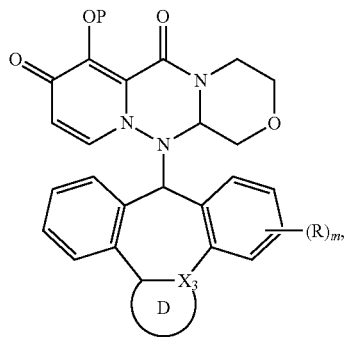
(VIII)

wherein ring D, $X^3$, R, P and m have definitions as described in the present invention.

In other embodiments, the compound of the present invention is a compound having Formula (IX), or a stereoisomer, a tautomer, an N-oxide, a solvate, a metabolite, a pharmaceutically acceptable salt or a prodrug thereof,

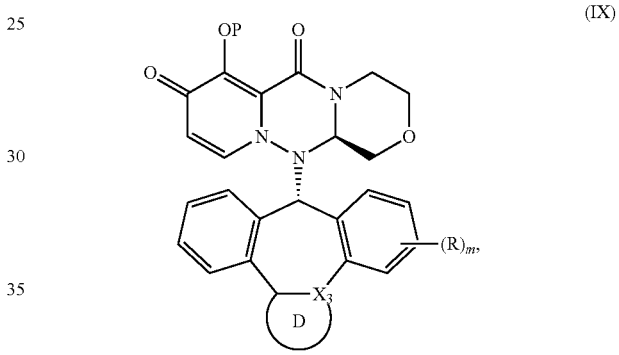
(IX)

wherein ring D, $X^3$, R, P and m have definitions as described in the present invention.

In other embodiments, the compound of the present invention is a compound having Formula (X), or a stereoisomer, a tautomer, an N-oxide, a solvate, a metabolite, a pharmaceutically acceptable salt or a prodrug thereof,

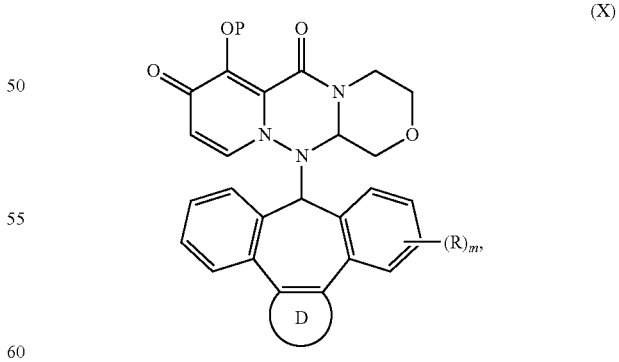
(X)

wherein ring D, R, P and m have definitions as described in the present invention.

In other embodiments, the compound of the present invention is a compound having Formula (XI), or a stereoisomer, a tautomer, an N-oxide, a solvate, a metabolite, a pharmaceutically acceptable salt or a prodrug thereof, (XI)
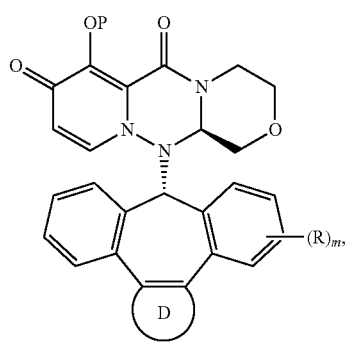
wherein ring D, R, P and m have definitions as described in the present invention.
In other embodiments, the present invention relates to one of the following compounds, or a stereoisomer, a tautomer, an N-oxide, a solvent, a metabolite, a pharmaceutically acceptable salt or a prodrug thereof, but is by no means limited to these compounds:
(1)
(2)
(3)
(4)
(5)
(6)
(7)
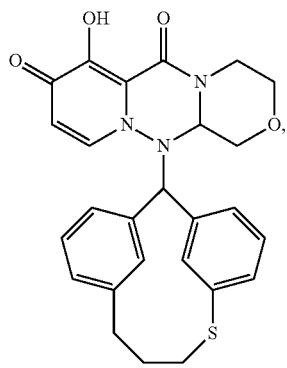
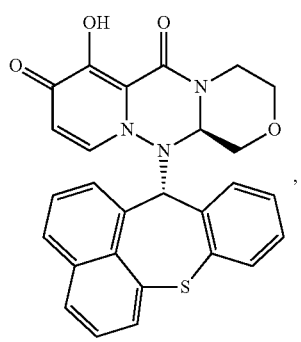
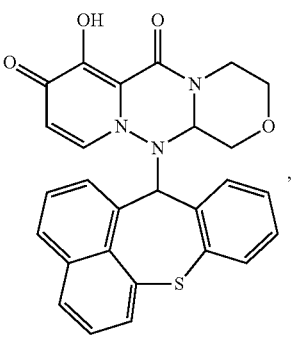
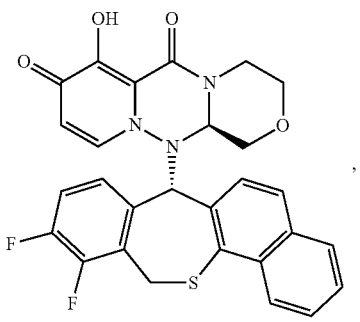

-continued
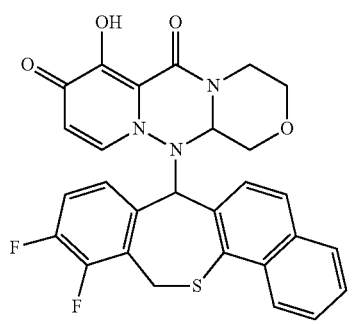
(8)
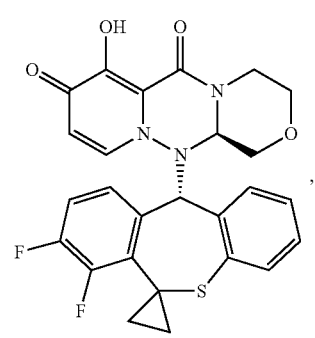
(9)
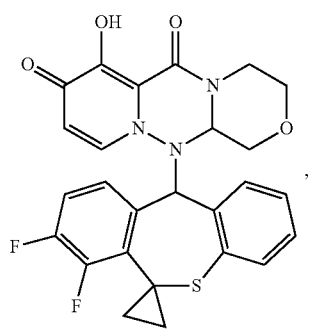
(10)
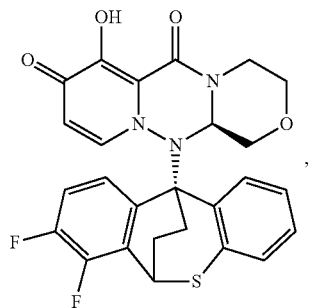
(11)
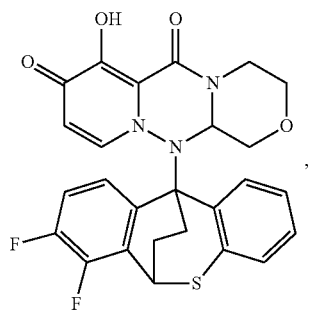
(12)
-continued
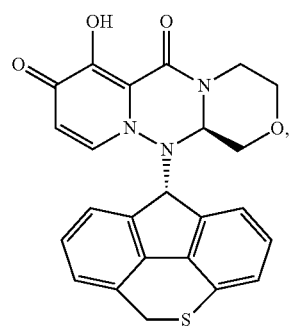
(13)
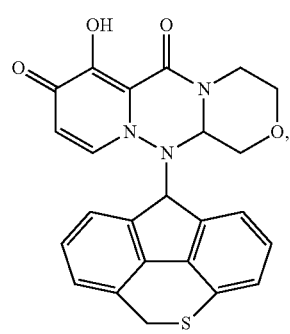
(14)
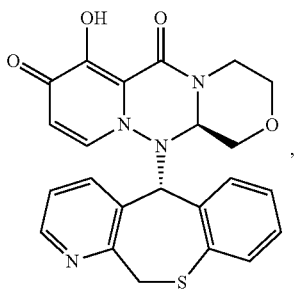
(15)
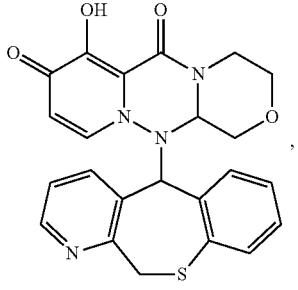
(16)
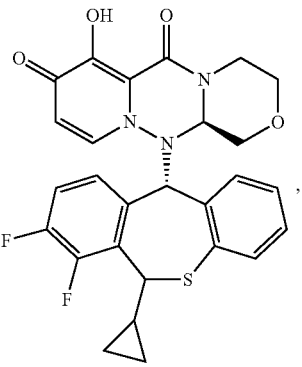
(17)

(18)
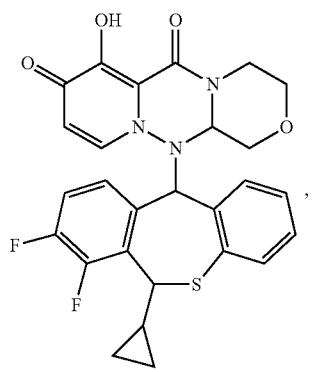
(19)
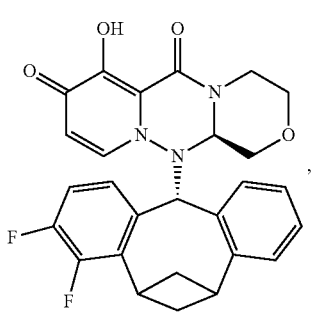
(20)
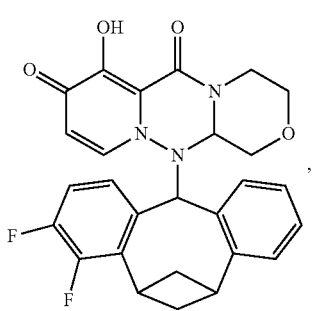
(21)
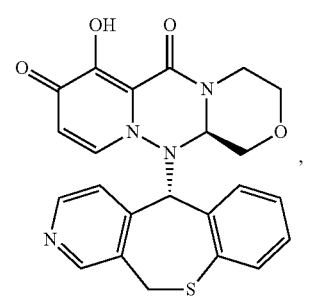
(22)
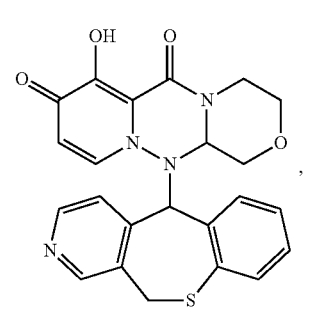
(23)
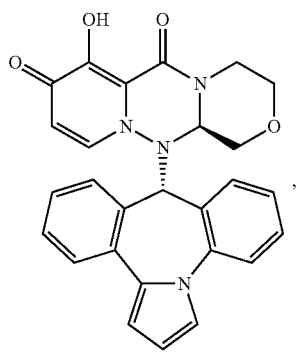
(24)
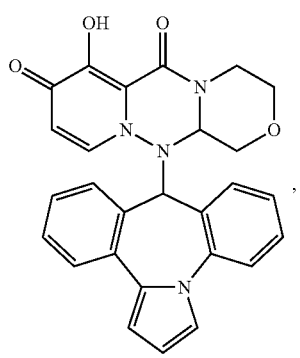
(25)
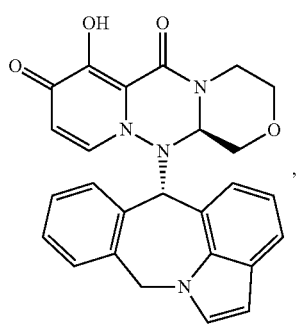
(26)
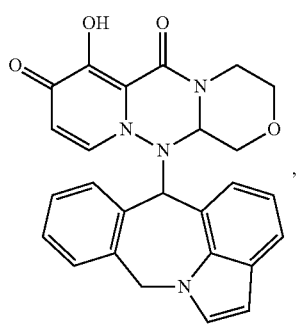

87
-continued
(27)
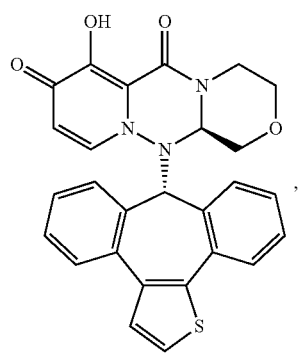
(28)
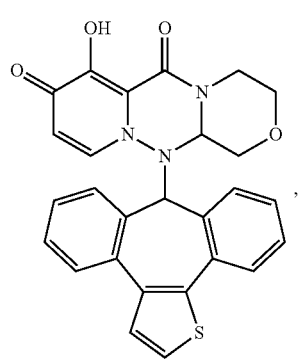
(29)
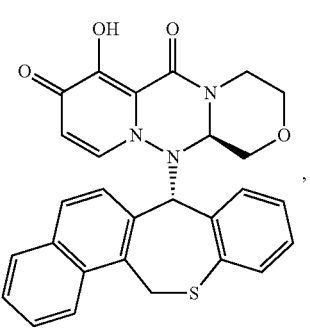
(30)
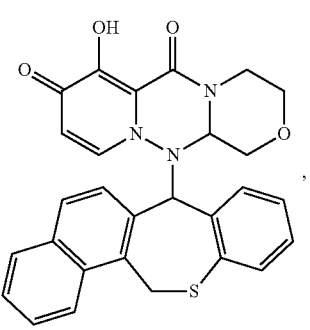
88
-continued
(31)
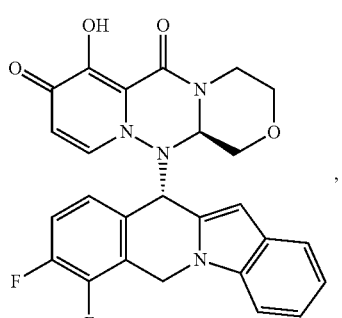
(32)
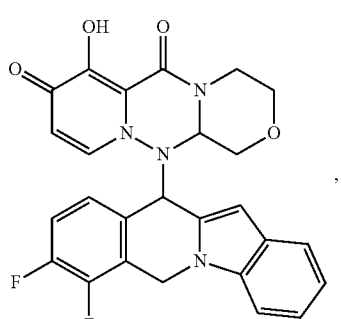
(33)
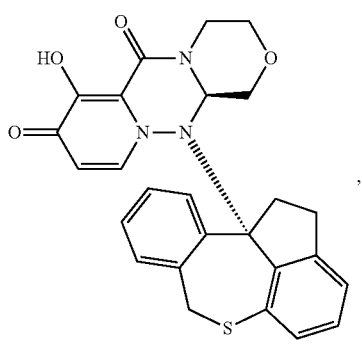
(34)
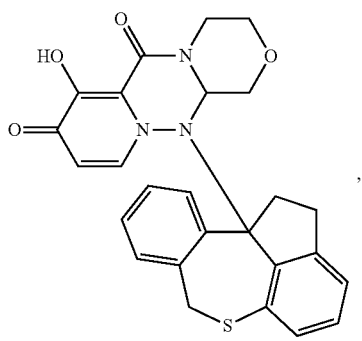

-continued
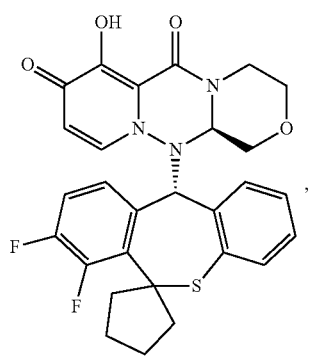
(35)
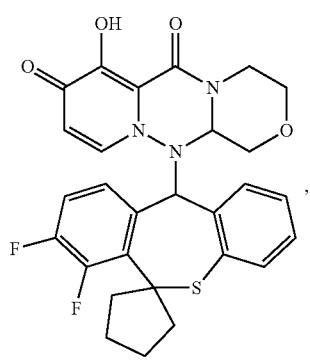
(36)
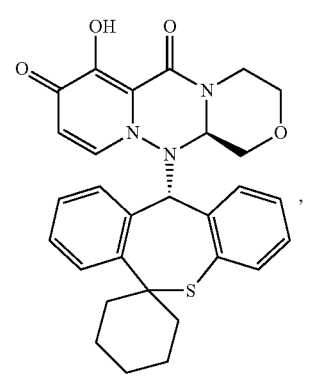
(37)
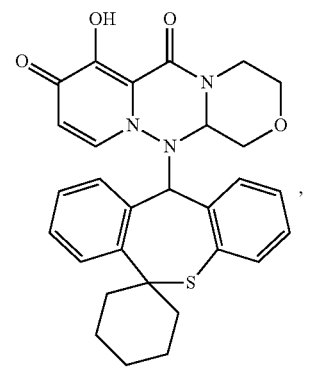
(38)
-continued
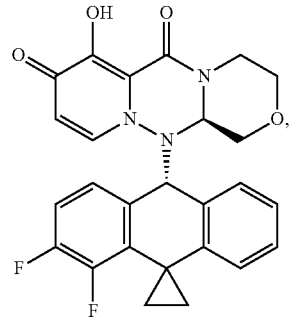
(39)
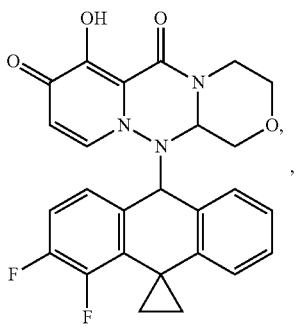
(40)
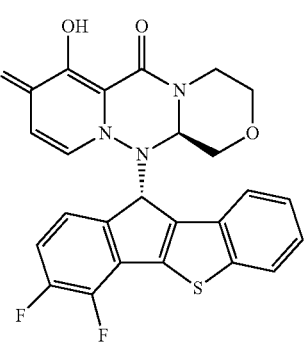
(41)
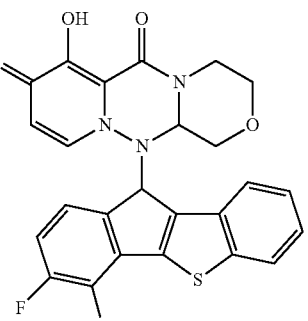
(42)
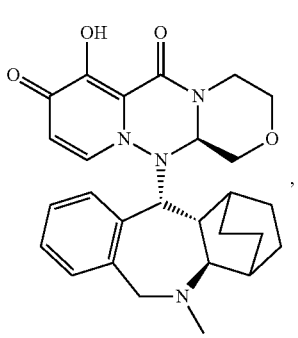
(43)

-continued
(44)
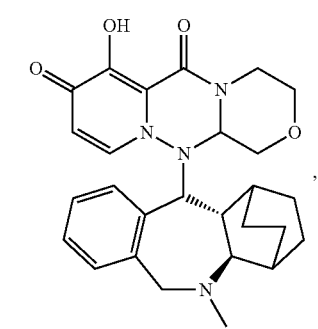
(45)
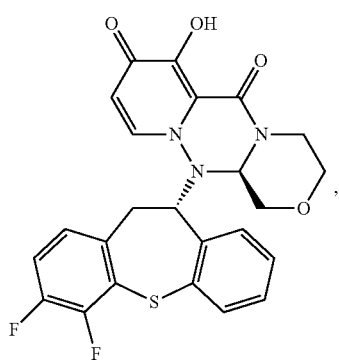
(46)
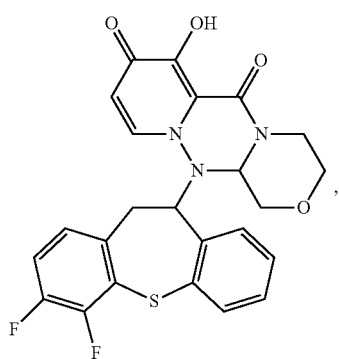
(47)
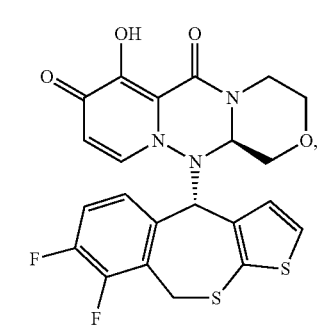
-continued
(48)
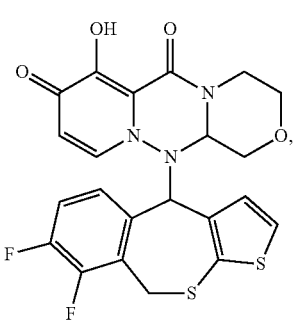
(49)
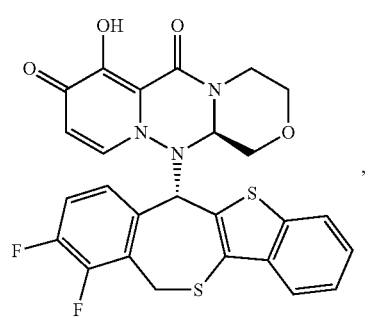
(50)
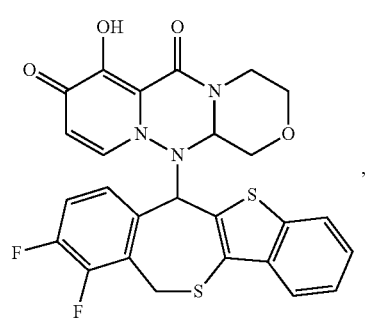
(51)
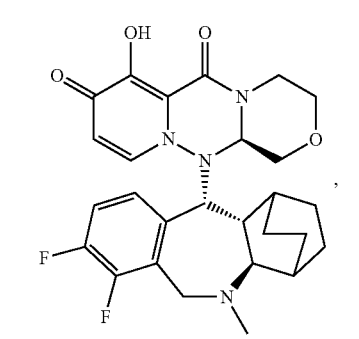
(52)
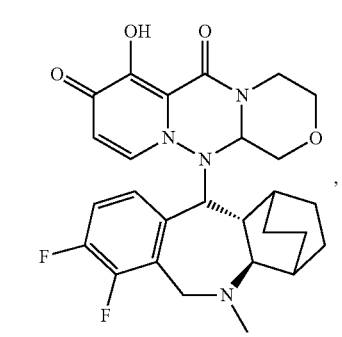

-continued
(53)
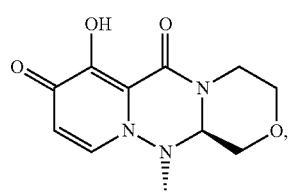
(54)
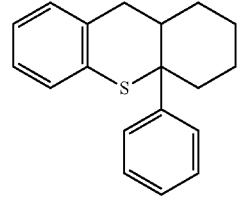
(55)
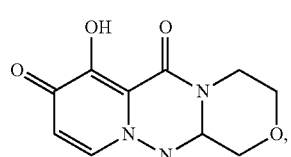
(56)
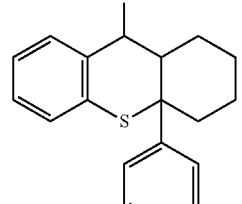
(57)
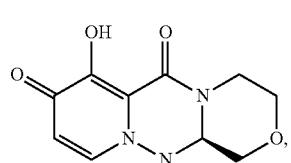
-continued
(58)
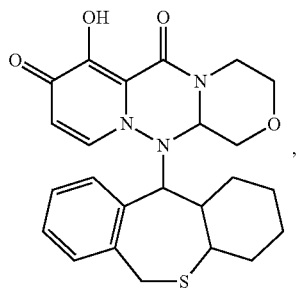
(59)
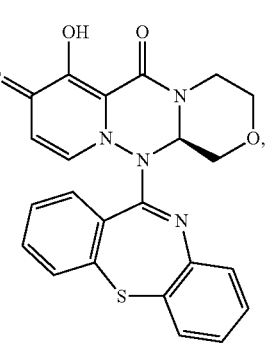
(60)
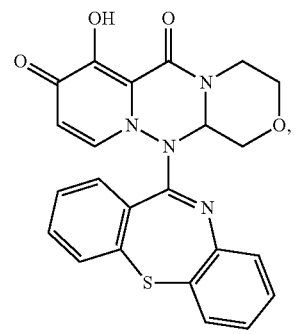
(61)
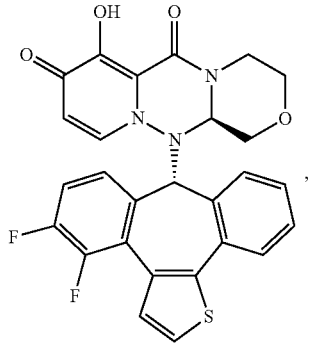

(62) 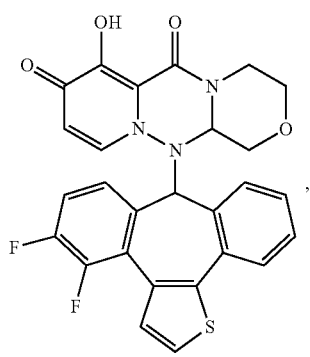
(63) 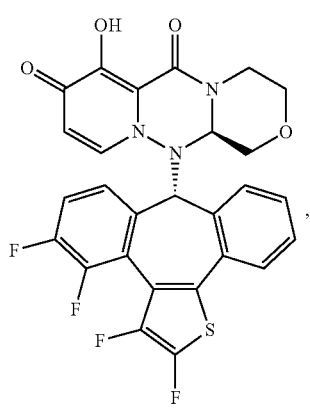
(64) 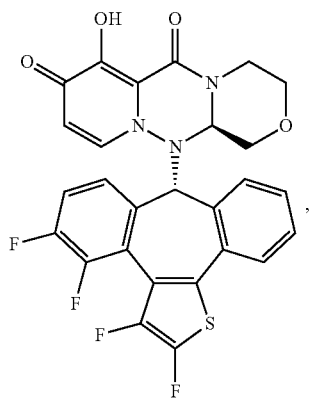
(65) 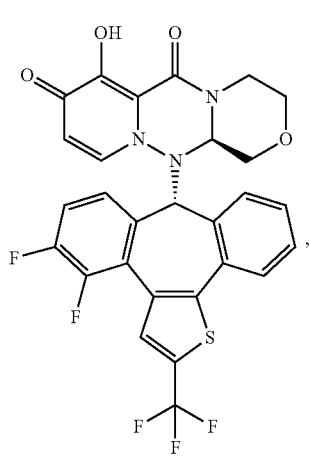
(66) 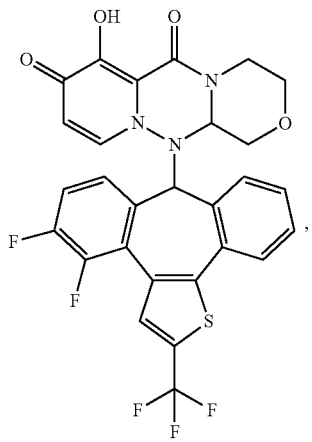
(67) 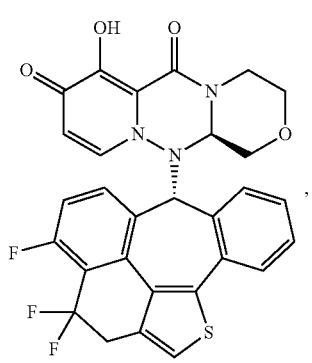
(68) 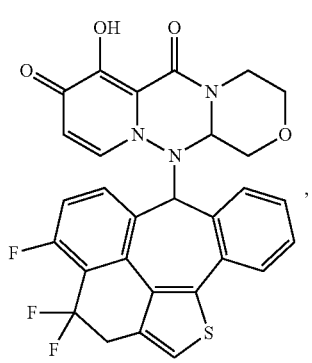
(69) 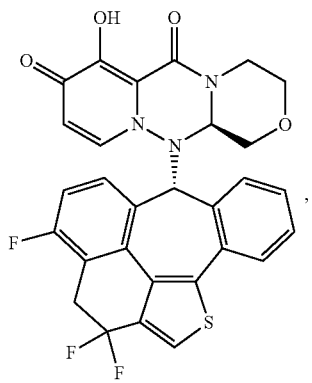

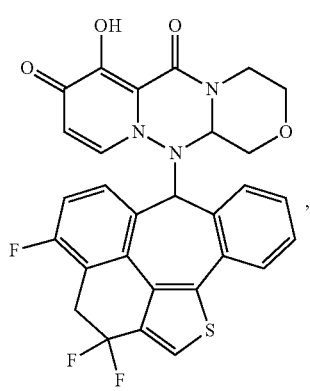
(70)
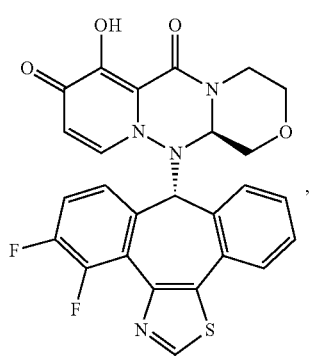
(71)
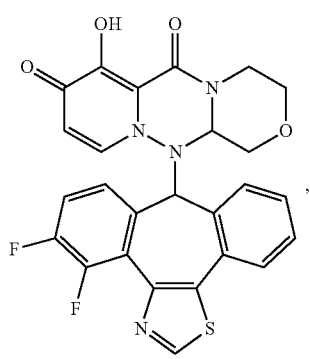
(72)
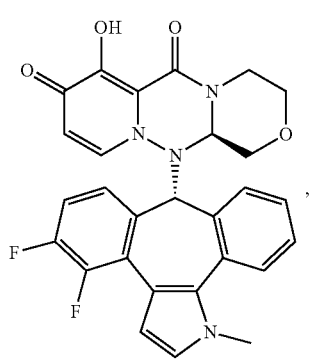
(73)
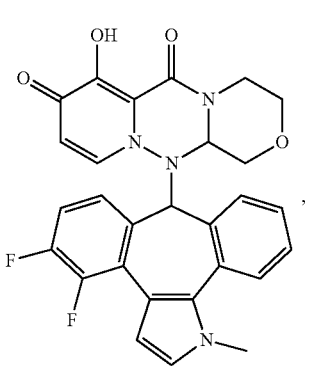
(74)
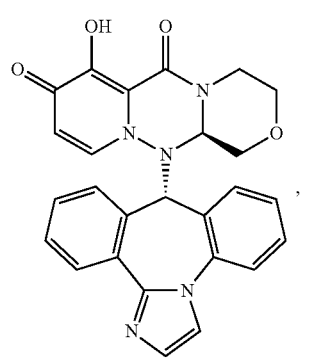
(75)
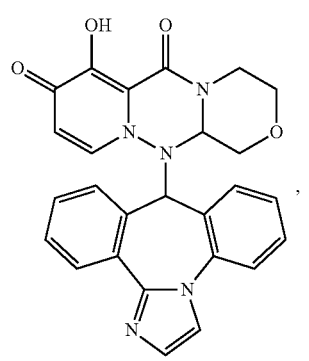
(76)
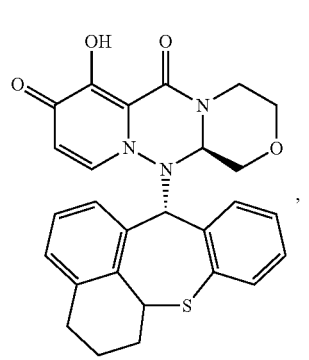
(77)

-continued
(78)
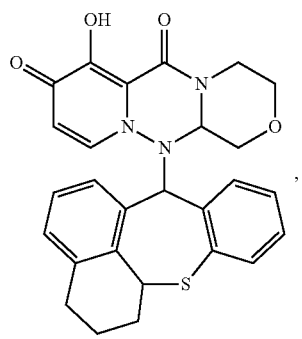
(79)
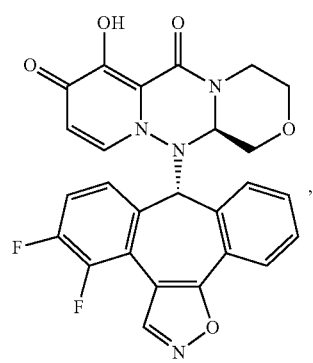
(80)
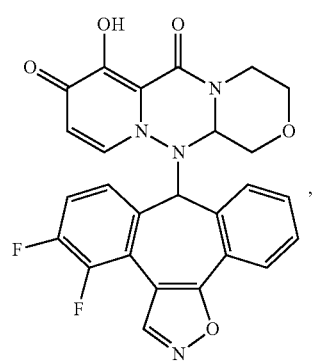
(81)
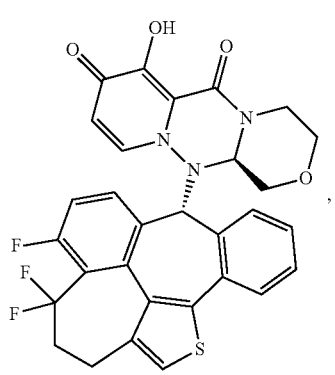
-continued
(82)
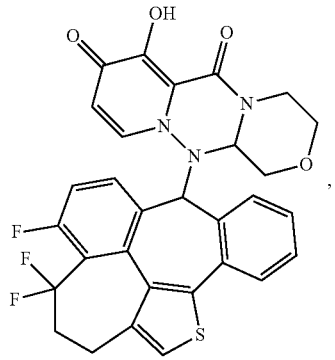
(83)
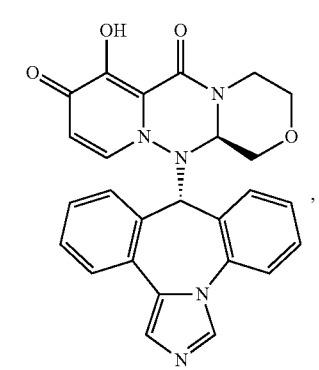
(84)
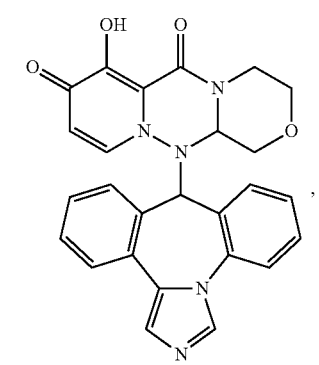
(85)
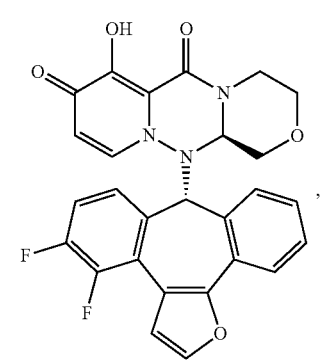

101
-continued
(86)
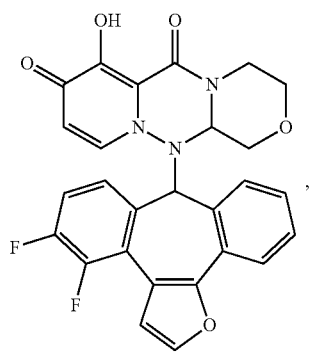
(87)
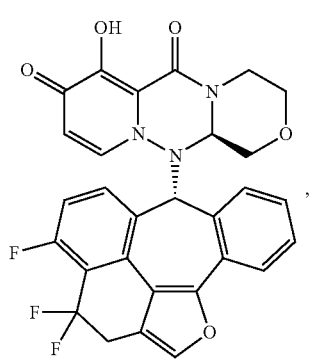
(88)

(89)
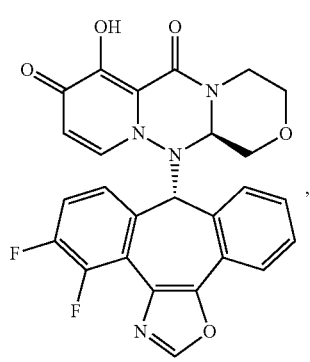
102
-continued
(90)
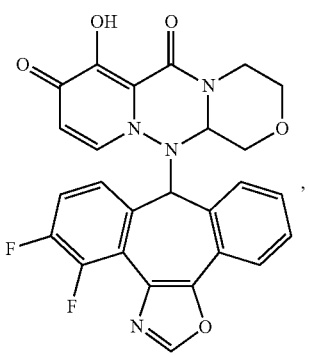
(91)
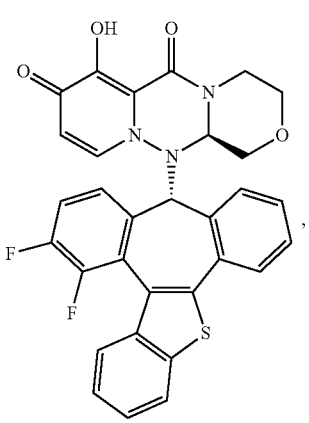
(92)
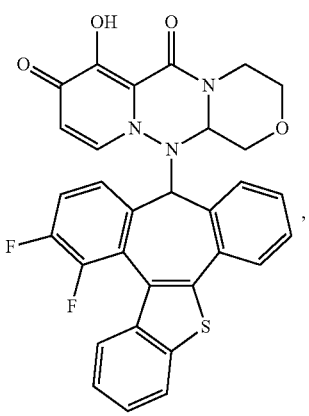
(93)
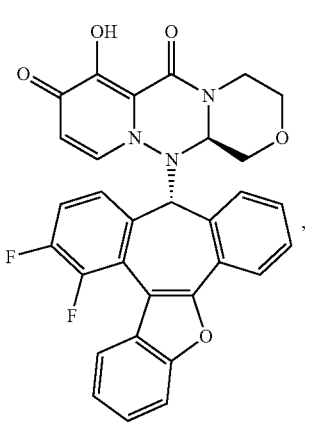

(94)
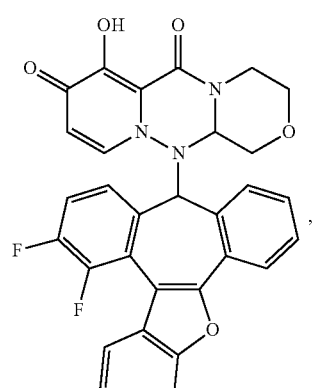
(95)
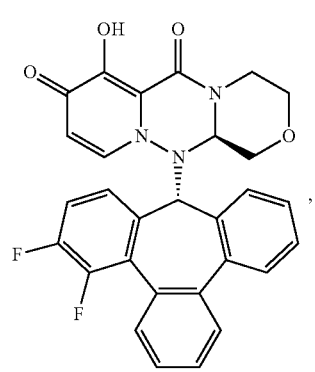
(96)
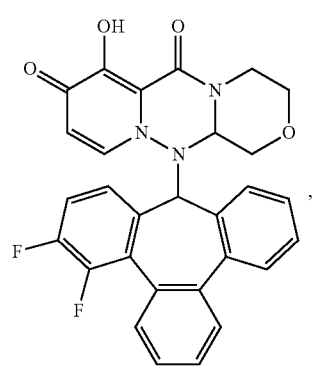
(97)
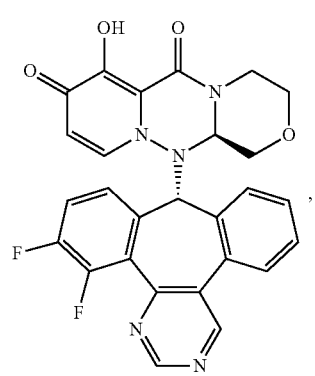
(98)
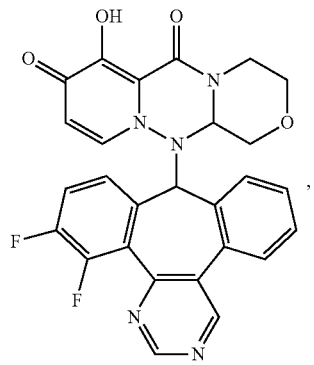
(99)
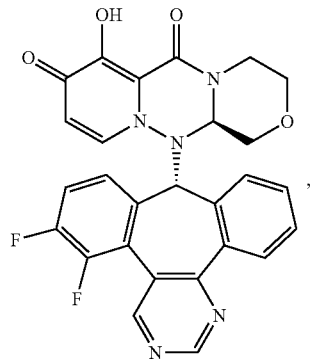
(100)
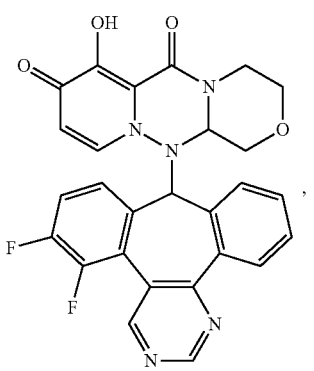
(101)

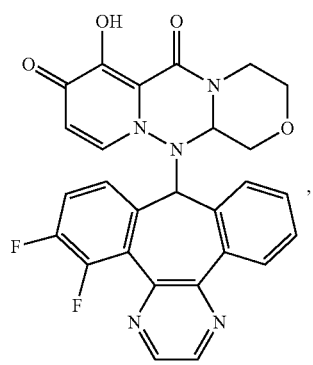
(102)
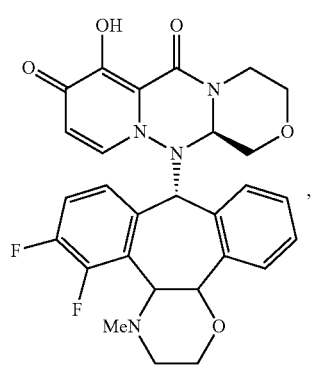
(103)
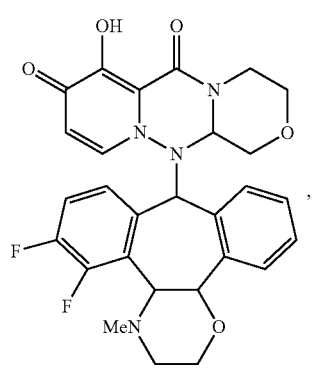
(104)
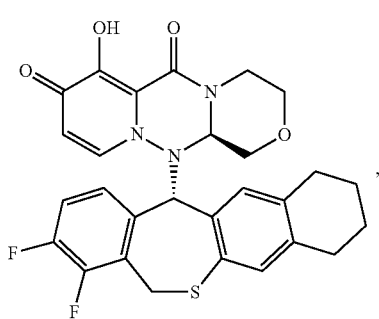
(105)
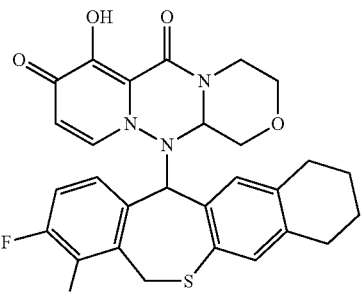
(106)
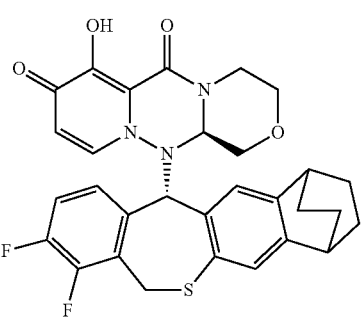
(107)
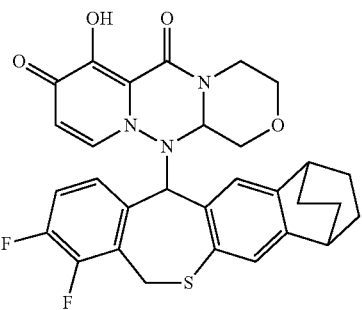
(108)
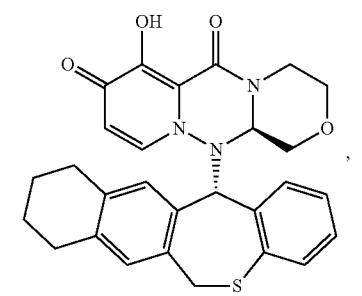
(109)
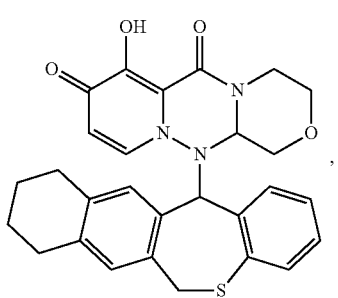
(110)

107
-continued
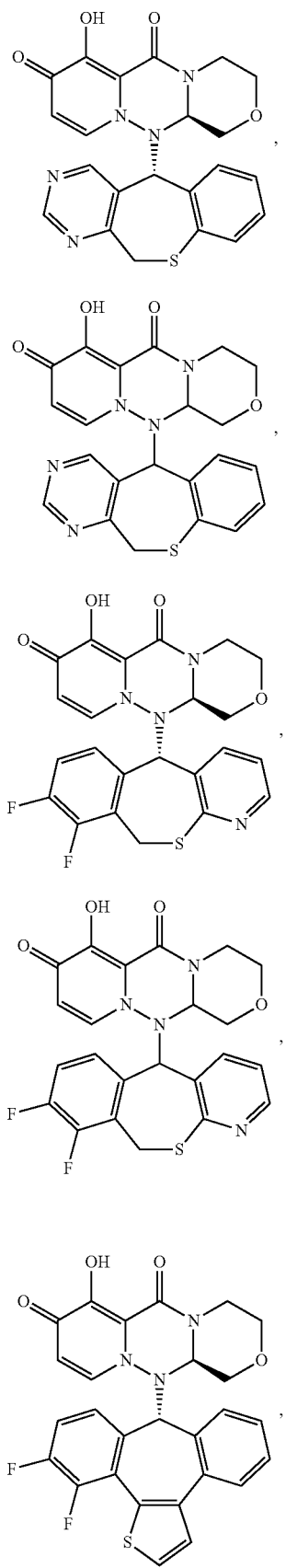
108
-continued
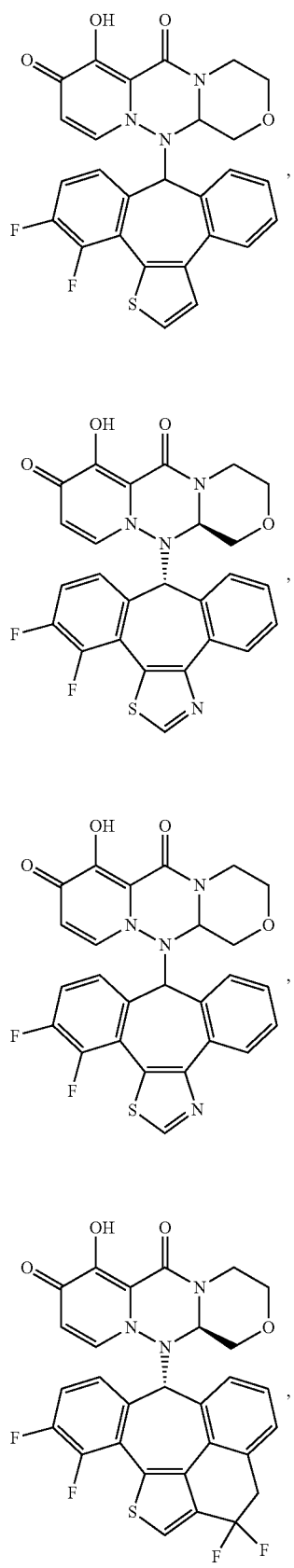

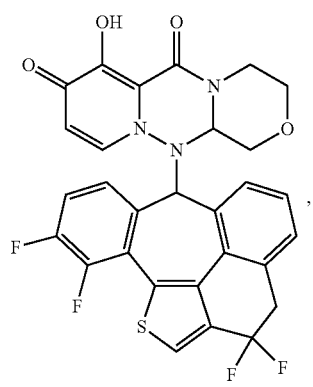 (120)
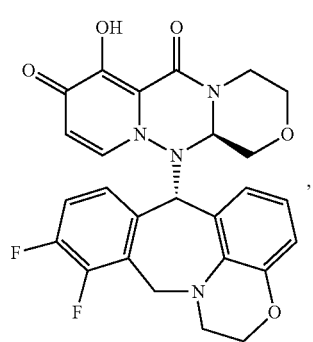 (121)
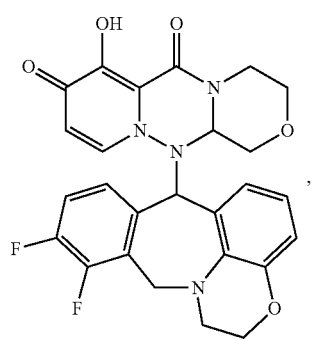 (122)
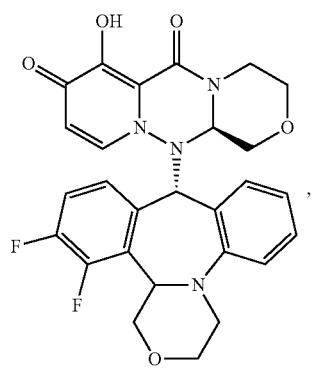 (123)
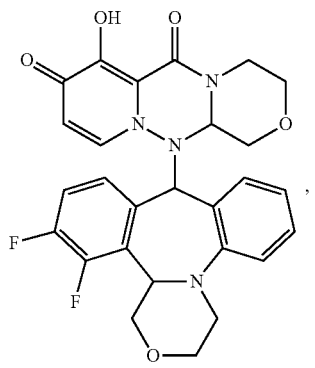 (124)
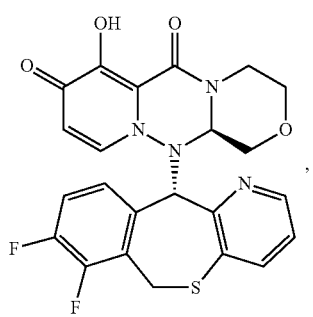 (125)
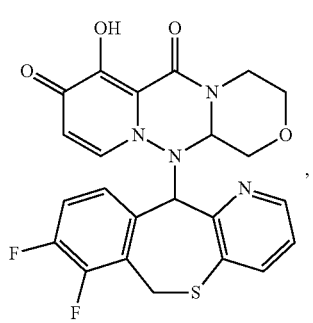 (126)
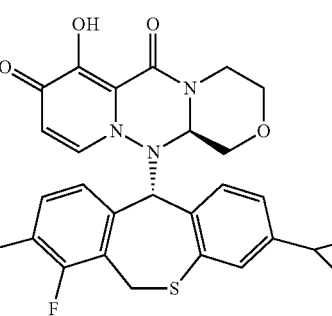 (127)
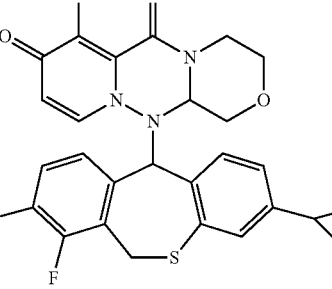 (128)

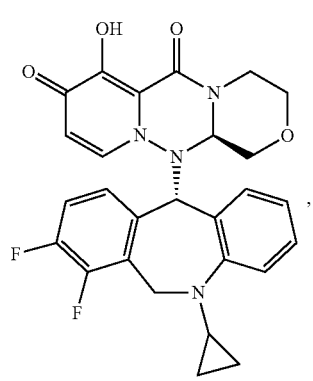
(129)
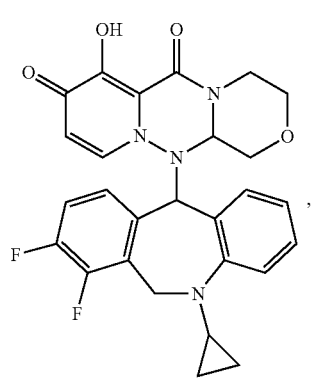
(130)
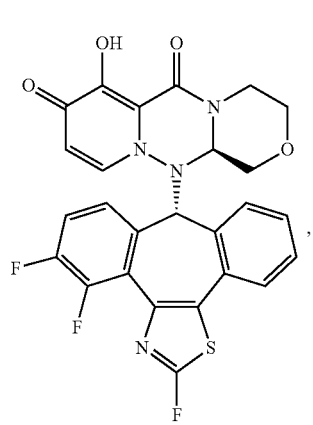
(131)
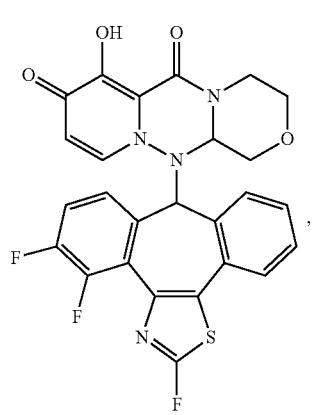
(132)
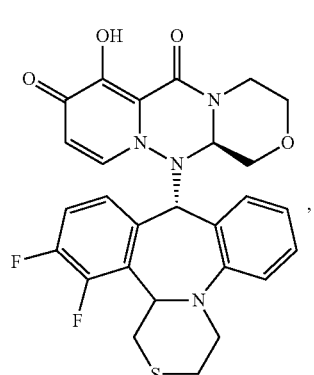
(133)
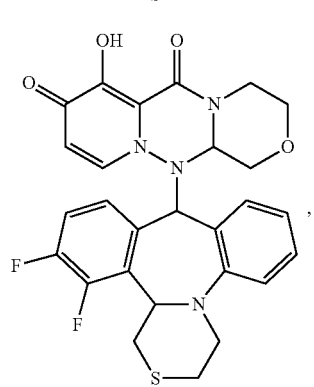
(134)
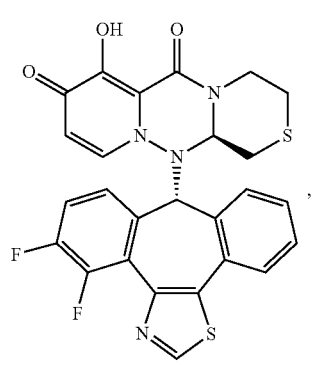
(135)
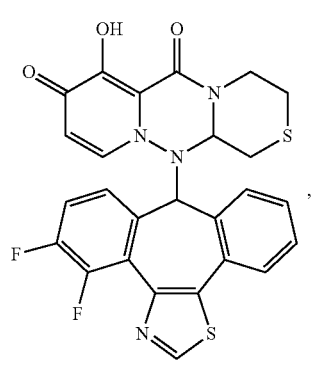
(136)

(137) 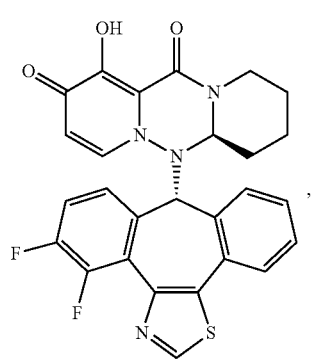
(138) 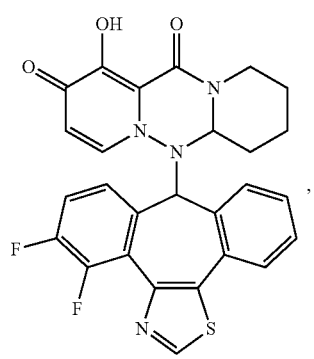
(139) 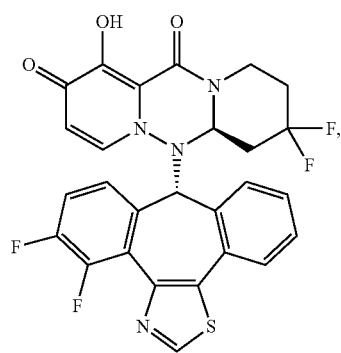
(140) 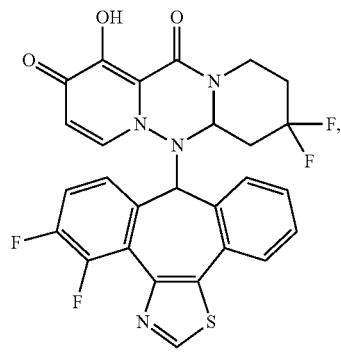
(141) 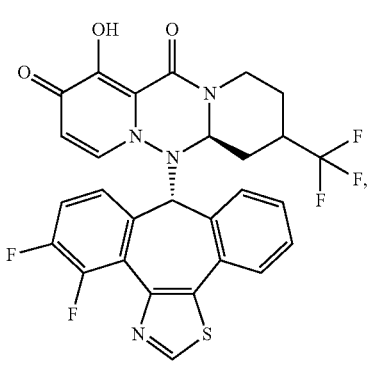
(142) 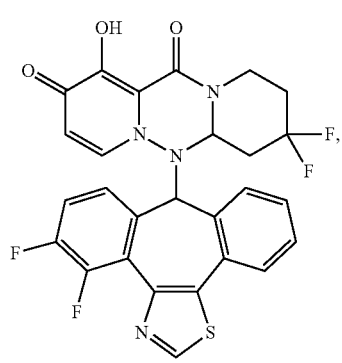
(143) 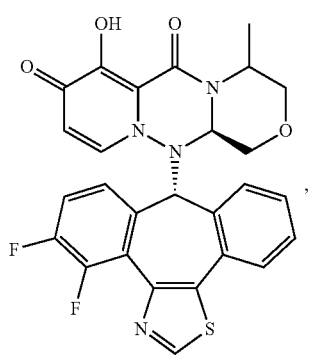
(144) 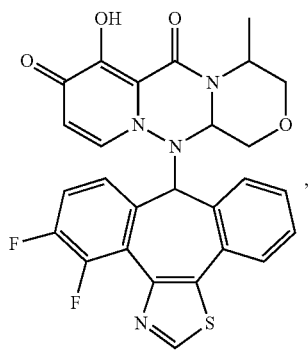

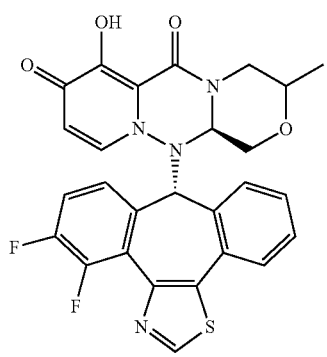
(145)
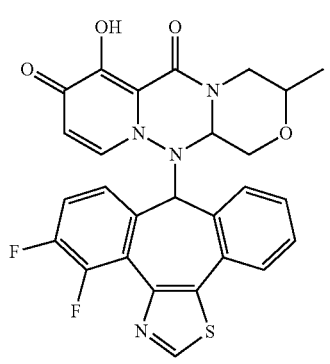
(146)
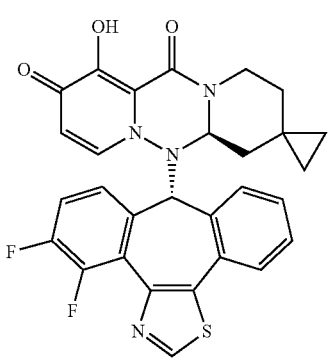
(147)
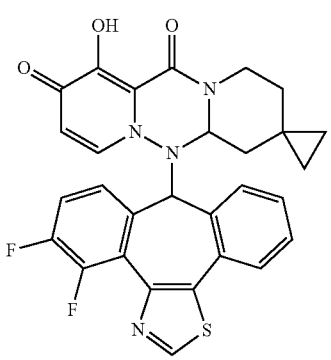
(148)
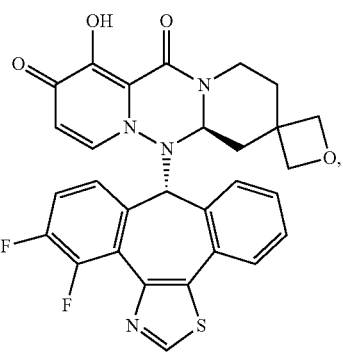
(149)
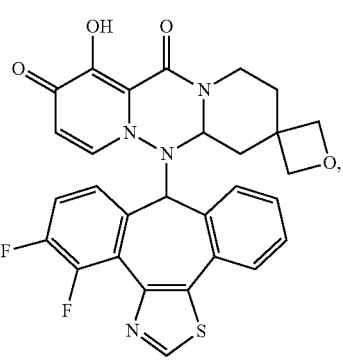
(150)
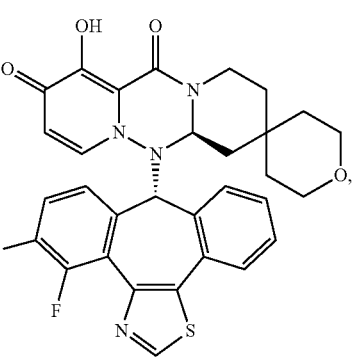
(151)
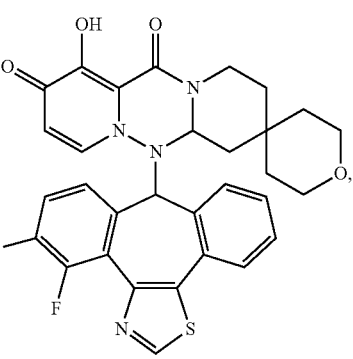
(152)

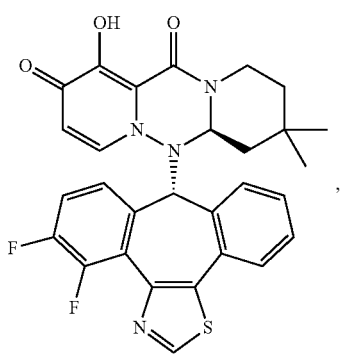 (153)
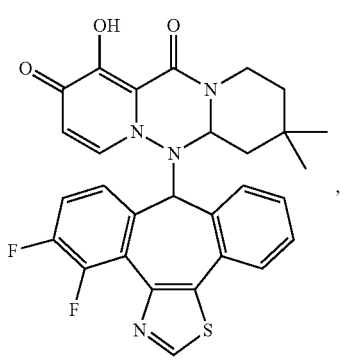 (154)
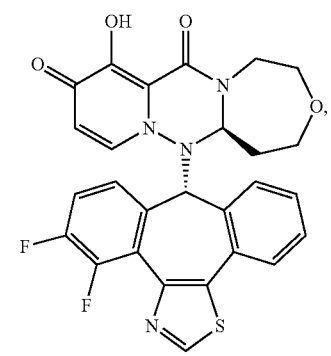 (155)
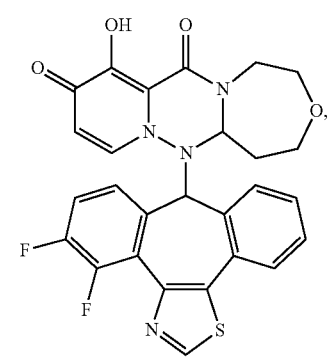 (156)
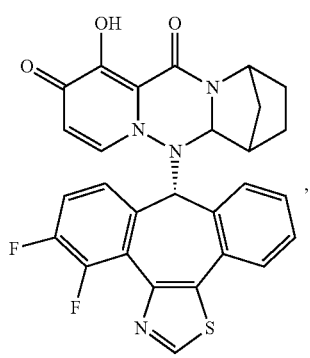 (157)
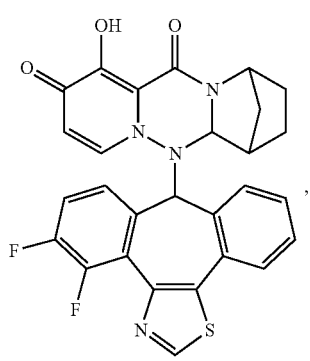 (158)
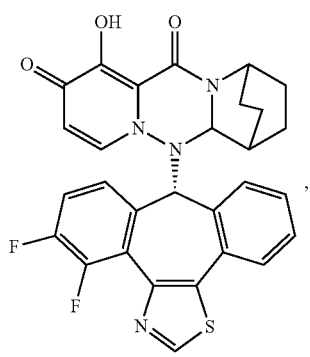 (159)
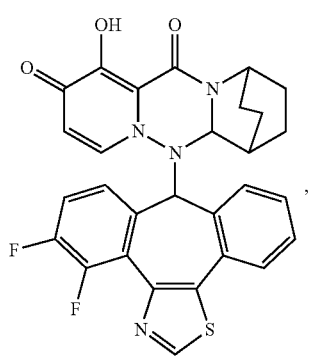 (160)

(161)
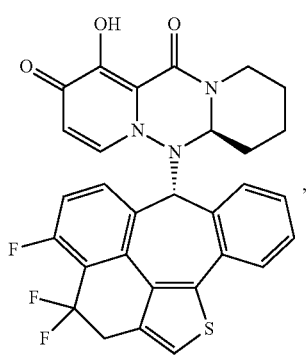
(162)
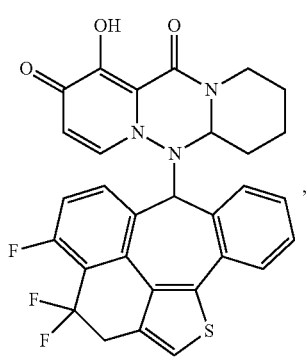
(163)
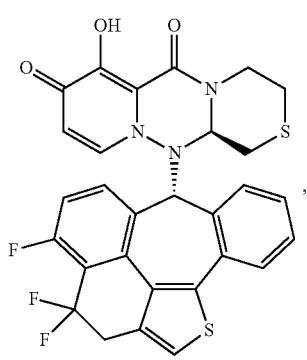
(164)
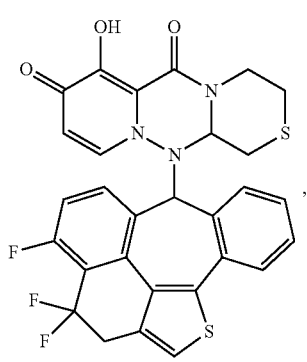
(165)
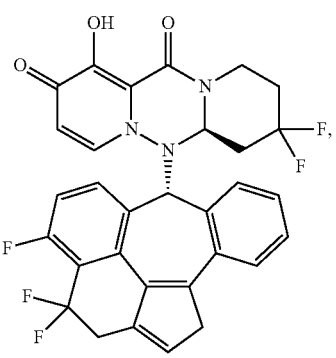
(166)
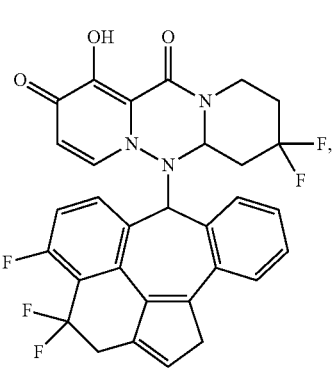
(167)
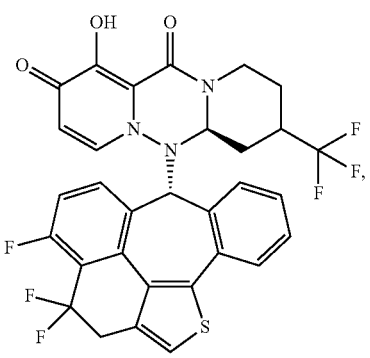
(168)
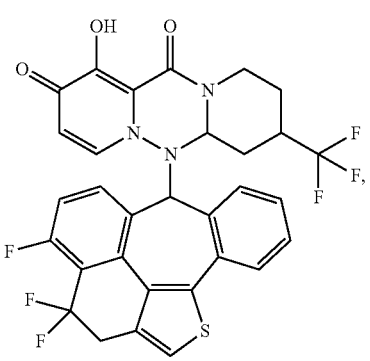

(169) 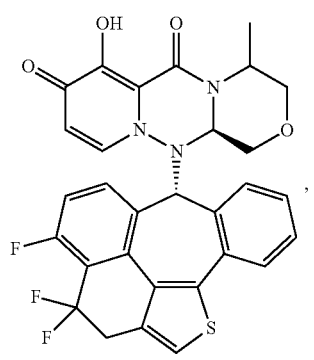
(170) 
(171) 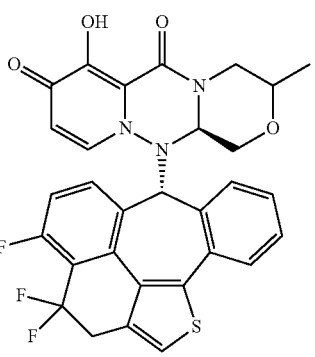
(172) 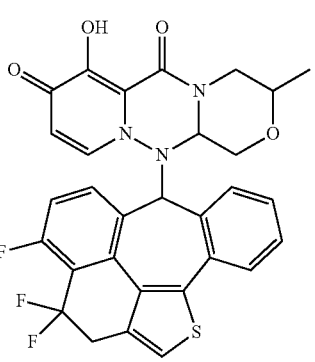
(173) 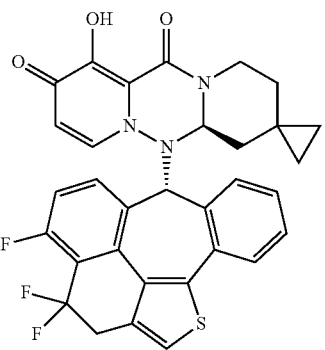
(174) 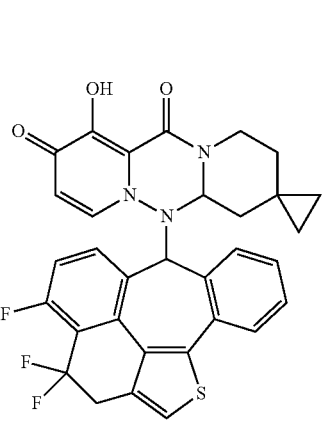
(175) 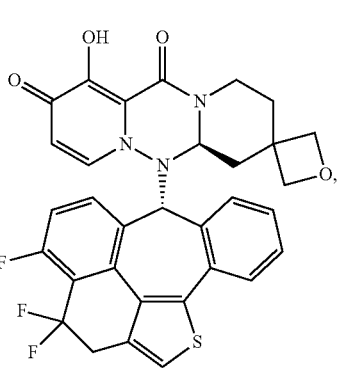
(176) 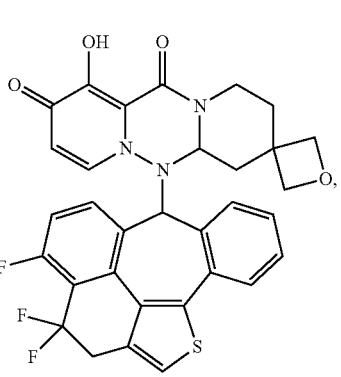

-continued
(177) 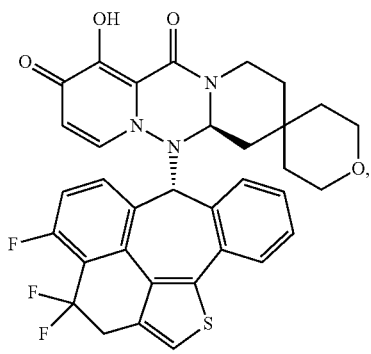
(178) 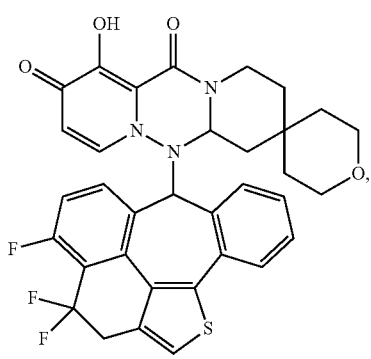
(179) 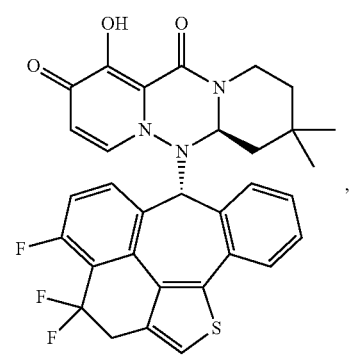
(180) 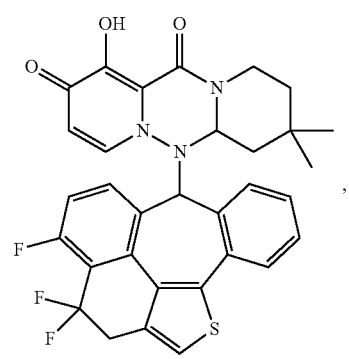
-continued
(181) 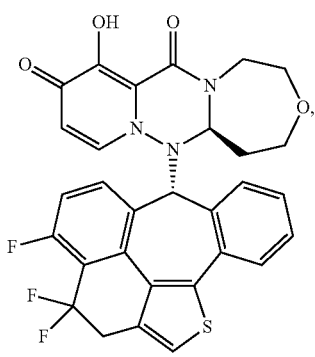
(182) 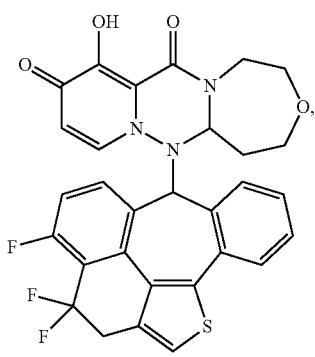
(183) 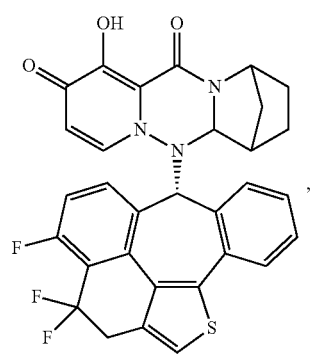
(184) 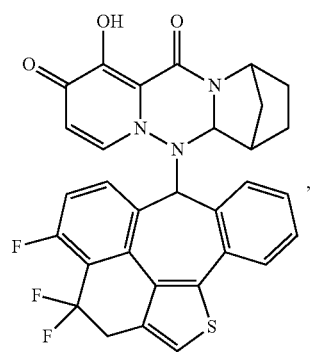

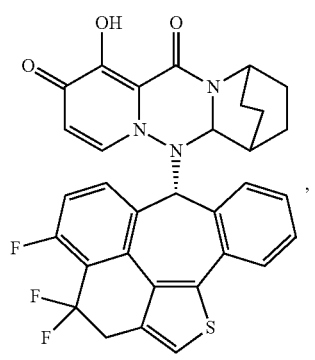
(185)
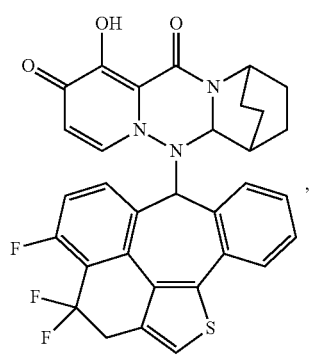
(186)
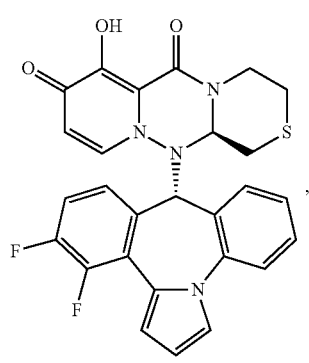
(187)
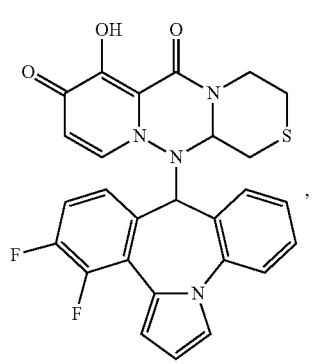
(188)
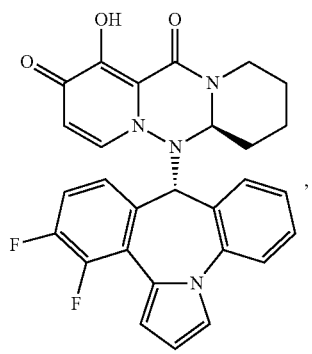
(189)
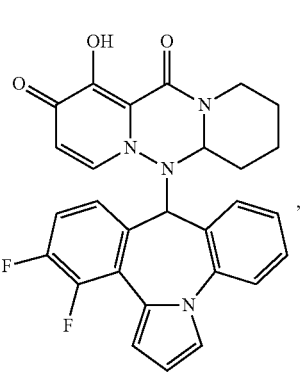
(190)
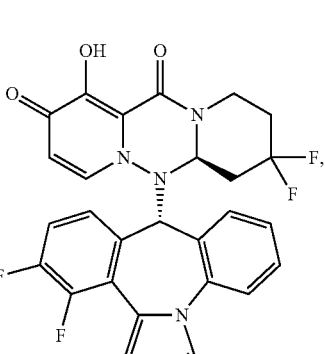
(191)
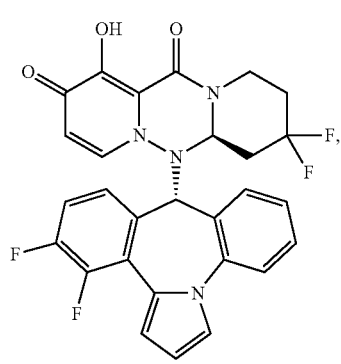
(192)

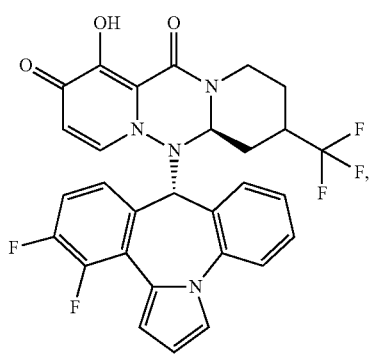
(193)
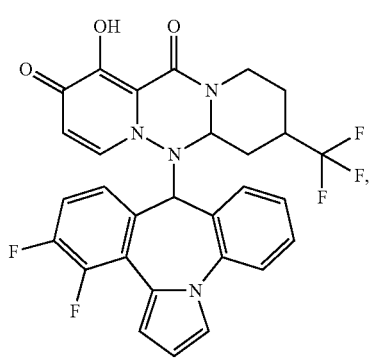
(194)
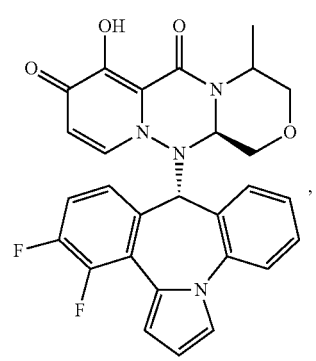
(199)
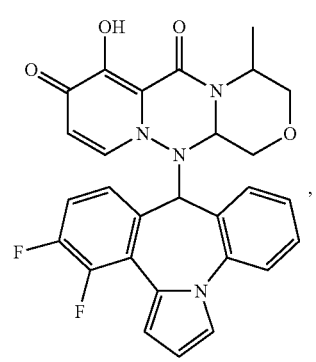
(200)
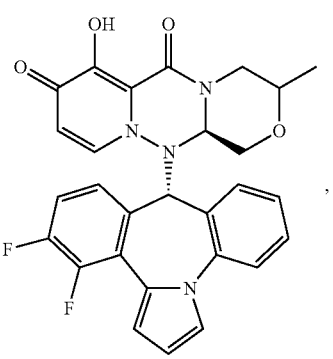
(201)
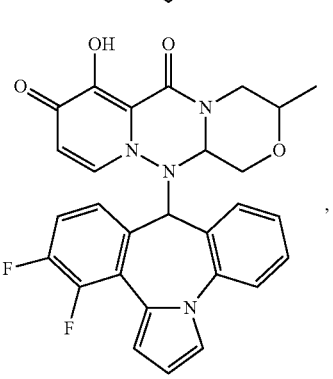
(202)
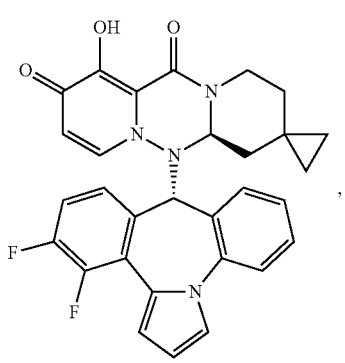
(203)
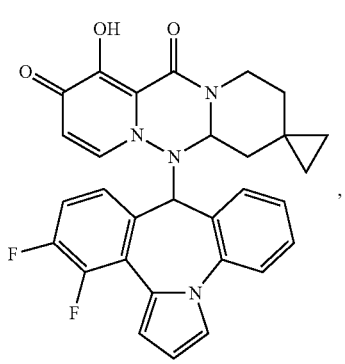
(204)

(205)
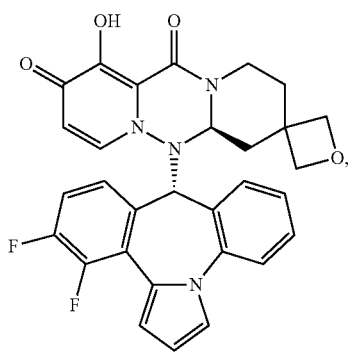
(206)

(207)
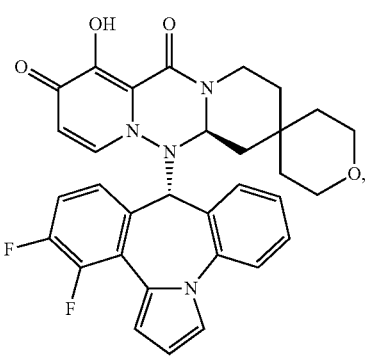
(208)
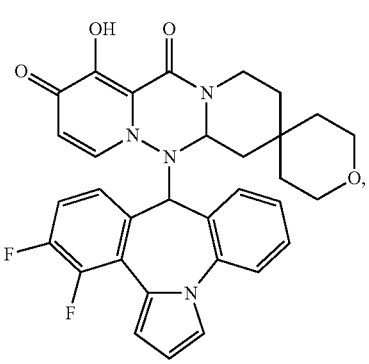
(209)
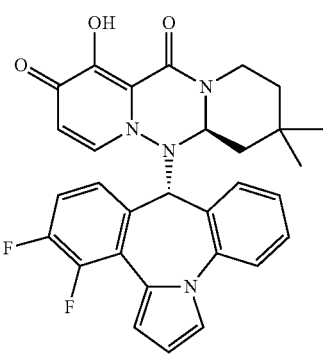
(210)
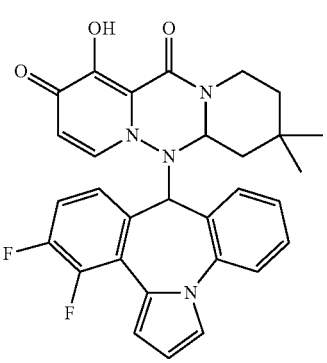
(211)
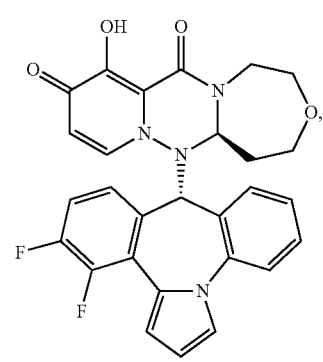
(212)
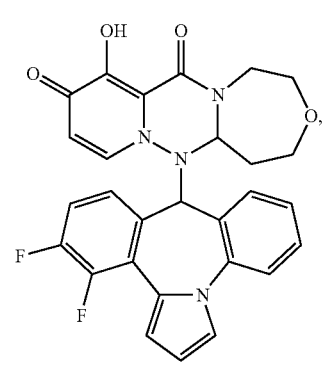

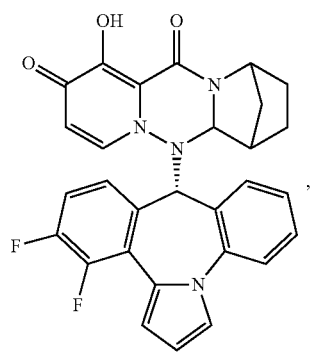
(213)
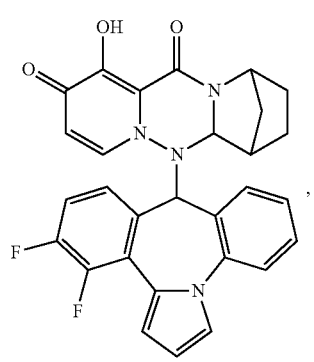
(214)
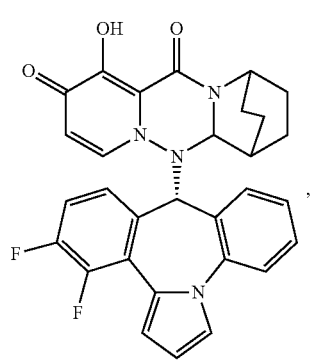
(215)
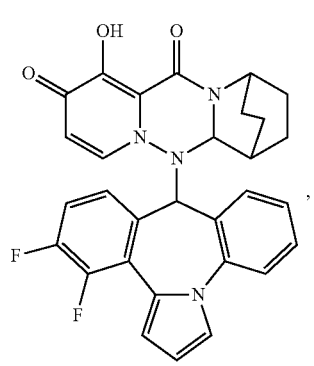
(216)
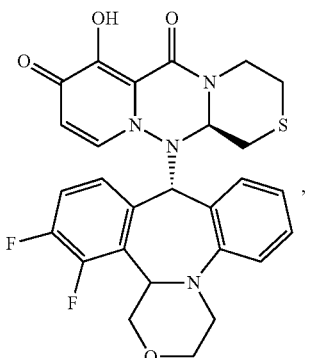
(217)
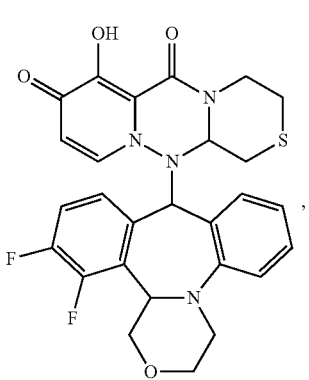
(218)
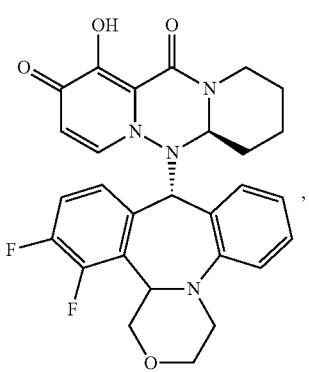
(219)
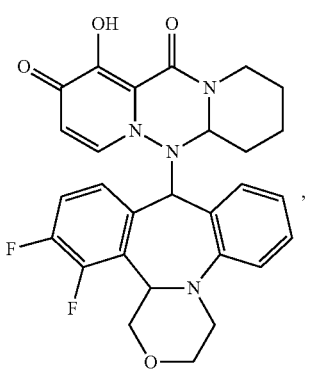
(220)

-continued
(221) 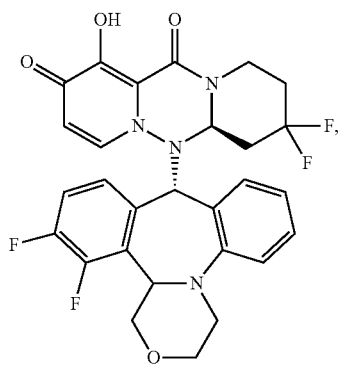
(222) 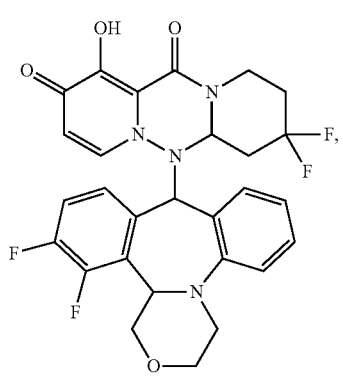
(223) 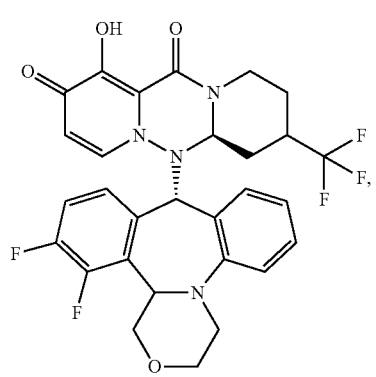
(224) 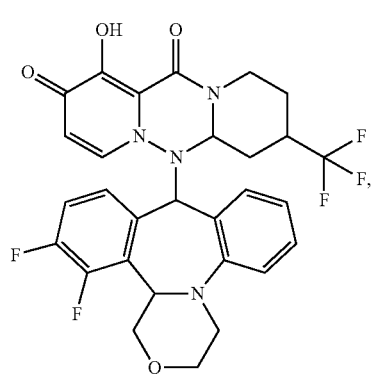
(225) 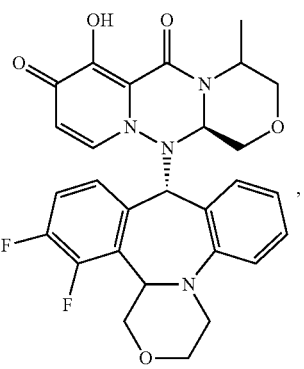
(226) 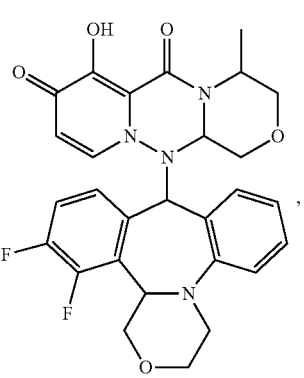
(227) 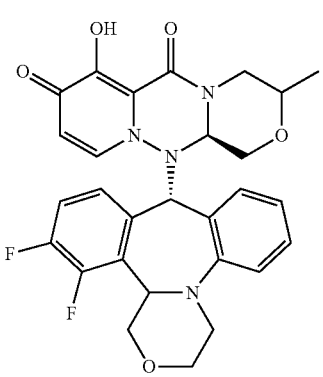
(228) 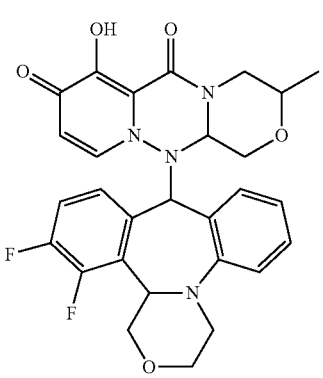

(229) 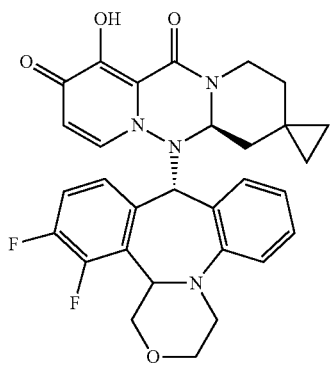
(230) 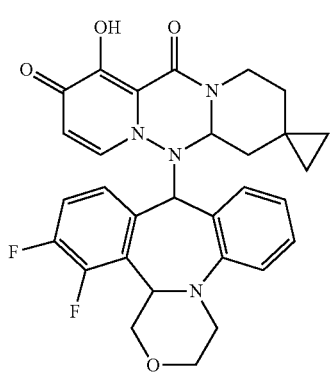
(231) 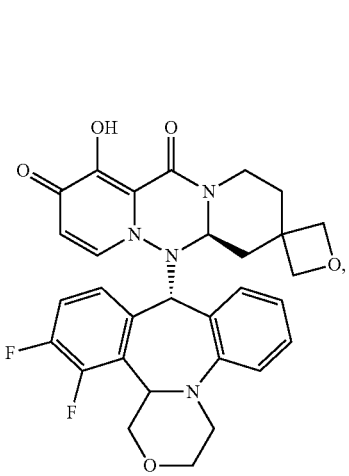
(232) 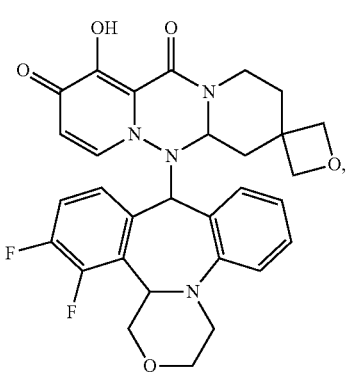
(233) 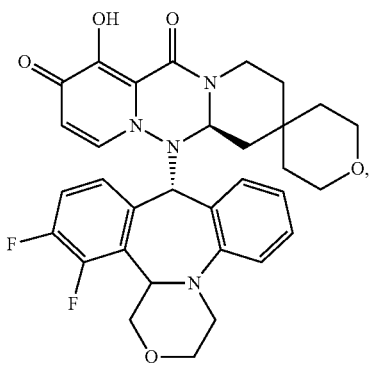
(234) 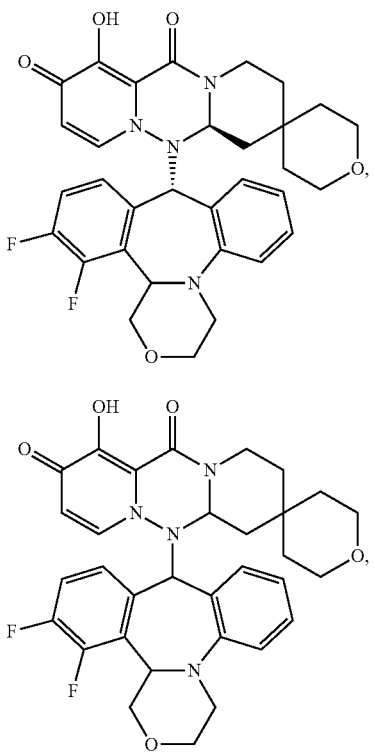
(235) 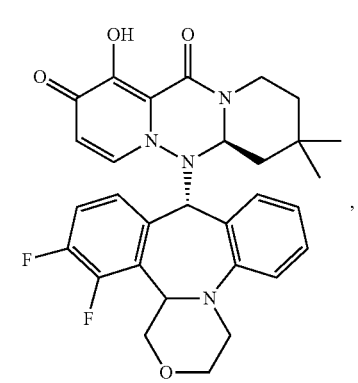
(236) 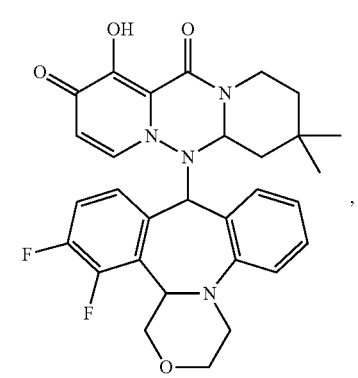

137
-continued
(237)
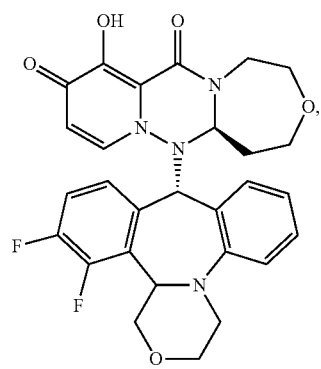
(238)
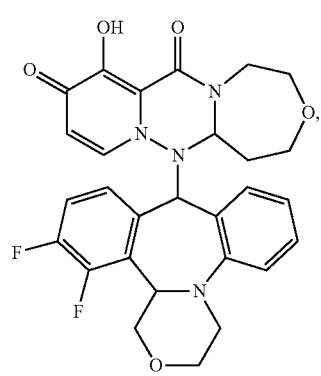
(239)
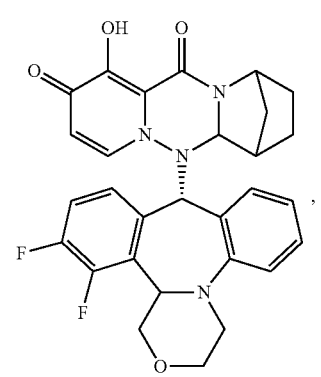
(240)
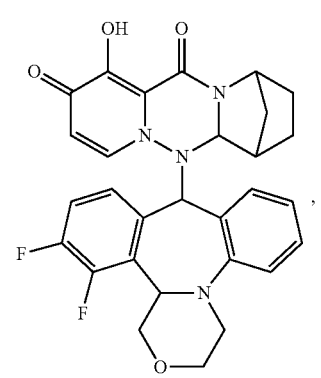
138
-continued
(241)
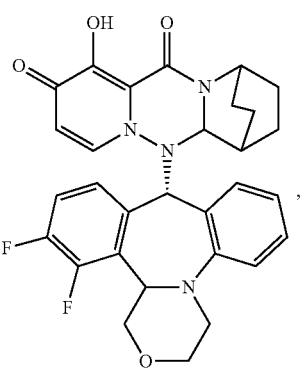
(242)
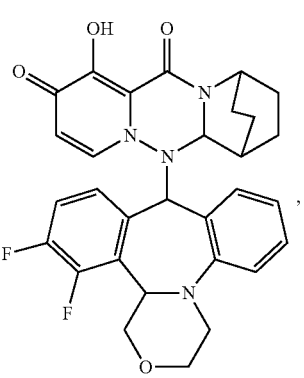
(243)
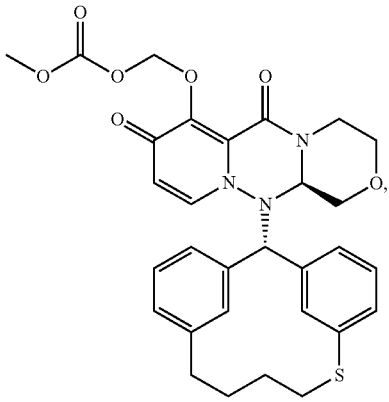
(244)
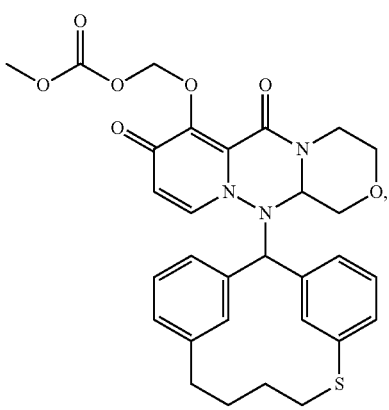

139
-continued
(245)
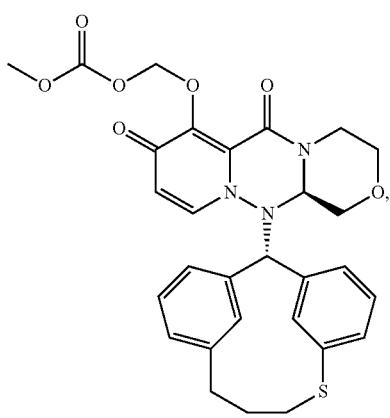
(246)
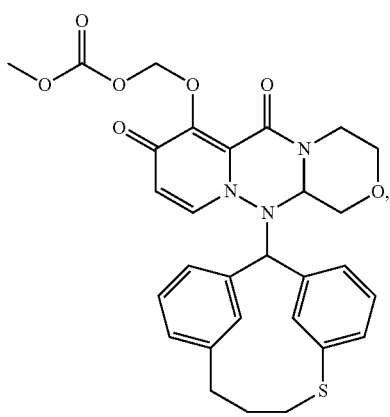
(247)
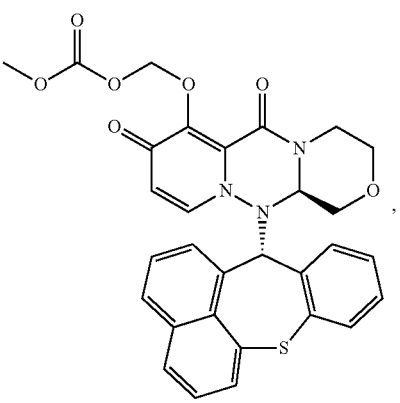
(248)
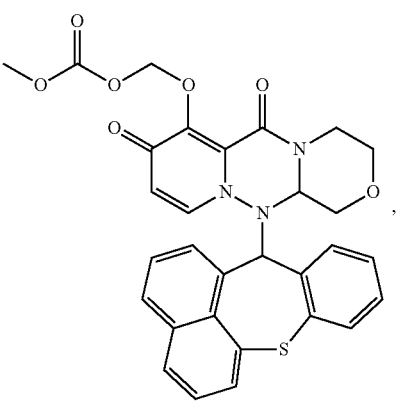
140
-continued
(249)
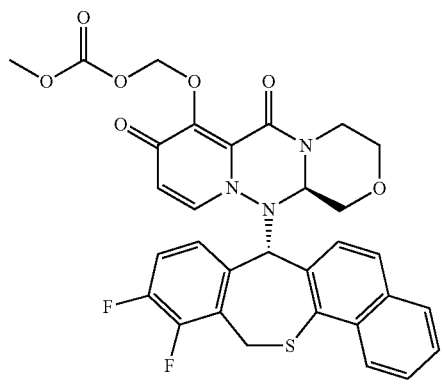
(250)
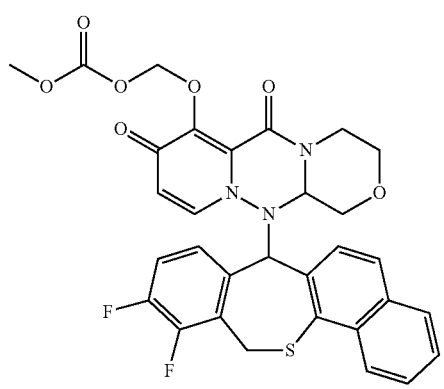
(251)
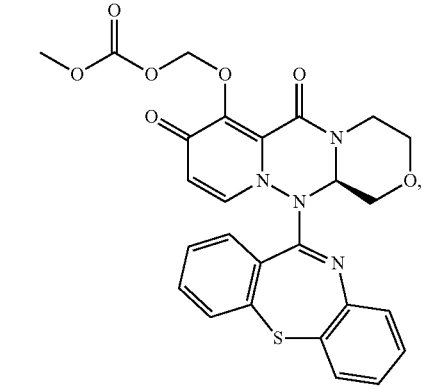
(252)
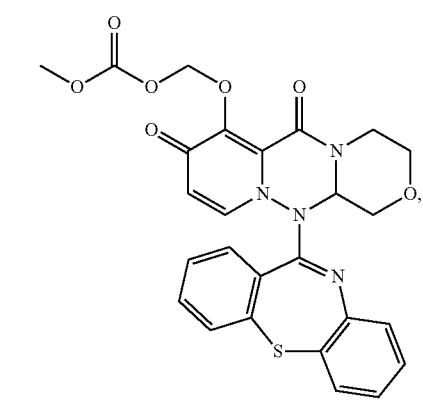

(253) 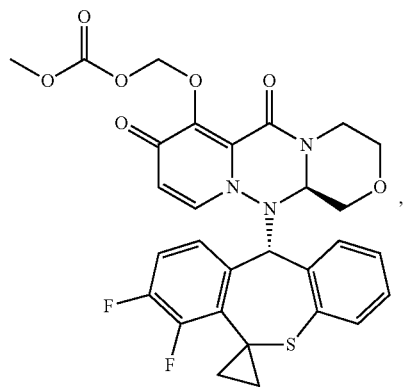
(254) 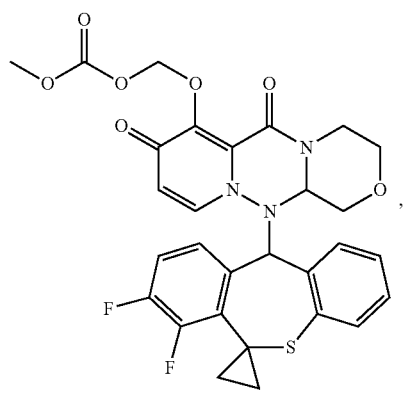
(255) 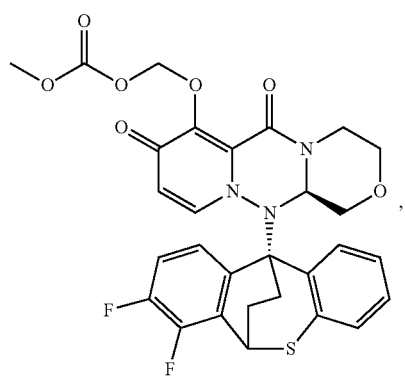
(256) 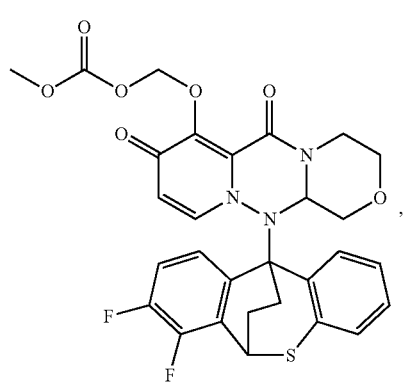
(257) 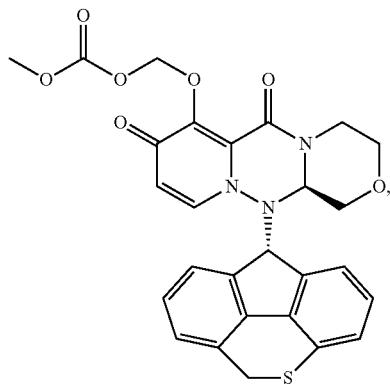
(258) 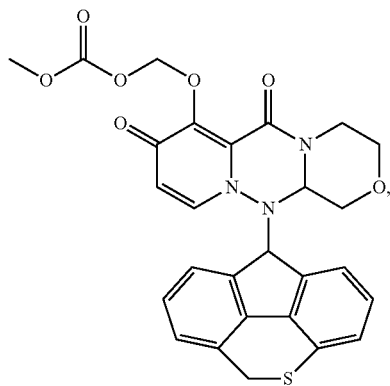
(259) 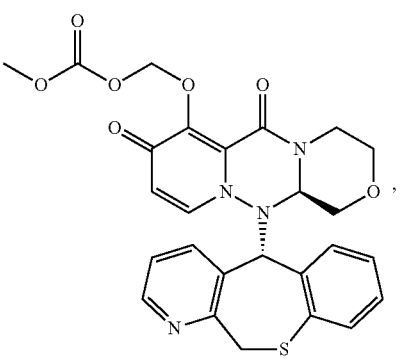
(260) 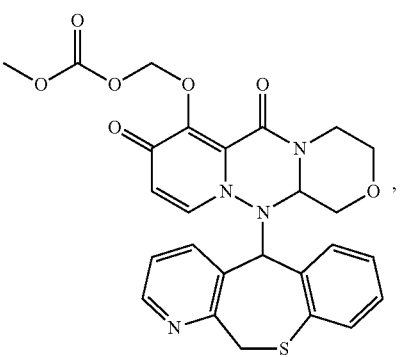

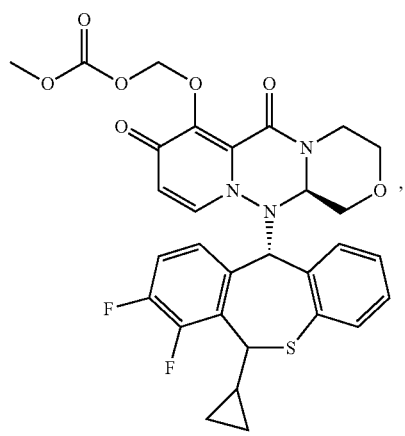
(261)
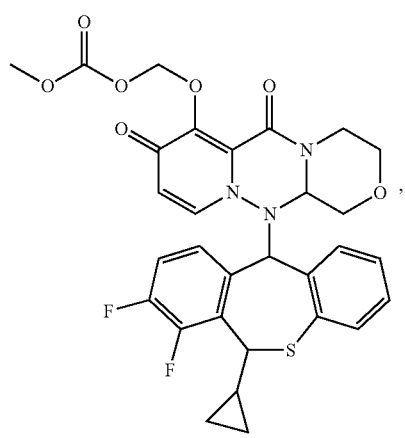
(262)
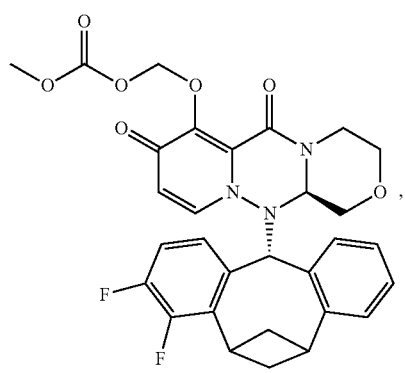
(263)
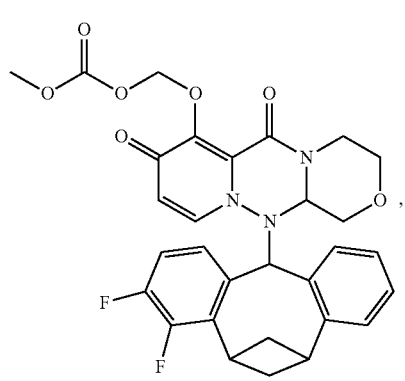
(264)
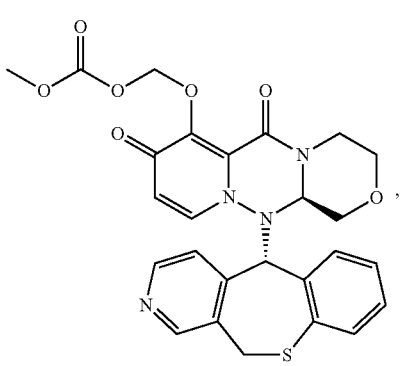
(265)
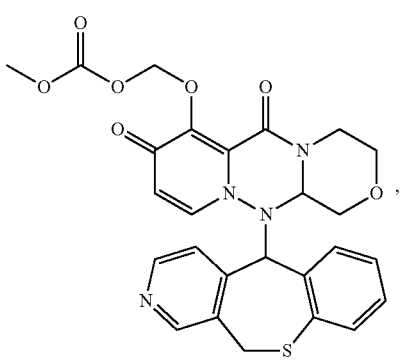
(266)
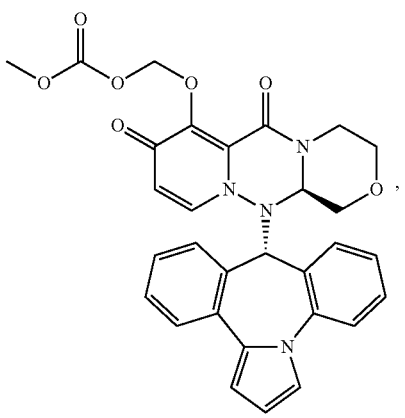
(267)
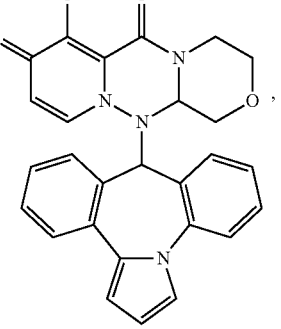
(268)

(269)
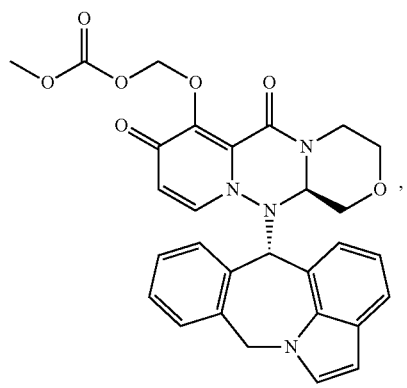
(270)
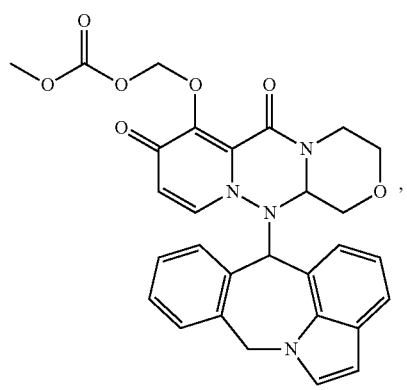
(271)
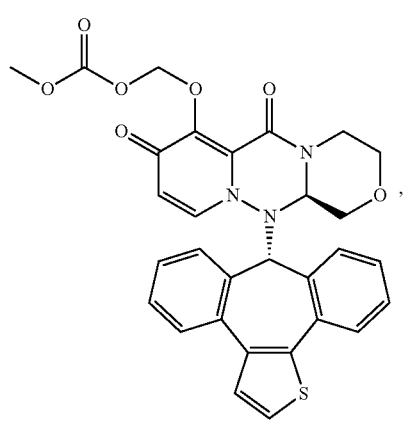
(272)
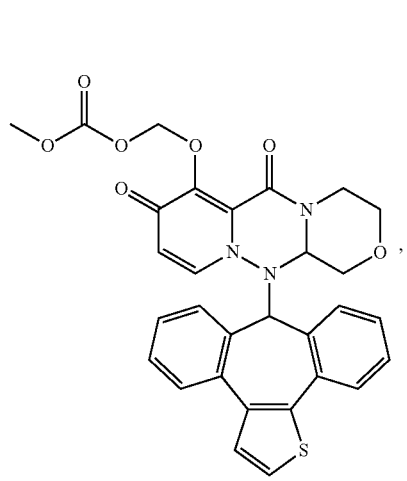
(273)
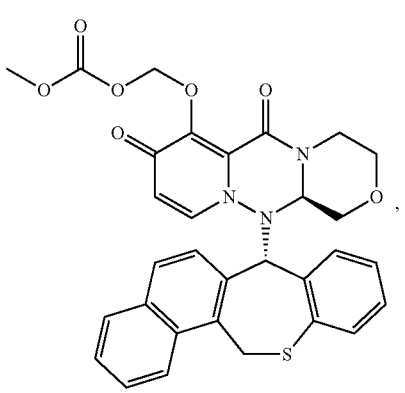
(274)
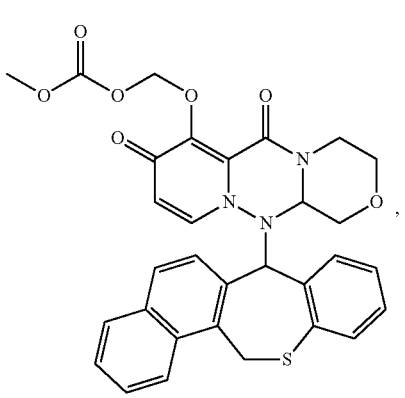
(275)
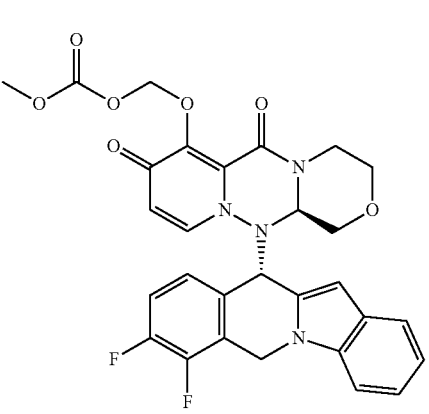
(276)
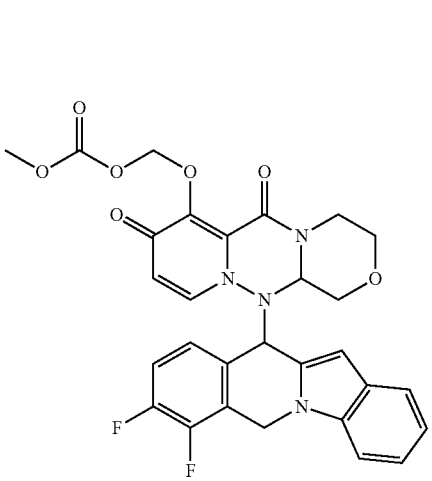

(277)

(278)

(279)

(280)

(281)

(282)

(283)

(284)

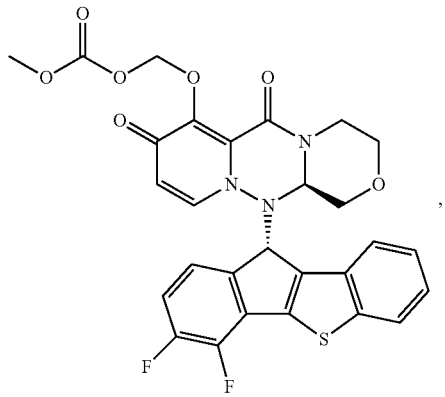
(285)
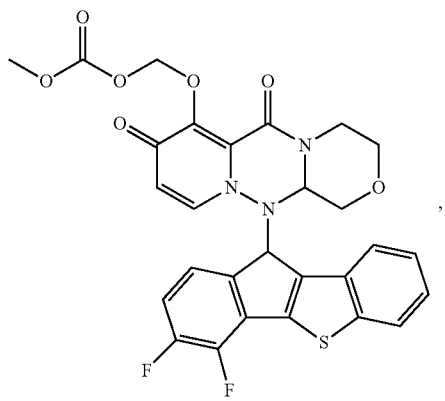
(286)
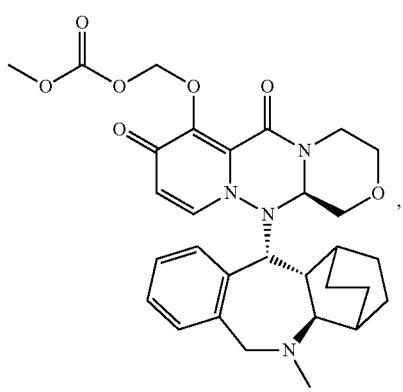
(287)
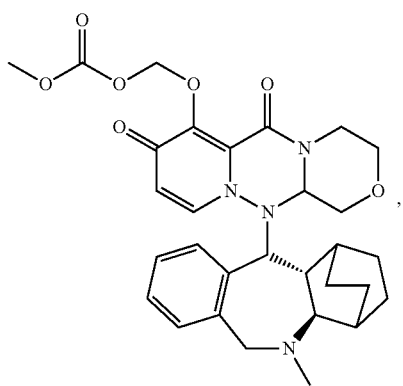
(288)
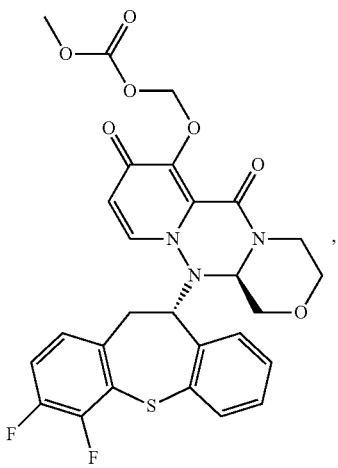
(289)
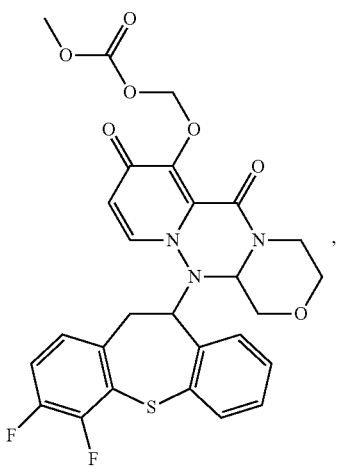
(290)
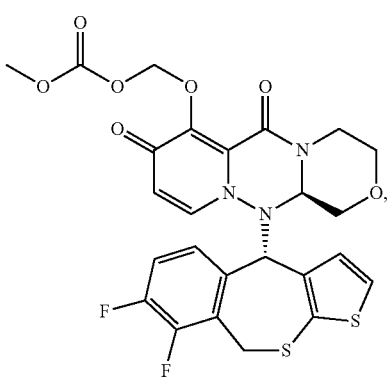
(291)

151
-continued
(292)
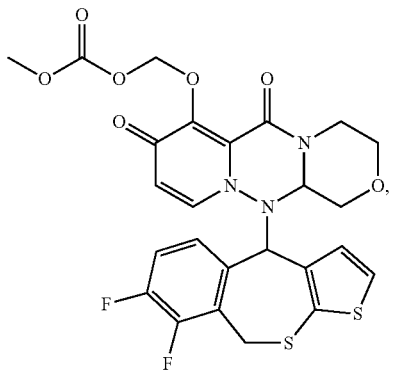
(293)
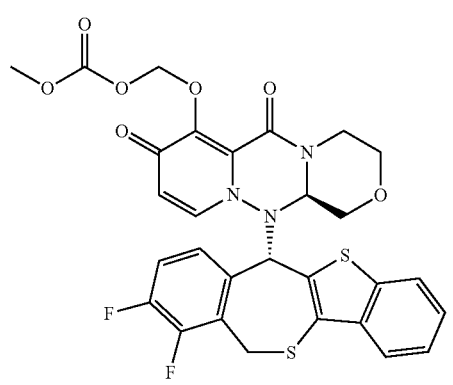
(294)
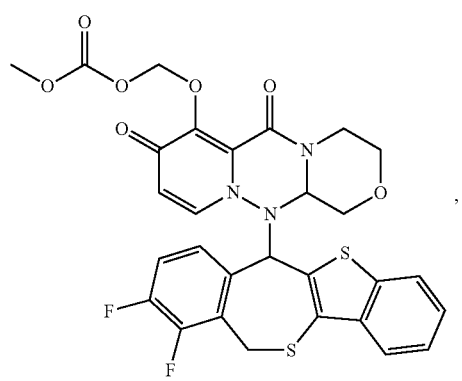
(295)
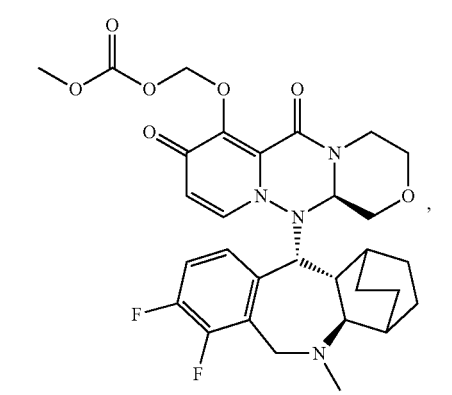
152
-continued
(296)
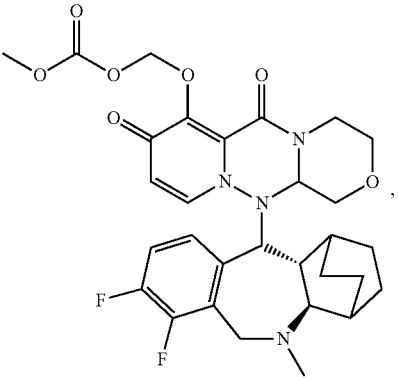
(297)
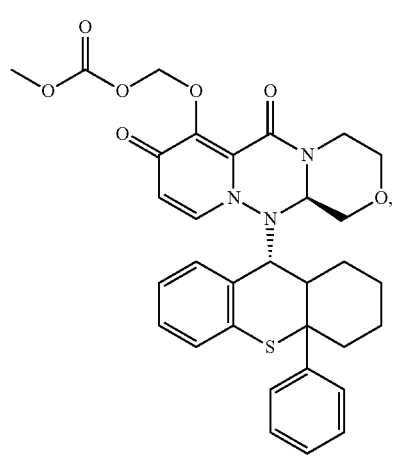
(298)
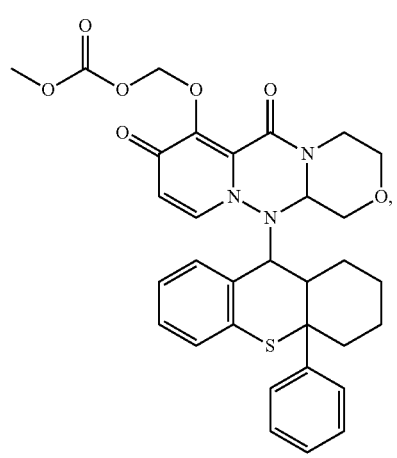
(299)
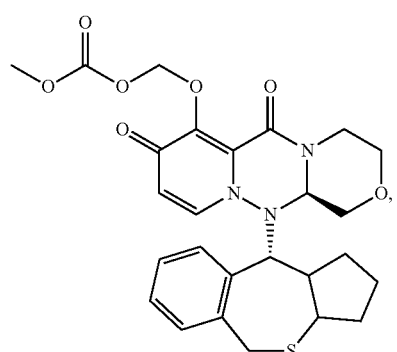

153
-continued
(300)
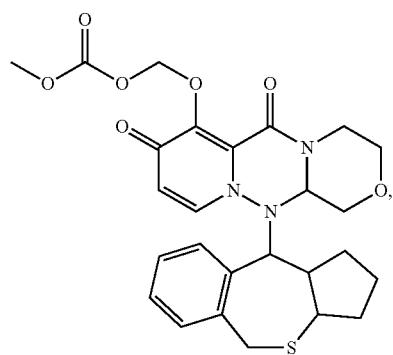
(301)
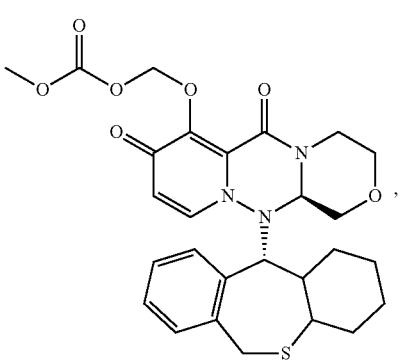
(302)
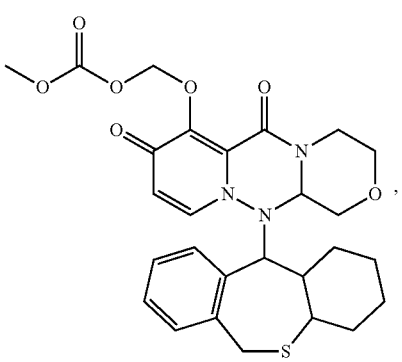
(303)
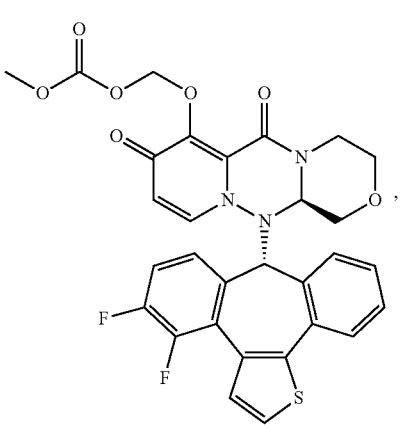
154
-continued
(304)
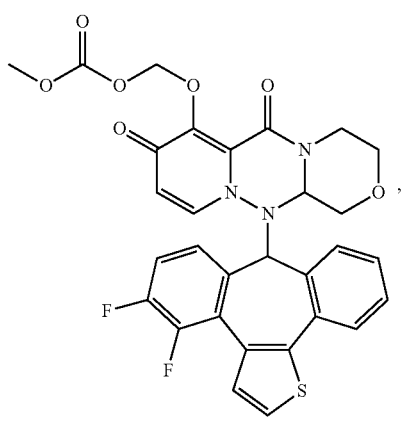
(305)
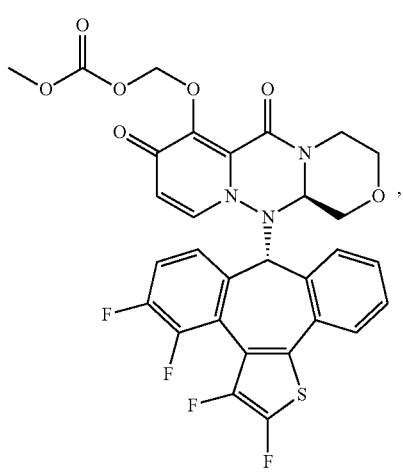
(306)
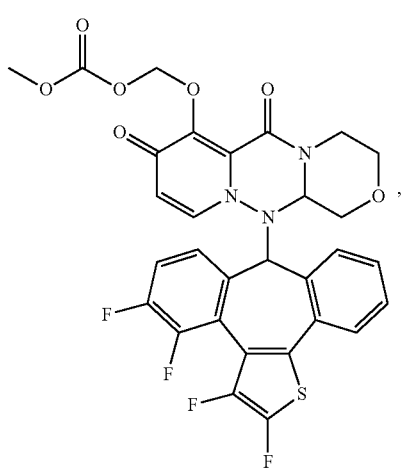

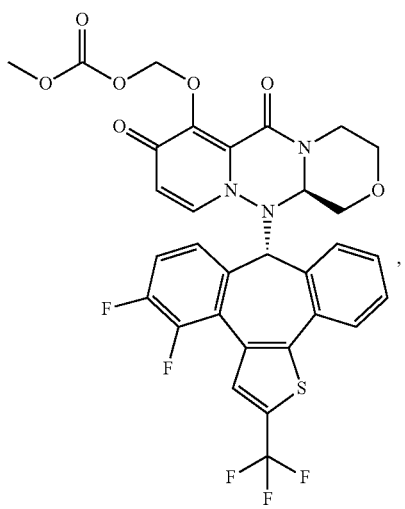
(307)
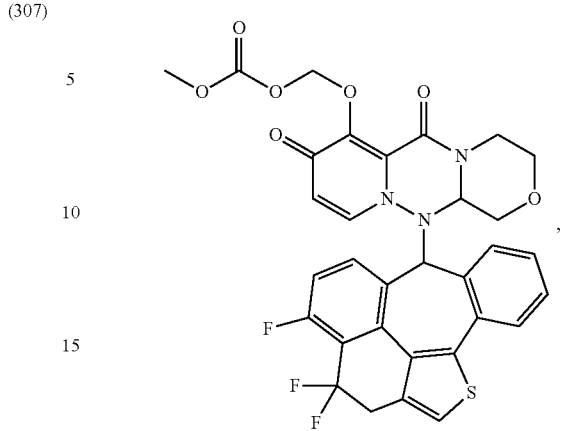
(310)
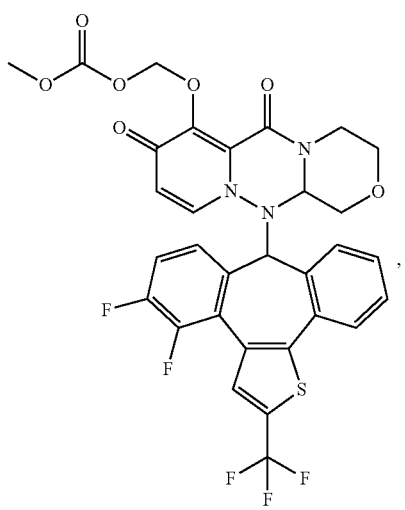
(308)
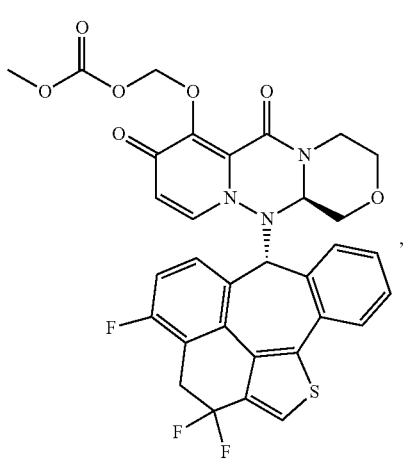
(311)
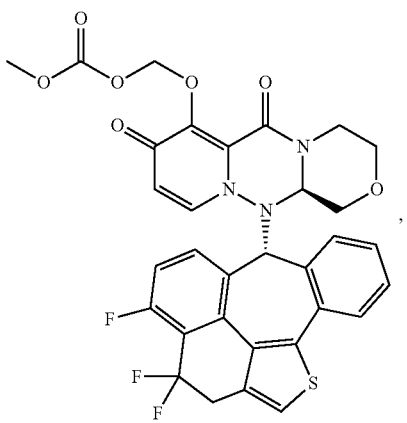
(309)
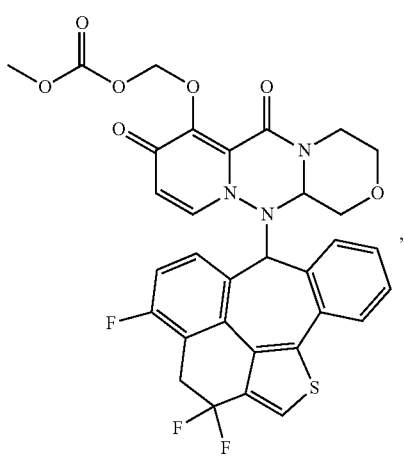
(312)

157
-continued
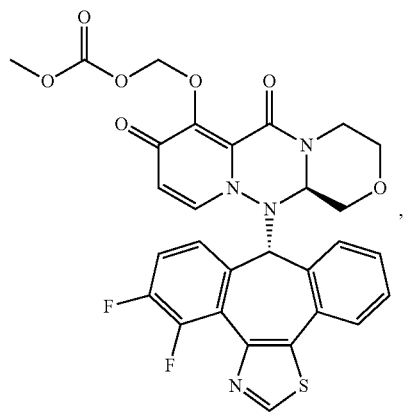
158
-continued
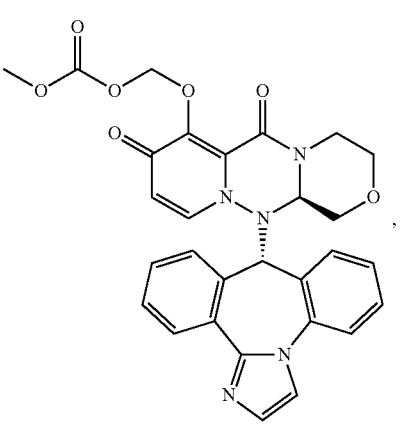

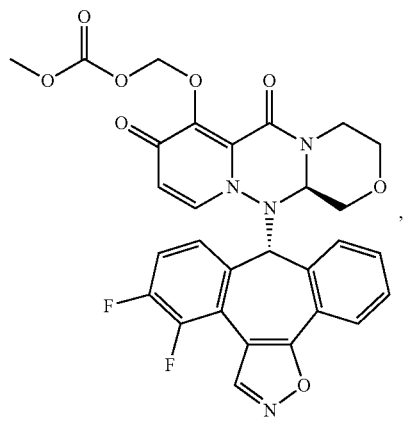 (321)
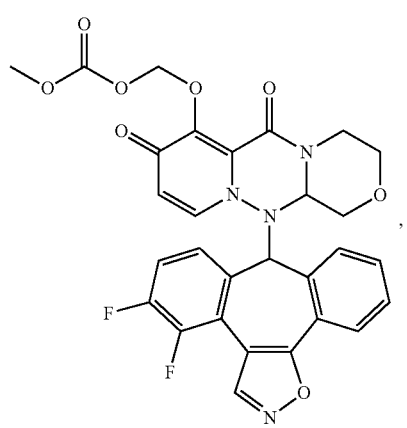 (322)
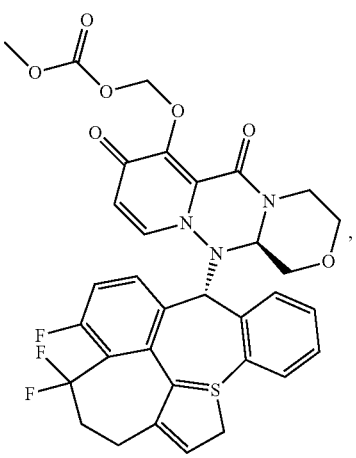 (323)
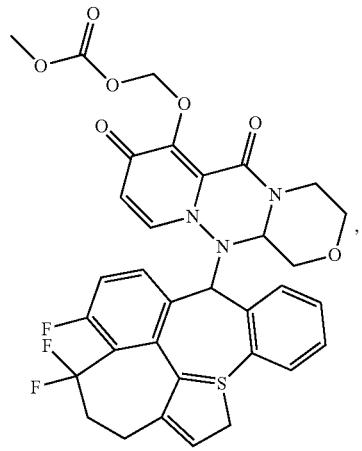 (324)
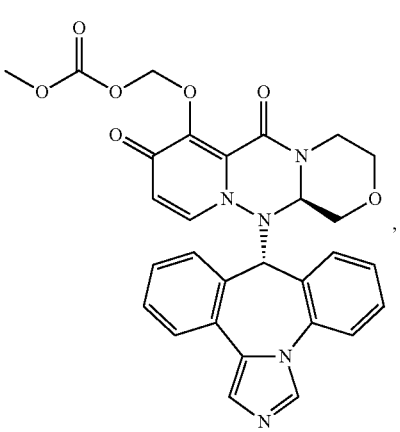 (325)
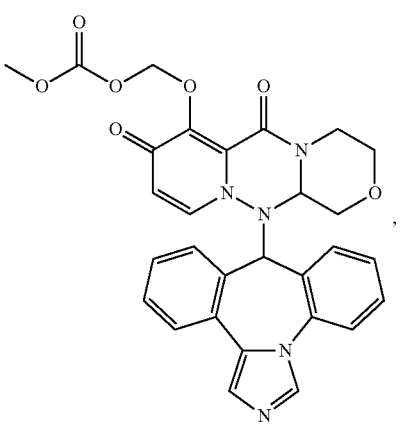 (326)

161
-continued
(327)
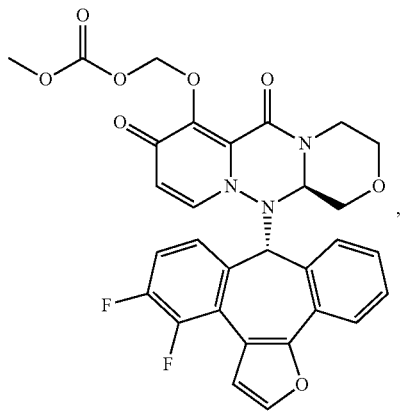
(328)
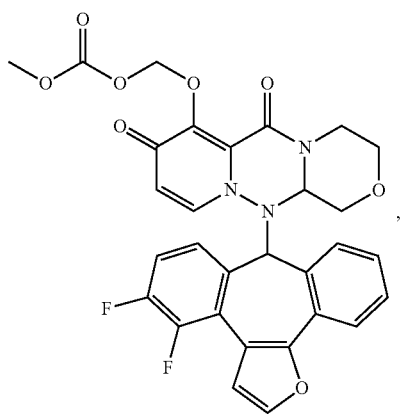
(329)
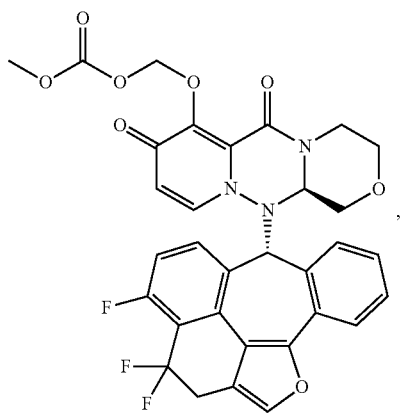
(330)
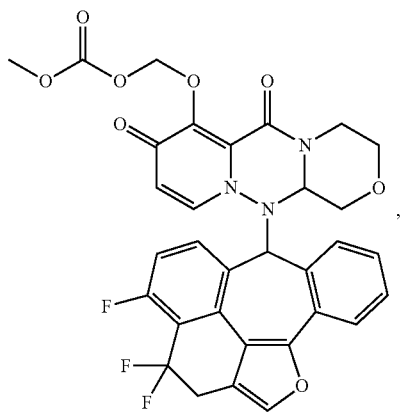
162
-continued
(331)
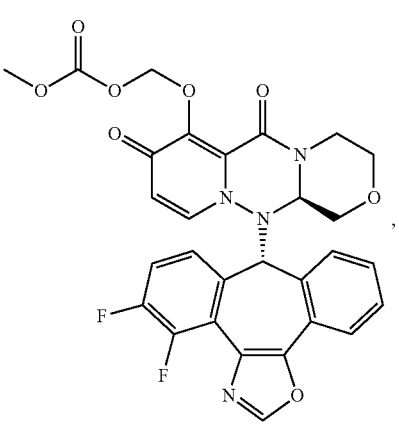
(332)
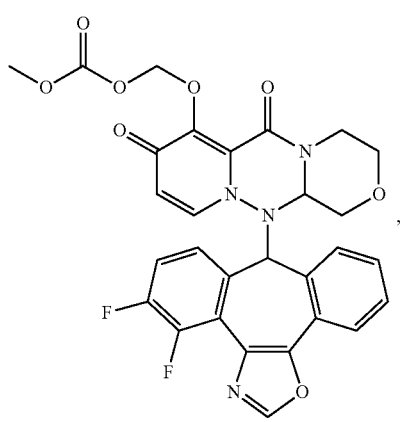
(333)
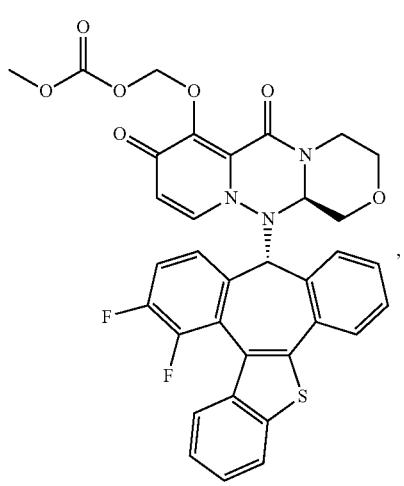

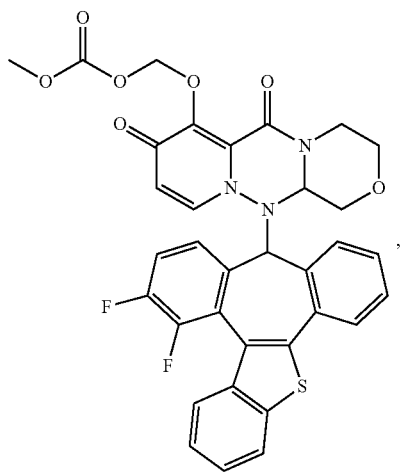
(334)
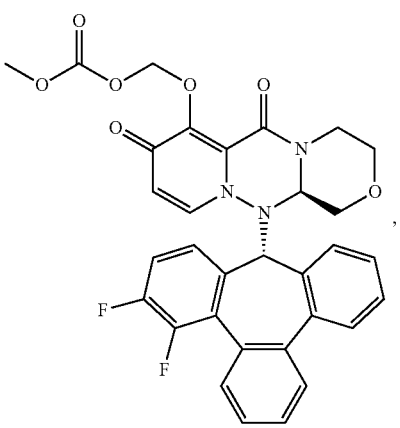
(337)
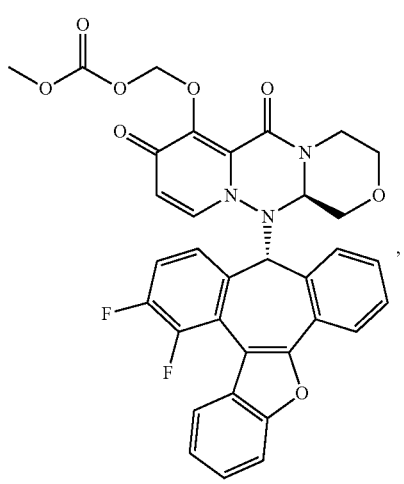
(335)
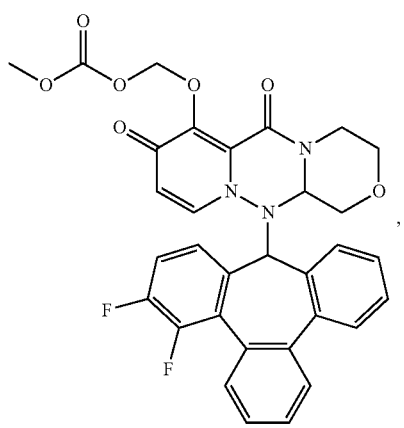
(338)
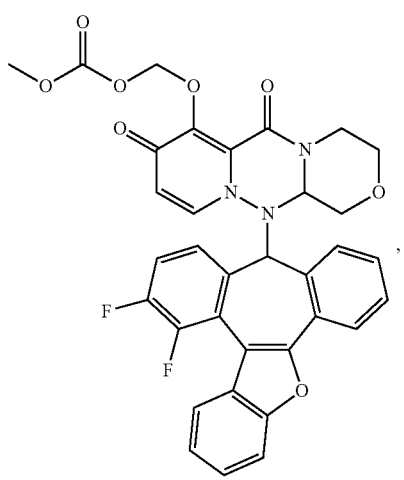
(336)
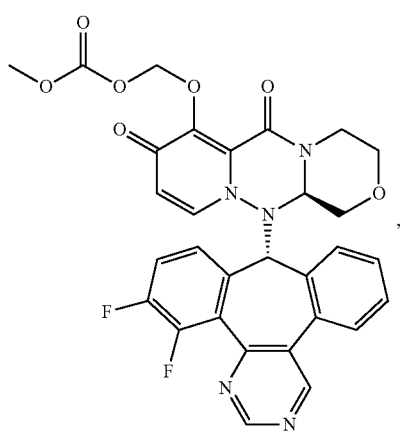
(339)

(340)
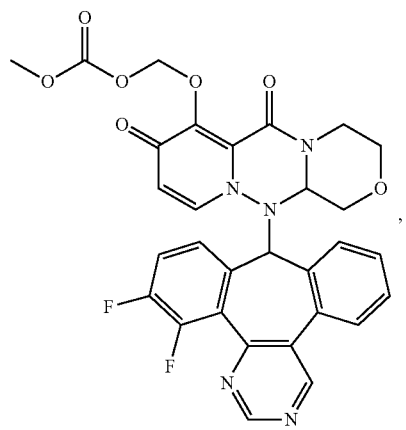
(341)
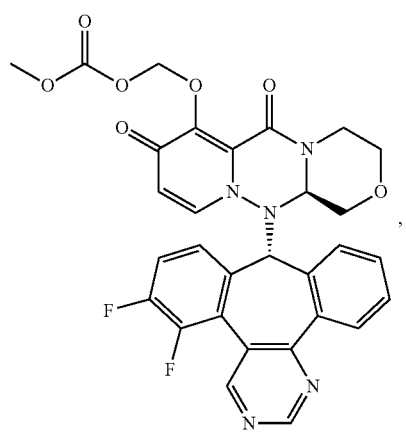
(342)
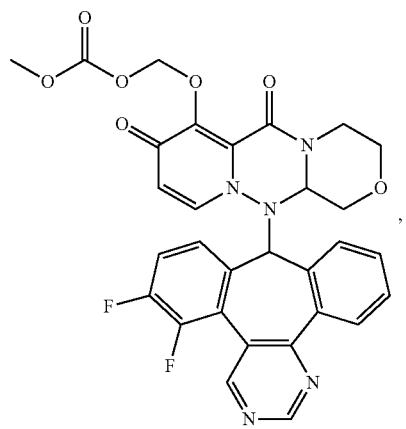
(343)
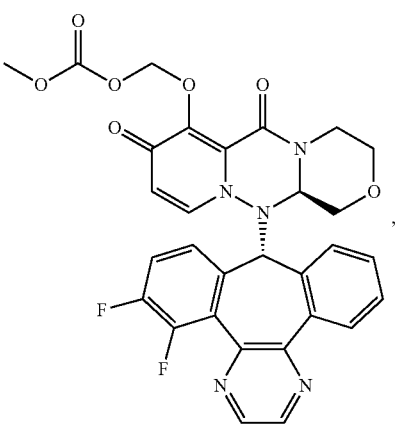
(344)
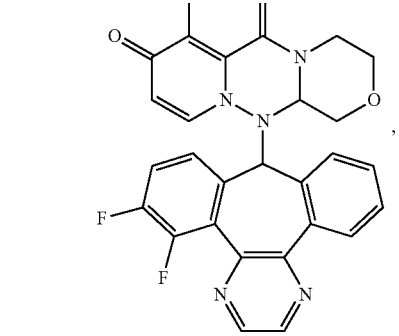
(345)
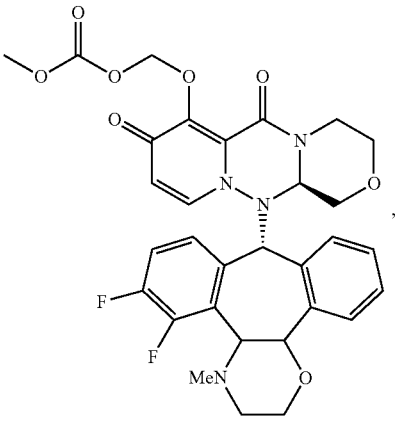

(346)
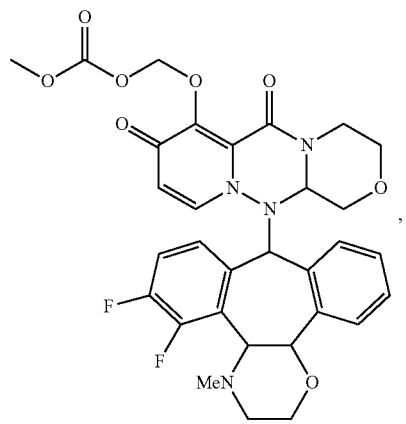
(347)
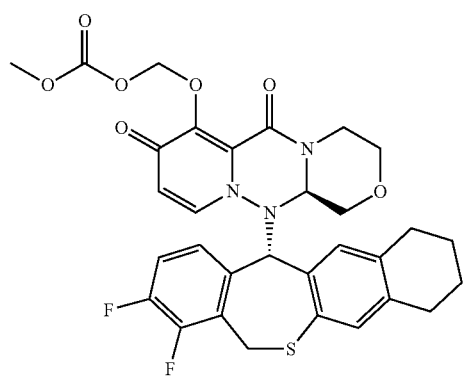
(348)
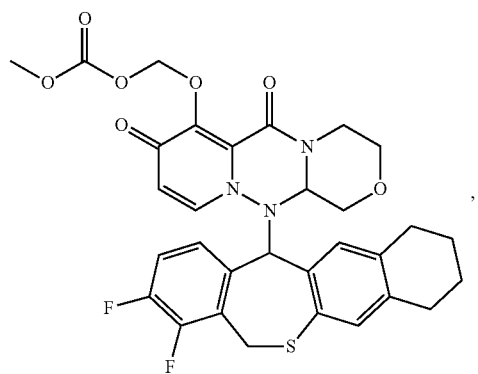
(349)
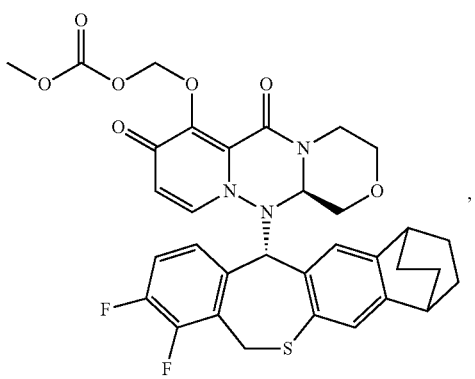
(350)
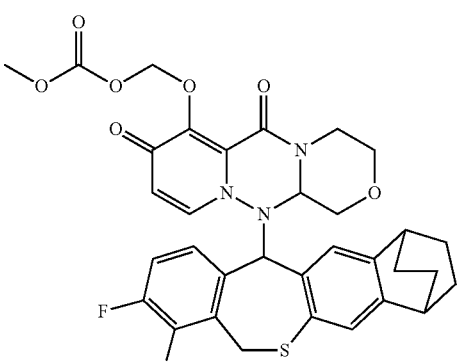
(351)
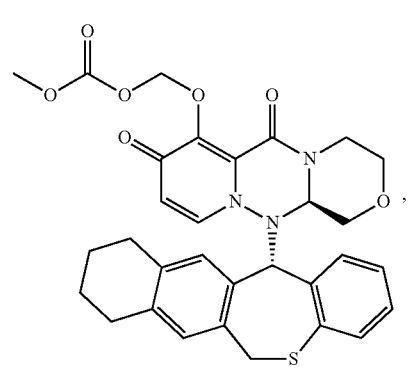
(352)
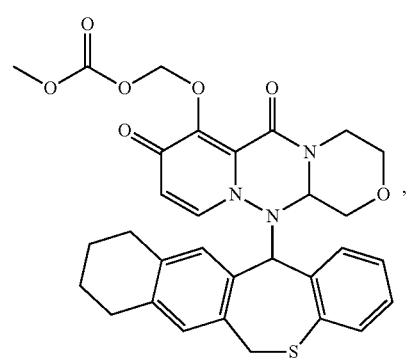
(353)
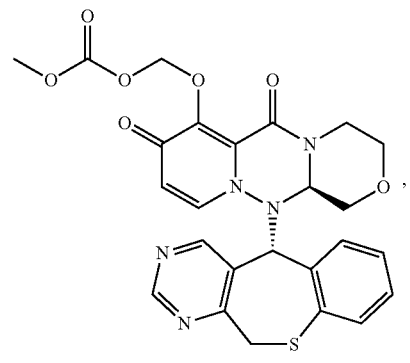

(354)
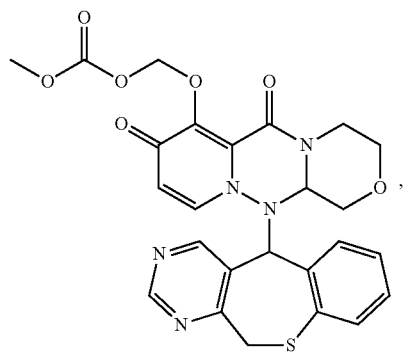
(355)
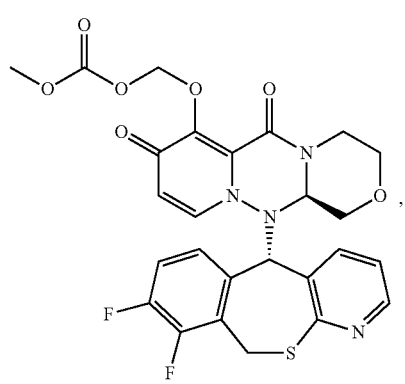
(356)
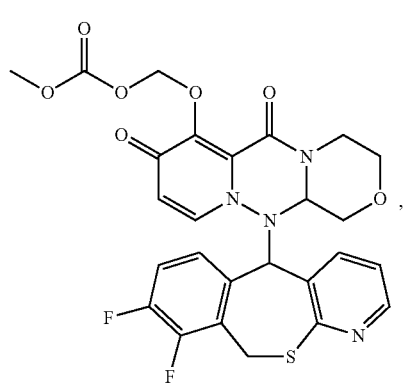
(357)
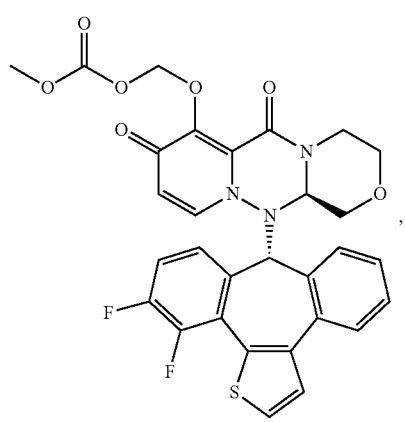
(358)
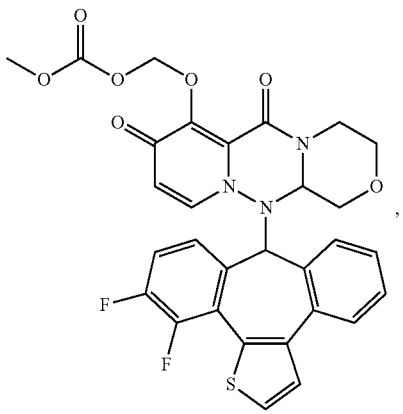
(359)
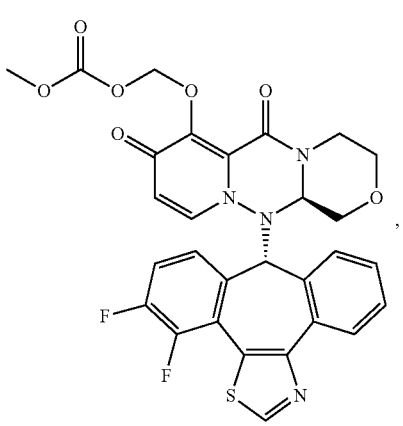
(360)
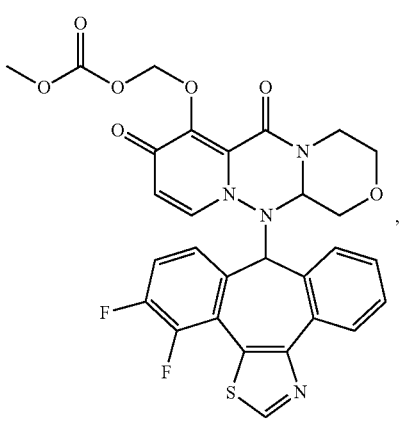

171
-continued
(361)
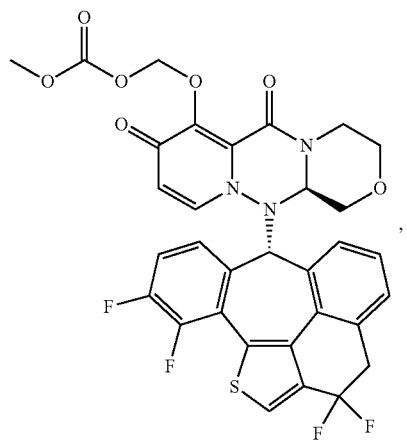
(362)
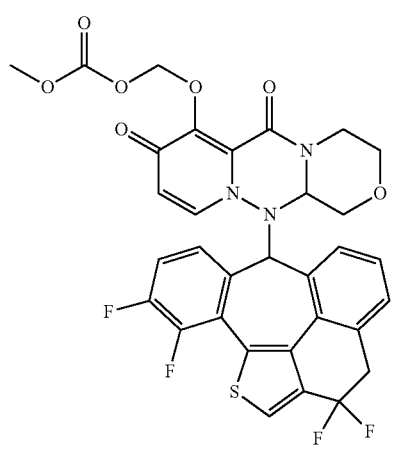
(363)
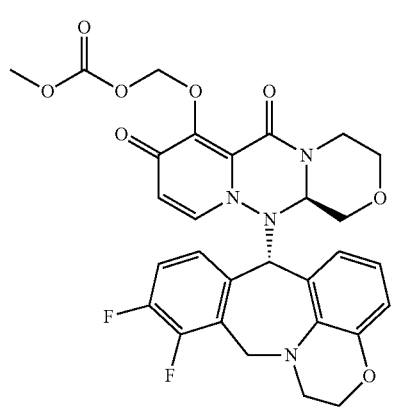
172
-continued
(364)
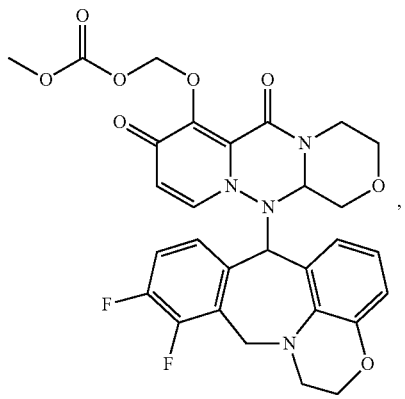
(365)
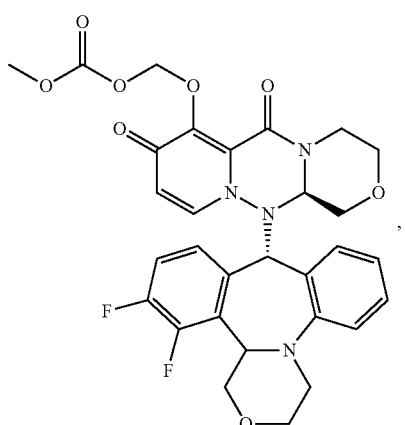
(366)
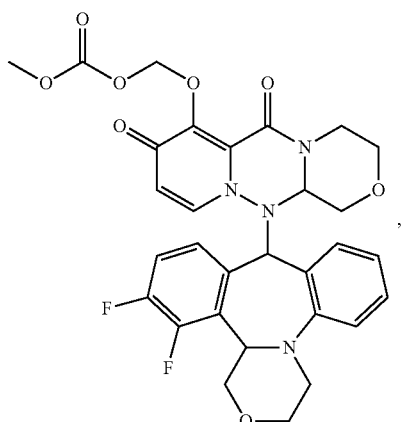
(367)
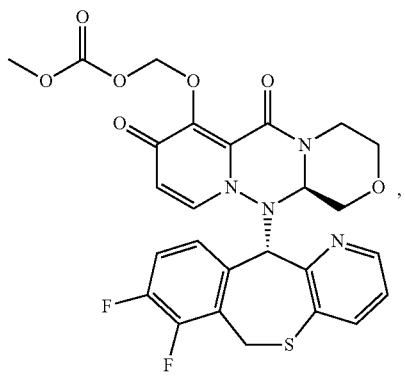

173
-continued
(368)
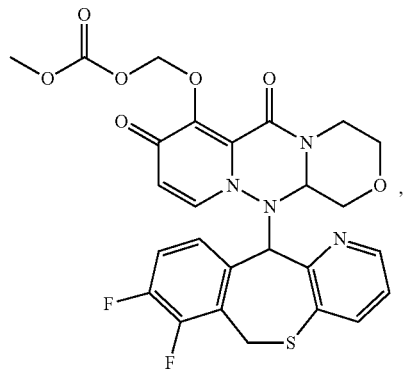
(369)
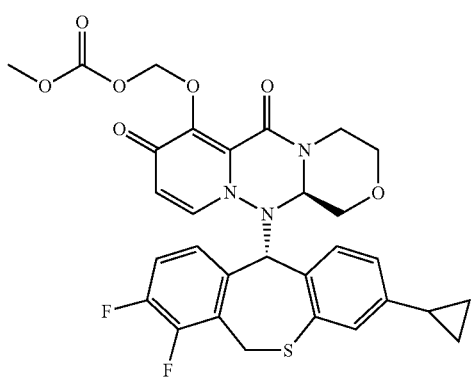
(370)
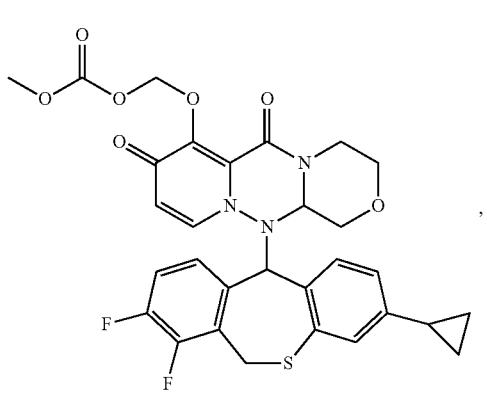
(371)
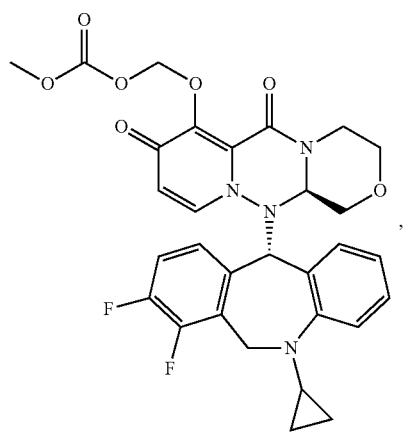
174
-continued
(372)
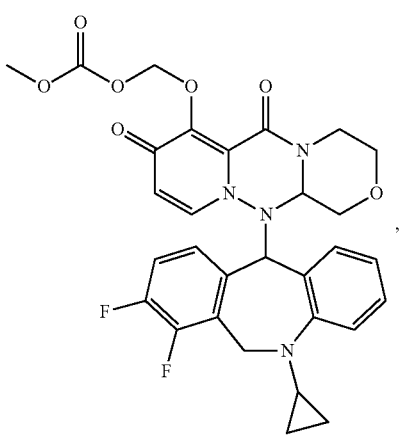
(373)
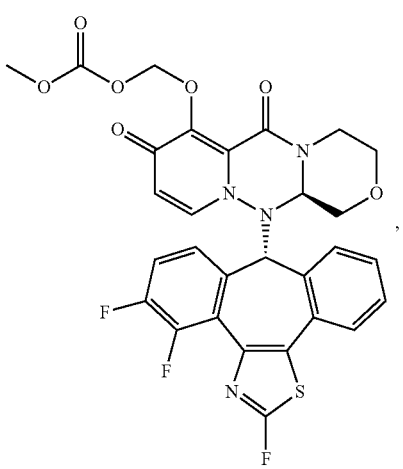
(374)
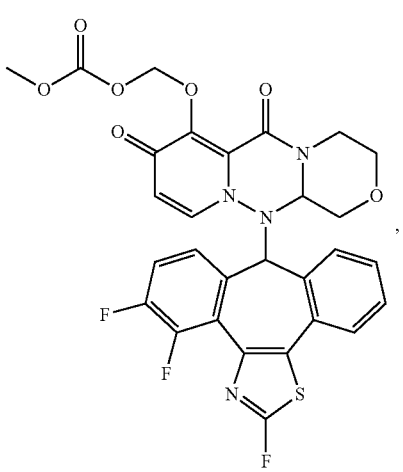

(375) 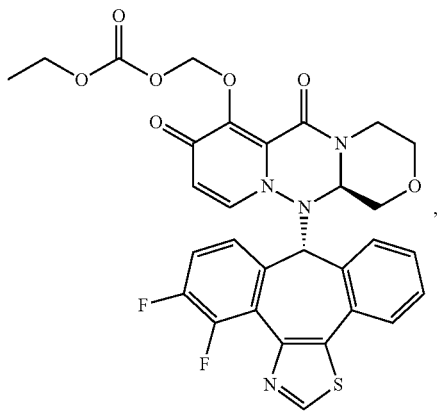
(376) 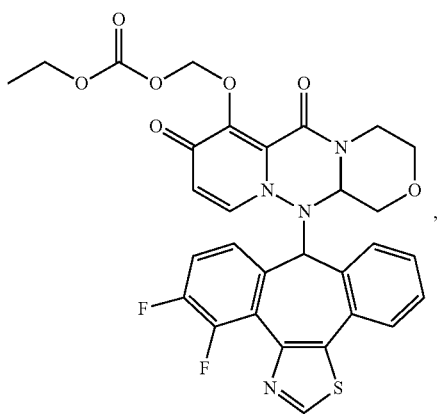
(377) 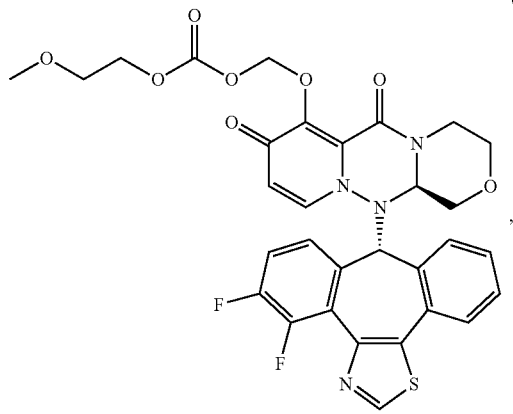
(378) 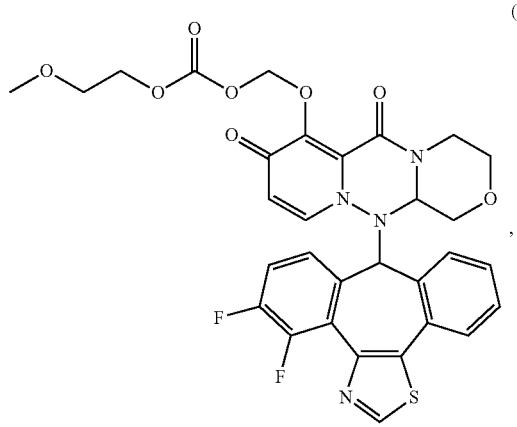
(379) 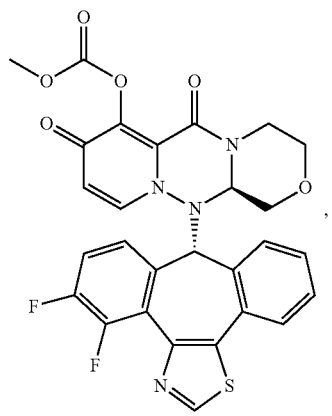
(380) 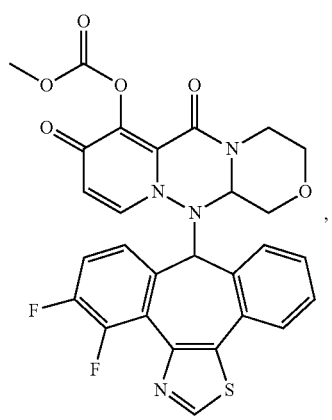
(381) 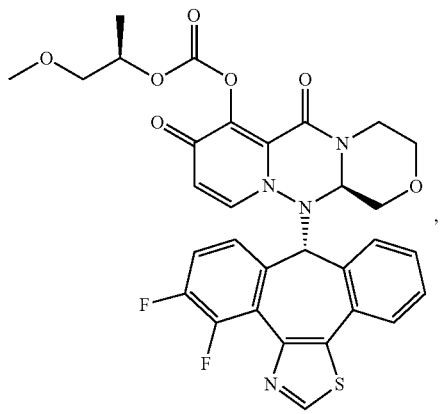
(382) 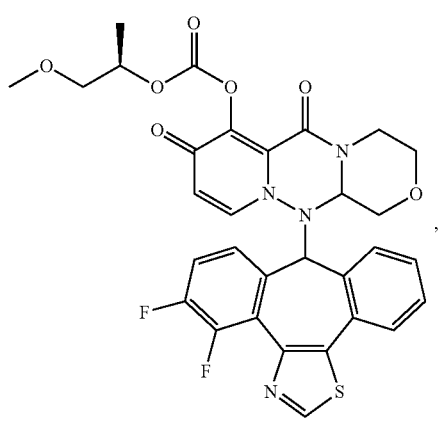

177
-continued
(383)
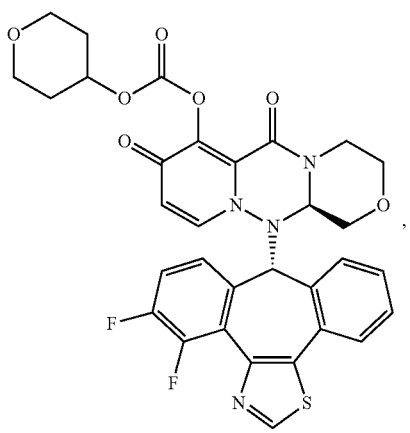
(384)
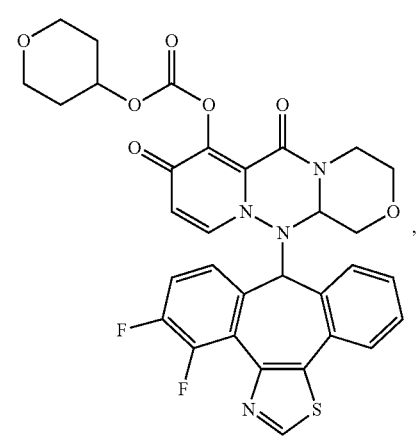
(385)
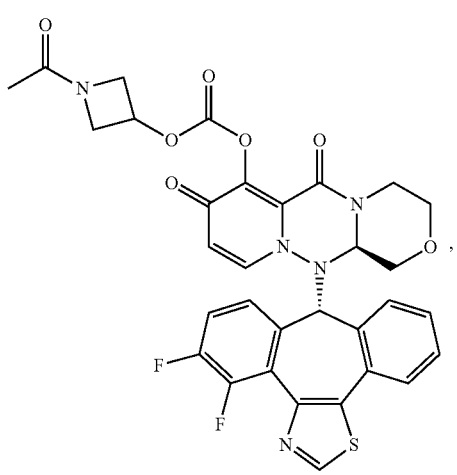
178
-continued
(386)
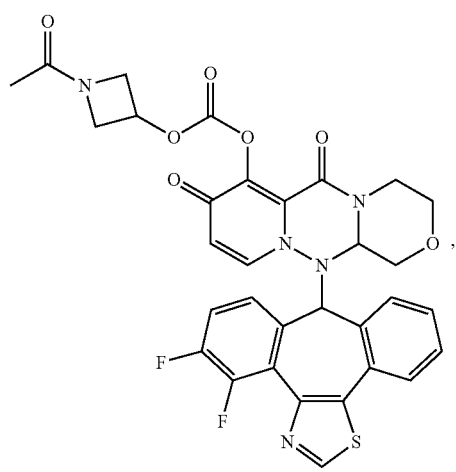
(387)
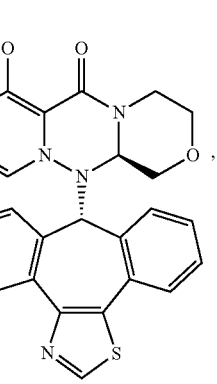
(388)
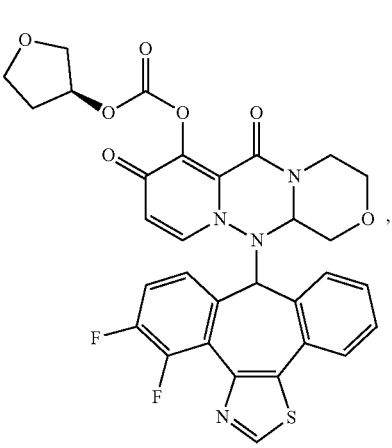

179
-continued
(389)
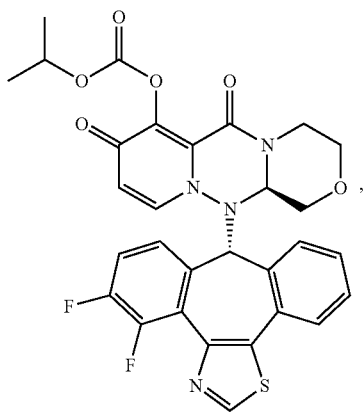
(390)
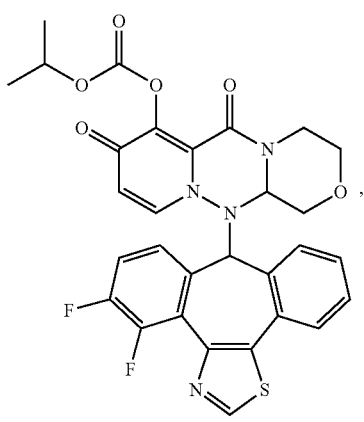
(391)
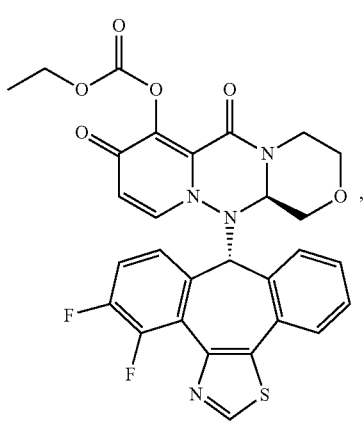
(392)
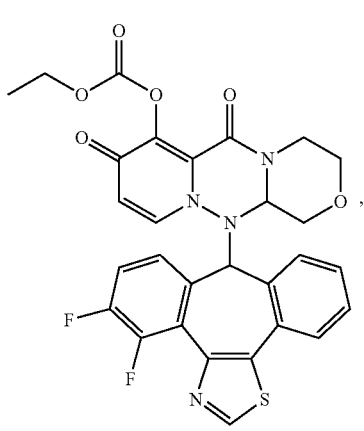
180
-continued
(393)
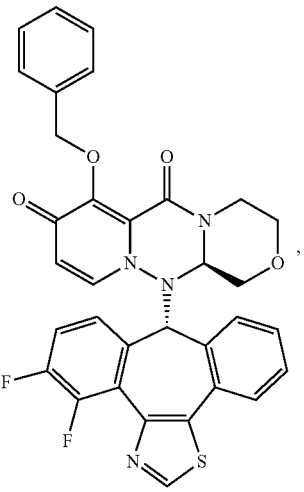
(394)
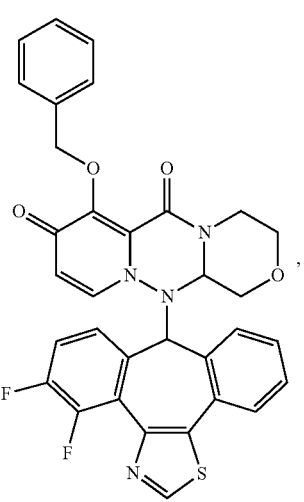
(395)
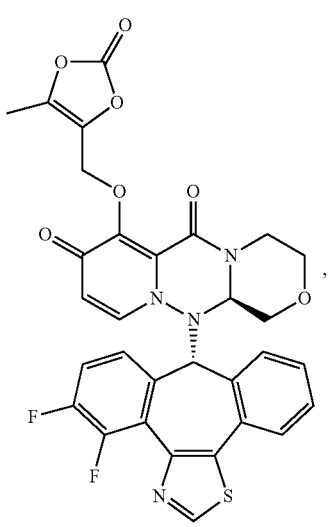

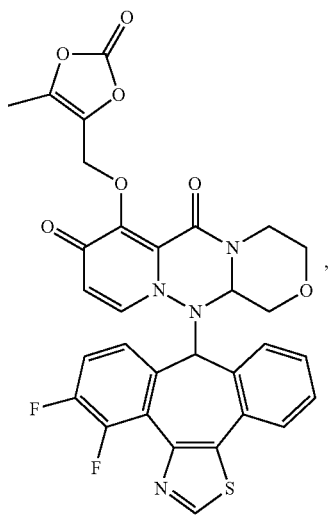
(396)
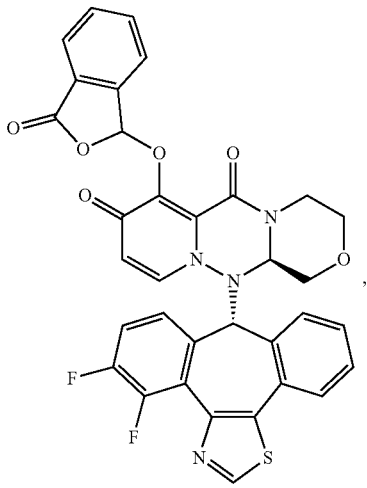
(399)
(397)
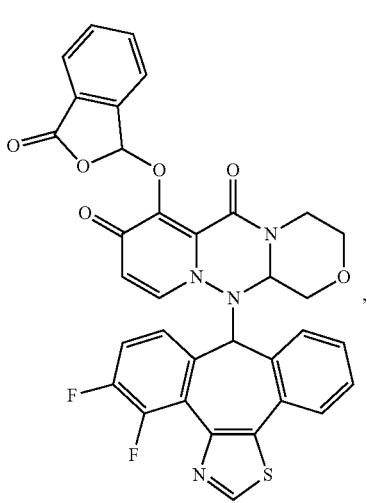
(400)
(398)
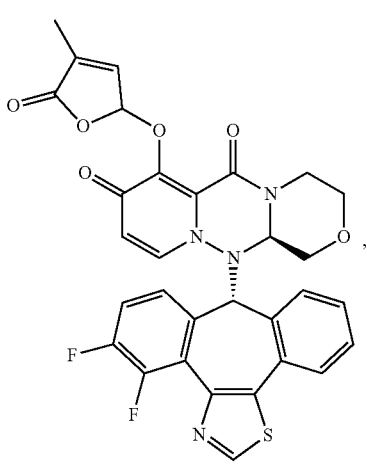
(401)

(402)
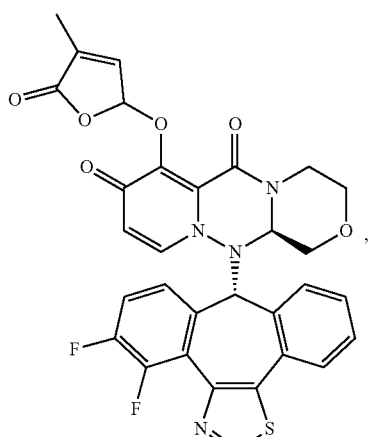
(403)
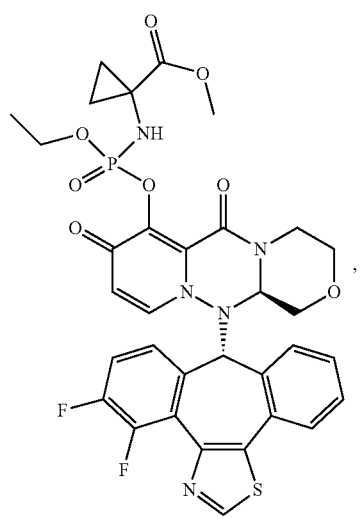
(404)
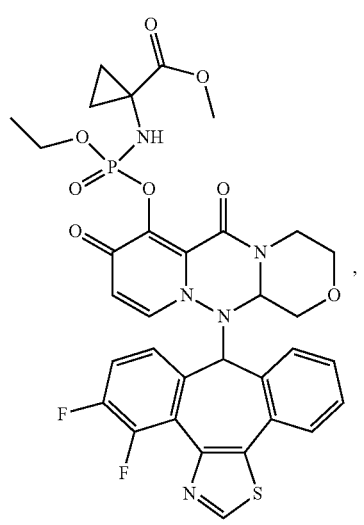
(405)
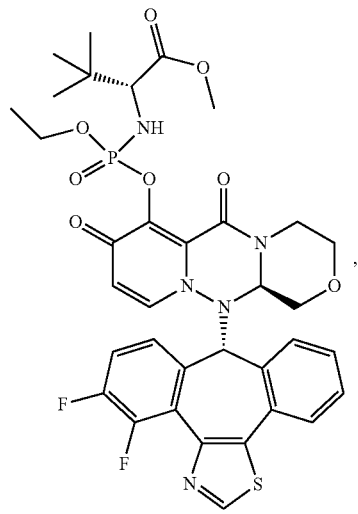
(406)
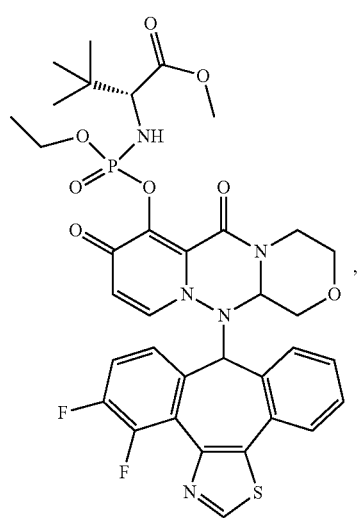
(407)
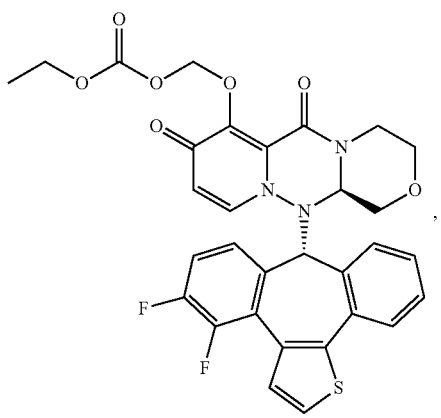

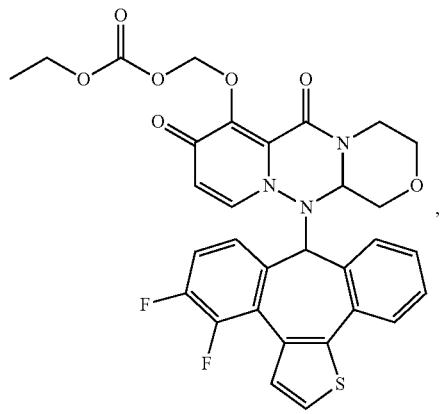
(408)
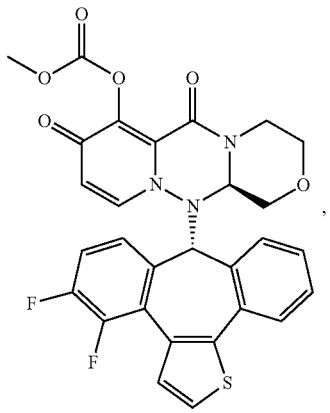
(411)
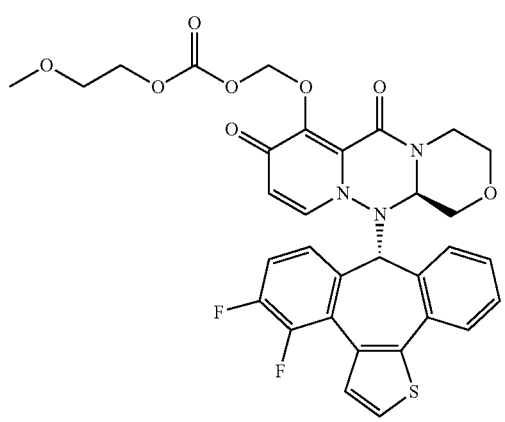
(409)
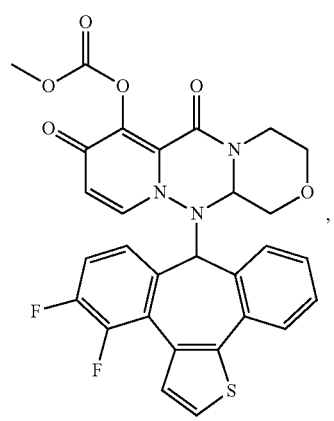
(412)
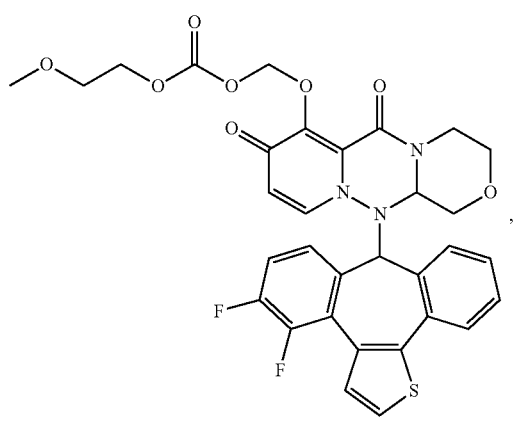
(410)
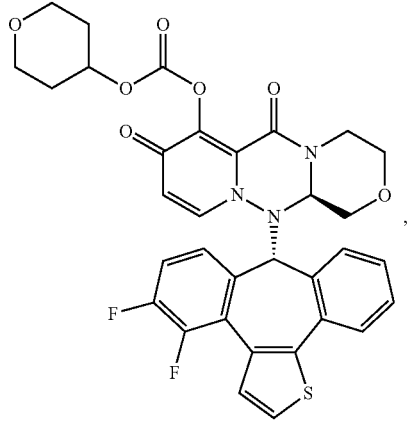
(413)

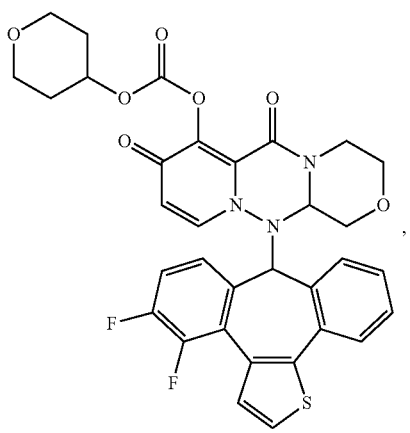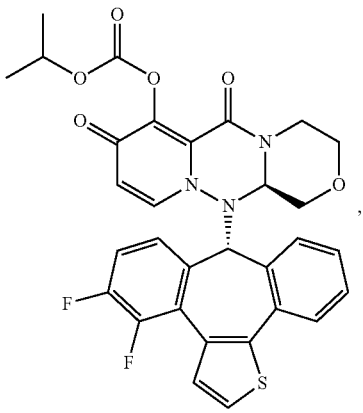

(421)
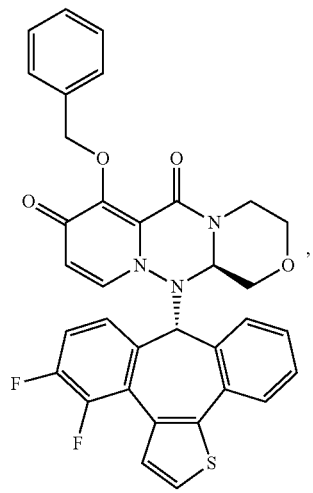
(422)
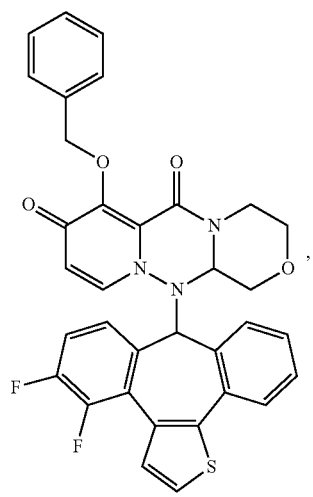
(423)
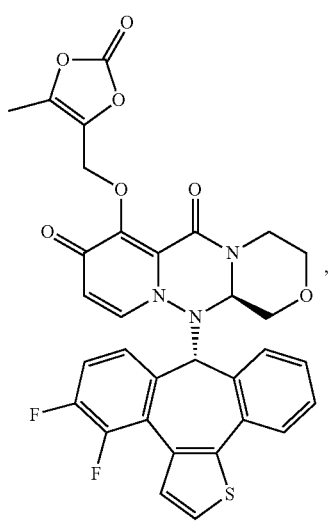
(424)
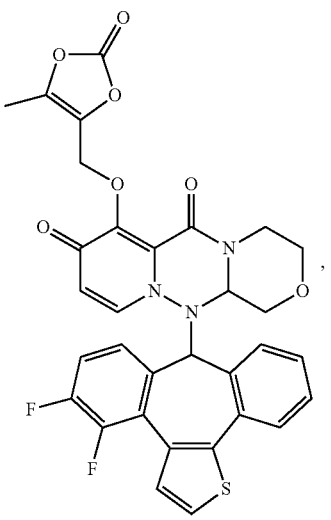
(425)
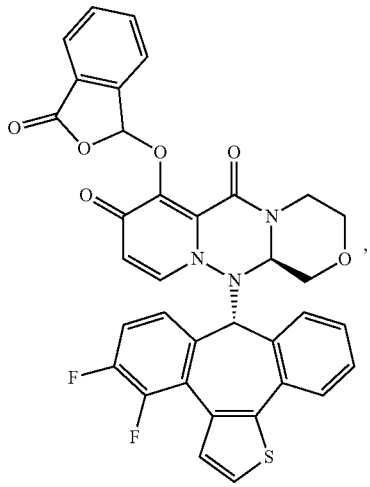
(426)
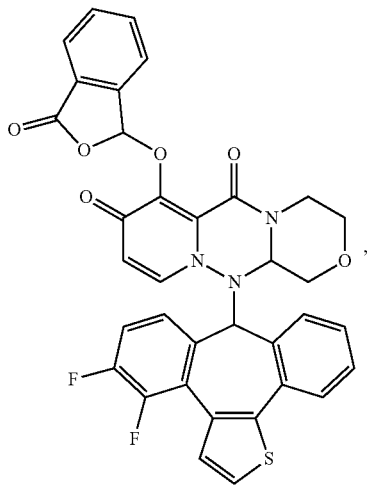

(427)
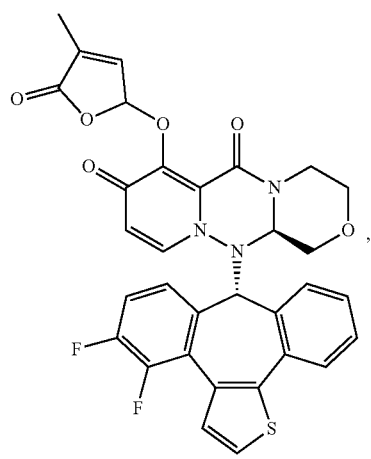
(428)
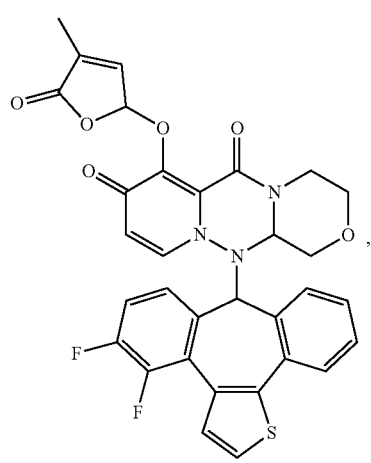
(429)
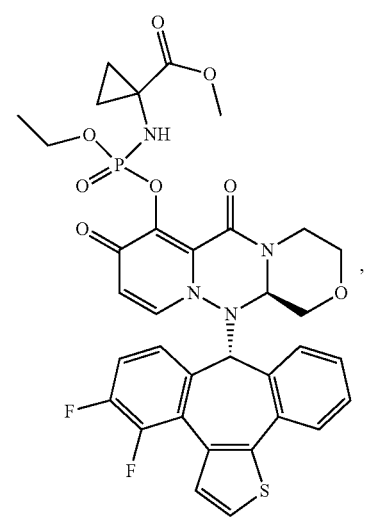
(430)
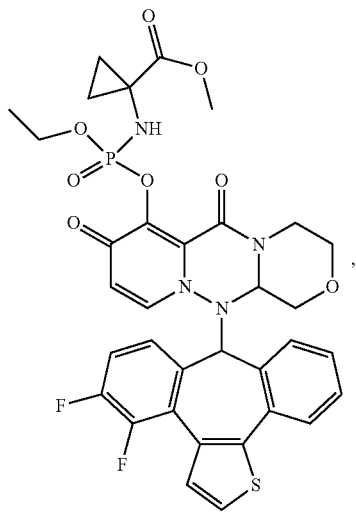
(431)
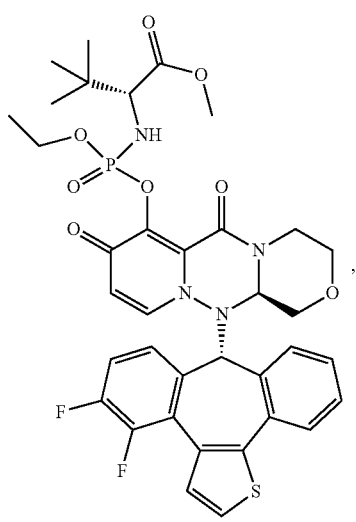
(432)
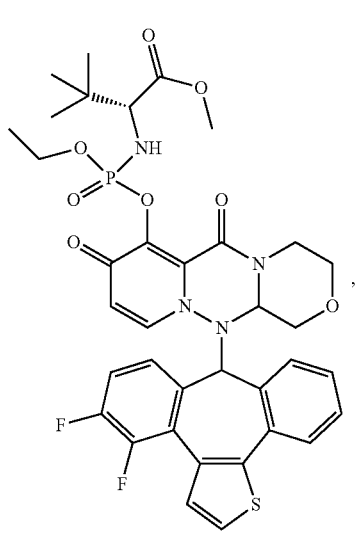

-continued
(433)
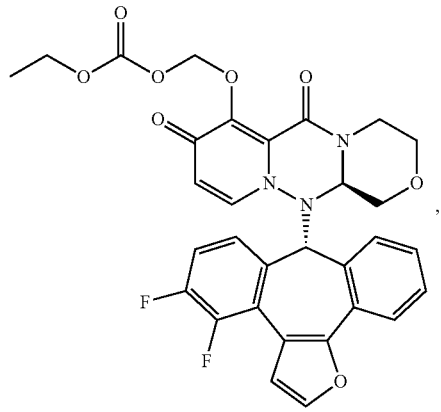
(434)
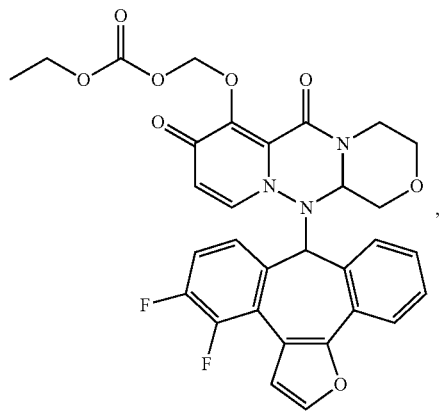
(435)
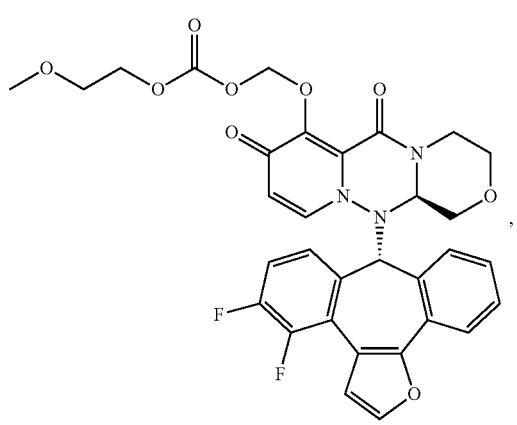
-continued
(436)
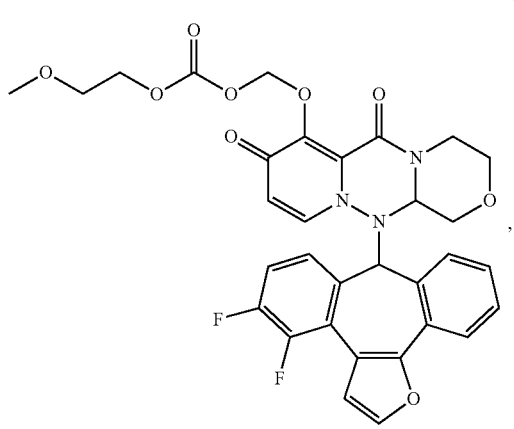
(437)
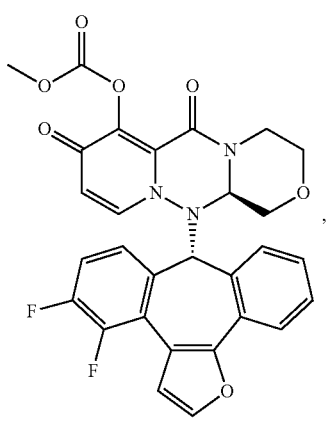
(438)
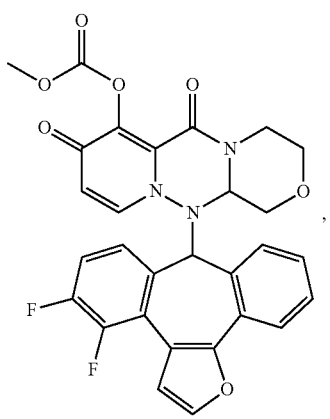

(439)
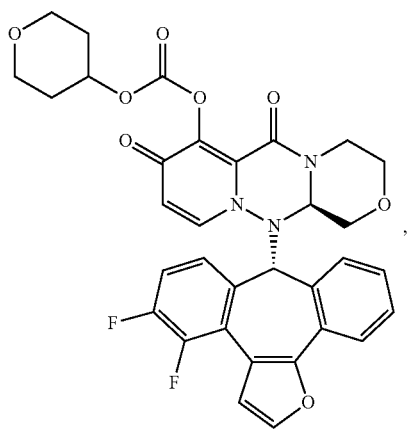
,
(440)
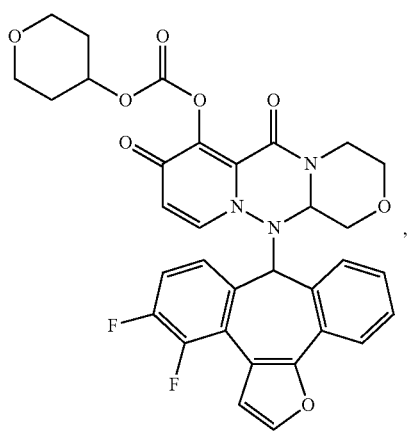
,
(441)
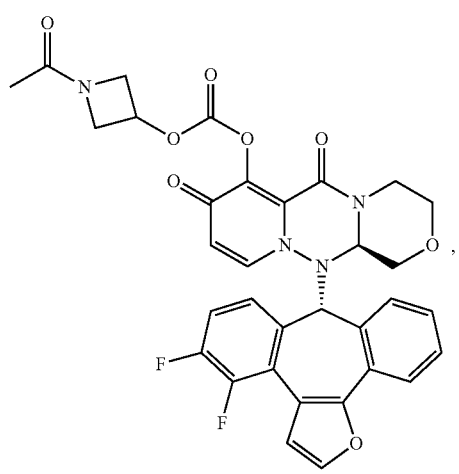
,
(442)
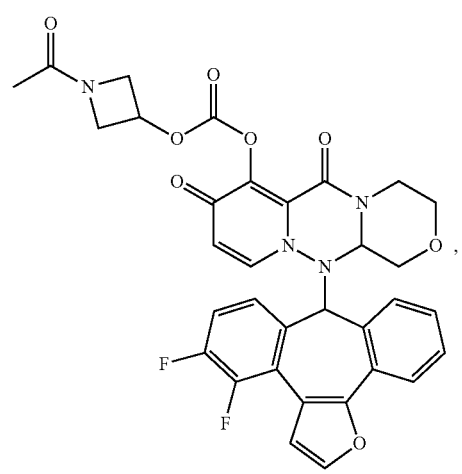
,
(443)
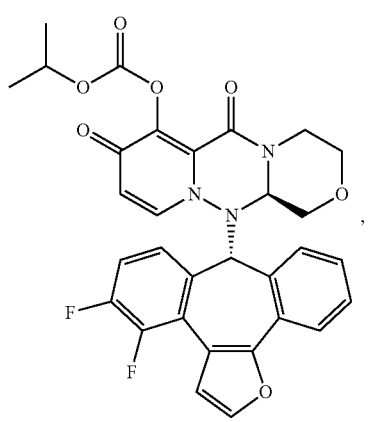
,
(444)
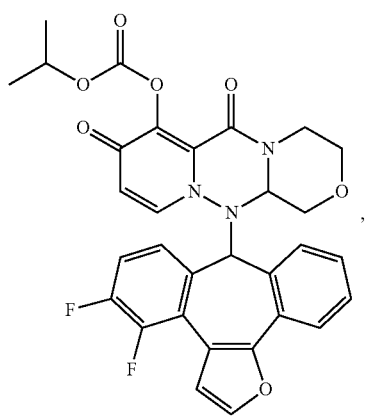
,

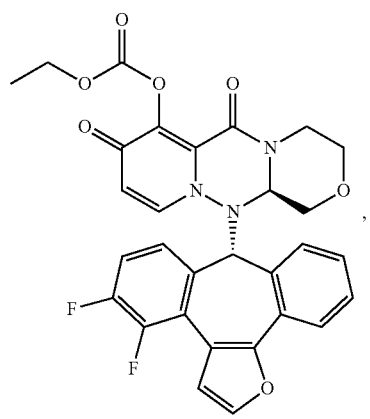
(445)
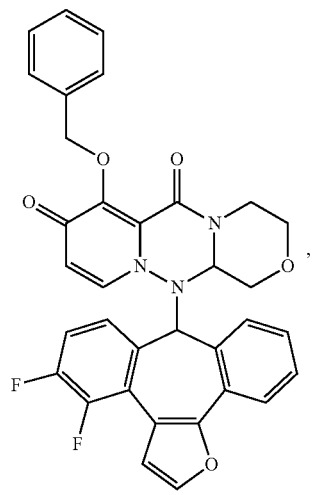
(448)
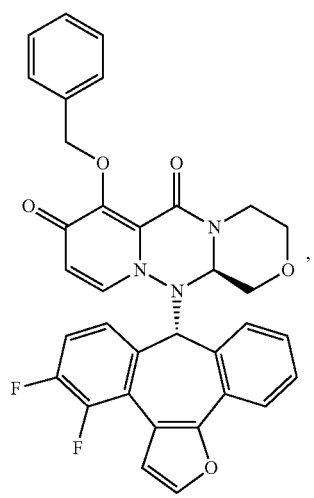
(446)
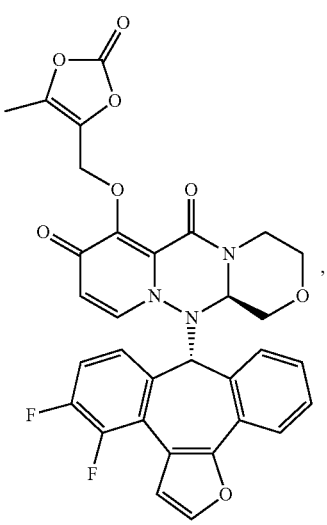
(449)
(447)
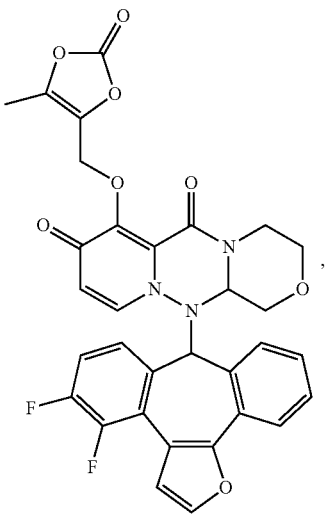
(450)

(451)
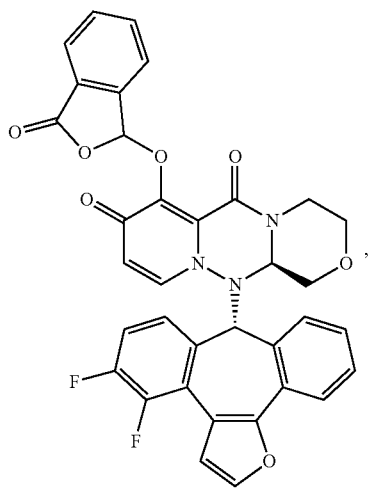
(452)
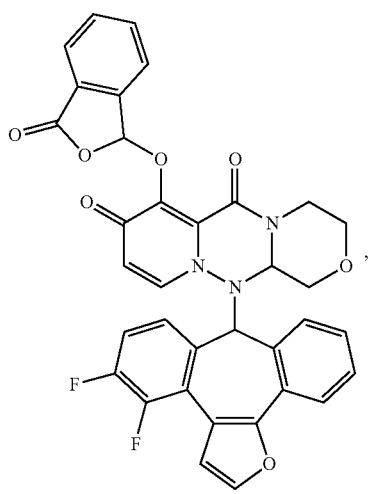
(453)
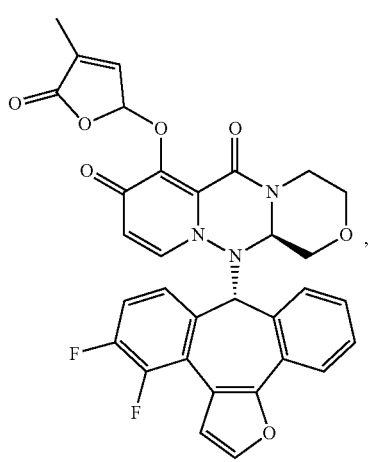
(454)
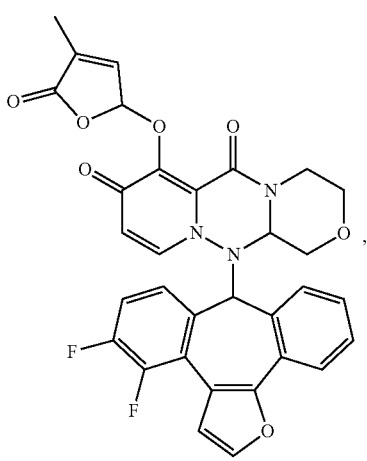
(455)
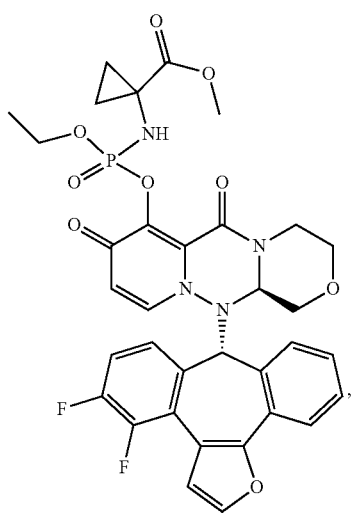
(456)
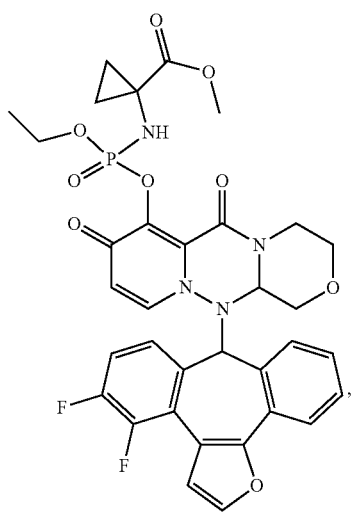

201
-continued
(457)
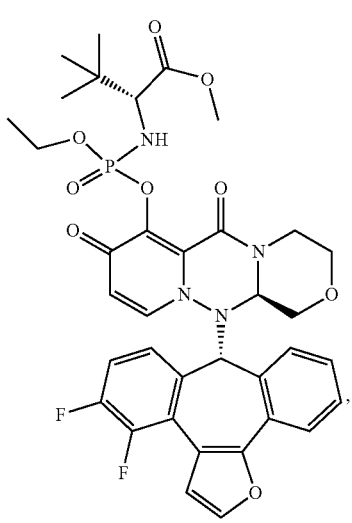
(458)
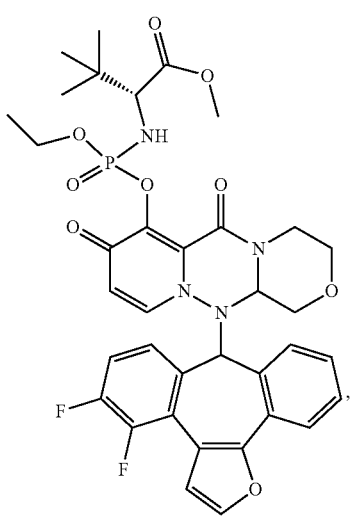
(459)
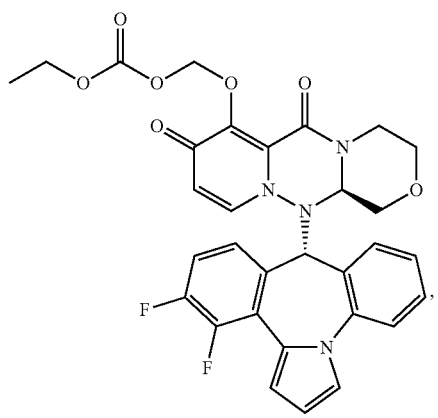
202
-continued
(460)
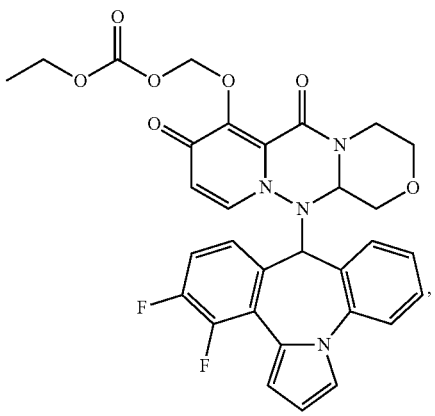
(461)
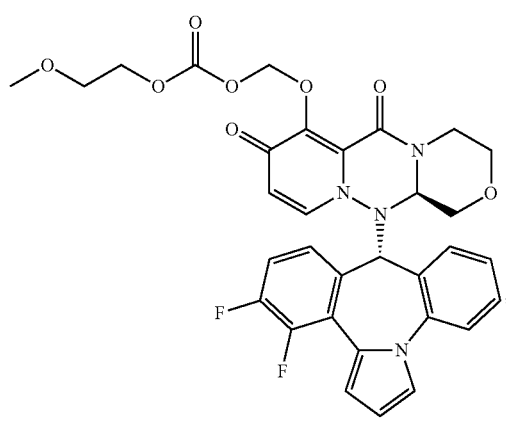
(462)
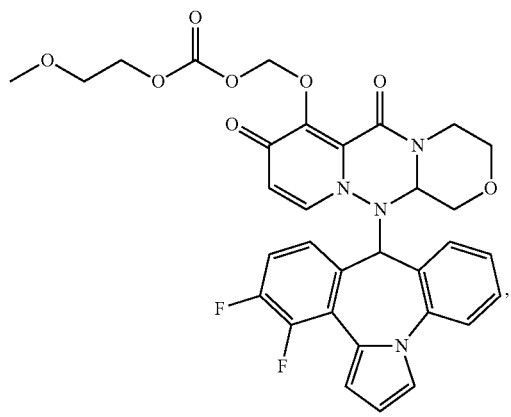

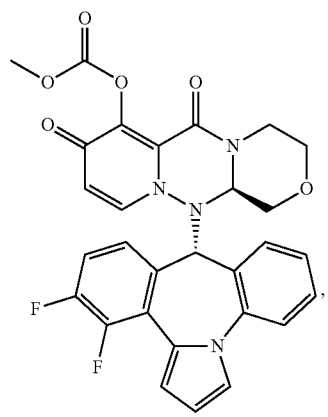
(463)
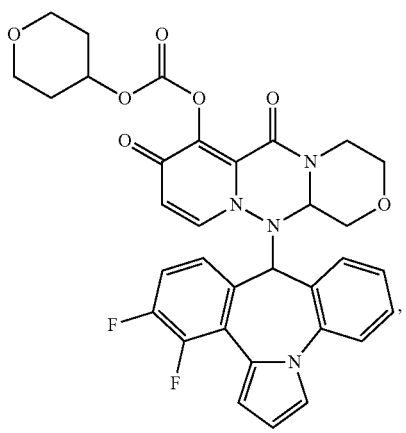
(466)
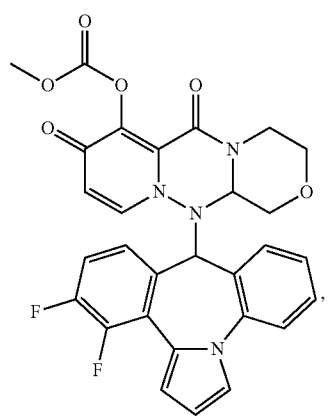
(464)
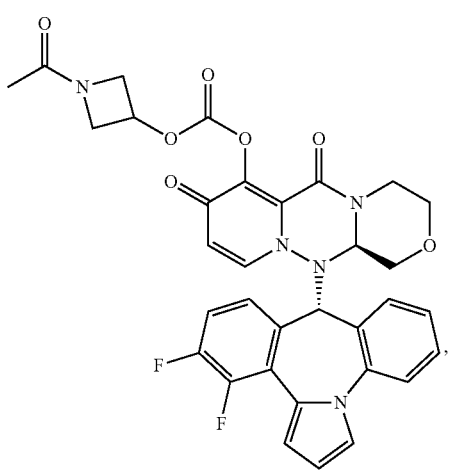
(467)
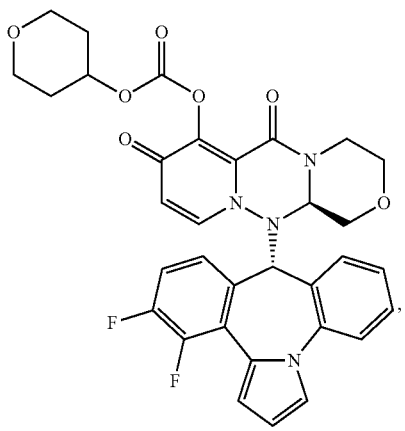
(465)
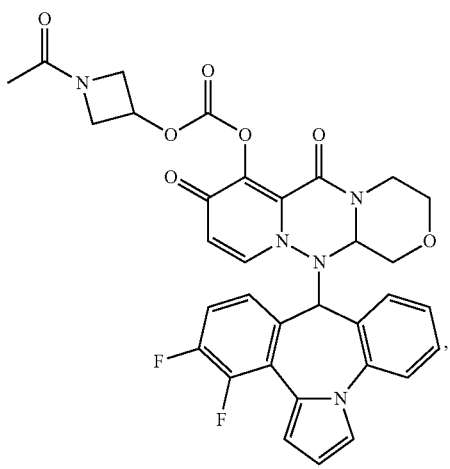
(468)

(469)
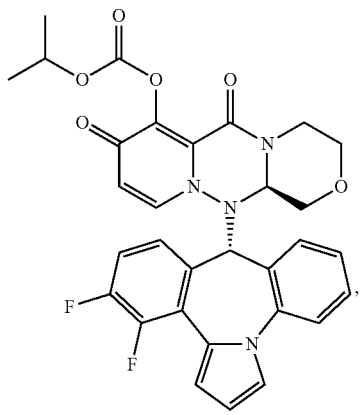
(470)
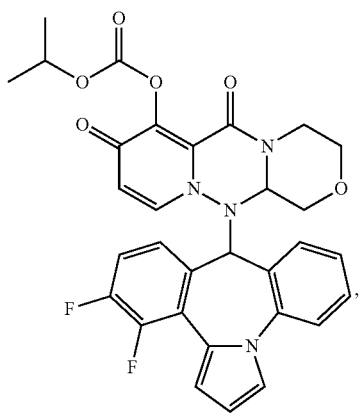
(471)
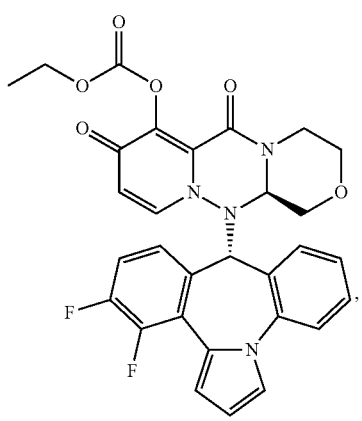
(472)
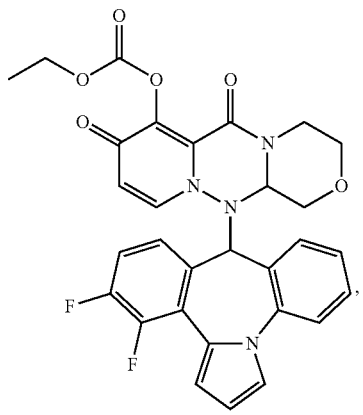
(473)
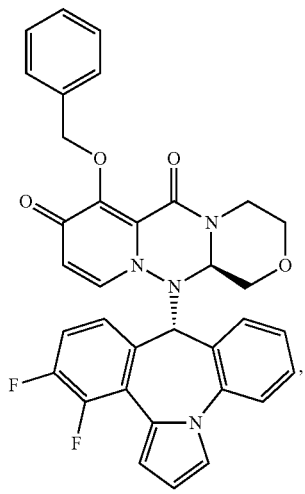
(474)
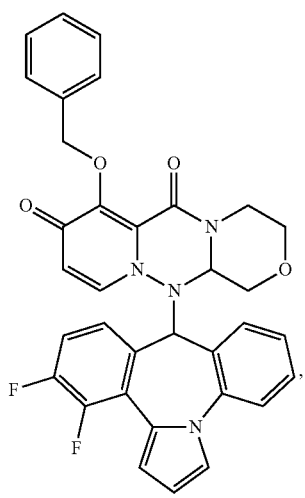

(475)
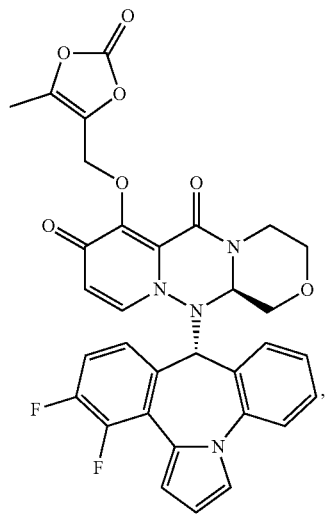
(476)
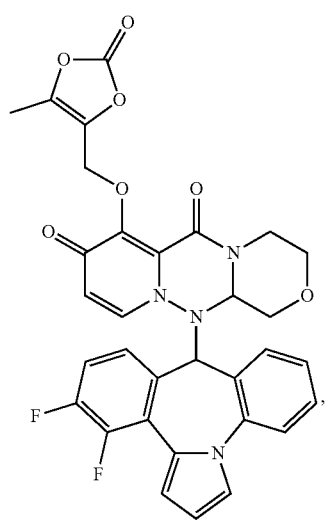
(477)
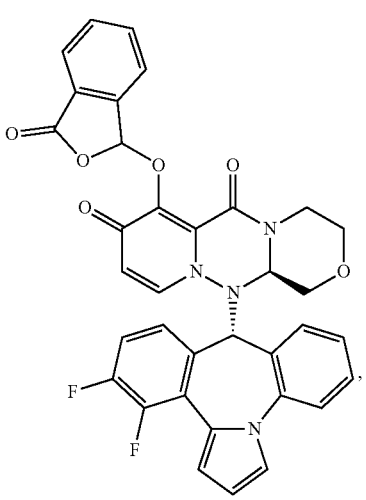
(478)
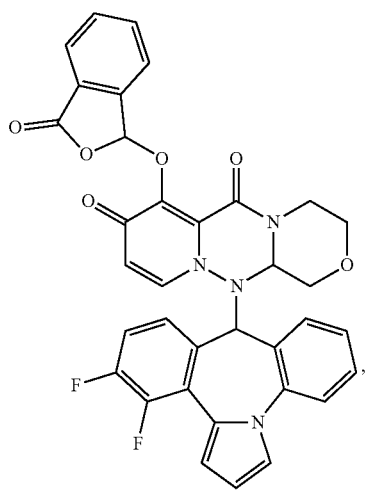
(479)
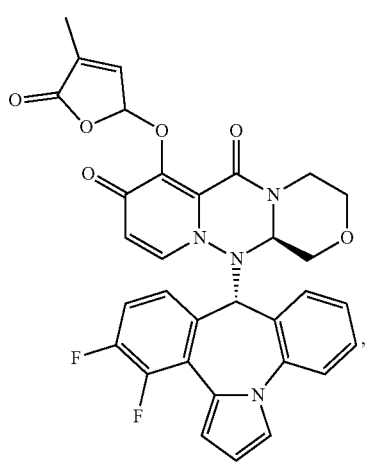
(480)
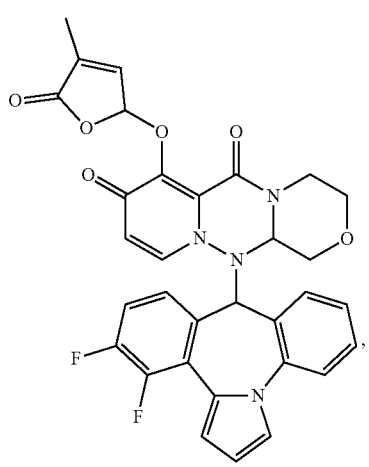

(481)
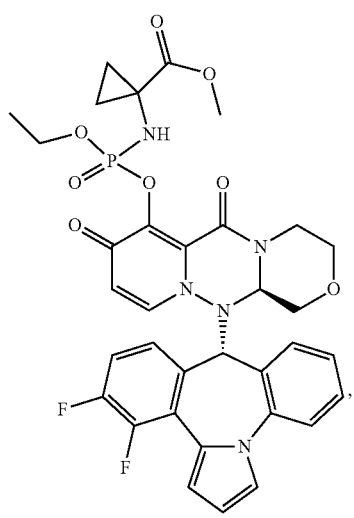
(482)
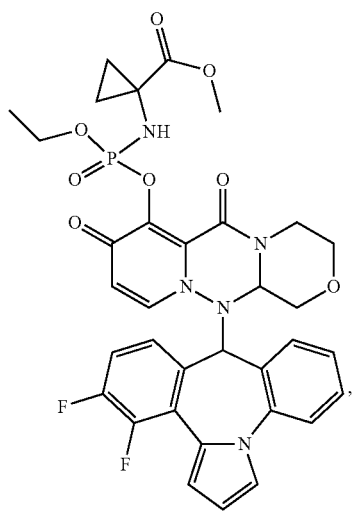
(483)
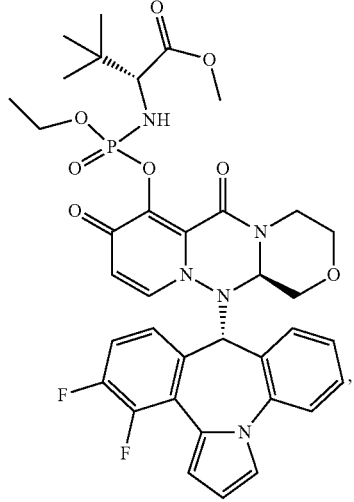
(484)
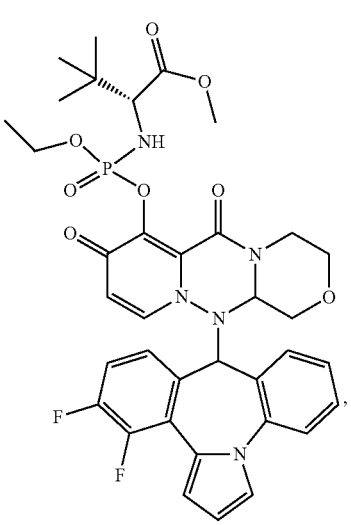
(485)
(486)
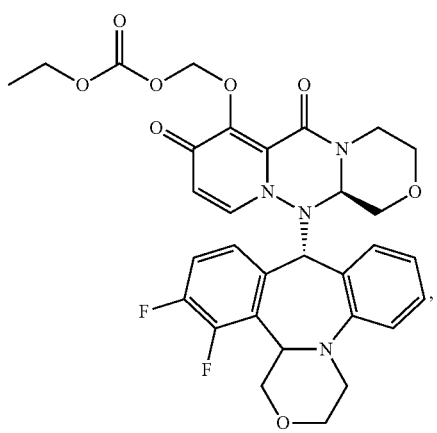

211
-continued
(487)
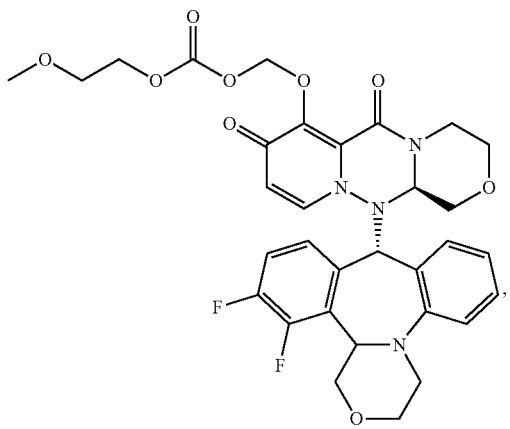
(488)
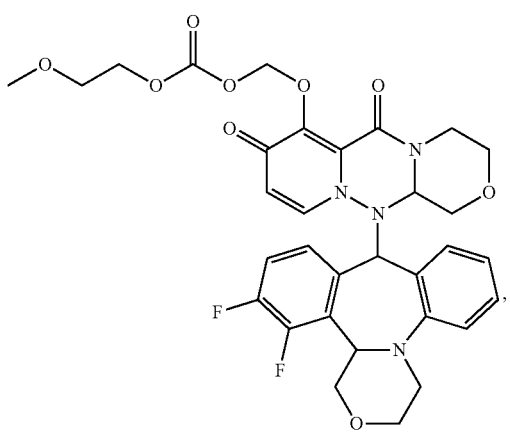
(489)
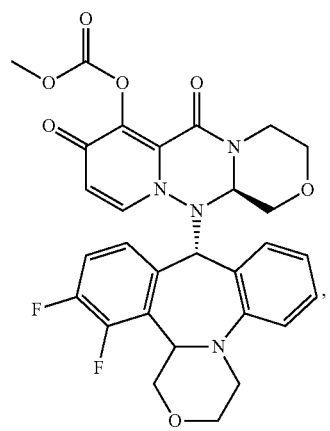
212
-continued
(490)
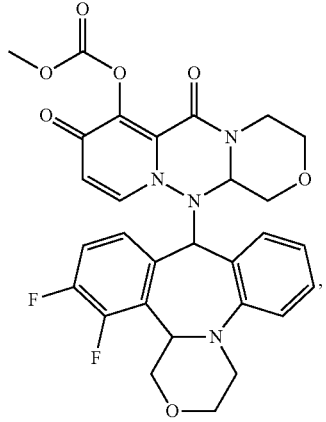
(491)
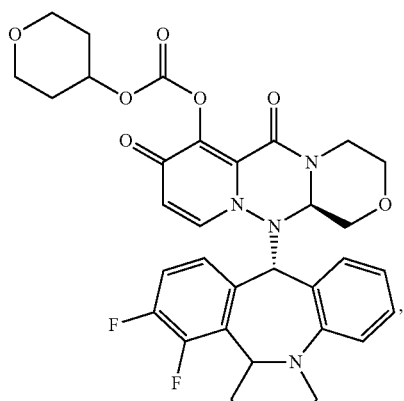
(492)
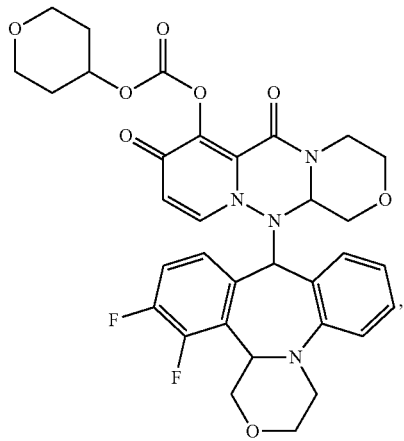

(493)
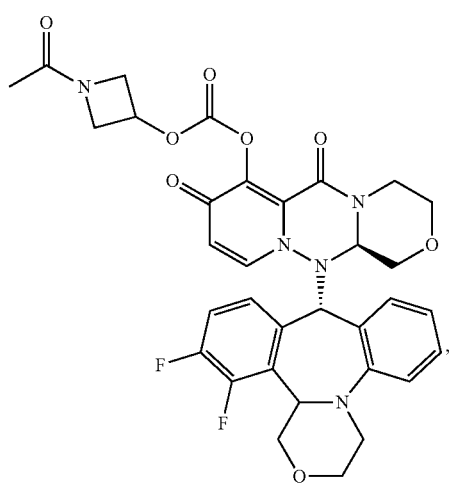
(494)
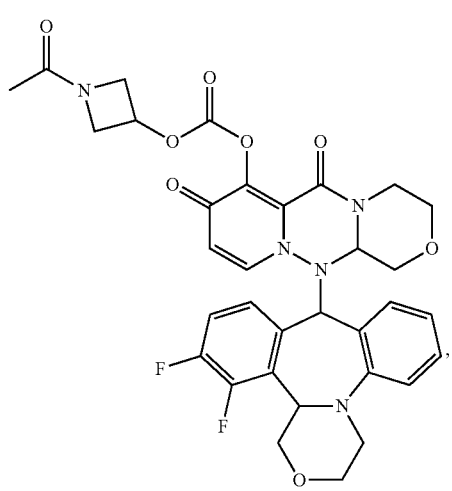
(495)
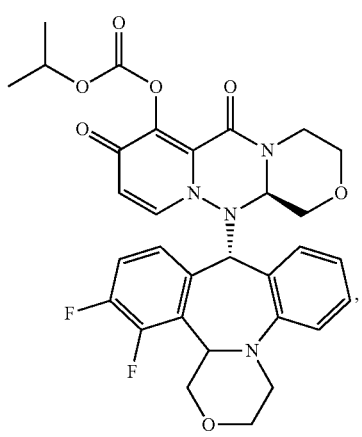
(496)
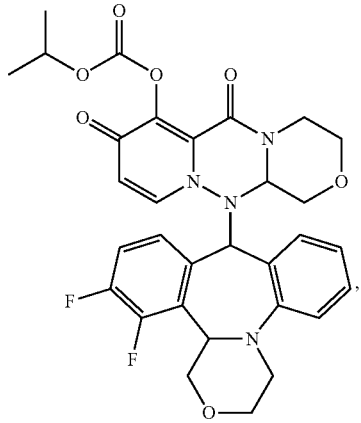
(497)
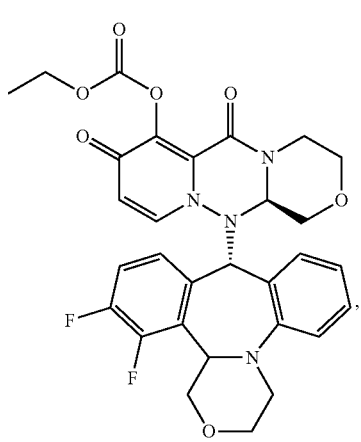
(498)
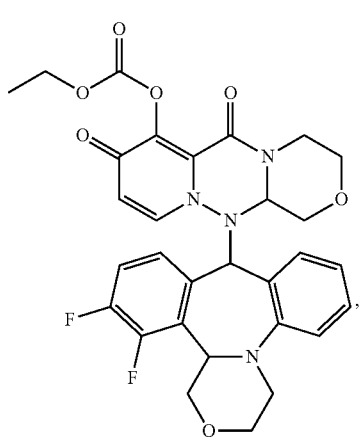

(499)
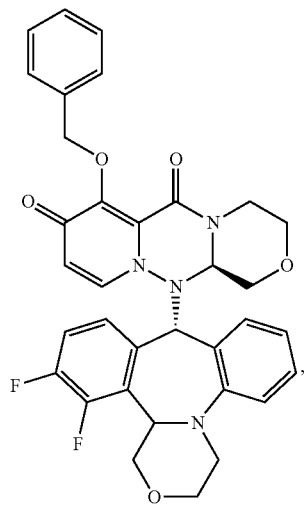
(500)
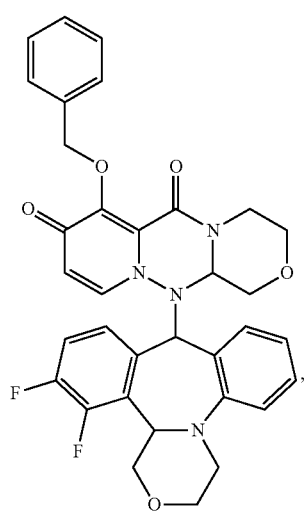
(501)
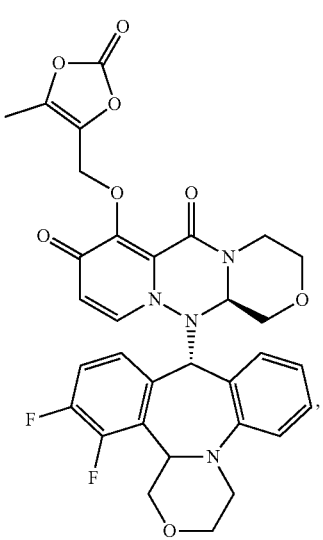
(502)
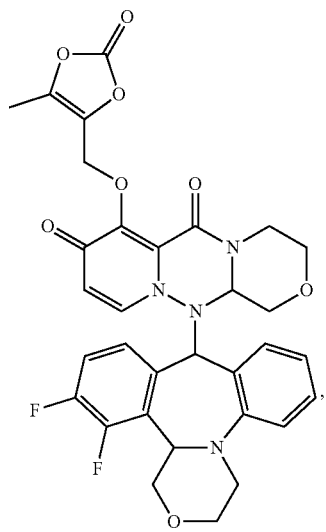
(503)
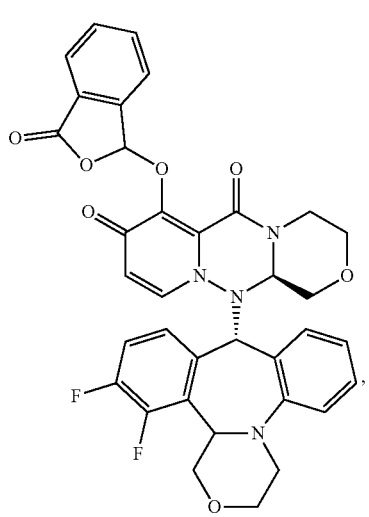
(504)
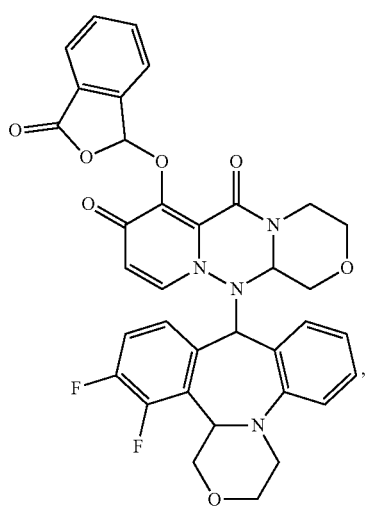

(505)
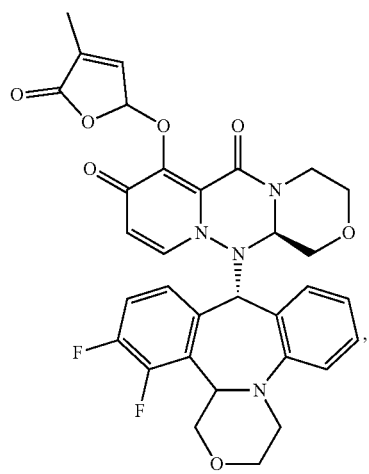
(506)
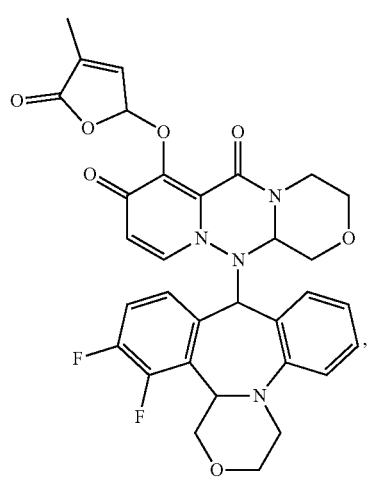
(507)
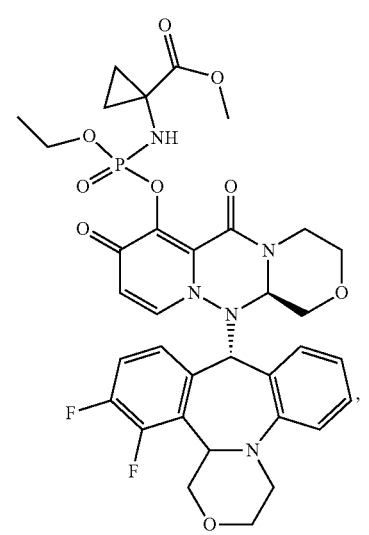
(508)
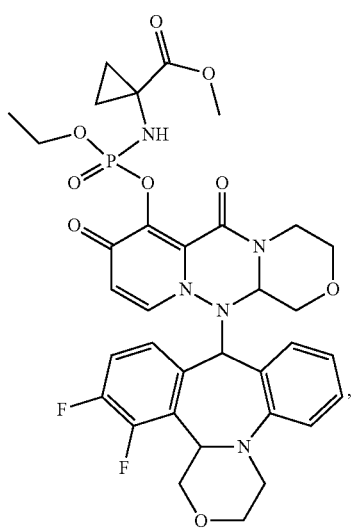
(509)
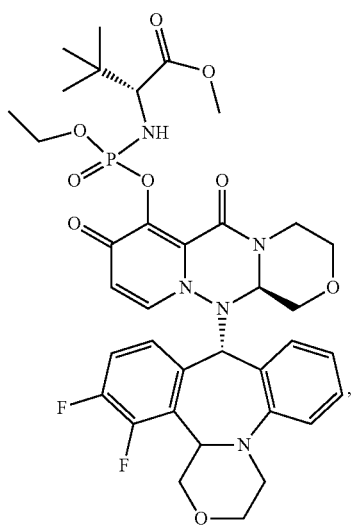
(510)
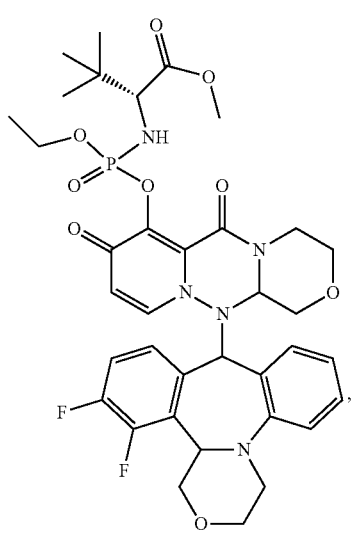

(511)
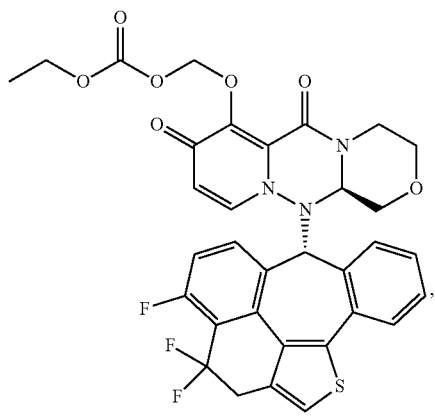
(512)
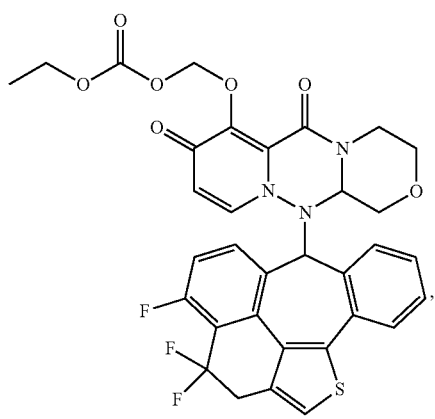
(513)
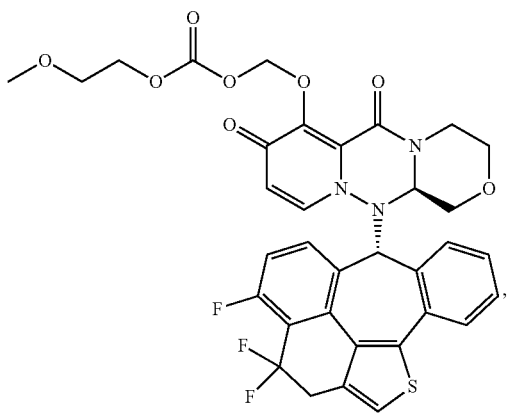
(514)
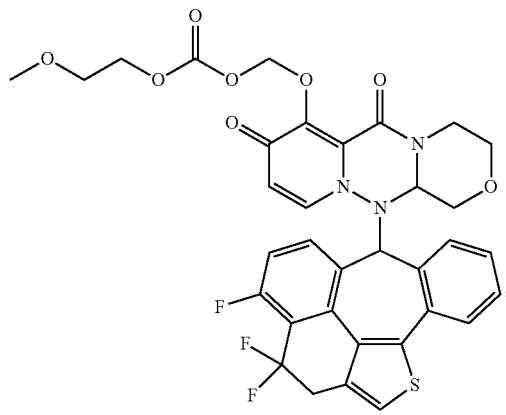
(515)
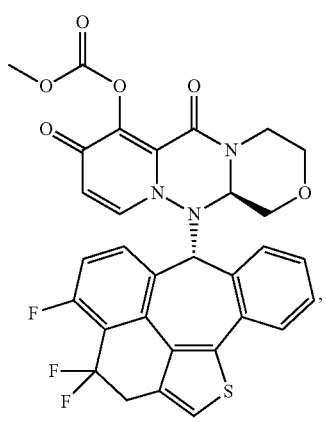
(516)
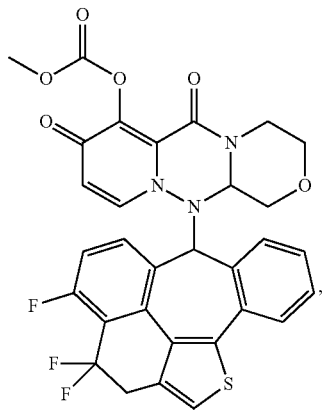

221
-continued
(517)
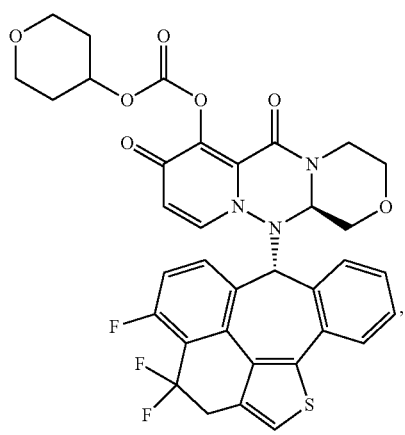
(518)
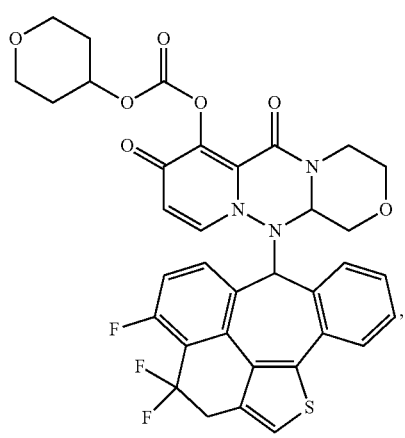
(519)
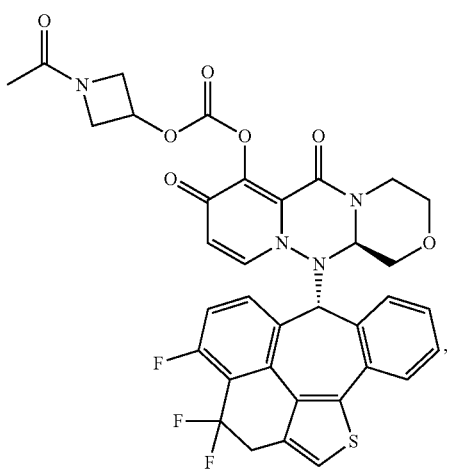
222
-continued
(520)
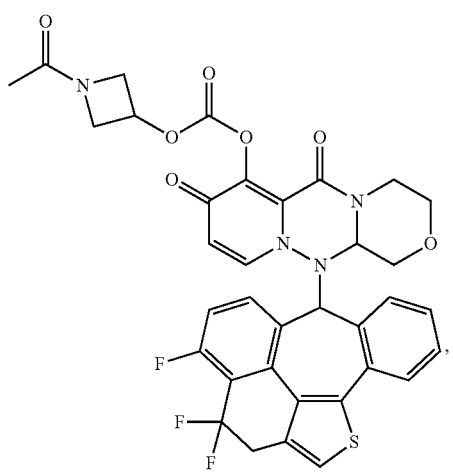
(521)
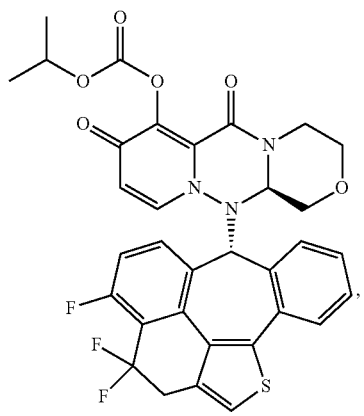
(522)
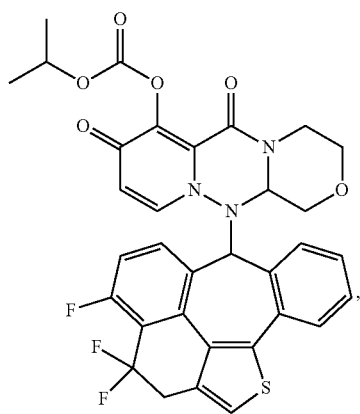

-continued
(523)
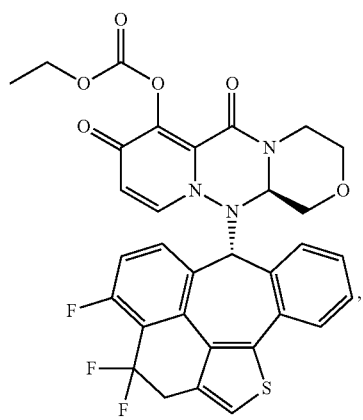
(524)
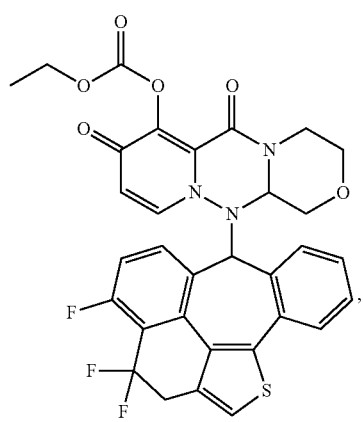
(525)
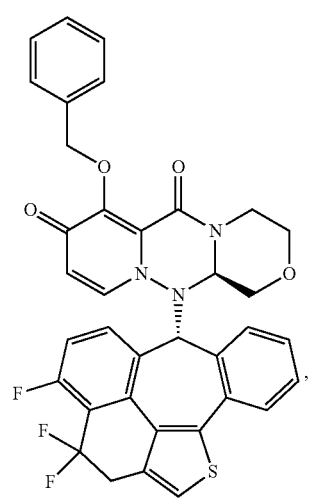
-continued
(526)
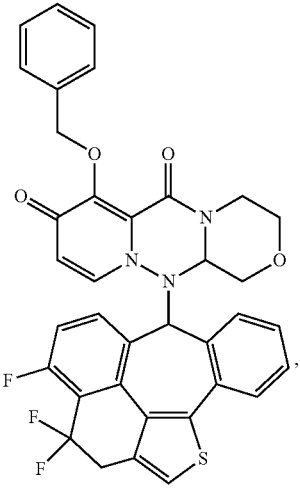
(527)
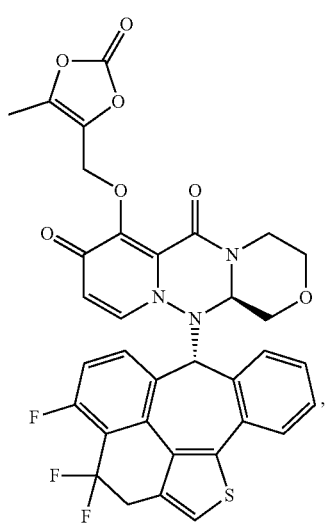
(528)
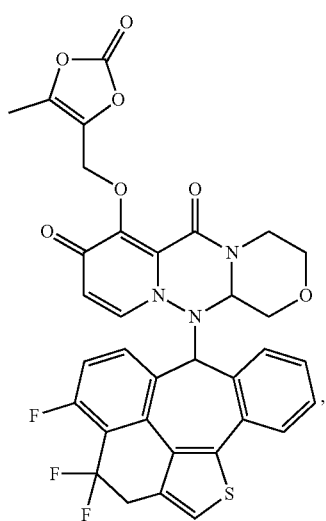

(529)
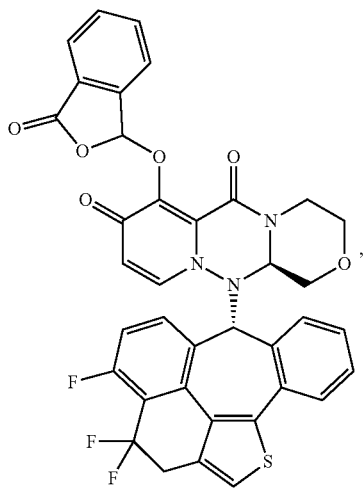
(530)
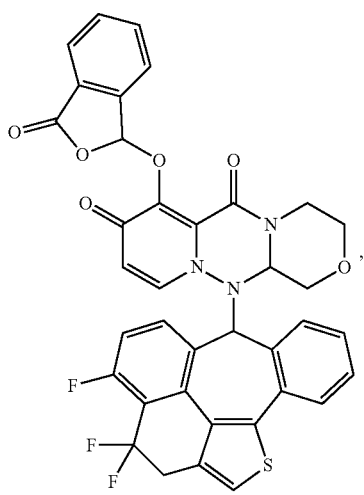
(531)
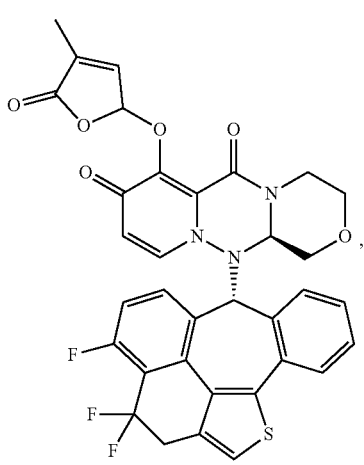
(532)
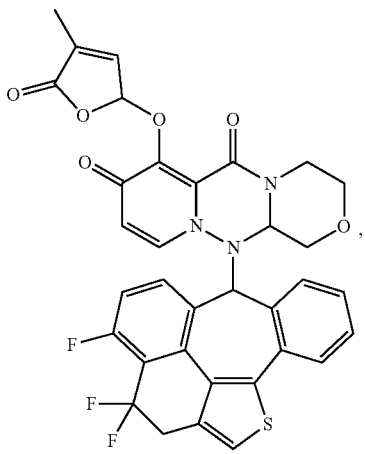
(533)
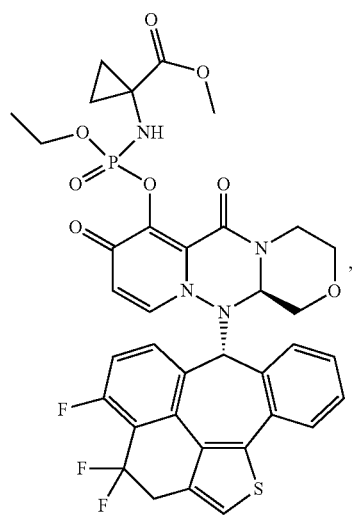
(534)
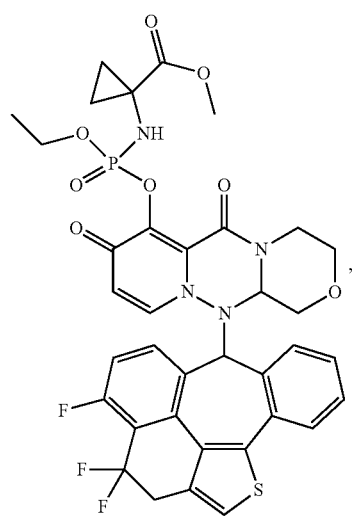

227
-continued
(535)
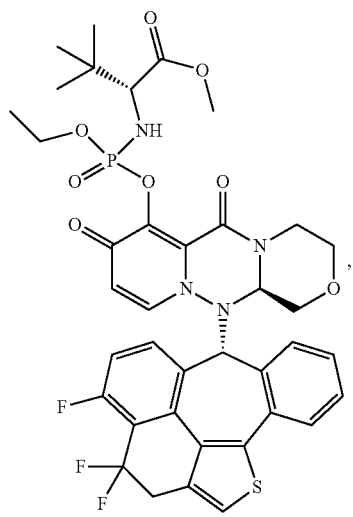
(536)
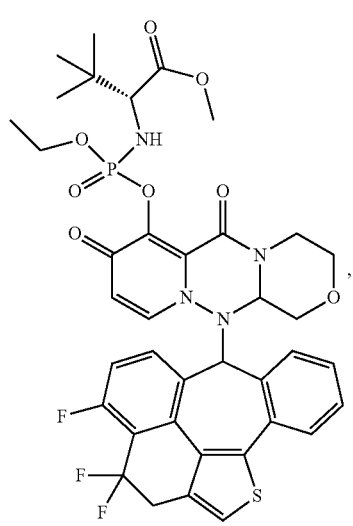
(537)
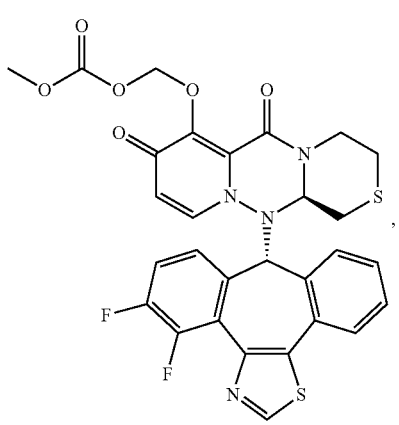
228
-continued
(538)
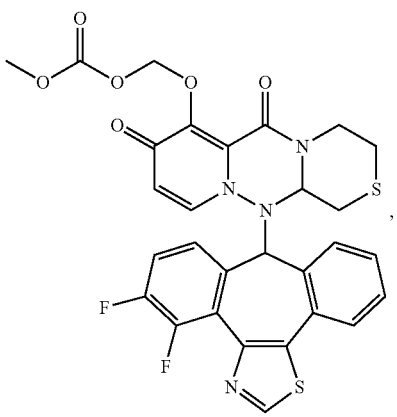
(539)
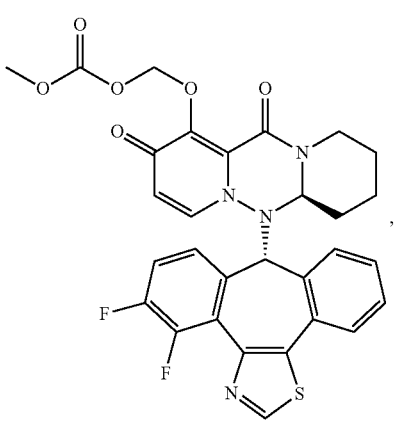
(540)
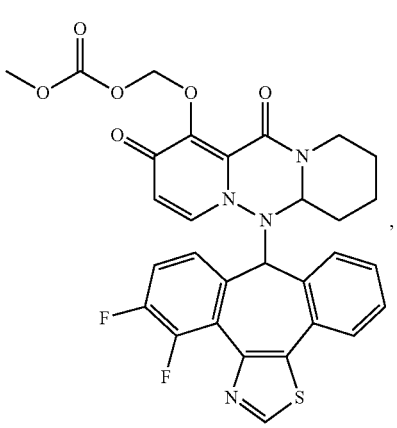
(541)
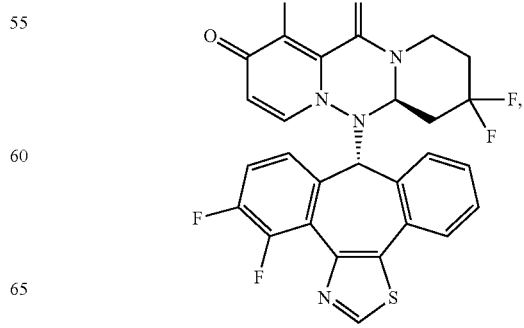

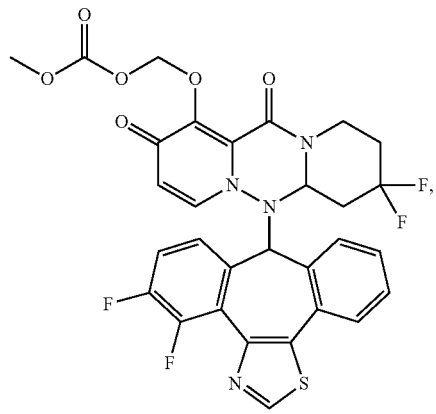
(542)
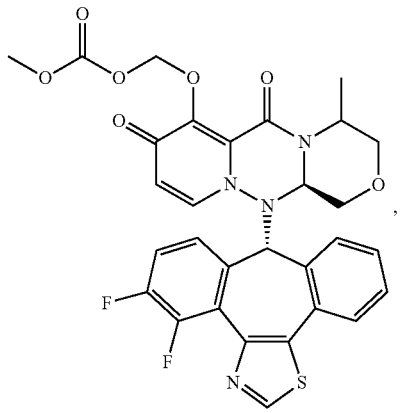
(545)
(543)
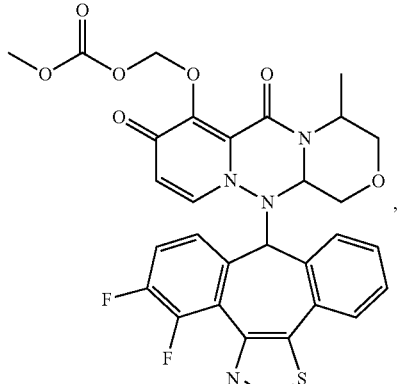
(546)
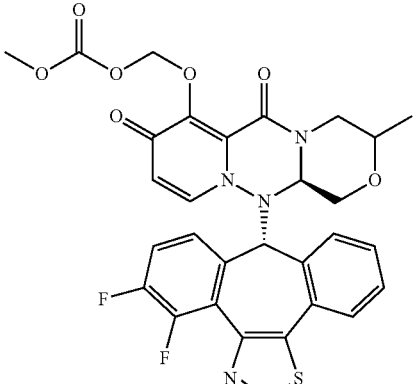
(547)
(544)
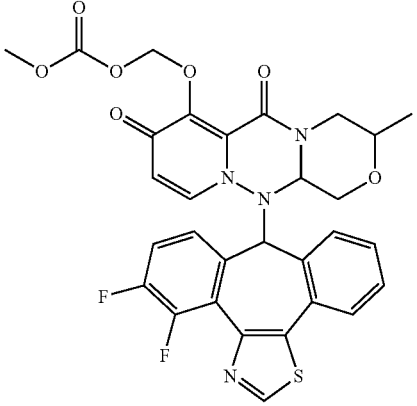
(548)

231
-continued
(549)
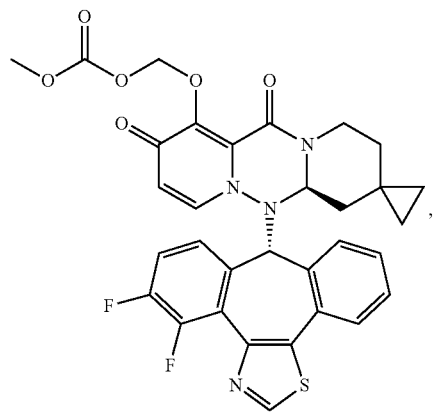
(550)
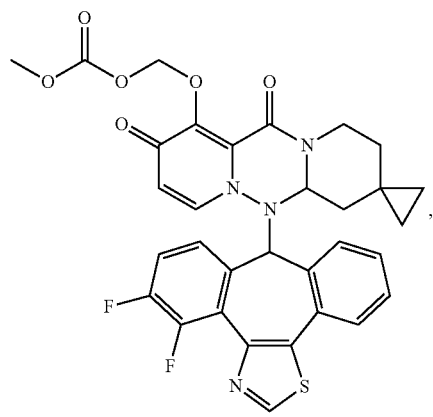
(551)
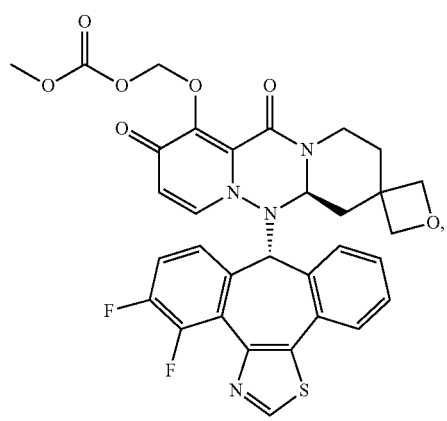
(552)
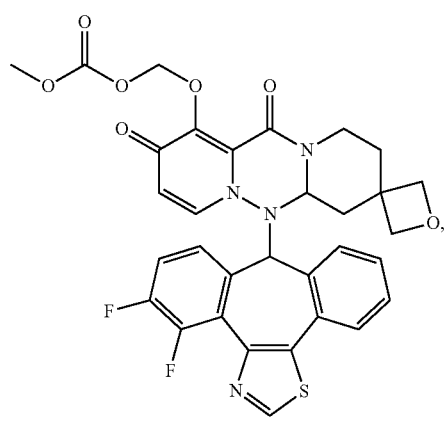
232
-continued
(553)
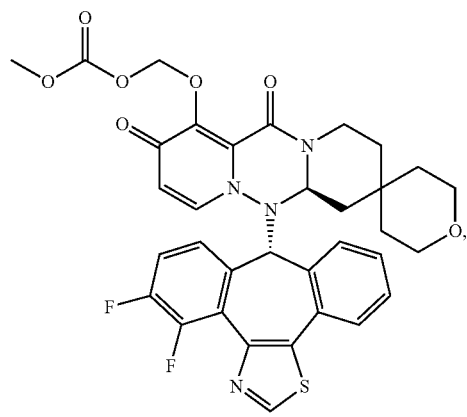
(554)
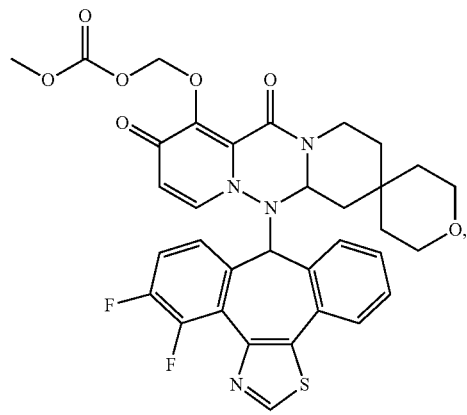
(555)
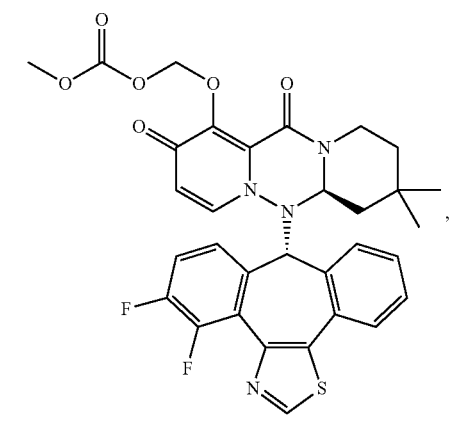
(556)
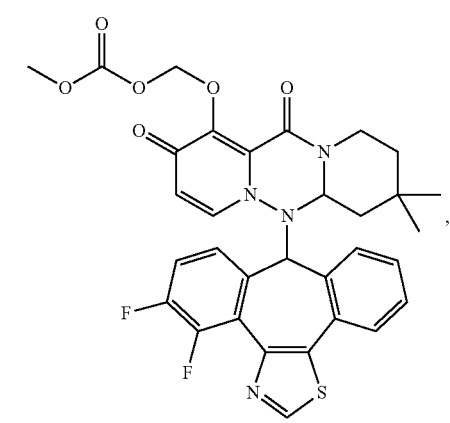

(557) 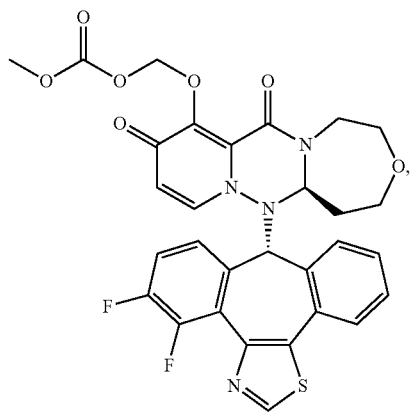
(558) 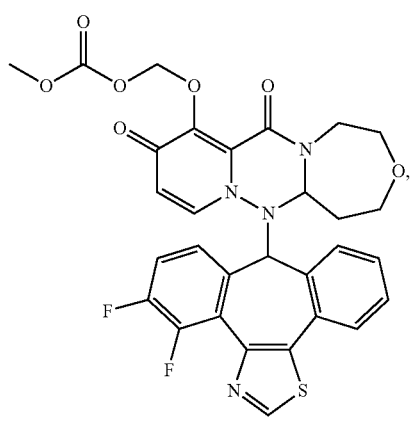
(559) 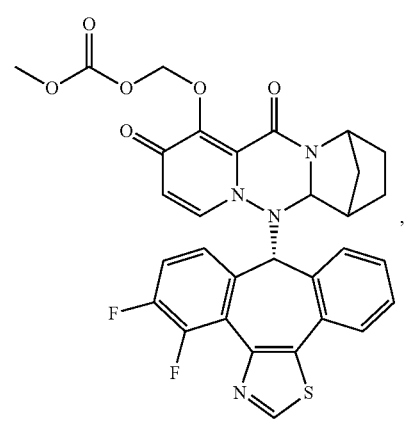
(560) 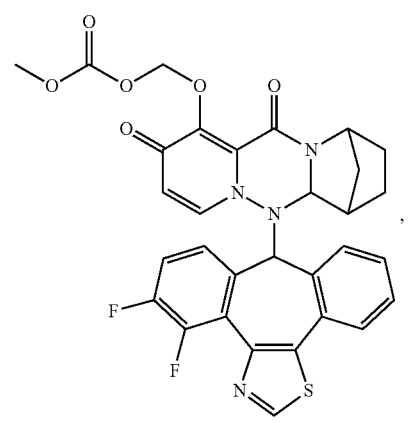
(561) 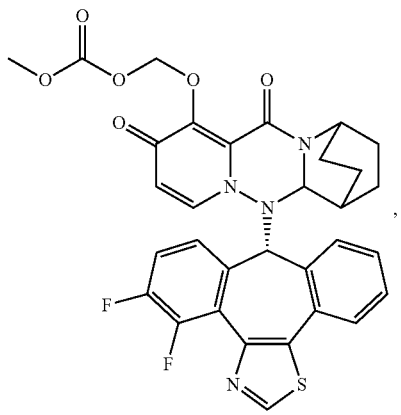
(562) 
(563) 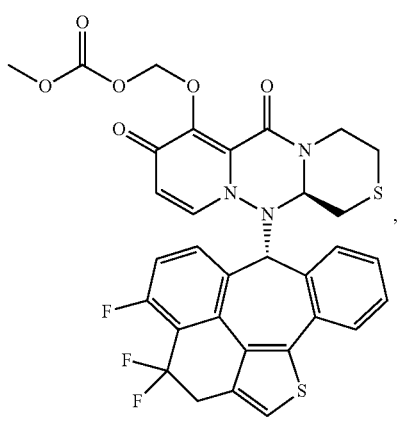
(564) 

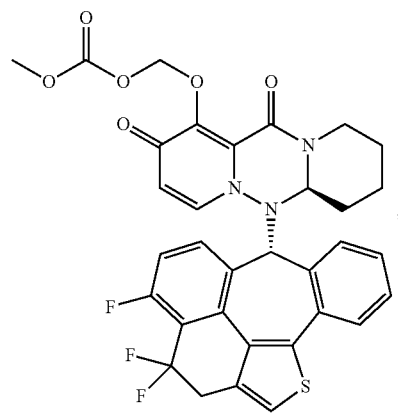
(565)
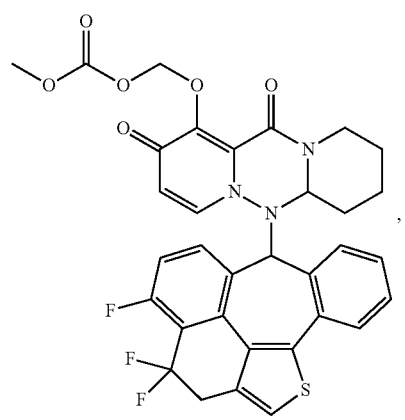
(566)
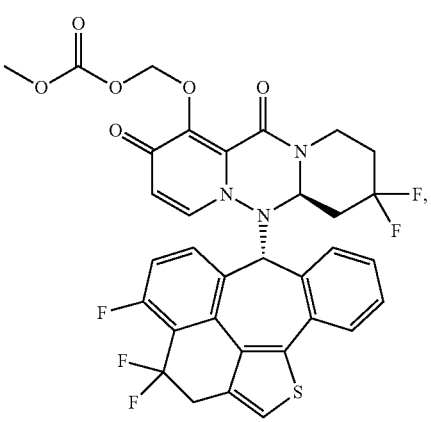
(567)
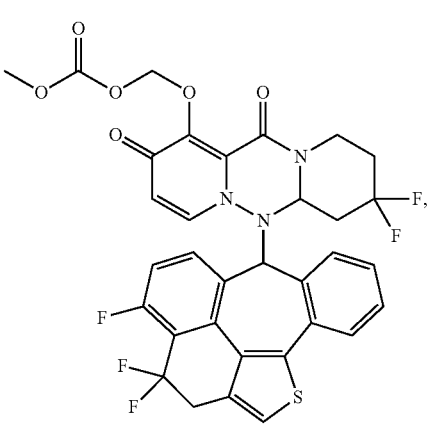
(568)
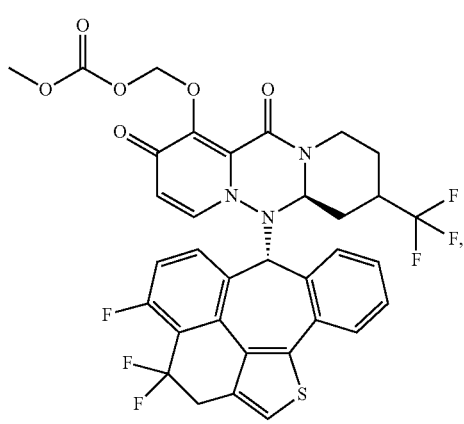
(569)
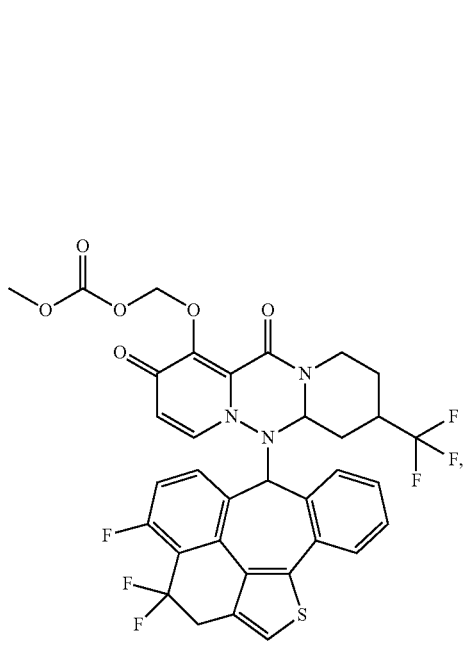
(570)
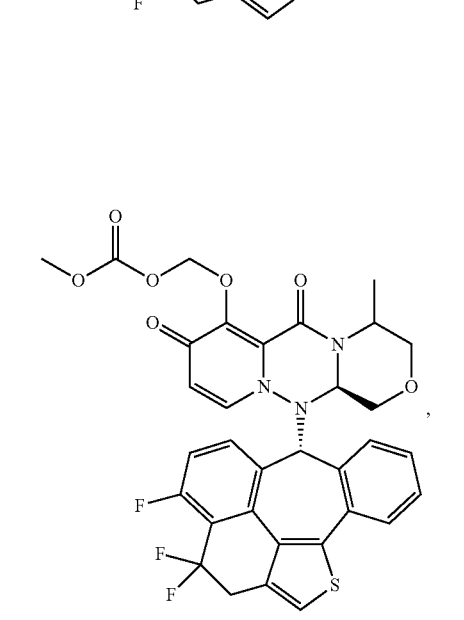
(571)

(572) 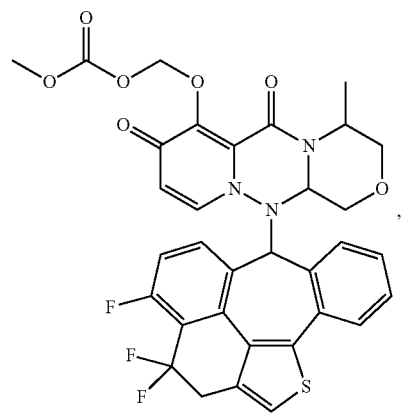,
(573) 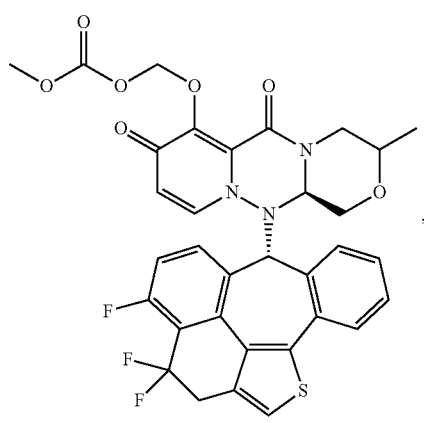,
(574) 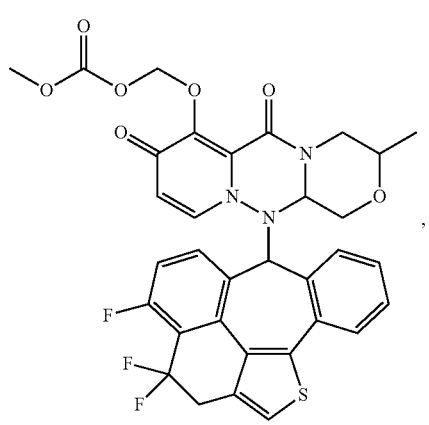,
(575) 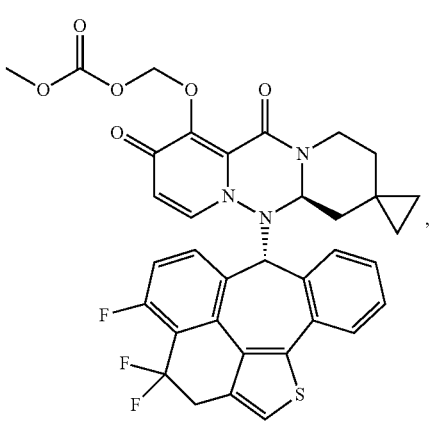,
(576) 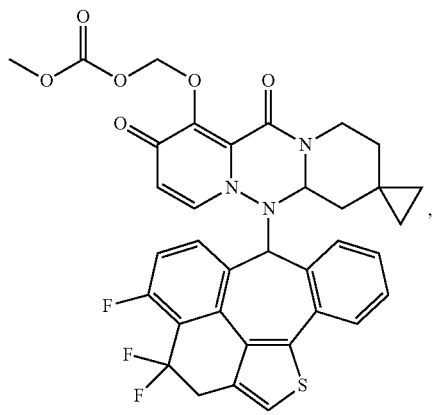,
(577) 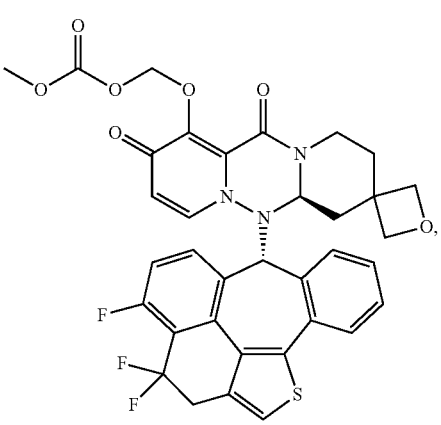,
(578) 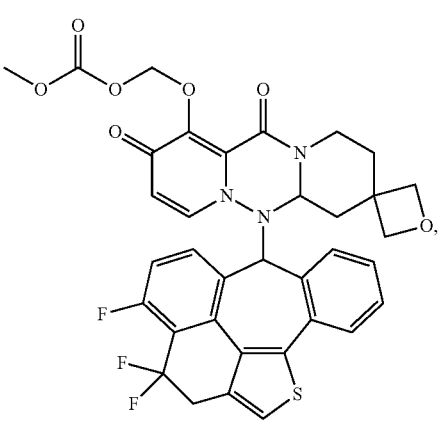,
(579) 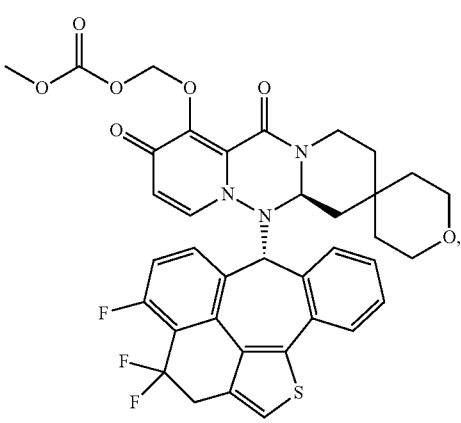, 239
-continued
(580)
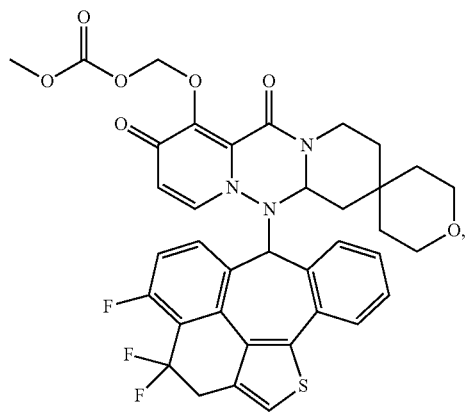
(581)
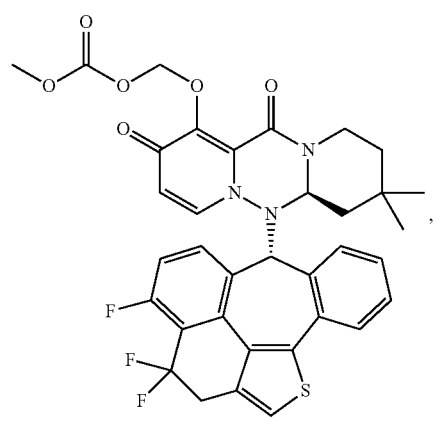
(582)
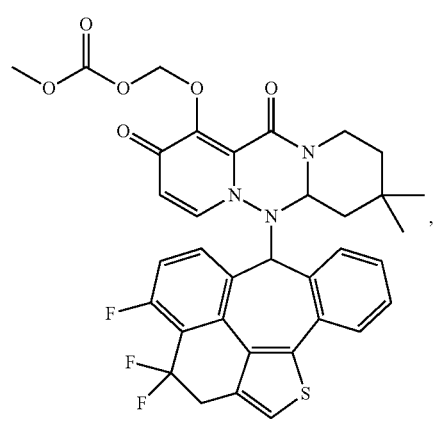
(583)
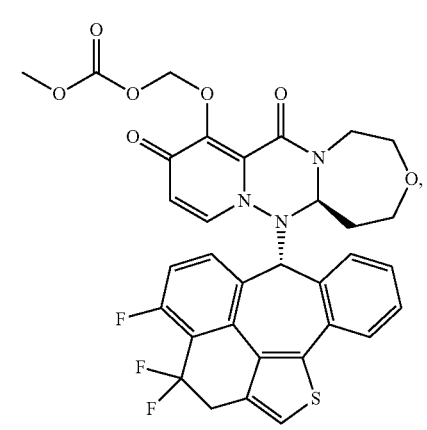
240
-continued
(584)
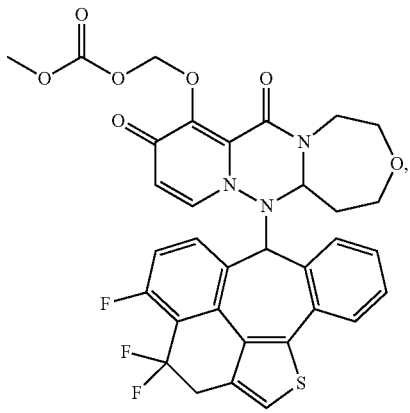
(585)
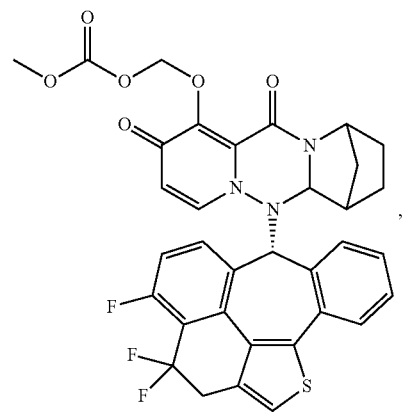
(586)
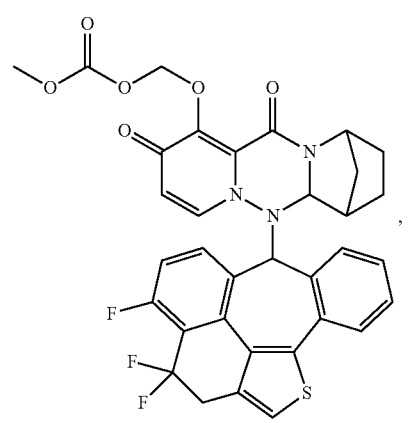
(587)
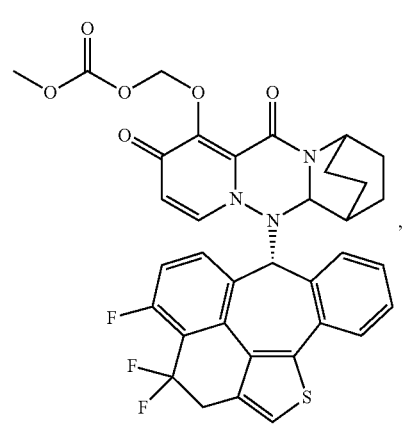

(588) 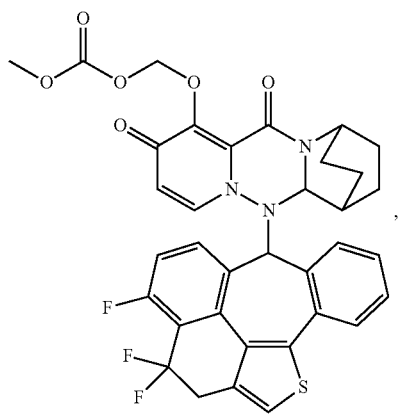
(589) 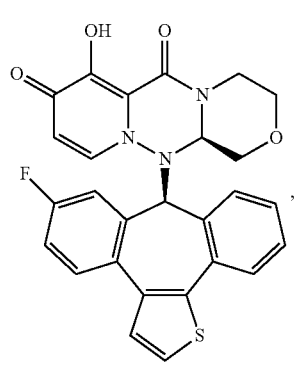
(590) 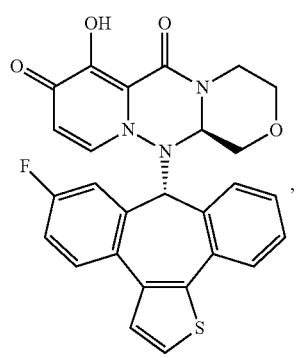
(591) 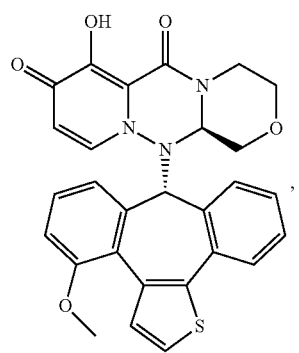
(592) 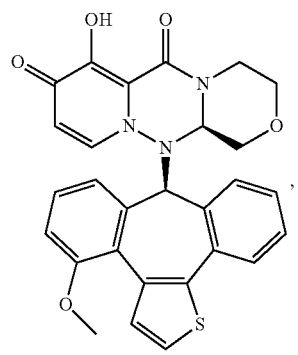
(593) 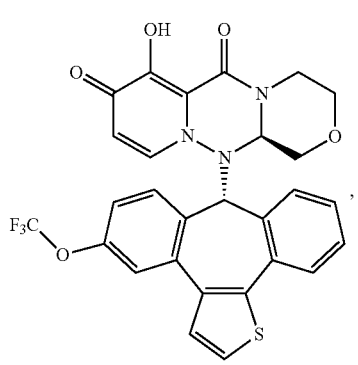
(594) 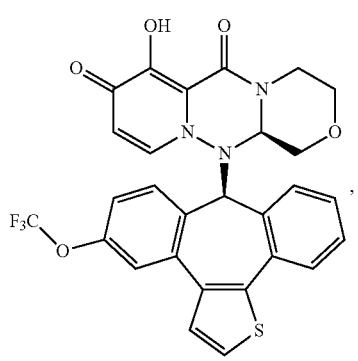
(595) 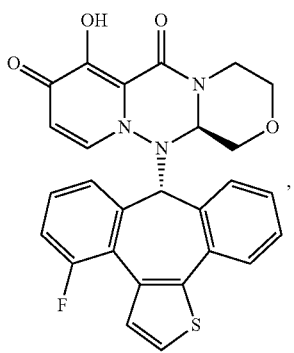

(596) 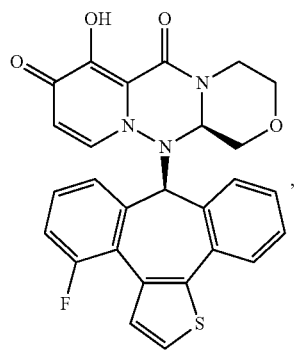
(597) 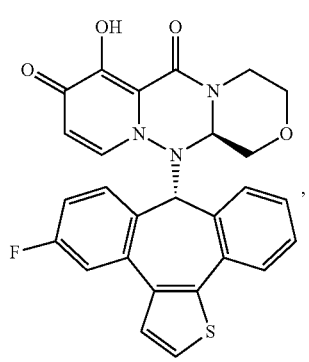
(598) 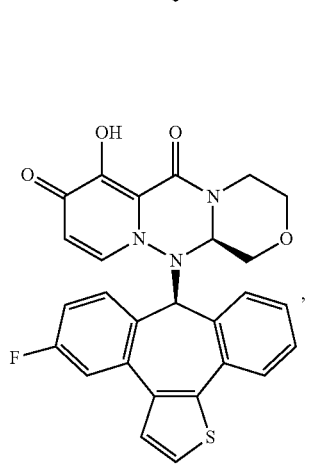
(599) 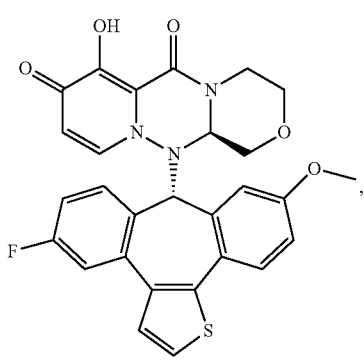
(600) 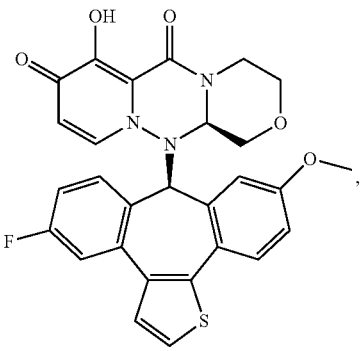
(601) 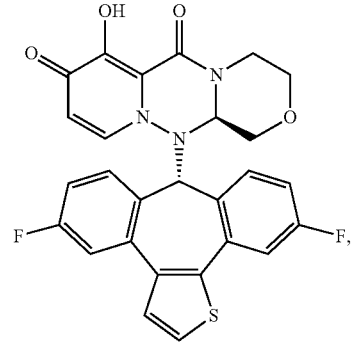
(602) 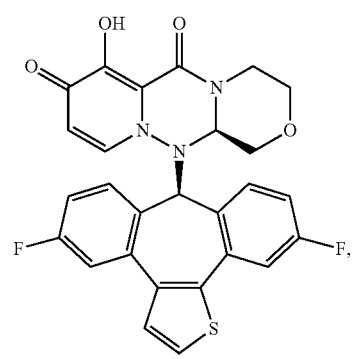
(604) 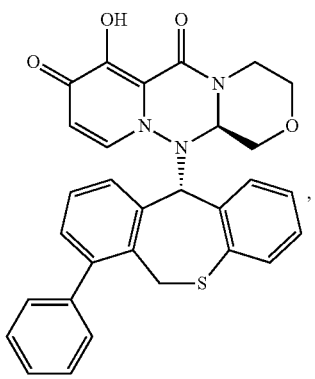

245
-continued
(605)
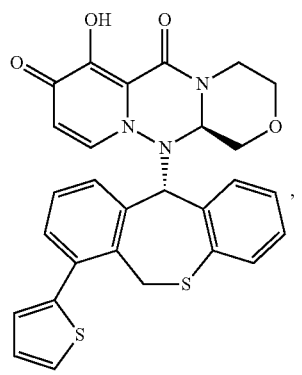
(606)
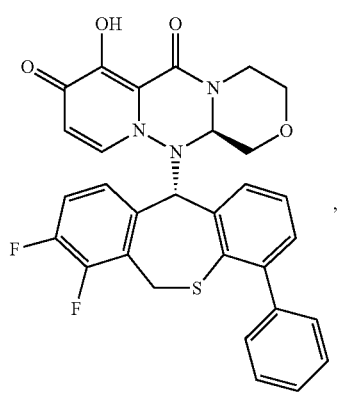
(607)
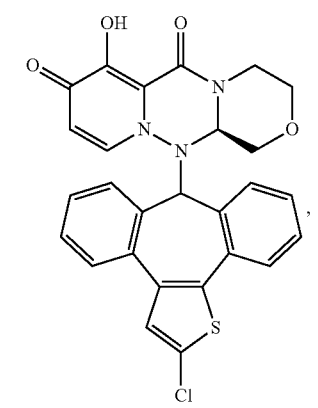
(608)
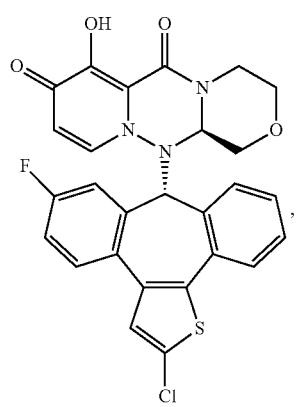
246
-continued
(609)
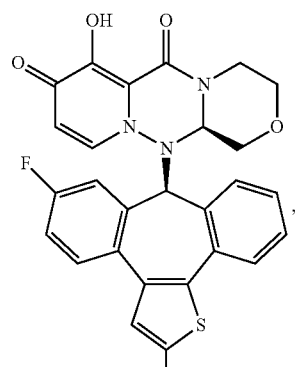
(610)
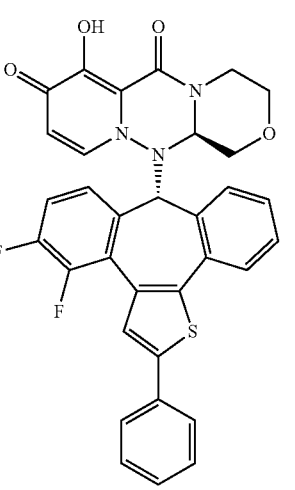
(611)
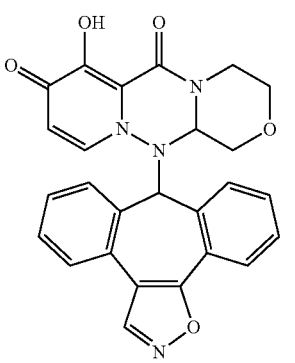
(612)
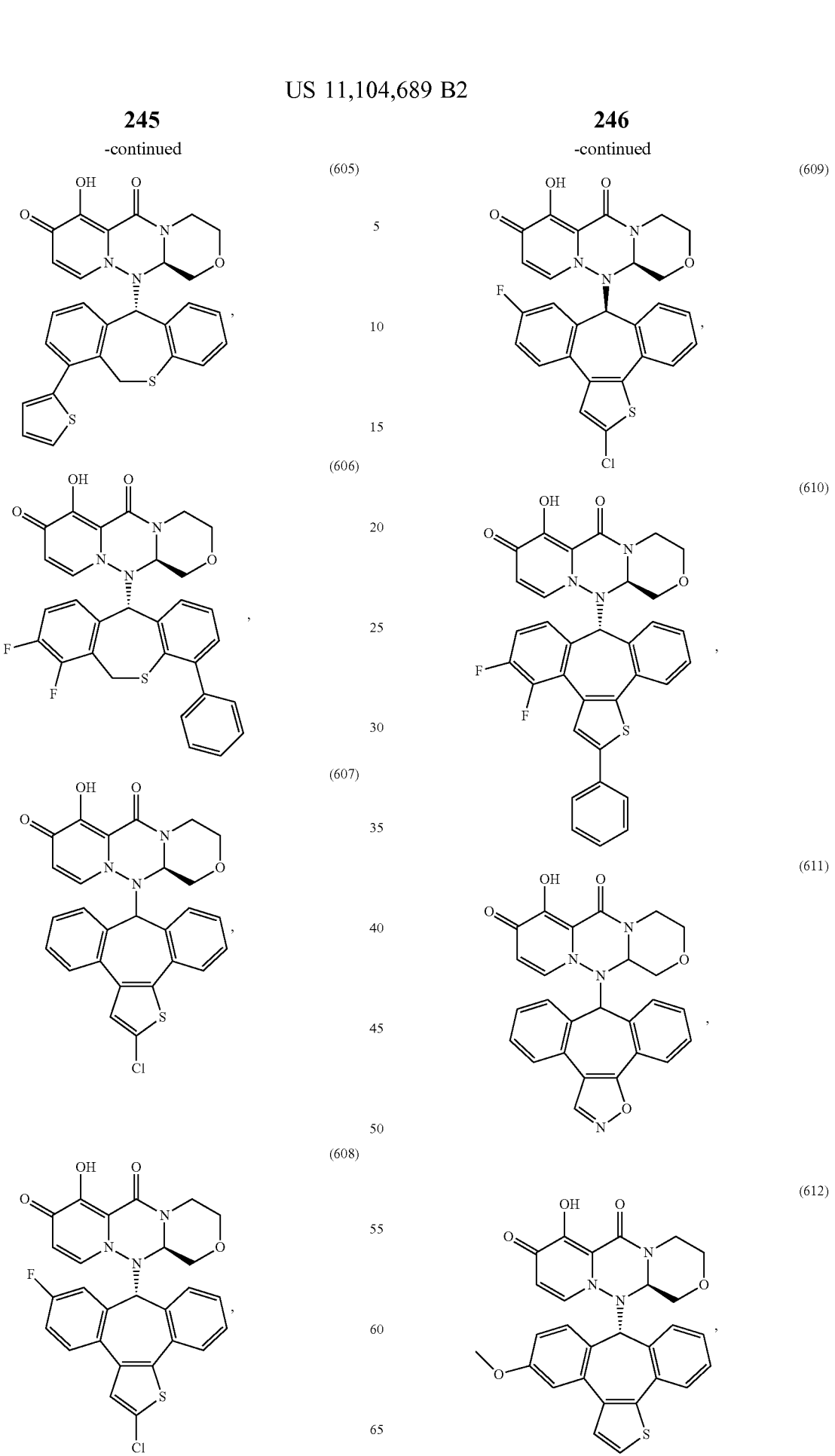

(613)
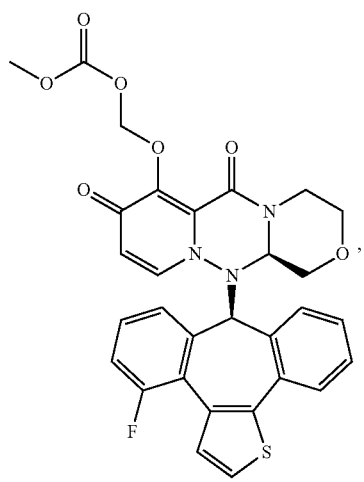
(614)
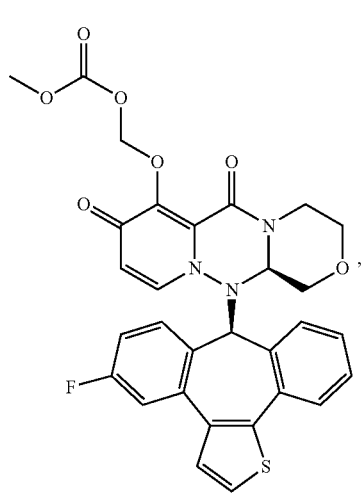
(616)
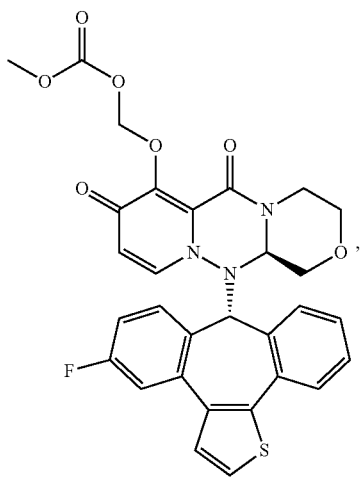
(617)
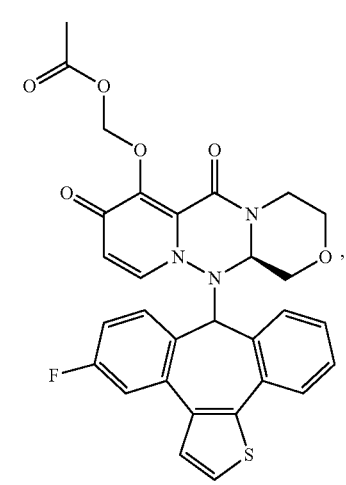

249
-continued
(619)
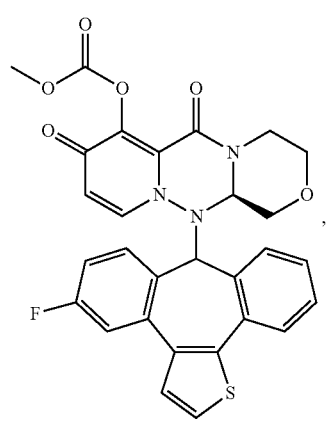,
(620)
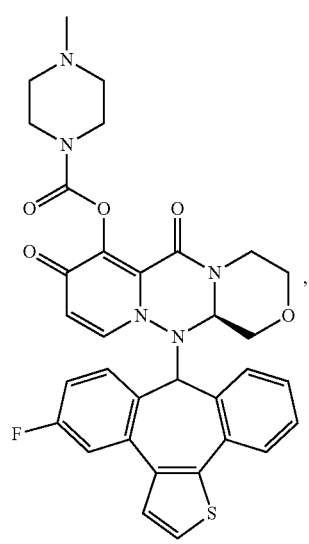,
(621)
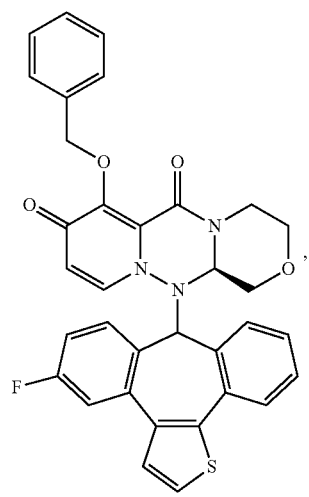,
250
-continued
(622)
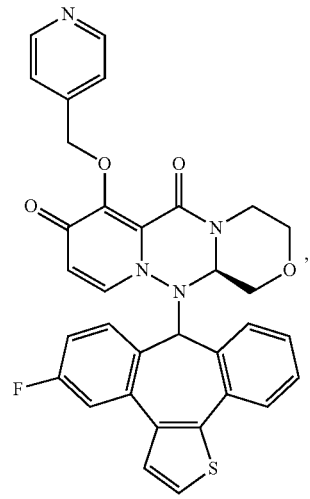,
(623)
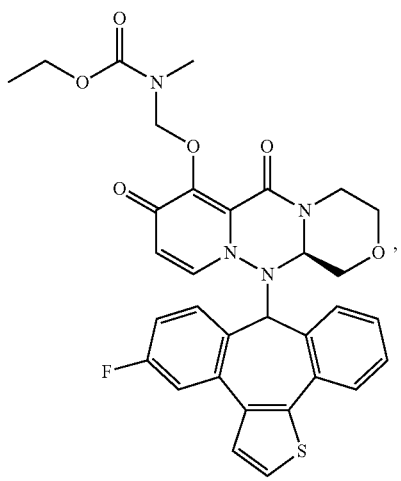,
(624)
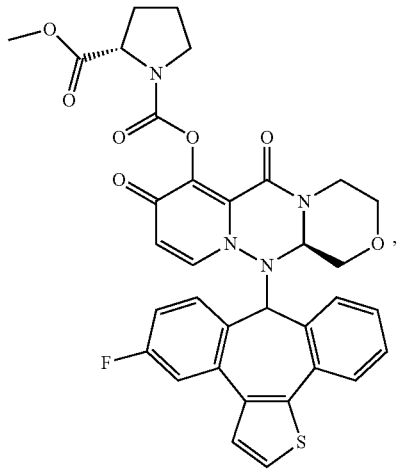, (625)
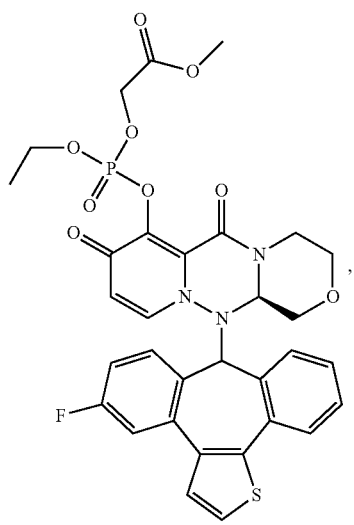
(626)
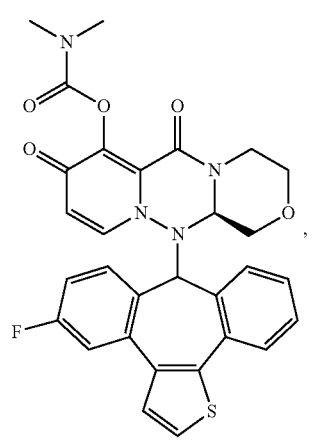
(627)
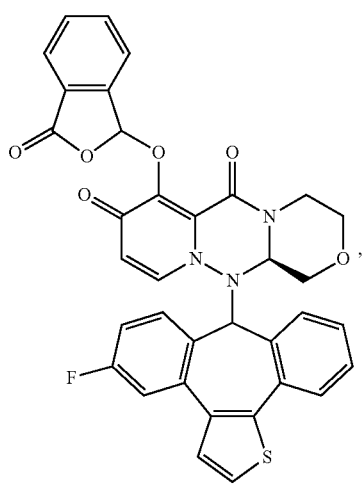
(628)
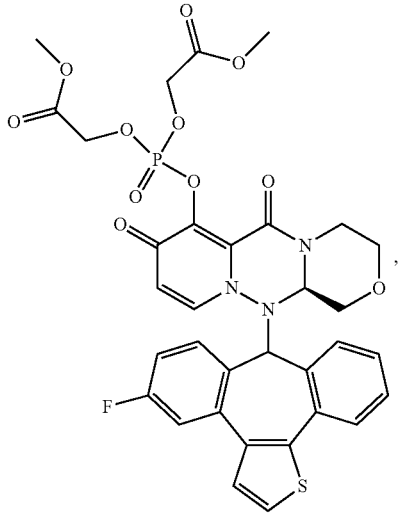
(629)
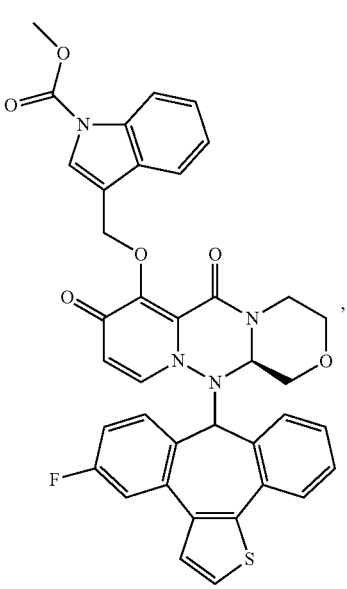
(630)
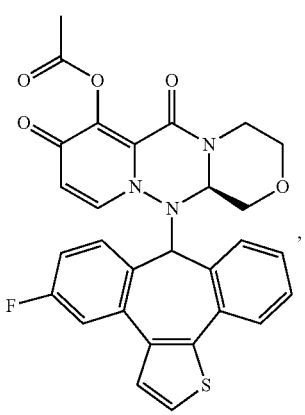

(631)
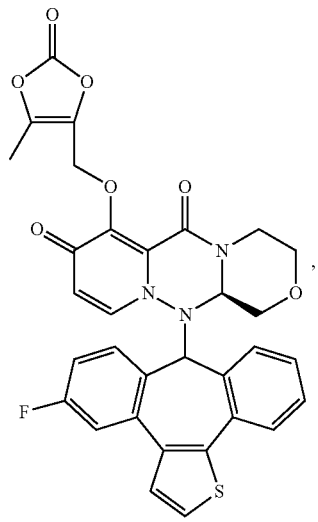
(632)
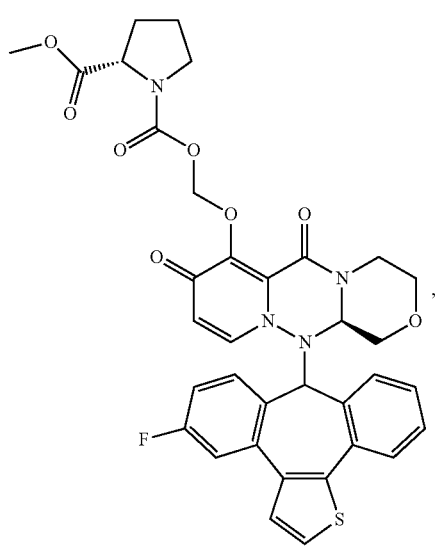
(633)
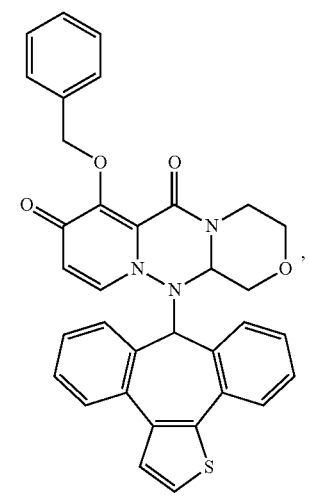
(634)
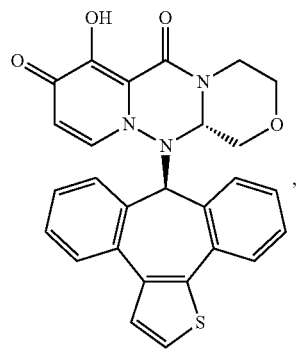
(635)
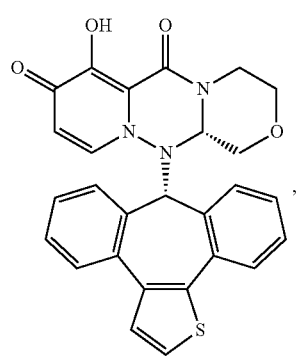
(636)
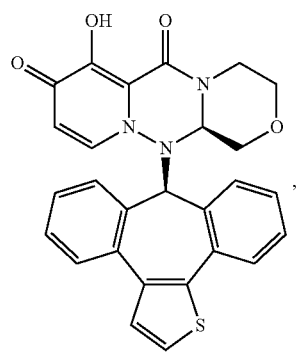
(637)
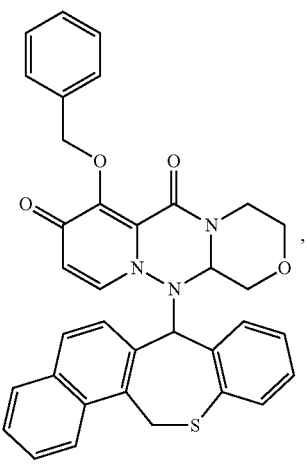

255
-continued
(638)
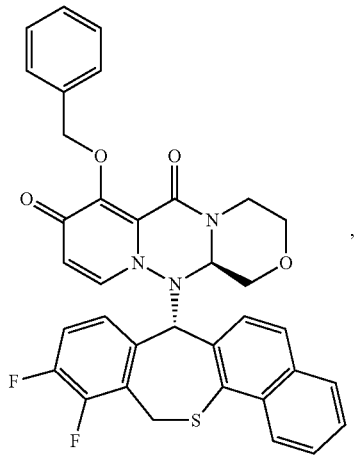
(639)
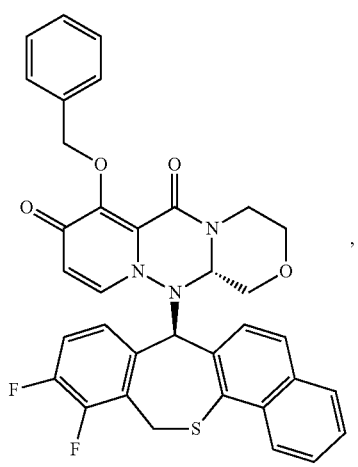
(640)
256
-continued
(641)
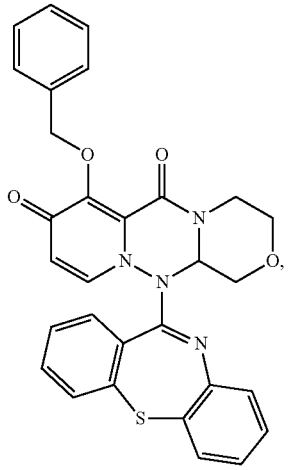
(643)
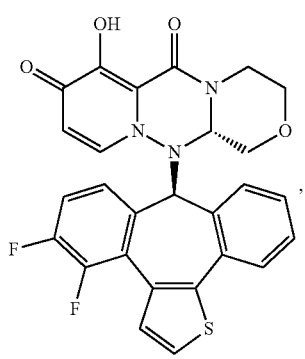
(644)
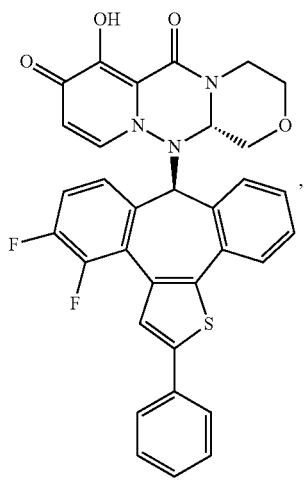

-continued
(645)
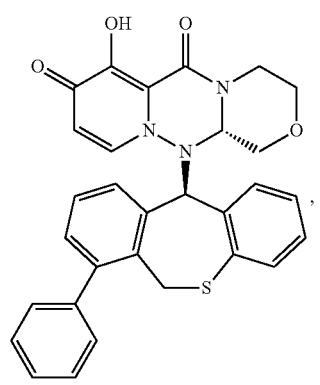
(646)
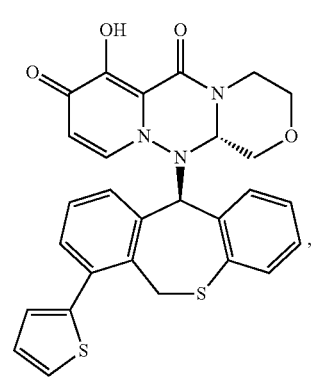
(647)
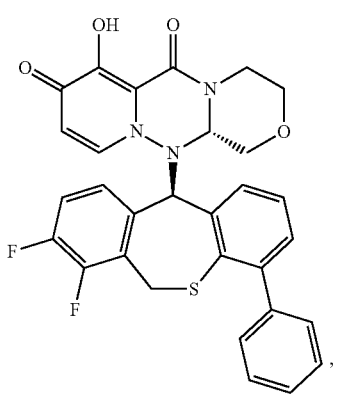
(648)
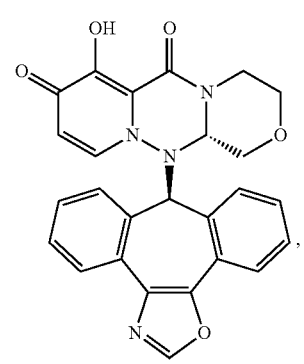
-continued
(649)
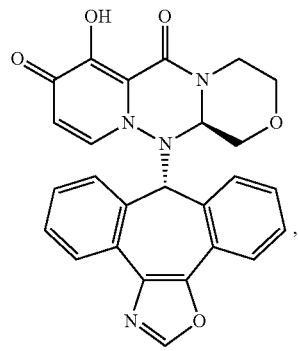
(650)
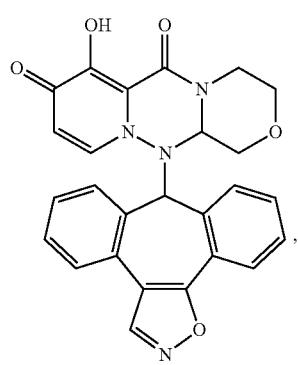
(651)
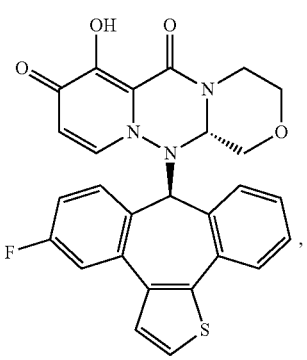
(652)
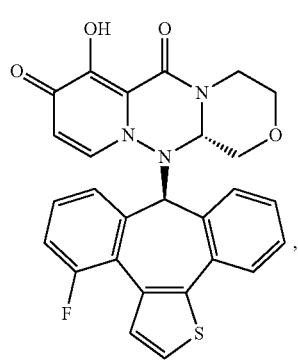

(653)

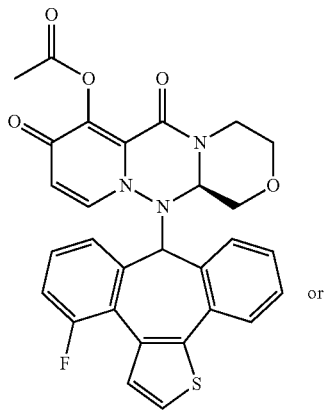

or (654)

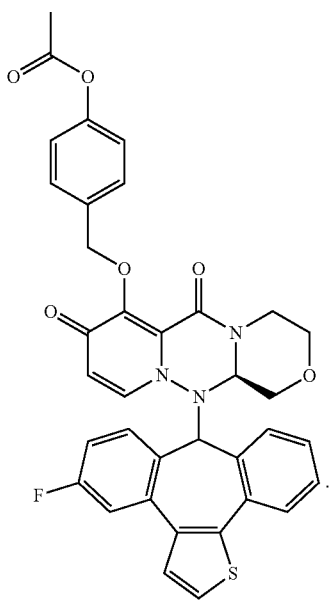

In other aspect, provided herein is a pharmaceutical composition comprising the compound disclosed herein.

In some embodiments, the compound further comprises at least one pharmaceutically acceptable carrier, adjuvant, vehicle and a combination thereof.

In some embodiments, the pharmaceutical composition of the present invention further comprises one or more other therapeutic agents.

In other embodiments, the other therapeutic agent is selected from anti-influenza agents or vaccines.

In other embodiments, the pharmaceutical composition can be liquid, solid, semisolid, gel or spray.

In other embodiments, other therapeutic agent of the pharmaceutical compositions relates to Amantadine, Rimantadine, Oseltamivir, Zanamivir, Peramivir, Lanimamivir, Lanimitine Laninamivir Octanoate Hydrate, Favipiravir, Arbidol, Ribavirin, Steffren, Ingavirin, Influenza Fludase), CAS No. 1422050-75-6, pimodivir, S-033188, Flu Vaccine (FluMist Quadrivalent®, Fluarix® Quadrivalent, Fluzone® Quadrivalent, Flucelvax® or FluBlok®), or their combination.

In other aspect, provided herein is use of the compound or the pharmaceutical composition disclosed herein in the manufacture a medicament for preventing, treating or reducing viral infectious diseases.

In some embodiments, the viral infection is an influenza virus infection.

In other aspect, provided herein is use of the compound or the pharmaceutical composition disclosed herein in the manufacture a medicament for inhibiting RNA polymerase of influenza virus.

In some embodiments, RNA polymerase is cap-dependent endonuclease.

Unless otherwise stated, all stereoisomers, geometric isomers, tautomers, solvates, hydrates, metabolites, salts and pharmaceutically acceptable prodrugs of the compounds disclosed herein are within the scope of the invention.

In some embodiments, the salt refers to a pharmaceutically acceptable salt. The term "pharmaceutically acceptable" means that a substance or composition must be chemically and/or toxically compatible with other components of the preparation and/or with mammals treated with it.

Other salts of compounds provided herein are also included, which are not necessarily pharmaceutically acceptable salts and can be used as intermediates for the preparation and/or purification of compounds of the present invention and/or for the separation of enantiomers of compounds of the present invention.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Moreover, the compounds of the present invention, including their salts, can also be obtained in the form of hydrates, or in the form of other solvents for their crystallization. The compounds of the present invention may inherently or by design form solvates with pharmaceutically acceptable solvents (including water); therefore, it is intended that the invention embrace both solvated and unsolvated forms.

In other aspect, the compounds of the present invention may contain several asymmetric centers or the forms of racemic mixtures commonly described. The invention also further comprises racemic mixtures, partial racemic mixtures and separated enantiomers and non-enantiomers.

Compounds of the invention may exist in the form of a possible isomer, a rotamer, an atropisomer, a tautomer or a mixture thereof. The invention may further comprise a mixture of isomer, rotamer, atropisomer and tautomer of the compounds of the invention, or a partial mixture of isomer, rotamer, atropisomer, tautomer or separated isomer, rotamer, atropisomer and tautomer.

Any formula given herein is also intended to represent isotopically unlabeled forms as well as isotopically labeled forms of the compounds. Isotope-labeled compounds have a structure described in the general formula provided by the present invention, except that one or more atoms are replaced by atoms with selected atomic weight or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$ $^{32}P$, $^{36}S$, $^{37}Cl$, or $^{125}I$, respectively.

In another aspect, the compounds of the invention include isotopically labeled compounds as defined herein, for example those within radioactive isotopes, such as $^3H$, $^{14}C$ and $^{18}F$, or those within non-radioactive isotopes, such as $^2H$ and $^{13}C$. Such isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$-labeled compound may be particularly desirable for PET or SPECT studies. Isotopically-labeled compounds of Formula (I) can generally be prepared by conventional techniques known to those skilled in the art or by processes analogous to those described in the accompanying examples and preparations using an appropriate isotopically-labeled reagent in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index, for example increased in vivo half-life or reduced dosage requirements or an improvement in therapeutic index. It is understood that deuterium in this context is regarded as a substituent of a compound of Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, $d_6$-acetone, DMSO-$d_6$.

In other aspect, provided herein is a method of preparing, separating or purifying the compound of Formula (I).

Pharmaceutical Composition of the Compound of the Invention and Preparations and Administration The invention provides a pharmaceutical composition comprising the compounds or stereoisomers, racemic or non-racemic mixtures of isomers or pharmaceutically acceptable salts or solvents thereof. The pharmaceutical composition further comprises at least one pharmaceutically acceptable carrier, diluent, adjuvant or vector, and optionally other therapeutic and/or preventive components. In some embodiments, the pharmaceutical composition comprises an effective amount of at least one pharmaceutically acceptable carrier, diluent, adjuvant or vector.

Pharmaceutically acceptable carriers may contain inert components that do not unduly inhibit the biological activity of compounds. Pharmaceutically acceptable carriers should be biocompatible, such as non-toxic, non-inflammatory, non-immunogenic or without other adverse reactions or side effects once applied to patients. Standard pharmaceutical technology is available.

As described above, the pharmaceutical compositions or pharmaceutically acceptable compositions disclosed herein further comprise a pharmaceutically acceptable carrier, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, disclosed various carriers for use in formulating pharmaceutically acceptable compositions and known methods of preparation thereof. Except insofar as any conventional carrier medium incompatible with the compounds disclosed herein, such as by producing any undesirable biological effect or otherwise interacting in a deleterious manner with any other components of the pharmaceutically acceptable composition, its use is contemplated to be within the scope of this invention.

Some examples of materials that can be used as pharmaceutically acceptable carriers include, but are not limited to ion exchanger, alumina, aluminum stearate, lecithin, serum protein (eg. human serum albumin), buffer substances (eg. Tween 80, phosphate, glycine, sorbic acid or potassium sorbate), saturated plant fatty acids Partial glyceride mixture, water, salt or electrolyte (eg. protamine sulfate, disodium hydrogen phosphate, potassium hydrogen phosphate, sodium chloride or zinc salt), silica gel, magnesium trisilicate, polyvinyl pyrrolidone, polyacrylate, wax, Polyethylene-polyoxypropylene-block copolymer, methylcellulose, hydroxypropylmethylcellulose, lanolin, sugars (eg. lactose, glucose and sucrose), starch (eg. corn starch and potato starch), fiber And its derivatives (eg. sodium carboxymethyl cellulose, ethyl cellulose and cellulose acetate), powdered tragacanth, malt, gel, talc, excipients (eg. cocoa butter and suppository wax), oil (eg. peanut oil, cottonseed oil, safflower oil, sesame oil, olive oil, corn oil and soybean oil), ethylene glycol (eg. propylene glycol or polyethylene glycol), esters (eg. ethyl oleate and ethyl dodecanoate)), agar, buffer (eg. magnesium hydroxide and aluminum hydroxide), alginic acid, pyrogen-free water, isotonic saline, Ringer's solution (Ringer's solution), ethanol, and phosphate buffer, other non-toxic compatible lubricants (eg. sodium lauryl sulfate and magnesium stearate), and colorants, anti-adhesives, coatings, sweeteners and flavoring agents, preservatives and antioxidants may also be present in the compositions according to the formulator's judgment.

The compounds or compositions of the invention may be administered by any suitable means, which are administered to humans or other animals orally, rectally, parenterally, intracisternally, intravaginally, intraperitoneally, topically (as with powders, ointments or drops), etc., to humans or other animals according to the severity of the infection.

Liquid dosage forms for oral administration include, but are not limited to, pharmaceutically acceptable emulsions, microemulsions, solutions, suspensions, syrups and elixirs. In addition to the active compound, the liquid dosage forms may contain inert diluent commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butanediol, dimethylformamide, oils (in particular, cottonseed oil, peanut oil, corn oil, germ oil, olive oil, castor oil and sesame oil), glycerol, tetrahydrofuryl alcohol, polyethylene glycols and fatty acid esters of sorbitan, and mixtures thereof. In addition to the inert diluent, the oral compositions may also contain adjuvants such as wetting agents, emulsifying or suspending agents, sweetening agents, flavoring agents and fragrances.

Injectable preparations, such as sterile injectable aqueous or oily suspensions, may be formulated using suitable dispersing or wetting agents and suspensions in accordance with common techniques. The sterile injectable preparation may also be a non-toxic parenterally acceptable diluent or sterile injectable solution in solvent, a suspension or an emulsion such as a solution in 1,3-butanediol. Among the acceptable vehicles and solvents, what can be employed are water, Ringer's solution, U.S.P., and isotonic sodium chloride solution. In addition, sterile fixed oils are conventionally employed as a solvent or suspension medium. For this purpose, any odorless, fixed oil may be employed including synthetic monoglycerides or diglycerides. In addition, fatty acids, such as oleic acid, are used in the preparation of injectables.

For example, the injectable preparation can be sterilized by filtration through a bacterial retention filter or by the addition of a bactericidal agent which is previously dissolved or dispersible in sterile water or other sterile injectable medium.

In order to prolong the action of the compounds or compositions of the invention, it is often desirable to slow the absorption of the compound by subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of the parenterally administered compound can be achieved by dissolving or suspending the compound in an oil vehicle. Injectable storage forms are made by forming a microcapsule matrix of a compound in a biodegradable polymer such as polylactide-polyglycolic acid. The rate of compound release can be controlled based on the ratio of compound to polymer and the nature of the particular polymer employed. Examples of other biodegradable polymers include polyorthoesters and polyanhydrides. Injectable depot formulations are also prepared by entrapping the compound in liposomes or microemulsions which are compatible with body tissues.

Compositions for rectal or vaginal administration may in particular be by mixing a compound of the invention together with a suitable non-irritating excipient or carrier which is solid at ambient temperature but liquid at body temperature and thus melting and releasing the active compound in the rectum or vaginal cavity.

Oral solid dosage forms include capsules, tablets, pills, powders and granules. In these solid dosage forms, the active compounds are mixed with at least one pharmaceutically acceptable inert excipient or carrier such as sodium citrate or calcium phosphate or a filler or a) fillers such as starch, lactose, sucrose, glucose, mannitol and silicic acid, b) binders such as carboxymethylcellulose, alginates, gelatin, polyvinylpyrrolidone, sucrose and acacia, c) humectants such as glycerol, d) disintegrating agents such as agar, calcium carbonate, potato starch or tapioca starch, alginic acid, certain silicates and sodium carbonate, e) blocker solutions such as paraffin, f) absorption enhancers such as quaternary amines, g) wetting agents such as cetyl alcohol and glyceryl monostearate, h) absorbents such as kaolin and bentonite, i) lubricants such as talc, calcium stearate, magnesium stearate, solid polyethylene glycol, sodium lauryl sulfate, and mixtures thereof. In the case of capsules, tablets and pills, the formulations may also comprise buffering agents.

Solid compositions of a similar type may also be employed as fillers in soft and hard gel capsules using such excipients as lactose or milk sugar as well as high molecular weight polyethylene glycols. Solid dosage forms of tablets, lozenges, capsules, pills and granules can be prepared with coatings and shells, for example enteric coatings and other coatings well known in the pharmaceutical arts. They may optionally contain opacifying agents and may also be of a nature such that the active ingredient is optionally released in a delayed manner or, preferably, in a portion of the intestinal tract. Examples of embedding compositions that can be used include polymeric substances and waxes. Solid compositions of a similar type may also be employed as fillers in soft and hard gel capsules using such excipients as lactose or milk sugar as well as high molecular weight polyethylene glycols.

The active compounds may also be presented in microencapsulated form with one or more of the above-mentioned excipients. Solid dosage forms of tablets, lozenges, capsules, pills, and granules can be prepared with coatings and shells such as enteric coatings, controlled release coatings, and other coatings well known in the pharmaceutical arts. In these solid dosage forms, the active compound may be mixed with at least one inert diluent, such as sucrose, lactose or starch. In general, such dosage forms may also contain additional materials other than inert diluents, such as tableting lubricants and other tableting aids, eg. magnesium stearate and microcrystalline cellulose. In the case of capsules, tablets and pills, the formulations may also comprise buffering agents. They may optionally contain opacifying agents and may also be of a nature such that the active ingredient is optionally released in a delayed manner or, preferably, in a portion of the intestinal tract. Examples of embedding compositions that can be used include polymeric substances and waxes.

Topical or transdermal administration forms of the compounds of the invention include ointments, ointments, creams, lotions, gels, powders, solutions, sprays, inhalants or patches. Under sterile conditions, the active compound is combined with a pharmaceutically acceptable carrier and any required preservatives or buffers which may be required. Ophthalmic formulations, ear drops, and eye drops are also considered as being within the scope of the invention. Additionally, the present invention contemplates the use of a dermal patch that provides the added benefit of controlling the delivery of the compound to the body. This dosage form can be prepared by dissolving or dispersing the compound in an appropriate medium. Absorption accelerant can also be used to increase the flow of compounds through the skin. The rate can be controlled by providing a rate controlling membrane or by dispersing the compound in a polymer matrix or gel.

The composition of the invention may also be administered orally, parenterally, by inhalation spray via topical, rectal, nasal, buccal, vaginal or by implantation of a kit. The term "parenteral" as used in the present invention includes, but is not limited to, subcutaneous, intravenous, intramuscular, intra-articular, intrasynovial, intrasternal, intrathecal, intrahepatic, intralesional, and intracranial injection or infusion techniques. The composition of the invention is administered orally, intraperitoneally or intravenously particularly.

The sterile injectable form of the composition of the prevention may be water or oil suspension. These suspensions can be prepared following techniques known in the art using suitable dispersing or wetting agents and suspension. The sterile injectable preparation may also be a non-toxic parenterally acceptable diluent or sterile injectable solution in solvent or a suspension, such as a solution in 1,3-butanediol. Among the acceptable vehicles and solvents, what can be employed are water, Ringer's solution, and isotonic sodium chloride solution. In addition, sterile fixed oils are conventionally employed as a solvent or suspension medium. For this purpose, any odorless, fixed oil may be employed including synthetic monoglycerides or diglycerides. In addition, it is as with that natural pharmaceutically acceptable oils, especially in the form of polyoxyethylenated, such as olive oil or castor oil, fatty acids such as oleic acid and its glyceride derivatives are used in the preparation of injectables. These oil solutions or suspensions may also contain a long-chain alcohol diluent or dispersant, such as carboxymethylcellulose or similar dispersants which are conventionally employed in the formulation of pharmaceutically acceptable dosage forms (including emulsions and suspensions). Other commonly used surfactants, such as Tweens, Spans, and other emulsifiers or bioavailability enhancers commonly used in the manufacture of pharmaceutically acceptable solid, liquid or other dosage forms can also be used for formulation purposes.

The pharmaceutical compositions of the present invention can be orally administered in any orally acceptable dosage form including, but not limited to, capsules, tablets, aqueous suspensions or solutions. In the case of oral tablets, conventional carriers include, but are not limited to, lactose and starch. A lubricant such as magnesium stearate is also usually added. For oral administration in capsule form, useful diluents include lactose and dried cornstarch. When an aqueous suspension is required orally, the active ingredient is combined with emulsifier and suspension. Some sweeteners, flavor enhancers or colorants may also be added if desired.

Alternatively, the pharmaceutical compositions of the invention may be administered in the form of a suppository for rectal use. These pharmaceutical compositions can be prepared by mixing agents and non-irritating excipients which are solid at room temperature but liquid at the rectal temperature and therefore will melt in the rectum to release the drug. Such substances include, but are not limited to, cocoa butter, beeswax, and polyethylene glycol.

The pharmaceutical compositions of the present invention may also be administered topically, especially when the therapeutic target includes areas or organs that are readily accessible by topical administration, including ocular, cutaneous or low intestinal disease. It is easy to prepare suitable topical formulations for each of these areas or organs.

Topical administration to the lower intestinal tract can be achieved in a rectal suppository formulation (seen above) or a suitable enema formulation. A topical skin patch can also be used.

For topical administration, the pharmaceutical compositions may be formulated as a suitable ointment containing the active component suspended or dissolved in one or more carriers. Suitable carriers of compounds for topical administration of the present invention include, but are not limited to, mineral oil, vaseline oil, white petrolatum, propylene glycol, polyoxyethylene, polyoxypropylene compounds, emulsified waxes and water. For topical application, the pharmaceutical compositions may be formulated as a suitable ointment containing the active component suspended or dissolved in one or more carriers. Suitable carriers include, but are not limited to, mineral oil, sorbitan monostearate, polysorbate 60, cetyl ester wax, cetostearyl alcohol, 2-octyl dodecanol, benzyl alcohol and water.

For ophthalmic use, the pharmaceutical compositions may be formulated as micronized suspensions in isotonic pH adjusted sterile saline, or especially solution in isotonic pH adjusted sterile saline, with or without a preservative such as benzalkonium chloride. Alternatively, for ophthalmic use, the pharmaceutical composition can be formulated as a salve, such as petrolatum.

The pharmaceutical composition can also be administered by nasal aerosolized spray or by inhalation. This composition is prepared according to techniques well known in the pharmaceutical arts and prepared into solutions using benzyl alcohol and other suitable preservatives, absorption enhancer for improving bioavailability, fluorocarbons and/or other conventional solubilizers or dispersants.

The compounds used in the methods of the invention can be formulated in unit dosage form. The term "unit dosage form" refers to physically discrete units suitable as unitary dosages of the subject, each unit containing a predetermined amount of active substance calculated to produce the desired therapeutic effect, optionally in association with a suitable pharmaceutical carrier. The unit dosage form can be one of a single daily dose or multiple daily doses (e.g., about 1-4 or more times per day). When multiple daily doses are used, the unit dosage form for each dose may be the same or different.

Use of the Compounds and Pharmaceutical Compositions

The above compounds and pharmaceutical compositions provided by the present invention are used in the manufacture of medicaments for preventing, treating or ameliorating a viral infectious disease in a patient. Preferably, the viral infection is an influenza virus infection.

The present invention also provides the use of the above compound or a pharmaceutical composition thereof in the manufacture of a medicament for inhibiting influenza virus RNA polymerase, preferably the RNA polymerase is a cap-dependent endonuclease.

The present invention provides a method for treating, preventing or delaying an infection caused by a virus, the method comprising administering to a patient in need of treatment a therapeutically effective amount of the above compound or a pharmaceutical composition thereof. Wherein the virus is an influenza virus. Furthermore, the above compounds or pharmaceutical compositions thereof provided by the present invention may be co-administered with other therapies or therapeutic agents. The mode of administration can be simultaneous, sequential or at regular intervals.

The dosage of the compound or pharmaceutical composition required for the treatment, prevention or delay will generally depend on the particular compound being administered, the patient, the particular disease or condition and its severity, the route and frequency of administration, etc., and it is judged by attending physician according to the specific situation. For example, when the compound or pharmaceutical composition provided by the present invention is administered by the intravenous route, it can be administered once a week or even at a longer interval.

In summary, the present invention provides a novel compound which is useful as an influenza virus RNA polymerase inhibitor. The compounds of the present invention are suitable for the manufacture of a variety of dosage forms and are widely used in the treatment of seasonal influenza, avian influenza, swine influenza, and Tamiflu resistant strains of influenza virus.

Besides being useful for human treatment, these compounds are also useful for veterinary treatment of animals such as companion animals, exotic animals and farm animals. In other embodiments, the animals disclosed herein include horses, dogs, and cats. As used herein, the compounds disclosed herein include the pharmaceutically acceptable derivatives thereof.

General Synthetic Procedures

In the present invention, if the chemical name of the compound doesn't match the corresponding structure, the compound is characterized by the corresponding structure.

Examples are listed below to describe the invention. It is to be understood that the invention is not limited to these examples, but merely provides a method of practicing the invention.

Generally, the compounds disclosed herein may be prepared by methods described herein, wherein the substituents are as defined for Formula (I), except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, J&K Scientific Ltd., and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Tianjin Fuchen Reagent Chemical Factory, Wuhan Xinhuayuan Technology Development Co., Ltd. Qingdao Tenglong Reagent Chemical Ltd., and Qingdao Ocean Chemical Factory, Beijing Coupling Technology Co., Ltd., Shanghai Tebo Chemical Technology Co., Ltd. and Accela ChemBio Co., Ltd (Shanghai).

Anhydrous THF, 1,4-dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Glassware was oven dried and/or heat dried.

Column chromatography was conducted using a silica gel column. Silica gel (300-400 mesh) was purchased from Qingdao Ocean Chemical Factory.

1H NMR spectra were recorded at room temperature with a Bruker 400 MHz or 600 MHz spectrometer using $CDCl_3$, $d_6$-DMSO, $CD_6OD$ or $d_6$-acetone as solutions (reported in ppm), and using TMS (0 ppm) or chloroform (7.26 ppm) as the reference standard. When peak multiplicities were reported, the following abbreviations were used: s (singlet), d (doublet), t (triplet), m (multiplet), br (broadened), dd (doublet of doublets), and dt (doublet of triplets). Coupling constant, expressed in J, in Hertz (Hz).

Low-resolution mass spectral (MS) data were determined on an Agilent 6120 Quadrupole HPLC-MS spectrometer equipped with an Agilent Zorbax SB-C18 (2.1×30 mm, 3.5 μm). The flow rate was 0.6 mL/min; the mobile phases consisted of a combination of A (0.1% formic acid in $CH_3CN$) and B (0.1% formic acid in $H_2O$) in gradient mode (5% to 95%), and an ESI source was used, the peak of HPLC was recorded with UV-Vis detection at 210 nm/254 nm.

Purification of compound by preparative chromatography was implemented on Agilent 1260 Series high performance liquid chromatography (Pre-HPLC) or Calesep Pump 250 Series high performance liquid chromatography (Pre-HPLC) with UV detection at 210/254 nm (NOVASEP, 50/80 mm, DAC).

The LC/MS/MS system for analysis in bioassay experiments includes Agilent 1200 Series Vacuum Degassing Furnace, Binary Syringe Pump, Orifice Autosampler, Column Incubator, Electrospray Ionization (ESI) Source AB Sciex 4000 Triple Four Polar mass spectrometer. Quantitative analysis is performed in MRM mode. The parameters of MRM conversion are shown in Table A:

TABLE A

| | |
|---|---|
| Multiple reaction detection scan | 590.1→265.0/ |
| | 502.3→265.2 |
| De-clustered voltage | 80 V/90 V |
| Collision voltage | 32 V/22 V |
| Dryer temperature | 550° C. |
| Atomizing gas | 50 psi |
| Air curtain | 20 psi |

Waters Xbridge-C18, 2.1×30 mm, 3.5 m column with 5 µL of sample injected was used for analysis. Analysis condition: the mobile phase is 0.5% aqueous formic acid (A) and the mixture solution (B) of acetonitrile:isopropanol (v/v: 2:1). Flow rate is 0.5 mL/min. The mobile phase gradient is shown in Table B:

TABLE B

| Time | The gradient of mobile phase B |
|---|---|
| 0.5 min | 20% |
| 1.0 min | 90% |
| 1.8 min | 90% |
| 1.83 min | 20% |
| 2.2 min | 20% |
| 2.3 min | 90% |
| 3.0 min | 90% |
| 3.01 min | 20% |
| 4.0 min | termination |

The following abbreviations are used throughout the specification:
2-MeTHF 2-methyltetrahydrofuran
Alloc allyl oxycarbonyl
AIBN Azobisisobutyronitrile
BOC, Boc tert-butoxycarbonyl
Bn Benzyl
BPO Benzoyl peroxide
OBn Benzyloxy
BocNHNH$_2$, Boc-NHNH$_2$ tert-butyl carbazate
CHCl$_3$ chloroform
CDCl$_3$ chloroform-d
CD3OD methyl alcohol-d4
DBU 1,5-diazabicyclo[5.4.0]undec-5-ene, 1,8-diazabicyclo[5.4.0]undec-7-ene
DCM dichloromethane
DIBAL-H Diisobutyl aluminium hydride
DMAC, DMAc N,N-dimethyl acetamide
DMF N,N-dimethylformamide, dimethylformamide
DMSO dimethylsulfoxide
DMF-DMA N,N-dimethylformamide dimethyl acetal
DIAD Diisopropyl azodiformate
DMSO-d$_6$ dimethyl sulfoxide-d$_6$, deuterated dimethyl sulfoxide
EtOAc, EA ethyl acetate
EtOH ethyl alcohol
Et ethyl
Me methyl
g gram, grams
h hour, hours
H$_2$ hydrogen
H$_2$O water
HCl Hydrochloric acid
HPLC high performance liquid chromatography
HPTLC high performance thin layer chromatography
KI potassium iodide
mL, ml milliliter
moL, mol mole
mmol, mmoL millimole
MeOH methanol
min minute, minutes
N$_2$ nitrogen
NH$_3$ Ammonia
NBS N-bromosuccinimide
NCS N-chlorosuccinimide
NaBH$_4$ Sodium borohydride
PE petroleum ether (60--90° C.)
P$_2$O$_5$ Phosphorus pentoxide
PPA Polyphosphoric acids
Pd(OH)$_2$/C Hydroxide palladium carbon
THF tetrahydrofuran
T3P 1-propylphosphonic anhydride
RT, rt, r.t. room temperature
Rt retention time
TI Therapeutic index
µL microlitre
N,M,mol/L mole every liter The experimental procedure for preparing the compound disclosed in the present invention was listed in following synthetic schemes. Wherein each $Y^1$, $Y^2$, $Y^3$, $Y^4$, R, n, m and ring A has a definition as described in the present invention, wherein each $Y^1$, $Y^2$ and $Y^4$ is independently preferably —CH$_2$—; n is preferably 0 or 1. PG is a hydroxy-protective group, preferably benzyl.

Scheme 1

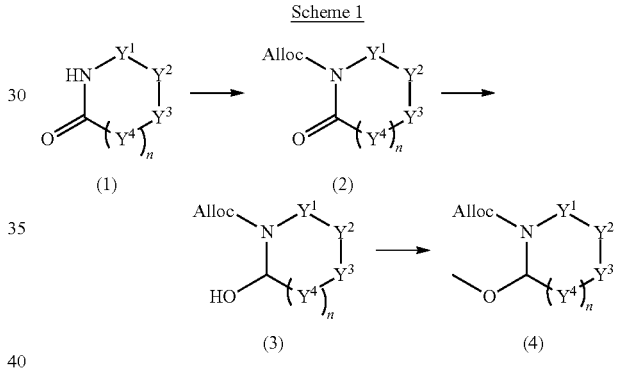

The intermediate of Formula (4) can be synthesized by the method disclosed in the scheme 1. First, compound (1) can react with allyl chloroformate under strong base condition to give a compound (2). Then, the compound (2) can be subjected to a reduction reaction under a low temperature condition to obtain a compound (3). Compound (3) can react with methanol under acid catalysis to give an intermediate (4).

Scheme 2

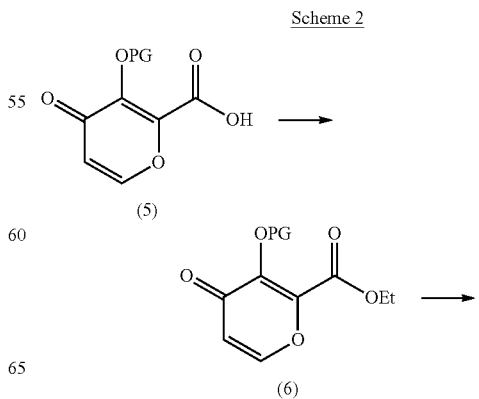

-continued

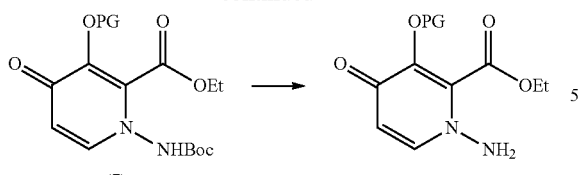

The intermediate of Formula (8) can be synthesized by the method disclosed in the scheme 2. First, a compound (5) can react with halogenated alkane such as ethyl iodide to give a compound (6). Then, the compound (6) can react with pyridinium p-toluenesulfonate and BocNHNH$_2$ to give a compound (7). Finally, the amino-protecting group Boc of the compound (7) can be removed to give a compound (8).

Scheme 3

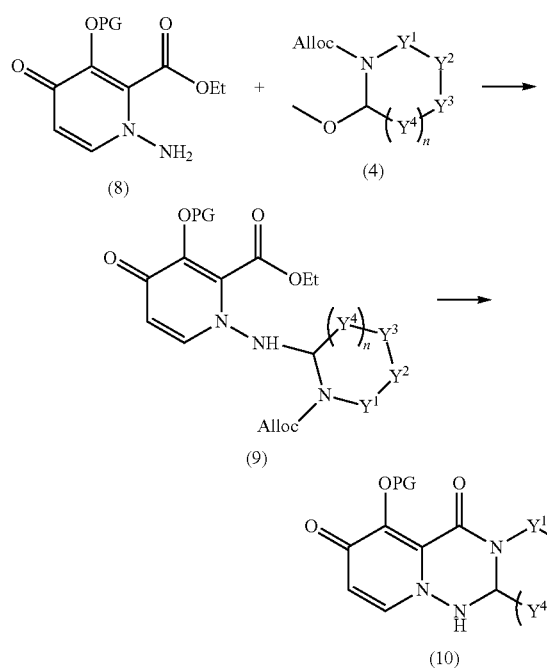

The intermediate of Formula (10) can be synthesized by the method disclosed in the scheme 3. First, the intermediate (8) can react with the intermediate (4) under the action of stannic chloride catalyst to obtain a compound (9). The compound (9) can undergo ring-closing under the action of Pd catalyst to give the intermediate (10).

Scheme 4

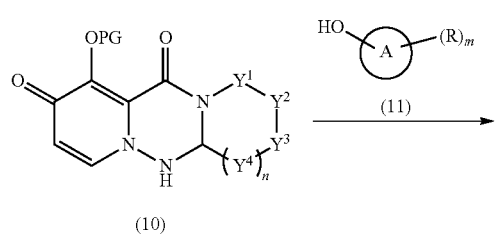

-continued

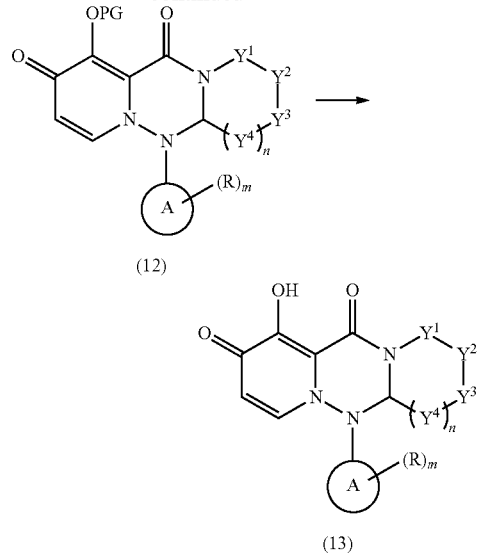

A compound of Formula (12) and a compound of Formula (13) can be prepared by the method disclosed in the scheme 4. A compound (10) can react with a compound (11) in the present of condensing agent such as 1-propylphosphoric anhydride to give a compound (12). The hydrogen-protecting group of compound (12) can be removed 1 under reducing condition to give a compound (13). Compound (13) can be isolated under preparative chromatography to give the corresponding isomer.

Scheme 5

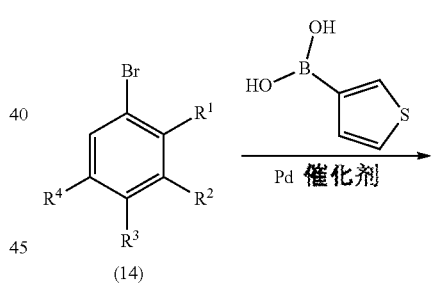

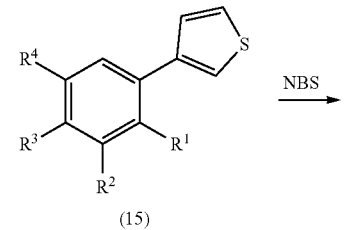

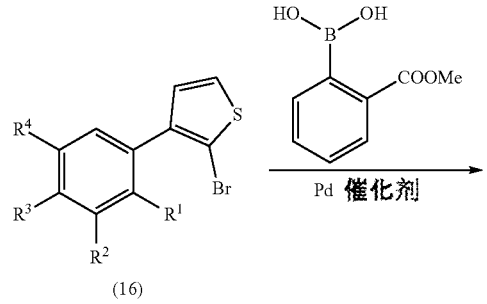

-continued

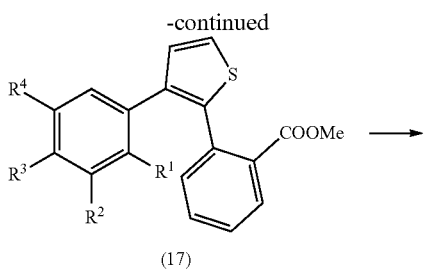

(17)

(18)

(19)

(20)

The intermediate of Formula (20) can be prepared by the method disclosed in scheme 5. Wherein $R^1$, $R^2$, $R^3$ and $R^4$ are as defined herein. First, a compound (14) can react with 3-thienylboronic acid under the action of Pd catalyst to give compound (15). The compound (15) can react with N-bromosuccinimide to give a compound (16). Then, the compound (16) can react with methyl benzoate-2-boric acid under the action of Pd catalyst to give a compound (17); the compound (17) can be hydrolyzed under basic condition to give a compound (18); the compound (18) can undergo ring-closing under the action of polyphosphoric acid to give a compound (19). Finally, the compound (19) can react under the action of sodium borohydride to give the intermediate (20). The intermediate (20) which can replace the compound (11) can react with the intermediate (10) to prepare the compound of the invention by the method described in scheme 4.

Scheme 6

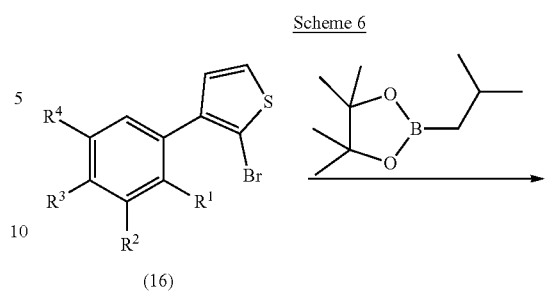

(16)

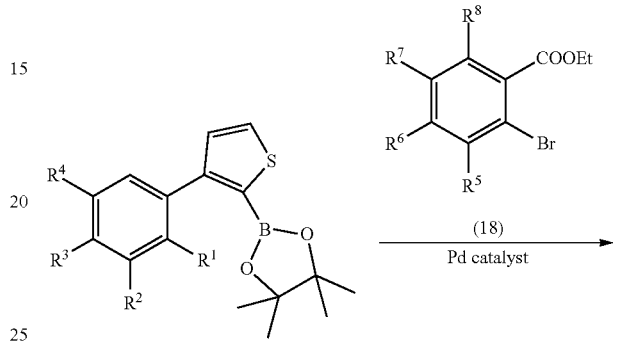

(17)

(19)

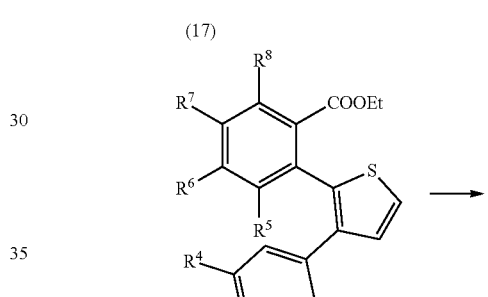

(20)

(21)

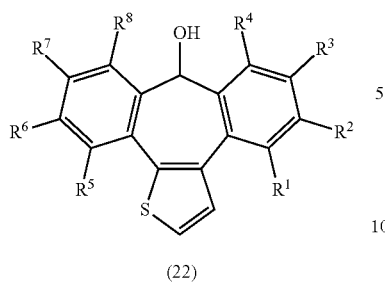

(22)

The intermediate of Formula (22) can be prepared by the method disclosed in the scheme 6. Wherein $R^1$, $R^2$, $R^3$, $R^4$, $R^5$, $R^6$, $R^7$ and $R^8$ have the same definition as R according to the invention. First, the compound (16) can react with 2-isopropoxy-4,4,5,5-tetramethyl-1,3,2-dioxaborolan at a low temperature to give a compound (17); the compound (17) can react with a compound (18) to give a compound (19) under the action of Pd catalyst; the compound (19) can be hydrolyzed under basic condition to give a compound (20); the compound (20) can undergo ring-closing under the action of polyphosphoric acid to give a compound (21). Finally, the compound (21) can react under the action of sodium borohydride to give the intermediate (22). The intermediate (22) which can replace the compound (11) can react with the intermediate (10) to prepare the compound of the invention by the method described in scheme 4.

Scheme 7

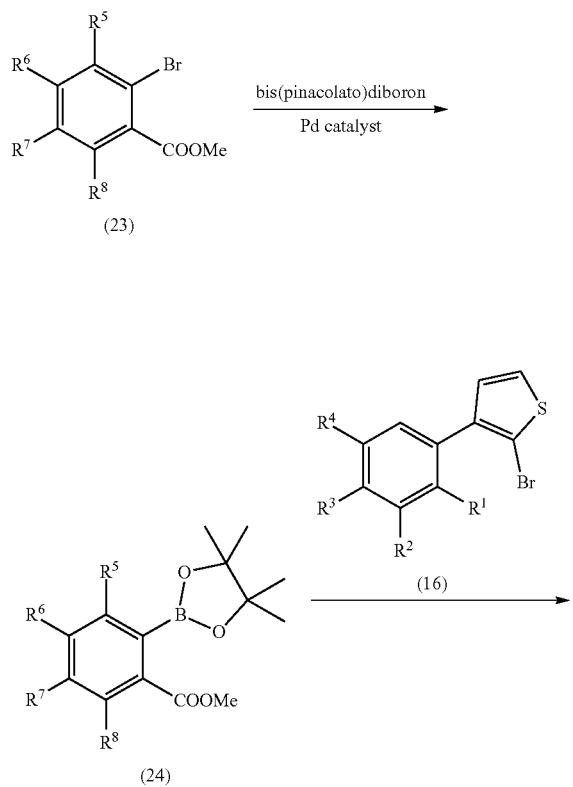

(23)

(24)

(16)

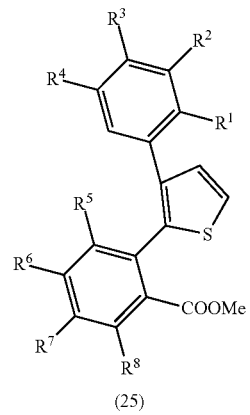

(25)

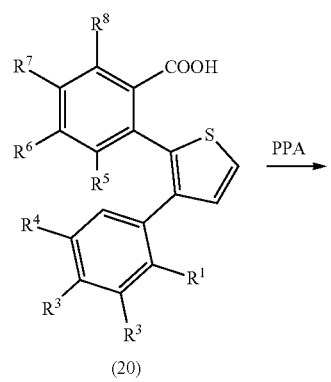

(20)

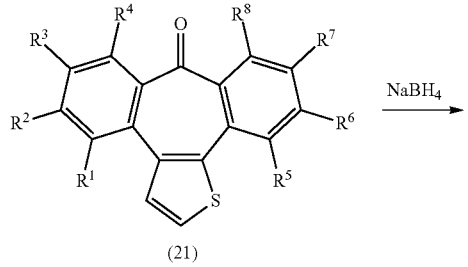

(21)

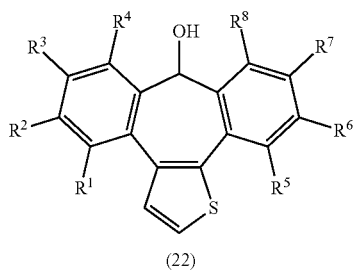

(22)

The intermediate of Formula (22) can be prepared by the method disclosed in the scheme 7. Wherein $R^1$, $R^2$, $R^3$, $R^4$, $R^5$, $R^6$, $R^7$ and $R^8$ have the same definition as R according to the invention. First, the compound (23) can react with bis(pinacolato)diboron under the action of Pd catalyst to give a compound (24); the compound (24) can react with a compound (16) to give a compound (25) under the action of Pd catalyst; the compound (25) can be hydrolyzed under basic condition to give a compound (20); the compound (20) can undergo ring-closing under the action of polyphosphoric acid to give a compound (21). Finally, the compound (21) can react under the action of sodium borohydride to give the intermediate (22). The intermediate (22) which can replace the compound (11) can react with the intermediate (10) to prepare the compound of the invention by the method described in scheme 4.

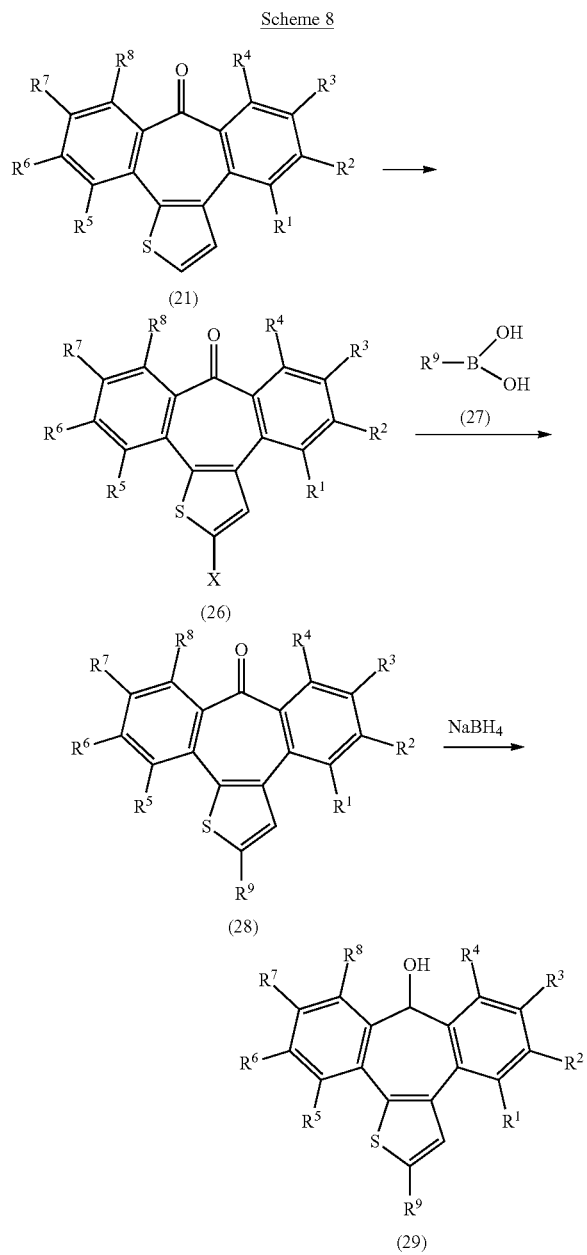

The intermediate of Formula (29) can be prepared by the method disclosed in the scheme 8. wherein $R^1$, $R^2$, $R^3$, $R^4$, $R^5$, $R^6$, $R^7$, $R^8$ and $R^9$ have the same definition as R according to the invention; X is halogen. First, the compound (21) with a halogenated alkane can undergo halogenation reaction to give a compound (26); then the compound (26) can react with a compound (27) under the action of Pd catalyst to give a compound (28); finally, the compound (28) can react under the action of sodium borohydride to give the intermediate (29). The intermediate (29) which can replace the compound (11) can react with the intermediate (10) to prepare the compound of the invention by the method described in scheme 4.

DESCRIPTION OF THE PREFERRED EMBODIMENTS

The following examples are intended to illustrate the invention but are not intended to limit the scope of the invention Example 1 7-(Benzyloxy)-12-(8H-dibenzo[3,4:6,7]cycloheptyl[1,2-b]thiophen-8-yl)-3,4,12,12a-tetrahydro-1H-[1,4]oxazino[3,4-c]pyrido[2,1-f][1,2,4]triazin-6,8-dione

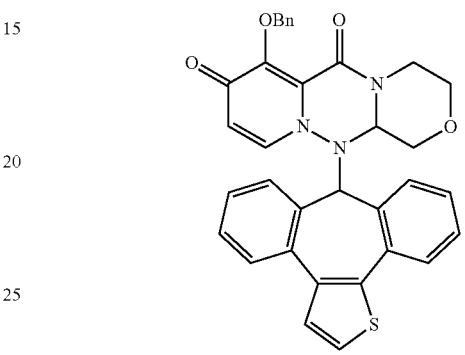

Step 1) allyl 3-oxomorpholin-N-formate

Morpholine-3-one (1.01 g, 9.99 mmol) was dissolved in anhydrous THF (20 mL) and cooled to 0° C. under the protection of nitrogen. Potassium tert-butoxide/tetrahydrofuran solution (1 M, 11.90 mL, 11.90 mmol) was added slowly, and the resulting mixture was warmed to room temperature and reacted for 1 hour, then cooled to 0° C. Then allyl chloroformate (1.16 mL, 10.9 mmol) was dripped. After addition, the resulting mixture was warmed to room temperature naturally and then stirred at room temperature for 4 hours. The reaction mixture was quenched with saturated aqueous ammonium chloride (30 mL). The resulting mixture was extracted with ethyl acetate (30 mL×3). The combined organic phases were washed with saturated brine (60 mL), dried over anhydrous sodium sulfate and filtered, then the filtrate was concentrated in vacuo, and the residue was purified by silica gel column chromatography (PE/EtOAc (v/v)=6/1) to give the title compound as colorless oil (1.50 g, 81%).

MS (ESI, pos. ion) m/z: 186.0 [M+H]$^+$;

$^1$H NMR (400 MHz, CDCl$_3$) δ (ppm): 5.98 (m, 1H), 5.45 (dd, J=17.2, 1.4 Hz, 1H), 5.30 (dd, J=10.5, 1.1 Hz, 1H), 4.78 (d, J=5.6, 2H), 4.26 (s, 2H), 3.95-3.89 (m, 2H), 3.87-3.80 (m, 2H).

Step 2) allyl 3-hydroxymorpholine-N-formate

Allyl 3-oxymorpholine-N-formate (1.50 g, 8.10 mmol) was dissolved in anhydrous THF (15 mL) and cooled to −30° C. DIBAL-H (1.5 M, 11.00 mL, 16.50 mmol) was added slowly and the resulting mixture was reacted at −30° C. for 3 hours. Acetone (5 mL) was added to the reaction solution which was then stirred for 10 minutes. To the reaction mixture was added saturated potassium sodium tartrate aqueous solution (30 mL), and the resulting mixture was extracted with ethyl acetate (30 mL×3). The combined organic phases were washed with saturated saline solution (60 mL) and dried over anhydrous sodium sulfate and filtered, then the filtrate was concentrated to give the title compound as light yellow oil (0.77 g, 51%).

Step 3) allyl 3-methoxymorpholine-N-formate

Allyl 3-hydroxymorpholine-N-formate (0.76 g, 4.10 mmol) was dissolved in methanol (10 mL), p-toluenesulfonic acid monohydrate (0.16 g, 0.84 mmol) was added, and the resulting mixture was reacted at room temperature for 4 hours. The reaction mixture was concentrated in vacuo to remove the solvent, and to the residue was added saturated sodium bicarbonate aqueous solution (20 mL). The resulting mixture was extracted with ethyl acetate (20 mL×3). The combined organic phases were washed with saturated saline solution (60 mL), dried over anhydrous sodium sulfate and filtered, then the filtrate was concentrated in vacuo, and the residue was purified by silica gel column chromatography (PE/EtOAc (v/v)=5/1) to give the title compound as a yellow solid (0.50 g, 61%).
$^1$H NMR (400 MHz, CDCl$_3$) δ (ppm): 5.94 (m, 1H), 5.32 (d, J=17.2 Hz, 1H), 5.24 (dd, J=10.4, 1.1 Hz, 1H), 5.14 (d, J=37.3 Hz, 1H), 4.63 (d, J=5.1 Hz, 2H), 4.00-3.85 (m, 2H), 3.84-3.71 (m, 1H), 3.52 (t, J=9.3 Hz, 2H), 3.41 (m, 1H), 3.33 (s, 3H).

Step 4) ethyl 3-(benzyloxy)-4-oxo-4H-pyran-2-formate 3-(Benzyloxy)-4-oxo-4H-pyran-2-formic acid (1.70 g, 6.90 mmol) was dissolved in anhydrous DMF (15 mL), then iodoethane (1.20 mL, 12.40 mmol) and DBU (1.58 mL, 10.40 mmol) were added. The resulting mixture was reacted overnight under rt, and then to the mixture was added saturated aqueous ammonium chloride (40 mL). The resulting mixture was extracted with ethyl acetate (30 mL×3). The combined organic phases were washed with saturated saline solution (60 mL×3) and dried over anhydrous sodium sulfate and concentrated. The residue was purified by silica gel column chromatography (PE/EtOAc (v/v)=3/1) to give the title compound as a light yellow solid (1.75 g, 92%).
MS (ESI, pos. ion) m/z: 275.0 [M+H]$^+$;
$^1$H NMR (400 MHz, CDCl$_3$) δ (ppm): 7.75 (d, J=5.6 Hz, 1H), 7.48 (d, J=7.0 Hz, 2H), 7.40-7.32 (m, 3H), 6.49 (d, J=5.6 Hz, 1H), 5.32 (s, 2H), 4.35 (q, J=7.1 Hz, 2H), 1.32 (t, J=7.1 Hz, 3H).

Step 5) Ethyl 3-(benzyloxy)-1-((tert-butoxycarbonyl)amino)-4-oxo-1,4-dihydropyridine-2-formate Ethyl 3-(benzyloxy)-4-oxo-4H-pyran-2-formate (1.75 g, 6.38 mmol) was dissolved in DMAc (20 mL), pyridinium p-toluenesulfonate (4.92 g, 19.20 mmol) and BocNHNH$_2$ (1.27 g, 9.61 mmol) were added. The resulting mixture was stirred at 60° C. for 6 hours. To the reaction mixture was added water (40 mL), and the mixture was extracted with ethyl acetate (40 mL×3). The combined organic phases were washed with saturated brine (100 mL×3), dried over anhydrous sodium sulfate and filtered, then the filtrate was concentrated in vacuo, and the residue was purified by silica gel column chromatography (PE/EtOAc (v/v)=1/1) to give the title compound as a light yellow solid (1.45 g, 59%).
MS (ESI, pos. ion) m/z: 389.3 [M+H]$^+$;
$^1$H NMR (400 MHz, CDCl$_3$) δ (ppm): 7.44 (s, 1H), 7.42 (s, 1H), 7.37-7.31 (m, 3H), 7.28 (s, 1H), 6.40 (d, J=7.8 Hz, 1H), 5.27 (s, 2H), 4.28 (q, J=7.1 Hz, 2H), 1.47 (s, 9H), 1.25 (t, J=7.2 Hz, 3H).

Step 6) Ethyl 1-amino-3-(benzyloxy)-4-oxo-1,4-dihydropyridine-2-carboxylate

Ethyl 3-(benzyloxy)-1-((tert-butoxycarbonyl)amino)-4-oxo-1,4-dihydropyridine-2-formate (1.45 g, 3.73 mmol) was dissolved in dichloromethane (10 mL), and trifluoroacetate (8.40 g, 112 mmol) was added. The resulting mixture was reacted at rt for 6 hours. The reaction mixture was concentrated and the residue was extracted with sodium bicarbonate solution (30 mL) and ethyl acetate (30 mL×3). The combined organic phases were washed with saturated brine (50 mL) and dried over anhydrous sodium sulfate and filtered, then the filtrate was concentrated, and the residue was purified by silica gel column chromatography (DCM/methanol (v/v)=15/1) to give the title compound as a light yellow solid (0.68 g, 63%).
MS (ESI, pos. ion) m/z: 289.1 [M+H]$^+$;
$^1$H NMR (400 MHz, CDCl$_3$) δ (ppm): 7.43 (s, 1H), 7.41 (s, 2H), 7.38-7.31 (m, 3H), 6.37 (d, J=7.6 Hz, 1H), 5.30 (s, 2H), 5.23 (s, 2H), 4.33 (q, J=7.1 Hz, 2H), 1.29 (t, J=7.1 Hz, 3H).

Step 7) allyl 3-((3-(benzyloxy)-2-(ethoxycarbonyl)-4-oxopyridin-1(4H)-yl)amino) morpholine-4-formate Ethyl 1-amino-3-(benzyloxy)-4-oxo-1,4-dihydropyridine-2-formate (0.68 g, 2.40 mmol) and allyl 3-methoxymorpholine-N-formate (0.57 g, 2.80 mmol) were dissolved in anhydrous acetonitrile (10 mL). The mixture was cooled to −30° C. under protection of nitrogen and to the mixture was added slowly anhydrous tin tetrachloride (0.42 mL, 3.50 mmol). After addition, the resulting mixture was reacted at −30° C. for 6 hours. To the reaction solution was added dichloromethane (10 mL), then saturated sodium bicarbonate solution (30 mL) was slowly added into the mixture. The resulting mixture was stirred for 10 minutes and filtered through a celite pad. The filter cake was washed with dichloromethane (30 mL), and the filtrate was partitioned, then the aqueous phase was extracted with dichloromethane (30 mL×2). The combined organic phases were washed with saturated brine (60 mL) and dried over anhydrous sodium sulfate and filtered, then the filtrate was concentrated in vacuo, and the residue was purified by silica gel column chromatography (DCM/methanol (v/v)=20/1) to give the title compound as a light yellow solid (0.68 g, 56%).
MS (ESI, pos. ion) m/z: 458.3 [M+H]$^+$ Step 8) 7-(benzyloxy)-3,4,12,12a-tetrahydro-1H-[1,4]oxazino[3,4-c]pyrido[2,1-f][1,2,4]triazine-6,8-diketone Allyl 3-((3-(benzyloxy)-2-(ethoxycarbonyl)-4-oxopyridin-1(4H)-yl)amino) morpholine-4-formate (0.60 g, 1.30 mmol) was dissolved in anhydrous THF (10 mL), then tetrakis triphenylphosphine palladium (0.15 g, 0.13 mmol) and morpholine (1.20 mL, 14.00 mmol) were added under protection of nitrogen. Then the mixture was stirred for 3 hours. To the reaction solution was added ethyl ether (10 mL) and the mixture was stirred at rt for 10 minutes, then filtered. The filter cake was washed with ether (5 mL) and dried to give the title compound as a light yellow solid (386 mg, 90%).
MS (ESI, pos. ion) m/z: 328.2 [M+H]$^+$;
$^1$H NMR (400 MHz, CDCl$_3$) δ (ppm): 7.71 (d, J=7.6 Hz, 1H), 7.57 (s, 1H), 7.55 (s, 1H), 7.39-7.26 (m, 3H), 6.23 (d, J=7.6 Hz, 1H), 5.08 (s, 2H), 4.85-4.76 (m, 1H), 4.15 (dd, J=13.8, 2.1 Hz, 1H), 4.08-3.98 (m, 2H), 3.44 (m, 1H), 3.17-3.10 (m, 1H), 2.95 (td, J=13.5, 4.2 Hz, 1H).

Step 9) 3-tolylthiophene

Bromobenzene (5.01 g, 31.90 mmol), 3-thiopheneboronic acid (4.90 g, 38.30 mmol), bistriphenylphosphine palladium dichloride (2.26 g, 3.19 mmol) and sodium carbonate (10.21 g, 95.40 mmol) were added into the reaction flask, then THF (100 mL) and water (10 mL) were added. The reaction was kept overnight at 75° C. under protection of nitrogen. The reaction mixture was filtered and the filter cake was washed with ethyl acetate (50 mL). The filtrate was concentrated in vacuo and the residue was purified by silica gel column chromatography (PE) to give the title compound as light yellow liquid (4.97 g, 97%).

1H NMR (400 MHz, CDCl$_3$) δ (ppm): 7.64 (d, J=1.2 Hz, 1H), 7.62 (s, 1H), 7.49-7.46 (m, 1H), 7.45-7.39 (m, 4H), 7.32 (t, J=7.4 Hz, 1H).

Step 10) 2-bromo-3-phenylthiophene

3-Phenylthiophene (501 mg, 3.13 mmol) was dissolved in anhydrous DMF (5 mL), then a solution of NBS (680 mg, 3.74 mmol) in DMF (2 mL) was added into the reaction solution. The resulting mixture was reacted for 3 hours under rt, and extracted with saturated aqueous ammonium chloride (20 mL) and ethyl acetate (15 mL×3). The combined organic phases were washed with saturated saline solution (30 mL×3), dried over anhydrous sodium sulfate and concentrated in vacuo. The residue was purified by silica gel column chromatography (PE) to give the title compound as light yellow liquid (702 mg, 94%).

$^1$H NMR (400 MHz, CDCl$_3$) δ (ppm): 7.60-7.58 (m, 2H), 7.49-7.45 (m, 2H), 7.41-7.38 (m, 1H), 7.34 (d, J=5.6 Hz, 1H), 7.07 (d, J=5.6 Hz, 1H).

Step 11) methyl 2-(3-phenylthiophen-2-yl)benzoate

2-Bromo-3-phenylthiophene (200 mg, 0.84 mmol), methyl benzoate-2-boronic acid (180 mg, 1.00 mmol), bis(triphenylphosphine)palladium dichloride (60 mg, 0.08 mmol) and potassium carbonate (271 mg, 2.53 mmol) were added into the reaction flask, then THF (2 mL) and water (0.1 mL) were added, and the reaction was kept for 6 hours at 75° C. under the protection of nitrogen. The reaction solution was cooled to rt and filtered. The filter cake was washed with ethyl acetate (10 mL), and the filtrate was concentrated in vacuo, the residue was purified by silica gel column chromatography (PE) to give the title compound as a white solid (103 mg, 42%).

$^1$H NMR (400 MHz, CDCl$_3$) δ (ppm): 7.77 (dd, J=8.0, 1.1 Hz, 1H), 7.49-7.45 (m, 1H), 7.43-7.37 (m, 3H), 7.25-7.16 (m, 6H), 3.56 (s, 3H).

Step 12) 2-(3-phenylthiophen-2-yl)benzoic acid

Methyl 2-(3-phenylthiophen-2-yl)benzoate (0.27 g, 0.92 mmol) was dissolved in THF (5 mL) and ethanol (1 mL), then a solution of sodium hydroxide (0.37 g, 9.20 mmol) in water (5 mL) was added into the reaction solution above, the resulting mixture was reacted overnight at 60° C. Saturated saline (10 mL) was added and pH of the reaction solution was adjusted to pH 6 with 1N diluted hydrochloric acid. The resulting mixture was quenched with ethyl acetate (20 mL×3). The combined organic phases were washed with saturated saline (30 mL), dried over anhydrous sodium sulfate and concentrated in vacuo. The residue was purified by silica gel column chromatography (PE/EtOAc (v/v)=3/1) to give the title compound as a light yellow solid (175 mg, 68%).

MS (ESI, neg. ion) m/z: 279.2[M−H]$^−$

Step 13) 8H-dibenzo[3,4:6,7]cyclohepta[1,2-b]thiophene-8-one 2-(3-Phenylthiophene-2-yl) benzoic acid (0.17 g, 0.61 mmol) was added into the reaction flask, then polyphosphoric acid (5 mL) was added. The reaction was kept for 4 hours at 130° C. under the protection of nitrogen. The reaction was stopped, then the reaction mixture cooled and added into ice water (20 mL). The resulting mixture was stirred for 10 minutes, and quenched with ethyl acetate (20 mL×3). The combined organic phases were washed with saturated sodium bicarbonate aqueous solution (50 mL) and saturated brine (50 mL) in turn, dried over anhydrous sodium sulfate and filtered, then the filtrate was concentrated, and the residue was purified by silica gel column chromatography (PE/EtOAc (v/v)=10/1) to give the title compound as a light yellow solid (60 mg, 38%).

MS (ESI, pos. ion) m/z: 263.2[M+H]$^+$;

$^1$H NMR (400 MHz, CDCl$_3$) δ (ppm): 7.93 (dd, J=4.0, 1.0 Hz, 1H), 7.91 (dd, J=4.0, 1.0 Hz, 1H), 7.84 (d, J=2.5 Hz, 1H), 7.82 (d, J=2.4 Hz, 1H), 7.67-7.59 (m, 2H), 7.47-7.54 (m, 4H).

Step 14) 8H-dibenzo [3,4:6,7] cycloheptane [1,2-b] thiophene-8-ol

8H-Dibenzo[3,4:6,7]cycloheptane[1,2-b]thiophene-8-one (0.13 g, 0.47 mmol) was dissolved in THF (1 mL) and methanol (0.5 mL), the solution was cooled to 0° C., sodium borohydride (74 mg, 1.92 mmol) was added in batches, and the reaction was kept at 0° C. for 5 minutes, and then kept for 1 hours at rt. The resulting mixture was extracted with water (5 mL), and then extracted with ethyl acetate (5 mL×3). The combined organic phases were washed with saturated saline solution (10 mL), dried over anhydrous sodium sulfate and concentrated in vacuo. The residue was purified by silica gel column chromatography (PE/EtOAc (v/v)=20/1) to give the title compound as a white solid (40 mg, 79%).

MS (ESI, pos. ion) m/z: 287.1[M+Na]$^+$;

$^1$H NMR (400 MHz, CDCl$_3$) δ (ppm): 7.87 (s, 1H), 7.85 (s, 1H), 7.56 (s, 1H), 7.54 (s, 1H), 7.45 (dd, J=12.3, 5.3 Hz, 4H), 7.33 (t, J=7.4 Hz, 2H), 5.36 (s, 1H).

Step 15) 7-(benzyloxy)-12-(8H-dibenzo [3,4:6,7] cycloheptane [1,2-b] thiophen-8-yl)-3,4,12,12a-tetrahydro-1H-[1,4] oxazino [3,4-c] pyrido [2,1-f] [1,2,4] triazine-6,8-dione 8H-Dibenzo[3,4:6,7]cyclohepta[1,2-b]thiophene-8-ol (18 mg, 0.07 mmol) and 7-(benzyloxy)-3,4,12,12a-tetrahydro-1H-[1,4] oxazino [3,4-c] pyrido [2,1-f] [1,2,4]triazine-6,8-dione (20 mg, 0.06 mmol) were added into a microwave tube, then 1-propyl phosphate anhydride (ethyl acetate solution) (wt 50%, 1 mL) was added. The air in solution was exhausted with nitrogen bubbling for 10 minutes, then the tube was sealed, and the resulting solution in the tube was reacted at 110° C. under microwave heating for 2.5 hours. The reaction mixture was added into ice water (3 mL) and the mixture was extracted with ethyl acetate (5 mL×3). The combined organic phases were washed with sodium bicarbonate aqueous solution (10 mL) and dried over anhydrous sodium sulfate and filtered, then the filtrate was concentrated, and the residue was purified by silica gel column chromatography (PE/EtOAc (v/v)=25/1) to give the title compound as a light yellow solid (16 mg, 44%).

MS (ESI, pos. ion) m/z: 574.3[M+H]$^+$;

$^1$H NMR (400 MHz, CDCl$_3$) δ (ppm): 7.73 (d, J=7.7 Hz, 1H), 7.62-7.61 (m, 3H), 7.53-7.30 (m, 9H), 7.10 (t, J=7.5 Hz, 1H), 6.68 (dd, J=11.4, 7.7 Hz, 1H), 6.27 (dd, J=46.3, 7.7 Hz, 1H), 5.70 (dd, J=7.5, 6.4 Hz, 1H), 5.61 (dd, J=10.8, 7.0 Hz, 1H), 5.44 (dd, J=10.8, 1.7 Hz, 1H), 5.36 (d, J=4.9 Hz, 1H), 4.60 (d, J=13.1 Hz, 1H), 4.06 (dt, J=9.9, 3.2 Hz, 1H), 3.63 (d, J=11.8 Hz, 1H), 3.30-3.14 (m, 2H), 2.98 (t, J=10.4 Hz, 1H), 2.82-2.76 (m, 1H).

Example 2 The Enantiomer Mixture of (R)-12-((S)-8H-dibenzo [3,4:6,7] cycloheptyl [1,2-b] thiophen-8-yl)-7-hydroxy-3,4,12,12a-tetrahydro-1H-[1,4] oxazino[3,4-c] pyrido [2,1-f] [1,2,4] triazine-6,8-dione and (S)-12-((R)-8H-dibenzo [3,4:6,7] cycloheptyl [1,2-b]thiophen-8-yl)-7-hydroxy-3,4,12,12a-tetrahydro-1H-[1,4] oxazino[3,4-c] pyrido [2,1-f][1,2,4] triazine-6,8-dione mixture:

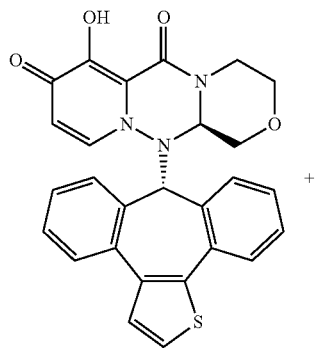

+

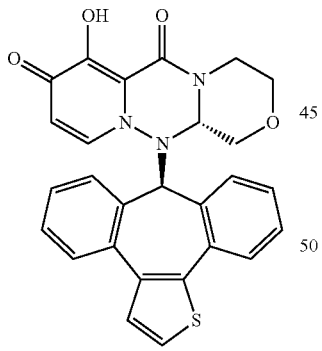

7-(benzyloxy)-12-(8H-dibenzo [3,4:6,7] cycloheptyl [1,2-b] thiophen-8-yl)-3,4,12,12a-tetrahydro-1H-[1,4] oxazino [3,4-c] pyrido [2,1-f] [1,2,4] triazine-6,8-dione (16 mg, 0.03 mmol) was dissolved in N,N'-dimethyl acetamide (1 mL), anhydrous lithium chloride (18 mg, 0.42 mmol) was added, the mixture was reacted overnight at 100° C. under nitrogen. Water (5 mL) was added into the reaction solution, the pH of which was adjusted to 6 with using 1M dilute hydrochloric acid. The resulting solution was extracted with ethyl acetate (10 mL×3). The combined organic phases were washed with saturated saline (20 mL×3), dried over anhydrous sodium sulfate and filtered, then the filtrate was concentrated, and the residue was purified by silica gel column chromatography (DCM/methanol/glacial acetic acid (v/v/v)=150/5/2) to give the title compound as a light yellow solid (11 mg, 85%), which was purified again by HPLC (Luna C$_{18}$, mobile phase: ACN/0.1% CF3COOH aqueous solution (v/v)=42/58) to give the title compound as a light yellow solid (4 mg, 31%).

MS (ESI, pos. ion) m/z: 484.0[M+H]$^+$;

HRMS (ESI, pos. ion) m/z: 484.1321, theoretical value of (C$_{27}$H$_{22}$N$_3$O$_4$S)[M+H]$^+$: 484.1331; $^1$H NMR (400 MHz, DMSO-d$_6$) δ (ppm): 7.78 (d, J=7.6 Hz, 1H), 7.72 (d, J=7.6 Hz, 1H), 7.55 (dd, J=15.9, 5.2 Hz, 3H), 7.47 (dd, J=14.6, 5.8 Hz, 4H), 7.27-7.23 (m, 1H), 6.97 (d, J=7.4 Hz, 1H), 6.41 (d, J=7.4 Hz, 1H), 6.15 (d, J=7.7 Hz, 1H), 5.45 (s, 1H), 4.60 (d, J=13.1 Hz, 1H), 4.29 (dd, J=9.9, 2.8 Hz, 1H), 3.74 (d, J=11.4 Hz, 1H), 3.36 (t, J=12.1 Hz, 2H), 3.18 (t, J=10.4 Hz, 1H), 2.98-2.90 (m, 1H).

Example 3 The Enantiomer Mixture of (S)-12-((S)-8H-dibenzo [3,4:6,7] cycloheptyl [1,2-b] thiophen-8-yl)-7-hydroxy-3,4,12,12a-tetrahydro-1H-[1,4] oxazino [3,4-c] pyrido [2,1-f] [1,2,4] triazine-6,8-dione and (R)-12-((R)-8H-dibenzo [3,4:6,7] cycloheptyl [1,2-b]thiophen-8-yl)-7-hydroxy-3,4,12,12a-tetrahydro-1H-[1,4] oxazino [3,4-c] pyrido [2,1-f] [1,2,4] triazine-6,8-dione Mixture:

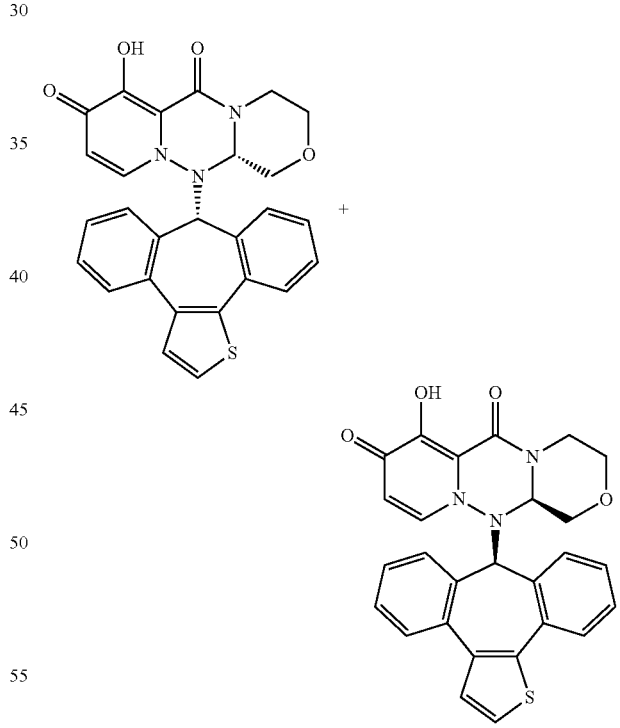

The title compound was prepared according to the method illustrated in Example 2 and purified by preparative HPLC to give other enantiomer mixture as a light yellow solid (5 mg, 38%).

MS (ESI, pos. ion) m/z: m/z 484.0 [M+H]$^+$.

$^1$H NMR (400 MHz, CDCl$_3$) δ (ppm): 7.78 (d, J=7.6 Hz, 1H), 7.71 (d, J=7.7 Hz, 1H), 7.59-7.54 (m, 1H), 7.53-7.42 (m, 5H), 7.25 (t, J=7.6 Hz, 1H), 6.97 (d, J=7.4 Hz, 1H), 6.49 (d, J=7.4 Hz, 1H), 6.10 (d, J=7.4 Hz, 1H), 5.44 (s, 1H), 4.60

(d, J=12.2 Hz, 1H), 4.27 (dd, J=9.9, 2.9 Hz, 1H), 3.74 (d, J=8.7 Hz, 1H), 3.35 (t, J=10.9 Hz, 2H), 3.17 (t, J=10.5 Hz, 1H), 2.93 (td, J=13.1, 3.2 Hz, 1H).

Example 4 7-(benzyloxy)-12-(7,13-dihydrobenzo[b] naphtho [2,1-e] thiepanyl-7-yl)-3,4,12,12a-tetrahydro-1H-[1,4] oxazino [3,4-c] pyrido [2,1-f] [1,2,4] triazine-6,8-dione

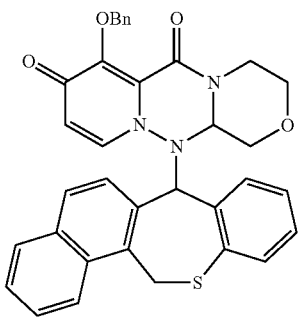 [SMILES: O=C1c2c(OCc3ccccc3)c(=O)ccn2N(C2c3ccccc3SCc3c2ccc2ccccc32)C2COCCN12]

Step 1) Ethyl 1-bromo-2-naphthalate

1-Bromo-2-naphthalic acid (2.00 g, 7.97 mmol) was dissolved in DMF (20 mL), then potassium carbonate (3.31 g, 23.90 mmol) and iodine ethane (0.96 mL, 12.00 mmol) were added. The resulting mixture was reacted overnight at rt, and to the mixture was added water (50 mL). The resulting mixture was extracted with ethyl acetate (50 mL×3). The combined organic phases were washed with saturated saline solution (100 mL×3), dried over anhydrous sodium sulfate and concentrated in vacuo. The residue was purified by silica gel column chromatography (PE/EtOAc (v/v)=5/1) to give the title compound as light yellow liquid (2.12 g, 95%).

MS (ESI, pos. ion) m/z: 279.0[M+H]$^+$;
$^1$H NMR (400 MHz, CDCl$_3$) δ (ppm): 8.32 (d, J=8.4 Hz, 1H), 8.06 (t, J=7.1 Hz, 2H), 7.80-7.67 (m, 3H), 4.40 (q, J=7.1 Hz, 2H), 1.36 (t, J=7.1 Hz, 3H).

Step 2) Ethyl 1-methyl-2-naphthalate

Ethyl 1-bromo-2-naphthoate (100 mg, 0.36 mmol), trimethylcyclotriborane (0.12 mL, 0.42 mmol), tetrakis(triphenylphosphine)palladium (43 mg, 0.04 mmol) and potassium carbonate (149 mg, 1.08 mmol) were added into the reaction flask, then DMF (2 mL) and water (0.1 mL) were added, and the resulting mixture was kept for 5 hours at 120° C. under the protection of nitrogen. The reaction solution was cooled to rt and water (5 mL) was added. The mixture was extracted with ethyl acetate (5 mL×3). The combined organic phases were washed with saturated saline (10 mL×3), dried over anhydrous sodium sulfate, filtered and the filtrate was concentrated. The residue was purified by silica gel column chromatography (PE) to give the title compound as light yellow liquid (53 mg, 69%).

MS (ESI, pos. ion) m/z: 215.1[M+H]$^+$;
$^1$H NMR (400 MHz, CDCl$_3$) δ (ppm): 8.23 (d, J=9.7 Hz, 1H), 8.00-7.95 (m, 1H), 7.85 (d, J=8.6 Hz, 1H), 7.73 (d, J=8.6 Hz, 1H), 7.68-7.62 (m, 2H), 4.37 (q, J=7.1 Hz, 2H), 2.84 (s, 3H), 1.36 (t, J=7.1 Hz, 3H).

Step 3) Ethyl 1-(bromomethyl)$_2$-naphthalene formate

Ethyl 1-methyl-2-naphthoate (0.58 g, 2.70 mmol) was dissolved in carbon tetrachloride (10 mL). NBS (0.58 g, 3.30 mmol) and AIBN (0.15 g, 0.90 mmol) were added. The mixture was heated to 80° C. and stirred for 3 hours under nitrogen protection. The reaction mixture was cooled to rt and quenched with water (20 mL), then extracted with dichloromethane (20 mL×3). The combined organic phases were washed with saturated brine (50 mL), dried over anhydrous sodium sulfate and filtered, then the filtrate was concentrated in vacuo, and the residue was purified by silica gel column chromatography (PE/EtOAc (v/v)=20/1) to give the title compound as a light yellow solid (0.57 g, 72%).

$^1$H NMR (400 MHz, CDCl$_3$) δ (ppm): 8.36 (d, J=8.5 Hz, 1H), 8.06 (s, 1H), 8.04 (s, 1H), 7.85 (d, J=8.6 Hz, 1H), 7.79-7.73 (m, 1H), 7.71-7.68 (m, 1H), 5.51 (s, 2H), 4.41 (q, J=7.1 Hz, 2H), 1.39 (t, J=7.1 Hz, 3H).

Step 4) Ethyl 1-((phenylthio)methyl)-2-naphthoate

Ethyl 1-(bromomethyl)-2-naphthoate (0.57 g, 1.90 mmol) was dissolved in DMF (10 mL), then potassium carbonate (0.40 g, 2.90 mmol), neutral alumina (0.24 g, 2.30 mmol) and thiophenol (0.24 mL, 2.30 mmol) were added. The resulting mixture was reacted for 1 hour at rt under protection of nitrogen, then to the mixture was added water (20 mL). The mixture was extracted with ethyl acetate (20 mL×3). The combined organic phases were washed with saturated saline solution (50 mL×3), dried over anhydrous sodium sulfate, filtered and the filtrate was concentrated. The residue was purified by silica gel column chromatography (PE/EtOAc (v/v)=20/1) to give the title compound as light yellow liquid (0.57 g, 91%).

$^1$H NMR (400 MHz, CDCl$_3$) δ (ppm): 8.28 (d, J=9.4 Hz, 1H), 8.03-7.98 (m, 1H), 7.95 (d, J=8.6 Hz, 1H), 7.78 (d, J=8.6 Hz, 1H), 7.68-7.61 (m, 2H), 7.38-7.29 (m, 4H), 7.27-7.23 (m, 1H), 5.07 (s, 2H), 4.26 (q, J=7.1 Hz, 2H), 1.28 (t, J=7.1 Hz, 3H).

Step 5) 1-((phenylthio)methyl)-2-naphthoic acid

Ethyl 1-((phenylthio)methyl)-2-benzoate (0.57 g, 1.80 mmol) was dissolved in THF (10 mL) and ethanol (5 mL), then a solution of sodium hydroxide (0.72 g, 18.00 mmol) in water (10 mL) was added into the reaction solution above, and the mixture was reacted overnight at 45° C. To the reaction mixture was added saturated saline (40 mL), adjusted with 1N dilute hydrochloric acid to pH about 6. The mixture was extracted with ethyl acetate (50 mL×3). The combined organic phases were washed with saturated brine (100 mL×3), dried over anhydrous sodium sulfate and filtered, then the filtrate was concentrated, and the residue was purified by silica gel column chromatography (PE/EtOAc (v/v)=1/1) to give the title compound as a light yellow solid (0.35 g, 67%).

MS (ESI, pos. ion) m/z: 317.0[M+Na]$^+$

Step 6) Benzo[b]naphtho[2,1-e]thiazepine-7-(13H)-one 1-((Phenylthio)methyl)-2-naphthoic acid (0.35 g, 1.20 mmol) was added into a reaction flask, polyphosphoric acid (5 mL) was added, and the reaction mixture was reacted at 120° C. for 5 hours under protection of nitrogen. Then the reaction was stopped and the reaction solution was cooled and added into ice water (10 mL). The resulting solution was extracted with ethyl acetate (5 mL×3). The combined organic phases were washed with saturated sodium bicarbonate aqueous solution (10 mL) and saturated brine (10 mL) in turn, dried over anhydrous sodium sulfate and filtered, then the filtrate was concentrated in vacuo, and the residue was purified by silica gel column chromatography (PE/EtOAc (v/v)=20/1) to give the title compound as a light yellow solid (0.14 g, 43%).

$^1$H NMR (400 MHz, CDCl$_3$) δ (ppm): 8.51 (d, J=8.2 Hz, 1H), 8.10 (dd, J=8.0, 1.1 Hz, 1H), 8.03 (d, J=7.5 Hz, 1H), 7.92 (d, J=8.5 Hz, 1H), 7.74-7.64 (m, 2H), 7.52-7.40 (m, 3H), 7.35 (t, J=7.5 Hz, 1H), 4.74 (s, 2H).

Step 7) 7,13-Dihydrobenzo[b]naphtho[2,1-e]thiazol-7-ol

Benzo[b]naphtho[2,1-e]thiazepine-7-(13H)-one (0.13 g, 0.47 mmol) was dissolved in THF (4 mL) and methanol (2 mL), the solution was cooled to 0° C., and sodium borohydride (0.18 g, 4.70 mmol) was added in batches. Then the reaction was kept at 0° C. for 5 minutes, and then kept for 1 hour at rt. To the resulting mixture was added water (20 mL), and the mixture was extracted with ethyl acetate (30 mL×3). The combined organic phases were washed with saturated saline solution (50 mL), dried over anhydrous sodium sulfate and concentrated in vacuo. The residue was purified by silica gel column chromatography (PE/EtOAc (v/v)=20/1) to give the title compound as a white solid (0.11 g, 84%).

$^1$H NMR (400 MHz, CDCl$_3$) δ (ppm): 8.32 (d, J=8.6 Hz, 1H), 7.89 (d, J=8.0 Hz, 1H), 7.82 (d, J=8.6 Hz, 1H), 7.66 (t, J=7.6 Hz, 2H), 7.58 (t, J=7.5 Hz, 1H), 7.49 (t, J=7.4 Hz, 1H), 7.09-6.99 (m, 2H), 6.92 (d, J=7.5 Hz, 1H), 6.50 (d, J=3.3 Hz, 1H), 6.31 (d, J=3.8 Hz, 1H), 5.02 (dd, J=37.7, 14.3 Hz, 2H).

Step 8) 7-(benzyloxy)-12-(7,13-dihydrobenzo [b] naphtho [2,1-e] thiepin-7-yl)-3,4,12,12a-tetrahydro-1H-[1,4] oxazino [3,4-c] pyrido [2,1-f] [1,2,4] triazine-6,8-dione 7,13-Dihydrobenzo [b] naphtho[2,1-e] thiepin-7-ol (18 mg, 0.06 mmol) and 7-(benzyloxy)-3,4,12,12a-tetrahydro-1H-[1,4] oxazino [3,4-c] pyrido [2,1-f] [1,2,4] triazine-6,8-dione (20 mg, 0.06 mmol) was added into microwave tube, then to the mixture was added a solution of 1-propyl phosphate anhydride in ethyl acetate (wt 50%, 1 mL). The resulting solution was exhausted with nitrogen bubbling for 10 minutes, then stirred at 110° C. by microwave-heating for 2.5 hours. Then the mixture was added into ice water (3 mL) and the resulting mixture was extracted with ethyl acetate (3 mL×3). The combined organic phases were washed with saturated sodium bicarbonate aqueous solution (10 mL), dried over anhydrous sodium sulfate and concentrated in vacuo. The residue was purified by silica gel column chromatography (DCM/methanol (v/v)=30/1) to give the title compound as a light yellow solid (10 mg, 28%).

MS (ESI, pos. ion) m/z: 588.1[M+H]$^+$;

$^1$H NMR (400 MHz, CDCl$_3$) δ (ppm): 8.21 (d, J=8.7 Hz, 1H), 7.91 (d, J=8.2 Hz, 1H), 7.81 (d, J=8.3 Hz, 1H), 7.70-7.66 (m, 3H), 7.62-7.58 (m, 1H), 7.41 (t, J=7.1 Hz, 2H), 7.36 (d, J=6.8 Hz, 1H), 7.29 (q, J=3.4 Hz, 3H), 7.09 (d, J=7.7 Hz, 1H), 7.06 (d, J=4.4 Hz, 1H), 6.68-6.67 (m, 1H), 6.46 (d, J=7.7 Hz, 1H), 5.86 (d, J=7.8 Hz, 1H), 5.68 (d, J=10.8 Hz, 1H), 5.50 (d, J=10.8 Hz, 1H), 5.41 (s, 1H), 4.70 (d, J=13.4 Hz, 1H), 4.61 (dd, J=10.0, 2.4 Hz, 1H), 4.45 (d, J=14.4 Hz, 1H), 3.88 (dd, J=10.9, 2.4 Hz, 1H), 3.69 (dd, J=11.8, 3.1 Hz, 1H), 3.40 (dd, J=13.9, 7.2 Hz, 1H), 3.33 (t, J=12.2 Hz, 1H), 2.93-2.84 (m, 1H).

Example 5 12-(7,13-Dihydrobenzo [b] naphtho [2,1-e] thiepin-7-yl)-7-hydroxy-3,4,12,12a-tetrahydro-1H-[1,4] oxazino [3,4-c] pyrido [2,1-f] [1,2,4]triazine-6,8-dione

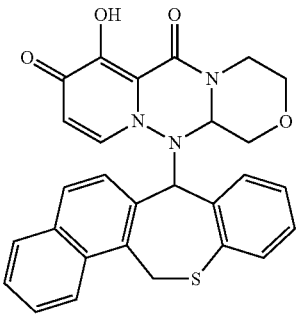 [SMILES: O=C1c2c(O)c(=O)ccn2N(C2c3ccccc3SCc3c2ccc2ccccc32)C2COCCN12]

7-(Benzyloxy)-12-(7,13-dihydrobenzo [b] naphtho [2,1-e] thiepin-7-yl)-3,4,12,12a-tetrahydro-1H-[1,4] oxazino [3,4-c] pyrido [2,1-f] [1,2,4] triazine-6,8-dione (29 mg, 0.05 mmol) was dissolved in N,N' dimethyl acetamide (2 mL), then anhydrous lithium chloride (32 mg, 0.75 mmol) was added, and the mixture was reacted overnight at 100° C. under protection of nitrogen. To the reaction mixture was added water (5 mL), adjusted with 1M diluted hydrochloric acid to pH about 6, quenched with ethyl acetate (10 mL×3). The combined organic phases were washed with saturated brine (20 mL×3), dried over anhydrous sodium sulfate and filtered, then the filtrate was concentrated in vacuo, and the residue was purified by silica gel column chromatography (dichloromethane/methanol/glacial acetic acid (v/v/v)=150/5/2) to give the title compound as a light yellow solid (80 mg, 81%).

MS (ESI, pos. ion) m/z: 498.1[M+H]$^+$;

HRMS (ESI, pos. ion) m/z: Theoretical value of 498.1488, (C$_{28}$H$_{24}$N$_3$O$_4$S)[M+H]$^+$: 498.1488;

$^1$H NMR (400 MHz, DMSO-d$_6$) δ (ppm): 8.24 (d, J=8.7 Hz, 1H), 7.93 (d, J=8.0 Hz, 1H), 7.85 (d, J=8.4 Hz, 1H), 7.74-7.69 (m, 1H), 7.65-7.60 (m, 1H), 7.33 (d, J=8.5 Hz, 1H), 7.27 (d, J=7.9 Hz, 1H), 7.17-7.09 (m, 2H), 6.85 (t, J=7.3 Hz, 1H), 6.69 (d, J=7.6 Hz, 1H), 6.21 (d, J=7.5 Hz, 1H), 5.86 (d, J=14.5 Hz, 1H), 5.46 (s, 1H), 4.81 (dd, J=10.1, 2.8 Hz, 1H), 4.70 (d, J=11.9 Hz, 1H), 4.51 (d, J=14.3 Hz, 1H), 3.99 (dd, J=11.1, 2.8 Hz, 1H), 3.81 (dd, J=12.2, 3.1 Hz, 1H), 3.67-3.60 (m, 1H), 3.50 (t, J=10.6 Hz, 1H), 3.08-2.99 (m, 1H).

Example 6 The enantiomer mixture of (R)-7-(benzyloxy)-12-((S)-10, 11-difluoro-7, 12-dihydrobenzo [e] naphtho [1, 2-b] thiepin-7-yl)-3, 4, 12, 12a-tetrahydro-1H-[1, 4] oxazino [3, 4-c] pyrido [2, 1-f] [1, 2, 4] triazine-6, 8-dione and (S)-7-(benzyloxy)-12-((R)-10, 11-difluoro-7, 12-dihydrobenzo [e] naphtho [1, 2-b] thiepin-7-yl)-3, 4, 12, 12a-tetrahydro-1H-[1, 4] oxazino [3, 4-c] pyrido [2, 1-f] [1, 2, 4] triazine-6, 8-dione Mixture:

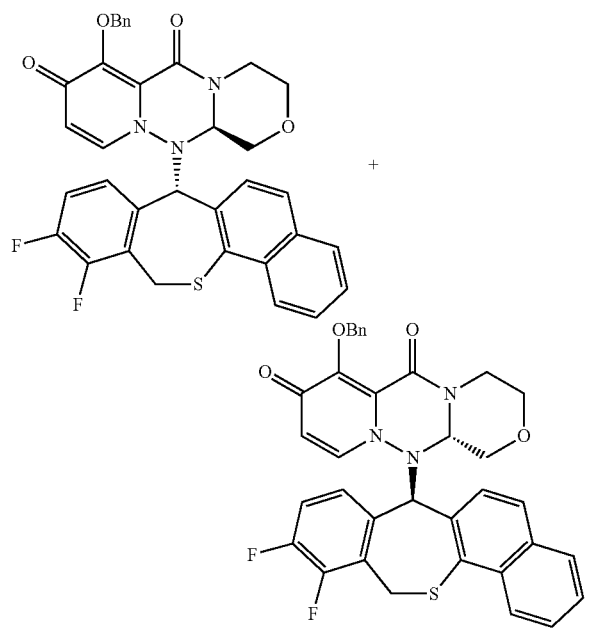

Step 1) Ethyl 3,4-difluoro-2-methylbenzoate 3,4-Difluoro-2-methylbenzoic acid (6.80 g, 0.40 mol) was dissolved in DMF (80 mL), then potassium carbonate (16.50 g, 1.19 mol) and iodine ethane (4.80 mL, 0.60 mol) was added. The resulting mixture was reacted overnight at rt, and quenched with water (200 mL). The mixture was extracted with ethyl acetate (100 mL×3). The combined organic phases were washed with saturated saline solution (200 mL×3), dried over anhydrous sodium sulfate, filtered and concentrated. The residue was purified by silica gel column chromatography (PE/EtOAc (v/v)=10/1) to give the title compound as light yellow liquid (7.58 g, 96%).

$^1$H NMR (400 MHz, CDCl$_3$) δ (ppm): 7.71 (m, 1H), 7.04 (q, J=8.8 Hz, 1H), 4.37 (q, J=7.1 Hz, 2H), 2.55 (d, J=2.7 Hz, 3H), 1.40 (t, J=7.1 Hz, 3H).

Step 2) Ethyl 2-(bromomethyl)-3,4-difluorobenzoate

Ethyl 3,4-difluoro-2-methylbenzoate (7.58 g, 0.38 mol) was dissolved in carbon tetrachloride (20 mL). NBS (7.42 g, 0.42 mol) and benzoyl peroxide (0.94 g, 3.80 mmol) were added. The mixture was heated to 78° C. and reacted for 6 hours. The reaction mixture was cooled to rt and saturated aqueous sodium thiosulfate solution (50 mL) was added. The resulting mixture was extracted with dichloromethane (50 mL×3). The combined organic phases were washed with saturated brine (100 mL) and dried over anhydrous sodium sulfate and filtered, then the filtrate was concentrated, and the residue was purified by silica gel column chromatography (PE/EtOAc (v/v)=20/1) to give the title compound as light yellow liquid (9.77 g, 93%).

$^1$H NMR (400 MHz, CDCl$_3$) δ (ppm): 7.83 (ddd, J=8.7, 5.0, 1.9 Hz, 1H), 7.20 (q, J=8.9 Hz, 1H), 5.03 (d, J=2.1 Hz, 2H), 4.43 (q, J=7.1 Hz, 2H), 1.44 (t, J=7.1 Hz, 3H).

Step 3) Ethyl 3,4-difluoro-2-((naphthalen-1-ylthio)methyl)benzoate

Ethyl 2-(bromomethyl)-3,4-difluorobenzoate (100 mg, 0.36 mmol) was dissolved in DMF (2 mL), then potassium carbonate (100 mg, 0.72 mmol) and naphthalene-1-thiol (0.06 mL, 0.40 mol) were added. The resulting mixture was reacted overnight at 45° C. under protection of nitrogen and then cooled to rt, and water (10 mL) was added. The mixture was extracted with ethyl acetate (10 mL×3). The combined organic phases were washed with saturated saline solution (20 mL×3), dried over anhydrous sodium sulfate, filtered and concentrated. The residue was purified by silica gel column chromatography (PE/EtOAc (v/v)=30/1) to give the title compound as light yellow liquid (105 mg, 82%).

$^1$H NMR (400 MHz, CDCl$_3$) δ (ppm): 8.45 (d, J=7.6 Hz, 1H), 7.90-7.80 (m, 2H), 7.65 (ddd, J=8.6, 5.1, 1.7 Hz, 1H), 7.59-7.49 (m, 3H), 7.38-7.32 (m, 1H), 7.05 (dd, J=16.7, 8.9 Hz, 1H), 4.60 (d, J=1.8 Hz, 2H), 4.12 (q, J=7.1 Hz, 2H), 1.31 (t, J=7.1 Hz, 3H).

Step 4) 3,4-difluoro-2-((naphthalen-1-ylthio)methyl)benzoic acid

Ethyl 3,4-difluoro-2-((naphthalen-1-ylthio)methyl)benzoate (220 mg, 0.61 mmol) was dissolved in THF (2 mL) and methanol (1 mL), and a solution of sodium hydroxide (0.25 g, 6.30 mmol) in water (2 mL) was added to the above reaction solution. The resulting mixture was reacted at 45° C. for 3 hours, added with saturated saline (6 mL), adjusted with 1M diluted hydrochloric acid to Ph about 6, and extracted with ethyl acetate (10 mL×3). The combined organic phases were washed with saturated saline solution (20 mL), dried over anhydrous sodium sulfate, filtered and concentrated to give the title compound as a light yellow solid (166 mg, 82%).

MS (ESI, pos. ion) m/z: 331.1[M+H]$^+$

Step 5) 10,11-difluorobenzo[e]naphtho[1,2-b] thiepin-7(12H)-one 3,4-Difluoro-2-((naphthalen-1-ylthio)methyl)benzoic acid (51 mg, 0.15 mmol) was added into the reaction flask, polyphosphoric acid (1 mL) was added under nitrogen protection, and the reaction mixture was reacted at 120° C. for 1 hour. The reaction was stopped and the reaction solution was cooled, then to the mixture was added ice water (10 mL). The resulting solution was stirred and extracted with ethyl acetate (10 mL×3). The combined organic phases were washed with saturated sodium bicarbonate aqueous solution (20 mL) and saturated brine (20 mL) in turn, dried over anhydrous sodium sulfate and filtered, then the filtrate was concentrated, and the residue was purified by silica gel column chromatography (PE/EtOAc (v/v)=5/1) to give the title compound as a light yellow solid (20 mg, 82%).

$^1$H NMR (400 MHz, CDCl$_3$) δ (ppm): 8.46 (d, J=8.3 Hz, 1H), 8.20 (d, J=8.9 Hz, 1H), 7.85 (d, J=7.6 Hz, 1H), 7.75 (d, J=8.8 Hz, 1H), 7.64-7.60 (m, 2H), 7.53-7.50 (m, 1H), 7.21-7.15 (m, 1H), 4.30 (s, 2H).

Step 6) 10,11-difluoro-7,12-dihydrobenzo[e]naphtho [1,2-b]thiepin-7-ol 10,11-Difluorobenzo[e]naphtho[1,2-b]thiepin-7(12H)-one (200 mg, 0.64 mmol) was dissolved in THF (2 mL) and methanol (2 mL), the solution was cooled to 0° C., sodium borohydride (75 mg, 1.94 mmol) was added in batches, and the reaction was kept at 0° C. for 5 minutes, and then kept for 1 hours at rt. The resulting mixture was added with saturated aqueous ammonium chloride solution (10 mL) and then extracted with ethyl acetate (5 mL×3). The combined organic phases were washed with saturated sodium bicarbonate aqueous solution (20 mL) and saturated saline solution (10 mL), dried over anhydrous sodium sulfate, filtered and concentrated. The residue was purified by silica gel column chromatography (PE/EtOAc (v/v)=6/1) to give the title compound as a light yellow solid (85 mg, 42%).

$^1$H NMR (400 MHz, CDCl$_3$) δ (ppm): 8.51 (d, J=8.4 Hz, 1H), 7.81 (d, J=7.7 Hz, 1H), 7.75 (d, J=8.5 Hz, 1H), 7.65 (d, J=8.5 Hz, 1H), 7.58-7.49 (m, 2H), 7.41-7.34 (m, 1H), 7.05 (dd, J=17.6, 8.6 Hz, 1H), 6.61 (d, J=3.5 Hz, 1H), 4.52 (d, J=15.6 Hz, 1H), 4.25 (d, J=15.6, 1H), 3.21 (d, J=4.3 Hz, 1H).

Step 7) The enantiomer mixture of (R)-7-(benzyloxy)-12-((S)-10,11-difluoro-7,12-dihydrobenzo [e] naphtho [1,2-b] thiepin-7-yl)-3, 4, 12,12a-tetrahydro-1H-[1, 4] oxazino [3, 4-c] pyridio [2, 1-f] [1, 2, 4] triazine-6, 8-dione and (S)-7-(benzyloxy)-12-((R)-10, 11-difluoro-7, 12-dihydrobenzo [e] naphtho [1, 2-b] thiepin-7-yl)-3, 4,12, 12a-tetrahydro-1H-[1, 4] oxazino [3, 4-c] pyridine [2, 1-f] [1, 2, 4] triazine-6, 8-dione 10,11-Difluoro-7,12-dihydrobenzo[e]naphtho[1,2-b]thiepin-7-ol (11 mg, 0.03 mmol) and 7-(benzyloxy)-3,4,12,12a-tetrahydro-1H-[1,4] oxazino [3,4-c] pyrido [2,1-f] [1,2,4]triazine-6,8-dione (10 mg, 0.03 mmol) were added into microwave tube, then a solution of 1-propyl phosphate anhydride in ethyl acetate (50%, 1 mL) was added. The air in resulting solution was exhausted with nitrogen bubbling for 10 minutes. The tube was sealed, and the solution was stirred at 110° C. by microwave-heating for 2.5 hours, and then added into ice water (2 mL). The resulting mixture was extracted with ethyl acetate (2 mL×3). The combined organic phases were washed with saturated sodium bicarbonate aqueous solution (5 mL) and saturated saline (5 mL), dried over anhydrous sodium sulfate and concentrated. The residue was purified by silica gel column chromatography (dichloromethane/methanol (v/v)=30/1) to give the title compound as a light yellow solid (10 mg, 52%).

MS (ESI, pos. ion) m/z: 624.3 [M+H]$^+$;

$^1$H NMR (400 MHz, CDCl$_3$) δ (ppm): 8.34 (dd, J=6.3, 3.5 Hz, 1H), 7.68 (dd, J=6.3, 3.3 Hz, 1H), 7.65 (s, 1H), 7.63 (s, 1H), 7.54-7.50 (m, 2H), 7.43-7.36 (m, 3H), 7.23 (d, J=8.4 Hz, 1H), 7.10 (q, J=8.6 Hz, 1H), 7.03 (dd, J=8.5, 3.9 Hz, 1H), 6.99 (d, J=7.8 Hz, 1H), 6.51 (d, J=8.5 Hz, 1H), 5.63 (d, J=5.5 Hz, 1H), 5.61 (d, J=2.2 Hz, 1H), 5.49 (d, J=10.8 Hz, 1H), 5.45 (s, 1H), 5.38 (dd, J=13.8, 2.1 Hz, 1H), 4.70 (dd, J=13.5, 1.9 Hz, 1H), 4.53 (dd, J=9.9, 2.9 Hz, 1H), 4.30 (d, J=13.8 Hz, 1H), 3.92 (dd, J=10.8, 2.8 Hz, 1H), 3.76 (dd, J=11.8, 3.2 Hz, 1H), 3.42-3.37 (m, 1H), 3.37-3.31 (m, 1H), 2.96-2.88 (m, 1H).

Example 7 The Enantiomer Mixture of (R)-12-((S)-10,11-difluoro-7,12-dihydrobenzo [e] naphtho [1,2-b]thiepin-7-yl)-7-hydroxy-3,4,12,12a-tetrahydro-11H-[1,4] oxazino [3,4-c] pyrido [2,1-f] [1,2,4] triazine-6, 8-dione and (S)-12-((R)-10,11-difluoro-7, 12-dihydrobenzo[e]naphtho[1,2-b]thiepin-7-yl)-7-hydroxy-3,4,12,12a-tetrahydro-1H-[1,4]oxazino[3,4-c]pyrido[2,1-f][1,2,4]triazine-6, 8-dione Mixture:

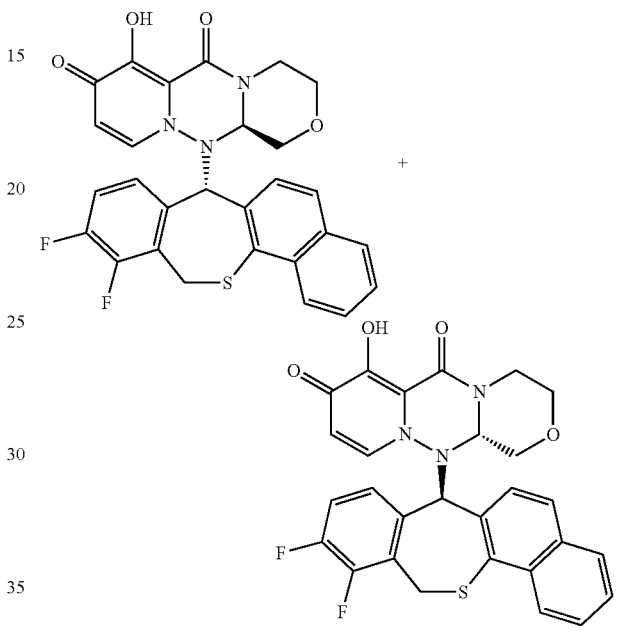

The enantiomer mixture 1 of 7-(benzyloxy)-12-(10,11-difluoro-7,12-dihydrobenzo[e]naphtho[1,2-b]thiepin-7-yl)-3,4,12,12a-tetrahydro-1H-[1,4]oxazino[3,4-c]pyrido[2,1-f][1,2,4]triazine-6,8-dione (64 mg, 0.10 mmol) which was the title compound of example 7 was dissolved in N,N'-dimethyl acetamide (2 mL), then anhydrous lithium chloride (66 mg, 1.54 mmol) was added. The mixture was reacted overnight at 100° C. under protection of nitrogen. To the reaction mixture was added water (5 mL), and adjusted with 1M dilute hydrochloric acid to pH about 6, filtered. The filter cake was washed with water (10 mL), dried, and the residue was purified by silica gel column chromatography (dichloromethane/methanol/glacial acetic acid (v/v/v)=150/10/1) to give the title compound as a light yellow solid (40 mg, 73%).

MS (ESI, pos. ion) m/z: 534.2[M+H]$^+$;

HRMS (ESI, pos. ion) m/z: Theoretical value of 534.1302, (C$_{28}$H$_{22}$F$_2$N$_3$O$_4$S)[M+H]$^+$: 534.1299

$^1$H NMR (400 MHz, DMSO-d$_6$) δ (ppm): 8.38-8.31 (m, 1H), 7.69-7.63 (m, 1H), 7.53-7.51 (m, 2H), 7.27-7.22 (m, 2H), 7.18-7.06 (m, 2H), 6.91 (d, J=6.5 Hz, 1H), 6.86 (d, J=8.1 Hz, 1H), 5.85 (d, J=6.3 Hz, 1H), 5.77 (s, 1H), 5.32 (d, J=13.6 Hz, 1H), 5.15 (s, 1H), 4.77 (d, J=13.7 Hz, 1H), 4.61 (d, J=7.7 Hz, 1H), 4.31 (d, J=13.8 Hz, 1H), 3.88 (d, J=7.9 Hz, 1H), 3.76-3.71 (m, 1H), 3.51 (t, J=10.4 Hz, 1H), 2.86 (t, J=11.3 Hz, 1H).

Example 8 7-(Benzyloxy)-12-(dibenzo [b,f] [1,4]thiazepin-11-yl)-3,4,12,12a-tetrahydro-1H-[1,4]oxazino[3,4-c]pyrido[2,1-f] [1,2,4]triazine-6,8-dione

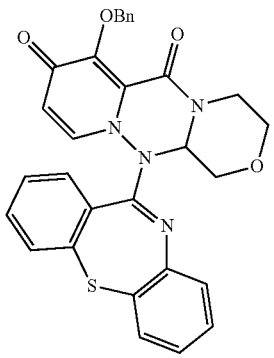 [SMILES: O=C1c2c(OCc3ccccc3)c(=O)ccn2N(C2=Nc3ccccc3Sc3ccccc32)C2COCCN12]

Step 1) 2-(Phenylthio)aniline

2-Aminothiophenol (5.00 g, 39.94 mmol), potassium carbonate (6.07 g, 43.90 mmol), iodobenzene (8.15 g, 39.90 mmol), iron powder (670 mg, 12.00 mmol) and copper powder (761 mg, 11.97 mmol) were mixed in DMF (30 mL), and the mixture was heated to 120° C. and stirred for 3 hours. The reaction was stopped, then the reaction mixture was filtered through a celite pad and quenched with ethyl acetate (60 mL×3). The combined organic phases were washed with saturated brine (80 mL) and dried over anhydrous sodium sulfate, then the filtrate was concentrated, and the residue was purified by silica gel column chromatography (PE/EtOAc (v/v)=10/1) to give the title compound as oil (7.96 g, 99.0%).

MS (ESI, pos. ion) m/z: 202.3 [M+H]$^+$;

$^1$H NMR (400 MHz, CDCl$_3$) δ (ppm): 7.98 (s, 1H), 5.11 (s, 2H), 0.31 (s, 9H)

Step 2) Phenyl (2-(phenylthio)phenyl)carbamate 2-(Phenylthio)aniline (7.66 g, 38.10 mmol) was dissolved in toluene (50 mL), then the mixture was cooled to 4° C. Phenyl chloroformate (7.15 g, 45.70 mmol) was dissolved in toluene (30 mL), and the resulting solution of phenyl chloroformate in toluene (15 mL) was added slowly to the solution of 2-(phenylthio)aniline in toluene above which was then stirred for 5 minute. A solution of sodium hydroxide (14.00 g, 28.5 mmol) and sodium carbonate (3.53 g, 33.30 mmol) in water (15 mL) with the remaining solution of phenyl chloroformate in toluene (15 mL) were added slowly into the above reaction solution which was then stirred at 4° C. for 1.5 hours. The reaction was stopped, and the reaction solution was extracted with ethyl acetate (30 mL). Aqueous phase was washed with ethyl acetate (10 mL), the combined organic phases were washed with 1M dilute hydrochloric acid (30 mL) and saturated saline (40 mL) in turn, dried over anhydrous sodium sulfate and concentrated to give the title compound as a white solid (12.20 g, 99.8%).

MS (ESI, pos. ion) m/z: 322.0 [M+H]$^+$;

$^1$H NMR (600 MHz, CDCl$_3$) δ (ppm): 8.30 (d, J=7.9 Hz, 1H), 8.13 (s, 1H), 7.69-7.61 (m, 1H), 7.50 (m, 1H), 7.46 (t, J=8.0 Hz, 1H), 7.41 (t, J=7.9 Hz, 2H), 7.31 (t, J=7.7 Hz, 2H), 7.29-7.20 (m, 3H), 7.16 (t, J=7.0 Hz, 5H).

Step 3) Dibenzo[b,f][1,4]thiazepin-11(1 OH)-one

P$_2$O$_5$ (9.13 g, 64.34 mmol) was suspended in methanesulfonic acid (30 mL), and the mixture was heated to 80° C. After solid was dissolved completely, phenyl (2-(phenylthio)phenyl)carbamate (10.34 g, 32.17 mmol) was added, the resulting solution was heated to 110° C. and stirred for 2.5 hours. Water (80 mL) was added into the reaction solution, large amounts of solid was precipitated, which was filtered under reduced pressure and washed with water (60 mL) and petroleum ether (60 mL) in turn, dried in vacuo to give a dark white solid (7.03 g, 96%).

MS (ESI, pos. ion) m/z: 228.0 [M+H]$^+$

Step 4) 11-chlorodibenzo [b, f] [1,4] thiazepine

Dibenzo[b,f][1,4]thiazepin-11(10H)-one (700 mg, 3.08 mmol) was dissolved in phosphorus oxychloride (10 mL), then N,N-dimethylaniline (0.59 mL, 4.7 mmol) was added, and the resulting mixture was reacted at 120° C. for 3 hours. The reaction was stopped and the reaction mixture was concentrated in vacuo. Dichloromethane (30 mL) and ice water (30 mL) were added in turn. The mixture was extracted with dichloromethane (30 mL×2), washed with saturated saline (40 mL), dried over anhydrous sodium sulfate, concentrated. The residue was purified by silica gel column chromatography (PE/EA (v/v)=5/1) to give the title compound as a yellow solid (470 mg, 62%).

$^1$H NMR (400 MHz, CDCl$_3$) δ (ppm): 7.77 (dd, J=7.6, 1.1 Hz, 1H), 7.49-7.28 (m, 6H), 7.22-7.16 (m, 1H)

Step 5) 7-(Benzyloxy)-12-(dibenzo[b,f][1,4]thiazepin-11-yl)-3,4,12,12a-tetrahydro-1H-[1, 4]oxazino[3,4-c]pyrido[2,1-f][1,2,4]triazine-6,8-dione 7-(Benzyloxy)-12-(10,11-difluoro-7,12-dihydrobenzo[e]naphtho[1,2-b]thiepin-7-yl)-3,4,12,12a-tetrahydro-1H-[1,4]oxazino[3,4-c]pyrido[2,1-f][1,2,4]triazine-6,8-dione (25 mg, 0.07 mmol) was dissolved in DMSO (8 mL), then potassium carbonate (22 mg, 0.16 mmol) was added under protection of nitrogen. The solution was stirred at rt for 15 minutes, then a solution of 11-chlorodibenzo[b,f][1,4]thiazepine (20 mg, 0.08 mmol) in DMSO (3 mL) was added into the reaction system. The resulting mixture was stirred for 30 minutes, heated to 80° C., and stirred overnight. The reaction was stopped, and the reaction solution was added to water (30 mL) for quenching reaction. The resulting solution was extracted with ethyl acetate (30 mL×3), washed with saturated saline (20 mL×3), dried over anhydrous sodium sulfate and concentrated in vacuo to give the title compound as a light white solid (19 mg, 46%).

MS (ESI, pos. ion) m/z: 537.3 [M+H]$^+$;

$^1$H NMR (400 MHz, DMSO-d$_6$) δ(ppm): 8.05 (d, J=7.7 Hz, 1H), 7.93 (d, J=7.5 Hz, 1H), 7.66 (d, J=6.1 Hz, 2H), 7.59 (t, J=6.7 Hz, 1H), 7.48 (d, J=6.9 Hz, 2H), 7.45 (d, J=7.7 Hz, 1H), 7.31-7.24 (m, 4H), 7.15 (t, J=7.5 Hz, 1H), 6.84 (d, J=7.7 Hz, 1H), 6.48 (d, J=7.7 Hz, 1H), 5.13 (q, J=10.7 Hz, 2H), 4.84 (d, J=7.8 Hz, 1H), 4.32 (d, J=12.7 Hz, 1H), 3.65 (t, J=10.5 Hz, 2H), 3.51 (s, 1H), 3.35-3.30 (m, 1H), 3.09 (t, J=6.9 Hz, 1H).

Example 9 12-(Dibenzo[b,f] [1,4]thiazepin-11-yl)-7-hydroxy-3,4,12,12a-tetrahydro-H-[1,4] oxazino [3,4-c]pyrido[2,1-f] [1,2,4]triazine-6,8-dione

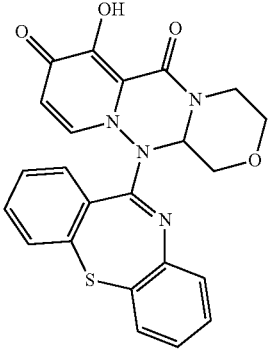 [SMILES: O=C1c2c(O)c(=O)ccn2N(C2=Nc3ccccc3Sc3ccccc32)C2COCCN12]

7-(Benzyloxy)-12-dibenzo[b,f][1,4]thiazepin-11-yl)-3,4, 12,12a-tetrahydro-1H-[1, 4]oxazino[3,4-c]pyrido[2,1-f][1, 2,4]triazine-6,8-dione (80 mg, 0.15 mmol) and lithium chloride (65 mg, 1.5 mmol) were mixed in DMSO (5 mL). The solution was heated to 110° C. and stirred overnight under protection of nitrogen. The reaction solution was added to water (10 mL) for quenching reaction, and adjusted with 0.5 M HCl to pH about 6. The resulting solution was extracted with 2-MeTHF (10 mL×3), washed with saturated saline (30 mL), dried over anhydrous sodium sulfate and concentrated. The residue was purified by silica gel column chromatography (DCM/MeOH (v/v)=20/1) to give the title compound as a pale solid (29 mg, 43%).

MS (ESI, pos. ion) m/z: 447.2 [M+H]+;

HRMS (ESI, pos. ion) m/z: Theoretical value of 447.1118, ($C_{23}H_{19}N_4O_4S$)[M+H]+: 447.1127; $^1$H NMR (600 MHz, DMSO-$d_6$) δ (ppm): 8.06 (s, 1H), 7.95 (s, 1H), 7.67 (s, 3H), 7.44 (s, 2H), 7.27 (s, 1H), 7.14 (s, 1H), 6.80 (s, 1H), 4.99 (s, 1H), 4.39 (s, 1H), 4.23 (s, 1H), 3.71 (d, J=14.9 Hz, 1H), 3.25 (s, 1H), 3.17 (s, 1H), 1.99 (s, 1H).

Example 10 The Mixture of (12aR)-12-((8R)-4,5-difluoro-8H-dibenzo [3,4:6,7]cyclohepta[1,2-b]thiophen-8-yl)-7-hydroxy-3,4,12,12a-tetrahydro-1H-[1, 4]oxazino[3,4-c]pyrido [2,1-f][1,2,4]triazine-6, 8-dione and (12aS)-12-((8S)-4,5-difluoro-8H-dibenzo [3,4:6,7]cyclohepta[1,2-b]thiophen-8-yl)-7-hydroxy-3,4,12,12a-tetrahydro-1H-[1,4]oxazino[3,4-c]pyrido[2,1-f] [1,2,4]triazine-6, 8-dione Mixture:

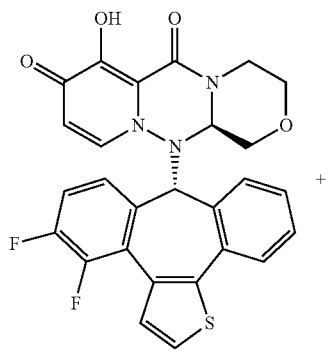

+

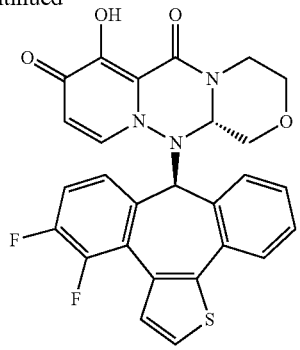

Step 1) Synthesis of 3-(2,3-difluorophenyl)thiophene 2,3-Difluorobromobenzene (5.01 g, 26.00 mmol), 3-thiopheneboronic acid (3.98 g, 31.10 mmol), bistriphenylphosphine palladium dichloride (1.85 g, 2.61 mmol) and sodium carbonate (8.33 g, 77.80 mmol) were added into reaction flask. THF (100 mL) and water (10 mL) were then added. The resulting mixture was warmed to 75° C. under the protection of nitrogen and reacted overnight. The reaction was stopped and the reaction mixture was filtered. The filter cake was washed with ethyl acetate (50 mL), the filtrate was concentrated in vacuo and the crude product was purified by silica gel column chromatography (PE) to give the title compound as light yellow liquid (4.06 g, 80%).

$^1$H NMR (400 MHz, CDCl$_3$) δ (ppm): 7.95-7.91 (m, 1H), 7.71 (dd, J=5.0, 3.0 Hz, 1H), 7.55-7.51 (m, 2H), 7.42-7.33 (m, 1H), 7.30-7.23 (m, 1H).

Step 2) Synthesis of 2-bromo-3-(2,3-difluorophenyl)thiophene 3-(2,3-Difluorophenyl)thiophene (4.06 g, 20.70 mmol) was dissolved in anhydrous DMF (80 mL), then solution of NBS (5.53 g, 30.40 mmol) in DMF (20 mL) was added to reaction solution. The resulting mixture was reacted for 3 hours under rt. The reaction was stopped and saturated sodium thiosulfate aqueous solution (200 mL) was added to reaction solution. The resulting mixture was quenched with ethyl acetate (100 mL×3). The combined organic phases were washed with saturated saline solution (200 mL×3), dried over anhydrous sodium sulfate and concentrated. The residue was purified by silica gel column chromatography (PE) to give the title compound as light yellow liquid (5.45 g, 96%).

Step 3) Synthesis of methyl 2-(3-(2,3-difluorophenyl)thiophen-2-yl)benzoate

2-Bromo-3-(2,3-difluorophenyl)thiophene (5.45 g, 19.80 mmol), methyl benzoate-2-boronic acid (7.15 g, 39.70 mmol), bis(triphenylphosphine)palladium dichloride (1.43 g, 2.02 mmol) and potassium carbonate (8.38 g, 59.40 mmol) were added into a reaction flask, then THF (50 mL) and water (5 mL) were added, and the mixture was stirred overnight at 75° C. under the protection of nitrogen. The reaction solution was cooled to rt and filtered, the filter cake was washed with ethyl acetate (50 mL), the filtrate was concentrated, and the residue was purified by silica gel column chromatography (PE/EA (v/v)=10/1) to give the title compound as a white solid (3.06 g, 47%).

$^1$H NMR (400 MHz, CDCl$_3$) δ (ppm): 7.73 (d, J=5.2 Hz, 1H), 7.64 (dd, J=7.7, 0.9 Hz, 1H), 7.58 (td, J=7.6, 1.3 Hz, 1H), 7.47 (td, J=7.6, 1.1 Hz, 1H), 7.42 (d, J=7.6 Hz, 1H), 7.35-7.26 (m, 1H), 7.23 (dd, J=5.2, 1.7 Hz, 1H), 7.08-7.03 (m, 1H), 6.85-6.81 (m, 1H), 3.48 (s, 3H).

Step 4) Synthesis of 2-(3-(2,3-difluorophenyl)thiophen-2-yl)benzoic acid

Methyl 2-(3-(2,3-difluorophenyl)thiophen-2-yl)benzoate (3.06 g, 9.26 mmol) was dissolved in THF (30 mL) and ethanol (10 mL), then a solution of sodium hydroxide (3.71 g, 92.80 mmol) in water (30 mL) was added into the reaction solution above, and the mixture was reacted overnight at 50° C. The reaction was stopped, and to the reaction mixture was added saturated saline (50 mL), adjusted with 1 N diluted hydrochloric acid to pH about 6, and partitioned. The aqueous phase was quenched with ethyl acetate (50 mL×2). The combined organic phases were washed with saturated brine (100 mL) and dried over anhydrous sodium sulfate and filtered, then the filtrate was concentrated, and the residue was purified by silica gel column chromatography (PE/EA (v/v)=3/1) to give the title compound as a light yellow solid (2.92 g, 99%).

MS (ESI, pos. ion) m/z: 317.0[M+H]+

Step 5) Synthesis of 4,5-difluoro-8H-dibenzo[3,4:6, 7]cyclohepta[1,2-b]thiophene-8-one 2-(3-(2,3-Difluorophenyl)thiophen-2-yl)benzoic acid (1.01 g, 3.19 mmol) was added into the reaction flask, then polyphosphoric acid (20 mL) was added, and the resulting mixture was stirred for 4 hours at 130° C. under the protection of nitrogen. The reaction was stopped, and the reaction mixture was cooled and then added into ice water (100 mL). The resulting mixture was stirred for 10 minutes, and quenched with ethyl acetate (100 mL×3). The combined organic phases were washed with saturated sodium bicarbonate aqueous solution (200 mL) and saturated brine (200 mL) in turn, and dried over anhydrous sodium sulfate and filtered, then the filtrate was concentrated in vacuo, and the residue was purified by silica gel column chromatography (PE/EA (v/v)=10/1) to give the title compound as a light yellow solid (0.46 g, 48%).

$^1$H NMR (400 MHz, CDCl$_3$) δ (ppm): 7.90 (d, J=5.4 Hz, 1H), 7.86 (d, J=7.8 Hz, 1H), 7.76 (t, J=6.9 Hz, 2H), 7.68 (t, J=6.0 Hz, 2H), 7.62 (t, J=7.1 Hz, 2H).

Step 6) Synthesis of 4,5-difluoro-8H-dibenzo[3,4:6, 7]cyclohepta[1,2-b]thiophene-8-ol 4,5-Difluoro-8H-dibenzo[3,4:6,7]cyclohepta[1,2-b]thiophene-8-one (0.46 g, 1.50 mmol) was dissolved in THF (10 mL) and methanol (5 mL), and the mixture was cooled to 0° C. Sodium borohydride (0.61 g, 16.00 mmol) was added in batches, the resulting mixture was reacted at 0° C. for 5 minutes, and then reacted at rt for 1 hour. Then the reaction was stopped and water (20 mL) was added to the reaction solution. The resulting solution was quenched with ethyl acetate (30 mL×3). The combined organic phases were washed with saturated saline solution (50 mL), dried over anhydrous sodium sulfate and concentrated in vacuo. The residue was purified by silica gel column chromatography (PE/EA (v/v)=20/1) to give the title compound as a white solid (0.45 g, 97%).

MS (ESI, pos. ion) m/z: 323.0[M+Na]$^+$;
$^1$H NMR (400 MHz, CDCl$_3$) δ (ppm): 7.81 (d, J=5.3 Hz, 1H), 7.77 (d, J=7.8 Hz, 1H), 7.60 (dd, J=9.4, 4.1 Hz, 2H), 7.55-7.44 (m, 3H), 7.34 (t, J=7.5 Hz, 1H), 6.44 (d, J=4.3 Hz, 1H), 5.00 (d, J=4.1 Hz, 1H).

Step 7) Synthesis of 7-(benzyloxy)-12-(4,5-difluoro-8H-dibenzo[3,4:6,7]cyclohepta[1,2-b]thiophen-8-yl)-3,4,12,12a-tetrahydro-1H-[1,4]oxazino[3,4-c]pyrido[2,1-f][1,2,4]triazine-6,8-dione 4,5-Difluoro-8H-dibenzo[3,4:6,7]cyclohepta[1,2-b]thiophene-8-ol (345 mg, 1.15 mmol) and 7-(benzyloxy)-3,4,12,12a-tetrahydro-1H-[1,4]oxazino[3,4-c]pyrido[2,1-f][1,2, 4]triazine-6, 8-dione (250 mg, 0.76 mmol) were added to a sealing tube, then 1-propylphosphoric anhydride (ethyl acetate solution) (wt 50%, 10 mL) was added, nitrogen was blowed in the mixture and the sealing tube was sealed. The reaction system was warmed to 100° C. and reacted for 2 hours. The reaction solution was added into ice water (30 mL) and resulting mixture was extracted with ethyl acetate (30 mL×3). The combined organic phases were washed with saturated sodium bicarbonate aqueous solution (50 mL), dried over anhydrous sodium sulfate, filtered and the filtrate was concentrated. The residue was purified by silica gel column chromatography (dichloromethane/methanol (v/v)=25/1) to give the title compound as a light yellow solid (174 mg, 37%).

MS (ESI, pos. ion) m/z: 610.0[M+H]$^+$

Step 8) Synthesis of the Mixture of (12aR)-12-((8R)-4,5-difluoro-8H-dibenzo[3,4:6,7]cyclohepta[1, 2-b]thiophen-8-yl)-7-hydroxy-3,4,12,12a-tetrahydro-1H-[1,4]oxazino[3,4-c]pyrido[2, 1-f][1,2,4]triazine-6, 8-dione and (12aS)-12-((8S)-4,5-difluoro-8H-dibenzo[3,4:6,7]cyclohepta[1,2-b]thiophen-8-yl)-7-hydroxy-3,4,12,12a-tetrahydro-1H-[1,4]oxazino[3,4-c]pyrido[2, 1-f][1,2,4]triazine-6, 8-dione 7-(Benzyloxy)-12-(4,5-difluoro-8H-dibenzo[3,4:6,7]cyclohepta[1,2-b]thiophen-8-yl)-3,4,12,12a-tetrahydro-1H-[1, 4]oxazino[3,4-c]pyrido[2,1-f][1,2,4]triazine-6,8-dione (174 mg, 0.29 mmol) was dissolved in N,N'-dimethyl acetamide (4 mL), anhydrous lithium chloride (123 mg, 2.87 mmol) was added, and the resulting mixture was reacted overnight at 100° C. under protection of nitrogen. The reaction was stopped and water (10 mL) was added. The reaction solution was adjusted with 1N dilute hydrochloric acid to pH 6. The mixture was extracted with ethyl acetate (10 mL×3). The combined organic phases were washed with saturated brine (20 mL×3), dried over anhydrous sodium sulfate and filtered, then the filtrate was concentrated in vacuo, and the residue was purified by LUNA preparative column chromatography (acetonitrile/0.1% trifluoroacetate aqueous solution (v/v)=12/13) to give the title compound as a light yellow solid (45 mg, 30%).

MS (ESI, pos. ion) m/z: 520.3[M+H]$^+$;
HRMS (ESI, pos. ion) m/z: 520.1131, (C$_{27}$H$_{20}$F$_2$N$_3$O$_4$S) [M+H]$^+$, theoretical value: 520.1143;
$^1$H NMR (400 MHz, DMSO-d$_6$) δ (ppm): 7.73 (d, J=7.6 Hz, 1H), 7.64 (t, J=5.4 Hz, 1H), 7.53 (d, J=5.3 Hz, 1H), 7.48 (t, J=7.5 Hz, 1H), 7.33-7.26 (m, 2H), 7.14 (s, 2H), 6.97 (d, J=7.5 Hz, 1H), 6.48 (d, J=7.4 Hz, 1H), 6.14 (d, J=7.4 Hz, 1H), 5.44 (s, 1H), 4.60 (d, J=13.0 Hz, 1H), 4.30 (dd, J=9.8, 2.8 Hz, 1H), 3.77 (dd, J=11.9, 2.6 Hz, 1H), 3.42-3.28 (m, 2H), 3.20 (t, J=10.5 Hz, 1H), 3.01-2.90 (m, 1H).

Example 11 12-(11,12-Difluoro-8H-dibenzo [3,4:6,7] cycloheptyl [1,2-b]thiophen-8-yl)-7-Hydroxy-3,4,12,12a-tetrahydro-1H-[1,4]oxazino[3,4-c]pyrido[2,1-f][1,2,4]triazine-6,8-dione

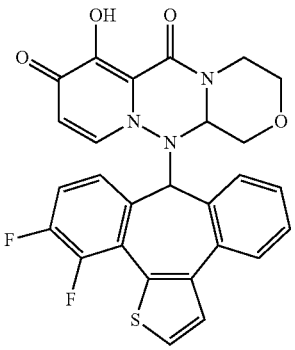 [SMILES: O=C1c2c(O)c(=O)ccn2N(C2c3ccccc3-c3ccsc3-c3c2ccc(F)c3F)C2COCCN12]

Step 1) Synthesis of 3-phenylthiophene

Bromobenzene (5.01 g, 31.90 mmol), 3-thiopheneboronic acid (4.90 g, 38.30 mmol), bis(triphenylphosphine)palladium dichloride (2.26 g, 3.19 mmol) and sodium carbonate (10.21 g, 95.40 mmol) were added into the reaction flask, then THF (100 mL) and water (10 mL) were added, and the reaction was stirred overnight at 75° C. under the protection of nitrogen. The reaction solution was filtered, the filter cake was washed with ethyl acetate (50 mL), and the filtrate was concentrated in vacuo. The residue was purified by silica gel column chromatography (eluent: PE) to give the title compound as light yellow liquid (4.97 g, 97%).
$^1$H NMR (400 MHz, CDCl$_3$) δ (ppm): 7.64 (d, J=1.2 Hz, 1H), 7.62 (s, 1H), 7.49-7.46 (m, 1H), 7.45-7.39 (m, 4H), 7.32 (t, J=7.4 Hz, 1H).

Step 2) Synthesis of 2-bromo-3-phenylthiophene

3-Phenylthiophene (501 mg, 3.13 mmol) was dissolved in DMF (5 mL), then a solution of NBS (680 mg, 3.74 mmol) in DMF (2 mL) was added to reaction solution. The resulting mixture was reacted for 3 hours at rt. The reaction was stopped and saturated sodium thiosulfate aqueous solution (20 mL) was added to quench the reaction. The resulting solution was extracted with ethyl acetate (15 mL×3). The combined organic phases were washed with saturated saline solution (30 mL×3), dried over anhydrous sodium sulfate and concentrated in vacuo. The residue was purified by silica gel column chromatography (PE) to give the title compound as light yellow liquid (702 mg, 94%).
$^1$H NMR (400 MHz, CDCl$_3$) δ (ppm): 7.59 (m, 2H), 7.47 (m, 2H), 7.40 (m, 1H), 7.34 (d, J=5.6 Hz, 1H), 7.07 (d, J=5.6 Hz, 1H).

Step 3) Synthesis of 4,4,5,5-tetramethyl-2-(3-phenylthiophen-2-yl)-1,3,2-dioxaborolane 2-Bromo-3-phenylthiophene (3.00 g, 12.50 mmol) was dissolved in anhydrous THF (50 mL), the resulting mixture was cooled to −78° C. under protection of nitrogen and a solution of N-butyllithium in n-hexane (2.5 M, 5.50 mL, 14.00 mmol) was added slowly. The resulting mixture was reacted at −78° C. for 2 hours, and then 2-isopropoxy-4,4,5,5-tetramethyl-1,3,2-dioxaborolan (3.05 g, 16.40 mmol) was added. The mixture was then reacted at −78° C. for 3 hours and further reacted at rt for 4 hours. The reaction was stopped, and to the reaction mixture was added water (50 mL). The resulting mixture was stirred for 10 minutes, and extracted with ethyl acetate (15 mL×3). The combined organic phases were washed with saturated brine (30 mL×3) and dried over anhydrous sodium sulfate and filtered, then the filtrate was concentrated, and the residue was purified by silica gel column chromatography (PE/EA (v/v)=5/1) to give the title compound as yellow oil (3.04 g, 85%).
MS (ESI, pos. ion) m/z: 287.0[M+H]$^+$

Step 4) Synthesis of ethyl 3,4-difluoro-2-(3-phenylthiophen-2-yl)benzoate

Ethyl 3,4-difluoro-2-bromobenzoate (2.80 g, 10.60 mmol), 4,4,5,5-tetramethyl-2-(3-phenylthiophen-2-yl)-1,3,2-dioxaborolane (3.04 g, 10.60 mmol), bis(triphenylphosphine)palladium dichloride (0.75 g, 1.10 mmol) and potassium carbonate (4.48 g 31.80 mmol) were added into the reaction flask, then THF (60 mL) and water (6 mL) were added, and the reaction mixture was stirred overnight at 75° C. under the protection of nitrogen. The reaction solution was cooled to rt and filtered, then the filter cake was washed with ethyl acetate (50 mL). The filtrate was concentrated in vacuo, and the residue was purified by silica gel column chromatography (PE/EA (v/v)=10/1) to give the title compound as a light yellow solid (2.00 g, 55%).
MS (ESI, pos. ion) m/z: 345.1[M+H]$^+$

Step 5) Synthesis of 3,4-difluoro-2-(3-phenylthiophen-2-yl)benzoic acid

Ethyl 3,4-difluoro-2-(3-phenylthiophen-2-yl)benzoate (2.00 g, 5.81 mmol) was dissolved in THF (15 mL) and methanol (10 mL), then a solution of sodium hydroxide (2.331 g, 58.30 mmol) in water (15 mL) was added into the reaction solution above. The resulting mixture was reacted overnight at 60° C. Saturated saline (50 mL) was added into the mixture and pH of the reaction mixture was adjusted to about 6 with 1 N diluted hydrochloric acid. The resulting mixture was partitioned, and the aqueous phase was extracted with ethyl acetate (50 mL×2). The combined organic phases were washed with saturated saline solution (100 mL), dried over anhydrous sodium sulfate and concentrated. The residue was purified by silica gel column chromatography (PE/EtOAc (v/v)=3/1) to give 3,4-difluoro-2-(3-phenylthiophen-2-yl)benzoic acid as a light yellow solid (1.80 g, 98%).
MS (ESI, neg. ion) m/z: 315.0[M−H]$^-$

Step 6) Synthesis of 11,12-difluoro-8H-dibenzo[3,4:6,7]cyclohepta[1,2-b]thiophene-8-one 3,4-Difluoro-2-(3-phenylthiophen-2-yl)benzoic acid (40 mg, 0.13 mmol) was added into the reaction flask, polyphosphoric acid (1 mL) was added, and the reaction mixture was reacted at 120° C. for 2 hour under protection of nitrogen. The reaction was stopped, then the reaction mixture was cooled and added into ice water (10 mL). The resulting solution was stirred for 10 min and extracted with ethyl acetate (10 mL×3). The combined organic phases were washed with saturated sodium bicarbonate aqueous solution (200 mL) and saturated brine (20 mL) in turn, dried over anhydrous sodium sulfate and filtered, then the filtrate was concentrated in vacuo. The residue was purified by silica gel column chromatography (PE/EA (v/v)=20/1) to give the title compound as a light yellow solid (15 mg, 40%).

$^1$H NMR (400 MHz, CDCl$_3$) δ (ppm): 8.04 (d, J=5.4 Hz, 1H), 7.94 (d, J=7.8 Hz, 1H), 7.78-7.72 (m, 2H), 7.70-7.64 (m, 3H), 7.64-7.60 (m, 1H).

Step 7) Synthesis of 11,12-difluoro-8H-dibenzo[3,4: 6,7]cyclohepta[1,2-b]thiophene-8-ol 11,12-Difluoro-8H-dibenzo[3,4:6,7]cyclohepta[1,2-b] thiophene-8-one (0.14 g, 0.47 mmol) was dissolved in THF (5 mL) and methanol (2 mL), and the mixture was cooled to 0° C. Sodium borohydride (0.18 g, 4.70 mmol) was added in batches, the resulting mixture was reacted at 0° C. for 5 minutes, and then reacted at rt for 30 minutes. Then the reaction was stopped and water (10 mL) was added to the reaction solution. The resulting mixture was extracted with ethyl acetate (10 mL×3). The combined organic phases were washed with saturated saline solution (20 mL), dried over anhydrous sodium sulfate and concentrated in vacuo. The residue was purified by silica gel column chromatography (PE/EA (v/v)=20/1) to give the title compound as a white solid (0.13 g, 92%).

$^1$H NMR (400 MHz, DMSO-d$_6$) δ (ppm): 7.96 (d, J=5.2 Hz, 1H), 7.74 (d, J=7.7 Hz, 1H), 7.65-7.55 (m, 3H), 7.55-7.49 (m, 1H), 7.48-7.43 (m, 1H), 7.34 (t, J=7.3 Hz, 1H), 6.42 (d, J=4.2 Hz, 1H), 4.98 (d, J=3.5 Hz, 1H).

Step 8) Synthesis of 7-(benzyloxy)-12-(11,12-difluoro-8H-dibenzo[3,4:6,7]cyclohept[1,2-b]thiophen-8-yl)-3,4,12,12a-tetrahydro-1H-[1,4]oxazino[3,4-c]pyrido[2,1-f][1,2,4]triazine-6,8-dione 11,12-Difluoro-8H-dibenzo[3,4:6,7]cyclohepta[1,2-b] thiophen-8-ol (166 mg, 0.55 mmol) and 7-(benzyloxy)-3,4, 12,12a-tetrahydro-1H-[1,4]oxazino[3,4-c]pyrido[2,1-f] [1,2, 4]triazine-6-,8-dione (120 mg, 0.37 mmol) were added to a sealing tube, then 1-propylphosphoric anhydride (ethyl acetate solution) (wt 50%, 6 mL) was added, nitrogen was blowed in and the sealing tube was sealed. The reaction mixture was heated to 100° C. and reacted for 2 hours. The reaction was stopped, and the reaction mixture was added into ice water (20 mL) and then the resulting mixture was extracted with ethyl acetate (20 mL×3). The combined organic phases were washed with saturated sodium bicarbonate aqueous solution (50 mL), dried over anhydrous sodium sulfate, filtered and the filtrate was concentrated in vacuo. The residue was purified by silica gel column chromatography (dichloromethane/methanol (v/v)=25/1) to give the title compound as a light yellow solid (100 mg, 45%).

MS (ESI, pos. ion) m/z: 610.1[M+H]$^+$

Step 9) Synthesis of 12-(11,12-difluoro-8H-dibenzo [3,4:6,7]cyclohept[1,2-b]thiophen-8-yl)-7-hydroxy 3,4,12,12a-tetrahydro-1H-[1,4]oxazino[3,4-c]pyrido [2, 1-f][1,2,4]triazine-6,8-dione 7-(Benzyloxy)-12-(11,12-difluoro-8H-dibenzo[3,4:6,7] cyclohept[1,2-b]thiophen-8-yl)-3,4,12,12a-tetrahydro-1H-[1,4]oxazino[3,4-c]pyrido[2,1-f][1,2,4]triazine-6,8-dione (100 mg, 0.16 mmol) was dissolved in N,N'-dimethyl acetamide (3 mL), and anhydrous lithium chloride (71 mg, 1.66 mmol) was added, then the mixture was reacted overnight at 100° C. under protection of nitrogen. To the reaction mixture was added water (10 mL), and the mixture was adjusted with 1N diluted hydrochloric acid to pH about 6, then extracted with ethyl acetate (10 mL×3). The combined organic phases were washed with saturated brine (20 mL×3), dried over anhydrous sodium sulfate and filtered, then the filtrate was concentrated in vacuo. The residue was purified by silica gel column chromatography (dichloromethane/methanol/glacial acetic acid (v/v/v)=150/5/2) to give the title compound as a light yellow solid (50 mg, 59%).

MS (ESI, pos. ion) m/z: 520.3[M+H]$^+$;

HRMS (ESI, pos. ion) m/z: 520.1153, (C$_{27}$H$_{20}$F$_2$N$_3$O$_4$S) [M+H]$^+$, theoretical value: 520.1143; $^1$H NMR (400 MHz, DMSO-d$_6$) δ(ppm): 7.80-7.65 (m, 2H), 7.62-7.43 (m, 3H), 7.12-6.76 (m, 2H), 6.57-6.36 (m, 1H), 6.20 (d, J=7.3 Hz, 1H), 6.12 (d, J=7.4 Hz, 1H), 5.42 (d, J=4.4 Hz, 1H), 4.59 (t, J=13.0 Hz, 1H), 4.30-4.19 (m, 1H), 3.81-3.69 (m, 1H), 3.37-3.26 (m, 2H), 3.17 (q, J=10.1 Hz, 1H), 2.96-2.88 (m, 1H).

Example 12 The Mixture of (12aR)-12-((8R)-4,5-difluoro-2-phenyl-8H-dibenzo[3,4:6,7]cyclohept[1, 2-b]thiophen-8-yl)-7-hydroxy-3,4,12,12a-tetrahydro-1H-[1,4]oxazino[3,4-c]pyrido[2,1-f] [1,2,4] triazine-6,8-dione and (12aS)-12-((8S)-4,5-difluoro-2-phenyl-8H-dibenzo[3,4:6,7]cyclohept[1,2-b] thiophen-8-yl)-7-hydroxy-3,4,12,12a-tetrahydro-1H-[1,4] oxazino [3,4-c] pyrido [2,1-f][1,2,4] triazine-6,8-dione Mixture:

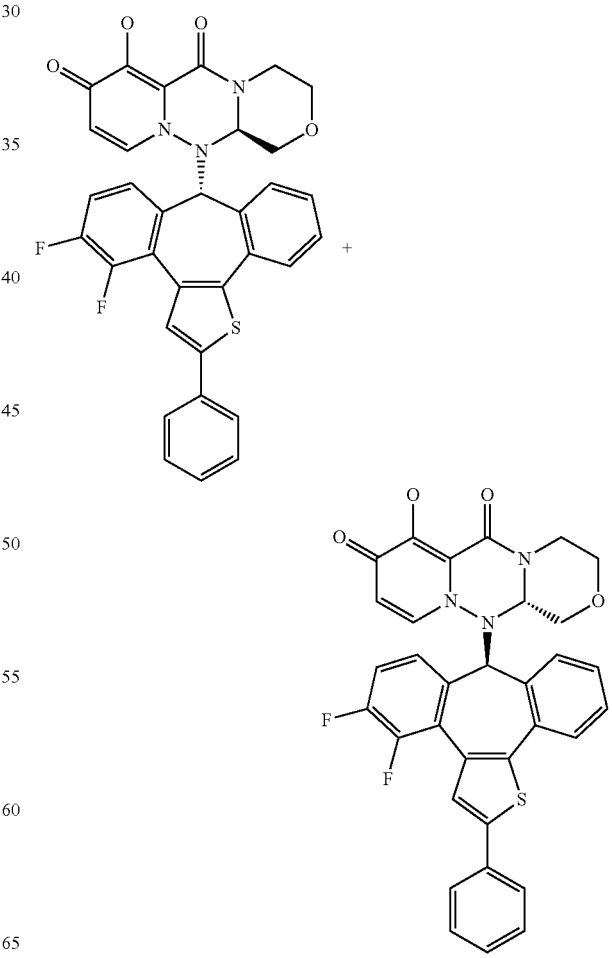

Step 1) Synthesis of 2-bromo-4, 5-difluoro-8H-dibenzo[3,4:6,7]cyclohept[1,2-b]thiophene-8-one 4,5-Difluoro-8H-dibenzo[3,4:6,7]cyclohept[1,2-b]thiophene-8-one (50 mg, 0.17 mmol) was dissolved in DMF (3 mL). The solution was stirred at rt and a solution of NBS (32 mg, 0.18 mmol) in DMF (3 mL) was added. The resulting mixture was reacted at rt for 48 hours. The reaction was stopped, and the reaction mixture was added to water (25 mL). The resulting mixture was extracted with ethyl acetate (15 mL×3). The combined organic phases were washed with saturated brine (15 mL×3), dried over anhydrous sodium sulfate, and concentrated. The residue was purified by silica gel column chromatography (PE/EA (v/v)=50/1) to give the title compound as a solid (51 mg, 80.66%).

$^1$H NMR (400 MHz, CDCl$_3$) δ (ppm) 7.86-7.81 (m, 1H), 7.70 (d, J=7.2 Hz, 1H), 7.63 (dd, J=8.6, 6.6 Hz, 3H), 7.54 (dd, J=10.7, 4.2 Hz, 1H), 7.35-7.29 (m, 1H).

Step 2) Synthesis of 2-phenyl-4,5-difluoro-8H-dibenzo[3,4:6,7] cyclohept[1,2-b]thiophen-8-one 2-Bromo-4,5-difluoro-8H-dibenzo[3,4:6,7]cyclohept[1,2-b]thiophene-8-one (130 mg, 0.34 mmol), phenylboronic acid (67 mg, 0.55 mmol), potassium carbonate (142 mg, 1.0 mmol), and bis(triphenylphosphine)palladium(II) chloride (24 mg, 0.03 mmol) were mixture in tetrahydrofuran (15 mL) and water (1 mL). The resulting mixture was reacted at 70° C. for 25 hours under nitrogen protection. The reaction was stopped and the reaction solution was concentrated. The residue was purified by silica gel column chromatography (PE/EA (v/v)=15/1) to give the title compound as a light yellow solid (77 mg, 60%).

$^1$H NMR (400 MHz, CDCl$_3$) δ (ppm) 7.85 (dd, J=7.4, 3.3 Hz, 3H), 7.71 (d, J=7.2 Hz, 2H), 7.65 (dd, J=8.7, 5.3 Hz, 2H), 7.53 (dd, J=11.5, 4.5 Hz, 1H), 7.47 (t, J=7.4 Hz, 2H), 7.38 (t, J=7.4 Hz, 1H), 7.35-7.29 (m, 1H).

Step 3) Synthesis of 4,5-difluoro-2-phenyl-8H-dibenzo[3,4:6,7]cyclohept[1,2-b]thiophen-8-ol 2-Phenyl-4,5-difluoro-8H-dibenzo[3,4:6,7]cyclohept[1,2-b]thiophene-8-one (80 mg, 0.21 mmol) was dissolved in methanol (3 mL) and tetrahydrofuran (3 mL). Sodium borohydride (42 mg, 1.1 mmol) was added and the resulting mixture was stirred at rt for 15 minutes. The reaction was stopped and the reaction mixture was quenched with saturated aqueous ammonium chloride (10 mL), then extracted with ethyl acetate (20 mL×3). The combined organic phases were washed with saturated brine (20 mL), dried over anhydrous sodium sulfate and filtered, then the filtrate was concentrated in vacuo, and the residue was purified by silica gel column chromatography (PE/EtOAc (v/v)=3/1) to give the title compound as a white solid (83 mg, 103%).

Step 4) Synthesis of 7-(benzyloxy)-12-(4,5-difluoro-2-phenyl-8H-dibenzo[3,4:6,7]cyclohept[1,2-b]thiophen-8-yl)-3,4,12,12a-tetrahydro-1H-[1,4]oxazino[3,4-c]pyrido[2,1-f][1,2,4]triazine-6,8-dione 4,5-Difluoro-2-phenyl-8H-dibenzo[3,4:6,7]cyclohept[1,2-b]thiophen-8-ol (80 mg, 0.21 mmol) and 7-(benzyloxy)-3,4,12,12a-tetrahydro-1H-[1,4]oxazino[3,4-c]pyrido[2,1-f][1, 2, 4]triazine-6,8-dione (69 mg, 0.21 mmol) were added into a sealing tube, then T3P (50 mass % ethyl acetate solution) (3 mL, 5.0 mmol, 50 mass %) was added, and the tube was sealed. The mixture was reacted at 100° C. in an oil bath for 1 hour. The reaction mixture was added in to water (15 mL) and the resulting mixture was extracted with ethyl acetate (20 mL×3). The combined organic phases were washed with saturated brine (15 mL), dried over anhydrous sodium sulfate and filtered, then the filtrate was concentrated in vacuo, and the residue was purified by silica gel column chromatography (PE/EtOAc (v/v)=1/2) to give the title compound as a white solid (31 mg, 21%).

MS (ESI, pos. ion) m/z: 686.2[M+H]$^+$

Step 5) Synthesis of the Mixture of (12aR)-12-((8R)-4,5-difluoro-2-phenyl-8H-dibenzo[3,4:6,7]cyclohept[1,2-b]thiophen-8-yl)-7-hydroxy-3,4,12,12a-tetrahydro-1H-[1,4]oxazino[3,4-c]pyrido[2, 1-f][1,2,4]triazine-6,8-dione and (12aS)-12-((8S)-4,5-difluoro-2-phenyl-8H-dibenzo[3,4:6,7]cyclohept[1,2-b]thiophen-8-yl)-7-hydroxy-3,4,12,12a-tetrahydro-1H-[1,4]oxazino[3,4-c]pyrido[2,1-f][1,2,4 triazine-6, 8-dione 7-(Benzyloxy)-12-(4,5-difluoro-8H-dibenzo[3,4:6,7]cyclohept[1,2-b]thiophen-8-yl)-3,4,12,12a-tetrahydro-1H-[1,4]oxazino[3,4-c]pyrido[2,1-f][1,2,4]triazine-6,8-dione (78 mg, 0.11 mmol) and lithium chloride (48 mg, 1.1 mmol) were dissolved in DMAc (8 mL). The mixture was reacted overnight at 110° C. under protection of nitrogen. The reaction was stopped and water (10 mL) was added. The resulting mixture was adjusted with 0.5 M HCl to be weakly acidic, stirred for 10 minutes, and then extracted with 2-MeTHF (10 mL×3). The combined organic phases were washed with saturated brine (30 mL), dried over anhydrous sodium sulfate and filtered, then the filtrate was concentrated in vacuo, and the residue was purified by LUNA preparative column chromatography (acetonitrile/0.1% trifluoroacetate aqueous solution (v/v)=12/13) to give the title compound as a light yellow solid (45 mg, 66%).

MS (ESI, pos. ion) m/z: 596.1[M+H]$^+$;

HRMS (ESI, pos. ion) m/z: 596.1444, (C$_{33}$H$_{23}$F$_2$N$_3$O$_4$S) [M+H]$^+$, theoretical value: 596.1456;

$^1$H NMR (600 MHz, CDCl$_3$) δ (ppm) 7.85 (d, J=5.5 Hz, 2H), 7.77 (d, J=7.2 Hz, 3H), 7.55-7.45 (m, 4H), 7.42 (d, J=7.3 Hz, 1H), 7.31 (d, J=6.7 Hz, 1H), 6.98 (d, J 7.7 Hz, 1H), 6.54 (d, J=7.6 Hz, 1H), 6.09 (d, J=7.5 Hz, 1H), 5.41 (d, J=30.4 Hz, 1H), 4.63 (d, J=12.1 Hz, 1H), 4.33 (dd, J=9.9, 3.0 Hz, 1H), 3.78 (dd, J=12.0, 2.9 Hz, 1H), 3.44-3.31 (m, 2H), 3.20 (t, J=10.6 Hz, 1H), 3.09-2.90 (m, 1H).

Example 13 (R)-7-hydroxy-12-((S)-5-(trifluoromethoxy)-8H-dibenzo[3,4:6,7]cyclohept[1,2-b]thiophen-8-yl)-3,4,4,12,12a-tetrahydro-1H-[1,4]oxazino [3,4-c]pyrido [2,1-f] [1,2,4 triazine-6,8-dione (13-1) and (R)-7-hydroxy-12-((R)-5-(trifluoromethoxy)-8H-dibenzo [3,4:6,7]cyclohept[1,2-b]thiophen-8-yl)-3,4,4,12,12a-tetrahydro-1H-[1,4]oxazino [3,4-c]pyrido [2,1-f] [1,2,4 triazine-6,8-dione (13-2)

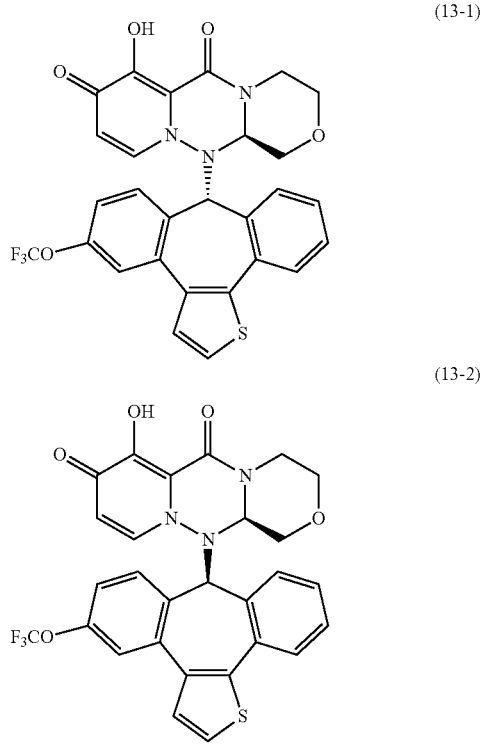

Step 1) Synthesis of (R)-7-(benzyloxy)-3,4,12,12a-tetrahydro-1H-[1,4]oxazino[3,4-c]pyrido[2, 1-f][1,2, 4]triazine-6,8-dione

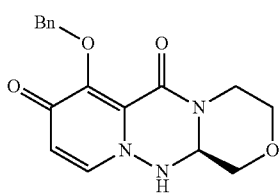 [SMILES: O=C1c2c(OCc3ccccc3)c(=O)ccn2N[C@@H]2COCCN12]

The title compound was prepared by the synthetic method disclosed in the patent application WO 2017221869.

Step 2) Synthesis of 3-(3-trifluoromethoxyphenyl)thiophene

3-Trifluoromethoxybromobenzene (1.00 g, 4.15 mmol), 3-thiopheneboronic acid (584 mg, 4.56 mmol), tetratriphenylphosphine palladium (247 mg, 0.21 mmol) and sodium carbonate (1.32 g, 12.40 mmol) were added into a reaction flask, then DMF (20 mL) and water (3 mL) were added. The reaction mixture was reacted overnight at 85° C. under protection of nitrogen. The reaction was stopped and the reaction solution was filtered. The filter cake was washed with ethyl acetate (50 mL), the filtrate was concentrated and the crude product was purified by silica gel column chromatography (PE) to give the title compound as light yellow liquid (670 mg, 66%).

$^1$H NMR (400 MHz, CDCl$_3$) δ (ppm): 7.56 (d, J=7.8 Hz, 1H), 7.52 (dd, J=2.8, 1.2 Hz, 1H), 7.47 (d, J=3.2 Hz, 1H), 7.45-7.37 (m, 3H), 7.19 (dd, J=8.1, 0.9 Hz, 1H).

Step 3) Synthesis of 2-bromo-3-(3-trifluoromethoxyphenyl)thiophene 3-(3-Trifluoromethoxyphenyl)thiophene (670 mg, 2.74 mmol) was dissolved in DMF (10 mL), and a solution of NBS (463 mg, 2.60 mmol) in DMF (10 mL) was added to the solution above. The resulting mixture was reacted at rt for 3 hours. The reaction was stopped, to the reaction mixture was added saturated sodium thiosulfate aqueous solution (200 mL) for quenching reaction, and the resulting mixture was extracted with ethyl acetate (100 mL×3). The combined organic phases were washed with saturated brine (200 mL×3), dried over anhydrous sodium sulfate and filtered, then the filtrate was concentrated in vacuo, and the residue was purified by silica gel column chromatography (PE) to give the title compound as light yellow liquid (863 mg, 97%).

Step 4) Synthesis of methyl 2-(3-(3-(trifluoromethoxy)phenyl)thiophen-2-yl)benzoate 2-Bromo-3-(3-trifluoromethoxyphenyl)thiophene (817 mg, 3.23 mmol), methyl benzoate-2-boronic acid (1.01 g, 3.87 mmol), bis(triphenylphosphine)palladium(II) chloride (228 mg, 0.32 mmol) and potassium carbonate (1.47 g, 10.60 mmol) were added into a reaction flask. THF (50 mL) and water (5 mL) were then added. The resulting mixture was warmed to 75° C. under the protection of nitrogen and reacted overnight. The reaction was stopped and the reaction solution was cooled to rt and filtered. The filter cake was washed with ethyl acetate (50 mL), the filtrate was concentrated and the crude product was purified by silica gel column chromatography (PE/EA (v/v)=10/1) to give the title compound as a white solid (245 mg, 25%).

$^1$H NMR (400 MHz, CDCl$_3$) δ (ppm): 7.81 (d, J=7.5 Hz, 1H), 7.56-7.46 (m, 2H), 7.41 (dd, J=12.9, 6.5 Hz, 3H), 7.23-7.21 (m, 1H), 7.13 (d, J=7.8 Hz, 1H), 7.04 (d, J=10.9 Hz, 2H), 3.58 (s, 3H).

Step 5) Synthesis of 2-(3-(3-trifluoromethoxyphenyl)thiophen-2-yl)benzoic acid

Methyl 2-(3-(3-trifluoromethoxyphenyl)thiophen-2-yl)benzoate (5.18 g, 13.70 mmol) was dissolved in THF (30 mL) and methanol (10 mL), then a solution of sodium hydroxide (2.19 g, 54.80 mmol) dissolved in water (30 mL) was added into the reaction solution above, and the mixture was reacted overnight at 50° C. The reaction was stopped, and to the reaction mixture was added saturated saline (50 mL). The mixture was adjusted with 1 N diluted hydrochloric acid to pH about 6, and partitioned. The aqueous phase was extracted with ethyl acetate (50 mL×2). The combined organic phases were washed with saturated brine (100 mL), dried over anhydrous sodium sulfate and filtered, then the filtrate was concentrated in vacuo, and the residue was purified by silica gel column chromatography (PE/EA (v/v)=3/1) to give the title compound as a light yellow solid (4.98 g, 99%).

MS (ESI, neg. ion) m/z: 363.1[M−H]⁻

Step 6) Synthesis of 3-trifluoromethoxy-8H-dibenzo[3,4:6,7]cyclohepta[1,2-b]thiophen-8-one 2-(3-(3-Trifluoromethoxyphenyl)thiophen-2-yl)benzoic acid (1.12 g, 3.07 mmol) was dissolved in dichloromethane (10 mL), and oxalyl chloride (0.52 mL, 6.1 mmol) was slowly added. The reaction solution was stirred for 30 minutes at rt. After the reaction was completed, the reaction mixture was concentrated in vacuo. Dichloromethane (10 mL) and aluminum chloride (820 mg, 6.14 mmol) were added into the residue. The resulting mixture was stirred for 8 minutes at rt. The reaction was stopped and the reaction mixture was quenched with saturated sodium bicarbonate solution (30 mL) and then extracted with dichloromethane (30 mL×3). The combined organic phases were washed with saturated brine (30 mL), dried over anhydrous sodium sulfate and filtered, then the filtrate was concentrated, and the residue was purified by silica gel column chromatography (PE/DCM (v/v)=3/1) to give the title compound as a light yellow solid (679 mg, 63.8%).

$^1$H NMR (400 MHz, CDCl$_3$) δ (ppm): 7.97 (d, J=8.7 Hz, 1H), 7.93 (dd, J=7.8, 0.9 Hz, 1H), 7.83 (d, J=7.9 Hz, 1H), 7.67-7.60 (m, 2H), 7.57-7.52 (m, 1H), 7.51-7.47 (m, 2H), 7.35 (d, J=8.6 Hz, 1H).

Step 7) Synthesis of 3-trifluoromethoxy-8H-dibenzo[3,4:6,7]cyclohepta[1,2-b]thiophen-8-ol 3-Trifluoromethoxy-8H-dibenzo[3,4:6,7]cyclohepta[1,2-b]thiophene-8-one (1.70 g, 4.91 mmol) was dissolved in THF (10 mL) and methanol (5 mL). The solution was cooled to 0° C. and sodium borohydride (1.93 g, 49.10 mmol) was added in batches. The resulting mixture was reacted at 0° C. for 5 minutes and at rt for 1 hour. The reaction was stopped, and the reaction mixture was added with water (20 mL) to quench the reaction, and then the resulting mixture was extracted with ethyl acetate (30 mL×3). The combined organic phases were washed with saturated brine (50 mL), dried over anhydrous sodium sulfate and filtered, then the filtrate was concentrated in vacuo, and the residue was purified by silica gel column chromatography (PE/EA (v/v)=20/1) to give the title compound as a white solid (1.68 g, 98%).

$^1$H NMR (400 MHz, CDCl$_3$) δ (ppm): 7.87 (dd, J=11.6, 8.4 Hz, 2H), 7.56 (d, J=7.7 Hz, 1H), 7.47 (dt, J=13.9, 6.4 Hz, 4H), 7.38 (s, 1H), 7.36-7.31 (m, 1H), 5.36 (s, 1H).

Step 8) Synthesis of (12aR)-7-(benzyloxy)-12-(5-(trifluoromethoxy)-8H-dibenzo[3,4:6,7]cyclohept[1,2-b]thiophen-8-yl)-3,4,12,12a-tetrahydro-1H-[1,4]oxazino[3,4-c]pyrido[2,1-f][1,2,4] triazine-6,8-dione 3-Trifluoromethoxy-8H-dibenzo[3,4:6,7]cyclohept[1,2-b]thiophen-8-ol (150 mg, 0.43 mmol) and (R)-7-(benzyloxy)-3,4,12,12a-tetrahydro-1H-[1,4]oxazino[3,4-c]pyrido[2,1-f][1,2,4]triazine-6,8-dione (155 mg, 0.47 mmol) were added into a sealing tube, and 1-propyl phosphate anhydride (ethyl acetate solution) (wt 50%, 1 mL) was added. The air in solution was exhausted with nitrogen bubbling, and the resulting solution was reacted at 110° C. for 2 hours. The reaction was stopped, and the mixture was added into ice water (30 mL), then the resulting mixture was extracted with ethyl acetate (30 mL×3). The combined organic phases were washed with saturated sodium bicarbonate aqueous solution (50 mL), dried over anhydrous sodium sulfate, filtered and the filtrate was concentrated. The residue was purified by silica gel column chromatography (dichloromethane/methanol (v/v)=25/1) to give the title compound as a light yellow solid (160 mg, 56%).

MS (ESI, pos. ion) m/z: 658.3[M+H]⁺

$^1$H NMR (400 MHz, CDCl$_3$) δ (ppm) 7.74 (d, J=7.6 Hz, 1H), 7.62 (d, J=7.6 Hz, 2H), 7.54 (d, J=7.3 Hz, 1H), 7.52-7.42 (m, 4H), 7.42-7.32 (m, 3H), 7.29 (s, 1H), 7.15-6.88 (m, 1H), 6.68-6.61 (m, 1H), 6.24 (m, 1H), 5.74-5.58 (m, 2H), 5.45 (dd, J=10.9, 3.8 Hz, 1H), 5.37 (d, J=7.7 Hz, 1H), 4.61 (dd, J=13.3, 2.8 Hz, 1H), 4.03 (d, J=8.7 Hz, 1H), 3.70-3.60 (m, 1H), 3.21 (m, 2H), 2.99 (t, J=10.4 Hz, 1H), 2.80 (td, J=14.7, 3.4 Hz, 1H).

Step 9) Synthesis of (R)-7-hydroxy-12-((S)-5-(trifluoromethoxy)-8H-dibenzo[3,4:6,7]cyclohept[1,2-b]thiophen-8-yl)-3,4,4,12,12a-tetrahydro-1H-[1,4]oxazino[3,4-c]pyrido[2,1-f] [1,2,4 triazine-6,8-dione (13-1) and (R)-7-hydroxy-12-((R)-5-(trifluoromethoxy)-8H-dibenzo[3,4:6,7]cyclohept[1,2-b]thiophen-8-yl)-3,4,4,12,12a-tetrahydro-1H-[1,4]oxazino[3,4-c]pyrido[2,1-f] [1,2,4 triazine-6,8-dione (13-2)

(12aR)-7-(benzyloxy)-12-(5-trifluoromethoxy-8H-dibenzo[3,4:6,7]cyclohept[1,2-b]thiophen-8-yl)-3,4,12,12a-tetrahydro-1H-[1,4]oxazino[3,4-c]pyrido[2,1-f][1,2,4]triazine-6, 8-dione (180 mg, 0.27 mmol) was dissolved in N,N'-dimethyl acetamide (4 mL), then anhydrous lithium chloride (116 mg, 2.74 mmol) was added, and the resulting mixture was reacted overnight at 100° C. under protection of nitrogen. The reaction was stopped and water (10 mL) was added. The reaction solution was adjusted with 1N diluted hydrochloric acid to pH about 6, and partitioned. The aqueous phase was quenched with ethyl acetate (10 mL×3). The combined organic phases were washed with saturated brine (20 mL×3), dried over anhydrous sodium sulfate and filtered, then the filtrate was concentrated in vacuo, and the residue was purified by LUNA preparative column chromatography (acetonitrile/0.1% trifluoroacetate aqueous solution (v/v)=12/13) to give the title compound (13-1) as a light yellow solid (18 mg, 12%) and the title compound (13-2) as a light yellow solid (17 mg, 10%).

MS (ESI, pos. ion) m/z: 568.2[M+H]⁺;

(R)-7-hydroxy-12-((S)-5-(trifluoromethoxy)-8H-dibenzo[3,4:6,7]cyclohept[1,2-b]thiophen-8-yl)-3,4,4,12,12a-tetrahydro-1H-[1,4]oxazino[3,4-c]pyrido[2,1-f] [1,2,4 triazine-6,8-dione (13-1)

HRMS (ESI, pos. ion) m/z: 568.1154, (C$_{28}$H$_{21}$F$_3$N$_3$O$_5$S) [M+H]⁺, theoretical value: 568.1166;

$^1$H NMR (400 MHz, DMSO-d$_6$) δ (ppm): 7.69 (d, J=7.6 Hz, 1H), 7.58 (s, 1H), 7.55-7.49 (m, 2H), 7.49-7.41 (m, 2H), 7.32 (s, 1H), 7.25 (d, J=7.3 Hz, 1H), 7.01 (d, J=7.5 Hz, 1H), 6.32 (d, J=7.7 Hz, 1H), 5.67 (d, J=7.7 Hz, 1H), 5.47 (s, 1H), 4.61 (d, J=13.1 Hz, 1H), 4.17 (dd, J=9.9, 2.9 Hz, 1H), 3.74 (dd, J=11.9, 2.7 Hz, 1H), 3.35 (dd, J=13.8, 6.1 Hz, 2H), 3.20 (t, J=10.5 Hz, 1H), 2.96-2.85 (m, 1H);

(R)-7-hydroxy-12-((R)-5-(trifluoromethoxy)-8H-dibenzo[3,4:6,7] cyclohept[1,2-b]thiophene-8-yl)-3,4,4,12,12a-tetrahydro-1H-[1,4]oxazino[3,4-c]pyrido[2,1-f] [1,2,4 triazine-6,8-dione (13-2)

HRMS (ESI, pos. ion) m/z: 568.1171, ($C_{28}H_{21}F_3N_3O_5S$) [M+H]$^+$, theoretical value: 568.1166;

$^1$H NMR (400 MHz, DMSO-d$_6$) δ (ppm): 7.77 (d, J=7.5 Hz, 1H), 7.59-7.44 (m, 6H), 7.06 (d, J=8.8 Hz, 2H), 6.23 (d, J=7.6 Hz, 1H), 5.70 (d, J=7.6 Hz, 1H), 5.47 (s, 1H), 4.59 (d, J=13.0 Hz, 1H), 4.16 (dd, J=9.8, 3.0 Hz, 1H), 3.72 (dd, J=11.8, 2.6 Hz, 1H), 3.35 (dd, J=14.3, 6.4 Hz, 2H), 3.22 (t, J=10.5 Hz, 1H), 2.95-2.83 (m, 1H).

Example 14 (R)-12-((S)-2-chloro-6-fluoro-8H-dibenzo [3,4:6,7]cyclohepta[1,2-b]thiophen-8-yl)-7-hydroxy-3,4,12,12a-tetrahydro-1H-[1,4]oxazino [3,4-c] pyrido [2,1-f] [1,2,4]triazine-6,8-dione (14-1) and (R-12-((R)-2-chloro-6-fluoro-8H-dibenzo[3,4:6,7]cyclohept[1,2-b]thiophen-8-yl)-7-hydroxy-3,4,12,12a-tetrahydro-1H-[1,4]oxazino [3,4-c] pyrido [2,1-f] [1,2,4]triazine-6,8-dione (14-2)

(14-1)

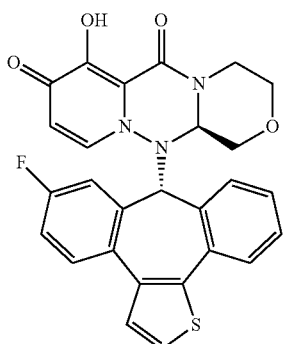

(14-2)

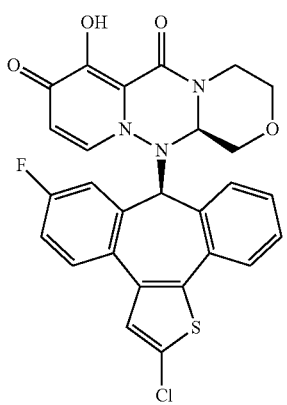

Step 1) Synthesis of 2-chloro-6-fluoro-8H-dibenzo [3,4:6,7]cyclohept[1,2-b]thiophen-8-one 6-Fluoro-8H-dibenzo[3,4:6,7]cyclohept[1,2-b]thiophen-8-one (703 mg, 2.50 mmol) was dissolved in DMF (5 mL). The solution was stirred at rt and added with a solution of NCS (683 mg, 5.01 mmol) in DMF (0.6 mL). The resulting mixture was stirred at rt for 3 hours, then heated to 40° C. and stirred for 23 hours. The reaction was stopped, and the reaction solution was added to saturated sodium thiosulfate solution (20 mL), and then ethyl acetate (30 mL) was added. The resulting mixture was stirred for 10 minutes and filtered to give the title compound as a light yellow solid (663 mg, 84%).

$^1$H NMR (400 MHz, CDCl$_3$) δ (ppm) 7.91 (d, J=7.7 Hz, 1H), 7.74-7.67 (m, 2H), 7.62 (ddd, J=6.6, 5.9, 2.0 Hz, 2H), 7.53 (t, J=7.5 Hz, 1H), 7.38-7.32 (m, 1H), 7.31 (s, 1H).

Step 2) Synthesis of 2-chloro-6-fluoro-8H-dibenzo [3,4:6,7]cyclohept[1,2-b]thiophen-8-ol 2-Chloro-6-fluoro-8H-dibenzo[3,4:6,7]cyclohept[1,2-b]thiophen-8-one (50 mg, 0.16 mmol) was dissolved in THF (10 mL) and methanol (5 mL). The solution was cooled to 0° C. and sodium borohydride (31 mg, 0.78 mmol) was added in batches. The resulting mixture was reacted at 0° C. for 5 minutes and then at rt for 1 hour. The reaction was stopped, to the reaction mixture was added water (20 mL). The resulting mixture was extracted with ethyl acetate (30 mL×3). The combined organic phases were washed with saturated brine (50 mL), dried over anhydrous sodium sulfate and filtered, then the filtrate was concentrated in vacuo, and the residue was purified by silica gel column chromatography (PE/EA (v/v)=20/1) to give the title compound as a white solid (38 mg, 76%).

$^1$H NMR (400 MHz, CDCl$_3$) δ (ppm): 7.80 (d, J=7.8 Hz, 1H), 7.62 (d, J=5.4 Hz, 1H), 7.61-7.56 (m, 1H), 7.49 (t, J=7.7 Hz, 2H), 7.42 (d, J=7.3 Hz, 1H), 7.32 (t, J=7.4 Hz, 1H), 7.14 (td, J=8.5, 2.7 Hz, 1H), 6.49 (d, J=4.3 Hz, 1H), 5.11 (d, J=4.1 Hz, 1H).

Step 3) Synthesis of (12aR)-7-(benzyloxy)-12-(2-chloro-6-fluoro-8H-dibenzo[3,4:6,7] cyclohept[1,2-b]thiophen-8-yl)-3,4,4,12,12a-tetrahydro-1H-[1,4] oxazino[3,4-c]pyrido[2, 1-f] [1,2,4] triazine-6,8-dione 2-Chloro-6-fluoro-8H-dibenzo[3,4:6,7]cyclohept[1,2-b]thiophen-8-ol (150 mg, 0.43 mmol) and (R)-7-(benzyloxy)-3,4,12,12a-tetrahydro-1H-[1,4]oxazino[3,4-c]pyrido[2,1-f][1,2,4]triazine-6,8-dione (170 mg, 0.52 mmol) were added into a sealing tube, then 1-propyl phosphate anhydride (ethyl acetate solution) (wt 50%, 10 mL) was added. The air in solution was exhausted with nitrogen bubbling, and the resulting solution was reacted at 110° C. for 2 hours. The reaction solution was added to ice water (30 mL) and resulting mixture was extracted with ethyl acetate (30 mL×3). The combined organic phases were washed with saturated sodium bicarbonate aqueous solution (50 mL), dried over anhydrous sodium sulfate, filtered and the filtrate was concentrated. The residue was purified by silica gel column chromatography (dichloromethane/methanol (v/v)=25/1) to give the title compound as a light yellow solid (181 mg, 61%).

MS (ESI, pos. ion) m/z: 626.0[M+H]$^+$

Step 4) Synthesis of (R)-12-((S)-2-chloro-6-fluoro-8H-dibenzo[3,4:6,7]cyclohept[1,2-b]thiophen-8-yl)-7-hydroxy-3,4,12,12a-tetrahydro-1H-[1,4]oxazino[3,4-c]pyrido[2,1-f][1,2,4]triazine-6,8-dione (14-1) and (R)-12-((R)-2-chloro-6-fluoro-8H-dibenzo[3,4:6,7] cyclohept[1,2-b]thiophen-8-yl)-7-hydroxy-3,4,12,12a-tetrahydro-1H-[1,4]oxazino[3,4-c]pyrido[2,1-f] [1,2,4]triazine-6,8-dione (14-2)

(12aR)-7-(benzyloxy)-12-(2-chloro-6-fluoro-8H-dibenzo [3,4:6,7]cyclohept[1,2-b]thiophene-8-yl)-3,4,12,12a-tetrahydro-1H-[1,4]oxazino[3,4-c]pyrido[2,1-f][1,2,4]triazine-6,8-dione (150 mg, 0.24 mmol) was dissolved in N,N'-dimethyl acetamide (4 mL), then anhydrous lithium chloride (101 mg, 2.38 mmol) was added, and the resulting mixture was reacted overnight at 100° C. under protection of nitrogen. The reaction was stopped and water (10 mL) was added. The reaction solution was adjusted with 1N diluted hydrochloric acid to pH about 6. The resulting mixture was extracted with ethyl acetate (10 mL×3). The combined organic phases were washed with saturated brine (20 mL×3) and dried over anhydrous sodium sulfate and filtered, then the filtrate was concentrated, and the residue was purified by LUNA preparative column chromatography (acetonitrile/0.1% trifluoroacetate aqueous solution (v/v)=12/13) to give the title compound (14-1) as a light yellow solid (30 mg, 23%) and the title compound (14-2) as a light yellow solid (30 mg, 23%).

MS (ESI, pos. ion) m/z: 536.0[M+H]+;

(R)-12-((S)-2-chloro-6-fluoro-8H-dibenzo[3,4:6,7]
cyclohept[1,2-b]thiophen-8-yl)-7-hydroxy-3,4,12,
12a-tetrahydro-1H-[1,4]oxazino[3,4-c]pyrido[2,1-f]
[1,2,4]triazine-6,8-dione (14-1)

HRMS (ESI, pos. ion) m/z: 536.0857, (C$_{27}$H$_{20}$ClFN$_3$O$_4$S)[M+H]$^+$, theoretical value: 536.0847;
$^1$H NMR (400 MHz, DMSO-d$_6$) δ (ppm): 7.66 (dd, J=8.0, 5.5 Hz, 1H), 7.56 (d, J=7.5 Hz, 1H), 7.41 (t, J=7.4 Hz, 1H), 7.31-7.20 (m, 4H), 6.99 (d, J=7.5 Hz, 1H), 6.34 (d, J=7.6 Hz, 1H), 5.65 (d, J=7.6 Hz, 1H), 5.38 (s, 1H), 4.63 (d, J=13.3 Hz, 1H), 4.22-4.13 (m, 1H), 3.75 (d, J=10.0 Hz, 1H), 3.35 (m, 3H), 2.95 (t, J=11.1 Hz, 1H).

(R)-12-((R)-2-chloro-6-fluoro-8H-dibenzo[3,4:6,7]
cyclohepta[1,2-b]thiophen-8-yl)-7-hydroxy-3,4,12,
12a-tetrahydro-1H-[1,4]oxazino[3,4-c]pyrido[2,1-f]
[1,2,4]triazine-6,8-dione (14-2)

HRMS (ESI, pos. ion) m/z: 536.0855, (C$_{27}$H$_{20}$ClFN$_3$O$_4$S)[M+H]$^+$, theoretical value: 536.0847;
$^1$H NMR (400 MHz, DMSO-d$_6$) δ (ppm): 7.64 (d, J=7.6 Hz, 1H), 7.61-7.44 (m, 4H), 7.35 (s, 1H), 7.13 (dd, J=11.0, 5.1 Hz, 1H), 6.78 (d, J=8.4 Hz, 1H), 6.29 (d, J=7.7 Hz, 1H), 5.72 (d, J=7.7 Hz, 1H), 5.39 (s, 1H), 4.59 (d, J=13.4 Hz, 1H), 4.14 (dd, J=9.5, 5.7 Hz, 1H), 3.73 (d, J=11.7 Hz, 1H), 3.48-3.22 (m, 3H), 2.88 (dm, 1H).

Example 15 (12aR)-12-(2-chloro-8H-dibenzo [3,4:6,7] cyclohept[1,2-b]thiophen-8-yl)-7-hydroxy-3,4,12,12a-tetrahydro-1H-[1,4] oxazino [3,4-c] pyrido [2,1-f] [1,2,4]triazine-6,8-dione

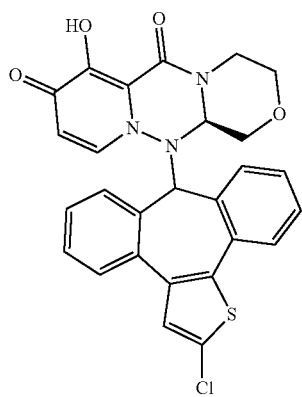 [SMILES: O=C1c2c(O)c(=O)ccn2N(C2c3ccccc3-c3cc(Cl)sc3-c3ccccc32)[C@@H]2COCCN12]

Step 1) Synthesis of 2-chloro-8H-dibenzo[3,4:6,7]
cyclohept[1,2-b]thiophen-8-ol

8H-Dibenzo[3,4:6,7]cyclohept[1,2-b]thiophen-8-ol (59 mg, 0.22 mmol) was dissolved in DMF (10 mL). NCS (61 mg, 0.45 mmol) was added. The resulting mixture was stirred at rt for 4 hours. The reaction was stopped, to the reaction mixture was added sodium thiosulfate solution (20 mL), and then the resulting mixture was extracted with ethyl acetate (30 mL×3). The combined organic phases were washed with saturated brine (50 mL×3), dried over anhydrous sodium sulfate and filtered, then the filtrate was concentrated in vacuo, and the residue was purified by silica gel column chromatography (PE/EA (v/v)=20/1) to give the title compound as a white solid (31 mg, 46%).
$^1$H NMR (400 MHz, CDCl$_3$) δ (ppm): 7.84 (d, J=7.5 Hz, 2H), 7.49-7.43 (m, 4H), 7.36-7.31 (m, 2H), 7.30 (s, 1H), 5.35 (d, J=4.5 Hz, 1H).

Step 2) Synthesis of (12aR)-7-(benzyloxy)-12-(2-chloro-8H-dibenzo[3,4:6,7]cyclohept[1,2-b]thiophen-8-yl)-3,4,12,12a-tetrahydro-1H-[1,4]oxazino[3,4-c]pyrido[2,1-f][1,2,4]triazine-6,8-dione 2-Chloro-8H-dibenzo[3,4:6,7]cyclohept[1,2-b]thiophen-8-ol (150 mg, 0.50 mmol) and (R)-7-(benzyloxy)-3,4,12,12a-tetrahydro-1H-[1,4]oxazino[3,4-c]pyrido[2, 1-f][1,2,4]triazine-6,8-dione (18 mg, 0.55 mmol) were added to a sealing tube, then 1-propylphosphoric anhydride (ethyl acetate solution) (wt 50%, 10 mL) was added, nitrogen was blowed in and the sealing tube was sealed. The reaction system was warmed to 110° C. and reacted for 2 hours. The reaction solution was added to ice water (30 mL) and resulting mixture was extracted with ethyl acetate (30 mL×3). The combined organic phases were washed with saturated sodium bicarbonate aqueous solution (50 mL), dried over anhydrous sodium sulfate, filtered and the filtrate was concentrated in vacuo. The residue was purified by silica gel column chromatography (dichloromethane/methanol (v/v)=25/1) to give the title compound as a light yellow solid (293 mg, 96%).

MS (ESI, pos. ion) m/z: 608.2[M+H]+

Step 3) Synthesis of (12aR)-12-(2-chloro-8H-dibenzo[3,4:6,7]cyclohept[1,2-b]thiophen-8-yl)-7-hydroxy-3,4,12,12a-tetrahydro-1H-[1,4]oxazino[3,4-c]pyrido[2, 1-f] [1,2,4]triazine-6,8-dione (12aR)-7-(benzyloxy)-12-(2-chloro-8H-dibenzo[3,4:6,7]cyclohept[1,2-b]thiophen-8-yl)-3,4,12,12a-tetrahydro-1H-[1,4]oxazino[3,4-c]pyrido[2,1-f][1,2,4]triazine-6,8-dione (293 mg, 0.48 mmol) was dissolved in N,N'-dimethyl acetamide (4 mL), then anhydrous lithium chloride (204 mg, 4.82 mmol) was added, and the mixture was reacted overnight at 100° C. under protection of nitrogen. The reaction was stopped and water (10 mL) was added. The reaction solution was adjusted with 1N dilute hydrochloric acid to pH about 6, and then mixture was extracted with ethyl acetate (10 mL×3). The combined organic phases were washed with saturated brine (20 mL×3), dried over anhydrous sodium sulfate and filtered, then the filtrate was concentrated in vacuo, and the residue was purified by LUNA preparative column chromatography (acetonitrile/0.1% trifluoroacetate aqueous solution (v/v)=12/13) to give the title compound as a light yellow solid (11 mg, 4.4%).

MS (ESI, pos. ion) m/z: 518.0[M+H]+;

HRMS (ESI, pos. ion) m/z: 518.0953, ($C_{27}H_{20}ClN_3O_4S$) [M+H]+, theoretical value: 518.0941;

$^1$H NMR (400 MHz, DMSO-$d_6$) δ (ppm): 7.67-7.54 (m, 2H), 7.43 (d, J=28.3 Hz, 4H), 6.98 (m, 1H), 6.28 (m, 1H), 5.65 (s, 1H), 5.44 (s, 1H), 5.40-5.20 (m, 1H), 4.60 (d, J=9.8 Hz, 1H), 4.14 (d, J=7.3 Hz, 1H), 3.72 (d, J=10.5 Hz, 1H), 3.39 (m, 2H), 3.24 (s, 1H), 2.81 (m, 1H), 2.04 (d, J=15.5 Hz, 1H).

Example 16 (R)-12-((S)-5-fluoro-10-methoxy-8H-dibenzo [3,4:6,7] cyclohept[1,2-b]thiophen-8-yl)-7-hydroxy-3,4,12,12a-tetrahydro-1H-[1,4]oxazino [3,4-c] pyrido [2,1-f] [1,2,4]pyrazine-6,8-dione (16-1) and (R)-12-((R)-5-fluoro-10-methoxy-8H-dibenzo [3,4:6,7] cyclohept[1,2-b]thiophen-8-yl)-7-hydroxy-3,4,12,12a-tetrahydro-1H-[1,4]oxazino [3,4-c] pyrido [2,1-f] [1,2,4]pyrazine-6,8-dione (16-2)

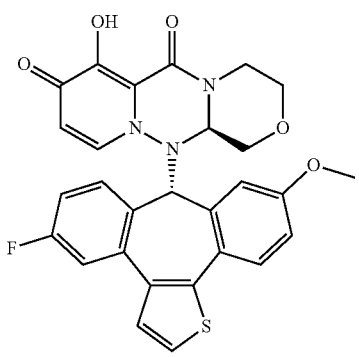

(16-1)

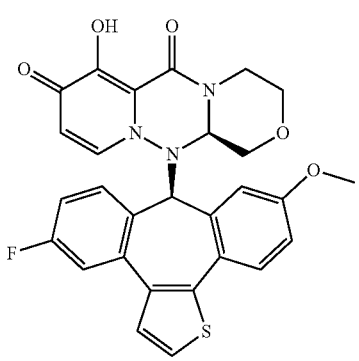

(16-2)

Step 1) Synthesis of methyl 5-methoxy-2-(4,4,5,5-tetramethyl-1,3,2-dioxaborolan-2-yl)benzoate Methyl 5-methoxy-2-bromobenzoate (300 mg, 1.22 mmol), ferrocene palladium dichloride (184 mg, 0.24 mmol), potassium acetate (360 mg, 3.67 mmol) and bis(pinacolato) diboron (491 mg, 1.84 mmol) were added into a round bottom flask, and dioxane (15 mL) was added. The resulting mixture was heated to 80° C. and reacted for 1 hour. The reaction was stopped and the reaction mixture was filtered, then the filtrate was concentrated in vacuo. The residue was purified by silica gel column chromatography (PE/EA (v/v)=15/1) to give the title compound as colorless liquid (293 mg, 82%).

MS (ESI, pos. ion) m/z: 293.1[M+1]+;

$^1$H NMR (400 MHz, CDCl$_3$) δ (ppm): 7.45 (d, J=8.5 Hz, 2H), 7.05 (dd, J=8.2, 2.5 Hz, 1H), 3.91 (s, 3H), 3.84 (s, 3H), 1.40 (s, 12H).

Step 2) Synthesis of methyl 2-(3-(3-fluorophenyl) thiophen-2-yl)-5-methoxybenzoate 2-Bromo-3-(3-fluorophenyl)thiophene (3.00 g, 11.66 mmol), methyl 5-methoxy-2-(4,4,5,5-tetramethyl-1,3,2-dioxaborolan-2-yl)benzoate (5.11 g, 17.50 mmol), bistriphenylphosphine palladium dichloride (830 mg, 1.17 mmol) and potassium carbonate (5.32 g, 38.50 mmol) were added into a reaction flask. THF (50 mL) and water (5 mL) were then added. The resulting mixture was heated to 75° C. under the protection of nitrogen and reacted overnight. The reaction was stopped, and the reaction mixture was cooled to rt and filtered. The filter cake was washed with ethyl acetate (50 mL), the filtrate was concentrated in vacuo and the residue was purified by silica gel column chromatography (PE/EA (v/v)=10/1) to give the title compound as a white solid (2.04 g, 51%).

$^1$H NMR (400 MHz, CDCl$_3$) δ (ppm): 7.37 (d, J=5.2 Hz, 1H), 7.33 (d, J=2.7 Hz, 1H), 7.29 (d, J=8.5 Hz, 1H), 7.22-7.16 (m, 2H), 7.02 (dd, J=8.5, 2.8 Hz, 1H), 6.97 (d, J=7.8 Hz, 1H), 6.89 (dd, J=9.0, 7.9 Hz, 2H), 3.87 (s, 3H), 3.60 (s, 3H).

Step 3) Synthesis of 2-(3-(3-fluorophenyl)thiophen-2-yl)-5-methoxybenzoic acid

Methyl 2-(3-(3-fluorophenyl)thiophen-2-yl)-5-methoxybenzoate (2.04 g, 5.96 mmol) was dissolved in THF (30 mL) and methanol (10 mL), then a solution of sodium hydroxide (953 mg, 23.80 mmol) in water (30 mL) was added into the reaction solution above, the resulting mixture was reacted overnight at 50° C. Saturated saline (50 mL) was added and pH of the reaction solution was adjusted to pH about 6 with 1N dilute hydrochloric acid. The resulting mixture was partitioned and aqueous phase was extracted with ethyl acetate (50 mL×2). The combined organic phases were washed with saturated saline solution (100 mL) and dried over anhydrous sodium sulfate and concentrated. The residue was purified by silica gel column chromatography (PE/EtOAc (v/v)=3/1) to give the title compound as a light yellow solid (1.69 g, 86%).

MS (ESI, pos. ion) m/z: 327.0[M−H]+.

Step 4) Synthesis of 5-fluoro-10-methoxy-8H-dibenzo[3,4:6,7]cyclohept[1,2-b]thiophen-8-one 2-(3-(3-Fluorophenyl)thiophen-2-yl)-5-methoxybenzoic acid (1.64 g, 4.99 mmol) was placed in PPA (13 mL), and the resulting mixture was heated to 130° C. and reacted for 1 hour. The reaction was stopped, and saturated sodium bicarbonate solution (30 mL) was added into the reaction mixture, and then the resulting mixture was extracted with ethyl acetate (30 mL×3). The combined organic phases were washed with saturated brine (30 mL), dried over anhydrous sodium sulfate and filtered, then the filtrate was concentrated, and the residue was purified by silica gel column chromatography (PE/DCM (v/v)=3/1) to give the title compound as a light yellow solid (241 mg, 16%).

¹H NMR (400 MHz, CDCl₃) δ (ppm): 7.95 (dd, J=8.7, 6.0 Hz, 1H), 7.77 (d, J=8.7 Hz, 1H), 7.51-7.38 (m, 4H), 7.24-7.16 (m, 2H), 3.94 (s, 3H).

Step 5) Synthesis of 5-fluoro-10-methoxy-8H-dibenzo[3,4:6,7]cyclohept[1,2-b]thiophen-8-ol 5-Fluoro-10-methoxy-8H-dibenzo[3,4:6,7]cyclohept[1,2-b]thiophen-8-one (241 mg, 0.78 mmol) was dissolved in THF (10 mL) and methanol (5 mL). The mixture was cooled to 0° C. and sodium borohydride (306 mg, 7.77 mmol) was added in batches. The resulting mixture was reacted at 0° C. for 5 minutes and at rt for 1 hour. The reaction was stopped, to the reaction mixture was added water (20 mL), and the resulting mixture was extracted with ethyl acetate (30 mL×3). The combined organic phases were washed with saturated brine (50 mL), dried over anhydrous sodium sulfate and filtered, then the filtrate was concentrated, and the residue was purified by silica gel column chromatography (PE/EA (v/v)=20/1) to give the title compound as a white solid (240 mg, 99%).
¹H NMR (400 MHz, CDCl₃) δ (ppm): 7.79 (dd, J=8.5, 6.0 Hz, 1H), 7.46 (d, J=8.5 Hz, 1H), 7.39 (d, J=5.7 Hz, 3H), 7.21 (dd, J=9.7, 2.4 Hz, 1H), 7.13 (td, J=8.5, 2.4 Hz, 1H), 6.86 (dd, J=8.4, 2.4 Hz, 1H), 5.34 (s, 1H), 3.89 (s, 3H).

Step 6) Synthesis of (12aR)-7-(benzyloxy)-12-(5-fluoro-10-methoxy-8H-dibenzo[3,4:6,7]cyclohept[1,2-b]thiophen-8-yl)-3,4,4,12,12a-tetrahydro-1H-[1,4]oxazino[3,4-c]pyrido[2,1-f][1,2, 4] triazine-6,8-dione 5-Fluoro-10-methoxy-8H-dibenzo[3,4:6,7]cyclohept[1,2-b]thiophen-8-ol (157 mg, 0.50 mmol) and (R)-7-(benzyloxy)-3,4,12,12a-tetrahydro-1H-[1,4]oxazino[3,4-c]pyrido[2,1-f][1,2,4]triazine-6,8-dione (150 mg, 0.46 mmol) were added into a sealing tube, then 1-propyl phosphate anhydride (ethyl acetate solution) (wt 50%, 10 mL) was added. The air in solution was exhausted with nitrogen bubbling, and the resulting solution was reacted at 110° C. for 2 hours. The reaction solution was added into ice water (30 mL) and the resulting mixture was extracted with ethyl acetate (30 mL×3). The combined organic phases were washed with saturated sodium bicarbonate aqueous solution (50 mL), dried over anhydrous sodium sulfate, filtered and the filtrate was concentrated in vacuo. The residue was purified by silica gel column chromatography (dichloromethane/methanol (v/v)=25/1) to give the title compound as a light yellow solid (281 mg, 99%).

Step 7) Synthesis of (R)-12-((S)-5-fluoro-10-methoxy-8H-dibenzo[3,4:6,7]cyclohept[1,2-b]thiophen-8-yl)-7-hydroxy-3,4,12,12a-tetrahydro-1H-[1, 4]oxazino[3,4-c]pyrido[2,1-f][1,2,4]triazine-6,8-dione (16-1) and (R)-12-((R)-5-fluoro-10-methoxy-8H-dibenzo[3,4:6,7]cyclohept[1,2-b]thiophen-8-yl)-7-hydroxy 3,4,12,12a-tetrahydro-1H-[1,4]oxazino[3,4-c]pyrido[2,1-f][1,2,4]triazine-6,8-dione (16-2)

(12aR)-7-(benzyloxy)-12-(5-fluoro-10-methoxy-8H-dibenzo[3,4:6,7]cyclohept[1,2-b]thiophen-8-yl)-3,4-4,12,12a-tetrahydro-1H-[1,4]oxazino[3,4-c]pyrido[2,1-f][1,2,4]triazine-6,8-dione (110 mg, 0.18 mmol) was dissolved in N,N'-dimethyl acetamide (4 mL), then anhydrous lithium chloride (75 mg, 1.77 mmol) was added, and the mixture was reacted overnight at 100° C. under protection of nitrogen. The reaction was stopped and water (10 mL) was added. The reaction solution was adjusted with 1N diluted hydrochloric acid to pH about 6. The resulting mixture was extracted with ethyl acetate (10 mL×3). The combined organic phases were washed with saturated brine (20 mL×3) and dried over anhydrous sodium sulfate and filtered, then the filtrate was concentrated in vacuo, and the residue was purified by LUNA preparative column chromatography (acetonitrile/0.1% trifluoroacetate aqueous solution (v/v)=12/13) to give the title compound (16-1) as a light yellow solid (8 mg, 9%) and the title compound (16-2) as a light yellow solid (16 mg, 17%).
MS (ESI, pos. ion) m/z: 532.1[M+H]⁺;
HRMS (ESI, pos. ion) m/z: 532.1356, 532.1354, (C₂₈H₂₂FN₃O₅S)[M+H]⁺, theoretical value: 532.1342;

(R)-12-((S)-5-fluoro-10-methoxy-8H-dibenzo[3,4:6, 7]cyclohept[1,2-b]thiophen-8-yl)-7-hydroxy-3,4,12, 12a-tetrahydro-1H-[1,4]oxazino[3,4-c]pyrido[2, 1-f] [1,2,4] pyrazine-6,8-dione (16-1)

¹H NMR (400 MHz, DMSO-d₆) δ (ppm): 7.61 (d, J=8.6 Hz, 1H), 7.46 (dd, J=15.9, 10.7 Hz, 4H), 7.21-7.07 (m, 1H), 7.00-6.93 (m, 1H), 6.48 (d, J=13.9 Hz, 2H), 5.96 (d, J=6.8 Hz, 1H), 5.36 (s, 1H), 4.60 (d, J=11.9 Hz, 1H), 4.20 (d, J=7.0 Hz, 1H), 3.90 (d, J=2.8 Hz, 1H), 3.72 (s, 3H), 3.41-3.29 (m, 2H), 3.19 (t, J=10.4 Hz, 1H), 2.99-2.87 (m, 1H).

(R)-12-((R)-5-fluoro-10-methoxy-8H-dibenzo[3,4:6, 7]cyclohept[1,2-b]thiophen-8-yl)-7-hydroxy 3,4,12, 12a-tetrahydro-1H-[1,4]oxazino[3,4-c]pyrido[2,1-f] [1,2,4]triazine-6,8-dione (16-2)

¹H NMR (400 MHz, DMSO-d₆) δ (ppm): 7.69 (d, J=8.6 Hz, 1H), 7.46 (dd, J=10.6, 5.3 Hz, 2H), 7.36 (d, J=9.4 Hz, 1H), 7.08 (dd, J=8.6, 2.4 Hz, 1H), 6.96 (dd, J=15.0, 5.5 Hz, 3H), 6.29 (d, J=7.4 Hz, 1H), 5.86 (d, J=7.2 Hz, 1H), 5.36 (s, 1H), 4.62 (d, J=13.5 Hz, 1H), 4.28 (dd, J=9.9, 2.8 Hz, 1H), 3.90 (s, 3H), 3.74 (d, J=11.8 Hz, 1H), 3.44-3.30 (m, 2H), 3.20 (t, J=10.5 Hz, 1H), 3.02-2.89 (m, 1H).

Example 17 (R)-12-((S)-5,11-difluoro-8H-dibenzo [3,4:6,7]cyclohept[1,2-b]thiophen-8-yl)-7-hydroxy-3,4,12,12a-tetrahydro-1H-[1,4]oxazino[3,4-c]pyrido [2,1-f][1,2,4]triazine-6, 8-dione (17-1) and (R)-12-((R)-5,11-difluoro-8H-dibenzo [3,4:6,7]cyclohept[1, 2-b]thiophen-8-yl)-7-hydroxy-3,4,12,12a-tetrahydro-1H-[1,4]oxazino [3,4-c] pyrido [2,1-f] [1,2,4] triazine-6, 8-dione (17-2)

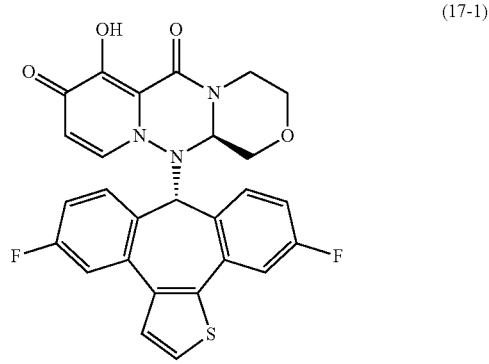

(17-1)

-continued (17-2)

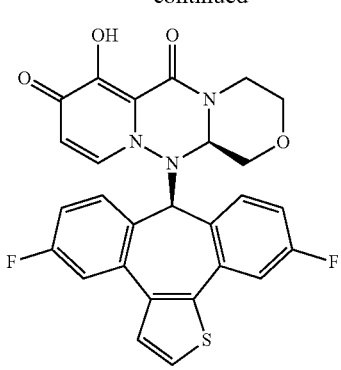

Step 1) Synthesis of methyl 4-fluoro-2-(4,4,5,5-tetramethyl-1,3,2-dioxaborolan-2-yl)benzoate Methyl 4-fluoro-2-bromobenzoate (300 mg, 1.29 mmol), ferrocene palladium dichloride (194 mg, 0.26 mmol), potassium acetate (379 mg, 3.86 mmol), and bis (pinacolato) diboron (413 mg, 1.55 mmol) were mixed in dioxane (15 mL). The resulting mixture was heated to 80° C. and reacted for 1 hour. The reaction was stopped. The reaction mixture was filtered and the filtrate was concentrated in vacuo. The residue was purified by silica gel column chromatography (PE/EA (v/v)=15/1) to give the title compound as colorless oil (287 mg, 80%).

MS (ESI, pos. ion) m/z: 281.2[M+1]$^+$;
$^1$H NMR (400 MHz, CDCl$_3$) δ (ppm): 7.93 (dd, J=8.6, 5.2 Hz, 1H), 7.13 (dd, J=8.6, 2.5 Hz, 1H), 7.08-7.01 (m, 1H), 3.87 (s, 3H), 1.39 (s, 12H).

Step 2) Synthesis of methyl 2-(3-(3-fluorophenyl)thiophen-2-yl)-4-fluoro-benzoate 2-Bromo-3-(3-fluorophenyl)thiophene (100 mg, 0.39 mmol), methyl 4-fluoro-2-(4,4,5,5-tetramethyl-1,3,2-dioxaborolan-2-yl)benzoate (163 mg, 0.58 mmol), bis(triphenylphosphine) palladium dichloride (27 mg, 0.38 mmol) and potassium carbonate (177 mg, 1.28 mmol) were added into a reaction flask. THF (50 mL) and water (5 mL) were then added. The resulting mixture was warmed to 75° C. under the protection of nitrogen and reacted overnight. The reaction was stopped and the reaction solution was filtered. The filter cake was washed with ethyl acetate (50 mL), then the filtrate was concentrated in vacuo and the residue was purified by silica gel column chromatography (PE/EA (v/v)=10/1) to give the title compound as a white solid (51 mg, 40%).

$^1$H NMR (400 MHz, CDCl$_3$) δ (ppm): 7.79 (dd, J=8.7, 5.9 Hz, 1H), 7.45 (d, J=5.2 Hz, 1H), 7.25-7.21 (m, 2H), 7.14 (dd, J=9.2, 2.6 Hz, 1H), 7.11-7.03 (m, 3H), 7.03-6.97 (m, 1H), 3.61 (s, 3H).

Step 3) Synthesis of 2-(3-(3-fluorophenyl)thiophen-2-yl)-4-fluorobenzoic acid

Methyl 2-(3-(3-fluorophenyl)thiophen-2-yl)-4-fluorobenzoate (3.06 g, 9.26 mmol) was dissolved in THF (30 mL) and methanol (10 mL), then a solution of sodium hydroxide (1.48 g, 37.00 mmol) in water (30 mL) was added into the reaction solution above, the resulting mixture was reacted overnight at 50° C. The reaction was stopped, saturated saline (50 mL) was added and the reaction solution was adjusted to pH about 6 with 1N diluted hydrochloric acid. The resulting mixture was partitioned, and the aqueous phase was extracted with ethyl acetate (50 mL×2). The combined organic phases were washed with saturated saline solution (100 mL), dried over anhydrous sodium sulfate and concentrated in vacuo. The residue was purified by silica gel column chromatography (PE/EtOAc (v/v)=3/1) to give methyl 2-(3-(3-fluorophenyl)thiophen-2-yl)-4-fluorobenzoate as a light yellow solid (2.63 g, 90%).

MS (ESI, neg ion) m/z: 315.0[M−H]$^-$

Step 4) Synthesis of 5,11-difluoro-8H-dibenzo[3,4:6,7]cyclohept[1,2-b]thiophen-8-one 2-(3-(3-Fluorophenyl)thiophen-2-yl)-4-fluorobenzoic acid (2.36 g, 7.46 mmol) was placed in PPA (13 mL), and the resulting mixture was heated and reacted for 1 hour at 160° C. in an oil bath. The reaction was stopped, saturated sodium bicarbonate solution (30 mL) was added into the reaction mixture, and the resulting mixture was extracted with ethyl acetate (30 mL×3). The combined organic phases were washed with saturated brine (30 mL), dried over anhydrous sodium sulfate and filtered, then the filtrate was concentrated in vacuo, and the residue was purified by silica gel column chromatography (PE/DCM (v/v)=3/1) to give the title compound as a light yellow solid (450 mg, 20%).

$^1$H NMR (400 MHz, CDCl$_3$) δ (ppm): 7.97 (dt, J=8.8, 5.6 Hz, 2H), 7.55-7.44 (m, 4H), 7.25-7.17 (m, 2H).

Step 5) Synthesis of 5,11-difluoro-8H-dibenzo[3,4:6,7]cyclohept[1,2-b]thiophen-8-ol 5,11-Difluoro-8H-dibenzo[3,4:6,7]cyclohept[1,2-b]thiophen-8-one (450 mg, 1.51 mmol) was dissolved in THF (10 mL) and methanol (5 mL). The solution was cooled to 0° C. and sodium borohydride (594 mg, 15.07 mmol) was added in batches. The resulting mixture was reacted at rt for 1 hour. The reaction was stopped, and to the reaction mixture was added water (20 mL), and then the resulting mixture was extracted with ethyl acetate (30 mL×3). The combined organic phases were washed with saturated brine (50 mL), dried over anhydrous sodium sulfate and filtered, then the filtrate was concentrated in vacuo, and the residue was purified by silica gel column chromatography (PE/EA (v/v)=20/1) to give the title compound as a white solid (451 mg, 99%).

$^1$H NMR (400 MHz, CDCl$_3$) δ (ppm): 7.80 (t, J=6.3 Hz, 2H), 7.48 (d, J=5.3 Hz, 1H), 7.41 (d, J=5.3 Hz, 1H), 7.27-7.20 (m, 2H), 7.15 (m, 2H), 5.30 (s, 1H).

Step 6) Synthesis of (12aR)-7-(benzyloxy)-12-(5,11-difluoro-8H-dibenzo[3,4:6,7]cyclohept[1,2-b]thiophen-8-3,4,12,12a-tetrahydro-1H-[1,4]oxazino[3,4-c]pyrido[2,1-f][1,2,4]triazine-6,8-dione 5,11-Difluoro-8H-dibenzo[3,4:6,7]cyclohept[1,2-b]thiophen-8-ol (150 mg, 0.50 mmol) and (R)-7-(benzyloxy)-3,4,12,12a-tetrahydro-1H-[1,4]oxazino[3,4-c]pyrido[2,1-f][1,2,4]triazine-6,8-dione (179 mg, 0.55 mmol) were added into a sealing tube, then 1-propyl phosphate anhydride (ethyl acetate solution) (wt 50%, 10 mL) was added. The air in solution was exhausted with nitrogen bubbling, and the resulting solution was reacted at 110° C. for 2 hours. The reaction was stopped, and the reaction mixture was added to ice water (30 mL), then the resulting mixture was extracted with ethyl acetate (30 mL×3). The combined organic phases were washed with saturated sodium bicarbonate aqueous solution (50 mL), dried over anhydrous sodium sulfate, filtered and the filtrate was concentrated. The residue was purified by silica gel column chromatography (dichloromethane/methanol (v/v)=25/1) to give the title compound as a light yellow solid (110 mg, 36%).

MS (ESI, pos. ion) m/z: 610.1 [M+1]+.

Step 7) Synthesis of (R)-12-((S)-5,11-difluoro-8H-dibenzo[3,4:6,7]cyclohept[1,2-b]thiophen-8-yl)-7-hydroxy-3,4,12,12a-tetrahydro-1H-[1,4]oxazino[3,4-c]pyrido[2,1-f][1,2,4]triazine-6, 8-dione (17-1) and (R)-12-((R)-5,11-difluoro-8H-dibenzo[3,4:6,7]cyclohept[1,2-b]thiophen-8-yl)-7-hydroxy-3,4,12,12a-tetrahydro-1H-[1,4]oxazino[3,4-c]pyrido[2,1-f][1,2,4]triazine-6, 8-dione (17-2)

(12aR)-7-(benzyloxy)-12-(5,11-difluoro-8H-dibenzo[3,4:6,7]cyclohept[1,2-b]thiophen-8-yl)-3,4,12,12a-tetrahydro-1H-[1,4]oxazino[3,4-c]pyrido[2,1-f][1,2,4]triazine-6,8-dione (110 mg, 0.18 mmol) was dissolved in N,N'-dimethyl acetamide (4 mL), then anhydrous lithium chloride (75 mg, 1.77 mmol) was added, and the resulting mixture was reacted overnight at 100° C. under protection of nitrogen. The reaction was stopped and water (10 mL) was added into the reaction mixture. The reaction solution was adjusted with 1N diluted hydrochloric acid to pH about 6. The resulting mixture was extracted with ethyl acetate (10 mL×3). The combined organic phases were washed with saturated brine (20 mL×3), dried over anhydrous sodium sulfate and filtered, then the filtrate was concentrated, and the residue was purified by LUNA preparative column chromatography (acetonitrile/0.1% trifluoroacetate aqueous solution (v/v)=12/13) to give the title compound (17-1) as a light yellow solid (15 mg, 16%) and the title compound (17-2) as a light yellow solid (16 mg, 17%).

MS (ESI, pos. ion) m/z: 520.0[M+H]+;

(R)-12-((S)-5,11-difluoro-8H-dibenzo[3,4:6,7]cyclohepta[1,2-b]thiophen-8-yl)-7-hydroxy-3,4,12,12a-tetrahydro-1H-[1,4]oxazino[3,4-c]pyrido[2,1-f][1,2,4]triazine-6,8-dione (17-1)

HRMS (ESI, pos. ion) m/z: 520.1154, ($C_{27}H_{19}F_2N_3O_4S$) [M+H]+, theoretical value: 520.1143;
$^1$H NMR (400 MHz, DMSO-$d_6$) δ (ppm): 7.54 (d, J=5.2 Hz, 1H), 7.51-7.42 (m, 3H), 7.38 (d, J=9.1 Hz, 1H), 7.19 (t, J=7.9 Hz, 1H), 6.98 (dd, J=11.6, 6.7 Hz, 2H), 6.36 (d, J=7.4 Hz, 1H), 5.84 (d, J=7.3 Hz, 1H), 5.43 (s, 1H), 4.60 (d, J=12.6 Hz, 1H), 4.20-4.12 (m, 1H), 3.74 (d, J=9.6 Hz, 1H), 3.42-3.29 (m, 2H), 3.20 (t, J=10.5 Hz, 1H), 2.90 (t, J=11.1 Hz, 1H).

(R)-12-((R)-5,11-difluoro-8H-dibenzo[3,4:6,7]cyclohepta[1,2-b]thiophen-8-yl)-7-hydroxy-3,4,12,12a-tetrahydro-1H-[1,4]oxazino[3,4-c]pyrido[2,1-f][1,2,4]triazine-6, 8-dione (17-2)

HRMS (ESI, pos. ion) m/z: 520.1158, ($C_{27}H_{19}F_2N_3O_4S$) [M+H]+, theoretical value: 520.1143;
$^1$H NMR (400 MHz, DMSO-$d_6$) δ (ppm): 7.57 (d, J=5.0 Hz, 1H), 7.49 (dd, J=22.5, 6.4 Hz, 3H), 7.38 (d, J=9.1 Hz, 1H), 7.19 (t, J=6.9 Hz, 1H), 6.97 (s, 2H), 6.32 (d, J=7.0 Hz, 1H), 6.01 (d, J=6.6 Hz, 1H), 5.45 (s, 1H), 4.60 (d, J=13.1 Hz, 1H), 4.22 (d, J=7.3 Hz, 1H), 3.75 (d, J=10.0 Hz, 1H), 3.42-3.33 (m, 2H), 3.24 (t, J=10.5 Hz, 1H), 2.93 (t, J=11.5 Hz, 1H).

Example 18 (R)-7-hydroxy-12-((S)-5-methoxy-8H-dibenzo[3,4:6,7]cyclohept[1,2-b]thiophen-8-yl)-3,4,12,12a-tetrahydro-1H-[1,4]oxazino[3,4-c]pyrido[2,1-f] [1,2,4]triazine-6, 8-dione

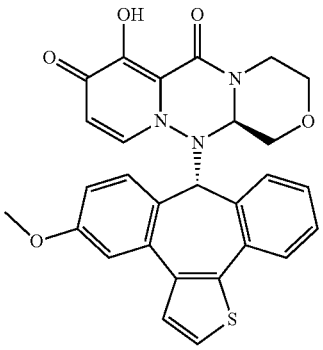 [SMILES: COc1ccc2c(c1)-c1ccsc1-c1ccccc1[C@H]2N1[C@@H]2COCCN2C(=O)c2c(O)c(=O)ccn21]

Step 1) Synthesis of 3-(3-methoxyphenyl)thiophene

3-Methoxybromobenzene (5.00 g, 26.70 mol), 3-thiopheneboronic acid (5.13 g, 40.10 mmol), tetratriphenylphosphine palladium (3.09 g, 2.67 mmol) and potassium carbonate (11.11 g, 80.38 mmol) were added into a reaction flask. 1,4-Dioxane (100 mL) and water (10 mL) were then added. The resulting mixture was heated to 100° C. under the protection of nitrogen and reacted overnight. The reaction solution was cooled to rt and filtered through a celite pad. The filter cake was washed with ethyl acetate (20 mL), then the filtrate was concentrated and the residue was purified by silica gel column chromatography (PE) to give the title compound as light yellow oil (3.36 g, 66%).
$^1$H NMR (400 MHz, CDCl$_3$) δ (ppm): 7.89 (dd, J=2.7, 1.1 Hz, 1H), 7.63 (dd, J=5.0, 2.9 Hz, 1H), 7.57 (dd, J=5.0, 1.1 Hz, 1H), 7.35-7.26 (m, 3H), 6.90-6.84 (m, 1H), 3.81 (s, 3H).

Step 2) Synthesis of 2-bromo-3-(3-methoxyphenyl)thiophene 3-(3-Methoxyphenyl)thiophene (3.36 g, 17.70 mmol) was dissolved in DMF (30 mL). The solution was cooled to −5° C. A solution of NBS (3.21 g, 17.70 mmol) in DMF (30 mL) was added slowly to the reaction solution above, and the resulting mixture was warmed to 0° C. and reacted overnight. The reaction was stopped, to the reaction mixture was added saturated sodium thiosulfate aqueous solution (40 mL) and the resulting mixture was stirred for 10 minutes, then to the mixture was added water (100 mL). The resulting mixture was extracted with ethyl acetate (50 mL×3). The combined organic phases were washed with saturated brine (100 mL×3), dried over anhydrous sodium sulfate and filtered, then the filtrate was concentrated, and the residue was purified by silica gel column chromatography (PE) to give the title compound as light yellow oil (4.50 g, 95%).

Step 3) Synthesis of methyl 2-(3-(3-methoxyphenyl)thiophen-2-yl)benzoate

2-Bromo-3-(3-methoxyphenyl)thiophene (4.50 g, 16.70 mmol), (2-(methoxycarbonyl)phenyl)boronic acid (6.02 g, 33.50 mmol), bis(triphenylphosphine) palladium(II) dichloride (1.19 g, 1.68 mmol) and potassium carbonate (7.07 g, 50.10 mmol) were added into a reaction flask. THF (60 mL)

and water (6 mL) were then added. The resulting mixture was warmed to 75° C. under the protection of nitrogen and reacted overnight. The reaction mixture was cooled to rt and filtered through a celite pad. The filter cake was washed with ethyl acetate (50 mL), the filtrate was concentrated in vacuo and the crude product was purified by silica gel column chromatography (PE/EA (v/v)=10/1) to give the title compound as a light yellow solid (3.06 g, 56%).

$^1$H NMR (400 MHz, CDCl$_3$) δ (ppm): 7.70 (dd, J=7.6, 0.8 Hz, 1H), 7.65 (d, J=5.2 Hz, 1H), 7.57 (td, J=7.5, 1.2 Hz, 1H), 7.52-7.47 (m, 1H), 7.38 (d, J=7.6 Hz, 1H), 7.28 (d, J=5.2 Hz, 1H), 7.15 (t, J=7.9 Hz, 1H), 6.76 (dd, J=11.2, 4.9 Hz, 2H), 6.64 (s, 1H), 3.55 (s, 3H), 3.48 (s, 3H).

Step 4) Synthesis of 2-(3-(3-methoxyphenyl)thiophen-2-yl)benzoic acid

Methyl 2-(3-(3-methoxyphenyl)thiophen-2-yl)benzoate (3.06 g, 9.43 mmol) was dissolved in THF (20 mL) and methanol (10 mL), the mixture was stirred at rt. A solution of sodium hydroxide (3.77 g, 94.30 mmol) in water (20 mL) was added into the reaction solution above, and the mixture was reacted overnight at 70° C. The reaction mixture was cooled to rt, and saturated saline (20 mL) was added into the mixture. The resulting mixture was adjusted with 1N diluted hydrochloric acid to pH about 6, and partitioned. The aqueous phase was extracted with ethyl acetate (10 mL×2). The combined organic phases were washed with saturated brine (20 mL), dried over anhydrous sodium sulfate and filtered, then the filtrate was concentrated to give the title compound as a white solid (1.43 g, 99%).

MS (ESI, pos. ion) m/z: 311.0[M+H]$^+$

Step 5) Synthesis of 5-methoxy-8H-dibenzo[3,4:6,7]cyclohepta[1,2-b]thiophene-8-one 2-(3-(3-Methoxyphenyl)thiophen-2-yl)benzoic acid (1.00 g, 3.22 mmol) was added to a reaction flask, then anhydrous dichloromethane (20 mL) and DMF (0.1 mL) were added, and then thionyl chloride (1.20 mL, 16.40 mmol) were added dropwise slowly. After addition, the resulting mixture was heated to 40° C. and reacted for 2 hours, then was cooled to rt. Aluminum trichloride (0.88 g, 6.50 mmol) was added. The solution was stirred at rt for 1 hour. The reaction solution was added dropwise slowly into saturated sodium bicarbonate solution (100 mL), and the resulting mixture was extracted with dichloromethane (50 mL×3). The combined organic phases were washed with saturated brine (100 mL), dried over anhydrous sodium sulfate and filtered, then the filtrate was concentrated in vacuo, and the residue was purified by silica gel column chromatography (PE/DCM (v/v)=1/1) to give the title compound as a light yellow solid (0.71 g, 75%).

$^1$H NMR (400 MHz, CDCl$_3$) δ (ppm): 7.88-7.82 (m, 3H), 7.82-7.77 (m, 2H), 7.74-7.70 (m, 1H), 7.58 (t, J=7.2 Hz, 1H), 7.41 (d, J=2.4 Hz, 1H), 7.16 (dd, J=8.7, 2.4 Hz, 1H), 3.93 (s, 3H).

Step 6) Synthesis of 5-methoxy-8H-dibenzo[3,4:6,7]cyclohepta[1,2-b]thiophen-8-ol 5-Methoxy-8H-dibenzo[3,4:6,7]cyclohepta[1,2-b]thiophene-8-one (0.71 g, 2.40 mmol) was dissolved in THF (10 mL) and methanol (5 mL). The mixture was cooled to 0° C., and sodium borohydride (0.47 g, 12.00 mmol) was added into the mixture. The resulting mixture was reacted at 0° C. for 5 minutes and reacted at rt for 30 minutes. The reaction was stopped, water (10 mL) was added, and the reaction mixture was extracted with dichloromethane (10 mL×3). The combined organic phases were washed with saturated brine (20 mL) dried over anhydrous sodium sulfate and filtered, then the filtrate was concentrated to give the title compound as a white solid (0.70 g, 98%).

MS (ESI, pos. ion) m/z: 317.1 [M+Na]$^+$

Step 7) Synthesis of (R)-7-hydroxy-12-((S)-5-methoxy-8H-dibenzo[3,4:6,7]cyclohepta[1,2-b]thiophen-8-yl)-3,4-12,12a-tetrahydro-1H-[1,4]oxazino[3,4-c]pyrido[2,1-f][1,2,4]triazine-6, 8-diketone 5-Methoxy-8H-dibenzo[3,4:6,7]cyclohepta[1,2-b]thiophen-8-ol (0.70 g, 2.40 mmol) and 7-(benzyloxy)-3,4,12,12a-tetrahydro-1H-[1,4]oxazino[3,4-c]pyrido[2,1-f][1,2, 4]triazine-6-, 8-dione (0.60 g, 1.80 mmol) were added to a sealing tube, then 1-propylphosphoric anhydride (ethyl acetate solution) (wt 50%, 3.5 g, 5.50 mmol) and ethyl acetate (5 mL) were then added. The tube was sealed and the resulting mixture was reacted for 2.5 hour at 110° C. The reaction was stopped, and the reaction mixture was added to ice water (50 mL). The resulting mixture was extracted with DCM (30 mL×3). The combined organic phases were washed with saturated saline solution (100 mL), dried over anhydrous sodium sulfate, filtered and the filtrate was concentrated. The residue was purified by silica gel column chromatography (dichloromethane/methanol (v/v)=20/1) to give the title compound as a light yellow solid (0.20 g, 21%).

MS (ESI, pos. ion) m/z: 514.1[M+H]$^+$

Example 19 (12aR)-7-hydroxy-12-((8R)-4-methoxy-8H-dibenzo [3,4:6,7] cyclohept[1,2-b]thiophen-8-yl)-3,4,12,12a-tetrahydro-1H-[1,4]oxazino[3,4-c]pyrido[2,1-f] [1,2,4]triazine-6, 8-dione

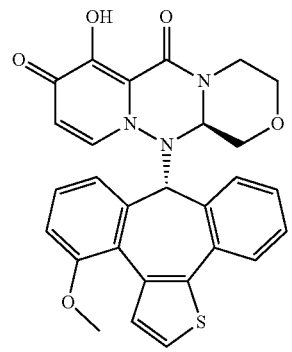 [SMILES: COc1cccc2c1-c1ccsc1-c1ccccc1[C@H]2N1[C@@H]2COCCN2C(=O)c2c(O)c(=O)ccn21]

Step 1) Synthesis of 3-(3-methoxyphenyl)thiophene

2-Methoxybromobenzene (3.00 g, 16.00 mol), 3-thiopheneboronic acid (3.08 g, 24.10 mmol), tetratriphenylphosphine palladium (1.85 g, 1.60 mmol) and potassium carbonate (6.66 g, 48.20 mmol) were added into a reaction flask. 1,4-Dioxane (100 mL) and water (10 mL) were then added. The resulting mixture was heated to 100° C. under the protection of nitrogen and reacted overnight. The reaction solution was cooled to rt and filtered through a celite pad. The filter cake was washed with ethyl acetate (20 mL), then the filtrate was concentrated in vacuo and the residue was purified by silica gel column chromatography (PE) to give the title compound as light yellow oil (1.05 g, 34%).

$^1$H NMR (400 MHz, CDCl$_3$) δ (ppm): 7.80-7.75 (m, 1H), 7.59-7.51 (m, 2H), 7.48 (dd, J=5.0, 0.8 Hz, 1H), 7.34-7.27 (m, 1H), 7.11 (d, J=8.2 Hz, 1H), 7.00 (t, J=7.4 Hz, 1H), 3.84 (s, 3H).

Step 2) Synthesis of 2-bromo-3-(2-methoxyphenyl)thiophene 3-(2-Methoxyphenyl)thiophene (1.05 g, 5.52 mmol) was dissolved in DMF (10 mL). The solution was cooled to −5° C., and a solution of NBS (1.00 g, 5.51 mmol) in DMF (10 mL) was added slowly to the reaction solution above, and the resulting mixture was warmed to 0° C. and reacted overnight. The reaction was stopped, to the reaction mixture was added with saturated sodium thiosulfate aqueous solution (50 mL) and stirred for 10 minutes at rt, then to the mixture was added water (100 mL). The resulting mixture was extracted with ethyl acetate (50 mL×3). The combined organic phases were washed with saturated brine (100 mL×3), dried over anhydrous sodium sulfate and filtered, then the filtrate was concentrated in vacuo, and the residue was purified by silica gel column chromatography (PE) to give the title compound as light yellow oil (0.64 g, 43%).

$^1$H NMR (400 MHz, CDCl$_3$) δ (ppm): 7.60 (d, J=5.6 Hz, 1H), 7.42-7.36 (m, 1H), 7.25 (dd, J=7.5, 1.6 Hz, 1H), 7.11 (d, J=8.2 Hz, 1H), 7.06-6.99 (m, 2H), 3.76 (s, 3H).

Step 3) Synthesis of methyl 2-(3-(2-methoxyphenyl)thiophen-2-yl)benzoate

2-Bromo-3-(2-methoxyphenyl)thiophene (0.64 g, 2.40 mmol), (2-(methoxycarbonyl)phenyl)boronic acid (0.86 g, 4.80 mmol), bis(triphenylphosphine) palladium (II) dichloride (0.17 g, 0.24 mmol) and potassium carbonate (1.00 g, 7.09 mmol) were added into a reaction flask. THF (10 mL) and water (1 mL) were then added into the flask. The resulting mixture was heated to 75° C. under the protection of nitrogen and reacted overnight. The reaction was cooled to rt and the reaction solution was filtered through a celite pad. The filter cake was washed with ethyl acetate (10 mL), the filtrate was concentrated and the residue was purified by silica gel column chromatography (PE/EA (v/v)=10/1) to give the title compound as a light yellow solid (0.44 g, 57%).

$^1$H NMR (400 MHz, CDCl$_3$) δ (ppm): 7.59 (s, 1H), 7.57 (s, 1H), 7.52 (t, J=7.5 Hz, 1H), 7.40 (t, J=7.2 Hz, 1H), 7.30 (d, J=7.6 Hz, 1H), 7.23-7.17 (m, 1H), 7.13 (d, J=5.2 Hz, 1H), 6.93 (s, 1H), 6.91 (d, J=1.8 Hz, 1H), 6.78 (t, J=7.4 Hz, 1H), 3.48 (s, 3H), 3.48 (s, 3H).

Step 4) Synthesis of 2-(3-(2-methoxyphenyl)thiophen-2-yl)benzoic acid

Methyl 2-(3-(2-methoxyphenyl)thiophen-2-yl)benzoate (0.44 g, 1.40 mmol) was dissolved in THF (2 mL) and methanol (1 mL), the mixture was stirred at rt. A solution of sodium hydroxide (0.54 g, 14.00 mmol) in water (2 mL) was added into the reaction solution above, and the mixture was reacted overnight at 60° C. The reaction was stopped. The reaction mixture was cooled to rt, and to the reaction mixture was added saturated saline (10 mL). The resulting mixture was adjusted with 1N diluted hydrochloric acid to pH about 6, and then partitioned. The aqueous phase was extracted with ethyl acetate (10 mL×2). The combined organic phases were washed with saturated brine (20 mL), dried over anhydrous sodium sulfate and filtered, then the filtrate was concentrated to give the title compound as a white solid (0.41 g, 97%).

MS (ESI, pos. ion) m/z: 333.0[M+Na]$^+$

Step 5) Synthesis of 4-methoxy-8H-dibenzo[3,4:6,7]cyclohepta[1,2-b]thiophen-8-one 2-(3-(2-Methoxyphenyl)thiophen-2-yl)benzoic acid (50 mg, 0.16 mmol) was added into a reaction flask, then polyphosphoric acid (1 mL) was added, and the resulting mixture was stirred for 5 hours at 120° C. under the protection of nitrogen. The reaction was stopped, and the reaction solution was added to ice water (10 mL) and then the resulting mixture was extracted with DCM (10 mL×3). The combined organic phases were washed with saturated saline solution (20 mL), dried over anhydrous sodium sulfate, filtered and the filtrate was concentrated in vacuo. The residue was purified by silica gel column chromatography (PE/EA (v/v)=10/1) to give the title compound as a light yellow solid (20 mg, 42%).

$^1$H NMR (400 MHz, CDCl$_3$) δ (ppm): 7.78 (d, J=7.7 Hz, 1H), 7.72-7.65 (m, 4H), 7.59-7.50 (m, 2H), 7.39 (d, J=8.0 Hz, 1H), 7.26 (d, J=7.6 Hz, 1H), 3.89 (s, 3H).

Step 6) Synthesis of 4-methoxy-8H-dibenzo[3,4:6,7]cyclohepta[1,2-b]thiophen-8-ol 4-Methoxy-8H-dibenzo[3,4:6,7]cyclohepta[1,2-b]thiophene-8-one (0.31 g, 1.10 mmol) was dissolved in THF (4 mL) and methanol (2 mL). The mixture was cooled to 0° C., and sodium borohydride (0.20 g, 5.20 mmol) was added into the mixture. The resulting mixture was reacted at 0° C. for 5 minutes and reacted at rt for 30 minutes. The reaction was stopped, water (10 mL) was added, and the reaction mixture was quenched with dichloromethane (10 mL×3). The combined organic phases were washed with saturated brine (20 mL) and dried over anhydrous sodium sulfate and filtered, then the filtrate was concentrated to give the title compound as a white solid (70 mg, 22%).

$^1$H NMR (400 MHz, CDCl$_3$) δ (ppm): 7.72 (d, J=7.7 Hz, 1H), 7.61 (q, J=5.3 Hz, 2H), 7.47-7.35 (m, 5H), 7.29 (t, J=7.2 Hz, 1H), 6.16 (d, J=4.2 Hz, 1H), 4.94 (d, J=4.1 Hz, 1H), 3.76 (s, 3H).

Step 7) Synthesis of (12aR)-7-(benzyloxy)-12-(4-methoxy-8H-dibenzo[3,4:6,7]cyclohepta[1,2-b]thiophen-8-3,4,12,12a-tetrahydro-1H-[1,4]oxazino[3,4-c]pyrido[2,1-f][1,2,4]triazine-6,8-dione 4-Methoxy-8H-dibenzo[3,4:6,7]cyclohepta[1,2-b]thiophen-8-ol (70 mg, 0.24 mmol) and (R)-7-(benzyloxy)-3,4,12,12a-tetrahydro-1H-[1,4]oxazino[3,4-c]pyrido[2,1-f][1,2,4]triazine-6,8-dione (80 mg, 0.24 mmol) were added to a sealing tube, 1-propylphosphoric anhydride (ethyl acetate solution) (wt 50%, 47 mg, 0.07 mmol) and ethyl acetate (1 mL) were then added. The tube was sealed and the resulting mixture was reacted for 2 hour at 100° C. in an oil bath. The reaction solution was added into ice water (20 mL) and the resulting mixture was extracted with DCM (10 mL×3). The combined organic phases were washed with saturated aqueous sodium bicarbonate solution (20 mL), dried over anhydrous sodium sulfate, filtered and the filtrate was concentrated. The residue was purified by silica gel column chromatography (dichloromethane/methanol (v/v)=20/1) to give the title compound as a light yellow solid (40 mg, 28%).

MS (ESI, pos. ion) m/z: 604.2[M+H]$^+$

Step 8) Synthesis of (12aR)-7-hydroxy-12-((8R)-4-methoxy-8H-dibenzo[3,4:6,7]cyclohept[1,2-b]thiophen-8-yl)-3,4,12,12a-tetrahydro-1H-[1,4]oxazino[3,4-c]pyrido[2,1-f][1,2,4]triazine-6, 8-dione (12aR)-7-(benzyloxy)-12-(4-methoxy-8H-dibenzo[3,4:6,7]cyclohepta[1,2-b]thiophen-8-yl)-3,4,12,12a-tetrahydro-1H-[1,4]oxazino[3,4-c]pyrido[2,1-f][1,2,4]triazine-6,8-dione (40 mg, 0.07 mmol) was dissolved in N,N'-dimethyl acetamide (1 mL), lithium chloride (28 mg, 0.65 mmol) was then added, and the mixture was heated to 100° C. and reacted overnight. The reaction was stopped, and to the reaction mixture was added water (5 mL). The reaction mixture was adjusted with 1N diluted hydrochloric acid to pH about 6. The combined organic phases were extracted with ethyl acetate (5 mL×3). The combined organic phases were washed with saturated brine (10 mL×3), dried over anhydrous sodium sulfate and filtered, then the filtrate was concentrated in vacuo, and the residue was purified by HPLC to give the title compound as a light yellow solid (10 mg, 29.5%).

MS (ESI, pos. ion) m/z: 514.1[M+H]$^+$

Example 20 (R)-12-((S)-5-fluoro-8H-dibenzo [3,4:6,7] cyclohept[1,2-b]thiophen-8-yl)-7-hydroxy-3,4,12,12a-tetrahydro-1H-[1,4]oxazino[3,4-c]pyrido[2,1-f][1,2,4]triazine-6,8-diketone (20-1) and (R)-12-((R)-5-fluoro-8H-dibenzo [3,4:6,7]cyclohept[1,2-b]thiophen-8-yl)-7-hydroxy-3,4,12,12a-tetrahydro-1H-[1,4]oxazino[3,4-c]pyrido[2,1-f] [1,2,4]triazine-6,8-diketone (20-2)

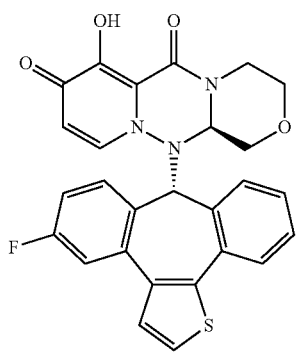

(20-1)

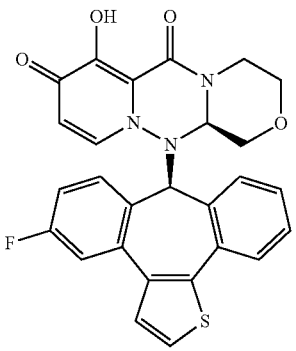

(20-2)

Step 1) Synthesis of 2-bromo-3-(3-fluorophenyl)thiophene 3-(3-Fluorophenyl)thiophene (4.79 g, 26.90 mmol) was dissolved in DMF (70 mL) and the mixture was cooled to −5° C. A solution of NBS (4.88 g, 26.90 mmol) in DMF (20 mL) was added slowly to the reaction solution above. The reaction solution was warmed to 0° C. and reacted overnight. The reaction was stopped, to the reaction mixture was added saturated sodium thiosulfate aqueous solution (200 mL) and the mixture was stirred for 10 minutes at rt. The resulting mixture was extracted with ethyl acetate (100 mL×3). The combined organic phases were washed with saturated brine (200 mL×3), dried over anhydrous sodium sulfate and filtered, then the filtrate was concentrated in vacuo, and the residue was purified by silica gel column chromatography (PE) to give the title compound as light yellow liquid (6.53 g, 95%).

$^1$H NMR (400 MHz, CDCl$_3$) δ (ppm): 7.44-7.39 (m, 1H), 7.37-7.34 (m, 2H), 7.33-7.29 (m, 1H), 7.12-7.06 (m, 1H), 7.05 (d, J=5.7 Hz, 1H).

Step 2) Synthesis of methyl 2-(3-(3-fluorophenyl)thiophen-2-yl)benzoate

2-Bromo-3-(3-fluorophenyl)thiophene (1.36 g, 5.29 mmol), (2-(methoxycarbonyl)phenyl)boronic acid (1.90 g, 10.60 mmol), bi(triphenylphosphine) palladium(II) dichloride (0.38 g, 0.54 mmol) and potassium carbonate (2.25 g, 16.00 mmol) were added into a reaction flask. THF (30 mL) and water (3 mL) were then added. The resulting mixture was reacted overnight at 75° C. under the protection of nitrogen. The reaction was stopped, and the reaction mixture was cooled to rt and filtered through a celite pad. The filter cake was washed with ethyl acetate (10 mL), then the filtrate was concentrated in vacuo and the residue was purified by silica gel column chromatography (PE/EA (v/v)=10/1) to give the title compound as a light yellow solid (1.06 g, 64%).

MS (ESI, pos. ion) m/z: 334.9[M+Na]$^+$;
$^1$H NMR (400 MHz, CDCl$_3$) δ (ppm): 7.80 (dd, J=7.7, 0.8 Hz, 1H), 7.52-7.46 (m, 1H), 7.44-7.38 (m, 3H), 7.21-7.15 (m, 2H), 6.95 (d, J=7.7 Hz, 1H), 6.92-6.88 (m, 2H), 3.60 (s, 3H).

Step 3) Synthesis of 2-(3-(3-fluorophenyl)thiophen-2-yl)benzoic acid

Methyl 2-(3-(3-fluorophenyl)thiophen-2-yl)benzoate (1.06 g, 3.39 mmol) was dissolved in THF (10 mL) and methanol (5 mL), and the mixture was stirred at rt. A solution of sodium hydroxide (1.36 g, 34.00 mmol) in water (10 mL) was added into the reaction solution above, and the mixture was heated to 60° C. and reacted overnight. The reaction was stopped. The reaction mixture was cooled to rt, and to the mixture was added saturated saline (20 mL). The resulting mixture was adjusted with 1 N diluted hydrochloric acid to pH about 6, and then partitioned. The aqueous phase was extracted with ethyl acetate (20 mL×2). The combined organic phases were washed with saturated brine (50 mL), dried over anhydrous sodium sulfate and filtered, then the filtrate was concentrated in vacuo, and the residue was purified by silica gel column chromatography (PE/EA (v/v)=3/1) to give the title compound as a white solid (0.93 g, 92%).

MS (ESI, pos. ion) m/z: 299.1[M+H]$^+$

Step 4) Synthesis of 5-fluoro-8H-dibenzo[3,4:6,7]cyclohepta[1,2-b]thiophene-8-one 2-(3-(3-Fluorophenyl)thiophen-2-yl)benzoic acid (100 mg, 0.34 mmol) was dissolved in anhydrous DCM (2 mL), then anhydrous DMF (0.02 mL) were added, and then thionyl chloride (0.13 mL, 1.80 mmol) were added dropwise under stirring at rt. The resulting mixture was heated to 40° C. and reacted for 3.5 hours, then was cooled to rt. Aluminum trichloride (92 mg, 0.68 mmol) was added. The solution was reacted at rt for 1 hour. The reaction was stopped, and the reaction solution was added to saturated sodium bicarbonate aqueous solution (20 mL), and then the resulting mixture was extracted with DCM (10 mL×3). The combined organic phases were washed with saturated saline solution (20 mL), dried over anhydrous sodium sulfate, filtered and the filtrate was concentrated in vacuo. The residue was purified by silica gel column chromatography (PE/EA (v/v)=10/1) to give the title compound as a white solid (60 mg, 64%).

$^1$H NMR (400 MHz, CDCl$_3$) δ (ppm): 7.97-7.93 (m, 2H), 7.84 (d, J=7.8 Hz, 1H), 7.63 (td, J=7.7, 1.2 Hz, 1H), 7.53 (t, J=7.6 Hz, 1H), 7.50-7.46 (m, 3H), 7.21 (td, J=8.5, 2.4 Hz, 1H).

Step 5) Synthesis of 5-fluoro-8H-dibenzo[3,4:6,7]cyclohepta[1,2-b]thiophen-8-ol

5-Fluoro-8H-dibenzo[3,4:6,7]cyclohepta[1,2-b]thiophen-8-one (60 mg, 0.21 mmol) was dissolved in THF (2 mL) and methanol (1 mL). The mixture was cooled to 0° C., and to the mixture was added sodium borohydride (42 mg, 1.09 mmol). The resulting mixture was reacted at 0° C. for 5 minutes and reacted at rt for 30 minutes. The reaction was stopped, and to the reaction solution was added water (10 mL), then resulting mixture was extracted with DCM (10 mL×3). The combined organic phases were washed with saturated saline solution (20 mL), dried over anhydrous sodium sulfate, filtered and the filtrate was concentrated in vacuo. The residue was purified by silica gel column chromatography (PE/EA (v/v)=5/1) to give the title compound as a white solid (53 mg, 88%).

$^1$H NMR (400 MHz, CDCl$_3$) δ (ppm): 7.87-7.79 (m, 2H), 7.55 (d, J=7.7 Hz, 1H), 7.51-7.40 (m, 4H), 7.32 (t, J=7.6 Hz, 1H), 7.23 (dd, J=9.7, 2.5 Hz, 1H), 7.14 (td, J=8.6, 2.5 Hz, 1H), 5.35 (s, 1H).

Step 6) Synthesis of (12aR)-7-(benzyloxy)-12-(5-fluoro-8H-dibenzo[3,4:6,7]cyclohept[1,2-b]thiophen-8-yl)-3,4,12,12a-tetrahydro-1H-[1,4]oxazino[3,4-c]pyrido[2,1-f][1,2,4]triazine-6,8-dione 5-Fluoro-8H-dibenzo[3,4:6,7]cyclohepta[1,2-b]thiophen-8-ol (20 mg, 0.09 mmol) and (R)-7-(benzyloxy)-3,4,12,12a-tetrahydro-1H-[1,4]oxazino[3,4-c]pyrido[2, 1-f][1,2,4]triazine-6,8-dione (20 mg, 0.06 mmol) were added to a sealing tube, then 1-propylphosphoric anhydride (ethyl acetate solution) (wt 50%, 1 mL) was then added. The tube was sealed and the resulting mixture was reacted for 1.5 hour at 100° C. in an oil bath. The reaction solution was added to ice water (10 mL) and resulting mixture was extracted with ethyl acetate (10 mL×3). The combined organic phases were washed with saturated sodium bicarbonate aqueous solution (20 mL), dried over anhydrous sodium sulfate, filtered and the filtrate was concentrated in vacuo. The residue was purified by silica gel column chromatography (dichloromethane/methanol (v/v)=20/1) to give the title compound as a light yellow solid (10 mg, 28%).

MS (ESI, pos. ion) m/z: 592.3[M+H]$^+$

Step 7) Synthesis of (R) 12-((S)-5-fluoro-8H-dibenzo[3,4:6,7]cyclohept[1,2-b]thiophen-8-yl)-7-hydroxy-3, 4,12,12a-tetrahydro-1H-[1,4]oxazino[3, 4-c]pyrido[2,1-f][[1,2,4]triazine-6,8-dione (20-1) and (R) 12-((R)-5-fluoro-8H-dibenzo[3,4:6,7]cyclohept[1,2-b]thiophen-8-yl)-7-hydroxy-3, 4,12,12a-tetrahydro-1H-[1,4]oxazino[3,4-c]pyrido[2,1-f][1,2, 4]triazine-6,8-dione (20-2)

(12aR)-7-(benzyloxy)-12-((5-fluoro-8H-dibenzo[3,4:6,7]cyclohept[1,2-b]thiophen-8-yl)-3,4,12,12a-tetrahydro-1H-[1,4]oxazino[3,4-c]pyrido[2,1-f][1,2,4]triazine-6,8-dione (0.30 g, 0.51 mmol) was dissolved in N,N'-dimethyl acetamide (5 mL), then anhydrous lithium chloride (220 mg, 5.10 mmol) was added, and the mixture was warmed to 100° C. and reacted overnight. The reaction solution was cooled to rt and water (20 mL) was added. The reaction solution was adjusted with 1N diluted hydrochloric acid to pH about 6, and the resulting mixture was extracted with ethyl acetate (10 mL×3). The combined organic phases were washed with saturated brine (50 mL×3), dried over anhydrous sodium sulfate and filtered, then the filtrate was concentrated in vacuo, and the residue was purified by LUNA preparative column chromatography (acetonitrile/0.1% trifluoroacetate aqueous solution (v/v)=43/57) to give the title compound (20-1) as a light yellow solid (75 mg, 29%) and the title compound (20-2) as a light yellow solid (85 mg, 33%).

MS (ESI, pos. ion) m/z: 501.9[M+H]$^+$;

(R) 12-((S)-5-fluoro-8H-dibenzo[3,4:6,7]cyclohept[1,2-b]thiophen-8-yl)-7-hydroxy-3, 4,12,12a-tetrahydro-1H-[1,4]oxazino[3,4-c]pyrido[2,1-f][1,2,4]triazine-6,8-dione (20-1)

HRMS (ESI, pos. ion) m/z: 502.1251, (C$_{27}$H$_{21}$FN$_3$O$_4$S) [M+H]$^+$, theoretical value: 502.1237;
$^1$H NMR (400 MHz, CDCl$_3$) δ (ppm) 7.68 (d, J=7.6 Hz, 1H), 7.55-7.38 (m, 5H), 7.24 (t, J=7.5 Hz, 1H), 7.16 (td, J=8.2, 8.5 Hz, 1H), 6.99 (d, J=7.5 Hz, 1H), 6.31 (d, J=7.7 Hz, 1H), 5.66 (d, J=7.7 Hz, 1H), 5.43 (s, 1H), 4.60 (d, J=13.3 Hz, 1H), 4.17 (dd, J=9.8, 2.8 Hz, 1H), 3.73 (dd, J=11.8, 2.9 Hz, 1H), 3.34 (t, J=11.0 Hz, 2H), 3.19 (t, J=10.5 Hz, 1H), 2.95-2.85 (m, 1H).

(R) 12-((R)-5-fluoro-8H-dibenzo[3,4:6,7]cyclohept[1,2-b]thiophen-8-yl)-7-hydroxy-3, 4,12,12a-tetrahydro-1H-[1,4]oxazino[3,4-c]pyrido[2,1-f][1,2,4]triazine-6,8-diketone (20-2)

$^1$H NMR (400 MHz, CDCl$_3$) δ (ppm) 7.76 (d, J=7.5 Hz, 1H), 7.58-7.44 (m, 5H), 7.37 (dd, J=9.5 Hz, 2.3 Hz, 1H), 7.03-6.90 (m, 2H), 5.72 (d, J=7.7 Hz, 1H), 5.44 (s, 1H), 4.59 (d, J=13.3 Hz, 1H), 4.17 (dd, J=9.9, 3.0 Hz, 1H), 3.72 (dd, J=11.9, 3.1 Hz, 1H), 3.41-3.29 (m, 2H), 3.19 (t, J=10.5 Hz, 1H), 2.93-2.84 (m, 1H).

Example 21 (12aR)-12-((8R)-4-fluoro-8H-dibenzo [3,4:6,7] cyclohept[1,2-b]thiophen-8-yl)-7-hydroxy-3,4,12,12a-tetrahydro-1H-[1,4]oxazino[3,4-c]pyrido [2,1-f][1,2,4]triazine-6,8-dione (21-1) and (12aR)-12-((8S)-4-fluoro-8H-dibenzo [3,4:6,7] cyclohept[1,2-b]thiophen-8-yl)-7-hydroxy-3,4,12,12a-tetrahydro-1H-[1,4]oxazino[3,4-c]pyrido[2,1-f] [1,2,4]triazine-6,8-dione (21-2)

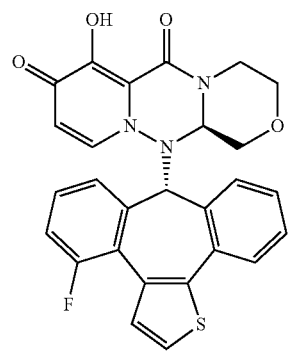

(21-1)

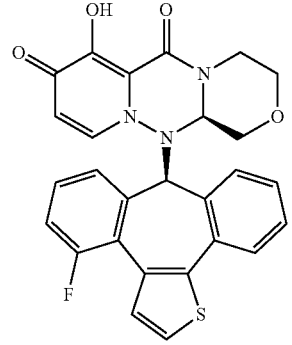

(21-2)

Step 1) Synthesis of 3-(2-fluorophenyl)thiophene

3-Bromothiophene (2.02 g, 12.40 mmol), 2-fluorobenzeneboronic acid (2.23 g, 15.90 mmol), tetratriphenylphosphine palladium (1.42 g, 1.23 mmol) and potassium carbonate (5.10 g, 36.90 mmol) were added into a reaction flask. 1,4-Dioxane (40 mL) and water (4 mL) were then added. The resulting mixture was warmed to 85° C. under the protection of nitrogen and reacted for 4 hours. The reaction was stopped, the reaction solution was cooled to rt and the reaction solution was filtered through a celite pad. The filter cake was washed with ethyl acetate (20 mL), the filtrate was concentrated and the crude product was purified by silica gel column chromatography (PE/EA (v/v)=10/1) to give the title compound as a light yellow solid (2.20 g, 99%).

$^1$H NMR (400 MHz, CDCl$_3$) δ (ppm): 7.68-7.64 (m, 1H), 7.62 (td, J=7.6, 1.6 Hz, 1H), 7.49-7.48 (m, 1H), 7.45-7.43 (m, 1H), 7.34-7.28 (m, 1H), 7.25-7.15 (m, 2H).

Step 2) Synthesis of 2-bromo-3-(3-fluorophenyl)thiophene 3-(2-Fluorophenyl)thiophene (2.20 g, 12.30 mmol) was dissolved in DMF (30 mL) and the mixture was cooled to −5° C. A solution of NBS (2.24 g, 12.30 mmol) in DMF (10 mL) was added slowly to the reaction solution above. The reaction solution was warmed to 0° C. and reacted overnight. The reaction was stopped, to the reaction mixture was added saturated sodium thiosulfate aqueous solution (60 mL), and the resulting mixture was stirred for 10 minutes at rt, then extracted with ethyl acetate (60 mL×3). The combined organic phases were washed with saturated brine (150 mL×3), dried over anhydrous sodium sulfate and filtered, then the filtrate was concentrated in vacuo, and the residue was purified by silica gel column chromatography (PE) to give the title compound as light yellow liquid (2.81 g, 89%).

$^1$H NMR (400 MHz, CDCl$_3$) δ (ppm): 7.50 (td, J=7.5, 1.7 Hz, 1H), 7.43-7.39 (m, 1H), 7.35 (d, J=5.6 Hz, 1H), 7.24 (td, J=7.6, 1.0 Hz, 1H), 7.19 (t, J=7.6 Hz, 1H), 7.06 (dd, J=5.6, 1.8 Hz, 1H).

Step 3) Synthesis of methyl 2-(3-(2-fluorophenyl)thiophen-2-yl)benzoate

2-Bromo-3-(2-fluorophenyl)thiophene (2.80 g, 10.90 mmol), (2-(methoxycarbonyl)phenyl)boronic acid (3.94 g, 21.90 mmol), bis(triphenylphosphine)palladium(II) chloride (0.78 g, 1.10 mmol) and sodium carbonate (4.62 g, 32.80 mmol) were added into a reaction flask. THF (40 mL) and water (4 mL) were then added. The resulting mixture was warmed to 75° C. and reacted overnight under the protection of nitrogen. The reaction was stopped, the reaction solution was cooled to rt and filtered through a celite pad. The filter cake was washed with ethyl acetate (10 mL), and the filtrate was concentrated in vacuo. The residue was purified by silica gel column chromatography (PE/EA (v/v)=10/1) to give the title compound as a light yellow solid (2.40 g, 70%).

MS (ESI, pos. ion) m/z: 313.2[M+H]$^+$;

$^1$H NMR (400 MHz, CDCl$_3$) δ (ppm): 7.74 (d, J=7.7 Hz, 1H), 7.51-7.45 (m, 1H), 7.44-7.36 (m, 3H), 7.25-7.18 (m, 2H), 7.07-7.00 (m, 2H), 6.95 (t, J=7.5 Hz, 1H), 3.61 (s, 3H).

Step 4) Synthesis of 2-(3-(2-fluorophenyl)thiophen-2-yl)benzoic acid

Methyl 2-(3-(2-fluorophenyl)thiophen-2-yl)benzoate (2.40 g, 7.69 mmol) was dissolved in THF (20 mL) and methanol (10 mL), the mixture was stirred at rt. A solution of sodium hydroxide (3.07 g, 76.80 mmol) in water (20 mL) was added into the reaction solution above, and the mixture was stirred overnight at 60° C. The reaction was stopped. The reaction mixture was cooled to rt, and to the mixture was added saturated saline (20 mL). The resulting mixture was adjusted with 1N diluted hydrochloric acid to pH about 6, and partitioned. The aqueous phase was extracted with ethyl acetate (20 mL×2). The combined organic phases were washed with saturated brine (50 mL), dried over anhydrous sodium sulfate and filtered, then the filtrate was concentrated in vacuo, and the residue was purified by silica gel column chromatography (PE/EA (v/v)=3/1) to give the title compound as a white solid (2.28 g, 99%).

MS (ESI, pos. ion) m/z: 299.1[M+H]$^+$.

Step 5) Synthesis of 4-fluoro-8H-dibenzo[3,4:6,7] cyclohepta[1,2-b]thiophen-8-one 2-(3-(2-Fluorophenyl)thiophen-2-yl)benzoic acid (100 mg, 0.34 mmol) was added into a reaction flask, PPA (2 mL) was added, and the reaction mixture was stirred at 120° C. for 8 hours. The reaction was stopped and the reaction solution was cooled to rt. The solution was added into ice water (10 mL). The resulting solution was stirred for 30 minutes and extracted with DCM (5 mL×3). The combined organic phases were washed with saturated brine (10 mL), dried over anhydrous sodium sulfate and filtered, then the filtrate was concentrated in vacuo, and the residue was purified by silica gel column chromatography (PE/EA (v/v)=10/1) to give the title compound as a white solid (10 mg, 11%).

$^1$H NMR (400 MHz, CDCl$_3$) δ (ppm): 7.82 (t, J=6.7 Hz, 2H), 7.69-7.65 (m, 1H), 7.65-7.60 (m, 2H), 7.54-7.49 (m, 1H), 7.49-7.43 (m, 2H), 7.40-7.36 (m, 1H).

Step 6) Synthesis of 4-fluoro-8H-dibenzo[3,4:6,7]cyclohepta[1,2-b]thiophen-8-ol

4-Fluoro-8H-dibenzo[3,4:6,7]cyclohepta[1,2-b]thiophen-8-one (0.37 g, 1.30 mmol) was dissolved in THF (8 mL) and methanol (4 mL). The mixture was cooled to 0° C., to the mixture was added sodium borohydride (0.5 g, 6.50 mmol). After addition, the resulting mixture was reacted at 0° C. for 5 minutes and reacted at rt for 30 minutes. The reaction was stopped, the reaction solution was added with water (20 mL) and the resulting mixture was extracted with DCM (20 mL×3). The organic phases were washed with saturated saline solution (50 mL), dried over anhydrous sodium sulfate, filtered and the filtrate was concentrated in vacuo. The residue was purified by silica gel column chromatography (PE/EA (v/v)=5/1) to give the title compound as a white solid (0.34 g, 91%).

$^1$H NMR (400 MHz, CDCl$_3$) δ (ppm): 7.83 (d, J=7.2 Hz, 1H), 7.65 (d, J=7.3 Hz, 1H), 7.61-7.56 (m, 2H), 7.53-7.36 (m, 4H), 7.36-7.30 (m, 1H), 7.11-6.99 (m, 1H), 5.34 (s, 1H).

Step 7) Synthesis of (12aR)-7-(benzyloxy)-12-(4-fluoro-8H-dibenzo[3,4:6,7]cyclohept[1,2-b]thiophen-8-yl)-3,4,12,12a-tetrahydro-1H-[1,4]oxazino[3,4-c]pyrido[2,1-f][1,2,4]triazine-6,8-dione 4-Fluoro-8H-dibenzo[3,4:6,7]cyclohepta[1,2-b]thiophen-8-ol (17 mg, 0.06 mmol) and (R)-7-(benzyloxy)-3,4,12,12a-tetrahydro-1H-[1,4]oxazino[3,4-c]pyrido[2,1-f][1,2,4]triazine-6,8-dione (20 mg, 0.06 mmol) were added to a sealing tube, then a solution of 1-propylphosphoric anhydride in ethyl acetate (wt 50%, 1 mL) was then added. The tube was sealed and the resulting mixture was reacted for 1.5 hour at 100° C. in an oil bath. The reaction was stopped, and the reaction mixture was added to ice water (10 mL), then the resulting mixture was extracted with ethyl acetate (10 mL×3). The combined organic phases were washed with saturated sodium bicarbonate aqueous solution (20 mL), dried over anhydrous sodium sulfate, filtered and the filtrate was concentrated in vacuo. The residue was purified by silica gel column chromatography (dichloromethane/methanol (v/v)=20/1) to give the title compound as a light yellow solid (11 mg, 34%).

MS (ESI, pos. ion) m/z: 592.3[M+H]

$^1$H NMR (400 MHz, CDCl3) δ (ppm): 7.75-7.60 (m, 4H), 7.53-7.30 (m, 7H), 7.27-7.03 (m, 2H), 6.56 (dd, J=54.0, 7.3 Hz, 1H), 6.31 (dd, J=7.7, 4.6 Hz, 1H), 5.76 (dd, J=29.8, 7.5 Hz, 1H), 5.61 (dd, J=10.8, 2.8 Hz, 1H), 5.45 (dd, J=10.9, 1.9 Hz, 1H), 5.36 (d, J=4.5 Hz, 1H), 4.60 (dd, J=13.6, 3.3 Hz, 1H), 4.06 (ddd, J=27.9, 10.0, 3.0 Hz, 1H), 3.69-3.60 (m, 1H), 3.26-3.13 (m, 2H), 2.97 (td, J=10.4, 5.1 Hz, 1H), 2.78 (td, J=12.8, 3.2 Hz, 1H).

Step 8) Synthesis of (12aR)-12-((8R)-4-fluoro-8H-dibenzo[3,4:6,7]cyclohept[1,2-b]thiophen-8-yl)-7-hydroxy-3,4,12,12a-tetrahydro-1H-[1,4]oxazino[3,4-c]pyrido[2,1-f][1,2,4]triazine-6,8-dione (21-1) and (12aR)-12-((8 S)-4-fluoro-8H-dibenzo[3,4:6,7]cyclohept[1,2-b]thiophen-8-yl)-7-hydroxy-3,4,12,12a-tetrahydro-1H-[1,4]oxazino[3,4-c]pyrido[2,1-f][1,2,4]triazine-6,8-dione (21-2)

(12aR)-7-(benzyloxy)-12-((4-fluoro-8H-dibenzo[3,4:6,7]cyclohept[1,2-b]thiophen-8-3,4,12,12a-tetrahydro-1H-[1,4]oxazino[3,4-c]pyrido[2,1-f][1,2,4]triazine-6,8-dione (0.16 g, 0.27 mmol) was dissolved in N,N'-dimethyl acetamide (3 mL), anhydrous lithium chloride (0.12 g, 2.80 mmol) was added, and the mixture was warmed to 100° C. and reacted overnight. The reaction was stopped, the reaction solution was cooled to rt and water (10 mL) was added. The resulting mixture was extracted with ethyl acetate (10 mL×3). The combined organic phases were washed with saturated brine (20 mL×3), dried over anhydrous sodium sulfate and filtered, then the filtrate was concentrated in vacuo, and the residue was purified by LUNA preparative column chromatography (acetonitrile/0.1% trifluoroacetate aqueous solution (v/v)=42/58) to give the title compound (21-1) as a light yellow solid (53 mg, 39%) and the title compound (21-2) as a light yellow solid (50 mg, 37%).

MS (ESI, pos. ion) m/z: 502.1[M+H]$^+$;

(12aR)-12-((8R)-4-fluoro-8H-dibenzo[3,4:6,7]cyclohept[1,2-b]thiophen-8-yl)-7-hydroxy-3,4,12,12a-tetrahydro-1H-[1,4]oxazino[3,4-c]pyrido[2,1-f][1,2,4]triazine-6,8-dione (21-1)

HRMS (ESI, pos. ion) m/z: 502.1253, (C$_{27}$H$_{21}$FN$_3$O$_4$S) [M+H]$^+$, theoretical value: 502.1237;

$^1$H NMR (400 MHz, CDCl$_3$) δ (ppm) 7.71 (d, J=7.7 Hz, 1H), 7.64 (t, J=5.5 Hz, 1H), 7.51-7.40 (m, 3H), 7.34-7.22 (m, 3H), 6.98 (d, J=7.6 Hz, 1H), 6.38 (d, J=7.6 Hz, 1H), 5.82 (d, J=7.6 Hz, 1H), 5.45 (s, 1H), 4.60 (d, J=11.7 Hz, 1H), 4.25 (dd, J=9.9, 3.0 Hz, 1H), 3.74 (dd, J=12.0, 3.2 Hz, 1H), 3.39-3.28 (m, 2H), 3.18 (t, J=10.5 Hz, 1H), 2.91 (td, J=13.1, 3.4 Hz, 1H).

(12aR)-12-((8 S)-4-fluoro-8H-dibenzo[3,4:6,7]cyclohept[1,2-b]thiophen-8-yl)-7-hydroxy-3,4,12,12a-tetrahydro-1H-[1,4]oxazino[3,4-c]pyrido[2,1-f][1,2,4]triazine-6,8-dione (21-2)

$^1$H NMR (400 MHz, CDCl$_3$) δ (ppm) 7.78 (d, J=7.6 Hz, 1H), 7.69 (t, J=5.4 Hz, 1H), 7.59-7.42 (m, 4H), 7.25-7.16 (m, 2H), 6.87-6.80 (m, 1H), 6.39 (d, J=7.6 Hz, 1H), 5.92 (d, J=7.6 Hz, 1H), 5.45 (s, 1H), 4.58 (d, J=11.8 Hz, 1H), 4.18 (dd, J=9.9, 3.0 Hz, 1H), 3.73 (dd, J=12.0, 3.2 Hz, 1H), 3.38-3.29 (m, 2H), 3.18 (t, J=10.5 Hz, 1H), 2.93-2.84 (m, 1H).

Example 22 The mixture of (R)-7-hydroxy-12-((S)-7-phenyl-6,11-dihydro-dibenzo [b,e]thiepane-11-yl)-3,4,12,12a-tetrahydro-1H-[1,4]oxazino[3,4-c]pyrido[2,1-f][1,2,4]triazine-6,8-dione and (S)-7-hydroxy-12-((R)-7-phenyl-6,11-dihydro-dibenzo [b,e]thiepane-11-yl)-3,4,12,12a-tetrahydro-1H-[1,4]oxazino[3,4-c]pyrido[2,1-f][1,2,4]triazine-6,8-dione Mixture:

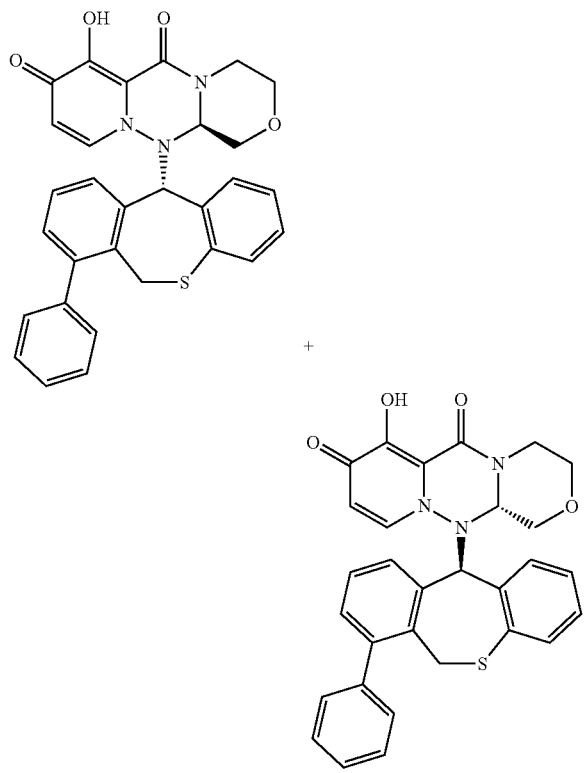

Step 1) Synthesis of methyl 2-methyl-[1,1'-biphenyl]-3-carboxylate

Methyl 3-bromo-2-methylbenzoate (3.00 g, 13.10 mmol), benzeneboronic acid (3.19 g, 26.20 mmol), palladium acetate (0.30 g, 1.30 mmol), S-PHOS (1.08 g, 2.63 mmol) and potassium phosphate (8.34 g, 39.30 mmol) were added into a reaction flask. Toluene (50 mL) and water (5 mL) were then added. The resulting mixture was warmed to 80° C. under the protection of nitrogen and reacted for 1.5 hours. The reaction was cooled to rt and the reaction solution was filtered. The filter cake was washed with ethyl acetate (30 mL), and the filtrate was concentrated in vacuo and the crude product was purified by silica gel column chromatography (PE/EA (v/v)=20/1) to give the title compound as a light yellow solid (2.90 g, 98%).

$^1$H NMR (400 MHz, CDCl$_3$) δ (ppm): 7.84 (dd, J=7.7, 1.2 Hz, 1H), 7.48-7.42 (m, 2H), 7.42-7.36 (m, 2H), 7.35-7.27 (m, 3H), 3.95 (s, 3H), 2.45 (s, 3H).

Step 2) Synthesis of methyl 2-(bromomethyl)-[1,1'-biphenyl]-3-carboxylate

Methyl 2-methyl-[1,1'-biphenyl]-3-carboxylate (2.90 g, 12.80 mmol) was dissolved in carbon tetrachloride (40 mL). NBS (2.52 g, 14.20 mmol) and BPO (0.32 g, 1.30 mmol) were added.

The mixture was heated to 78° C. and stirred for 3 hours. The reaction mixture was cooled to rt, and saturated aqueous sodium thiosulfate solution (50 mL) was added to quench the reaction. The resulting mixture was stirred at rt for 10 minutes and then extracted with dichloromethane (50 mL×3). The combined organic phases were washed with saturated brine (100 mL), dried over anhydrous sodium sulfate and filtered, then the filtrate was concentrated in vacuo, and the residue was purified by silica gel column chromatography (PE/EtOAc (v/v)=20/1) to give the title compound as light yellow liquid (3.55 g, 91%).

MS (ESI, pos. ion) m/z: 306.0[M+H]$^+$;

$^1$H NMR (400 MHz, CDCl$_3$) δ (ppm): 7.94 (dd, J=5.9, 3.3 Hz, 1H), 7.51-7.40 (m, 7H), 4.92 (s, 2H), 4.00 (s, 3H).

Step 3) Synthesis of methyl 2-((phenylthio)methyl)-[1,1'-biphenyl]-3-carboxylate Methyl 2-(bromomethyl)-[1,1'-biphenyl]-3-carboxylate (3.55 g, 11.30 mmol) was dissolved in DMF (40 mL), potassium carbonate (2.42 g, 17.50 mmol) and thiophenol (1.45 mL, 14.10 mmol) were then added, the resulting mixture was reacted for 1 hour at rt. The reaction was stopped, and to the reaction mixture was added water (60 mL). The resulting mixture was extracted with ethyl acetate (40 mL×3). The combined organic phases were washed with saturated brine (100 mL×3), dried over anhydrous sodium sulfate and filtered, then the filtrate was concentrated, and the residue was purified by silica gel column chromatography (PE/EA (v/v)=40/1) to give the title compound as a light yellow solid (2.55 g, 66%).

MS (ESI, pos. ion) m/z: 335.2 [M+H]$^+$;

$^1$H NMR (400 MHz, CDCl$_3$) δ (ppm): 7.85 (dd, J=6.3, 2.9 Hz, 1H), 7.41-7.30 (m, 5H), 7.24-7.10 (m, 7H), 4.49 (s, 2H), 3.92 (s, 3H).

Step 4) Synthesis of 2-((phenylthio)methyl)-[1,1'-biphenyl]-3-carboxylic acid

Methyl 2-((phenylthio)methyl)-[1,1'-biphenyl]-3-carboxylate (2.55 g, 7.63 mmol) was dissolved in THF (20 mL) and methanol (10 mL), the mixture was stirred at rt. A solution of sodium hydroxide (3.05 g, 76.30 mmol) in water (20 mL) was added into the reaction solution above, and the mixture was heated to 60° C. and reacted overnight. The reaction mixture was cooled to rt, and to the mixture was added saturated saline (20 mL). The resulting mixture was adjusted with 1N dilute hydrochloric acid to pH about 6, and partitioned. The aqueous phase was extracted with ethyl acetate (20 mL×2). The combined organic phases were washed with saturated brine (50 mL), dried over anhydrous sodium sulfate and filtered, then the filtrate was concentrated in vacuo, and the residue was purified by silica gel column chromatography (PE/EA (v/v)=3/1) to give the title compound as a white solid (2.40 g, 98%).

MS (ESI, pos. ion) m/z: 343.1[M+Na]$^+$

Step 5) Synthesis of 7-phenyl-dibenzo[b,e]thiepane-11-(6H)-one 2-((Phenylthio)methyl)-[1,1'-biphenyl]-3-carboxylic acid (100 mg, 0.31 mmol) was added into a reaction flask, PPA (2 mL) was added, and the mixture was warmed to 120° C. and stirred for 2 hours. The reaction was cooled to rt, the reaction solution was added to ice water (10 mL), stirred for 30 minutes, and the resulting mixture was extracted with DCM (10 mL×3). The organic phases were washed with saturated saline solution (20 mL), dried over anhydrous sodium sulfate, filtered and the filtrate was concentrated in vacuo. The residue was purified by silica gel column chromatography (PE/DCM (v/v)=1/1) to give the title compound as a white solid (35 mg, 37%).

MS (ESI, pos. ion) m/z: 303.2[M+H]+;

1H NMR (400 MHz, CDCl3) δ (ppm): 8.18 (dd, J=8.0, 1.1 Hz, 1H), 7.54-7.48 (m, 3H), 7.47-7.42 (m, 4H), 7.39 (t, J=7.6 Hz, 2H), 7.32 (dd, J=7.8, 0.6 Hz, 1H), 7.30-7.26 (m, 1H), 4.01 (s, 2H).

Step 6) Synthesis of
7-phenyl-dibenzo[b,e]thiepane-11-(6H)-ol

7-Phenyldibenzo[b,e]thiepane-11-(6H)-one (1.69 g, 5.59 mmol) was dissolved in THF (20 mL) and methanol (10 mL). The mixture was cooled to 0° C. and sodium borohydride (1.09 g, 28.20 mmol) was added. The resulting mixture was reacted for 5 minutes at 0° C. and reacted at rm for 30 minutes. The reaction was stopped, and to the reaction solution was added water (50 mL), and then the resulting mixture was extracted with DCM (30 mL×3). The combined organic phases were washed with saturated saline solution (80 mL), dried over anhydrous sodium sulfate, filtered and the filtrate was concentrated in vacuo. The residue was purified by silica gel column chromatography (DCM) to give the title compound as a white solid (1.59 g, 94%).

MS (ESI, pos. ion) m/z: 327.1[M+Na]+;

1H NMR (400 MHz, CDCl3) δ (ppm): 7.63-7.57 (m, 1H), 7.53-7.38 (m, 6H), 7.32 (t, J=7.6 Hz, 1H), 7.29-7.26 (m, 1H), 7.17-7.10 (m, 3H), 6.30 (d, J=2.2 Hz, 1H), 4.39 (dd, J=66.8, 13.8 Hz, 2H).

Step 7) Synthesis of 7-(benzyloxy)-12-(7-phenyl-6,
11-dihydro-dibenzo[b,e]thiepane-11-yl)-3,4,12,12a-
tetrahydro-1H-[1, 4]oxazino[3,4-c]pyrido[2,1-f][1,2,
4]triazine-6,8-dione 7-Phenyl-dibenzo[b,e]thiepane-11-(6H)-ol (22 mg, 0.07 mmol) and 7-(benzyloxy)-3,4,12,12a-tetrahydro-1H-[1,4] oxazino [3,4-c] pyrido [2,1-f] [1,2,4] triazine-6,8-dione (20 mg, 0.06 mmol) were added into a microwave tube, 1-propyl phosphate anhydride (ethyl acetate solution) (wt 50%, 1 mL) was added. The tube was sealed, and the resulting mixture in the tube was reacted at 100° C. for 1.5 hours. The reaction was stopped. The reaction solution was added into ice water (10 mL) and the resulting mixture was extracted with ethyl acetate (10 mL×3). The combined organic phases were washed with sodium bicarbonate aqueous solution (20 mL), dried over anhydrous sodium sulfate and filtered, then the filtrate was concentrated in vacuo, and the residue was purified by silica gel column chromatography (PE/EtOAc (v/v)=20/1) to give the title compound as a light yellow solid (50 mg, 53%).

MS (ESI, pos. ion) m/z: 614.3[M+H]+

Step 8) Synthesis of the mixture of (R)-7-hydroxy-
12-((S)-7-phenyl-6,11-dihydro-dibenzo[b,e]thi-
epane-11-yl)-3,4,12,12a-tetrahydro-1H-[1,4]oxazino
[3,4-c]pyrido[2,1-f][1,2,4]triazine-6,8-dione and
(S)-7-hydroxy-12-((R)-7-phenyl-6,11-dihydro-
dibenzo[b,e]thiepane-11-yl)-3,4,12,12a-tetrahydro-
1H-[1,4]oxazino[3,4-c]pyrido[2,1-f][1,2,4]triazine-6,
8-dione 7-(Benzyloxy)-12-(7-phenyl-6,11-dihydrodibenzo[b,e] thiepane-11-yl)-3,4,12,12a-tetrahydro-1H-[1,4]oxazino[3,4-c]pyrido[2, 1-f][1,2,4]triazin-6,8-dione (378 mg, 0.62 mmol) was dissolved in N,N'-dimethyl acetamide (8 mL), anhydrous lithium chloride (0.27 g, 6.30 mmol) was then added, and the mixture was warmed to 100° C. and reacted overnight. The reaction was cooled to rt and water (30 mL) was added. The reaction solution was adjusted with 1N dilute hydrochloric acid to pH 6, and quenched with ethyl acetate (20 mL×3). The combined organic phases were washed with saturated brine (50 mL×3), dried over anhydrous sodium sulfate and filtered, then the filtrate was concentrated in vacuo. The residue was purified by LUNA preparative column chromatography (acetonitrile/0.1% trifluoroacetate aqueous solution (v/v)=47/53) to give the title compound as a light yellow solid (120 mg, 37%).

MS (ESI, pos. ion) m/z: 524.1[M+H]+;

HRMS (ESI, pos. ion) m/z: 524.1663, (C27H21FN3O4S) [M+H]+, theoretical value: 524.1644;

1H NMR (400 MHz, DMSO-d6) δ (ppm): 7.52-7.46 (m, 6H), 7.36 (t, J=7.6 Hz, 1H), 7.29-7.21 (m, 3H), 7.17 (s, 2H), 6.87 (d, J=5.2 Hz, 1H), 6.69 (d, J=7.6 Hz, 1H), 6.13 (d, J=7.5 Hz, 1H), 5.41-5.30 (m, 2H), 4.83 (d, J=7.4 Hz, 1H), 4.72 (d, J=13.0 Hz, 1H), 3.98 (d, J=8.8 Hz, 1H), 3.87 (d, J=9.6 Hz, 1H), 3.76 (d, J=13.8 Hz, 1H), 3.64 (t, J=10.6 Hz, 1H), 3.53 (t, J=11.0 Hz, 1H), 3.13 (t, J=11.1 Hz, 1H).

Example 23 The mixture of (R)-7-hydroxy-12-((S)-
7-(thiophen-2-yl)-6,11-dihydro-dibenzo [b,e]thi-
epane-11-yl)-3,4,12,12a-tetrahydro-1H-[1,4]oxazino
[3,4-c] pyrido [2,1-f] [1,2,4]triazine-6,8-dione and
(S)-7-hydroxy-12-((R)-7-(thiophen-2-yl)-6,11-di-
hydro-dibenzo [b,e] thiepane-11-yl)-3,4,12,12a-
tetrahydro-1H-[1,4]oxazino [3,4-c] pyrido [2,1-f]
[1,2,4]triazine-6,8-dione Mixture:

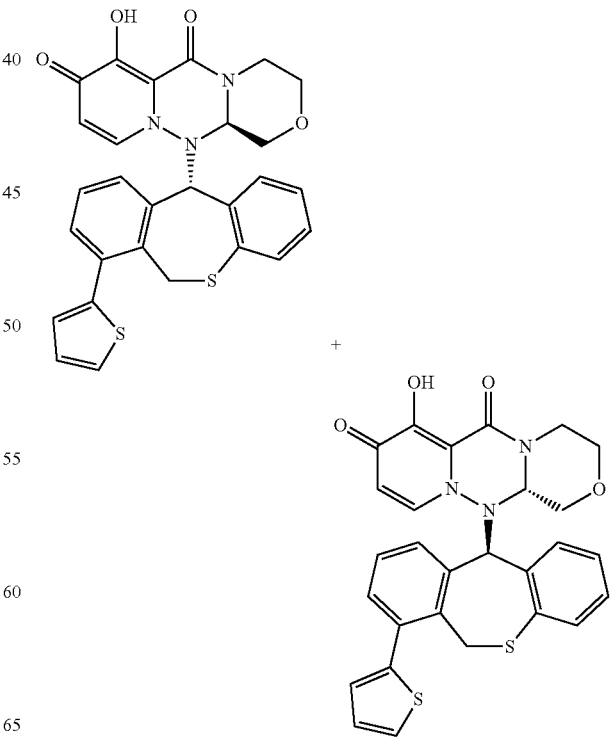

Step 1) Synthesis of methyl 2-methyl-3-(4,4,5,5-tetramethyl-1,3,2-dioxaborolan-2-yl)benzoate Methyl 3-bromo-2-methylbenzoate (0.50 g, 2.20 mmol), bis(pinacolato)diboron (0.83 g, 3.30 mmol), potassium acetate (0.64 g, 6.50 mmol) and [1,1'-Bis(diphenylphosphino)ferrocene]dichloropalladium(II)(0.16 g, 0.21 mmol) was suspended in 1,4-dioxane (10 mL). The mixture was warmed to 100° C. and reacted overnight under protection of nitrogen. The mixture was cooled to rm and filtered. The filter cake was washed with ethyl acetate (10 mL), the filtrate was concentrated, and the residue was purified by silica gel column chromatography (PE/EtOAc (v/v)=20/1) to give the title compound as a colorless oil (0.39 g, 65%).

MS (ESI, pos. ion) m/z: 277.1[M+H]$^+$;
$^1$H NMR (400 MHz, CDCl$_3$) δ (ppm): 7.87 (t, J=7.9 Hz, 2H), 7.24 (t, J=7.6 Hz, 1H), 3.91 (s, 3H), 2.76 (s, 3H), 1.38 (s, 12H).

Step 2) Synthesis of methyl 2-methyl-3-(thiophen-2-yl) benzoate

Methyl 2-methyl-3-(4,4,5,5-tetramethyl-1,3,2-dioxaborolan-2-yl) methyl benzoate (68 mg, 0.25 mmol), 2-bromothiophene (20 mg, 0.12 mmol), [1,1'-bis(diphenylphosphino)ferrocene]dichloropalladium(II) (8 mg, 0.01 mmol) and potassium carbonate (51 mg, 0.37 mmol) were added into a sealing tube, then 1,4-dioxane (1 mL) and water (0.1 mL) were added. The mixture was heated to 110° C. and reacted for 2.5 hours under protection of nitrogen, then was cooled to rt and filtered. The filter cake was washed with ethyl acetate (5 mL) and the filtrate was concentrated in vacuo. The residue was purified by silica gel column chromatography (PE/EtOAc (v/v)=20/1) to give the title compound as a light yellow solid (15 mg, 53%).

$^1$H NMR (400 MHz, CDCl$_3$) δ (ppm): 7.82 (d, J=7.8 Hz, 1H), 7.53 (d, J=7.6 Hz, 1H), 7.39 (d, J=5.1 Hz, 1H), 7.29 (d, J=7.7 Hz, 1H), 7.12 (dd, J=5.0, 3.6 Hz, 1H), 7.06-7.02 (m, 1H), 3.94 (s, 3H), 2.57 (s, 3H)

Step 3) Synthesis of methyl 2-(bromomethyl)-3-(thiophen-2-yl)benzoate

Methyl 2-methyl-3-(thiophen-2-yl)benzoate (0.45 g, 1.90 mmol) was dissolved in carbon tetrachloride (10 mL). NBS (0.38 g, 2.10 mmol) and BPO (50 mg, 0.20 mmol) were added. The mixture was heated to 78° C. and stirred for 2 hours under protection of nitrogen. The reaction was stopped, the reaction mixture was cooled to rt and quenched with saturated aqueous sodium thiosulfate solution (30 mL), stirred at rt for 10 minutes and extracted with dichloromethane (20 mL×3). The combined organic phases were washed with saturated brine (50 mL), dried over anhydrous sodium sulfate and filtered, then the filtrate was concentrated to give the title compound as fuchsia liquid (0.60 g, 100%).

Step 4) Synthesis of methyl 2-((phenylthio)methyl)-3-(thiophen-2-yl)benzoate Methyl 2-(bromomethyl)-3-(thiophen-2-yl)benzoate (0.60 g, 1.90 mmol) was dissolved in DMF (10 mL), potassium carbonate (0.40 g, 2.90 mmol) and thiophenol (0.25 mL, 2.40 mmol) were then added, the resulting mixture was reacted for 0.5 hour at rt. To the reaction mixture was added water (30 mL), and the mixture was extracted with ethyl acetate (20 mL×3). The combined organic phases were washed with saturated brine (50 mL×3) and dried over anhydrous sodium sulfate and filtered, then the filtrate was concentrated, and the residue was purified by silica gel column chromatography (PE/EtOAc (v/v)=40/1) to give the title compound as a light yellow solid (0.50 g, 76%).

MS (ESI, pos. ion) m/z: 341.0 [M+H]$^+$;
$^1$H NMR (400 MHz, CDCl$_3$) δ (ppm): 7.84 (d, J=7.6 Hz, 1H), 7.50 (dd, J=7.7, 1.1 Hz, 1H), 7.36-7.32 (m, 2H), 7.24-7.17 (m, 5H), 7.05-7.03 (m, 2H), 4.63 (s, 2H), 3.89 (s, 3H).

Step 5) Synthesis of 2-((phenylthio)methyl)-3-(thiophen-2-yl)benzoic acid

Methyl 2-((phenylthio)methyl)-3-(thiophen-2-yl)benzoate (0.50 g, 1.50 mmol) was dissolved in THF (5 mL) and methanol (2 mL). The mixture was stirred and a solution of sodium hydroxide (0.60 g, 15.00 mmol) in water (5 mL) was added. The resulting mixture was stirred overnight at rt. To the reaction mixture was added saturated brine (20 mL). The mixture was adjusted with 1N dilute hydrochloric acid to pH about 6, and partitioned. The aqueous phase was extracted with ethyl acetate (20 mL×2). The combined organic phases were washed with saturated brine (50 mL), dried over anhydrous sodium sulfate and filtered, then the filtrate was concentrated, and the residue was purified by silica gel column chromatography (PE/EtOAc (v/v)=3/1) to give the title compound as a white solid (0.45 g, 94%).

MS (ESI, pos. ion) m/z: 327.1[M+H]$^+$

Step 6) Synthesis of 7-(thien-2-yl)dibenzo[b,e]thiahepta-11-(6H)-one 2-((Phenylthio)methyl)-3-(thiophen-2-yl)benzoic acid (0.45 g, 1.40 mmol) was added into a reaction flask, PPA (10 mL) was added, and the mixture was heated to 120° C. and stirred for 2.5 hours. The reaction was cooled to rt, and to the reaction solution was added ice water (30 mL). The resulting mixture was stirred for 30 minutes, and the resulting mixture was extracted with DCM (20 mL×3). The combined organic phases were washed with saturated saline solution (50 mL), dried over anhydrous sodium sulfate, filtered and the filtrate was concentrated. The residue was purified by silica gel column chromatography (PE/EA (v/v)=1/1) to give the title compound as a white solid (200 mg, 47%).

MS (ESI, pos. ion) m/z: 309.1[M+H]$^+$;
$^1$H NMR (400 MHz, CDCl$_3$) δ (ppm): 8.16 (dd, J=8.0, 1.1 Hz, 1H), 7.58 (d, J=7.6 Hz, 1H), 7.50 (d, J=7.6 Hz, 1H), 7.47-7.44 (m, 1H), 7.41-7.37 (m, 2H), 7.34 (t, J=5.5 Hz, 1H), 7.30-7.26 (m, 1H), 7.20-7.16 (m, 2H), 4.15 (s, 2H).

Step 7) Synthesis of 7-(thien-2-yl)dibenzo[b,e]thiahepta-11-(6H)-ol 7-(Thien-2-yl)dibenzo[b,e]thiahepta-11-(6H)-one (200 mg, 0.65 mmol) was dissolved in THF (4 mL) and methanol (2 mL). The mixture was cooled to 0° C. and added with sodium borohydride (126 mg, 3.26 mmol). The resulting mixture was reacted for 5 minutes at 0° C. and reacted at rt for 30 minutes. To the reaction solution was added water (30 mL) and the resulting mixture was extracted with DCM (20 mL×3). The combined organic phases were washed with saturated saline solution (50 mL), dried over anhydrous sodium sulfate, filtered and the filtrate was concentrated in vacuo. The residue was purified by silica gel column chromatography (DCM) to give the title compound as a white solid (195 mg, 97%).

MS (ESI, pos. ion) m/z: 333.1[M+Na]⁺

Step 8) Synthesis of 7-(benzyloxy)-12-(7-(thiophen-2-yl)-6,11-dihydrodibenzo[b, e]thiahepta-11-yl)-3,4,12,12a-tetrahydro-1H-[1,4]oxazino[3,4-c]pyrido[2,1-f] [1,2,4]triazine-6,8-dione 7-(Thien-2-yl)dibenzo[b,e]thiahepta-11-(6H)-ol (190 mg, 0.61 mmol) and 7-(benzyloxy)-3,4,12,12a-tetrahydro-1H-[1,4]oxazino[3,4-c]pyrido[2,1-f][1,2, 4]triazine-6,8-dione (200 mg, 0.61 mmol) was added to a sealing tube, then 1-propylphosphoric anhydride (ethyl acetate solution) (wt 50%, 10 mL) was added, and the tube was sealed. The resulting mixture was warmed to 100° C. and reacted for 1.5 hours. The reaction was stopped. The reaction solution was cooled to rt, added into ice water (100 mL) and the resulting mixture was extracted with ethyl acetate (50 mL×3). The combined organic phases were washed with sodium bicarbonate aqueous solution (100 mL), dried over anhydrous sodium sulfate and filtered, then the filtrate was concentrated in vacuo, and the residue was purified by silica gel column chromatography (DCM/methanol (v/v)=20/1) to give the title compound as a light yellow solid (0.19 g, 50%).

MS (ESI, pos. ion) m/z: 620.2[M+H]⁺

Step 9) Synthesis of the mixture of (R)-7-hydroxy-12-((S)-7-(thiophen-2-yl)-6,11-dihydro-dibenzo[b,e]thiahepta-11-yl)-3,4,12,12a-tetrahydro-1H-[1,4]oxazino[3,4-c]pyrido[2,1-f][1,2,4]triazine-6,8-dione and (S)-7-hydroxy-12-((R)-7-(thiophen-2-yl)-6,11-dihydro-dibenzo[b, e]thiahepta-11-yl)-3,4,12,12a-tetrahydro-1H-[1,4]oxazino[3,4-c]pyrido[2,1-f][1,2, 4]triazine-6,8-dione 7-(Benzyloxy)-12-(7-(thiophen-2-yl)-6,11-dihydrodibenzo[b,e]thiahepta-11-yl)-3,4,12,12a-tetrahydro-1H-[1,4]oxazino[3,4-c]pyrido[2,1-f][1,2,4]triazin-6,8-dione (0.19 g, 0.31 mmol) was dissolved in N,N'-dimethyl acetamide (4 mL), anhydrous lithium chloride (0.13 g, 3.00 mmol) was added. The mixture was warmed to 100° C. and reacted overnight under protection of nitrogen. The reaction was cooled to rt and water (20 mL) was added. The reaction solution was adjusted with 1N dilute hydrochloric acid to pH about 6, and then extracted with ethyl acetate (20 mL×3). The combined organic phases were washed with saturated brine (50 mL×3), dried over anhydrous sodium sulfate and filtered, then the filtrate was concentrated, and the residue was purified by LUNA preparative column chromatography (acetonitrile/0.1% trifluoroacetate aqueous solution (v/v)=47/53) to give the title compound as a light yellow solid (120 mg, 37%).

MS (ESI, pos. ion) m/z: 530.3[M+H]⁺;
HRMS (ESI, pos. ion) m/z: 530.1181, (C₂₇H₂₁FN₃O₄S) [M+H]⁺, theoretical value: 530.1208; 1H NMR (400 MHz, DMSO-d6) δ (ppm): 7.58 (d, J=7.5 Hz, 1H), 7.48 (d, J=4.8 Hz, 1H), 7.34 (t, J=7.6 Hz, 1H), 7.29-7.17 (m, 6H), 6.86 (dd, J=9.5, 4.2 Hz, 1H), 6.68 (d, J=7.6 Hz, 1H), 6.16 (d, J=7.5 Hz, 1H), 5.42 (d, J=13.8 Hz, 1H), 5.36 (s, 1H), 4.82 (dd, J=10.0, 2.7 Hz, 1H), 4.72 (d, J=12.3 Hz, 1H), 4.05-3.96 (m, 2H), 3.90-3.84 (m, 1H), 3.62 (t, J=10.6 Hz, 1H), 3.52 (t, J=10.9 Hz, 1H), 3.15-3.08 (m, 1H).

Example 24 The mixture of (R)-7-hydroxy-12-((S)-7,8-difluoro-4-phenyl-6,11-dihydro-dibenzo [b,e]thiahepta-11-yl-3,4,12,12a-tetrahydro-1H-[1,4]oxazino [3,4-c] pyrido [2,1-f] [1,2,4]triazine-6,8-dione and (S)-7-hydroxy-12-((R)-7,8-difluoro-4-phenyl-6,11-dihydro-dibenzo [b,e]thiahepta-11-yl-3,4,12,12a-tetrahydro-1H-[1,4]oxazino[3,4-c]pyrido[2,1-f] [1,2,4]triazine-6, 8-dione Mixture:

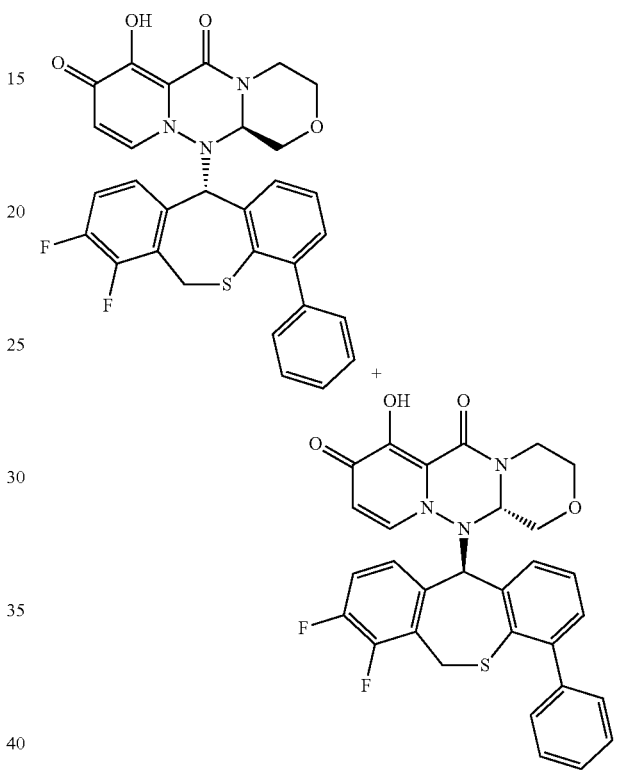

Step 1) Synthesis of ethyl 3,4-difluoro-2-methylbenzoate 3,4-Difluoro-2-methylbenzoic acid (6.80 g, 0.40 mol) was dissolved in DMF (80 mL), potassium carbonate (16.50 g, 1.19 mol) and iodine (4.80 mL, 0.60 mol) were then added, the resulting mixture was reacted overnight at rt. To the reaction mixture was added water (200 mL) and the resulting mixture was extracted with ethyl acetate (100 mL×3). The combined organic phases were washed with saturated brine (200 mL×3), dried over anhydrous sodium sulfate and filtered, then the filtrate was concentrated, and the residue was purified by silica gel column chromatography (PE/EtOAc (v/v)=10/1) to give the title compound as light yellow liquid (7.58 g, 96%).

¹H NMR (400 MHz, CDCl₃) δ (ppm): 7.71 (m, 1H), 7.04 (q, J=8.8 Hz, 1H), 4.37 (q, J=7.1 Hz, 2H), 2.55 (d, J=2.7 Hz, 3H), 1.40 (t, J=7.1 Hz, 3H).

Step 2) Synthesis of ethyl 2-(bromomethyl)-3,4-difluorobenzoate

Ethyl 3,4-difluoro-2-methylbenzoate (7.58 g, 0.38 mol) was dissolved in carbon tetrachloride (20 mL). NBS (7.42 g, 0.42 mol) and benzoyl peroxide (0.94 g, 3.80 mmol) were added. The mixture was heated to 78° C. and reacted for 6 hours under protection of nitrogen. The reaction mixture was cooled to rt, quenched with saturated aqueous sodium thiosulfate solution (50 mL), and the resulting mixture was extracted with dichloromethane (50 mL×3). The combined organic phases were washed with saturated brine (100 mL) and dried over anhydrous sodium sulfate and filtered, then the filtrate was concentrated in vacuo, and the residue was purified by silica gel column chromatography (PE/EtOAc (v/v)=20/1) to give the title compound as light yellow liquid (9.77 g, 93%).

$^1$H NMR (400 MHz, CDCl$_3$) δ (ppm): 7.83 (ddd, J=8.7, 5.0, 1.9 Hz, 1H), 7.20 (q, J=8.9 Hz, 1H), 5.03 (d, J=2.1 Hz, 2H), 4.43 (q, J=7.1 Hz, 2H), 1.44 (t, J=7.1 Hz, 3H).

Step 3) Synthesis of ethyl 2-(((2-bromophenyl)thio)methyl)-3,4-difluorobenzoate Ethyl 2-(bromomethyl)-3,4-difluorobenzoate (1.00 g, 3.58 mmol) was dissolved in DMF (15 mL), potassium carbonate (0.75 g, 5.40 mmol), alumina (0.45 g, 4.30 mmol) and 2-toluenethiol (0.52 mL, 4.30 mmol) were then added. The resulting mixture was reacted for 2 hour at rt. To the reaction mixture was added water (30 mL) and the mixture was stirred at rt for 10 minutes, extracted with ethyl acetate (20 mL×3). The combined organic phases were washed with saturated brine (50 mL×3), dried over anhydrous sodium sulfate and filtered, then the filtrate was concentrated in vacuo, and the residue was purified by silica gel column chromatography (PE/EtOAc (v/v)=40/1) to give the title compound as fuchsia liquid (0.98 g, 71%).

MS (ESI, neg. ion) m/z: 386.9 [M−H]$^-$ $^1$H NMR (400 MHz, CDCl$_3$) δ (ppm): 7.74 (ddd, J=8.7, 5.1, 1.8 Hz, 1H), 7.57 (dd, J=7.9, 1.2 Hz, 1H), 7.33 (dd, J=7.8, 1.4 Hz, 1H), 7.22 (td, J=7.6, 1.3 Hz, 1H), 7.15-7.06 (m, 2H), 4.63 (d, J=1.7 Hz, 2H), 4.33 (q, J=7.1 Hz, 2H), 1.37 (t, J=7.1 Hz, 3H).

Step 4) Synthesis of 2-(((2-bromophenyl)thio)methyl)-3,4-difluorobenzoic acid Ethyl 2-(((2-bromophenyl)thio)methyl)-3,4-difluorobenzoate (0.98 g, 2.50 mmol) was dissolved in THF (10 mL) and methanol (5 mL). The mixture was stirred and a solution of sodium hydroxide (1.00 g, 25.00 mmol) in water (10 mL) was added. The resulting mixture was warmed to 60° C. and stirred overnight. The reaction was stopped. Saturated saline (20 mL) was added into the reaction mixture. The resulting mixture was adjusted with 1N dilute hydrochloric acid to pH about 6 and partitioned. The aqueous phase was extracted with ethyl acetate (20 mL×2), and the organic phases were combined. The combined organic phases were washed with saturated brine (50 mL), dried over anhydrous sodium sulfate and filtered, then the filtrate was concentrated in vacuo, and the residue was purified by silica gel column chromatography (PE/EtOAc (v/v)=3/1) to give the title compound as a white solid (0.74 g, 81%).

MS (ESI, pos. ion) m/z: 360.0[M+H]$^+$

Step 5) Synthesis of 4-bromo-7,8-difluoro-dibenzo[b,e]thiahepta-11-(6H)-one 2-(((2-Bromophenyl)thio)methyl)-3,4-difluorobenzoic acid (0.74 g, 2.10 mmol) was added into a the reaction flask, PPA (20 mL) was added, and the mixture was warmed to 120° C. and stirred for 10 hours. The reaction was cooled to rt, and to the reaction solution was added ice water (100 mL). The resulting mixture was stirred for 30 minutes, and extracted with DCM (50 mL×3). The combined organic phases were washed with saturated saline solution (100 mL), dried over anhydrous sodium sulfate, filtered and the filtrate was concentrated. The residue was purified by silica gel column chromatography (PE/DCM (v/v)=1/1) to give the title compound as a white solid (0.25 g, 36%).

$^1$H NMR (400 MHz, CDCl$_3$) δ (ppm): 8.18 (dd, J=8.1, 1.3 Hz, 1H), 7.72 (dd, J=7.7, 1.3 Hz, 1H), 7.32 (ddd, J=8.5, 4.7, 1.6 Hz, 1H), 7.20-7.13 (m, 2H), 4.17 (s, 2H).

Step 6) Synthesis of 4-phenyl-7,8-difluoro-dibenzo[b,e]thiahepta-11-(6H)-one 4-Bromo-7,8-difluoro-dibenzo[b,e]thiahepta-11-(6H)-one (30 mg, 0.09 mmol), phenylboronic acid (22 mg, 0.18 mmol), potassium phosphate (56 mg, 0.26 mmol), palladium acetate (2 mg, 0.01 mmol) and S-PHOS (7 mg, 0.02 mmol) were added into a reaction flask, and then toluene (1 mL) and water (0.1 mL) were added. The mixture was warmed to 80° C. and reacted for 6 hours. The mixture was cooled to rt and filtered. The filter cake was washed with ethyl acetate (5 mL), and the filtrate was concentrated in vacuo, and the residue was purified by silica gel column chromatography (PE/EtOAc (v/v)=20/1) to give the title compound as a white solid (10 mg, 34%).

$^1$H NMR (400 MHz, CDCl$_3$) δ (ppm): 8.24 (dd, J=5.7, 4.0 Hz, 1H), 7.49-7.43 (m, 4H), 7.40-7.33 (m, 4H), 7.20-7.13 (m, 1H), 4.03 (s, 2H).

Step 7) Synthesis of 4-phenyl-7,8-difluoro-dibenzo[b,e] thiepane-11-(6H)-ol

4-Phenyl-7,8-difluoro-dibenzo[b,e] thiepane-11-(6H)-one (0.91 g, 2.70 mmol) was dissolved in THF (15 mL) and methanol (5 mL). The mixture was cooled to 0° C. and sodium borohydride (0.53 g, 14.00 mmol) was added. The resulting mixture was reacted for 5 minutes at 0° C. and reacted at rt for 30 minutes. The reaction was stopped. To the reaction solution was added water (30 mL), and the resulting mixture was extracted with DCM (20 mL×3). The combined organic phases were washed with saturated saline solution (50 mL), dried over anhydrous sodium sulfate, filtered and the filtrate was concentrated in vacuo. The residue was purified by silica gel column chromatography (PE/DCM (v/v)=1/1) to give the title compound as a white solid (0.89 g, 97%).

$^1$H NMR (400 MHz, CDCl$_3$) δ (ppm): 7.54 (dd, J=7.6, 0.8 Hz, 1H), 7.48-7.38 (m, 3H), 7.35-7.27 (m, 4H), 7.18 (dd, J=7.5, 1.3 Hz, 1H), 7.07 (dd, J=17.7, 8.5 Hz, 1H), 6.33 (d, J=3.9 Hz, 1H), 4.28 (dd, J=133.5, 15.6 Hz, 2H), 3.01 (d, J=4.3 Hz, 1H).

Step 8) Synthesis of 7-(benzyloxy)-12-(7,8-difluoro-4-phenyl-6, 11-dihydrodibenzo[b,e]thiepane-11-yl)-7-hydroxy-3,4,1,2,12a-tetrahydro-1H-[1,4]oxazino[3,4-c]pyrido[2, 1-f] [1,2,4]triazine-6,8-dione 4-Phenyl-7,8-difluoro-dibenzo[b,e]thiepane-11-(6H)-ol (27 mg, 0.07 mmol) and 7-(benzyloxy)-3,4,12,12a-tetrahydro-1H-[1,4]oxazino[3,4-c]pyrido[2,1-f] [1,2,4]triazine-6,8-dione (20 mg, 0.06 mmol) were added to a sealing tube, then 1-propylphosphoric anhydride (ethyl acetate solution) (wt 50%, 1 mL) was added, and the tube was sealed. The resulting mixture was warmed to 100° C. and reacted for 1.5 hours. The reaction was stopped. The reaction solution was added into ice water (10 mL) and extracted with ethyl acetate (10 mL×3).

The combined organic phases were washed with saturated sodium bicarbonate aqueous solution (20 mL), dried over anhydrous sodium sulfate and filtered, then the filtrate was concentrated in vacuo, and the residue was purified by silica gel column chromatography (DCM/methanol (v/v)=20/1) to give the title compound as a light yellow solid (20 mg, 50%).

MS (ESI, pos. ion) m/z: 650.2[M+H]$^+$ $^1$H NMR (400 MHz, CDCl$_3$) δ (ppm): 7.65 (d, J=6.9 Hz, 2H), 7.39 (dt, J=13.4, 5.3 Hz, 6H), 7.19 (t, J=6.4 Hz, 2H), 7.12 (dd, J=16.8, 8.6 Hz, 1H), 7.06-6.97 (m, 2H), 6.75 (t, J=7.6 Hz, 1H), 6.50 (d, J=7.0 Hz, 1H), 5.93 (d, J=7.7 Hz, 1H), 5.66 (d, J=10.9 Hz, 1H), 5.48 (d, J=10.8 Hz, 1H), 5.36 (s, 1H), 5.21 (d, J=15.4 Hz, 1H), 4.70 (d, J=12.5 Hz, 1H), 4.48 (dd, J=9.8, 2.6 Hz, 1H), 3.97 (d, J=13.9 Hz, 1H), 3.87 (dd, J=10.9, 2.5 Hz, 1H), 3.75-3.60 (m, 2H), 3.36 (dt, J=11.7, 10.1 Hz, 2H), 2.94 (dd, J=18.2, 7.1 Hz, 1H).

Step 9) Synthesis of the mixture of (R)-7-hydroxy-12-((S)-7,8-difluoro-4-phenyl-6,11-dihydro-dibenzo[b,e] thiepane-11-yl-3,4,12,12a-tetrahydro-1H-[1,4]oxazino[3,4-c]pyrido[2,1-f][1,2,4]triazine-6, 8-dione and (S)-7-hydroxy-12-((R)-7,8-difluoro-4-phenyl-6,11-dihydro-dibenzo[b,e] thiepane-11-yl-3,4,12,12a-tetrahydro-1H-[1,4]oxazino[3,4-c]pyrido[2,1-f][1,2,4]triazine-6, 8-dione 7-(Benzyloxy)-12-(7,8-difluoro-4-phenyl-6,11-dihydro-dibenzo[b,e]thiepane-11-yl)-7-hydroxy-3,4,12,12a-tetrahydro-1H-[1,4]oxazino[3,4-c]pyrido[2,1-f][1,2,4]triazine-6,8-dione (0.32 g, 0.49 mmol) was dissolved in N,N-dimethyl acetamide (8 mL), anhydrous lithium chloride (0.21 g, 4.90 mmol) was added. The mixture was warmed to 100° C. and reacted overnight. The reaction was cooled to rt and water (30 mL) was added. The reaction solution was adjusted with 1N diluted hydrochloric acid to pH about 6, and extracted with ethyl acetate (20 mL×3). The combined organic phases were washed with saturated brine (50 mL×3), dried over anhydrous sodium sulfate and filtered, then the filtrate was concentrated in vacuo, and the residue was purified by LUNA preparative column chromatography (acetonitrile/0.1% trifluoroacetate aqueous solution (v/v)=47/53) to give the title compound as a light yellow solid (120 mg, 44%).

MS (ESI, pos. ion) m/z: 560.1[M+H]$^+$;

MS (ESI, pos. ion) m/z: 560.1431, (C$_{30}$H$_{24}$F$_2$N$_3$O$_4$S)[M+H]$^+$, theoretical value: 560.1456;

$^1$H NMR (400 MHz, DMSO-d$_6$) δ (ppm): 7.48-7.40 (m, 3H), 7.30 (d, J=7.6 Hz, 1H), 7.24-7.19 (m, 2H), 7.19-7.12 (m, 1H), 7.11-7.05 (m, 2H), 6.93 (t, J=7.6 Hz, 1H), 6.71 (d, J=7.7 Hz, 1H), 6.12 (d, J=7.6 Hz, 1H), 5.41 (s, 1H), 5.23 (dd, J=14.0, 1.5 Hz, 1H), 4.71 (d, J=13.6 Hz, 1H), 4.66 (dd, J=10.0, 2.8 Hz, 1H), 4.02 (d, J=14.0 Hz, 1H), 3.98 (dd, J=11.3, 2.8 Hz, 1H), 3.86 (dd, J=11.9, 2.8 Hz, 1H), 3.64 (t, J=10.6 Hz, 1H), 3.51 (td, J=11.7, 1.9 Hz, 1H), 3.12-3.02 (m, 1H).

Example 25 Synthesis of the mixture of (R)-12-((S)-8H-dibenzo [3,4:6,7] cyclohept[1,2-d] oxazole-8-yl)-7-hydroxy-3,4,12,12a-tetrahydro-1H-[1,4]oxazino[3,4-c]pyrido[2,1-f][1,2,4]triazine-6,8-dione and (S)-12-((R)-8H-dibenzo [3,4:6,7] cyclohepta[1,2-d] oxazole-8-yl)-7-hydroxy-3,4,12,12a-tetrahydro-1H-[1,4]oxazino[3,4-c]pyrido[2,1-f][1,2,4]triazine-6, 8-dione Mixture:

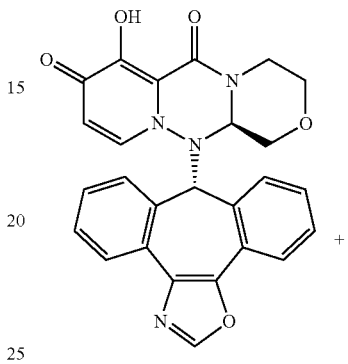

+

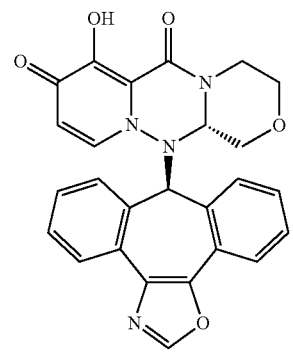

Step 1) Synthesis of 5H-dibenzo[a,d][7]annulene-5,10(11H)-dione

1H-Indene-1,3(2H)-dione (200 mg, 1.37 mmol), 2-(trimethylsilyl)phenyl trifluoromethanesulfonate (0.53 g, 1.80 mmol) and cesium fluoride (0.53 g, 3.50 mmol) were added into a reaction flask, then anhydrous acetonitrile (5 mL) was added. The reaction solution was warmed to 65° C. and reacted for 4 hours. The reaction was completed. Water (10 mL) was added into the reaction mixture. The resulting mixture was extracted with ethyl acetate (10 mL×3). The combined organic phases were washed with saturated brine (30 mL), dried over anhydrous sodium sulfate and filtered, then the filtrate was concentrated in vacuo, and the residue was purified by silica gel column chromatography (PE/EtOAc (v/v)=20/1) to give the title compound as light yellow liquid (100 mg, 33%).

MS (ESI, pos. ion) m/z: 223.2[M+H]$^+$;

$^1$H NMR (400 MHz, CDCl$_3$) δ (ppm): 8.21-8.16 (m, 1H), 8.09-8.04 (m, 1H), 7.75-7.66 (m, 3H), 7.50 (td, J=7.5, 1.2 Hz, 1H), 7.38 (dd, J=14.1, 7.5 Hz, 2H), 4.28 (s, 2H).

Step 2) Synthesis of 11-bromo-5H-dibenzo[a,d][7]annulene-5,10-(11H)-dione

5H-Dibenzo[a,d][7] annulene-5,10(11H)-dione (50 mg, 0.23 mmol) was dissolved in carbon tetrachloride (2 mL). BPO (12 mg, 0.05 mmol) and NBS (45 mg, 0.25 mmol) were added.

The mixture was heated to 78° C. and stirred for 8 hours. The reaction mixture was cooled to rt, and to the mixture was added with saturated aqueous sodium thiosulfate solution (5 mL). The resulting mixture was extracted with dichloromethane (5 mL×3). The combined organic phases were washed with saturated brine (10 mL), dried over anhydrous sodium sulfate and filtered, then the filtrate was concentrated in vacuo, and the residue was purified by silica gel column chromatography (PE/EtOAc (v/v)=10/1) to give the title compound as a light yellow solid (50 mg, 74%).

$^1$H NMR (400 MHz, CDCl$_3$) δ (ppm): 8.25-8.19 (m, 1H), 8.17-8.12 (m, 1H), 7.81-7.78 (m, 1H), 7.76-7.74 (m, 2H), 7.53-7.47 (m, 3H), 5.61 (s, 1H).

Step 3) Synthesis of 8H-dibenzo[3,4:6,7]cyclohepta[1,2-d]oxazole-8-one

11-Bromo-5H-dibenzo[a,d][7]annulene-5,10-(11H)-dione (50 mg, 0.17 mmol) was dissolved in ethyl acetate (2 mL). Formamide (10 mg, 0.22 mmol) and silver trifluoromethanesulfonate (54 mg, 0.21 mmol) were added. The mixture was heated to 78° C. and stirred for 3 hours under protection of nitrogen. The mixture was cooled to rt and filtered through a celite pad. The filter cake was washed with ethyl acetate (5 mL), the filtrate was concentrated, and the residue was purified by silica gel column chromatography (PE/EtOAc (v/v)=10/1) to give the title compound as a yellow solid (25 mg, 61%).

MS (ESI, pos. ion) m/z: 248.2[M+H]$^+$;
$^1$H NMR (400 MHz, CDCl$_3$) δ (ppm): 8.47 (d, J=7.9 Hz, 1H), 8.26 (d, J=8.0 Hz, 1H), 8.23 (d, J=8.0 Hz, 1H), 8.12 (s, 1H), 8.08 (d, J=7.9 Hz, 1H), 7.76 (dd, J=14.9, 7.4 Hz, 2H), 7.62 (dd, J=14.9, 7.4 Hz, 2H).

Step 4) Synthesis of 8H-dibenzo[3,4:6,7]cyclohepta[1,2-d]oxazole-8-ol

8H-Dibenzo[3,4:6,7]cyclohepta[1,2-d]oxazole-8-one (200 mg, 0.81 mmol) was dissolved in THF (2 mL) and methanol (1 mL). The mixture was cooled to 0° C. and sodium borohydride (0.32 g, 8.30 mmol) was added in batches. The resulting mixture was reacted for 5 minutes at 0° C. and reacted at rt for 30 minutes. The reaction was stopped. To the reaction solution was added water (20 mL) and the resulting mixture was extracted with DCM (15 mL×3). The combined organic phases were washed with saturated saline solution (50 mL), dried over anhydrous sodium sulfate, filtered, and the filtrate was concentrated. The residue was purified by silica gel column chromatography (PE/EA (v/v)=20/1) to give the title compound as a white solid (140 mg, 69%).

MS (ESI, pos. ion) m/z: 250.1[M+H]$^+$

Step 5) Synthesis of 7-(benzyloxy)-12-(8H-dibenzo[3,4:6,7]cyclohepta[1,2-d]oxazol-8-yl)-3,4,12,12a-tetrahydro-1H-[1,4]oxazino[3,4-c]pyrido[2,1-f][1,2,4]triazin-6,8-dione 8H-Dibenzo[3,4:6,7]cyclohepta[1,2-d]oxazole-8-ol (138 mg, 0.55 mmol) and 7-(benzyloxy)-3,4,12,12a-tetrahydro-1H-[1,4]oxazino[3,4-c]pyrido[2,1-f][1,2,4]triazine-6-,8-dione (150 mg, 0.46 mmol) were added to a reaction flask, then 1-propylphosphoric anhydride (ethyl acetate solution) (wt 50%, 10 mL) was added. The resulting mixture was heated to 70° C. and reacted for 1 hour. The reaction solution was added into ice water (100 mL) and the resulting mixture was extracted with ethyl acetate (100 mL×3). The combined organic phases were washed with sodium bicarbonate aqueous solution (200 mL), dried over anhydrous sodium sulfate and filtered, then the filtrate was concentrated, and the residue was purified by silica gel column chromatography (DCM/Methanol (v/v)=20/1) to give the title compound as a light yellow solid (50 mg, 20%).

MS (ESI, pos. ion) m/z: 559.3[M+H]$^+$

Step 6) Synthesis of the mixture of (R)-12 ((S)-8H-dibenzo[3,4:6,7]cyclohepta[1,2-d]oxazole-8-yl)-7-hydroxy-3,4,12,12a-tetrahydro-1H-[1,4]oxazino[3,4-C]pyrido[2,1-f][1,2,4]triazine-6,8-dione and (S)-12 ((R)-8H-dibenzo[3,4:6,7]cyclohepta[1,2-d]oxazole-8-yl)-7-hydroxy-3,4,12,12a-tetrahydro-1H-[1,4]oxazino[3,4-C]pyrido[2,1-f][1,2,4]triazine-6,8-dione 7-(Benzyloxy)-12-(8H-dibenzo[3,4:6,7]cyclohepta[1,2-d]oxazol-8-yl)-3,4,12,12a-tetrahydro-1H-[1,4]oxazino[3,4-c]pyrido[2,1-f][1,2,4]triazin-6,8-dione (40 mg, 0.07 mmol) was dissolved in methanol (5 mL), Pd(OH)$_2$/C (20 mg, 0.14 mmol) was added, and air was replaced by hydrogen for three times. The reaction solution was reacted at rt for 4 hours. The reaction was stopped. The reaction solution was filtered and the filter cake was washed with methanol (5 mL), and the filtrate was concentrated. The residue was purified by LUNA preparative column (acetonitrile/0.1% trifluoroacetate aqueous solution (v/v)=31/69) to give the title compound as a light yellow solid (10 mg, 30%).

MS (ESI, pos. ion) m/z: 469.0[M+H]$^+$;
HRMS (ESI, pos. ion) m/z: 469.1509, (C$_{26}$H$_{21}$N$_4$O$_5$)[M+H]$^+$, theoretical value: 469.1512;
$^1$H NMR (400 MHz, DMSO-d$_6$) δ (ppm): 8.20 (d, J=7.7 Hz, 1H), 8.17 (s, 1H), 8.03 (d, J=7.7 Hz, 1H), 7.71-7.66 (m, 1H), 7.61 (s, 2H), 7.59-7.53 (m, 1H), 7.37-7.30 (m, 1H), 6.99 (d, J=7.4 Hz, 1H), 6.30 (d, J=7.6 Hz, 1H), 5.91 (d, J=7.6 Hz, 1H), 5.58 (s, 1H), 4.64 (d, J=13.2 Hz, 1H), 4.09 (d, J=7.1 Hz, 1H), 3.75 (d, J=12.3 Hz, 1H), 3.51 (dd, J=11.1, 2.3 Hz, 1H), 3.37 (t, J=11.2 Hz, 1H), 3.23 (t, J=10.5 Hz, 1H), 2.98-2.89 (m, 1H).

Example 26 (R)-12-((S)-6-fluoro-8H-dibenzo [3,4:6,7]cyclohept[1,2-b]thiophen-8-yl)-7-hydroxy-3,4,12,12a-tetrahydro-1H-[1,4]oxazino[3,4-c]pyrido [2,1-f][1,2,4]triazine-6,8-dione (26-1) and (R)-12-((R)-6-fluoro-8H-dibenzo [3,4:6,7]cyclohept[1,2-b] thiophen-8-yl)-7-hydroxy-3,4,12,12a-tetrahydro-1H-[1,4]oxazino[3,4-c]pyrido[2,1-f] [1,2,4]triazine-6,8-dione (26-2)

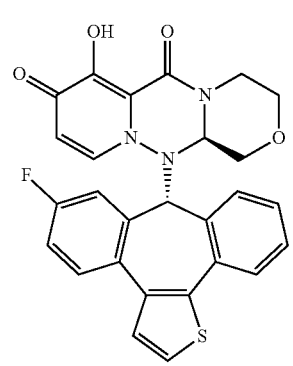

(26-1)

(26-2)

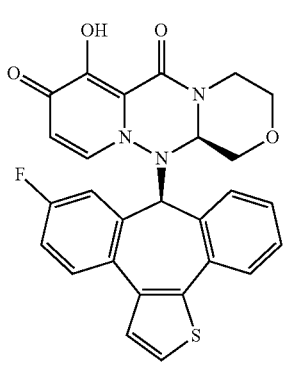

Step 1) Synthesis of 3-(4-fluorophenyl)thiophene p-Fluorobromobenzene (2.01 g, 11.50 mmol), thiophene-3-boronic acid (2.93 g, 22.90 mmol), palladium tetrakistriphenylphosphine (1.33 g, 1.15 mmol) and sodium carbonate (3.64 g, 34.30 mmol) were added into a reaction flask. DMF (40 mL) and water (4 mL) were then added. The resulting mixture was warmed to 85° C. under the protection of nitrogen and reacted for 2 hours. The reaction solution was cooled to rt, and to the mixture was added water (60 mL). The resulting mixture was stirred for 10 minutes at rt. The reaction mixture was extracted with ethyl acetate (50 mL×3). The combined organic phases were washed with saturated brine (100 mL×3), dried over anhydrous sodium sulfate and filtered, then the filtrate was concentrated in vacuo, and the residue was purified by silica gel column chromatography (PE) to give the title compound as a light yellow solid (1.61 g, 79%).

$^1$H NMR (400 MHz, CDCl$_3$) δ (ppm): 7.61-7.55 (m, 2H), 7.41 (d, J=3.0 Hz, 2H), 7.38-7.34 (m, 1H), 7.11 (t, J=8.7 Hz, 2H).

Step 2) Synthesis of 2-bromo-3-(4-fluorophenyl)thiophene 3-(4-Fluorophenyl)thiophene (1.61 g, 9.03 mmol) was dissolved in DMF (30 mL) and the mixture was cooled to −5° C. A solution of NBS (1.65 g, 9.09 mmol) in DMF (8 mL) was added slowly to the reaction solution above. The reaction solution was warmed to 0° C. and reacted overnight. After the reaction was completed, the reaction mixture was quenched with saturated sodium thiosulfate aqueous solution (60 mL) and the resulting mixture was stirred for 10 minutes at rt, then extracted with ethyl acetate (60 mL×3). The combined organic phases were washed with saturated brine (150 mL×3), dried over anhydrous sodium sulfate and filtered, then the filtrate was concentrated in vacuo, and the residue was purified by silica gel column chromatography (PE) to give the title compound as light yellow liquid (2.04 g, 88%).

$^1$H NMR (400 MHz, CDCl$_3$) δ (ppm): 7.58-7.51 (m, 2H), 7.34 (d, J=5.6 Hz, 1H), 7.15 (t, J=8.7 Hz, 2H), 7.03 (d, J=5.6 Hz, 1H).

Step 3) Synthesis of methyl 2-(3-(4-fluorophenyl)thiophen-2-yl)benzoate

2-Bromo-3-(4-fluorophenyl)thiophene (2.04 g, 7.93 mmol), (2-(methoxycarbonyl)phenyl)boronic acid (2.86 g, 15.90 mmol), ditriphenylphosphine palladium dichloride (0.57 g, 0.80 mmol) and potassium carbonate (3.36 g, 23.80 mmol) were added into a reaction flask. THF (40 mL) and water (4 mL) were then added. The resulting mixture was heated to 75° C. and reacted for 10 hours under the protection of nitrogen. The reaction was stopped, and the reaction solution was cooled to rt and filtered through a celite pad. The filter cake was washed with ethyl acetate (50 mL), the filtrate was concentrated in vacuo and the residue was purified by silica gel column chromatography (PE/EA (v/v)=10/1) to give the title compound as a light yellow solid (1.52 g, 61%).

MS (ESI, pos. ion) m/z: 313.0 [M+H]$^+$;

$^1$H NMR (400 MHz, CDCl$_3$) δ (ppm): 7.74 (d, J=7.7 Hz, 1H), 7.51-7.45 (m, 1H), 7.44-7.36 (m, 3H), 7.25-7.18 (m, 2H), 7.07-7.00 (m, 2H), 6.95 (t, J=7.5 Hz, 1H), 3.61 (s, 3H).

Step 4) Synthesis of 2-(3-(4-fluorophenyl)thiophen-2-yl)benzoic acid

Methyl 2-(3-(2-fluorophenyl)thiophen-2-yl)benzoate (1.52 g, 4.87 mmol) was dissolved in THF (15 mL) and methanol (8 mL), then a solution of sodium hydroxide (1.96 g, 76.80 mmol) in water (15 mL) was added into the reaction solution above, the resulting mixture was stirred overnight at 60° C. and then cooled to rt. Saturated saline (20 mL) was added and the reaction solution was adjusted to pH about 6 with 1 N diluted hydrochloric acid. The resulting mixture was partitioned and aqueous phase was extracted with ethyl acetate (20 mL×2). The combined organic phases were washed with saturated saline solution (50 mL), dried over anhydrous sodium sulfate and concentrated in vacuo. The residue was purified by silica gel column chromatography (PE/EtOAc (v/v)=3/1) to give the title compound as a white solid (1.43 g, 99%).

MS (ESI, neg. ion) m/z: 296.9[M−H]$^−$

Step 5) Synthesis of 6-fluoro-8H-dibenzo[3,4:6,7]cyclohepta[1,2-b]thiophene-8-one 2-(3-(4-Fluorophenyl)thiophen-2-yl)benzoic acid (100 mg, 0.34 mmol) was added into a reaction flask, PPA (2 mL) was added, and the mixture was warmed to 120° C. and stirred for 11 hours. The reaction was cooled to rt, the reaction solution was added to ice water (10 mL), stirred for 30 minutes, and the resulting mixture was extracted with DCM (5 mL×3). The combined organic phases were washed with saturated saline solution (10 mL), dried over anhydrous sodium sulfate, filtered and the filtrate was concentrated in vacuo. The residue was purified by silica gel column chromatography (PE/EA (v/v)=10/1) to give the title compound as a white solid (35 mg, 37%).

$^1$H NMR (400 MHz, CDCl$_3$) δ (ppm): 7.92 (dd, J=7.8, 1.0 Hz, 1H), 7.86-7.79 (m, 2H), 7.67-7.60 (m, 2H), 7.54-7.51 (m, 1H), 7.48 (s, 2H), 7.38-7.31 (m, 1H).

Step 6) Synthesis of 6-fluoro-8H-dibenzo[3,4:6,7]cyclohepta[1,2-b]thiophen-8-ol 6-Fluoro-8H-dibenzo[3,4:6,7]cyclohepta[1,2-b]thiophene-8-one (1.97 g, 7.03 mmol) was dissolved in THF (30 mL) and methanol (10 mL). The mixture was cooled to 0° C., and to the mixture was added sodium borohydride (1.36 g, 35.20 mmol). After addition, the resulting mixture was reacted at 0° C. for 5 minutes and reacted at rt for 30 minutes. After the reaction was completed, water (50 mL) was added. The resulting mixture was extracted with DCM (50 mL×3). The combined organic phases were washed with saturated saline solution (100 mL), dried over anhydrous sodium sulfate, filtered and the filtrate was concentrated in vacuo. The residue was purified by silica gel column chromatography (DCM) to give the title compound as a white solid (1.87 g, 94%).

$^1$H NMR (400 MHz, CDCl$_3$) δ (ppm): 7.84 (d, J=7.8 Hz, 1H), 7.60-7.52 (m, 2H), 7.52-7.45 (m, 2H), 7.42 (dd, J=11.1, 5.2 Hz, 2H), 7.32 (t, J=7.5 Hz, 1H), 7.01 (td, J=8.4, 2.6 Hz, 1H), 5.34 (s, 1H).

Step 7) Synthesis of (12aR)-7-(benzyloxy)-12-(6-fluoro-8H-dibenzo[3,4:6,7]cyclohepta[1,2-b]thiophen-8-yl)-3,4,12,12a-tetrahydro-1H-[1,4]oxazino[3,4-c]pyrido[2,1-f][1,2,4]triazine-6,8-dione 6-Fluoro-8H-dibenzo[3,4:6,7]cyclohepta[1,2-b]thiophen-8-ol (389 mg, 1.38 mmol) and (R)-7-(benzyloxy)-3,4,12,12a-tetrahydro-1H-[1,4]oxazino[3,4-c]pyrido[2, 1-f][1,2,4]triazine-6,8-dione (300 mg, 0.92 mmol) were added into a sealing tube, 1-propyl phosphate anhydride (ethyl acetate solution) (wt 50%, 10 mL) was added. The tube was sealed, and the resulting solution was reacted at 100° C. for 1.5 hours. The reaction solution was added to ice water (50 mL) and the resulting mixture was extracted with DCM (50 mL×3). The organic phases were washed with saturated sodium bicarbonate aqueous solution (100 mL), dried over anhydrous sodium sulfate, filtered and the filtrate was concentrated in vacuo. The residue was purified by silica gel column chromatography (DCM/methanol (v/v)=50/1) to give the title compound as a light yellow solid (145 mg, 27%).

MS (ESI, pos. ion) m/z: 593.2[M+H]$^+$

Step 8) Synthesis of (R)-12-((S)-6-fluoro-8H-dibenzo[3,4:6,7]cyclohept[1,2-b]thiophen-8-yl)-7-hydroxy-3,4,12,12a-tetrahydro-1H-[1,4]oxazino[3,4-c]pyrido[2,1-f][1,2,4]triazine-6,8-dione (26-1) and (R)-12-((R)-6-fluoro-8H-dibenzo[3,4:6,7]cyclohept[1,2-b]thiophen-8-yl)-7-hydroxy-3,4,12,12a-tetrahydro-1H-[1,4]oxazino[3,4-c]pyrido[2,1-f][1,2,4]triazine-6,8-dione (26-2)

(12aR)-7-(benzyloxy)-12-((6-fluoro-8H-dibenzo[3,4:6,7]cyclohepta[1,2-b]thiophene-8-yl)-3,4,12,12a-tetrahydro-1H-[1,4]oxazino[3,4-c]pyrido[2, 1-f][1,2,4]triazine-6,8-dione (0.14 g, 0.24 mmol) was dissolved in N,N'-dimethyl acetamide (3 mL), anhydrous lithium chloride (0.10 g, 2.30 mmol) was added, and the mixture was heated to 100° C. and reacted overnight. The reaction solution was cooled to rt and water (10 mL) was added. The reaction solution was extracted with ethyl acetate (10 mL×3). The combined organic phases were washed with saturated brine (20 mL×3), dried over anhydrous sodium sulfate and filtered, then the filtrate was concentrated, and the residue was purified by LUNA preparative column chromatography (acetonitrile/0.1% trifluoroacetate aqueous solution (v/v)=48/52) to give the title compound (26-1) as a light yellow solid (51 mg, 39%) and the title compound (26-2) as a light yellow solid (30 mg, 23%).

MS (ESI, pos. ion) m/z: 502.1[M+H]$^+$;
HRMS (ESI, pos. ion) m/z: 502.1255, (C$_{27}$H$_{21}$FN$_3$O$_4$S) [M+H]$^+$, theoretical value: 502.1237;

(R)-12-((S)-6-fluoro-8H-dibenzo[3,4:6,7]cyclohept[1,2-b]thiophen-8-yl)-7-hydroxy-3,4,12,12a-tetrahydro-1H-[1,4]oxazino[3,4-c]pyrido[2,1-f][1,2,4]triazine-6,8-dione (26-1)

$^1$H NMR (400 MHz, CDCl$_3$) δ (ppm) 7.74 (dd, J=8.5, 5.5 Hz, 1H), 7.68 (d, J=7.7 Hz, 1H), 7.46 (dt, J=8.7, 4.3 Hz, 2H), 7.41 (d, J=7.6 Hz, 1H), 7.28-7.18 (m, 3H), 7.00 (d, J=7.6 Hz, 1H), 6.33 (d, J=7.7 Hz, 1H), 5.66 (d, J=7.7 Hz, 1H), 5.38 (s, 1H), 4.62 (d, J=13.4 Hz, 1H), 4.20 (dd, J=9.9, 3.0 Hz, 1H), 3.74 (dd, J=11.9, 3.0 Hz, 1H), 3.39-3.29 (m, 2H), 3.20 (t, J=10.5 Hz, 1H), 3.03-2.90 (m, 1H).

(R)-12-((R)-6-fluoro-8H-dibenzo[3,4:6,7] cyclohept[1,2-b]thiophen-8-yl)-7-hydroxy-3,4,12,12a-tetrahydro-1H-[1,4]oxazino[3,4-c]pyrido[2,1-f][1,2,4]triazine-6,8-dione (26-2)

$^1$H NMR (400 MHz, CDCl$_3$) δ (ppm) 7.74 (d, J=7.6 Hz, 1H), 7.64 (dd, J=8.2, 5.4 Hz, 1H), 7.50 (dd, J=13.9, 7.1 Hz, 5H), 7.10 (t, J=7.0 Hz, 1H), 6.80 (d, J=7.4 Hz, 1H), 6.23 (d, J=7.1 Hz, 1H), 5.67 (d, J=6.2 Hz, 1H), 5.43 (s, 1H), 4.58 (d, J=13.1 Hz, 1H), 4.17-4.11 (m, 1H), 3.66 (d, J=9.9 Hz, 1H), 3.31 (d, J=10.3 Hz, 2H), 3.15 (t, J=10.4 Hz, 1H), 2.83 (t, J=11.8 Hz, 1H).

Example 27 methyl (((12aR)-12-((8R)-4-fluoro-8H-dibenzo [3,4:6,7] cyclohept[1,2-b]thiophen-8-yl)-6,8-dioxo-3,4,6,8,12,12a-hexahydro-1H-[1,4]oxazino [3,4-c]pyrido [2,1-f] [1,2,4]triazin-7-yl)oxy)methyl carbonate

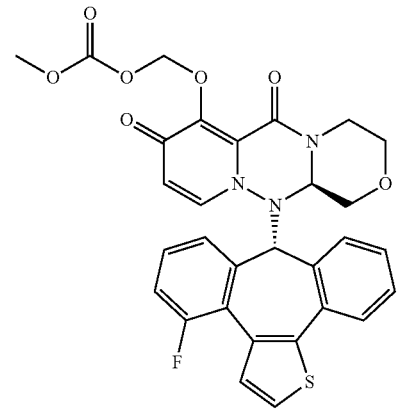 [SMILES: COC(=O)OCOc1c2n(ccc1=O)N([C@@H]1c3ccccc3-c3sccc3-c3c(F)cccc31)[C@@H]1COCCN1C2=O]

(12aR)-12-((8R)-4-fluoro-8H-dibenzo[3,4:6,7]cyclohept[1,2-b]thiophen-8-yl)-7-hydroxy-3,4,12,12a-tetrahydro-1H-[1,4]oxazino[3,4-c]pyrido[2,1-f][1,2,4]triazine-6,8-dione (300 mg, 0.60 mmol), potassium carbonate (165 mg, 1.18 mmol) and potassium iodide (99 mg, 0.60 mmol) was mixed in DMAc (3 mL), and the mixture was warmed to 60° C. and reacted overnight. After the reaction was completed, water (30 mL) was added, and the reaction mixture was extracted with ethyl acetate (20 mL×3). The combined organic phases were washed with saturated brine (25 mL), dried over Example 28 methyl (((R)-12-((S)-5-fluoro-8H-dibenzo [3,4:6,7] cyclohept[1,2-b] thiophen-8-yl)-6,8-dioxo 3,4,6,8,12,12a-hexahydro-1H-[1,4]oxazino [3,4-c]pyrido [2,1-f] [1,2, 4]triazin-7-yl)oxy)methyl carbonate

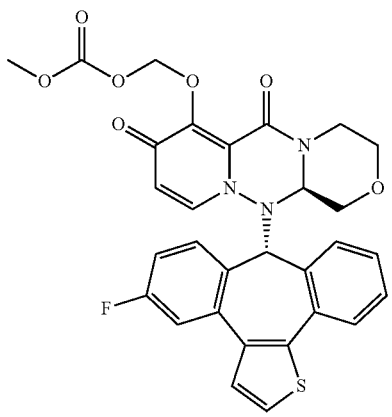 [SMILES: COC(=O)OCOc1c2n(ccc1=O)N([C@H]1c3ccc(F)cc3-c3ccsc3-c3ccccc31)[C@@H]1COCCN1C2=O]

(R)-12-((S)-5-fluoro-8H-dibenzo[3,4:6,7]cyclohept[1,2-b]thiophen-8-yl)-7-hydroxy-3,4,12,12a-tetrahydro-1H-[1,4]oxazino[3,4-c]pyrido[2,1-f][1,2,4]triazine-6,8-dione (273 mg, 0.54 mmol), potassium carbonate (150 mg, 1.10 mmol) and potassium iodide (90 mg, 0.54 mmol) were mixed in DMAc (3 mL), and the mixture was warmed to 60° C. and reacted overnight. After the reaction was completed, water (30 mL) was added, and the resulting mixture was extracted with ethyl acetate (20 mL×3). The combined organic phases were washed with saturated brine (25 mL), dried over anhydrous sodium sulfate and filtered, then the filtrate was concentrated in vacuo to give the title compound as an off-white solid (246 mg, 77%).

MS (ESI, pos. ion) m/z: 590.2[M+H]$^+$;

$^1$H NMR (400 MHz, CDCl$_3$) δ (ppm) 7.67 (d, J=7.1 Hz, 1H), 7.45 (dd, J=14.4, 9.0 Hz, 5H), 7.27 (d, J=10.3 Hz, 1H), 7.21-7.07 (m, 2H), 6.37 (d, J=7.4 Hz, 1H), 5.89 (s, 2H), 5.77 (d, J=7.5 Hz, 1H), 5.48 (s, 1H), 4.57 (d, J=13.3 Hz, 1H), 4.10 (d, J=8.6 Hz, 1H), 3.87 (s, 3H), 3.68 (d, J=10.7 Hz, 1H), 3.30 (d, J=9.7 Hz, 2H), 3.15 (t, J=10.1 Hz, 1H), 2.91-2.78 (m, 1H).

anhydrous sodium sulfate and filtered, then the filtrate was concentrated in vacuo to give the title compound as an off-white solid (298 mg, 84.49%).

MS (ESI, pos. ion) m/z: 590.1[M+H]$^+$;

$^1$H NMR (400 MHz, CDCl$_3$) δ (ppm) 7.68 (d, J=7.6 Hz, 1H), 7.62 (t, J=5.5 Hz, 1H), 7.49-7.36 (m, 3H), 7.25 (dd, J=6.8, 4.6 Hz, 3H), 7.10 (d, J=7.5 Hz, 1H), 6.39 (d, J=7.7 Hz, 1H), 5.88 (q, J=6.5 Hz, 2H), 5.78 (d, J=7.7 Hz, 1H), 5.49 (s, 1H), 4.56 (d, J=12.0 Hz, 1H), 4.16 (dd, J=9.9, 2.9 Hz, 1H), 3.86 (s, 3H), 3.68 (dd, J=11.7, 2.8 Hz, 1H), 3.30 (dt, J=10.7, 6.3 Hz, 2H), 3.14 (t, J=10.4 Hz, 1H), 2.90-2.78 (m, 1H).

Example 29 phenyl 4-((((12aR)-12-(5-fluoro-8H-dibenzo [3,4:6,7] cyclohepta[1,2-b]thiophen-8-yl)-6,8-dioxo-3,4,6,8,12,12a-hexahydro-1H-[1,4]oxazino [3,4-c] pyrido [2,1-f] [1,2,4]triazin-7-yl)oxy)methyl) acetate

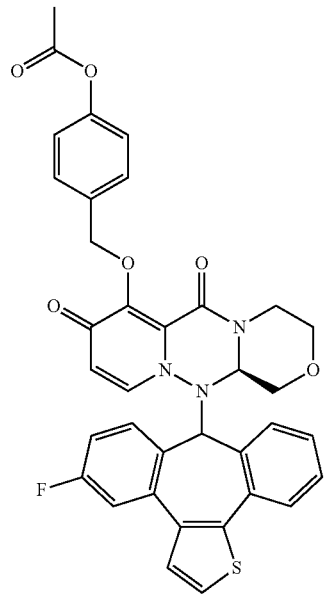 [SMILES: CC(=O)Oc1ccc(COc2c3n(ccc2=O)N(C2c4ccc(F)cc4-c4ccsc4-c4ccccc42)[C@@H]2COCCN2C3=O)cc1]

(12aR)-12-(5-fluoro-8H-dibenzo[3,4:6,7]cyclohepta[1,2-b]thiophen-8-yl)-7-hydroxy-3,4,12,12a-tetrahydro-1H-[1,4]oxazino[3,4-c]pyrido[2,1-f][1,2,4]triazin-6, 8-dione (50 mg, 0.09970 mmol), DMF (3 mL), 4-(chloromethyl)phenyl acetate (55 mg, 0.30 mmol), K$_2$CO$_3$ (41 mg, 0.30 mmol) and KI (50 mg, 0.30 mmol) were added into a three-necked flask, and the mixture was heated to 65° C. and reacted for 8 hours. At the end of the reaction, the reaction mixture was cooled to rt, and to the mixture was added EtOAc (15 mL) and water (20 mL), and then the resulting mixture was partitioned. The aqueous phase was extracted with EtOAc (15 mL×3). The combined organic phases were washed with saturated brine (15 mL×3), dried over anhydrous sodium sulfate and filtered, then the filtrate was concentrated in vacuo, and the residue was purified by silica gel column chromatography (EA) to give the title compound as a white solid (34 mg, 54%).

MS (ESI, pos. ion) m/z: 650.4 [M+H]$^+$

1H NMR (400 MHz, CDCl$_3$) δ (ppm) 777-7.61 (m, 3H), 7.54-7.34 (m, 5H), 7.33-6.78 (m, 4H), 6.75-6.65 (m, 1H), 6.30-6.19 (m, 1H), 5.74-5.67 (m, 1H), 5.63-5.56 (m, 1H), 5.41-5.38 (m, 1H), 5.34 (s, 1H), 4.58 (d, J=13.4 Hz, 1H), 4.19-3.98 (m, 1H), 3.64 (d, J=11.8 Hz, 1H), 3.27-3.16 (m, 2H), 2.99 (t, J=10.4 Hz, 1H), 2.88-2.70 (m, 1H), 2.27 (s, 3H).

Example 30 (12aR)-12-(5-fluoro-8H-dibenzo [3,4:6, 7]cyclohepta [1,2-b]thiophen-8-yl)-7-((3-oxo-1,3-dihydroisobenzofuran-1-yl)oxy)-3,4,12,12a-tetrahydro-1H-[1,4]oxazino[3,4-c]pyrido[2,1-f] [1,2,4]triazine-6,8-dione

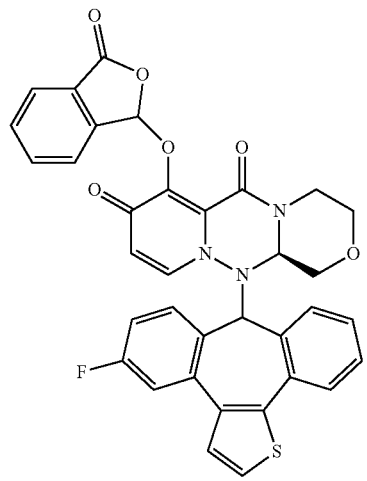 [SMILES: O=C1OC(Oc2c3n(ccc2=O)N(C2c4ccc(F)cc4-c4ccsc4-c4ccccc42)[C@@H]2COCCN2C3=O)c2ccccc21]

(12aR)-12-(5-fluoro-8H-dibenzo[3,4:6,7]cyclohepta[1,2-b]thiophen-8-yl)-7-hydroxy 3,4,12, 12a-tetrahydro-1H-[1,4]oxazino[3,4-c]pyrido[2,1-f][1,2,4]triazin-6,8-dione (50 mg, 0.10 mmol), DMF (3 mL), 3-chloro-3H-isobenzofuran-1-one (50 mg, 0.30 mmol), K₂CO₃ (41 mg, 0.30 mmol) and KI (50 mg, 0.30 mmol) were added into a 25 mL three-necked flask, and the mixture was heated to 65° C. and stirred for 3 hours. After the reaction was completed, the reaction solution was cooled to rt. To the reaction mixture was added EtOAc (15 mL) and water (20 mL), and the resulting mixture was partitioned. The aqueous phase was extracted with EtOAc (15 mL×3). The combined organic phases were washed with saturated brine (15 mL×3), dried over anhydrous sodium sulfate and filtered, then the filtrate was concentrated in vacuo, and the residue was purified by silica gel column chromatography (EA) to give the title compound as a white solid (25 mg, 40%).

MS (ESI, pos. ion) m/z: 634.5 [M+H]⁺

¹H NMR (400 MHz, CDCl₃) δ (ppm) 7.98 (t, J=7.8 Hz, 2H), 7.77-7.63 (m, 3H), 7.56-7.40 (m, 5H), 7.36-7.27 (m, 2H), 7.19-6.97 (m, 1H), 6.48-6.37 (m, 1H), 5.89-5.81 (m, 1H), 5.64 (s, 1H), 4.53 (d, J=13.6 Hz, 1H), 4.18-4.11 (m, 1H), 3.61-3.58 (m, 1H), 3.33 (td, J=11.0, 2.9 Hz, 1H), 3.19 (t, J=11.8 Hz, 1H), 3.11 (t, J=10.4 Hz, 1H), 2.88 (s, 1H), 2.81 (t, J=11.7 Hz, 1H).

Example 31 (12aR)-12-(5-fluoro-8H-dibenzo [3,4:6, 7]cyclohepta[1,2-b]thiophen-8-yl)-6,8-dioxo-3,4,6,8, 12,12a-hexahydro-1H-[1,4]oxazino [3,4-c]pyrido [2,1-f] [1,2,4]triazine-7-yl acetate

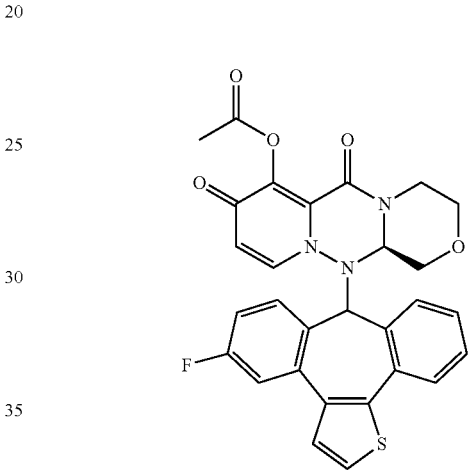

(12aR)-12-(5-fluoro-8H-dibenzo[3,4:6,7]cyclohepta[1,2-b]thiophen-8-yl)-7-hydroxy-3,4,1, 2, 12a-tetrahydro-1H-[1, 4]oxazino[3,4-c]pyrido[2,1-f][1,2,4]triazin-6,8-dione (50 mg, 0.09970 mmol), DCM (4 mL), acetic anhydride (28 mL, 0.30 mmol) and triethylamine (41 mL, 0.30 mmol) were added into a 25 mL three-necked flask, and the mixture was stirred at rt for 26 hours. At the end of the reaction, the reaction mixture was dried under reduced pressure by rotary evaporator. The residue was purified by silica gel column chromatography (EA) to give the title compound as a white solid (35 mg, 65%).

MS (ESI, pos. ion) m/z: 544.4 [M+H]⁺

¹H NMR (400 MHz, CDCl₃) δ (ppm) 7.75-7.65 (m, 1H), 7.52-7.37 (m, 5H), 7.35-7.20 (m, 1H), 7.18-6.91 (m, 2H), 6.41-6.31 (m, 1H), 5.85-5.77 (m, 1H), 5.50 (s, 1H), 4.56 (d, J=13.3 Hz, 1H), 4.25-4.10 (m, 1H), 3.68 (d, J=11.9 Hz, 1H), 3.47-3.24 (m, 2H), 3.18 (t, J=10.4 Hz, 1H), 2.84 (t, J=12.6 Hz, 1H), 2.45 (s, 3H).

Example 32 (12aR)-12-(5-fluoro-8H-dibenzo [3,4:6,7] cycloheptyl [1,2-b]thiophen-8-yl)-7-((5-methyl-)2-oxo-1,3-dioxol-4-yl)methoxy)-3,4,12,12a-tetrahydro-H-[1,4]oxazino [3,4-c]pyrido[2,1-f] [1,2,4] triazine-6,8-dione

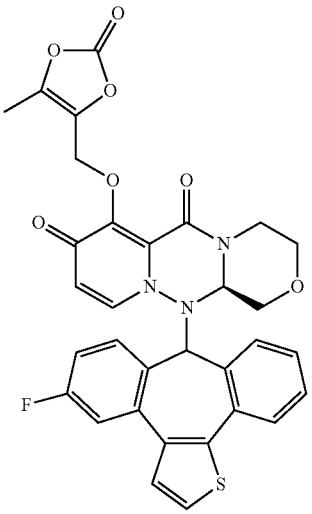 [SMILES: Cc1oc(=O)oc1COc1c2n(ccc1=O)N(C1c3ccc(F)cc3-c3ccsc3-c3ccccc31)[C@@H]1COCCN1C2=O]

(12aR)-12-(5-fluoro-8H-dibenzo[3,4:6,7]cyclohepta[1,2-b]thiophen-8-yl)-7-hydroxy-3,4,12,12a-tetrahydro-1H-[1,4]oxazino[3,4-c]pyrido[2,1-f][1,2,4]triazin-6,8-dione (50 mg, 0.09970 mmol), DMF (3 mL), 4-(chloromethyl)-5-methyl-1,3-dioxol-2-one (44 mg, 0.30 mmol), K₂CO₃ (41 mg, 0.30 mmol) and KI (50 mg, 0.30 mmol) were added into a 25 mL three-neck flask, and the mixture was heated to 65° C. and stirred for 23 hours. After the reaction was completed, the reaction solution was cooled to rt. To the reaction mixture was added EtOAc (15 mL) and water (20 mL), and the resulting mixture was partitioned. The aqueous phase was extracted with EtOAc (15 mL×3). The combined organic phases were washed with saturated brine (15 mL×3), dried over anhydrous sodium sulfate and filtered, then the filtrate was concentrated in vacuo, and the residue was purified by silica gel column chromatography (EA) to give the title compound as a white solid (44 mg, 52%).

MS (ESI, pos. ion) m/z: 614.0 [M+H]⁺

¹H NMR (400 MHz, CDCl₃) δ (ppm) 7.73-7.65 (m, 1H), 7.54-7.38 (m, 5H), 7.36-7.23 (m, 1H), 7.16-6.91 (m, 2H), 6.40-6.29 (m, 1H), 5.81-5.74 (m, 1H), 5.49 (d, J=2.5 Hz, 1H), 5.25-5.13 (m, 2H), 4.58 (d, J=13.5 Hz, 1H), 4.09 (d, J=3.2 Hz, 1H), 3.74-3.58 (m, 1H), 3.28 (dd, J=16.4, 6.8 Hz, 2H), 3.08 (t, J=10.4 Hz, 1H), 2.85-2.79 (m, 1H), 2.20 (s, 3H).

Example 33 (12aR)-12-(5-fluoro-8H-dibenzo [3,4:6,7] cyclohept[1,2-b]thiophen-8-yl)-6,8-dioxo-3,4,6,8,12,12a-hexahydro-1H-[1,4]oxazino [3,4-c]pyrido[2,1-f] [1,2,4]triazine-7-yl-methyl carbonate

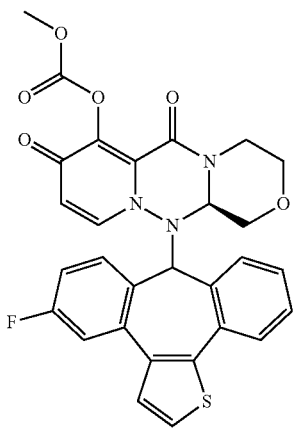 [SMILES: COC(=O)Oc1c2n(ccc1=O)N(C1c3ccc(F)cc3-c3ccsc3-c3ccccc31)[C@@H]1COCCN1C2=O]

(12aR)-12-(5-Fluoro-8H-dibenzo[3,4:6,7]cyclohepta[1,2-b]thiophen-8-yl)-7-hydroxy-3,4,12,12a-tetrahydro-1H-[1,4]oxazino[3,4-c]pyrido[2,1-f][1,2,4]triazin-6,8-dione (50 mg, 0.09970 mmol), DCM (3 mL), methyl chloroformate (19 mg, 0.20 mmol) and triethylamine (41 mg, 0.40 mmol) were added into a 25 mL three-neck flask, and the mixture was stirred at rt for 24 hours. At the end of the reaction, the reaction mixture was dried under reduced pressure by rotary evaporator. The residue was purified by silica gel column chromatography (EA) to give the title compound as a white solid (25 mg, 45%).

MS (ESI, pos. ion) m/z: 560.4 [M+H]⁺

¹H NMR (400 MHz, CDCl₃) δ (ppm) 7.75-7.65 (m, 1H), 7.54-7.38 (m, 5H), 7.37-7.25 (m, 1H), 7.16-6.92 (m, 2H), 6.42-6.32 (m, 1H), 5.88-5.80 (m, 1H), 5.51 (d, J=2.0 Hz, 1H), 4.58 (d, J=13.5 Hz, 1H), 4.18-4.14 (m, 1H), 3.99 (s, 3H), 3.83-3.61 (m, 1H), 3.47-3.22 (m, 2H), 3.18 (t, J=10.4 Hz, 1H), 2.93-2.79 (m, 1H).

Example 34 (12aR)-12-(5-fluoro-8H-dibenzo [3,4:6, 7] cyclohept[1,2-b]thiophen-8-yl)-7-(pyridin-4-yl-methoxy)-3,4,12,12a-tetrahydro-1H-[1,4] oxazino [3,4-c]pyrido [2,1-f] [1,2,4]triazine-6,8-dione

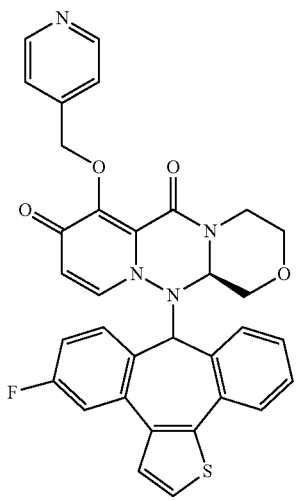 [SMILES: O=C1c2c(OCc3ccncc3)c(=O)ccn2N(C2c3ccc(F)cc3-c3ccsc3-c3ccccc32)[C@@H]2COCCN12]

(12aR)-12-(5-Fluoro-8H-dibenzo[3,4:6,7]cyclohepta[1,2-b]thiophen-8-yl)-7-hydroxy-3,4,12,12a-tetrahydro-1H-[1,4]oxazino[3,4-c]pyrido[2, 1-f][1,2,4]triazin-6,8-dione (50 mg, 0.09970 mmol), DCM (3 mL), triphenylphosphine (78 mg, 0.30 mmol), DIAD (37 mg, 0.20 mmol) and 4-pyridinemethanol (21 mg, 0.20 mmol) were added into a 25 mL three-neck flask, and the mixture was stirred at rt for 18 hours. At the end of the reaction, the reaction mixture was dried under reduced pressure by rotary evaporator. The residue was purified by silica gel column chromatography (ethyl acetate/methanol (v/v)=20/1) to give the title compound as a white solid (16 mg, 27%).

MS (ESI, pos. ion) m/z: 593.2 [M+H]$^+$ $^1$H NMR (400 MHz, CDCl$_3$) δ (ppm) 8.64-8.62 (m, 2H), 7.74-7.64 (m, 1H), 7.60-7.38 (m, 6H), 7.35-6.82 (m, 4H), 6.35-6.26 (m, 1H), 5.78-5.70 (m, 1H), 5.62-5.58 (m, 1H), 5.43 (s, 1H), 5.36-5.26 (m, 1H), 4.62 (d, J=13.5 Hz, 1H), 4.10 (d, J=8.9 Hz, 1H), 3.69-3.65 (m, 1H), 3.37-3.17 (m, 2H), 3.08 (t, J=10.4 Hz, 1H), 2.86-2.80 (m, 1H).

Example 35 (12aR)-12-(5-fluoro-8H-dibenzo [3,4:6, 7] cyclohept[1,2-b]thiophen-8-yl)-6,8-dioxo-3,4,6,8, 12,12a-hexahydro-1H-[1,4]oxazine [3,4-c]pyrido[2, 1-f] [1,2,4]triazine-7-yldimethylcarbamate

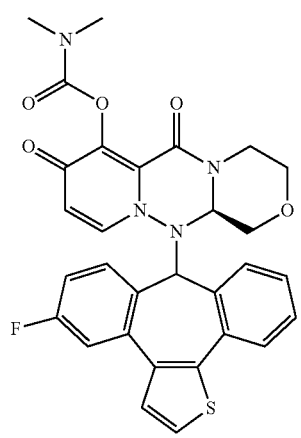 [SMILES: CN(C)C(=O)Oc1c2n(ccc1=O)N(C1c3ccc(F)cc3-c3ccsc3-c3ccccc31)[C@@H]1COCCN1C2=O]

(12aR)-12-(5-Fluoro-8H-dibenzo[3,4:6,7]cyclohepta[1,2-b]thiophen-8-yl)-7-hydroxy 3,4,12, 12a-tetrahydro-1H-[1,4]oxazino[3,4-c]pyrido[2,1-f][1,2,4]triazin-6, 8-dione (50 mg, 0.09970 mmol), pyridine (3 mL), and dimethylcarbamoyl chloride hydrochloride (31 mg, 0.30 mmol) were added into a 25 mL three-necked flask, and the mixture was stirred at 85° C. for 27 hours. At the end of the reaction, the reaction mixture was dried under reduced pressure. The residue was purified by silica gel column chromatography (ethyl acetate/methanol (v/v)=20/1) to give the title compound as a white solid (15 mg, 26%).

MS (ESI, pos. ion) m/z: 573.1[M+H]$^+$ $^1$H NMR (600 MHz, CDCl$_3$) δ (ppm) 7.73-0.63 (m, 1H), 749-7.35 (m, 5H), 7.34-6.94 (m, 3H), 6.39-6.29 (m, 1H), 5.86-5.72 (m, 1H), 5.59-5.48 (m, 1H), 4.60-4.52 (m, 1H), 4.15-4.10 (m, 1H), 3.68-3.61 (m, 1H), 3.36-3.28 (m, 2H), 3.26-3.23 (m, 4H), 3.11 (s, 2H), 2.98 (s, 1H), 2.83-2.79 (m, 1H).

Example 36 The mixture of (12aR)-12-((8R)-4-fluoro-8H-dibenzo [3,4:6,7]cyclohepta[1,2-b]thiophen-8-yl)-7-hydroxy-3,4,12,12a-tetrahydro-1H-[1,4]oxazino [3,4-c] pyrido [2,1-f] [1,2,4]triazine-6,8-dione and (12aR)-12-((8S)-4-fluoro-8H-dibenzo [3,4:6,7] cyclohept[1,2-b]thiophen-8-yl)-7-hydroxy-3,4,12,12a-tetrahydro-1H-[1,4]oxazino [3,4-c] pyrido [2,1-f] [1,2,4]triazine-6,8-dione Mixture:

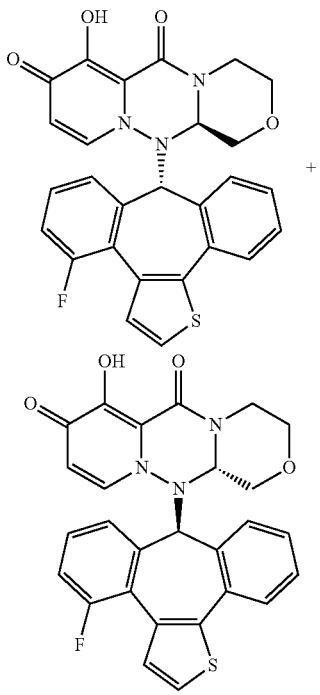

Step 1) Synthesis of 7-(benzyloxy)-12-(4-fluoro-8H-dibenzo[3,4:6,7]cyclohept[1,2-b]thiophen-8-yl)-3,4,12,12a-tetrahydro-1H-[1,4]oxazino[3,4-c]pyrido [2,1-f][1,2,4]triazin-6,8-dione 4-Fluoro-8H-dibenzo[3,4:6,7]cyclohepta[1,2-b]thiophene-8-ol (17 mg, 0.06 mmol) and 7-(benzyloxy)-3,4,12,12a-tetrahydro-1H-[1,4]oxazino[3,4-c]pyrido[2,1-f][1,2, 4]triazine-6, 8-dione (20 mg, 0.06 mmol) a solution of 1-propylphosphoric anhydride (wt 50%, 1 mL) in ethyl acetate were mixed in the sealing tube, which was reacted at 100° C. in an oil bath for 1.5 hours. After the reaction was completed, the reaction solution was added into ice water (10 mL) and extracted with ethyl acetate (10 mL×3). The combined organic phases were washed with sodium bicarbonate aqueous solution (20 mL), dried over anhydrous sodium sulfate and filtered, then the filtrate was concentrated in vacuo, and the residue was purified by silica gel column chromatography (DCM/Methanol (v/v)=20/1) to give the title compound as a light yellow solid (11 mg, 34%).

MS (ESI, pos. ion) m/z: 592.3[M+H]+

$^1$H NMR (400 MHz, CDCl$_3$) δ (ppm): 7.75-7.60 (m, 4H), 7.53-7.30 (m, 7H), 7.27-7.03 (m, 2H), 6.56 (dd, J=54.0, 7.3 Hz, 1H), 6.31 (dd, J=7.7, 4.6 Hz, 1H), 5.76 (dd, J=29.8, 7.5 Hz, 1H), 5.61 (dd, J=10.8, 2.8 Hz, 1H), 5.45 (dd, J=10.9, 1.9 Hz, 1H), 5.36 (d, J=4.5 Hz, 1H), 4.60 (dd, J=13.6, 3.3 Hz, 1H), 4.06 (ddd, J=27.9, 10.0, 3.0 Hz, 1H), 3.69-3.60 (m, 1H), 3.26-3.13 (m, 2H), 2.97 (td, J=10.4, 5.1 Hz, 1H), 2.78 (td, J=12.8, 3.2 Hz, 1H).

Step 2) Synthesis of (12aR)-12-((8R)-4-fluoro-8H-dibenzo[3,4:6,7]cyclohepta[1,2-b]thiophen-8-yl)-7-hydroxy-3,4,12,12a-tetrahydro-1H-[1,4]oxazino[3,4-c]pyrido[2,1-f][1,2,4]triazine-6,8-dione and (12aR)-12-((8S)-4-fluoro-8H-dibenzo[3,4:6,7]cyclohepta[1,2-b]thiophen-8-yl)-7-hydroxy-3,4,12,12a-tetrahydro-1H-[1,4]oxazino[3,4-c]pyrido[2,1-f][1,2,4]triazine-6, 8-dione 7-(Benzyloxy)-12-(4-fluoro-8H-dibenzo[3,4:6,7]cyclohepta[1,2-b]thiophen-8-yl)-3,4,12,12a-tetrahydro-1H-[1,4]oxazino[3,4-c]pyrido[2,1-f][1,2,4]triazin-6,8-dione (0.16 g, 0.27 mmol) was dissolved in N,N-dimethylacetamide (3 mL), then anhydrous lithium chloride (0.12 g, 2.80 mmol) was added, and the mixture was heated to 100° C. and reacted overnight. The reaction was cooled to rt and water (10 mL) was added. The reaction solution was extracted with ethyl acetate (10 mL×3). The combined organic phases were washed with saturated brine (20 mL×3), dried over anhydrous sodium sulfate and filtered, then the filtrate was concentrated, and the residue was purified by LUNA preparative column chromatography (acetonitrile/0.1% trifluoroacetate aqueous solution (v/v)=42/58) to give the title compound as a light yellow solid (53 mg, 39%).

MS (ESI, pos. ion) m/z: 502.1[M+H]+;

HRMS (ESI, pos. ion) m/z: 502.1253, (C$_{27}$H$_{21}$FN$_3$O$_4$S) [M+H]+, theoretical value: 502.1237;

$^1$H NMR (400 MHz, DMSO-d$_6$) δ (ppm): 8.81 (s, 1H), 7.73 (d, J=7.7 Hz, 1H), 7.65 (t, J=5.5 Hz, 1H), 7.54-7.41 (m, 3H), 7.34-7.24 (m, 3H), 6.96 (d, J=7.5 Hz, 1H), 6.51 (d, J=7.4 Hz, 1H), 6.17 (d, J=7.4 Hz, 1H), 5.46 (s, 1H), 4.60 (d, J=12.5 Hz, 1H), 4.33 (dd, J=9.9, 3.0 Hz, 1H), 3.76 (dd, J=11.9, 2.9 Hz, 1H), 3.41-3.28 (m, 2H), 3.19 (t, J=10.6 Hz, 1H), 2.99-2.91 (m, 1H).

Example 37 The mixture of (R)-12-((S)-5-fluoro-8H-dibenzo[3,4:6,7]cyclohepta[1,2-b]thiophen-8-yl)-7-hydroxy-3,4,12,12a-tetrahydro-1H-[1,4] oxazino[3,4-c]pyrido[2,1-f][1,2,4]triazine-6,8-dione and (S)-12-((R)-5-fluoro-8H-dibenzo [3,4:6,7]cyclohepta[1,2-b]thiophen-8-yl)-7-hydroxy-3,4,12,12a-tetrahydro-1H-[1,4]oxazino [3,4-c]pyrido [2,1-f][1,2,4]triazine-6,8-dione Mixture:

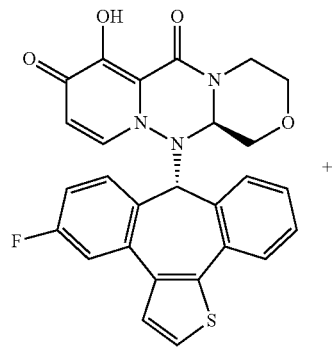

-continued

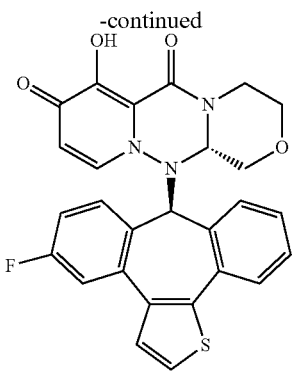

Step 1) Synthesis of 7-(benzyloxy)-12-(5-fluoro-8H-dibenzo[3,4:6,7]cyclohepta[1,2-b]thiophen-8-yl)-3,4,12,12a-tetrahydro-1H-[1,4]oxazino[3,4-c]pyrido[2,1-f][1,2,4]triazin-6,8-dione 5-Fluoro-8H-dibenzo[3,4:6,7]cyclohepta[1,2-b]thiophene-8-ol (20 mg, 0.09 mmol) and 7-(benzyloxy)-3,4,12,12a-tetrahydro-1H-[1,4]oxazino[3,4-c]pyrido[2,1-f][1,2, 4]triazine-6, 8-dione (20 mg, 0.06 mmol) were added into a sealing tube, then 1-propyl phosphate anhydride (ethyl acetate solution) (wt 50%, 1 mL) was added. The tube was sealed, and the resulting solution was reacted at 100° C. for 1.5 hours. After the reaction was completed, the reaction solution was added to ice water (10 mL), and resulting mixture was extracted with ethyl acetate (10 mL×3). The combined organic phases were washed with saturated sodium bicarbonate aqueous solution (20 mL), dried over anhydrous sodium sulfate, filtered and the filtrate was concentrated in vacuo. The residue was purified by silica gel column chromatography (dichloromethane/methanol (v/v)=20/1) to give the title compound as a light yellow solid (10 mg, 28%).

MS (ESI, pos. ion) m/z: 592.3[M+H]$^+$ $^1$H NMR (400 MHz, CDCl$_3$) δ (ppm): 7.74-7.55 (m, 4H), 7.53-7.30 (m, 9H), 7.16-7.10 (m, 1H), 6.67-6.56 (m, 1H), 6.25 (dd, J=35.7, 7.7 Hz, 1H), 5.74 (dd, J=19.2, 7.7 Hz, 1H), 5.67-5.58 (m, 1H), 5.45 (dd, J=10.9, 3.8 Hz, 1H), 5.34 (d, J=2.5 Hz, 1H), 4.61 (d, J=13.4 Hz, 1H), 4.04 (d, J=9.1 Hz, 1H), 3.65 (d, J=11.7 Hz, 1H), 3.30-3.12 (m, 2H), 2.98 (td, J=10.4, 2.5 Hz, 1H), 2.85-2.74 (m, 1H).

Step 2) Synthesis of (R)-12-((S)-5-fluoro-8H-dibenzo[3,4:6,7]cyclohepta[1,2-b]thiophen-8-yl)-7-hydroxy-3,4,12,12a-tetrahydro-1H-[1,4]oxazino[3,4-c]pyrido[2,1-f][1,2,4]triazine-6,8-dione and (S)-12-((R)-5-fluoro-8H-dibenzo[3,4:6,7]cyclohepta[1,2-b]thiophen-8-yl)-7-hydroxy-3,4,12,12a-tetrahydro-1H-[1,4]oxazino[3,4-c]pyrido[2,1-f][1,2,4]triazine-6,8-dione 7-(Benzyloxy)-12-(5-fluoro-8H-dibenzo[3,4:6,7]cyclohepta[1,2-b]thiophen-8-yl)-3,4,12,12a-tetrahydro-1H-[1,4]oxazino[3,4-c]pyrido[2,1-f][1,2,4]triazine-6,8-dione (0.13 g, 0.22 mmol) was dissolved in N,N-dimethyl acetamide (3 mL), then anhydrous lithium chloride (95 mg, 2.22 mmol) was added, and the mixture was warmed to 100° C. and reacted overnight. The reaction was cooled to rt and water (10 mL) was added. The resulting mixture was extracted with ethyl acetate (10 mL×3). The combined organic phases were washed with saturated brine (20 mL×3), dried over anhydrous sodium sulfate and filtered, then the filtrate was concentrated, and the residue was purified by LUNA preparative column chromatography (acetonitrile/0.1% trifluoroacetate aqueous solution (v/v)=43/57) to give the title compound as a light yellow solid (10 mg, 9%).

MS (ESI, pos. ion) m/z: 501.9[M+H]$^+$;

HRMS (ESI, pos. ion) m/z: 502.1251, (C$_{27}$H$_{21}$FN$_3$O$_4$S) [M+H]$^+$, theoretical value: 502.1237;

$^1$H NMR (400 MHz, DMSO-d$_6$) δ (ppm): 7.70 (d, J=7.7 Hz, 1H), 7.53-7.41 (m, 5H), 7.25 (d, J=7.4 Hz, 1H), 7.17 (td, J=8.1, 2.2 Hz, 1H), 6.98 (d, J=7.5 Hz, 1H), 6.38 (d, J=7.5 Hz, 1H), 5.86 (d, J=7.5 Hz, 1H), 5.44 (s, 1H), 4.61 (d, J=13.6 Hz, 1H), 4.21 (dd, J=9.9, 2.8 Hz, 1H), 3.74 (d, J=9.2 Hz, 1H), 3.35 (dd, J=12.6, 10.2 Hz, 2H), 3.19 (t, J=10.5 Hz, 1H), 2.92 (t, J=11.1 Hz, 1H).

Example 38 12-(8H-Dibenzo [3,4:6,7]cyclohepta[1,2-d]isoxazol-8-yl)-7-hydroxy-3,4,12,12a-tetrahydro-1H-[1,4]oxazino[3,4-c]pyrido[2,1-f] [1,2,4]triazin-6,8-dione

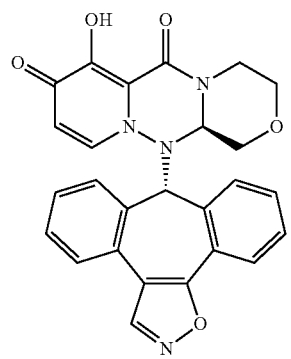 [SMILES: O=C1c2c(O)c(=O)ccn2N([C@H]2c3ccccc3-c3cnoc3-c3ccccc32)[C@@H]2COCCN12]

Step 1) Synthesis of 11-((Dimethylamino)methylene)-5H-dibenzo[a,d] [7] annulene-5,10-(11H)-dione 5H-Dibenzo[a,d][7] annulene-5,10(11H)-dione (300 mg, 1.35 mmol) was added to a sealing tube, and DMF-DMA (10 mL) was added. The tube was sealed and the mixture was warmed to 110° C. and reacted for 5 hours. The reaction was stopped, to the reaction mixture was added water (30 mL), and the resulting mixture was extracted with ethyl acetate (30 mL×3). The combined organic phases were washed with saturated brine (100 mL×3), dried over anhydrous sodium sulfate and filtered, then the filtrate was concentrated in vacuo, and the residue was purified by silica gel column chromatography (PE/EA (v/v)=8/1) to give the title compound as a light yellow solid (0.18 g, 48%).

MS (ESI, pos. ion) m/z: 278.1[M+H]$^+$;

$^1$H NMR (400 MHz, CDCl$_3$) δ (ppm): 8.22-8.18 (m, 2H), 7.60 (t, J=6.6 Hz, 2H), 7.57-7.53 (m, 1H), 7.48 (d, J=7.0 Hz, 1H), 7.42-7.38 (m, 1H), 7.22 (t, J=7.5 Hz, 1H), 7.06 (d, J=7.7 Hz, 1H), 2.87 (s, 6H).

Step 2) Synthesis of 8H-dibenzo[3,4:6,7]cyclohepta [1,2-d]isoxazole-8-one 11-((Dimethylamino)methylene)-5H-dibenzo[a,d] [7] annulene-5,10-(11H)-dione (30 mg, 0.11 mmol) was dissolved in ethanol (2 mL), hydroxylamine hydrochloride (16 mg, 0.23 mmol) was added, and the resulting mixture was heated to 78° C. and reacted for 3 hours. The reaction mixture was concentrated to remove the solvent. The residue was dissolved with ethyl acetate (5 mL), and then water (5 mL) was added. The resulting mixture was partitioned. The aqueous phase was extracted with ethyl acetate (5 mL×2). The combined organic phases were washed with saturated brine (10 mL), dried over anhydrous sodium sulfate and filtered, then the filtrate was concentrated in vacuo, and the residue was purified by silica gel column chromatography (PE/EA (v/v)=10/1) to give the title compound as yellow oil (10 mg, 37%).

MS (ESI, pos. ion) m/z: 248.2[M+H]$^+$;

$^1$H NMR (400 MHz, CDCl$_3$) δ (ppm): 8.88 (s, 1H), 8.27-8.22 (m, 1H), 8.16 (ddd, J=11.6, 7.9, 0.9 Hz, 2H), 7.82-7.78 (m, 2H), 7.74-7.69 (m, 2H), 7.60-7.55 (m, 1H).

Step 3) Synthesis of 8H-dibenzo[3,4:6,7]cyclohepta[1,2-d]isoxazole-8-ol 8H-dibenzo[3,4:6,7]cyclohepta[1,2-d]isoxazole-8-one (0.11 g, 0.44 mmol) was dissolved in THF (2 mL) and methanol (1 mL). The mixture was cooled to 0° C. and to the mixture was added sodium borohydride (0.17 g, 4.40 mmol) in batches. Then the resulting mixture was reacted at 0° C. for 5 minutes and reacted at rt for 30 minutes. After the reaction was completed, to the reaction solution was added water (10 mL) and the resulting mixture was extracted with DCM (10 mL×2). The combined organic phases were washed with saturated saline solution (20 mL), dried over anhydrous sodium sulfate, filtered and the filtrate was concentrated in vacuo. The residue was purified by silica gel column chromatography (PE/EA (v/v)=20/1) to give the title compound as a white solid (90 mg, 81%).

MS (ESI, pos. ion) m/z: 250.2[M+H]$^+$

Step 4) Synthesis of 7-(benzyloxy)-12-(8H-dibenzo[3,4:6,7]cyclohepta[1,2-d]isoxazole-8-yl)-3,4,12,12a-tetrahydro-1H-[1,4]oxazino[3,4-c]pyrido[2,1-f][1,2,4]triazine-6,8-dione 8H-Dibenzo[3,4:6,7]cyclohepta[1,2-d]isoxazole-8-ol (23 mg, 0.09 mmol) and 7-(benzyloxy)-3,4,12,12a-tetrahydro-1H-[1,4]oxazino[3,4-c]pyrido[2,1-f][1,2,4]triazine-6-,8-dione (20 mg, 0.06 mmol) were added into a sealing tube, then 1-propyl phosphate anhydride (ethyl acetate solution) (wt 50%, 1 mL) was added. Nitrogen was blowed in the mixture, and the tube was sealed, and then the resulting solution was heated to 90° C. and reacted for 2 hours. The reaction solution was added to ice water (5 mL) and resulting mixture was extracted with ethyl acetate (5 mL×3). The combined organic phases were washed with saturated sodium bicarbonate aqueous solution (10 mL), dried over anhydrous sodium sulfate, filtered and the filtrate was concentrated in vacuo. The residue was purified by silica gel column chromatography (DCM/methanol (v/v)=30/1) to give the title compound as a light yellow solid (15 mg, 44%).

MS (ESI, pos. ion) m/z: 559.2[M+H]$^+$;

$^1$H NMR (400 MHz, DMSO-d$_6$) δ (ppm): 8.86 (s, 1H), 8.15 (d, J=7.2 Hz, 1H), 7.70-7.66 (m, 2H), 7.66-7.62 (m, 3H), 7.56 (d, J=7.4 Hz, 1H), 7.43 (t, J=7.6 Hz, 1H), 7.39 (t, J=7.4 Hz, 3H), 7.35 (d, J=7.2 Hz, 1H), 7.14 (t, J=7.5 Hz, 1H), 6.70 (d, J=7.6 Hz, 1H), 6.15 (d, J=7.7 Hz, 1H), 5.65 (d, J=8.4 Hz, 1H), 5.45 (d, J=10.9 Hz, 1H), 4.63 (d, J=13.0 Hz, 1H), 3.88 (d, J=9.6 Hz, 1H), 3.65 (d, J=11.9 Hz, 1H), 3.41 (d, J=10.8 Hz, 1H), 3.19 (t, J=11.5 Hz, 1H), 3.01 (t, J=10.2 Hz, 1H), 2.81-2.76 (m, 1H).

Step 5) Synthesis of 12-(8H-dibenzo[3,4:6,7]cyclohepta[1,2-d]isoxazol-8-yl)-7-hydroxy-3,4,12,12a-tetrahydro-1H-[1,4]oxazino[3,4-c]pyrido[2,1-f] [1,2,4]triazin-6, 8-dione 7-(Benzyloxy)-12-(8H-dibenzo[3,4:6,7]cyclohepta[1,2-d]isoxazole-8-yl)-3,4,12,12a-tetrahydro-1H-[1,4]oxazino[3,4-c]pyrido[2,1-f][1,2,4]triazine-6,8-dione (0.11 g, 0.20 mmol) was dissolved in N,N'-dimethyl acetamide (3 mL), then anhydrous lithium chloride (85 mg, 1.99 mmol) was added, and the mixture was warmed to 100° C. and reacted overnight under protection of nitrogen. The reaction was stopped and water (10 mL) was added. The reaction solution was adjusted with 1N diluted hydrochloric acid to pH about 6, and the resulting mixture was extracted with ethyl acetate (10 mL×3). The combined organic phases were washed with saturated brine (20 mL×3), dried over anhydrous sodium sulfate and filtered, then the filtrate was concentrated in vacuo, and the residue was purified by LUNA preparative column chromatography (acetonitrile/0.1% trifluoroacetate aqueous solution (v/v)=19/31) to give the title compound as a light yellow solid (7 mg, 9%).

MS (ESI, pos. ion) m/z: 469.2[M+H]$^+$;

HRMS (ESI, pos. ion) m/z: 469.1504, (C$_{26}$H$_{21}$N$_4$O$_5$)[M+H]$^+$, theoretical value: 469.1512;

$^1$H NMR (400 MHz, DMSO-d$_6$) δ (ppm): 8.95 (d, J=40.3 Hz, 1H), 8.13 (dd, J=40.6, 7.5 Hz, 1H), 7.73-7.62 (m, 2H), 7.56 (dd, J=15.0, 7.3 Hz, 2H), 7.50-7.43 (m, 1H), 7.42-7.36 (m, 1H), 7.26 (d, J=7.8 Hz, 1H), 7.02 (dd, J=19.2, 7.4 Hz, 1H), 6.57 (dd, J=24.8, 6.6 Hz, 1H), 6.11 (dd, J=61.9, 6.4 Hz, 1H), 5.42 (d, J=4.3 Hz, 1H), 4.61 (d, J=13.1 Hz, 1H), 4.26 (d, J=7.6 Hz, 1H), 3.75 (d, J=10.8 Hz, 1H), 3.53 (dd, J=28.1, 9.7 Hz, 1H), 3.36 (t, J=12.4 Hz, 1H), 3.27-3.20 (m, 1H), 2.96-2.87 (m, 1H).

Activity Test

In the following examples, the inventors examined the antiviral activity and cytotoxicity, pharmacokinetic properties, and stability in liver microparticles of the compounds of the present invention by taking a part of the compounds of the present invention as examples.

Antiviral Activity and Cytotoxicity Tests

Example A: Cytopathic Effect Assay (CPE Assay)

Detection of the ability of compounds to inhibit viral H1N1 A/Weiss/43 inducing cytopathic effect (CPE) in vitro at the cell level.

Experimental Procedures: MDCK cells were seeded in a 384-well plate with 2000 cells per wells, which were incubated overnight at 37° C., 5% CO$_2$; The culture medium was changed to the fresh culture solution containing different concentrations of the compound and virus H1N1 A/Weiss/43 at a multiplicity of infection to yield 80-95% CPE on the second day. The test compound was serially diluted from the highest concentration of 100 nM in 1:3 dilutions to give 8 concentrations: 100 nM, 33.33 nM, 11.11 nM, 3.70 nM, 1.23 nM, 0.41 nM, 0.14 nM, 0.05 nM. At the same time, a non-medicated virus control group and a non-medicated cell control group free of virus were set up. No virus was added in the cytotoxicity test group but medium was added for replacement. Each group was set in duplicate, and incubated at 37° C. in 5% $CO_2$. The cell activity was measured according to the CCK-8 kit (source: Shanghai Liji Biotechnology Co., Ltd. #D3100L4057) and the data would be used to calculate the antiviral and cytotoxicity of the compound. Data were analyzed by GraphPad Prism, CPE inhibition rate was calculated, and the EC50 was obtained according to the fitted curve.

CPE inhibition rate=(absorbance of dosing hole-absorbance of virus control well)/(absorbance of cell control well-virus control well)×100%

Antiviral activity assays and cytotoxicity assays of the compounds of the invention indicates that the compounds provided herein have excellent antiviral toxicity, wherein the inhibitory activity of the compounds of the present invention against influenza virus (A/Weiss/43 (H1N1)) has an $EC_{50}$ less than 0.1 μM, and the $EC_{50}$ of the inhibitory activity of most compounds against influenza virus (A/Weiss/43 (H1N1)) are less than 0.05 μM. The compounds of the invention have very low cytotoxicity, wherein the compounds of the invention have a $CC_{50}$ greater than 5 μM while most of the compounds have a $CC_{50}$ greater than 30 μM.

TABLE 1

$EC_{50}$ data of some compounds of the present invention against influenza virus (A/Weiss/43(H1N1)) in vitro

| Example number | $EC_{50}$ (nM) | Example number | $EC_{50}$ (nM) |
| --- | --- | --- | --- |
| Example 2 | 22.82 | Example 3 | 23.54 |
| Example 11 | 48.7 | Example 12 | 49.3 |
| Example 17 Compound (17-1) | 18.78 | Example 19 | 34.1 |
| Example 20 Compound (20-1) | 4.90 | Example 21 Compound (21-1) | 5.81 |
| Example 21 Compound (21-2) | 18.9 | Example 36 | 9.87 |
| Example 37 | 14.9 | Example 38 | 38 |

TABLE 2

$CC_{50}$ data of some compounds of the present invention against influenza virus (A/Weiss/43(H1N1)) in vitro

| Example number | $CC_{50}$ (μM) | Example number | $CC_{50}$ (μM) |
| --- | --- | --- | --- |
| Example 2 | >100 | Example 3 | >100 |
| Example 5 | >100 | Example 7 | >100 |
| Example 12 | 112 | Example 15 | 39.4 |
| Example 17 Compound (17-1) | 77.5 | Example 19 | >100 |
| Example 21 | 62.8 | Example 36 | 36 |

TABLE 2-continued $CC_{50}$ data of some compounds of the present invention against influenza virus (A/Weiss/43(H1N1)) in vitro

| Example number | $CC_{50}$ (μM) | Example number | $CC_{50}$ (μM) |
| --- | --- | --- | --- |
| Compound (21-1) Example 37 | 104 | Example 38 | >100 |

Table 1 and Table 2 show that the compounds of the present invention have excellent anti-influenza activity and low cytotoxicity.

Pharmacokinetic Properties Test

Example B: Pharmacokinetic Evaluation after Intravenous or Oral Quantification of the Compound of the Present Invention Pharmacokinetic studies of compounds of the invention in healthy adult male SD rats, dogs or monkeys were evaluated. The compound of the present invention was administered in form of a solution containing 5% DMSO+5% Kolliphor HS 15+90% physiological saline solution. For intravenous (iv) administration, animals were given with a dose of 0.2 or 1 mg/kg, blood was taken at 0.083, 0.25, 0.5, 1.0, 2.0, 5.0, 7.0, and 24 hours (0.3 mL), and centrifugated at 3,000 or at 4,000 rpm for 10 minutes. For oral (po) administration, animals were given with a dose of 1 or 5 mg/kg, blood was taken at time points of 0.25, 0.5, 1.0, 2.0, 5.0, 7.0, and 24 hours (0.3 mL) and centrifuged at 3,000 or 4,000 rpm for 10 minutes. The plasma solution was collected and stored at −20° C. or −70° C. until the LC/MS/MS analysis was performed.

The test results show that the compound of the present invention has high exposure level, good absorption and good pharmacokinetic properties in rats, dogs or monkeys.

Example C: Pharmacokinetic Evaluation after Intravenous or Oral Quantification of the Compound of the Present Invention Pharmacokinetic studies of compounds of the invention in healthy adult male SD rats, dogs or monkeys were evaluated. The compound of the present invention was administered in form of a solution containing 10% DMSO+10% Kolliphor HS 15+80% physiological saline solution. For intravenous (iv) administration, animals were given with a dose of 0.2 or 1 mg/kg and blood was taken at 0.083, 0.25, 0.5, 1.0, 2.0, 5.0, 7.0, and 24 hours (0.3 mL) and centrifugated for 10 minutes at 3,000 or 4,000 rpm. For oral (po) administration, animals were given with a dose of 1 or 5 mg/kg, taken at 0.25, 0.5, 1.0, 2.0, 5.0, 7.0, and 24 hours (0.3 mL) and centrifugated at 3,000 or 4,000 rpm for 10 minutes. The plasma solution was collected and stored at −20° C. or −70° C. until the LC/MS/MS analysis was performed.

Table 3 shows pharmacokinetic data of some compounds of the invention in Beagle dogs

| Tests Compound | Species | Route of administration | dose mg/kg | $C_{max}$ ng/mL | $AUC_{last}$ hr*ng/mL | $AUC_{INF}$ hr*ng/mL | $t_{1/2}$ h | CLL/h/Kg | F % |
| --- | --- | --- | --- | --- | --- | --- | --- | --- | --- |
| Example 28 | Beagles | iv | 0.2 | 144 | 996 | 1030 | 4.91 | 3.22 | N/A |
|  |  | po | 1 | 311 | 2430 | 2580 | 5.72 | N/A | 57.6 |

Remarks: compound of Example 28 was converted to the compound of Example 21 (21-1) in animals;
AUClast—0-24 hours of AUC
AUCINF—0-infinite time of AUC The test results show that the compound of the present invention has high exposure level in the dog, good absorption, and good pharmacokinetic properties.

Stability in Liver Microsome

Example D: Stability Evaluation in Human Liver Microsome

The stability of the compound of the present invention in mixed rat and human liver microsome were evaluated. The compound of the present invention was incubated with mixed human and rat liver microsomes at 37° C., pH=7.4. By measuring the concentration of the sample at different incubation times, the speed constant was given by plotting curve according to "Log [drug concentration]" and the corresponding "incubation time", and the drug half-life and clearance rate in vivo $Cl_{in\ vivo}$ were calculated. Drug stability in liver microsomes was evaluated by values of drug half-life and clearance values in vivo $Cl_{in\ vivo}$. The specific experimental system was as follows

| Reference | Verapamil |
|---|---|
| Test concentration | 1 μM |
| Test system | Mixed human liver microsomes, tested at a concentration of 0.5 mg/ml |
| Test Conditions | 0, 15, 30, 60 min, pH 7.4, 37° C. |
| Number of duplicates | 2 |
| Analytical method | LC/MS/MS |

The test results show that the compounds of the present invention are stable in both rat and human liver microsome.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I), a stereoisomer, a tautomer, or a pharmaceutically acceptable salt thereof,

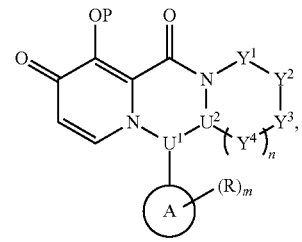

wherein, $U^1$ is N or CH;

$U^2$ is N or CH;

$Y^1$ is $CR^{1a}R^{1b}$, S or O;

$Y^2$ is $CR^{2a}R^{2b}$, S or O;

$Y^3$ is $CR^{3a}R^{3b}$, S or O;

each $Y^4$ is independently $CR^{4a}R^{4b}$, S or O;

each $R^{1a}$, $R^{1b}$, $R^{2a}$, $R^{2b}$, $R^{3a}$, $R^{3b}$, $R^{4a}$ and $R^{4b}$ is independently H, deuterium, F, Cl, Br, I, CN, $NO_2$, $OR^b$, $R^bO$—$C_{1-4}$ alkylene, $R^dR^cN$—$C_{1-4}$ alkylene, $C_{1-6}$ haloalkyl, $C_{1-6}$ alkyl, $C_{2-6}$ alkenyl, $C_{2-6}$ alkynyl, $C_{3-8}$ carbocyclyl, 3-8 membered heterocyclyl, $C_{6-10}$ aryl or 5-10 membered heteroaryl; wherein each $C_{1-6}$ haloalkyl, $C_{1-6}$ alkyl, $C_{2-6}$ alkenyl, $C_{2-6}$ alkynyl, $C_{3-8}$ carbocyclyl, 3-8 membered heterocyclyl, $C_{6-10}$ aryl and 5-10 membered heteroaryl is unsubstituted or substituted with 1, 2, 3 or 4 substituents independently selected from deuterium, F, Cl, Br, I, CN, OH, $NH_2$, $C_{1-6}$ alkyl, $C_{1-6}$ haloalkyl, $C_{1-6}$ alkoxy or $C_{1-6}$ alkylamino;

or optionally two $R^{1a}$, $R^{1b}$, $R^{2a}$, $R^{2b}$, $R^{3a}$, $R^{3b}$, $R^{4a}$, $R^{4b}$ together with the carbon atom to which they are attached, form a $C_{3-8}$ carbocyclic ring or 3-8 membered heterocyclic ring; wherein each $C_{3-8}$ carbocyclic ring and 3-8 membered heterocyclic ring is unsubstituted or substituted with 1, 2, 3 or 4 substituents independently selected from deuterium, F, Cl, Br, I, CN, OH, $NH_2$, $C_{1-6}$ alkyl, $C_{1-6}$ haloalkyl, $C_{1-6}$ alkoxy or $C_{1-6}$ alkylamino;

ring A is one of the following sub-formulae:

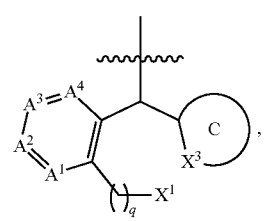

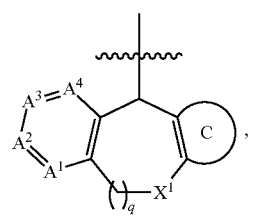

-continued (A-3) 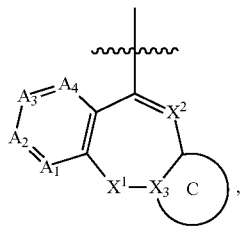

(A-4) 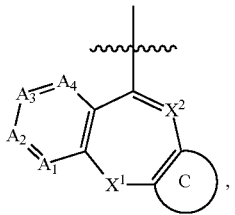

(A-5) 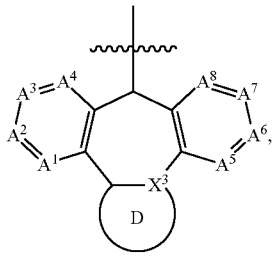

(A-6) 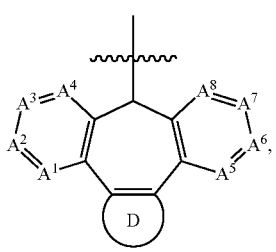

(A-7) 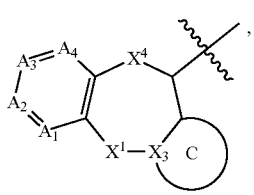

(A-8) 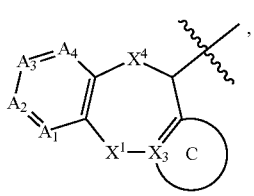

(A-10) 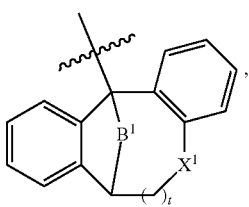

-continued (A-11) 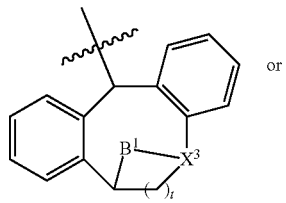 or (A-12) 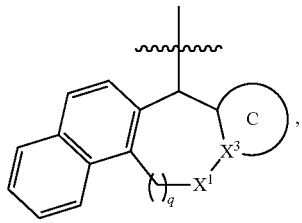

wherein,
each $X^1$ is independently S, S(=O), S(=O)$_2$, O, NH, CH$_2$ or absent;
each $X^2$ is independently CH or N;
each $X^3$ is independently CH or N;
each $X^4$ is independently S, O, NH or CH$_2$;
each $A^1$, $A^2$, $A^3$, $A^4$, $A^5$, $A^6$, $A^7$, and $A^8$ is independently C or N;
$B^1$ is —CH$_2$—, —CH$_2$CH$_2$—, —CH$_2$CH$_2$CH$_2$— or O;
ring C is benzocyclohexane, benzocyclopentane, naphthalene, benzoimidazole, benzopyrazole, benzothiophene, benzopyrimidine, indole, purine, quinoline, isoquinoline, bicyclic [2.2.2]octane, or benzobicyclic [2.2.2] octane;
ring D is C$_{3-8}$ carbocyclic ring, 3-8 membered heterocyclic ring, C$_{6-10}$ aromatic ring, C$_{11}$ aromatic ring, C$_{12}$ aromatic ring, or 5-10 membered heteroaromatic ring;
each q is independently 0, 1, 2, 3, 4, 5, or 6;
each t is independently 0, 1, 2, or 3;
each R is independently H, deuterium, F, Cl, Br, I, CN, NO$_2$, oxo(=O), —C(=O)R$^a$, —C(=O)OR$^b$, —C(=O)NR$^c$R$^d$, —OR$^b$, —NR$^c$R$^d$, R$^b$O—C$_{1-4}$ alkylene, R$^d$R$^c$N—C$_{1-4}$ alkylene, C$_{1-6}$ alkyl, C$_{1-6}$ haloalkyl, C$_{2-6}$ alkenyl, C$_{2-6}$ alkynyl, C$_{3-8}$ cycloalkyl, C$_{3-8}$ cycloalkyl-C$_{1-4}$ alkylene, 3-8 membered heterocyclyl, (3-8 membered heterocyclyl)-C$_{1-4}$ alkylene, C$_{6-10}$ aryl, C$_{6-10}$ aryl-C$_{1-4}$ alkylene, 5-10 membered heteroaryl, or (5-10 membered heteroaryl)-C$_{1-4}$ alkylene;
wherein each C$_{1-6}$ alkyl, C$_{1-6}$ haloalkyl, C$_{2-6}$ alkenyl, C$_{2-6}$ alkynyl, C$_{3-8}$ cycloalkyl, C$_{3-8}$ cycloalkyl-C$_{1-4}$ alkylene, 3-8 membered heterocyclyl, (3-8 membered heterocyclyl)-C$_{1-4}$ alkylene, C$_{6-10}$ aryl, C$_{6-10}$ aryl-C$_{1-4}$ alkylene, 5-10 membered heteroaryl and (5-10 atomic heteroaryl)-C$_{1-4}$ alkylene is independently unsubstituted or substituted with 1, 2, 3 or 4 substituents independently selected from deuterium, F, Cl, Br, I, CN, NO$_2$, —OR$^b$, —NR$^c$R$^d$, C$_{1-6}$ alkyl, C$_{1-6}$ haloalkyl, R$^b$O—C$_{1-4}$ alkylene or R$^d$R$^c$N—C$_{1-4}$ alkylene;
or optionally two R together with carbon atom or nitrogen atom to which they are attached form a C$_{3-8}$ carbocyclic ring, 3-8 membered heterocyclic ring, C$_{6-10}$ aromatic ring or a 5-10 membered heteroaryl ring; wherein the C$_{3-8}$ carbocyclic ring, 3-8 membered heterocyclic ring, C$_{6-10}$ aromatic ring, and 5-10 membered heteroaryl ring is independently unsubstituted or substituted with 1, 2, 3 or 4 substituents independently selected from deuterium, F, Cl, Br, I, CN, NO$_2$, —OR$^b$, —NR$^c$R$^d$, C$_{1-6}$ alkyl, C$_{1-6}$ haloalkyl, R$^b$O—C$_{1-4}$ alkylene or R$^d$R$^c$N—C$_{1-4}$ alkylene;

P is H, deuterium, C$_{1-6}$ alkyl, C$_{2-6}$ alkenyl, C$_{3-8}$ carbocyclyl, C$_{3-8}$ carbocyclyl-C$_{1-4}$ alkylene, 3-8 membered heterocyclyl, (3-8 member heterocyclyl)-C$_{1-4}$ alkylene, C$_{6-10}$ aryl, C$_{6-10}$ aryl-C$_{1-4}$ alkylene, 5-10 membered heteroaryl, (5-10 membered heteroaryl)-C$_{1-4}$ alkylene, —C(=O)—R$^{Pa}$, —C(=O)-L-R$^{Pe}$, —C(=O)-L-O—R$^{Pb}$, —C(=O)-L-O-L-O—R$^{Pb}$, —C(=O)-L-O—C(=O)—R$^{Pa}$, —C(=O)—NR$^{Pf}$R$^{Pd}$, —C(=O)—O—R$^{Pb}$, —S(=O)$_2$—R$^{Pk}$, —P(=O)—(R$^{Pg}$)(R$^{Ph}$), —C(=O)—O-L-O—R$^{Pb}$, —C(=N$^+$R$^{Pi}$R$^{Pj}$)(—NR$^{Pc}$R$^{Pd}$), R$^{Pb}$—O—C$_{1-4}$ alkylene, R$^{Pb}$—O-L-O—C$_{1-4}$ alkylene, R$^{Pa}$—(C=O)—O—C$_{1-4}$ alkylene, R$^{Pb}$—O—(C=O)—C$_{1-4}$ alkylene, R$^{Pb}$—O—(C=O)—NR$^{Pf}$—C$_{1-4}$ alkylene, R$^{Pb}$—O—(C=O)—O—C$_{1-4}$ alkylene, NR$^{Pf}$R$^{Pd}$—O—(C=O)—O—C$_{1-4}$ alkylene, R$^{Pb}$—O-L-O—(C=O)—O—C$_{1-4}$ alkylene, NR$^{Pe}$R$^{Pd}$-L-O—(C=O)—O—C$_{1-4}$ alkylene, R$^{Pb}$—O-L-NR$^{Pf}$—(C=O)—O—C$_{1-4}$ alkylene, NR$^{Pe}$R$^{Pd}$-L-N(R$^{Pf}$)—(C=O)—O—C$_{1-4}$ alkylene, R$^{Pb}$—O-L-O-L-O—(C=O)—O—C$_{1-4}$ alkylene, (HO)$_2$P(=O)—C$_{1-4}$ alkylene, (BnO)$_2$P(=O)—C$_{1-4}$ alkylene or R$^{Pa}$—(C=O)—NR$^{Pf}$-L-O—(C=O)—O—C$_{1-4}$ alkylene, wherein each of C$_{1-6}$ alkyl, C$_{2-6}$ alkenyl, C$_{3-8}$ carbocyclyl, C$_{3-8}$ carbocyclyl-C$_{1-4}$ alkylene, 3-8 membered heterocyclyl, (3-8 membered heterocyclyl)-C$_{1-4}$ alkylene, C$_{6-10}$ aryl, C$_{6-10}$ aryl-C$_{1-4}$ alkylene, 5-10 membered heteroaryl and (5-10 membered heterocyclyl)-C$_{1-4}$ alkylene is independently unsubstituted or substituted with 1, 2, 3 or 4 substituents independently selected from deuterium, F, Cl, Br, I, oxo(=O), CN, NO$_2$, —OR$^b$, —NR$^c$R$^d$, —C(=O)R$^a$, —O(C=O)R$^a$, —C(=O)OR$^b$, C$_{1-6}$ alkyl, R$^b$O—C$_{1-4}$ alkylene, —NR$^d$R$^c$C(=O)R$^a$ or R$^d$R$^c$N—C$_{1-4}$ alkylene;

each L is independently C$_{1-6}$ alkylene or C$_{2-6}$ alkenylene;
each R$^{Pf}$ is independently H or C$_{1-6}$ alkyl;
each R$^{Pa}$, R$^{Pb}$, R$^{Pc}$, R$^{Pd}$, R$^{Pe}$, R$^{Pi}$, R$^{Pj}$ and R$^{Pk}$ is independently C$_{1-6}$ alkyl, C$_{3-8}$ carbocyclyl, C$_{3-8}$ carbocyclyl-C$_{1-4}$ alkylene, 3-8 membered heterocyclyl, (3-8 membered heterocyclyl)-C$_{1-4}$ alkylene, C$_{6-10}$ aryl, C$_{6-10}$ aryl-C$_{1-4}$ alkylene, 5-10 membered heteroaryl, (5-10 membered heteroaryl)-C$_{1-4}$ alkylene, C$_{1-6}$ alkylamino, C$_{1-6}$ alkylthio or C$_{1-6}$ alkylsilyl, wherein each C$_{1-6}$ alkyl, C$_{3-8}$ carbocyclyl, C$_{3-8}$ carbocyclyl-C$_{1-4}$ alkylene, 3-8 membered heterocyclyl, (3-8 membered heterocyclyl)-C$_{1-4}$ alkylene, C$_{6-10}$ aryl, C$_{6-10}$ aryl-C$_{1-4}$ alkylene, 5-10 membered heteroaryl, (5-10 membered heteroaryl)-C$_{1-4}$ alkylene, C$_{1-6}$ alkylamino and C$_{1-6}$ alkylthio is independently unsubstituted or substituted with 1, 2, 3 or 4 substituents independently selected from deuterium, F, Cl, Br, I, oxo(=O), CN, NO$_2$, —OR$^b$, —NR$^c$R$^d$, —C(=O)R$^a$, —O(C=O)R$^a$, —C(=O)OR$^b$, C$_{1-6}$ alkyl, R$^b$O—C$_{1-4}$ alkylene, —NR$^d$R$^c$C(=O)R$^a$ or R$^d$R$^c$N—C$_{1-4}$ alkylene;

each R$^{Pg}$ and R$^{Ph}$ is independently C$_{1-6}$ alkoxy, C$_{1-6}$ alkylamino, C$_{3-8}$ carbocyclyloxy, C$_{3-8}$ carbocyclylamino, 3-8 membered heterocyclyloxy, 3-8 membered heterocyclylamino, C$_{6-10}$ aryloxy, C$_{6-10}$ arylamino, 5-10 membered heteroaryloxy or 5-10 membered heteroarylamino, wherein each of C$_{1-6}$ alkoxy, C$_{1-6}$ alkylamino, C$_{3-8}$ carbocyclyloxy and C$_{3-8}$ carbocyclylamino, 3-8 membered heterocyclyloxy, 3-8 membered heterocyclylamino, C$_{6-10}$ aryloxy, C$_{6-10}$ arylamino, 5-10 membered heteroaryloxy and 5-10 membered heteroarylamino is independently unsubstituted or substituted with 1, 2, 3 or 4 substituents independently selected from deuterium, F, Cl, Br, I, oxo(=O), CN, NO$_2$, —OR$^b$, —NR$^c$R$^d$, —C(=O)R$^a$, —O(C=O)R$^a$, —C(=O)OR$^b$, C$_{1-6}$ alkyl, R$^b$O—C$_{1-4}$alkylene, —NR$^d$R$^c$C(=O)R$^a$ or R$^d$R$^c$N—C$_{1-4}$ alkylene;

or R$^{Pg}$, R$^{Ph}$ together with phosphorus atom to which they are attached form a 3-8 membered heterocyclic ring, or 5-10 membered heteroaromatic ring; wherein each of the 3-8 membered heterocyclyl and 5-10 membered heteroaromatic ring is independently unsubstituted or substituted with 1, 2, 3 or 4 substituents independently selected from deuterium, F, Cl, Br, I, oxo(=O), CN, NO$_2$, —OR$^b$, —NR$^c$R$^d$, —C(=O)R$^a$, —O(C=O)R$^a$, —C(=O)OR$^b$, C$_{1-6}$ alkyl, R$^b$O—C$_{1-4}$ alkylene, —NR$^d$R$^c$C(=O)R$^a$ or R$^d$R$^c$N—C$_{1-4}$ alkylene;

each R$^a$, R$^b$, R$^c$ and R$^d$ is independently H, deuterium, C$_{1-6}$ haloalkyl, C$_{1-6}$ alkyl, C$_{1-6}$ alkenyl, C$_{2-6}$ alkynyl, C$_{3-6}$ carbocyclyl, C$_{3-6}$ carbocyclyl-C$_{1-4}$ alkylene, 3-6 membered heterocyclyl, (3-6 membered heterocyclyl)-C$_{1-4}$ alkylene, C$_{6-10}$ aryl, C$_{6-10}$ aryl —C$_{1-4}$ alkylene, 5-10 membered heteroaryl or (5-10 membered heteroaryl)-C$_{1-4}$ alkylene, wherein each C$_{1-6}$ alkyl, C$_{2-6}$ alkenyl, C$_{2-6}$ alkynyl, C$_{3-6}$ carbocyclyl, C$_{3-6}$ carbocyclyl-C$_{1-4}$ alkylene, 3-6 membered heterocyclyl, (3-6 membered heterocyclyl) C$_{1-4}$ alkylene, C$_{6-10}$ aryl, C$_{6-10}$ aryl-C$_{1-4}$ alkylene, 5-10 membered heteroaryl and (5-10 membered heteroaryl)-C$_{1-4}$ alkylene is independently unsubstituted or substituted with 1, 2, 3 or 4 substituents independently selected from deuterium, F, Cl, Br, I, CN, OH, NH$_2$, NO$_2$, C$_{1-6}$ alkyl, C$_{1-6}$ haloalkyl, C$_{1-6}$ alkoxy or C$_{1-6}$ alkylamino;

or R$^c$, R$^d$ together with the nitrogen atom to which they are attached form a 3-6 membered heterocyclic ring or 5-8 membered heteroaryl ring; wherein the 3-6 membered heterocyclic ring and 5-8 membered heteroaryl ring is independently unsubstituted or substituted with 1, 2, 3 or 4 substituents independently selected from deuterium, F, Cl, Br, I, CN, OH, NH$_2$, NO$_2$, C$_{1-6}$ alkyl, C$_{1-6}$ haloalkyl, C$_{1-6}$ alkoxy or C$_{1-6}$ alkylamino;

m is 0, 1, 2, 3, 4, 5, 6, 7 or 8; and
n is 0, 1, 2, or 3.

2. The compound of claim 1, wherein ring D is a C$_{3-6}$ carbocyclic ring, 5 membered atomic heterocyclic ring, 6 membered heterocyclic ring, C$_{6-10}$ aromatic ring, 5 membered heteroaromatic ring or 6 membered heteroaromatic ring.

3. The compound of claim 1, wherein ring C is benzocyclohexane, benzocyclopentane, naphthalene, benzoimidazole, benzopyrazole, benzothiophene, benzopyrimidine, indole, purine, quinoline, isoquinoline, bicyclic [2.2.2]octane or benzobicyclic [2.2.2] octane;

and ring D is cyclopropane, cyclobutane, cyclopentane, cyclohexane, cycloheptane, cyclopentene, cyclopentadiene, cyclohexene, cyclohexadiene, benzocyclohexane, benzocyclopentane, cyclopropyl ethane, azetidine, oxetane, pyrrolidine, piperidine, piperazine, tetrahydrofuran, tetrahydropyran, morpholine, thiomorpholine, benzene, naphthalene, furan, benzofuran, pyrrole, pyridine, pyrazole, imidazole, benzoimidazole, benzopyrazole, triazole, tetrazole, oxazole, isoxazole, oxadiazole, 1,3,5-triazine, thiazole, thiophene, benzothiophene, pyrazine, pyridazine, pyrimidine, benzopyrimidine, indole, purine, quinoline, isoquinoline, bicyclic [2.2.2] octane or benzobicyclic [2.2.2] octane.

4. The compound of claim 1, wherein ring A is one of the following sub-formulae:
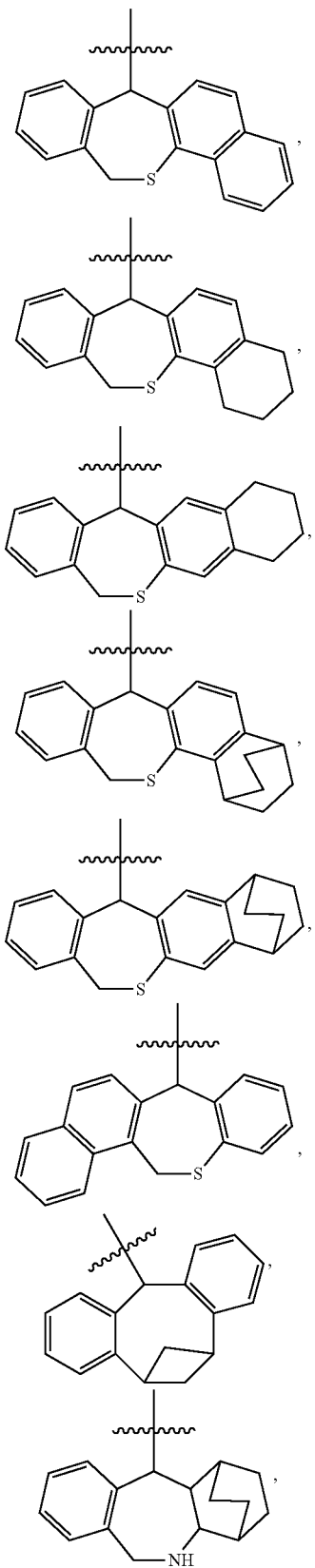
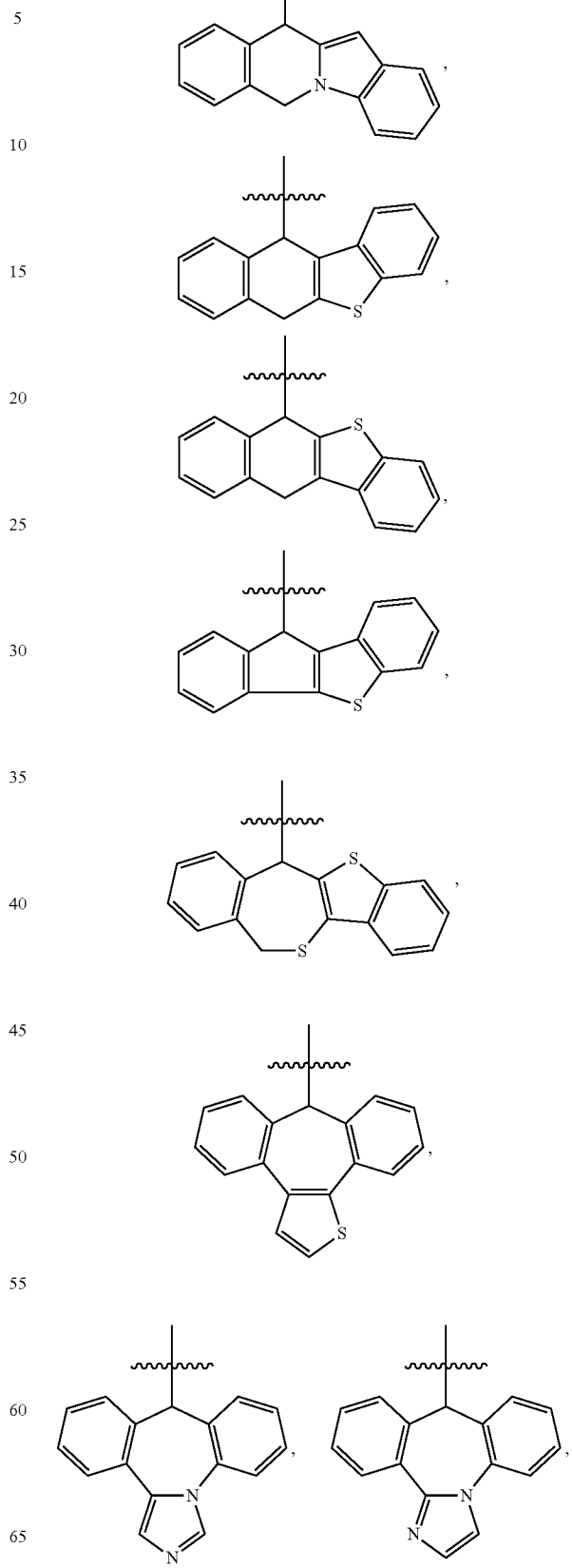

375
-continued

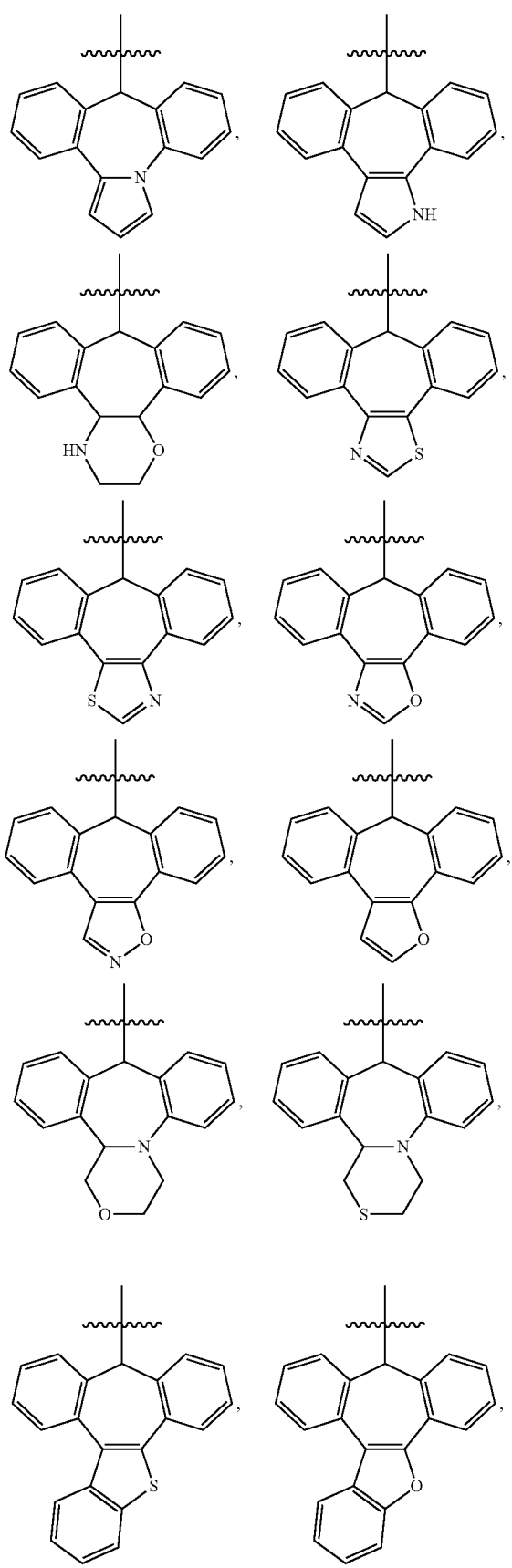

376
-continued

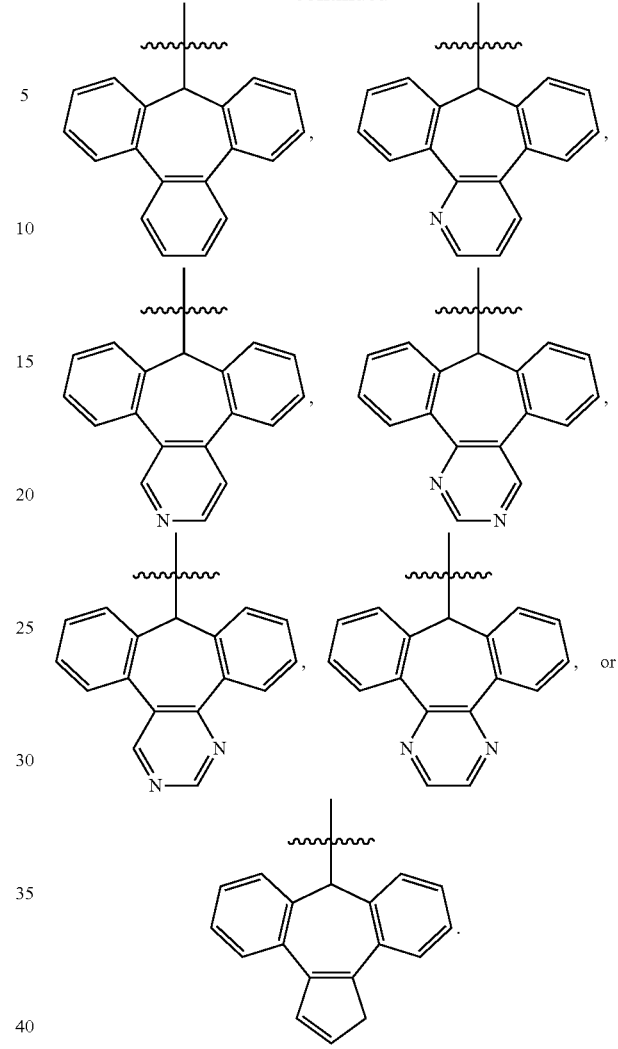

5. The compound of claim 1, wherein each R is independently H, deuterium, F, Cl, Br, I, CN, NO$_2$, oxo(=O), —C(=O)R$^a$, —C(=O)OR$^b$, —C(=O)NR$^c$R$^d$, —OR$^b$, —NR$^c$R$^d$, R$^b$O—C$_{1-4}$ alkylene, R$^d$R$^c$N—C$_{1-4}$ alkylene, C$_{1-4}$ alkyl, C$_{1-4}$ haloalkyl, C$_{2-4}$ alkenyl, C$_{2-4}$ alkynyl, C$_{3-6}$ cycloalkyl, C$_{3-6}$ cycloalkyl-C$_{1-2}$ alkylene, 3-6 membered heterocyclyl, (3-6 membered heterocyclyl)-C$_{1-2}$ alkylene, C$_{6-10}$ aryl, C$_{6-10}$ aryl-C$_{1-2}$ alkylene, 5-10 membered heteroaryl or (5-10 membered heteroaryl)-C$_{1-2}$ alkylene; wherein each C$_{1-4}$ alkyl, C$_{1-4}$ haloalkyl, C$_{2-4}$ alkenyl, C$_{2-4}$ alkynyl, C$_{3-6}$ cycloalkyl, C$_{3-6}$ cycloalkyl-C$_{1-2}$ alkylene, 3-6 membered heterocyclyl, (3-6 membered heterocyclyl)-C$_{1-2}$ alkylene, C$_{6-10}$ aryl, C$_{6-10}$ aryl-C$_{1-2}$ alkylene, 5-10 membered heteroaryl, and (5-10 membered heteroaryl)-C$_{1-2}$ alkylene is independently unsubstituted or substituted with 1, 2, 3 or 4 substituents independently selected from deuterium, F, Cl, Br, CN, NO$_2$, —OR$^b$, —NR$^c$R$^d$, C$_{1-4}$ alkyl, C$_{1-4}$ haloalkyl, R$^b$O—C$_{1-4}$ alkylene or R$^d$R$^c$N—C$_{1-4}$ alkylene;

or optionally two R together with the carbon atom or nitrogen atom to which they are attached form a C$_{3-8}$ carbocyclic ring, 3-8 membered heterocyclic ring, C$_{6-10}$ aromatic ring or 5-10 membered heteroaromatic ring; wherein the C$_{3-8}$ carbocyclic ring, 3-8 membered heterocyclic ring, C$_{6-10}$ aromatic ring, and 5-10 membered heteroaromatic ring is independently unsubstituted or substituted with 1, 2, 3 or 4 substituents independently selected from deuterium, F, Cl, Br, CN, $NO_2$, $-OR^b$, $-NR^cR^d$, $C_{1-4}$ alkyl, $C_{1-4}$ haloalkyl, $R^bO-C_{1-4}$ alkylene or $R^dR^cN-C_{1-4}$ alkylene.

6. The compound of claim 1, wherein each R is independently H, deuterium, F, Cl, Br, I, CN, $NO_2$, oxo(=O), $-C(=O)OH$, $-C(=O)OCH_3$, $-C(=O)NH_2$, $-OH$, $-OCH_3$, $-OCH_2CH_3$, $-OCF_3$, $-OCHF_2$, $-OCH_2CF_3$, $-NH_2$, methyl, ethyl, n-propyl, isopropyl, trifluoromethyl, trifluoroethyl, cyclopropyl, cyclobutyl, cyclopentyl, cyclohexyl, cycloheptyl, oxiranyl, azetidinyl, oxetanyl, pyrrolidinyl, piperidinyl, piperazinyl, tetrahydrofuranyl, tetrahydropyranyl, morpholinyl, phenyl, naphthyl, furanyl, benzofuranyl, pyrrolidinyl, pyridyl, pyrazolyl, imidazolyl, benzimidazolyl, benzopyrazolyl, triazolyl, tetrazolyl, oxazolyl, oxadiazolyl, 1,3,5-triazinyl, thiazolyl, thiophenyl, benzothiophenyl, pyrazinyl, pyrimidinyl, indolyl, purinyl, quinolinyl or isoquinolinyl, wherein each methyl, ethyl, n-propyl, isopropyl, trifluoromethyl, trifluoroethyl, cyclopropyl, cyclobutyl, cyclopentyl, cyclohexyl, cycloheptyl, oxiranyl, azetidinyl, oxetanyl, pyrrolidinyl, piperidinyl, piperazinyl, tetrahydrofuranyl, tetrahydropyranyl, morpholinyl, phenyl, naphthyl, furanyl, benzofuranyl, pyrrolidinyl, pyridyl, pyrazolyl, imidazolyl, benzimidazolyl, benzopyrazolyl, triazolyl, tetrazolyl, oxazolyl, oxadiazolyl, 1,3,5-triazinyl, thiazolyl, thiophenyl, benzothiophenyl, pyrazinyl, pyrimidinyl, indolyl, purinyl, quinolinyl and isoquinolinyl is independently unsubstituted or substituted with 1, 2, 3 or 4 substituents independently selected from deuterium, F, Cl, Br, CN, $NO_2$, OH, $-NH_2$, methyl, ethyl, n-propyl, isopropyl, trifluoromethyl or methoxy;

or optionally two R together with the carbon atom or nitrogen atom to which they are attached form cyclopropane, cyclobutane, cyclopentane, cyclohexane, cycloheptane, oxirane, azetidine, oxetane, pyrrolidine, piperidine, piperazine, tetrahydrofuran, tetrahydropyran, morpholine, thiomorphine, benzene, furan, pyrrole, pyridine, pyrazole, imidazole, triazole, tetrazole, oxazole, oxadiazole, 1,3,5-triazine, thiazole, thiophene, pyrazine, pyridazine or pyrimidine, wherein each of the cyclopropane, cyclobutane, cyclopentane, cyclohexane, cycloheptane, oxirane, azetidine, oxetane, pyrrolidine, piperidine, piperazine, tetrahydrofuran, tetrahydropyran, morpholine, thiomorphine, benzene, furan, pyrrole, pyridine, pyrazole, imidazole, triazole, tetrazole, oxazole, oxadiazole, 1,3,5-triazine, thiazole, thiophene, pyrazine, pyridazine and pyrimidine is independently unsubstituted or substituted with 1, 2, 3 or 4 substituents independently selected from deuterium, F, Cl, Br, CN, $NO_2$, OH, $-NH_2$, methyl, ethyl, n-propyl, isopropyl, trifluoromethyl or methoxy.

7. The compound of claim 1, wherein each $R^{1a}$, $R^{1b}$, $R^{2a}$, $R^{2b}$, $R^{3a}$, $R^{3b}$, $R^{4a}$ and $R^{4b}$ is independently H, deuterium, F, Cl, Br, I, CN, $NO_2$, $OR^b$, $R^bO-C_{1-2}$ alkylene, $R^dR^cN-C_{1-2}$ alkylene, $C_{1-4}$ haloalkyl, $C_{1-4}$ alkyl, $C_{2-4}$ alkenyl, $C_{2-4}$ alkynyl, $C_{3-6}$ carbocyclyl, 3-6 membered heterocyclyl, $C_{6-10}$ aryl or 5-10 membered heteroaryl; wherein each $C_{1-4}$ haloalkyl, $C_{1-4}$ alkyl, $C_{2-4}$ alkenyl, $C_{2-4}$ alkynyl, $C_{3-6}$ carbocyclyl, 3-6 membered heterocyclic ring, $C_{6-10}$ aryl and 5-10 membered heteroaryl is independently unsubstituted or substituted with 1, 2, 3 or 4 substituents independently selected from deuterium, F, Cl, Br, I, CN, OH, $NH_2$, $C_{1-4}$ alkyl, $C_{1-4}$ haloalkyl, $C_{1-4}$ alkoxy or $C_{1-4}$ alkyl amino;

or optionally two $R^{1a}$, $R^{1b}$, $R^{2a}$, $R^{2b}$, $R^{3a}$, $R^{3b}$, $R^{4a}$, $R^{4b}$ together with the carbon atom to which they are attached form a $C_{3-8}$ carbocyclic ring or 3-8 membered heterocyclic ring; wherein each $C_{3-8}$ carbocyclic ring and 3-8 membered heterocyclic ring is unsubstituted or substituted with 1, 2, 3 or 4 substituents independently selected from deuterium, F, Cl, Br, I, CN, OH, $NH_2$, $C_{1-4}$ alkyl, $C_{1-4}$ haloalkyl, $C_{1-4}$ alkoxy or $C_{1-4}$ alkylamino.

8. The compound of claim 1, wherein each $R^{1a}$, $R^{1b}$, $R^{2a}$, $R^{2b}$, $R^{3a}$, $R^{3b}$, $R^{4a}$ and $R^{4b}$ is independently H, deuterium, F, Cl, Br, I, CN, $NO_2$, $OR^b$ $R^bO-C_{1-2}$ alkylene, $R^dR^cN-C_{1-2}$ alkylene, trifluoromethyl, trifluoroethyl, methyl, ethyl, n-propyl, isopropyl, cyclopropyl, cyclobutyl, cyclopentyl, oxiranyl, azetidinyl, oxetanyl, pyrrolidinyl, piperidinyl, piperazinyl, tetrahydrofuranyl, tetrahydropyranyl, morpholinyl, phenyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, wherein each trifluoroethyl, methyl, ethyl, n-propyl, isopropyl, cyclopropyl, cyclobutyl, cyclopentyl, oxiranyl, azetidinyl, oxetanyl, pyrrolidinyl, piperidinyl, piperazinyl, tetrahydrofuranyl, tetrahydropyranyl, morpholinyl, phenyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with 1, 2, 3 or 4 substituents independently selected from deuterium, F, Cl, Br, I, CN, OH, $NH_2$, methyl, ethyl, n-propyl, isopropyl, trifluoromethyl, methoxy or ethoxy;

or any two $R^{1a}$, $R^{1b}$, $R^{2a}$, $R^{2b}$, $R^{3a}$, $R^{3b}$, $R^{4a}$, $R^{4b}$ together with carbon atom to which they are attached form cyclopropane, cyclobutane, cyclopentane, cyclohexane, cycloheptane, oxirane, oxetane, azetidine, pyrrolidine, piperidine, piperazine, tetrahydrofuran, tetrahydropyran or morpholine, wherein each cyclopropane, cyclobutane, cyclopentane, cyclohexane, cycloheptane, oxirane, oxetane, azetidine, pyrrolidine, piperidine, piperazine, tetrahydrofuran, tetrahydropyran and morpholine is independently unsubstituted or substituted with 1, 2, 3 or 4 substituents independently selected from deuterium, F, Cl, Br, I, CN, OH, $NH_2$, methyl, ethyl, n-propyl, isopropyl, trifluoromethyl, methoxy or ethoxy.

9. The compound of claim 1, wherein P is H, deuterium, $C_{1-4}$ alkyl, $C_{2-4}$ alkenyl, $C_{3-6}$ carbocyclyl, $C_{3-6}$ carbocyclyl-$C_{1-2}$ alkylene, 3-6 membered heterocyclyl, (3-6 membered heterocyclyl)-$C_{1-2}$ alkylene, $C_{6-10}$ aryl, $C_{6-10}$ aryl-$C_{1-2}$ alkylene, 5-10 membered heteroaryl, (5-10 membered heteroaryl)-$C_{1-2}$ alkylene, $-C(=O)-R^{Pa}$, $-C(=O)-O-R^{Pb}$, $-C(=O)-NR^{Pf}R^{Pd}$, $-P(=O)-(R^{Pg})(R^{Ph})$, $-C(=O)-O-L-O-R^{Pb}$, $R^{Pa}-(C=O)-O-C_{1-4}$ alkylene, $R^{Pb}-O-(C=O)-C_{1-4}$ alkylene, $R^{Pb}-O-(C=O)-NR^{Pf}-C_{1-4}$ alkylene, $R^{Pb}-O-(C=O)-O-C_{1-4}$ alkylene or $R^{Pb}-O-L-O-(C=O)-O-C_{1-4}$ alkylene, wherein each of $C_{1-4}$ alkyl, $C_{1-4}$ alkenyl, $C_{3-6}$ carbocyclyl, $C_{3-6}$ carbocyclyl-$C_{1-2}$ alkylene, 3-6 membered heterocyclyl, (3-6 membered heterocyclyl)-$C_{1-2}$ alkylene, $C_{6-10}$ aryl, $C_{6-10}$ aryl-$C_{1-2}$ alkylene, 5-10 membered heteroaryl, and (5-10 membered heteroaryl)-$C_{1-2}$ alkylene is independently unsubstituted or substituted with 1, 2, 3 or 4 substituents independently selected from deuterium, F, Cl, Br, I, oxo(=O), CN, $NO_2$, $-OR^b$, $-NR^cR^d$, $-C(=O)R^a$, $-O(C=O)R^a$, $-C(=O)OR^b$, $C_{1-6}$ alkyl, $R^bO-C_{1-4}$ alkylene, $-NR^dR^cC(=O)R^a$ or $R^dR^cN-C_{1-4}$ alkylene;

each of L is independently $C_{1-6}$ alkylene;
each of $R^{Pf}$ is independently H or $C_{1-6}$ alkyl;
each $R^{Pa}$, $R^{Pb}$, and $R^{Pd}$ is independently $C_{1-4}$ alkyl, $C_{3-6}$ carbocyclyl, $C_{3-6}$ carbocyclyl-$C_{1-2}$ alkylene, 3-6 membered heterocyclyl, (3-6 membered heterocyclyl)-$C_{1-2}$ alkylene, $C_{6-10}$ aryl, $C_{6-10}$ aryl-$C_{1-2}$ alkylene, 5-10 membered heteroaryl or (5-10 membered heteroaryl)-$C_{1-2}$ alkylene, wherein each $C_{1-4}$ alkyl, $C_{3-6}$ carbocyclyl, $C_{3-6}$ carbocyclyl-$C_{1-2}$ alkylene, 3-6 membered heterocyclyl, (3-6 membered heterocyclyl)-$C_{1-2}$ alkylene, $C_{6-10}$ aryl, $C_{6-10}$ aryl-$C_{1-2}$ alkylene, 5-10 membered heteroaryl and (5-10 membered heteroaryl)-$C_{1-2}$ alkylene is independently unsubstituted or substituted with 1, 2, 3 or 4 substituents independently selected from deuterium, F, Cl, Br, I, oxo(=O), CN, $NO_2$, —$OR^b$, —$NR^cR^d$, —C(=O)$R^a$, —O(C=O)$R^a$, —C(=O)$OR^b$, $C_{1-6}$ alkyl, $R^bO$—$C_{1-4}$ alkylene, —$NR^dR^cC$(=O)$R^a$ or $R^dR^cN$—$C_{1-4}$ alkylene;

each $R^{Pg}$ and $R^{Ph}$ is independently $C_{1-4}$ alkoxy, $C_{1-4}$ alkylamino, $C_{3-6}$ carbocyclyloxy, $C_{3-6}$ carbocyclylamino, 3-6 membered heterocyclyloxy, 3-6 membered heterocyclylamino, $C_{6-10}$ aryloxy, $C_{6-10}$ arylamino, 5-6 membered heteroaryloxy or 5-6 membered heteroarylamino, wherein each $C_{1-4}$ alkoxy, $C_{1-4}$ alkylamino, $C_{3-6}$ carbocyclyloxy, $C_{3-6}$ carbocyclylamino, 3-6 membered heterocyclyloxy, 3-6 membered heterocyclylamino, $C_{6-10}$ aryloxy, $C_{6-10}$ arylamino, 5-6 membered heteroaryloxy and 5-6 membered heteroarylamino is independently unsubstituted or substituted with 1, 2, 3 or 4 substituents independently selected from deuterium, F, Cl, Br, I, oxo(=O), CN, $NO_2$, —$OR^b$, —$NR^cR^d$, —C(=O)$R^a$, —O(C=O)$R^a$, —C(=O)$OR^b$, $C_{1-6}$ alkyl, $R^bO$—$C_{1-4}$ alkylene, —$NR^dR^cC$(=O)$R^a$ or $R^dR^cN$—$C_{1-4}$ alkylene;

or $R^{Pg}$, $R^{Ph}$ together with phosphorus atom to which they are attached form a 3-6 membered heterocyclic ring or 5-6 membered heteroaromatic ring; wherein the 3-6 membered heterocyclic ring and 5-6 membered heteroaromatic ring is independently unsubstituted or substituted with 1, 2, 3 or 4 substituents independently selected from deuterium, F, Cl, Br, I, oxo(=O), CN, $NO_2$, —$OR^b$, —$NR^cR^d$, —C(=O)$R^a$, —O(C=O)$R^a$, —C(=O)$OR^b$, $C_{1-6}$ alkyl, $R^bO$—$C_{1-4}$ alkylene, —$NR^dR^cC$(=O)$R^a$ or $R^dR^cN$—$C_{1-4}$ alkylene.

10. The compound of claim 1, wherein P is H, deuterium,

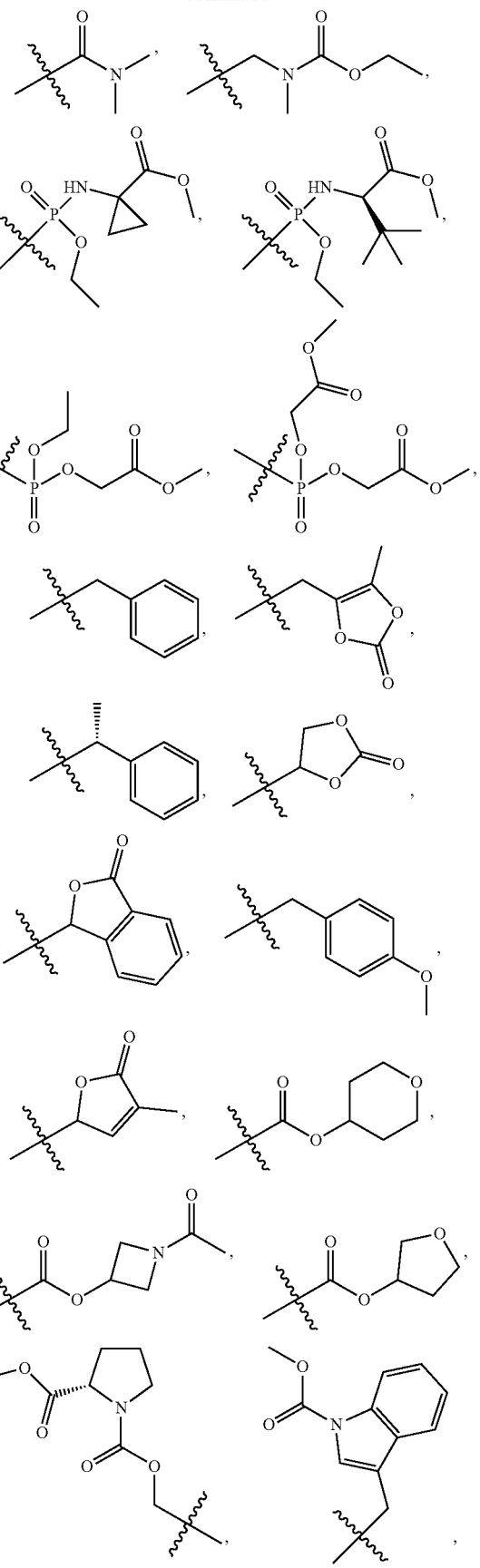

-continued

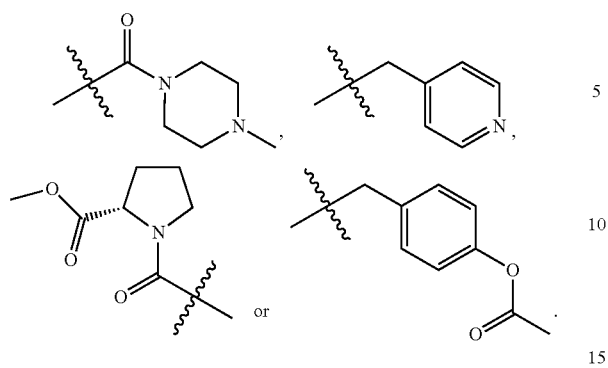

11. The compound of claim 1, wherein each $R^a$, $R^b$, $R^c$ and $R^d$ is independently H, deuterium, trifluoromethyl, trifluoroethyl, methyl, ethyl, n-propyl, isopropyl, tert-butyl, cyclopropyl, cyclobutyl, 3-6 membered heterocyclyl, phenyl or 5-10 membered heteroaryl, wherein each methyl, ethyl, n-propyl, isopropyl, tert-butyl, cyclopropyl, cyclobutyl, 3-6 membered heterocyclyl, phenyl and 5-10 membered heteroaryl is independently unsubstituted or substituted with 1, 2, 3 or 4 substituents independently selected from deuterium, F, Cl, CN, OH, $NH_2$, $NO_2$, methyl, ethyl, n-propyl, isopropyl, trifluoromethyl, methoxy;

or $R^c$, $R^d$ together with the phosphorus atom to which they are attached form a 3-6 membered heterocyclic ring or 5-6 membered heteroaromatic ring; wherein each of the 3-6 membered heterocyclic ring and 5-6 membered heteroaromatic ring is independently unsubstituted or substituted with 1, 2, 3 or 4 substituents; each substituent is independently selected from deuterium, F, Cl, CN, OH, $NH_2$, $NO_2$, methyl, ethyl, n-propyl, isopropyl, trifluoromethyl, methoxy.

12. The compound of claim 1 having Formula (II),

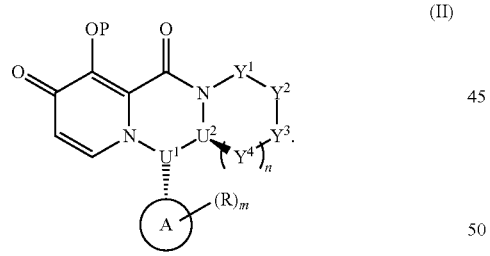

(II)

13. The compound of claim 1 having Formula (III), (IV), (V), (VI) or (VII):

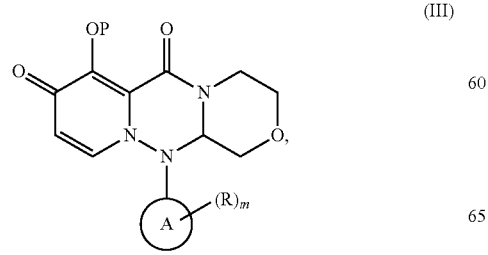

(III)

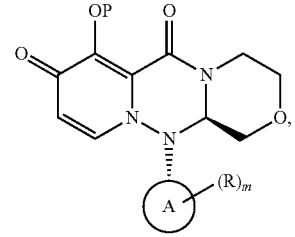

(IV)

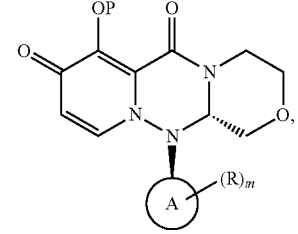

(V)

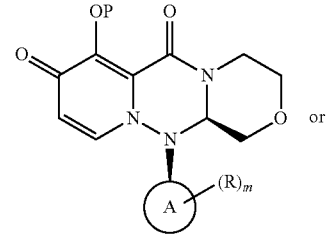

(VI)

or

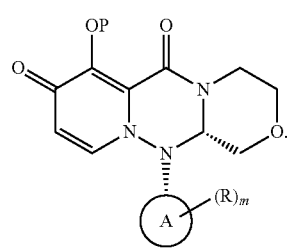

(VII)

14. The compound of claim 1 having Formula (VIII), (IX), (X), or (XI):

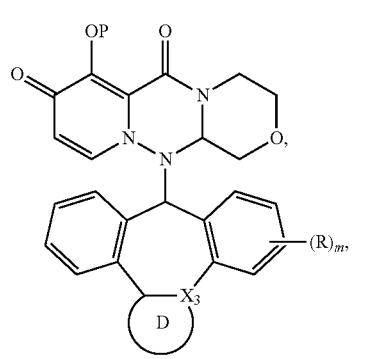

(VIII)

(IX)
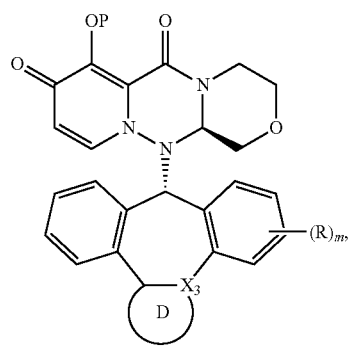
(X)
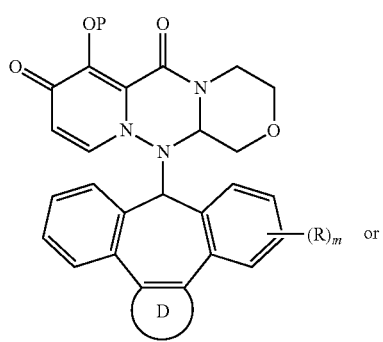
or
(XI)
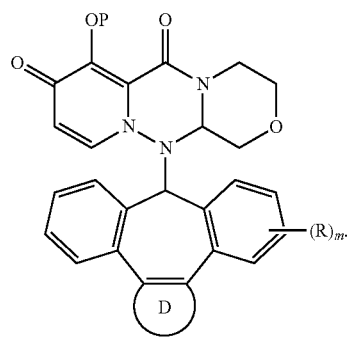
15. A compound having one of the following structures:
(7)
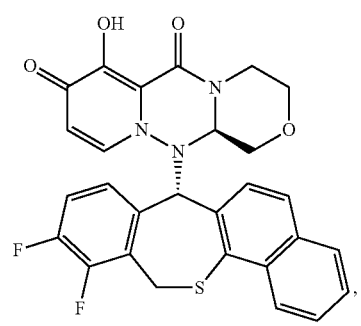
(8)
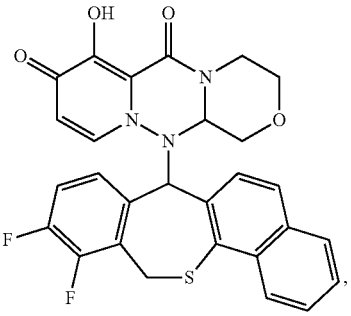
(19)
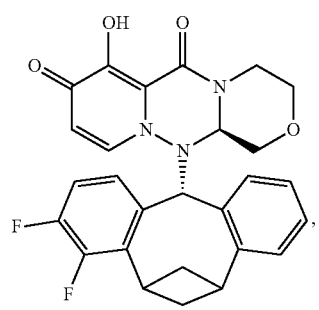
(20)
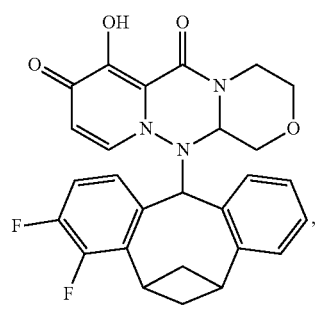
(23)
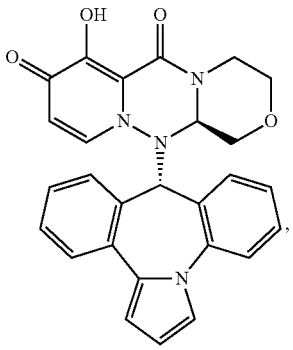
(24)

(27)
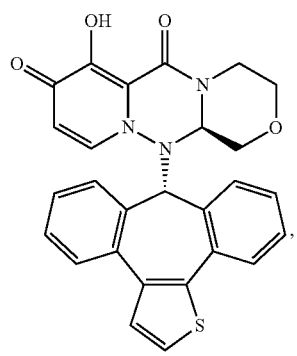
(28)
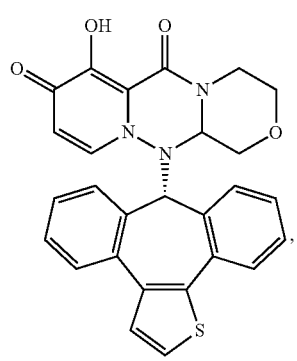
(29)
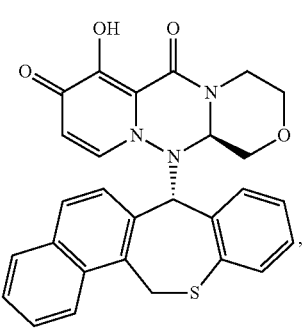
(30)
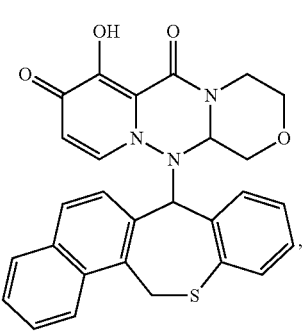
(31)
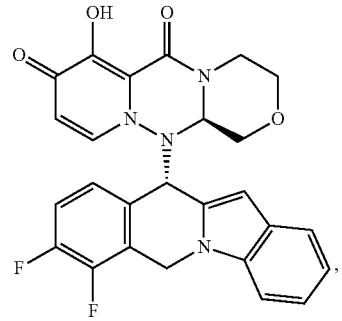
(32)
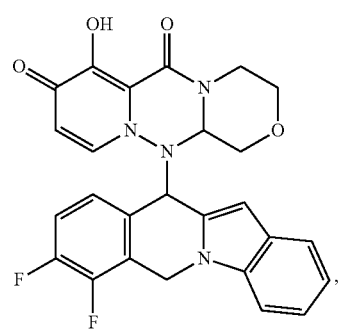
(41)
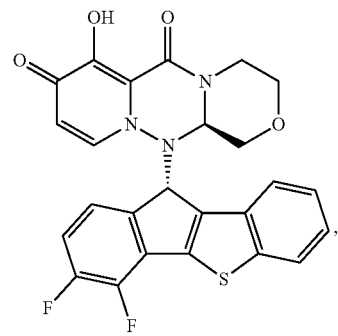
(42)
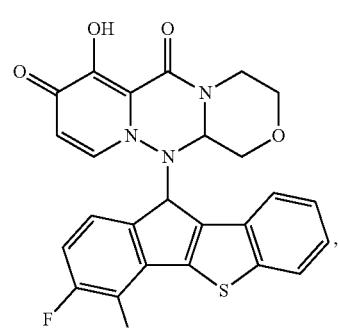
(43)
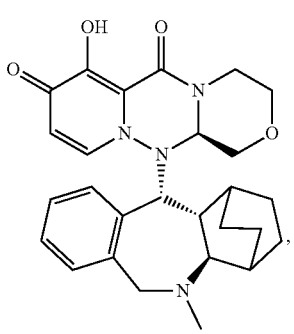

387
-continued
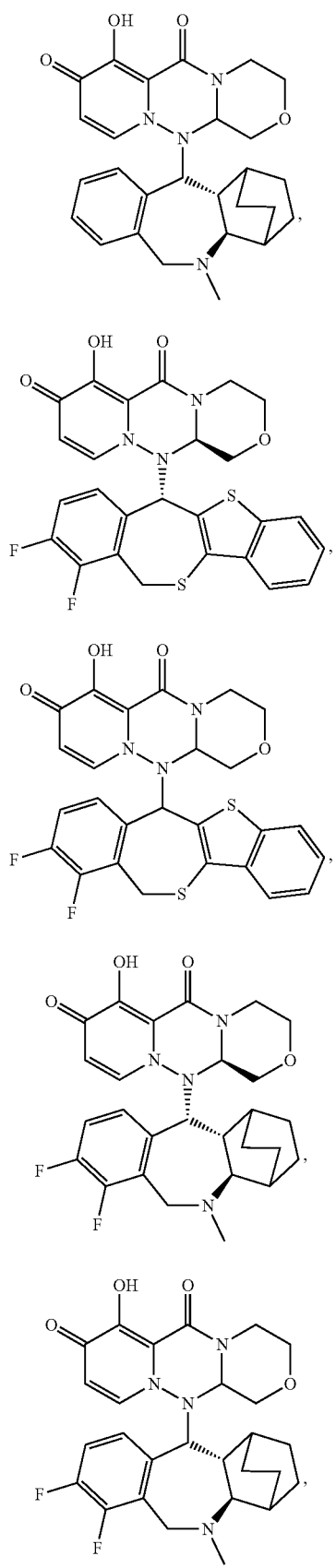
(44)
(49)
(50)
(51)
(52)
388
-continued
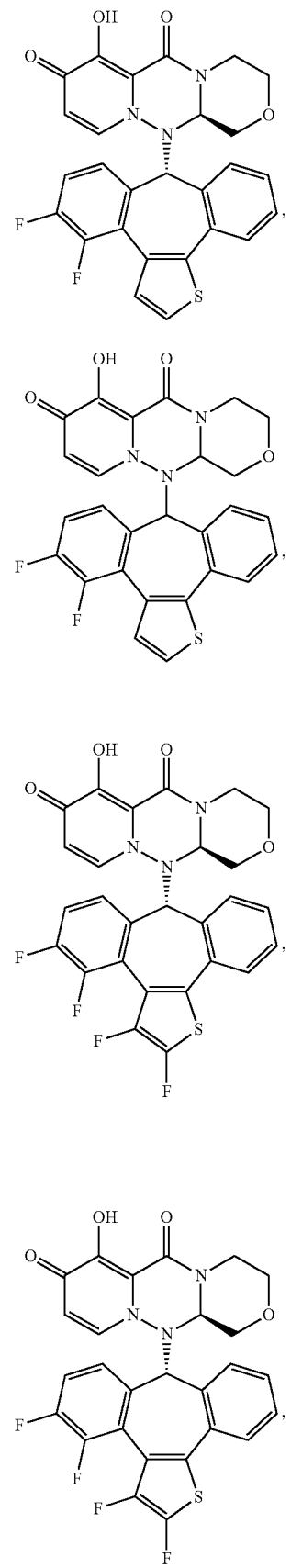
(61)
(62)
(63)
(64)

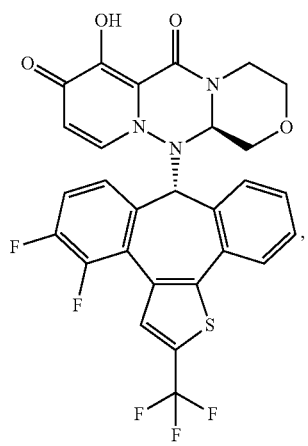
(65)
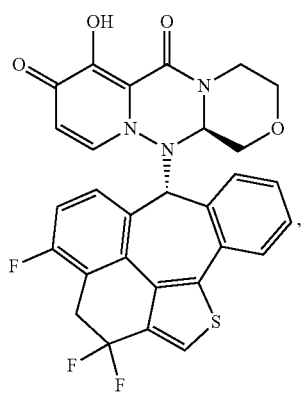
(69)
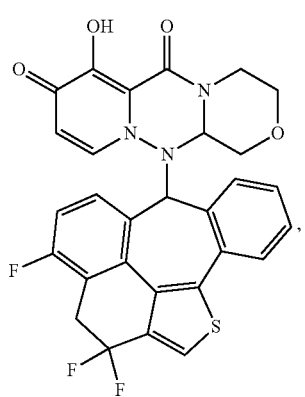
(66)
(70)
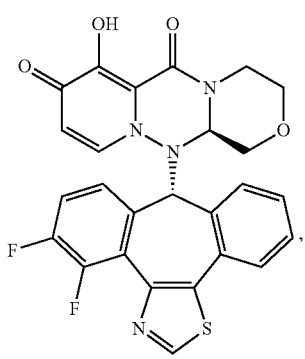
(67)
(71)
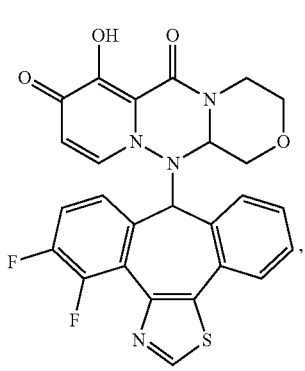
(68)
(72)

391
-continued
(73)
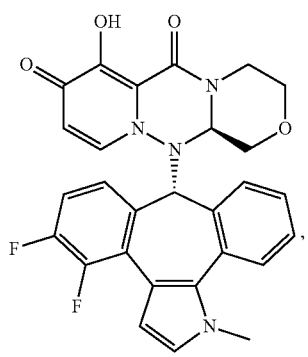
(74)
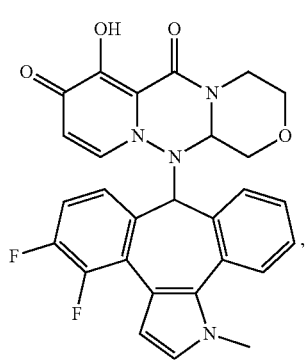
(75)
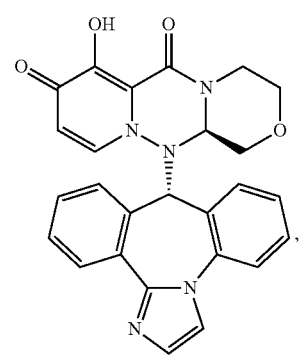
(76)
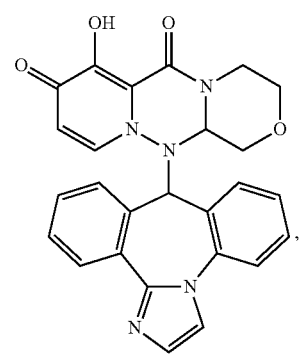
392
-continued
(79)
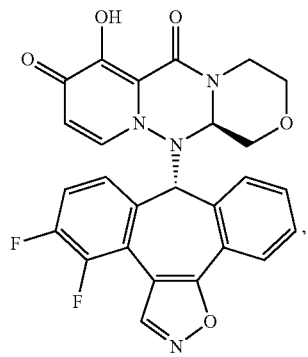
(80)
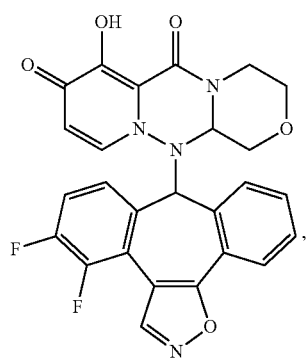
(81)
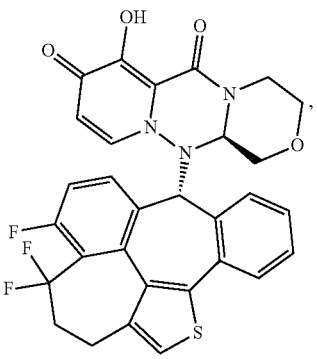
(82)
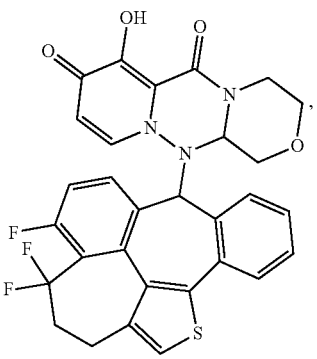

(83) 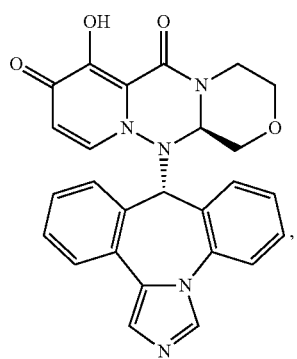
(84) 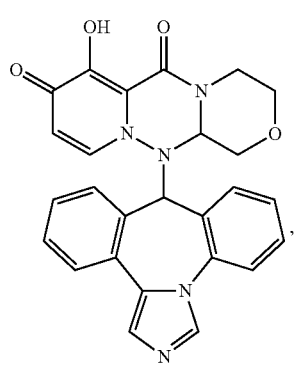
(85) 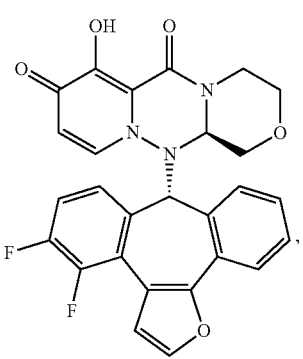
(86) 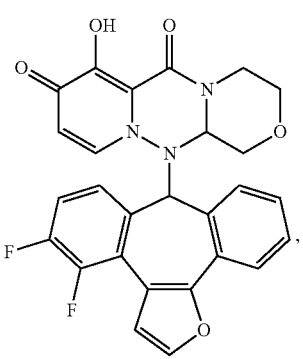
(87) 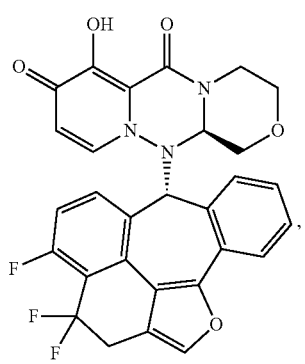
(88) 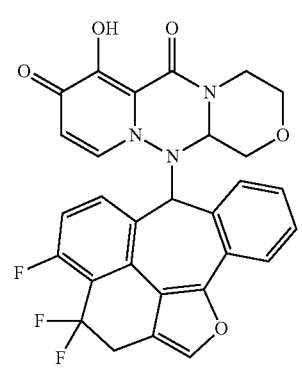
(89) 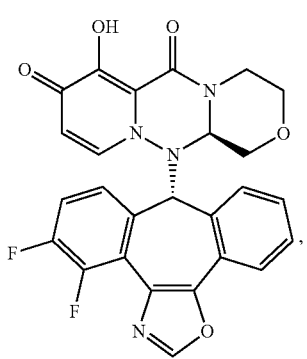
(90) 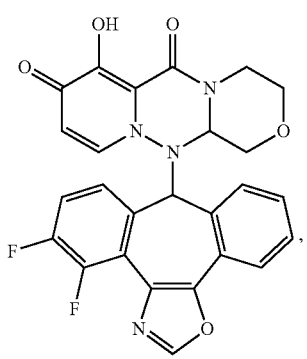

(91) 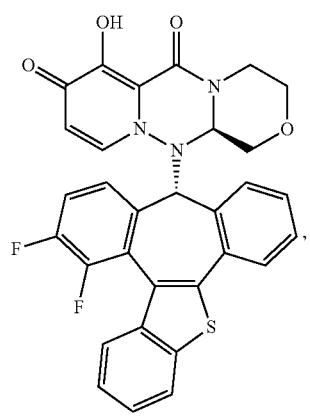
(92) 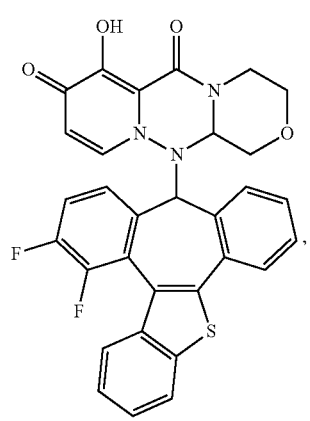
(93) 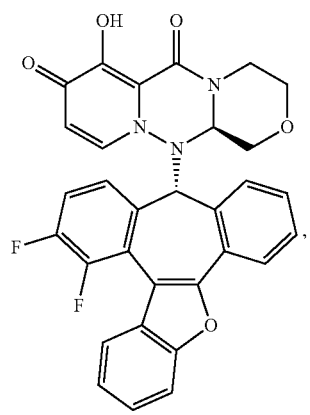
(94) 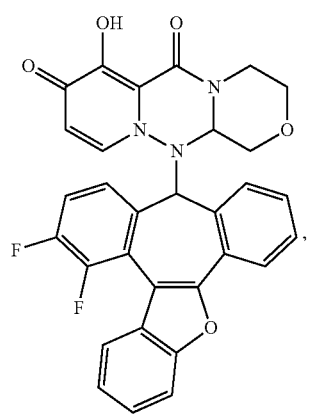
(95) 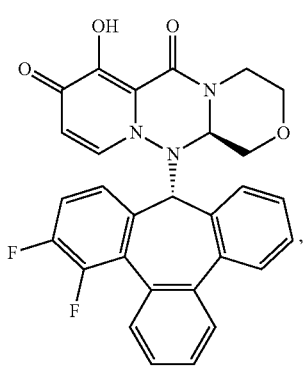
(96) 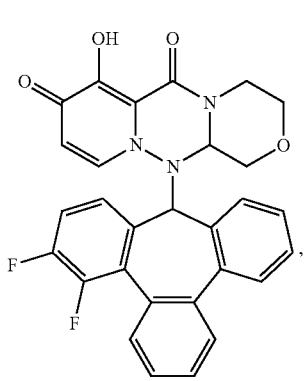
(97) 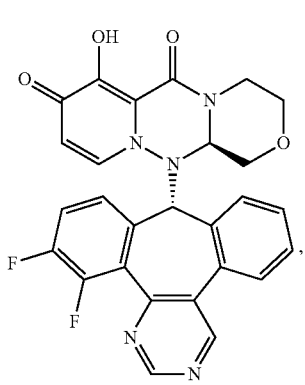
(98) 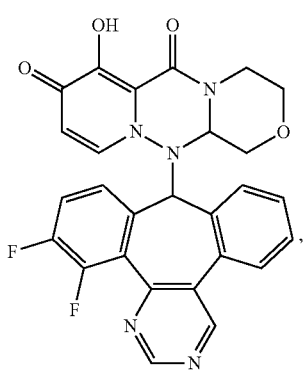

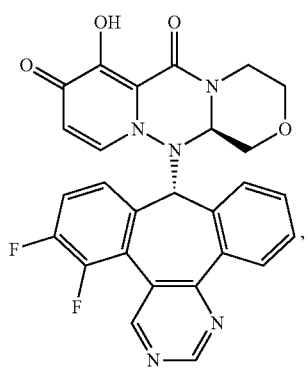
(99)
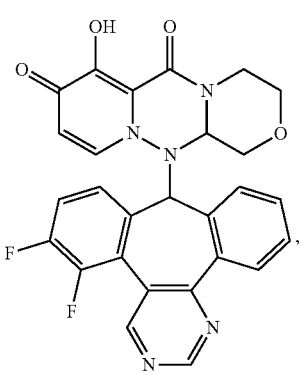
(100)
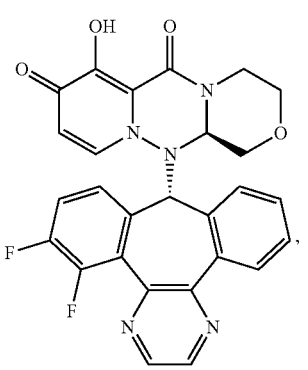
(101)
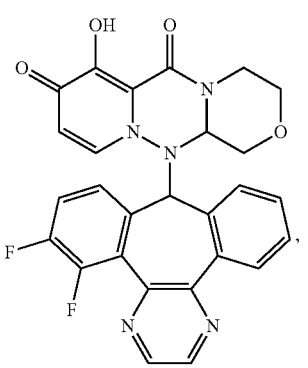
(102)
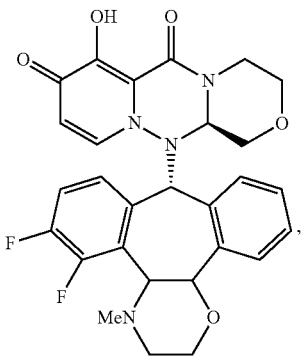
(103)
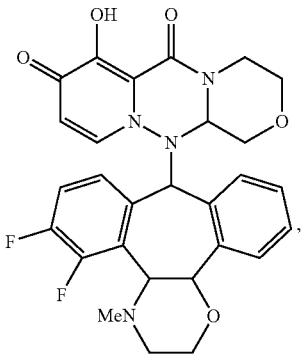
(104)
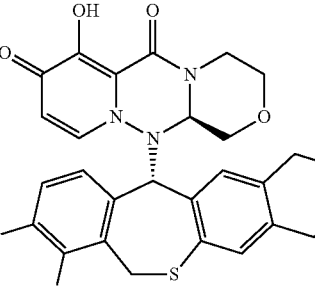
(105)
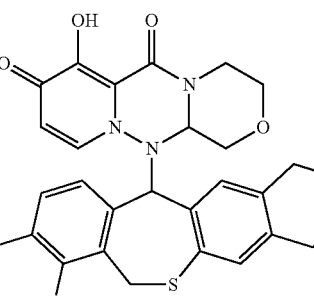
(106)
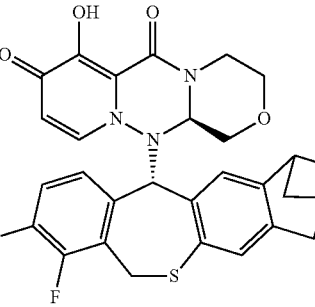
(107)

(108) 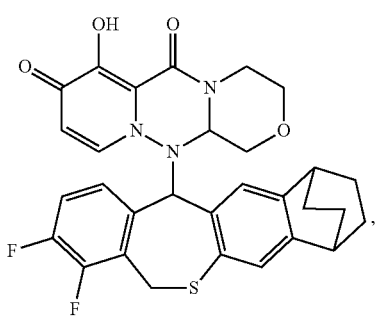
(109) 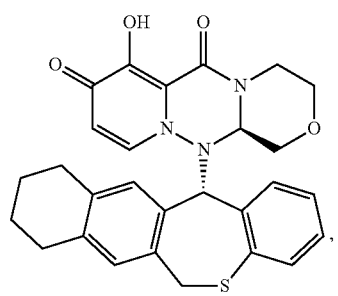
(110) 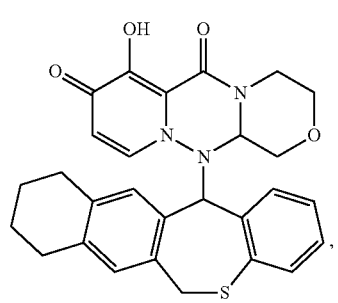
(115) 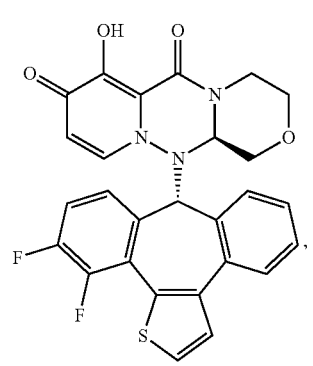
(116) 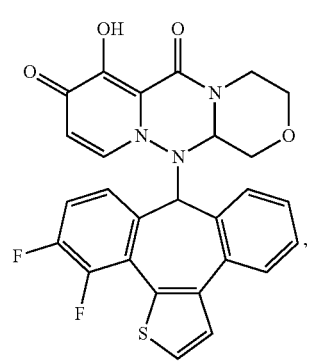
(117) 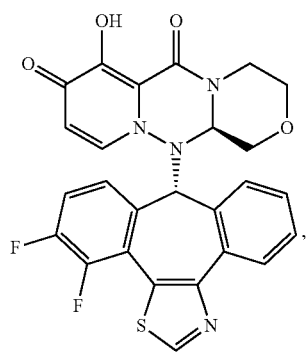
(118) 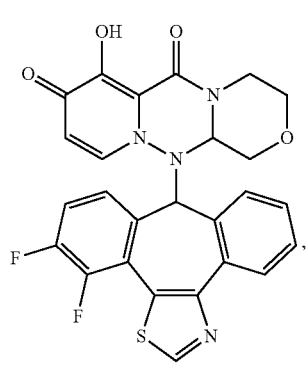
(119) 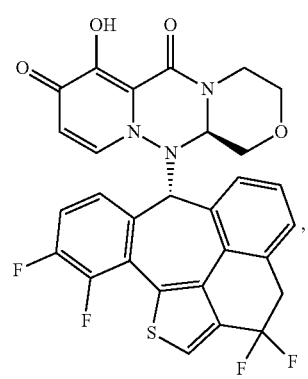
(120) 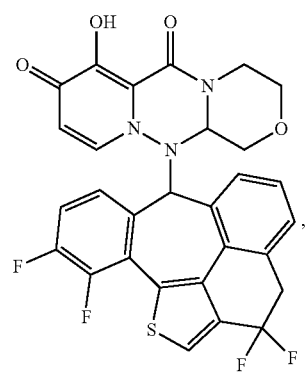

-continued
(123)
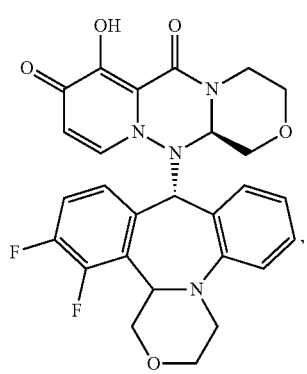
(124)
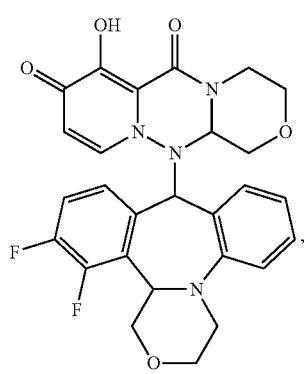
(131)
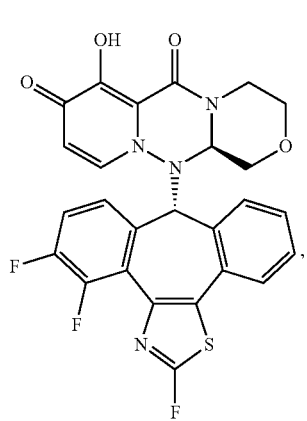
(132)
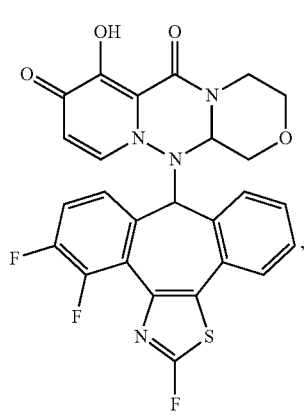
-continued
(133)
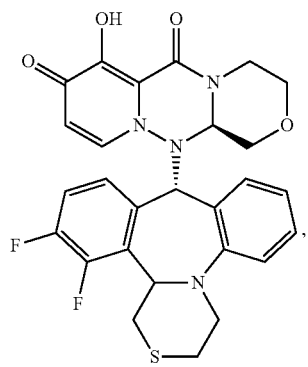
(134)
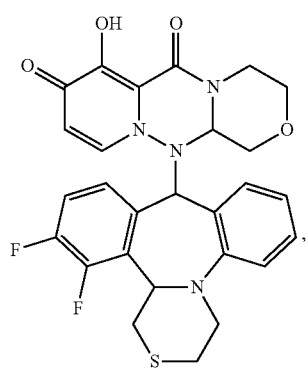
(135)
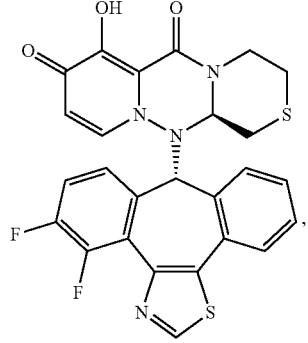
(136)

-continued
(137) 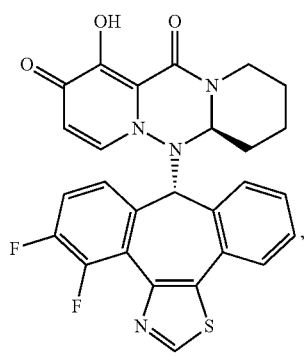
(138) 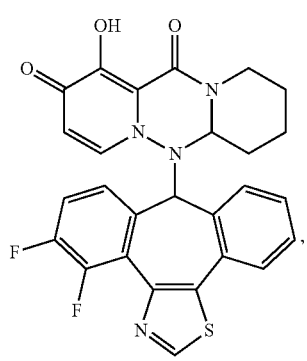
(139) 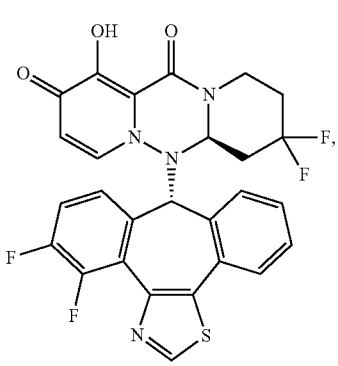
(140) 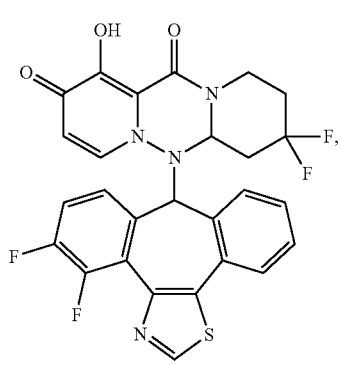
-continued
(141) 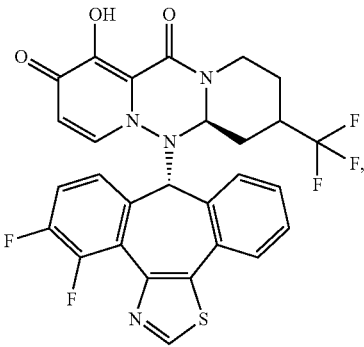
(142) 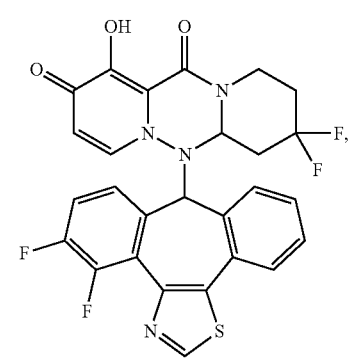
(143) 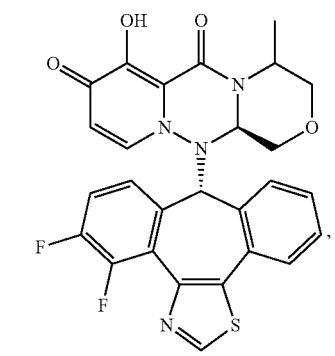
(144) 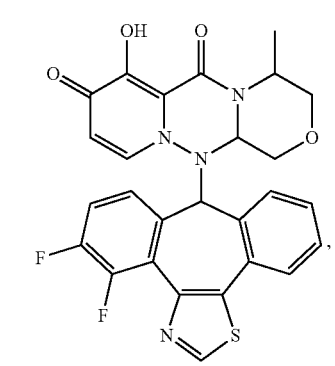

405
-continued
(145)
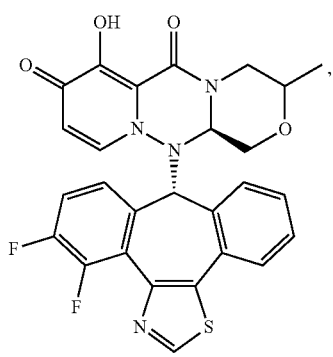
(146)
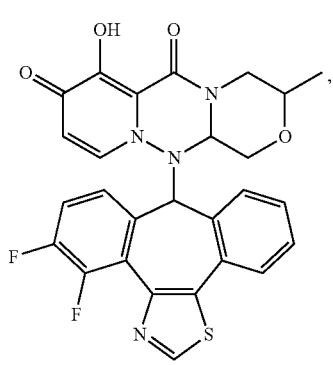
(147)
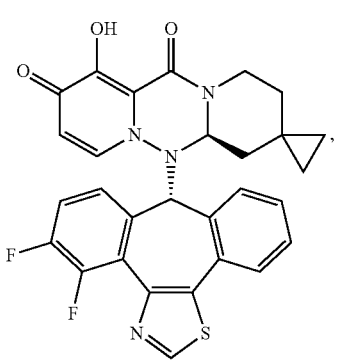
(148)
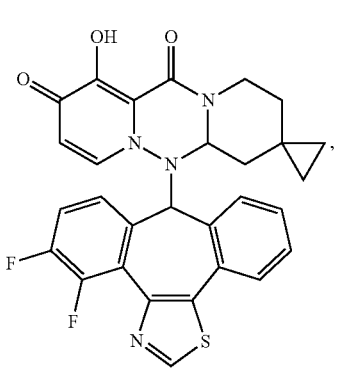
406
-continued
(149)
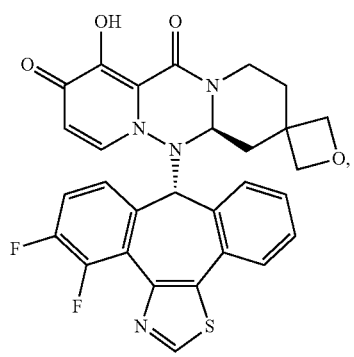
(150)
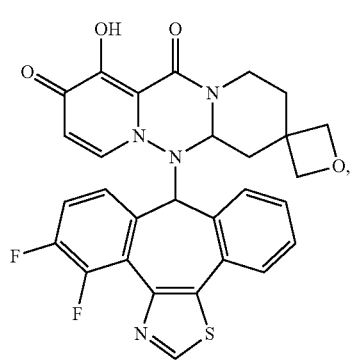
(151)
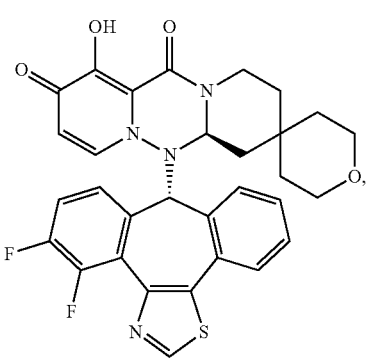
(152)
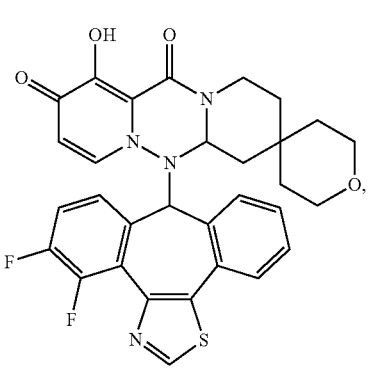

407
-continued
(153)
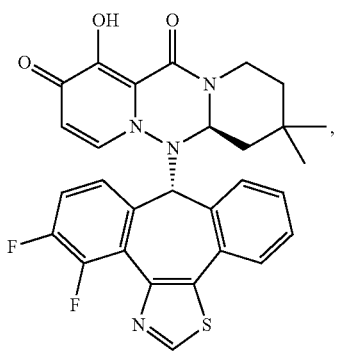
(154)
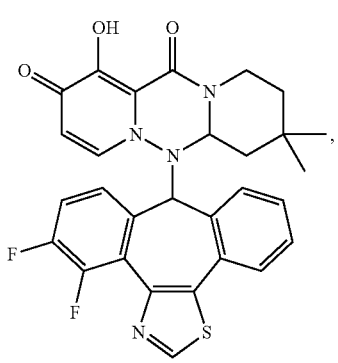
(155)
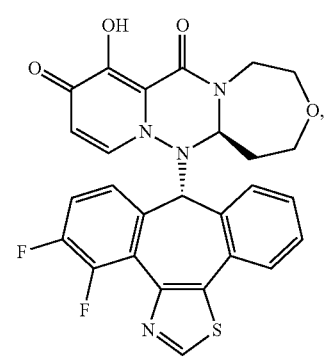
(156)
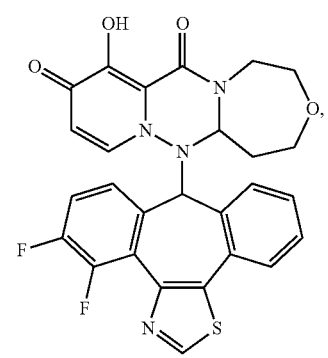
408
-continued
(157)
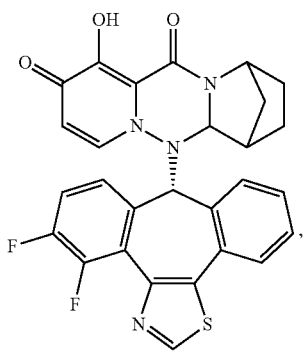
(158)
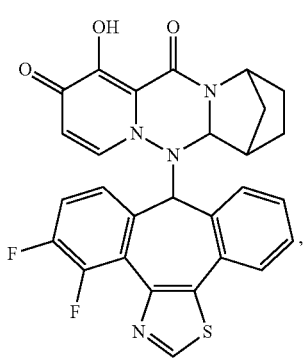
(159)
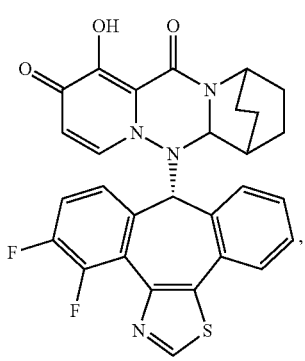
(160)
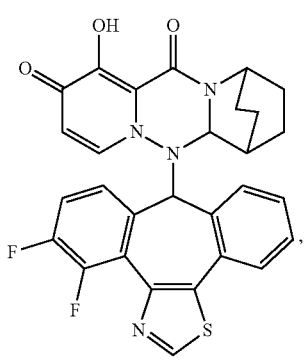

(161) 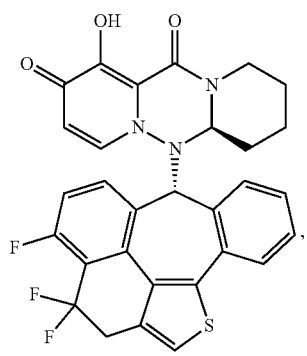
(162) 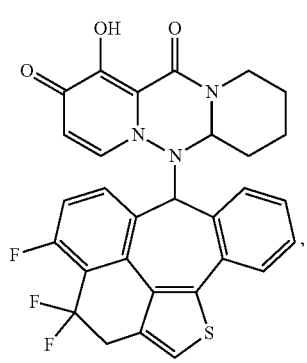
(163) 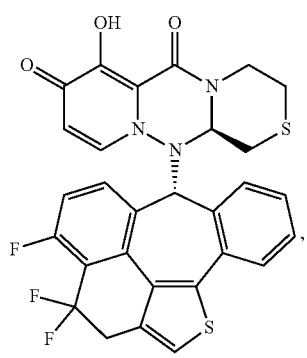
(164) 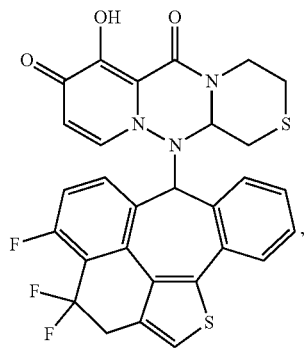
(165) 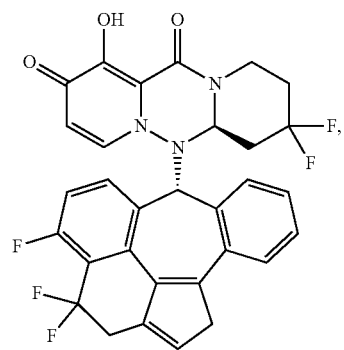
(166) 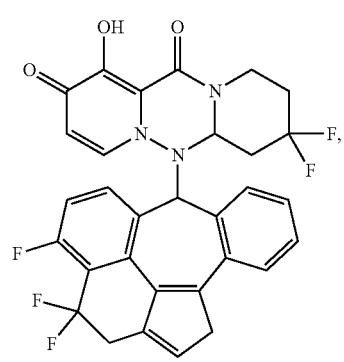
(167) 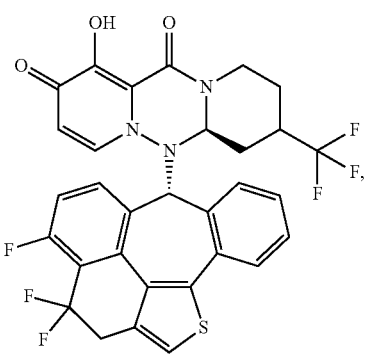
(168) 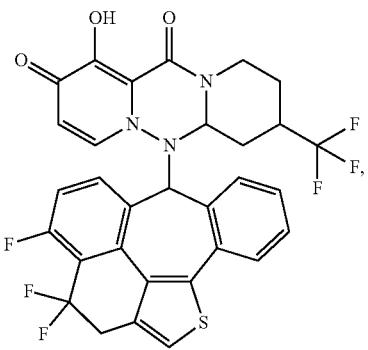

411
-continued
(169)
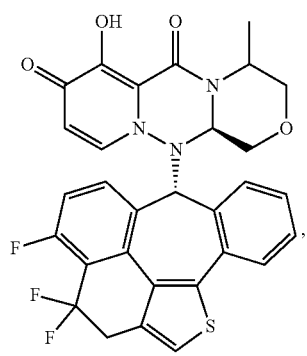
(170)
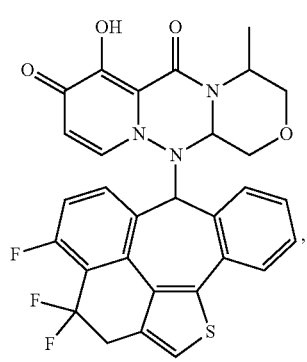
(171)
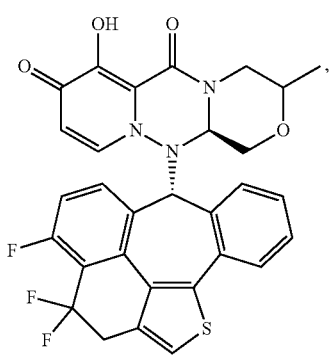
(172)
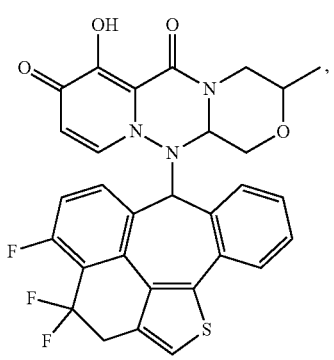
412
-continued
(173)
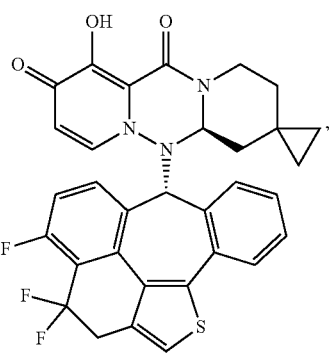
(174)
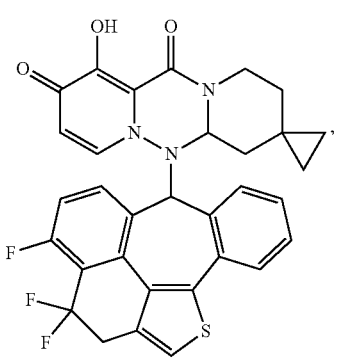
(175)
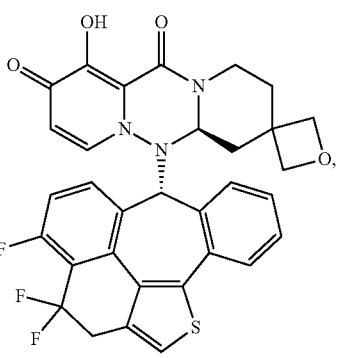
(176)
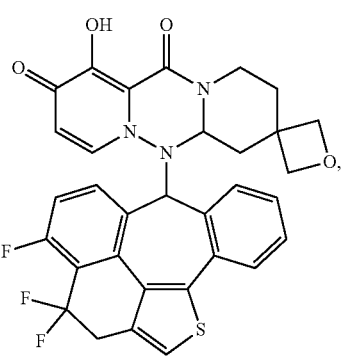

413
-continued
(177)
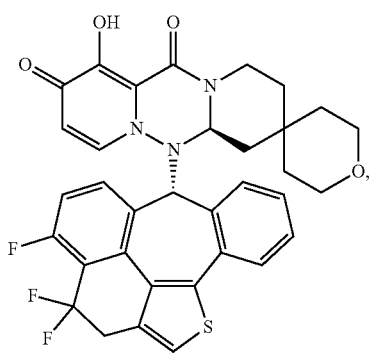
(178)
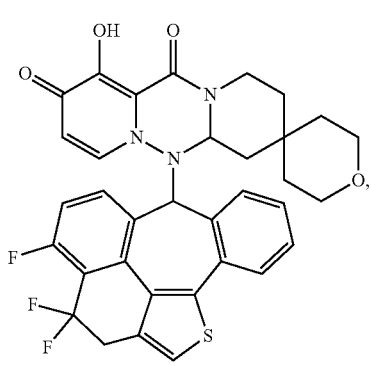
(179)
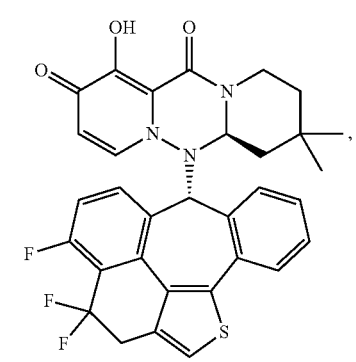
(180)
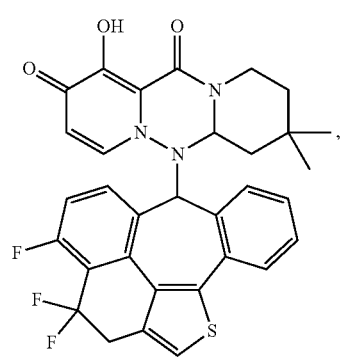
414
-continued
(181)
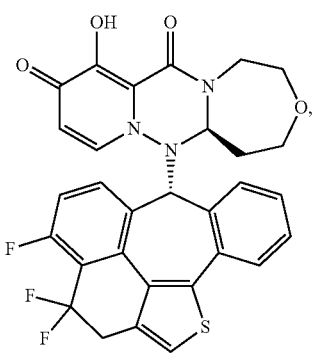
(182)
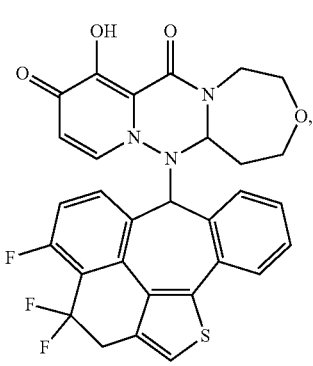
(183)
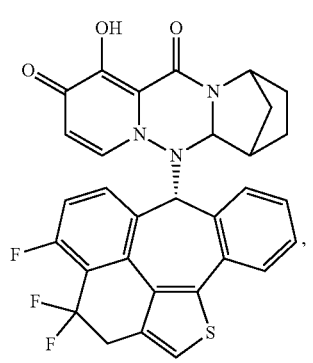
(184)
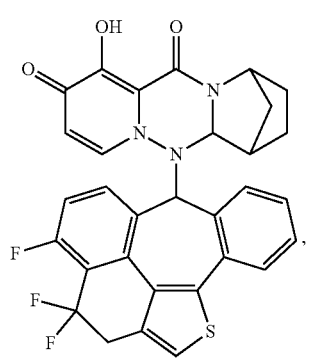

-continued
(185)
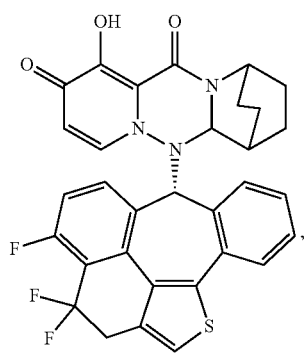
(186)
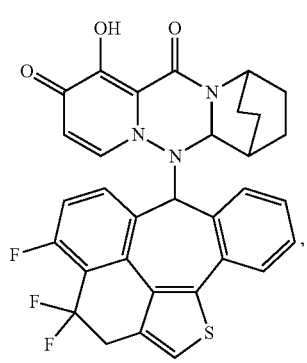
(187)
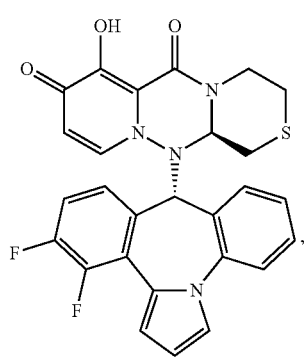
(188)
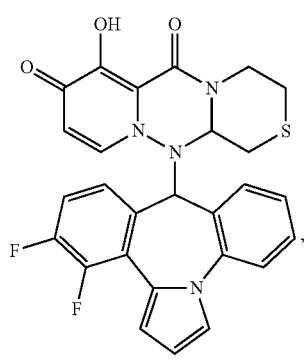
-continued
(189)
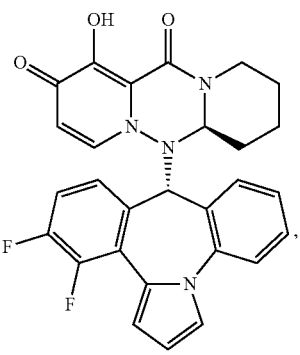
(190)
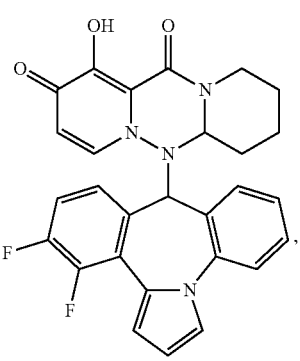
(191)
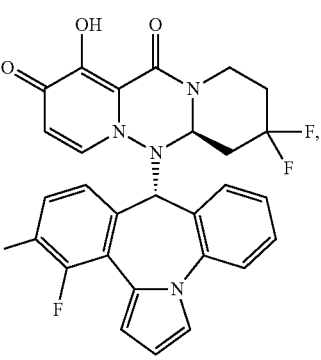
(192)
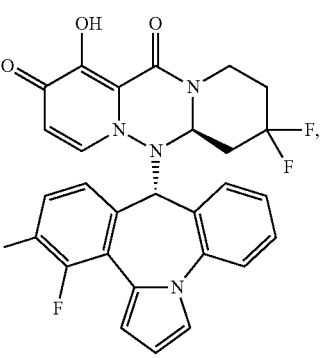

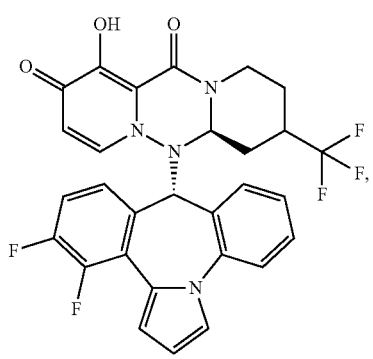
(193)
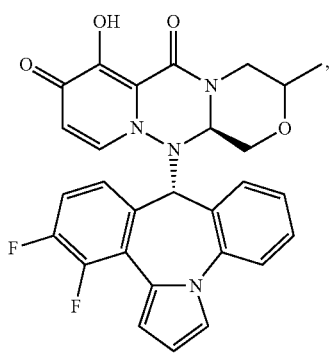
(201)
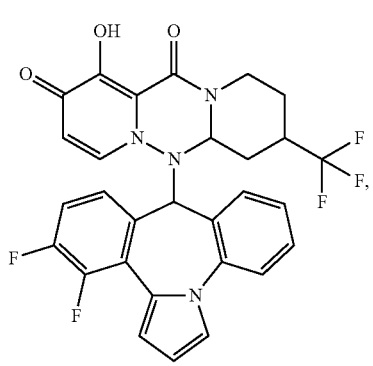
(194)
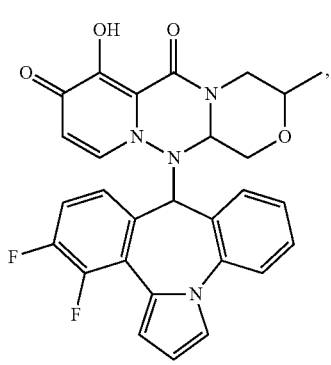
(202)
(199)
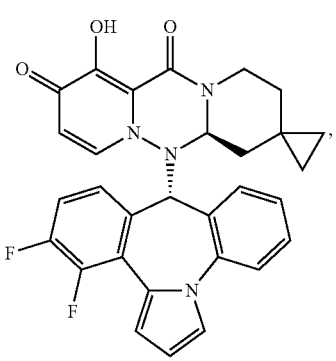
(203)
(200)
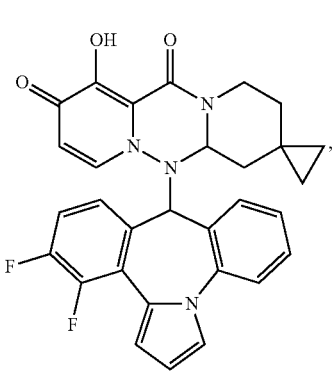
(204)

-continued
(205)
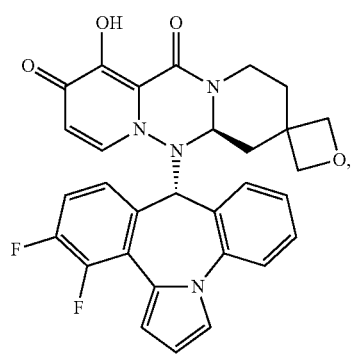
(206)
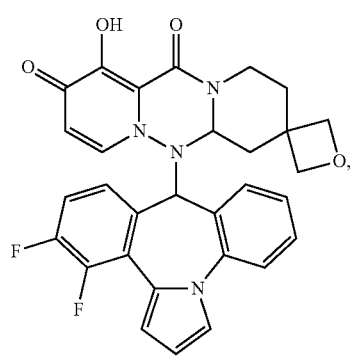
(207)
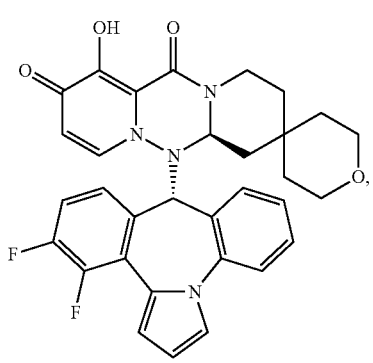
(208)
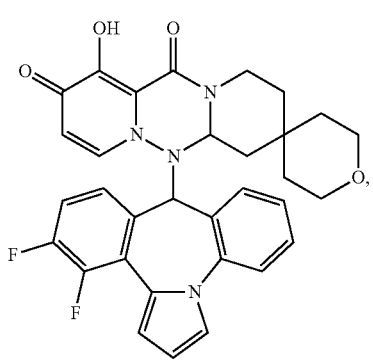
-continued
(209)
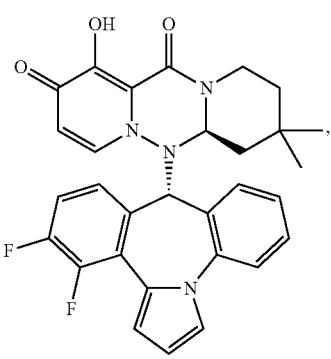
(210)
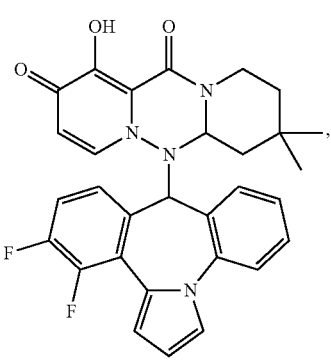
(211)
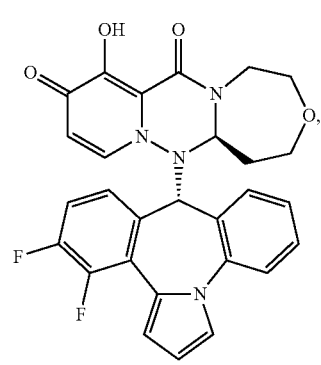
(212)
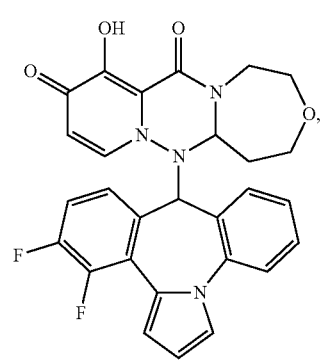

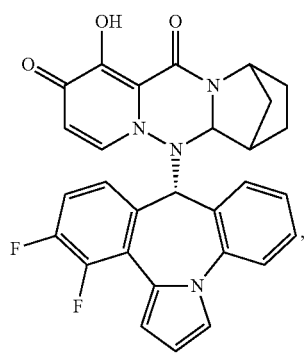
(213)
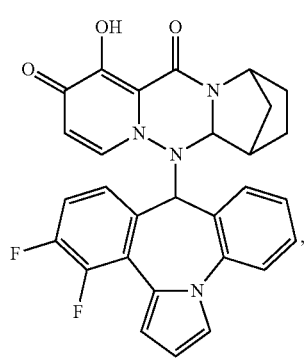
(214)
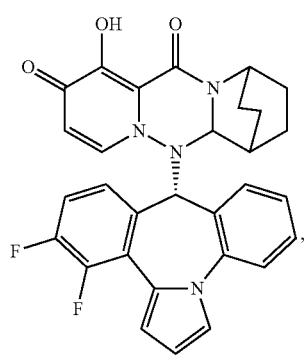
(215)
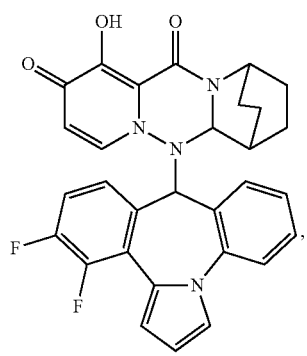
(216)
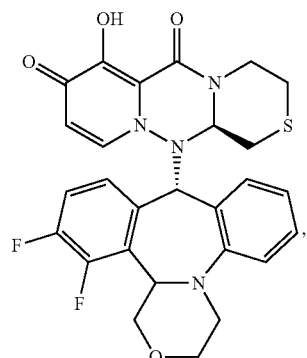
(217)
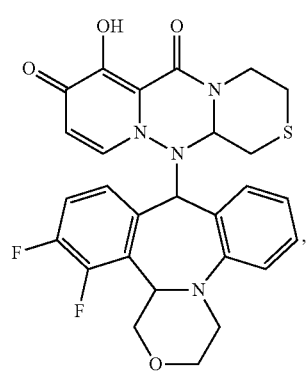
(218)
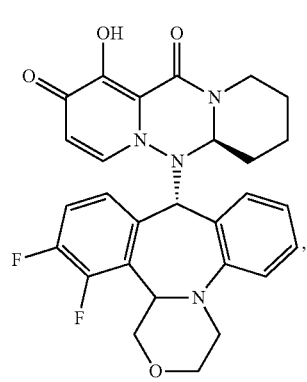
(219)
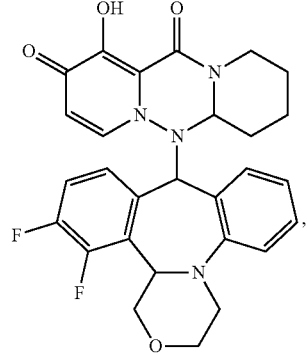
(220)

423
-continued
(221)
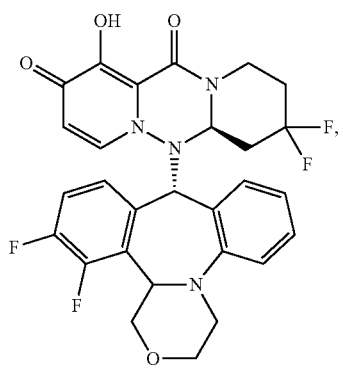
(222)
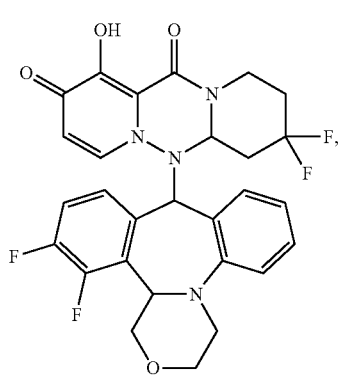
(223)
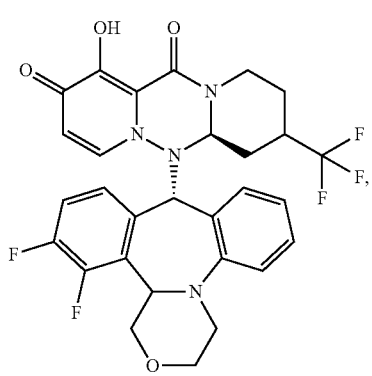
(224)
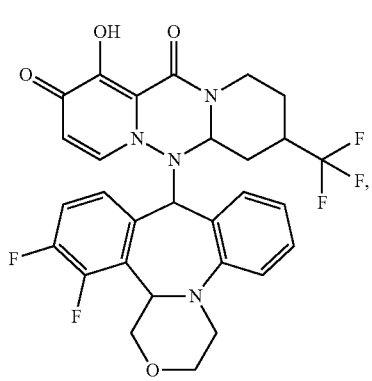
424
-continued
(225)
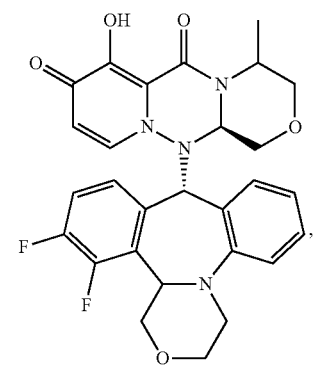
(226)
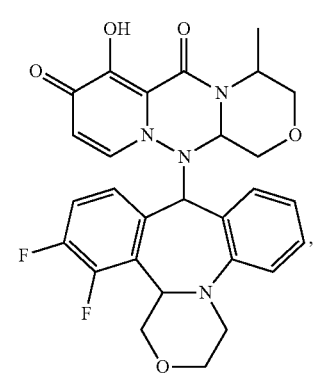
(227)
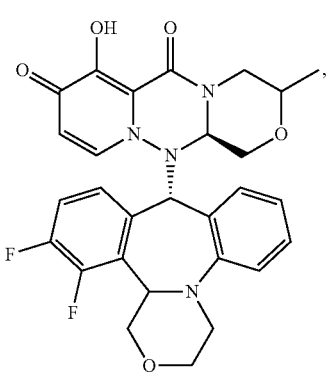
(228)
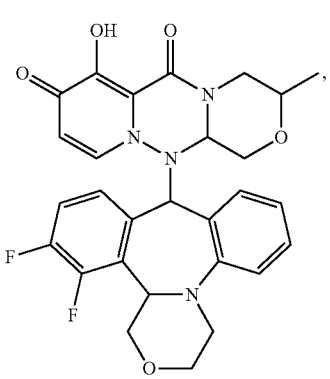

(229) 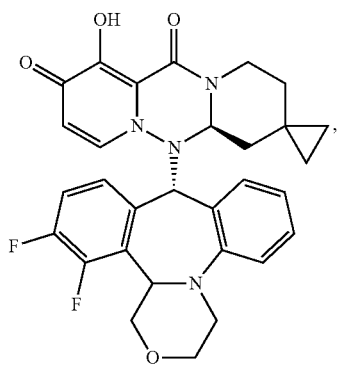
(230) 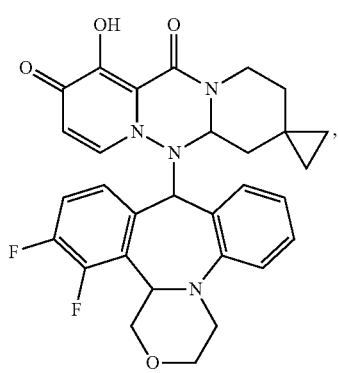
(231) 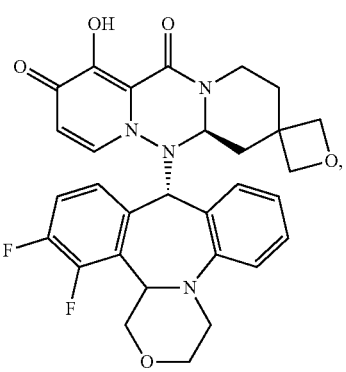
(232) 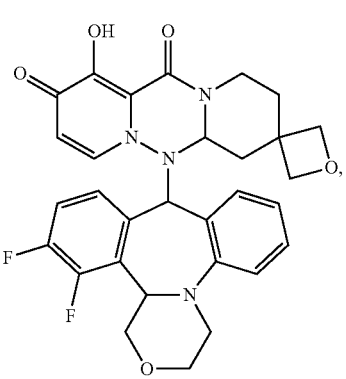
(233) 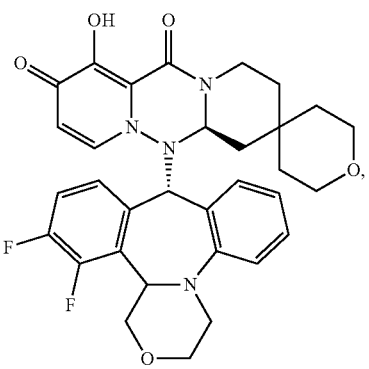
(234) 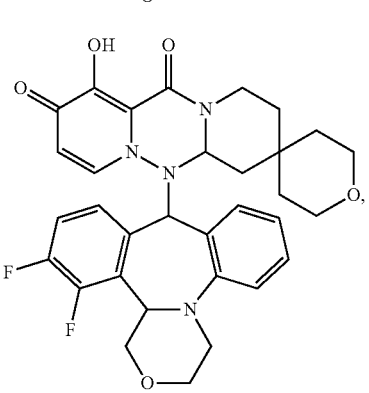
(235) 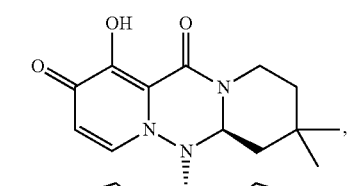
(236)

427
-continued
(237)
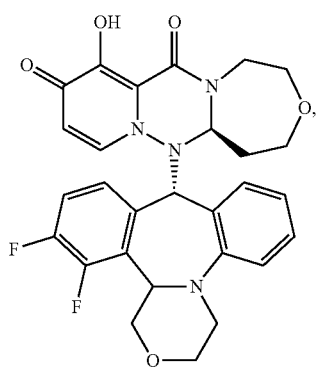
(238)
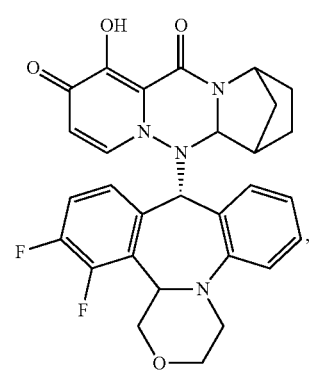
(239)
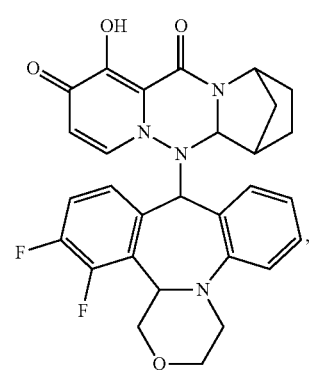
(240)
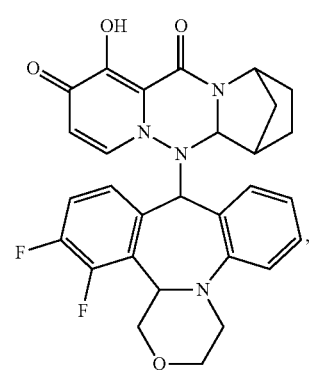
428
-continued
(241)
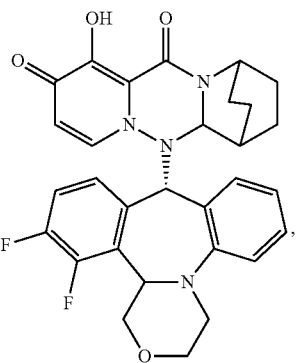
(242)
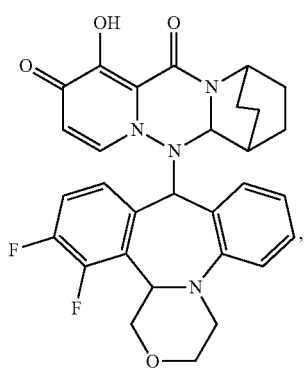
(249)
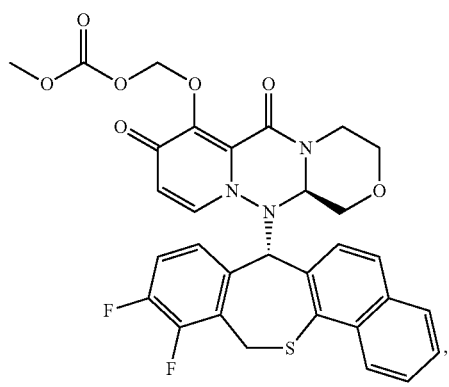
(250)
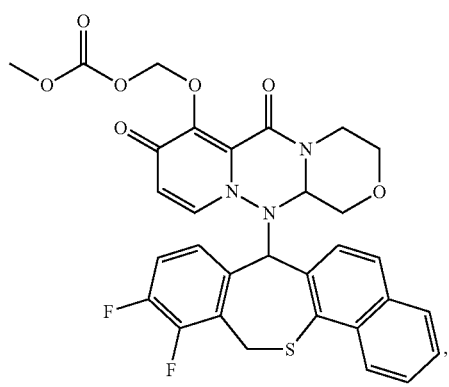

429
-continued
(263)
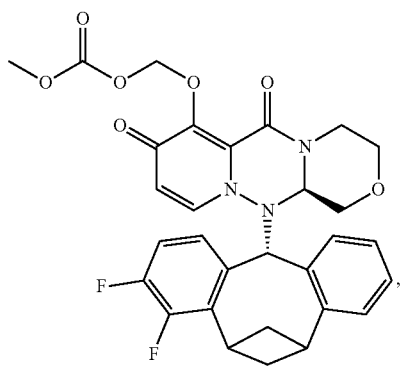
(264)
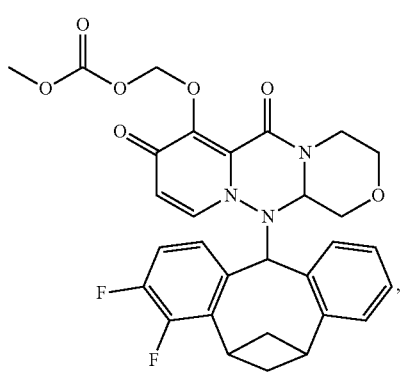
(267)
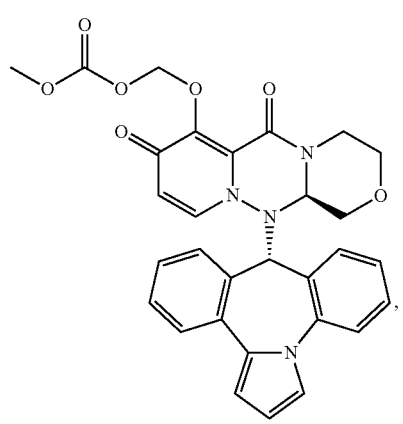
(268)
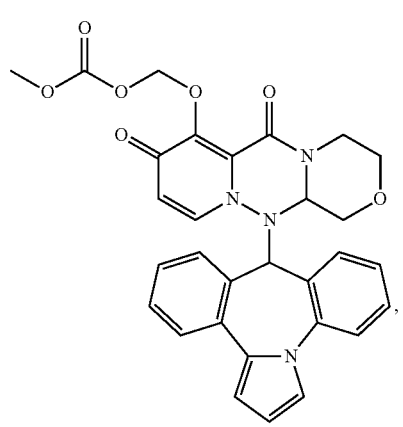
430
-continued
(271)
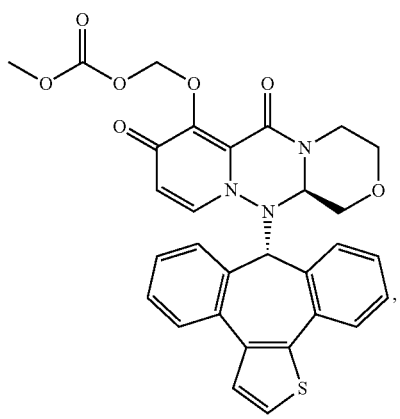
(272)
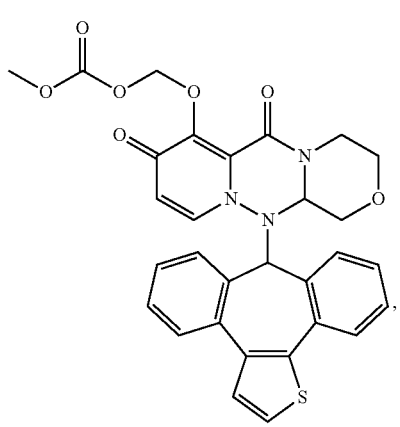
(273)
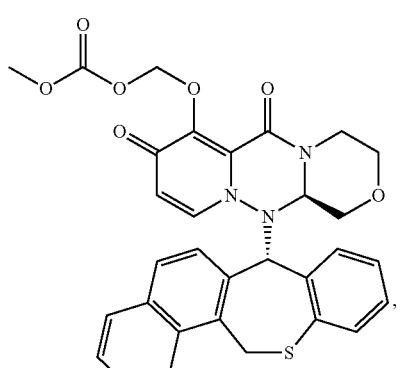
(274)
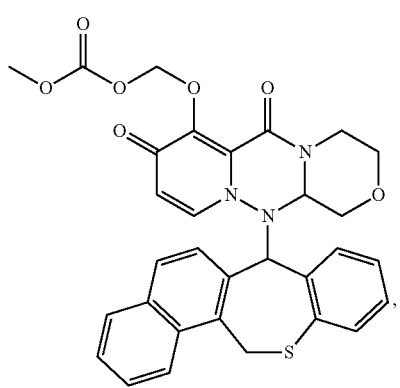

431
-continued
(275)
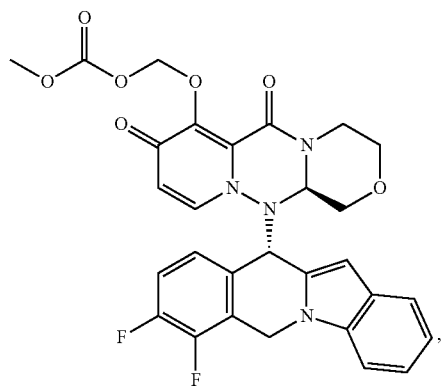
(276)
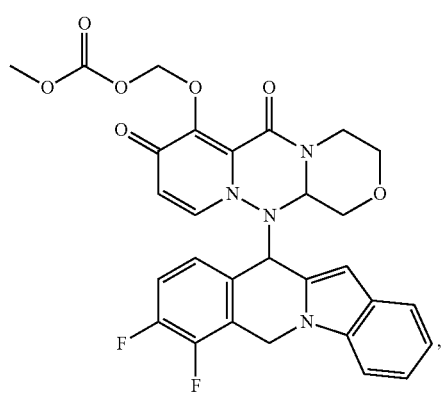
(285)
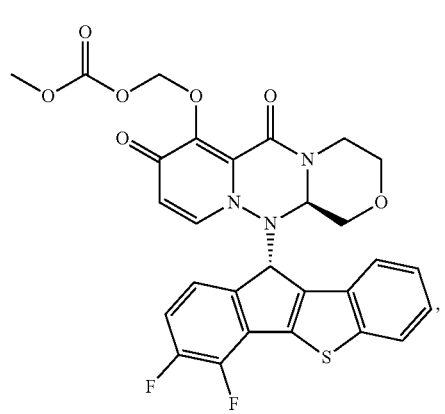
(286)
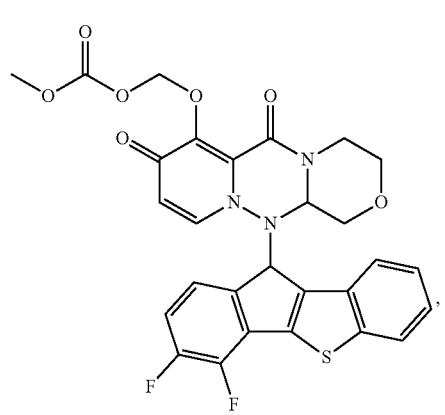
432
-continued
(287)
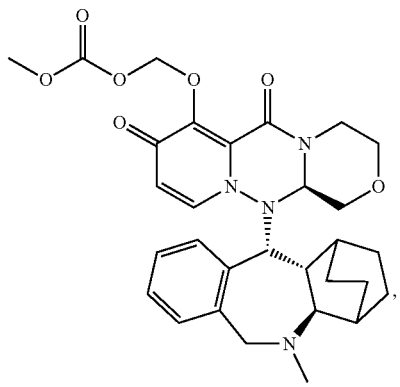
(288)
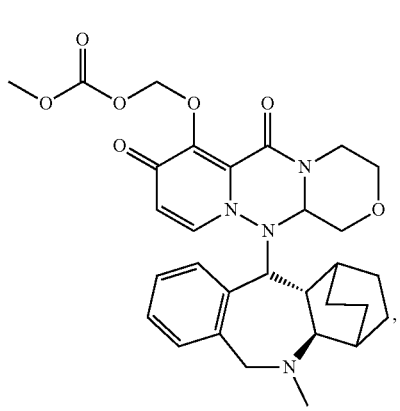
(293)
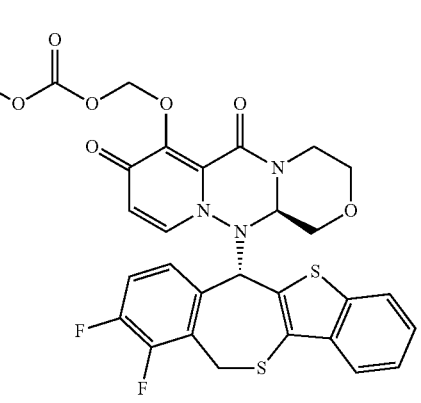
(294)
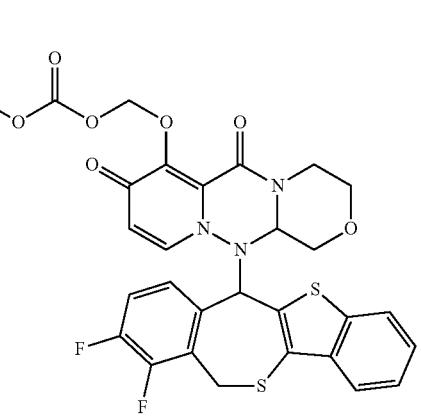

433
-continued
(295) 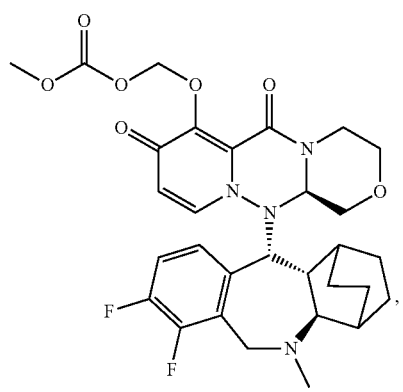
(296) 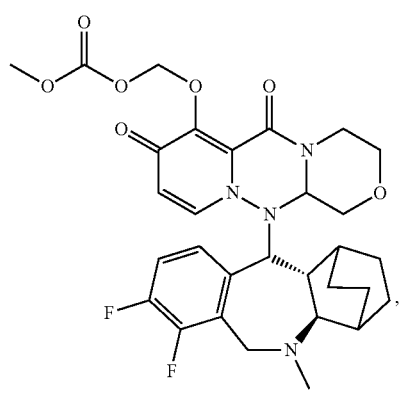
(303) 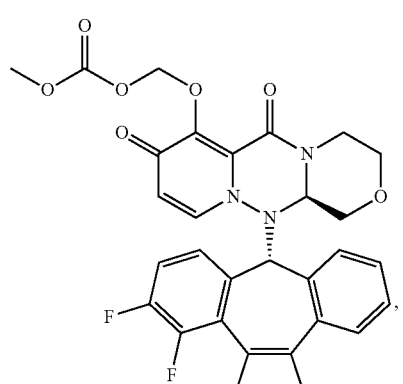
(304) 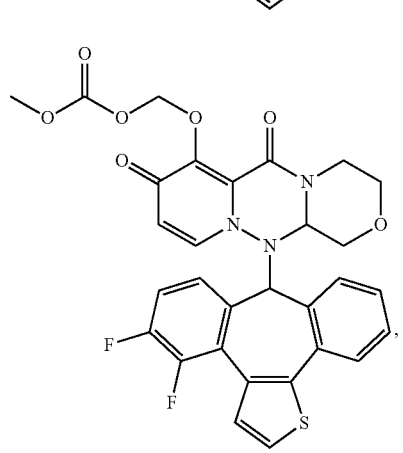
434
-continued
(305)
(306)
(307)

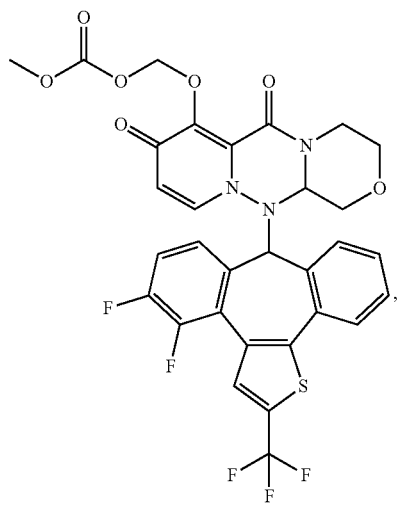
(308)
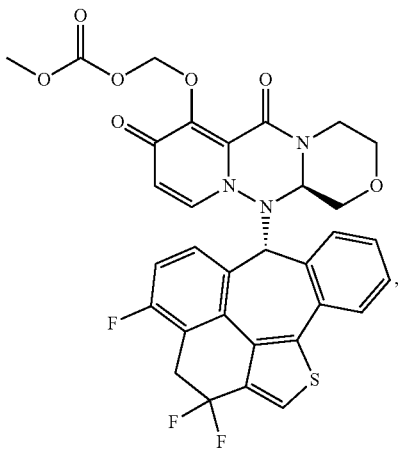
(311)
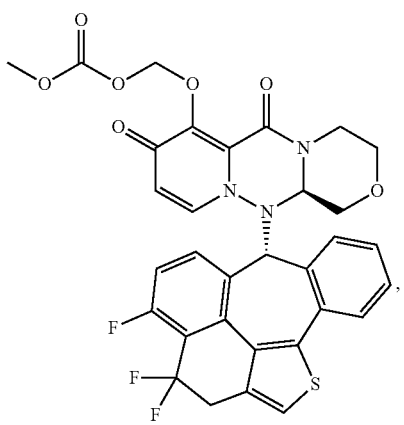
(309)
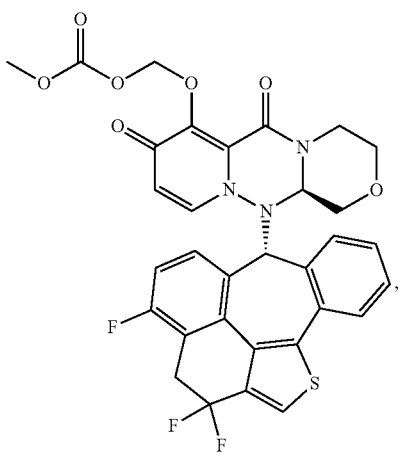
(312)
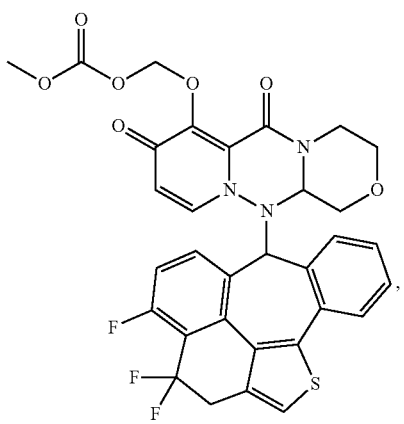
(310)
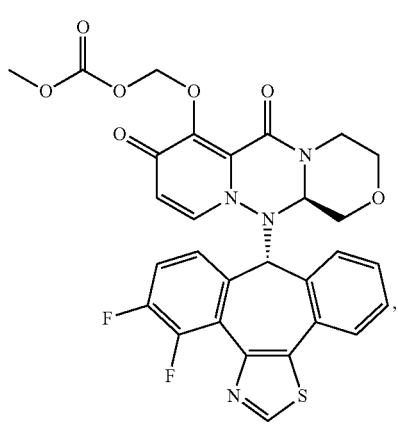
(313)

437
-continued
(314)
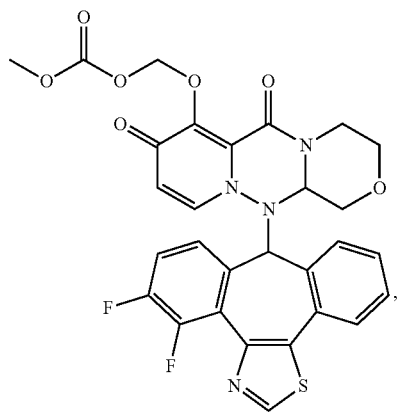
(315)
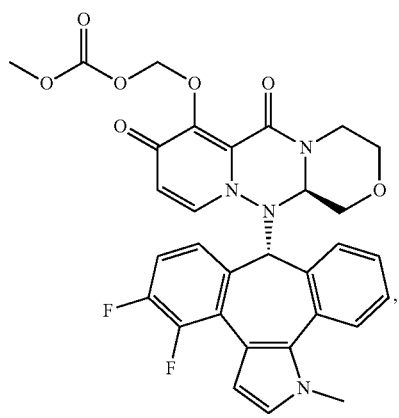
(316)
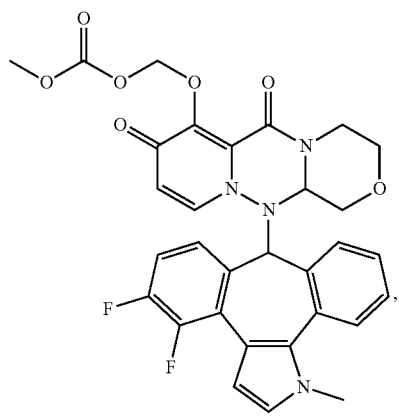
(317)
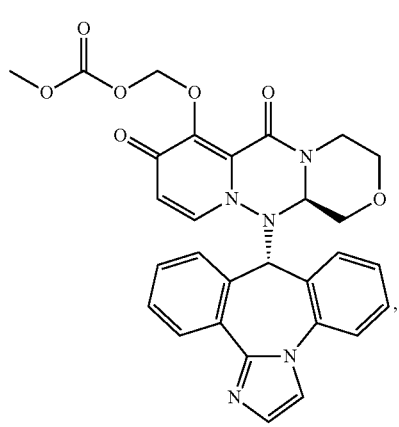
438
-continued
(318)
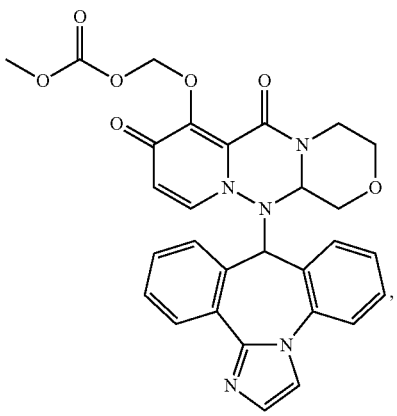
(321)
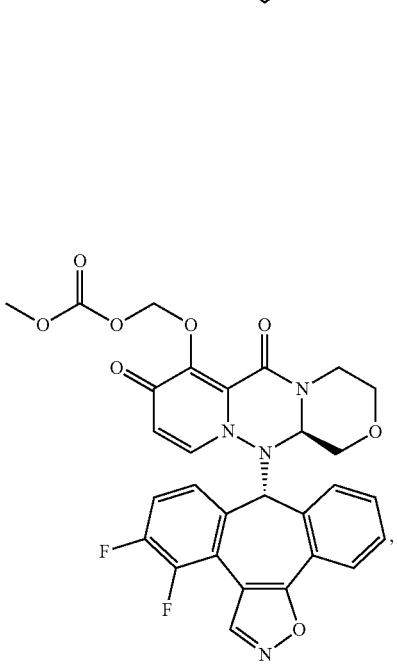
(322)
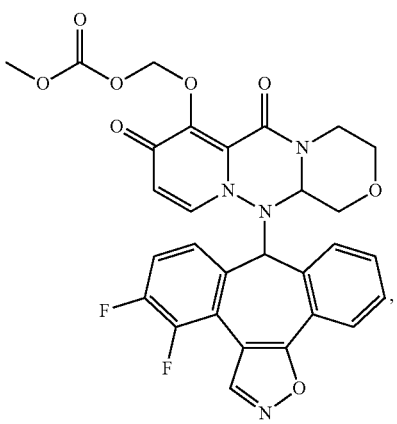

439
-continued
(323)
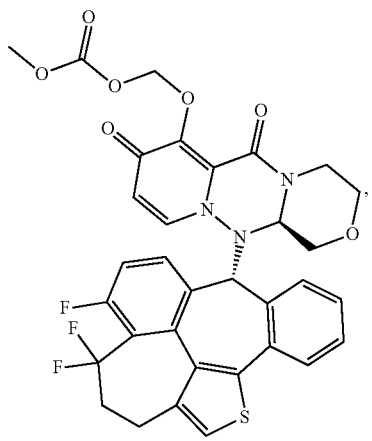
(324)
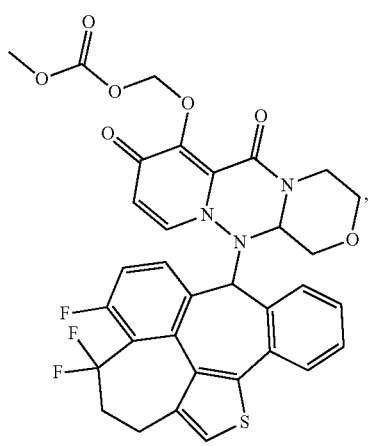
(325)
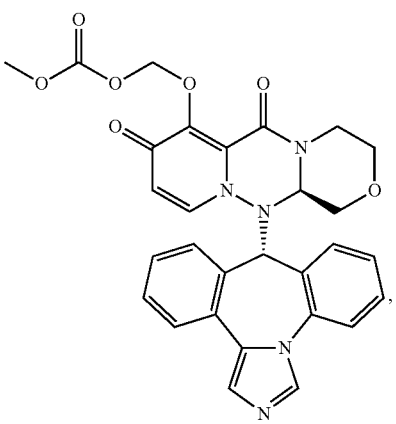
440
-continued
(326)
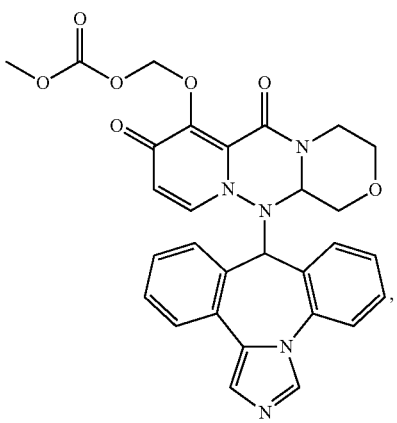
(327)
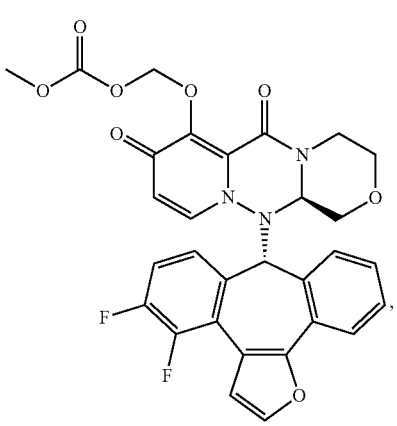
(328)
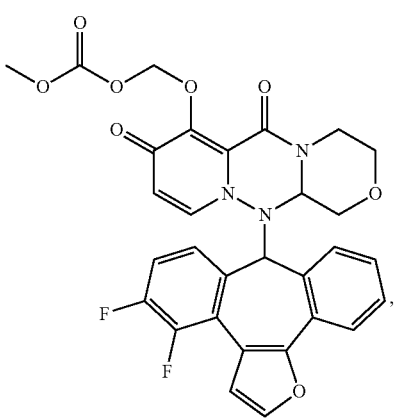

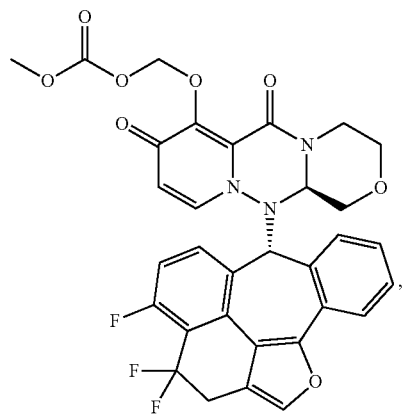
(329)
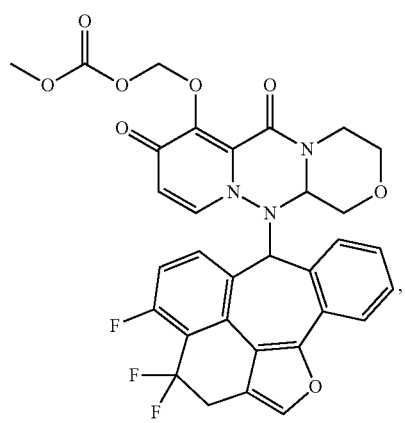
(330)
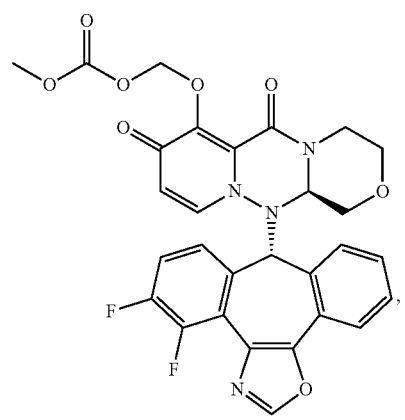
(331)
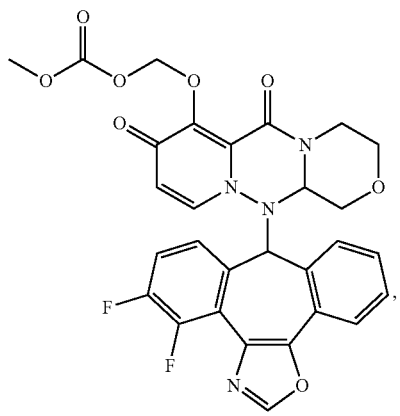
(332)
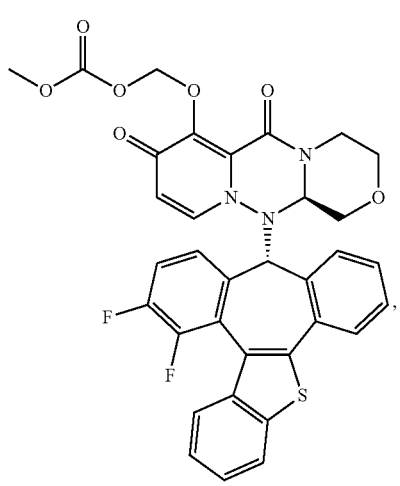
(333)
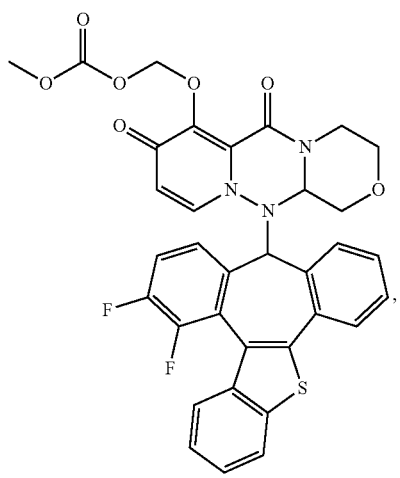
(334)

443
-continued
(335)
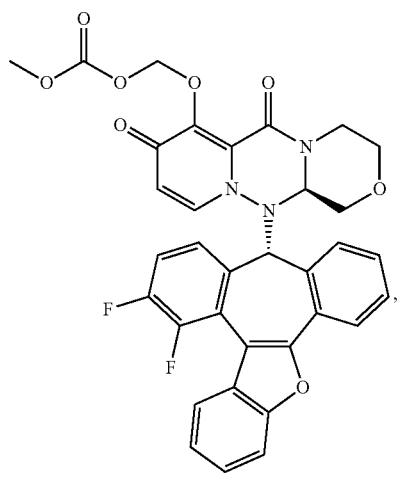
(336)
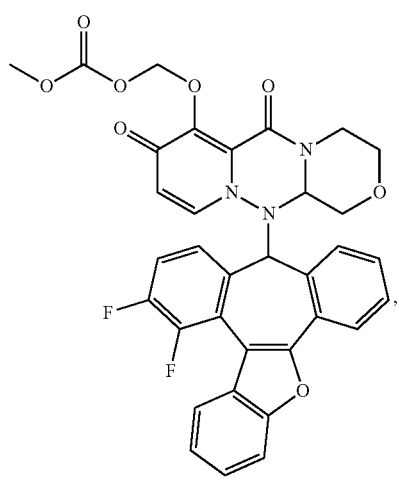
(337)
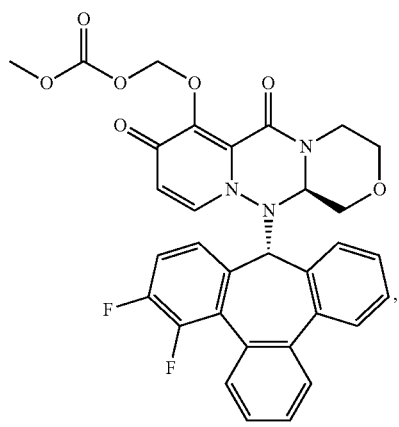
444
-continued
(338)
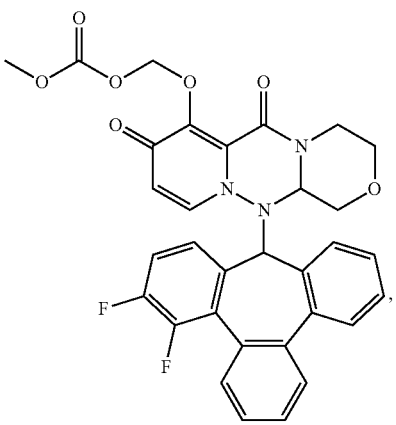
(339)
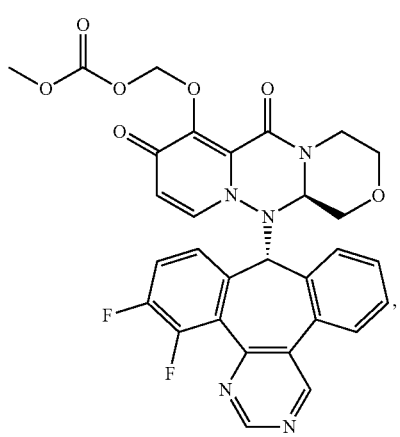
(340)
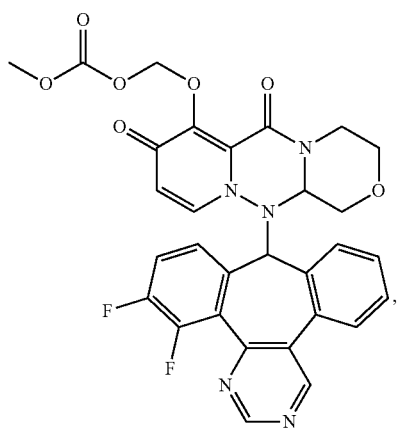

445
-continued
(341)
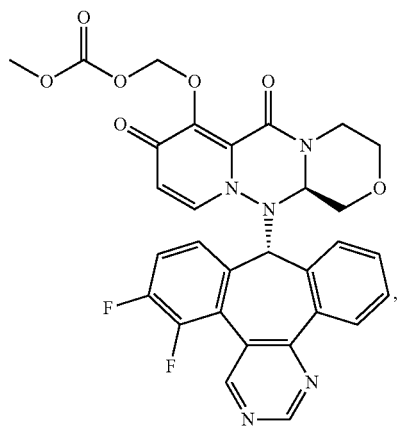
(342)
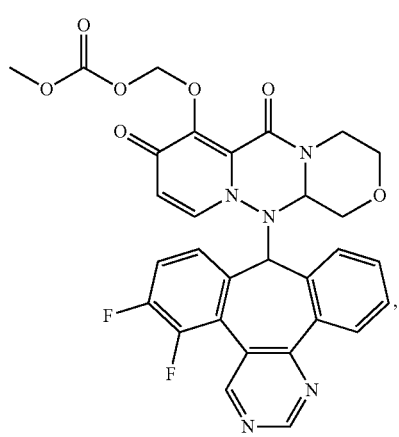
(343)
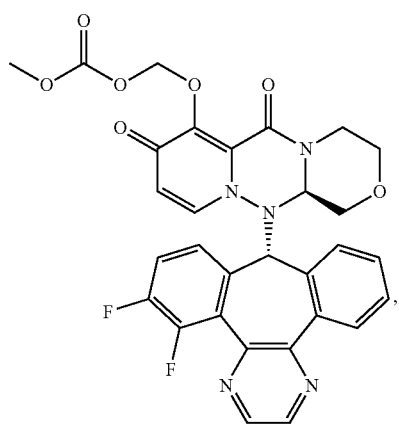
446
-continued
(344)
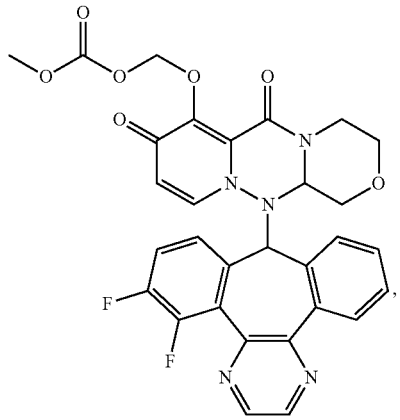
(345)
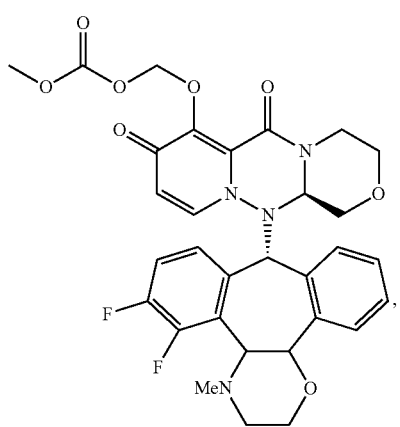
(346)
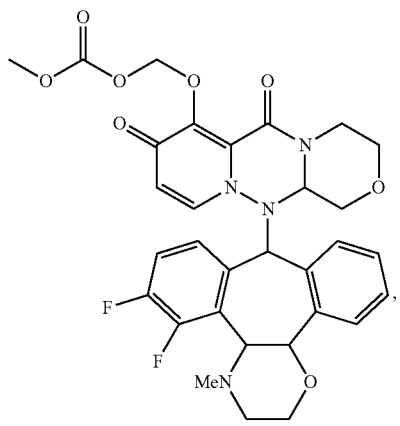
(347)
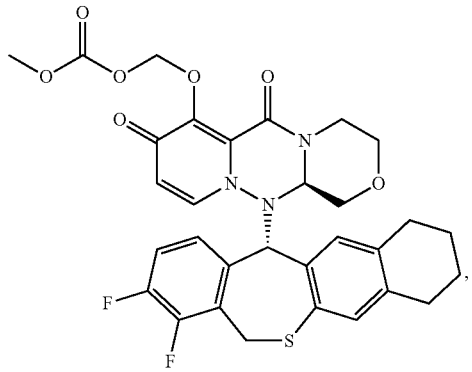

(348)
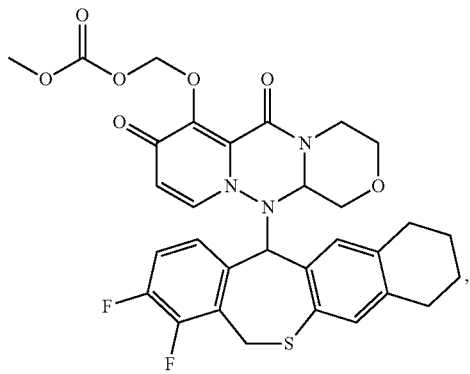
(349)
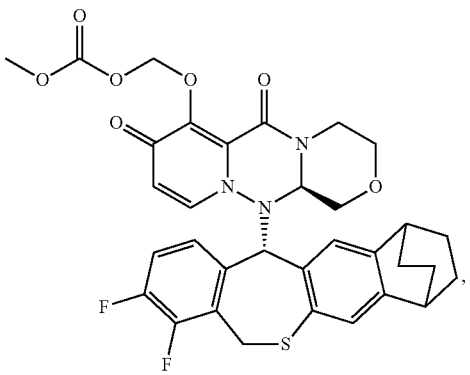
(350)
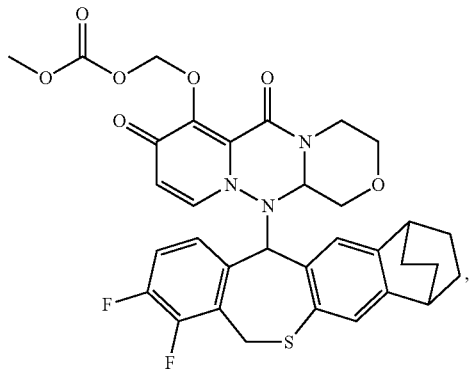
(351)
(352)
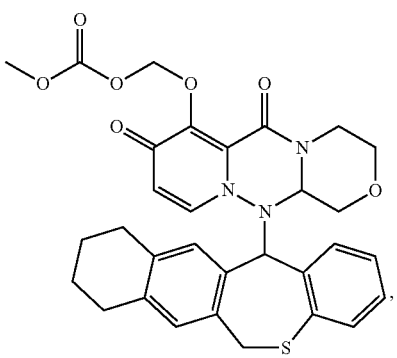
(357)
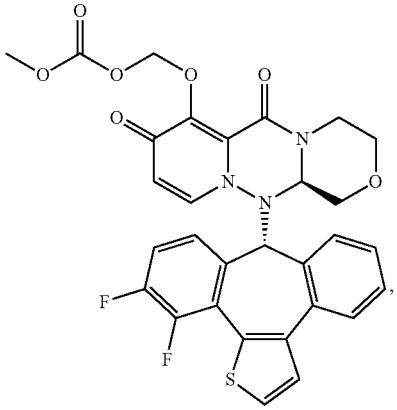
(358)
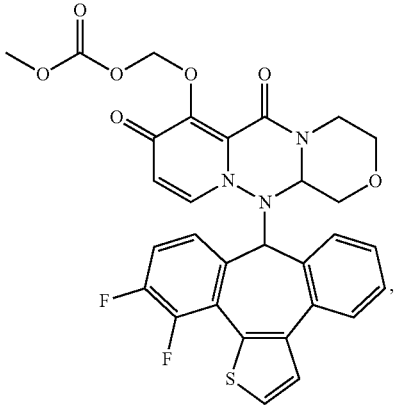
(359)
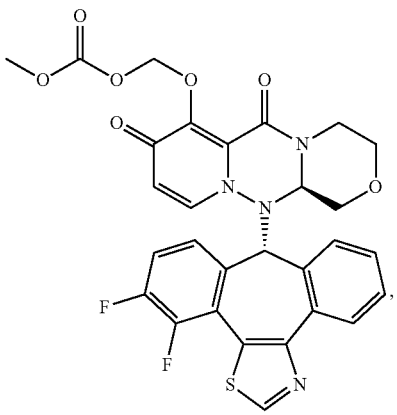

449
-continued
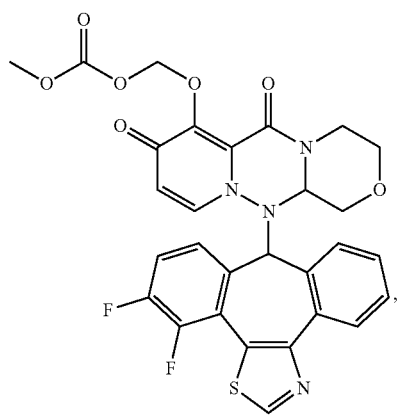
(360)
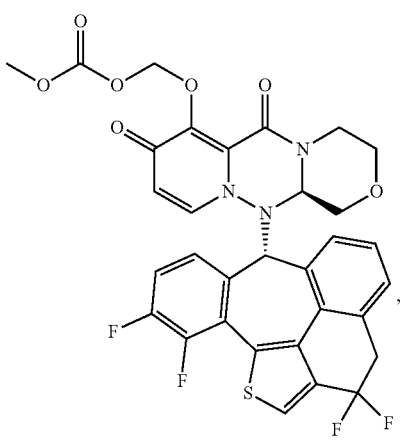
(361)
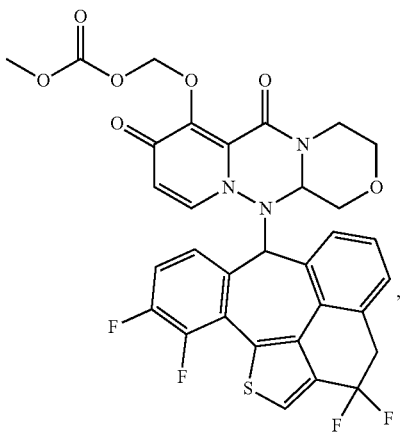
(362)
450
-continued
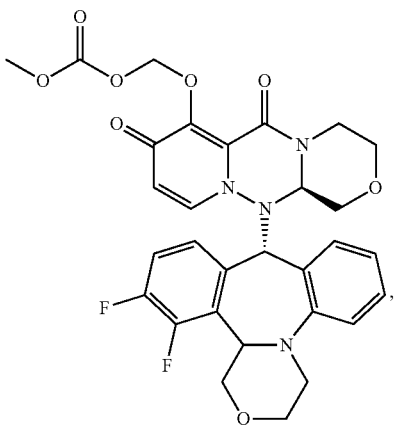
(365)
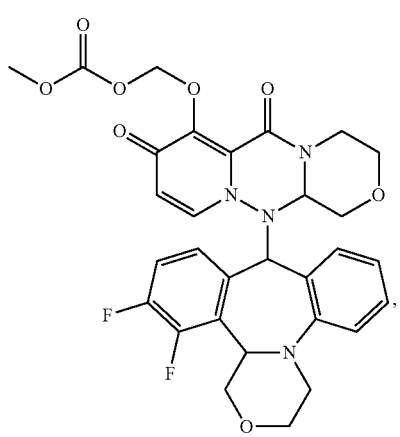
(366)
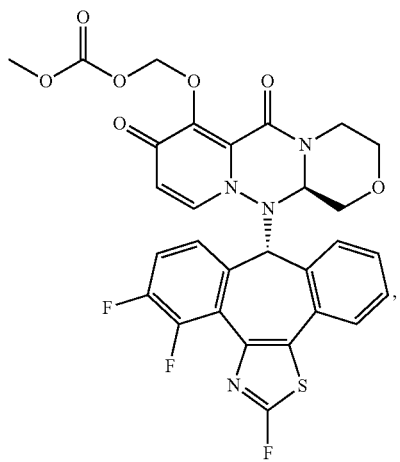
(373)

451
-continued
(374)
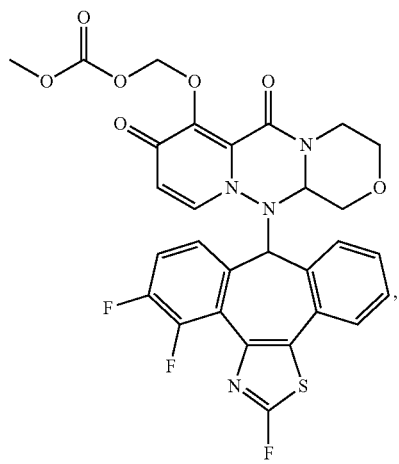
(375)
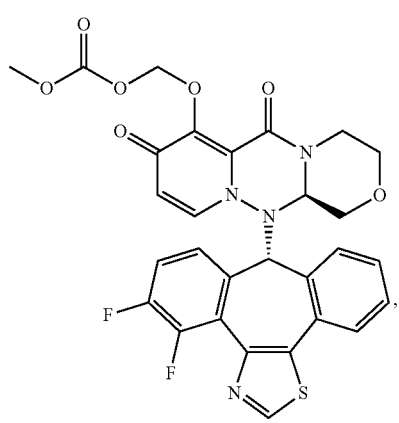
(376)
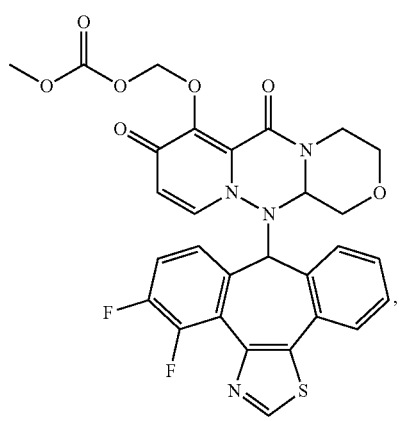
452
-continued
(377)
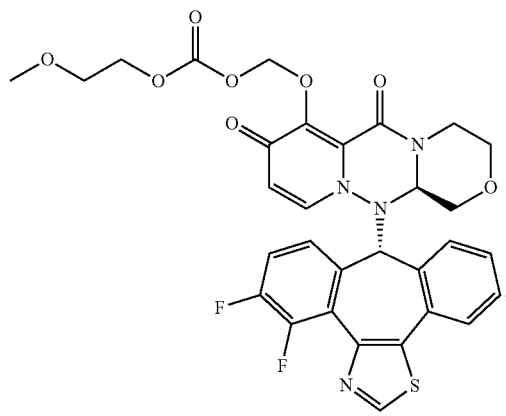
(378)
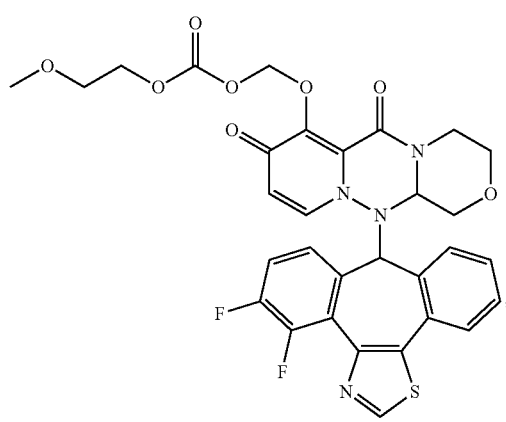
(379)
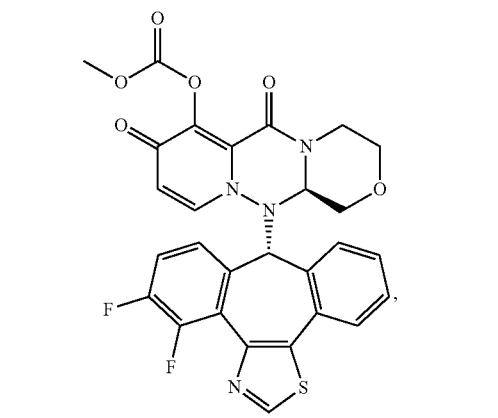
(380)
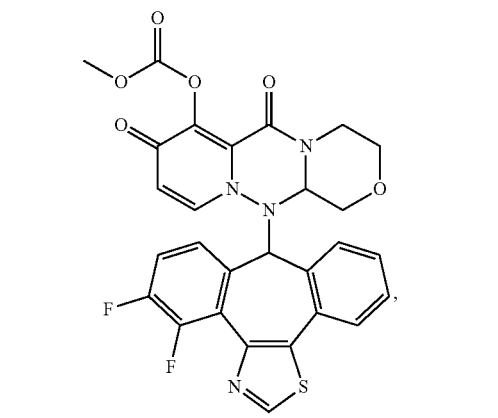

453
-continued
(381)
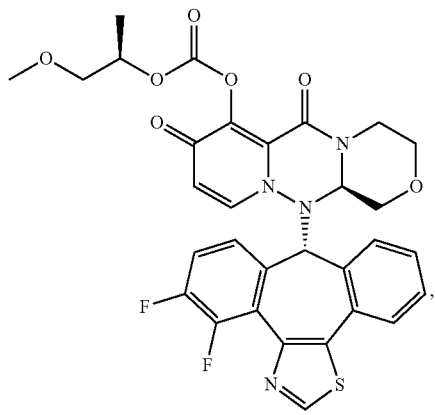
(382)
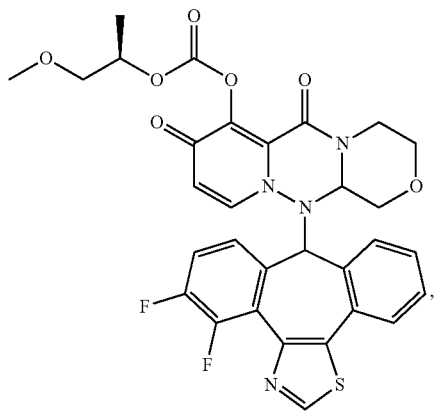
(383)
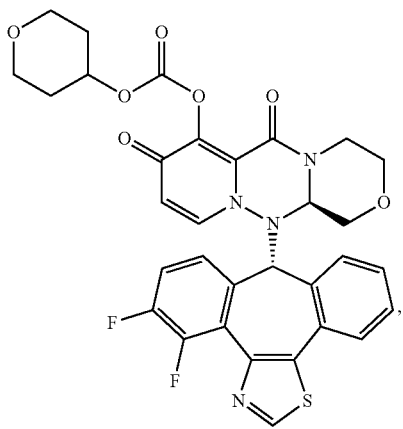
454
-continued
(384)
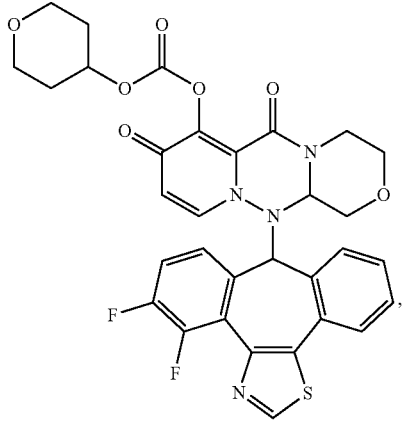
(385)
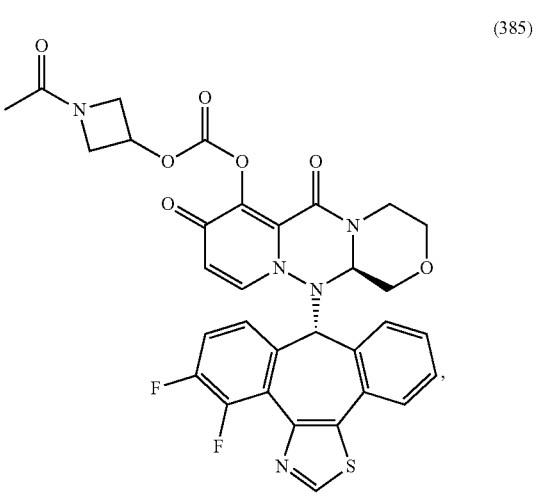
(386)
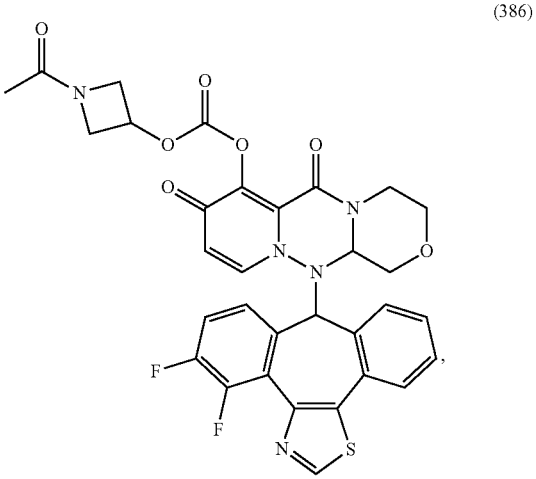

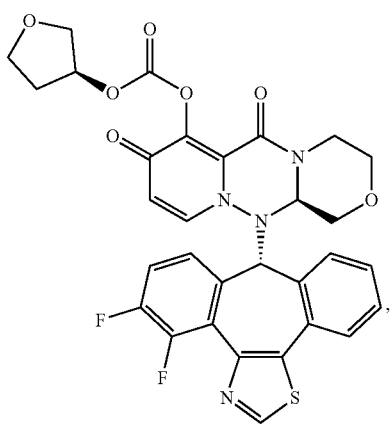
(387)
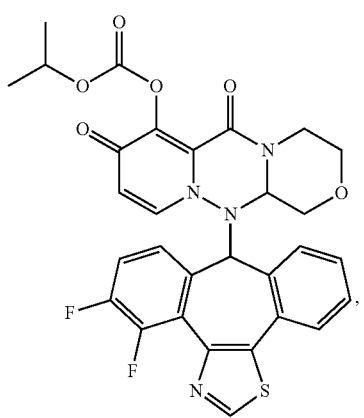
(390)
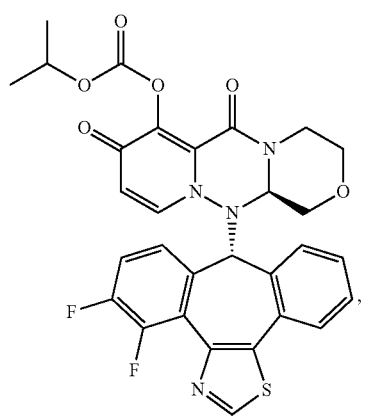
(388)
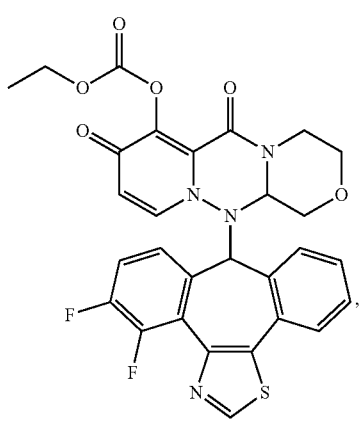
(391)
(389)
(392)

457
-continued
(393)
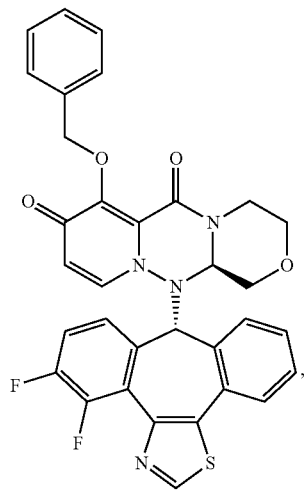
(394)
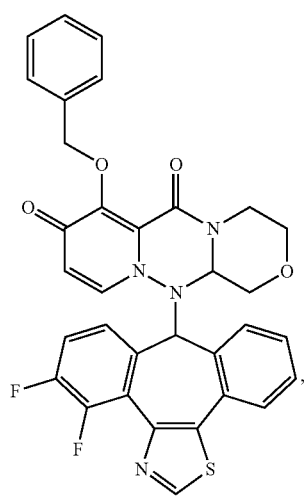
(395)
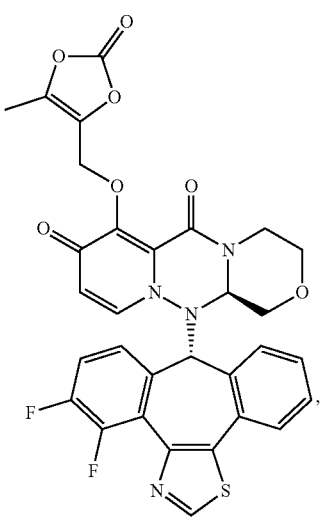
458
-continued
(396)
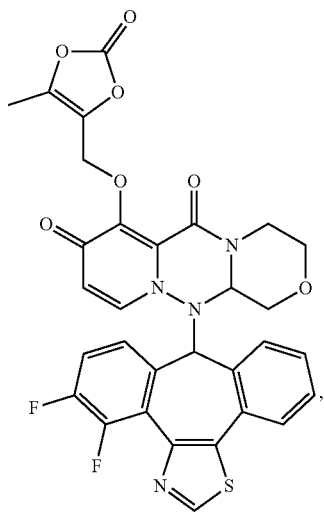
(397)
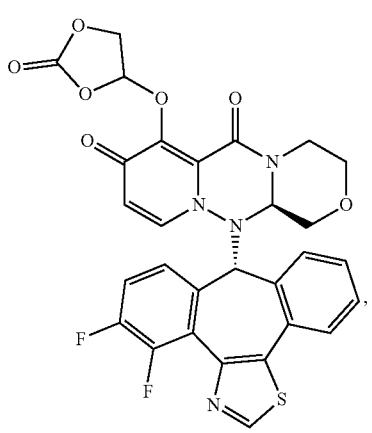
(398)
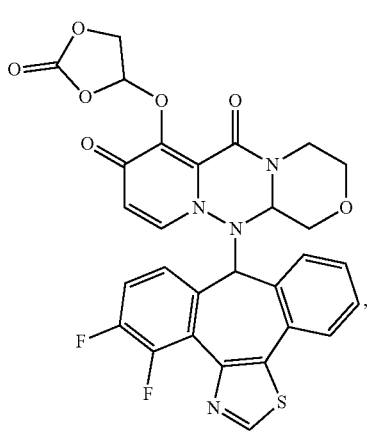

459
-continued
(399)
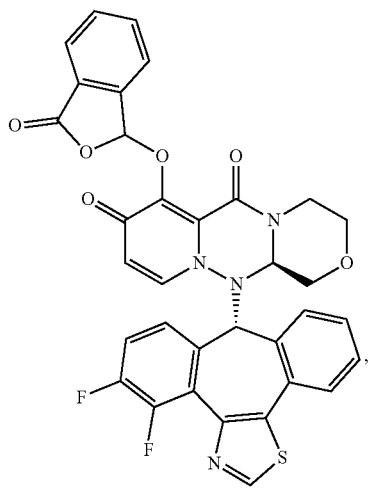
(400)
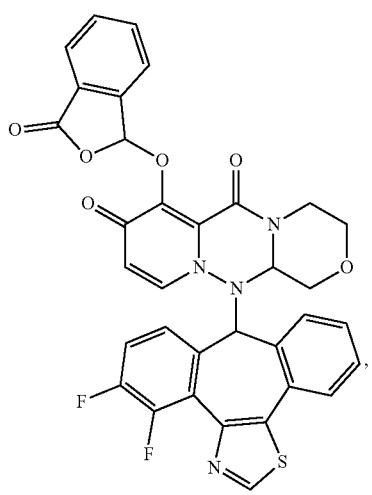
(401)
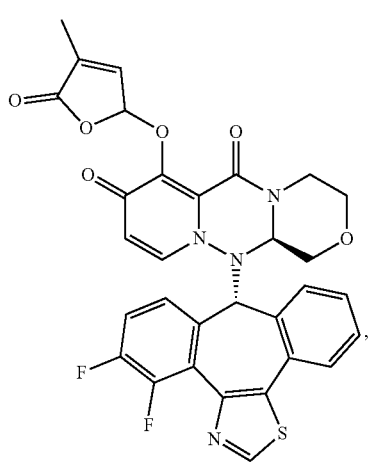
460
-continued
(402)
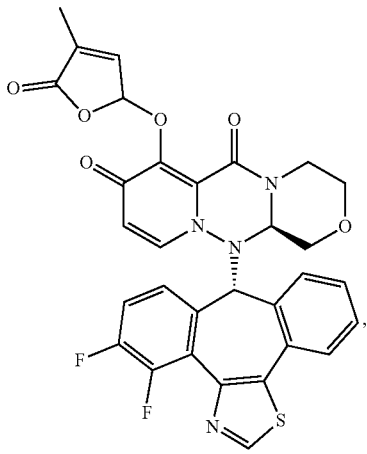
(403)
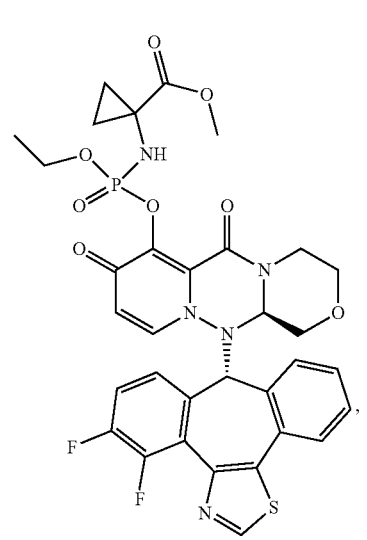
(404)
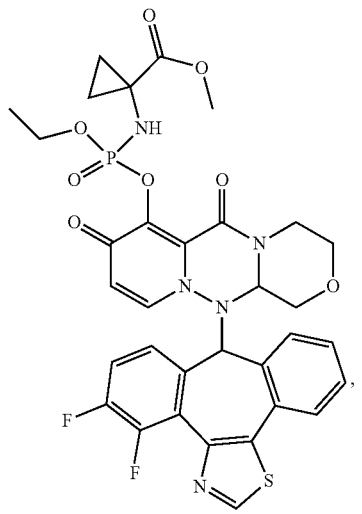

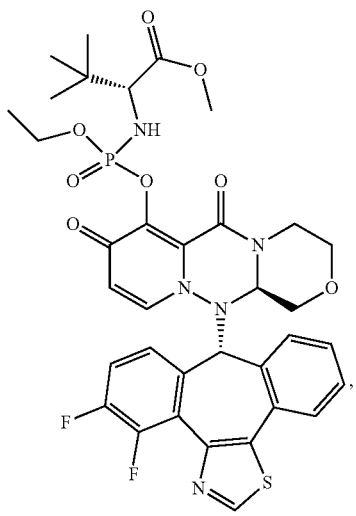
(405)
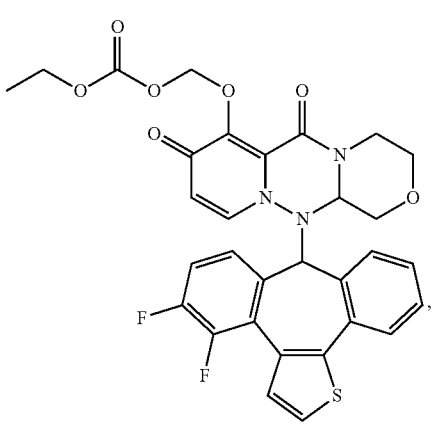
(408)
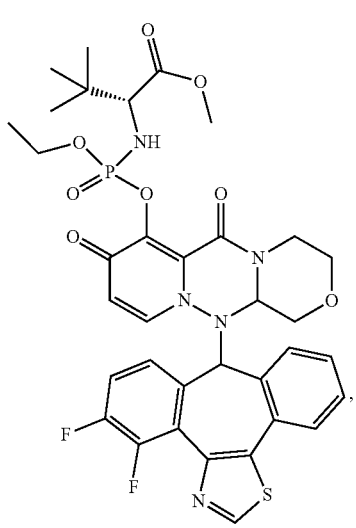
(406)
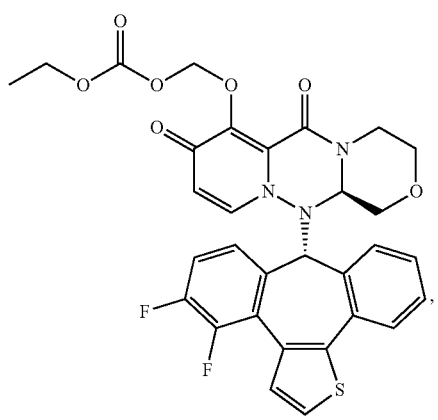
(407)
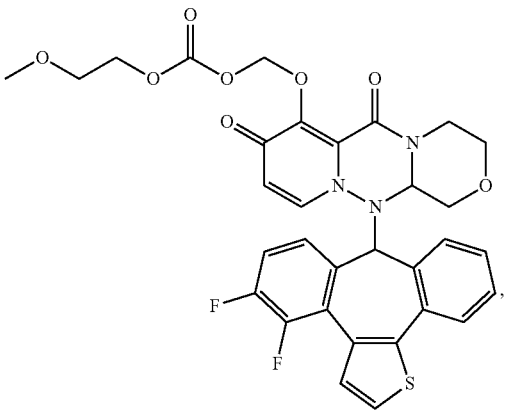
(409)
(410)

463
-continued
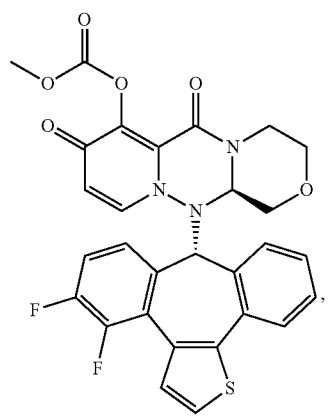
(411)
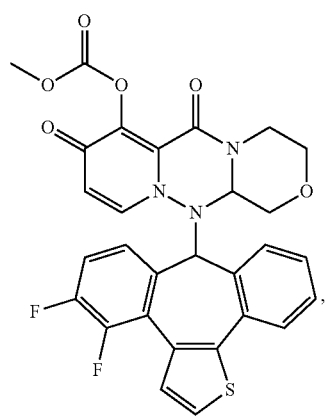
(412)
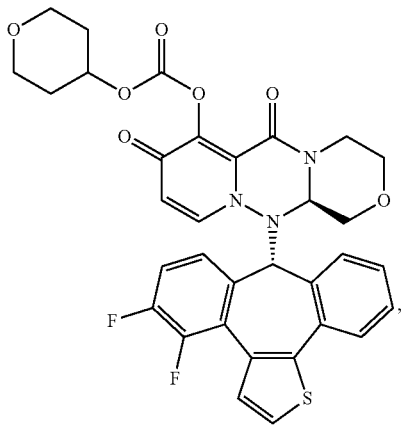
(413)
464
-continued
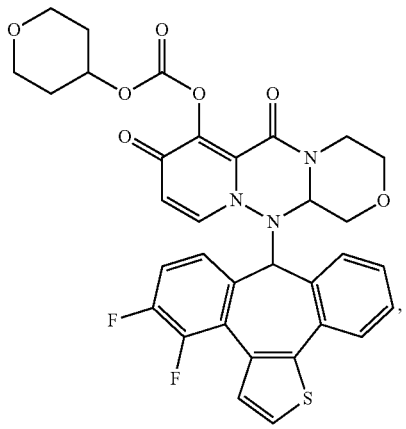
(414)
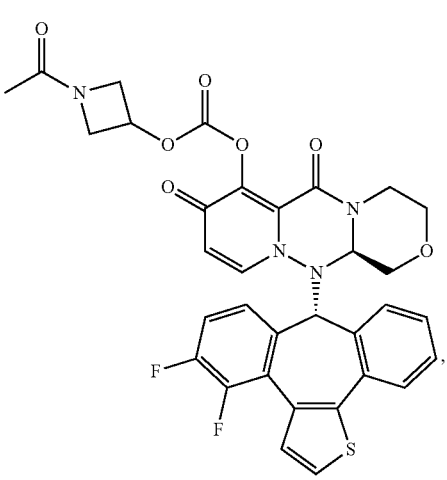
(415)
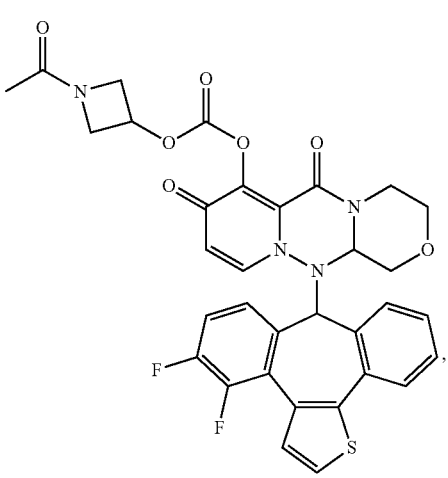
(416)

(417)
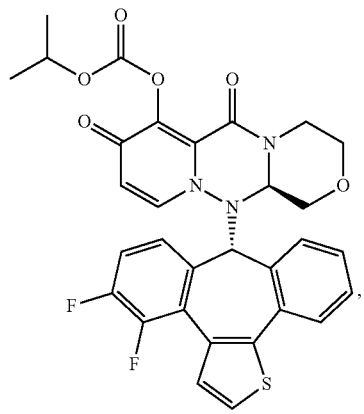
(418)
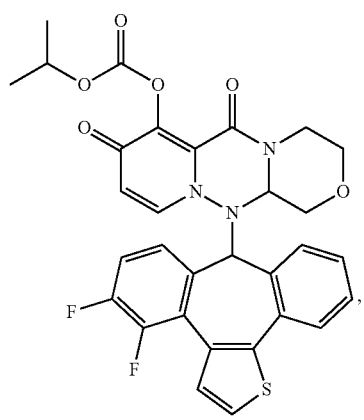
(419)
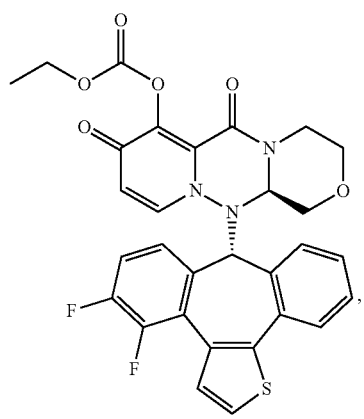
(420)
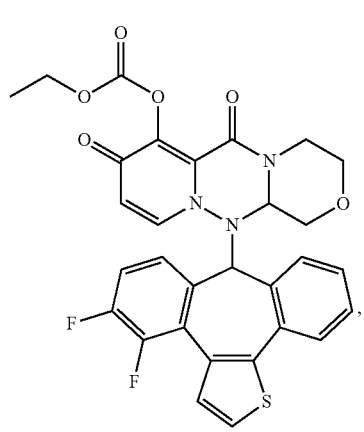
(421)
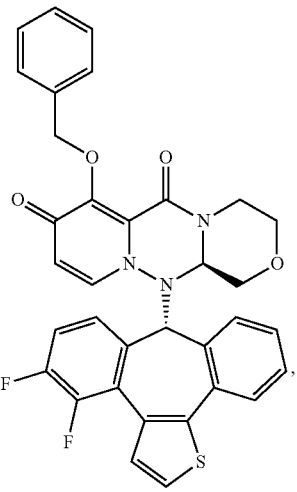
(422)
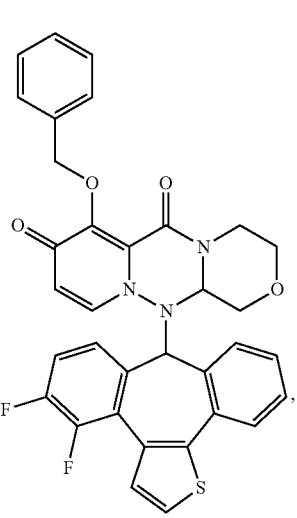
(423)
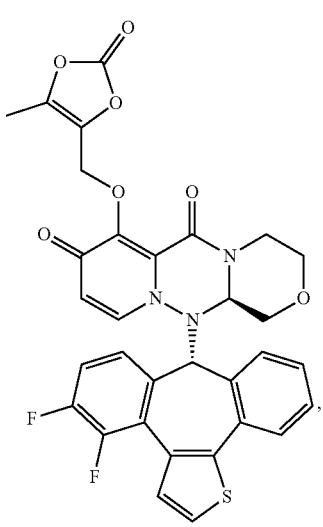

467
-continued
(424)
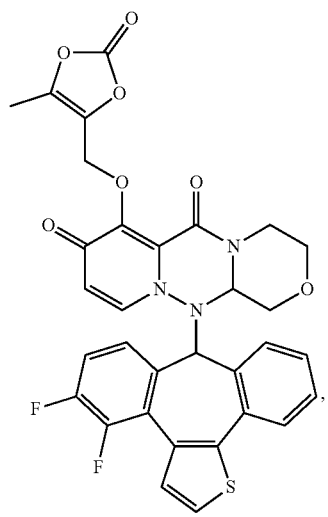
(425)
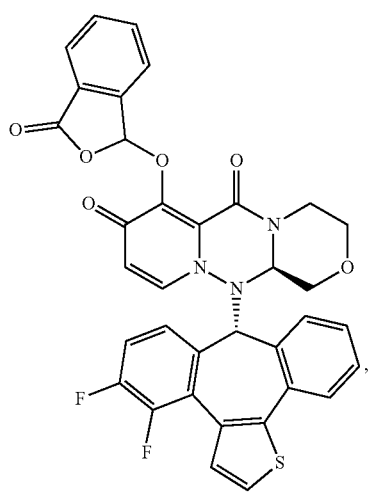
(426)
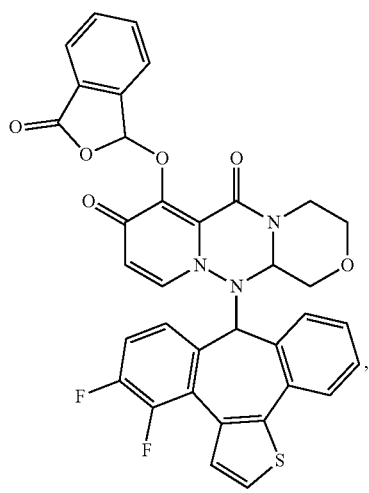
468
-continued
(427)
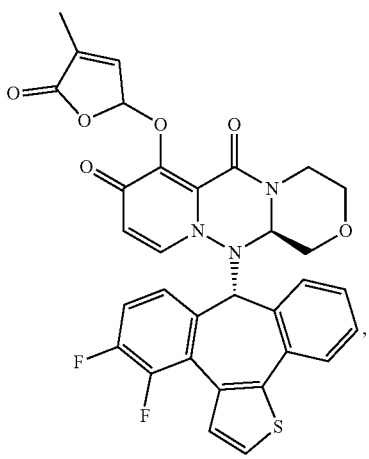
(428)
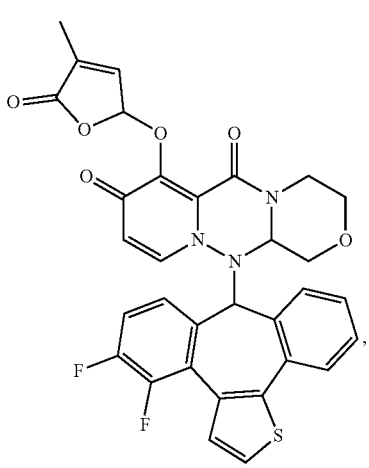
(429)
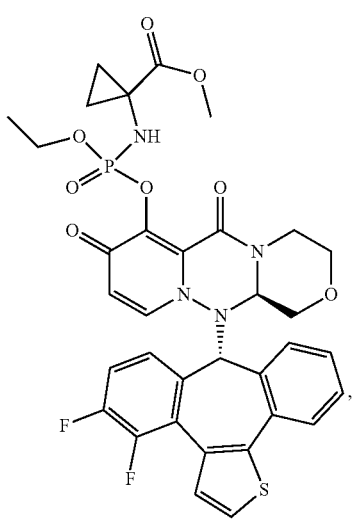

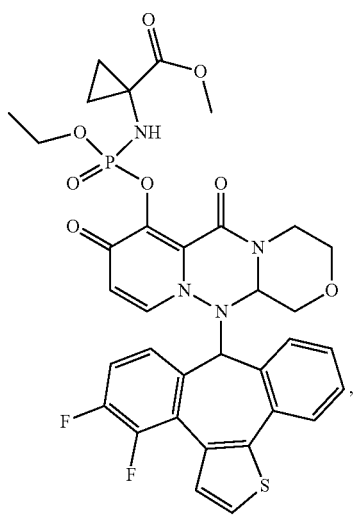
(430)
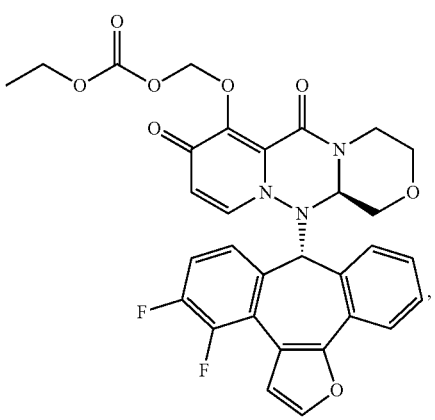
(433)
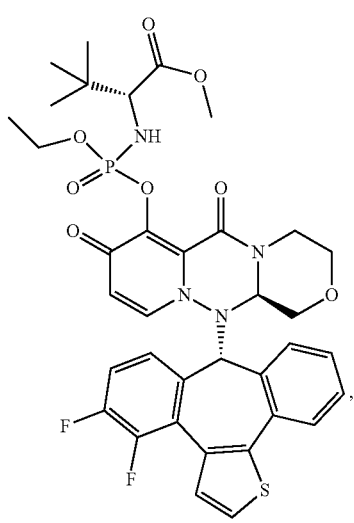
(431)
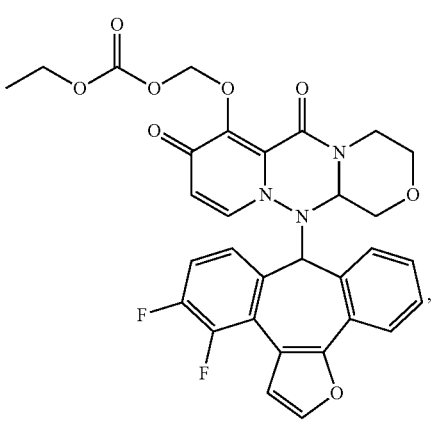
(434)
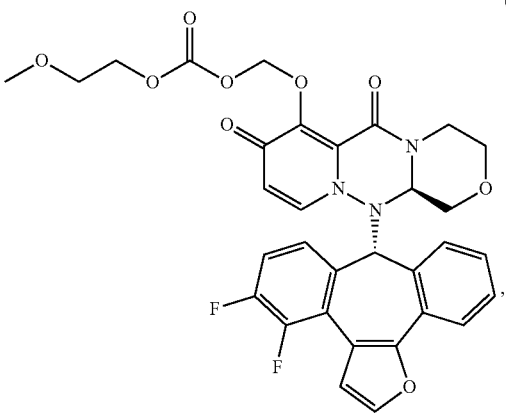
(435)
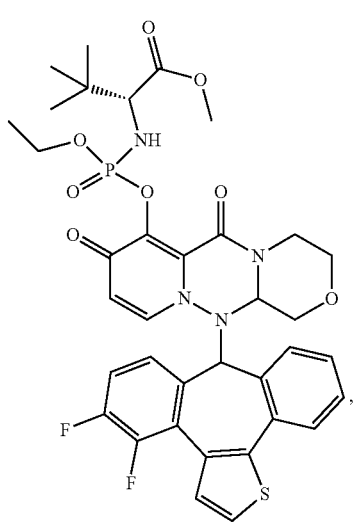
(432)
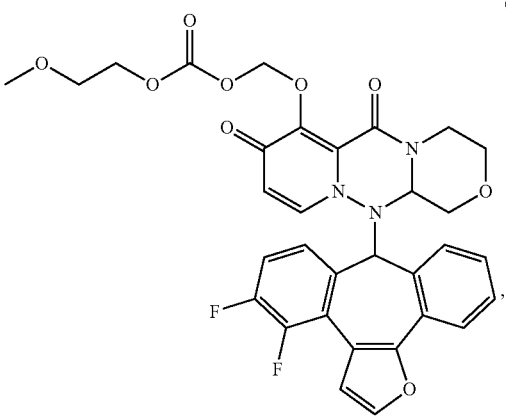
(436)

(437)
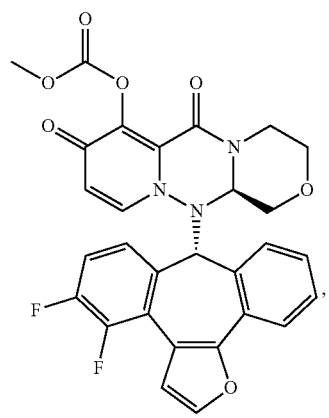
(438)
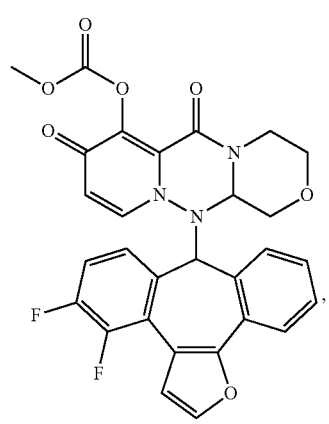
(439)
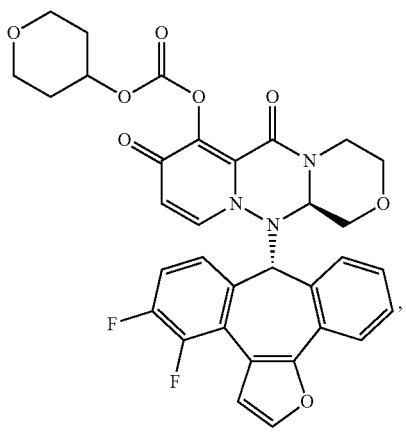
(440)
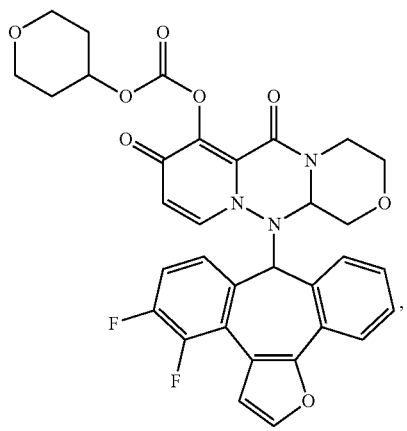
(441)
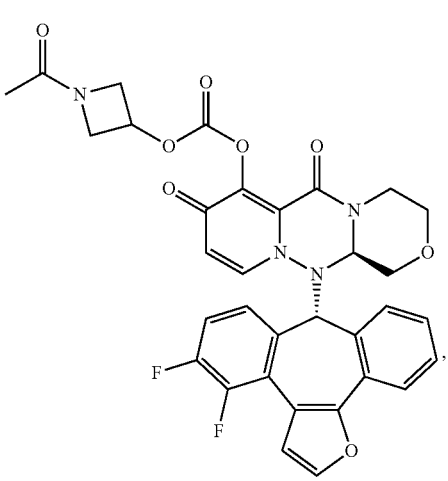
(442)
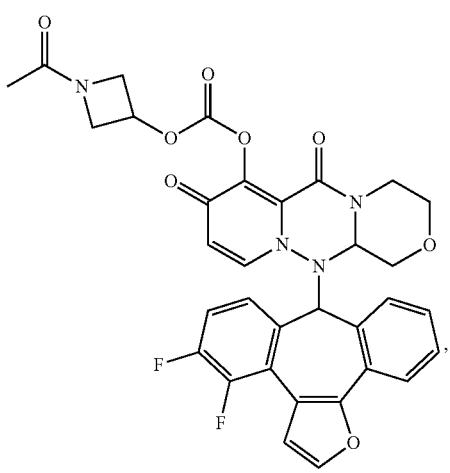

473
-continued
(443)
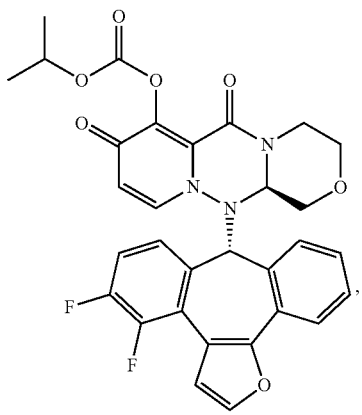
(444)
(445)
(446)
474
-continued
(447)
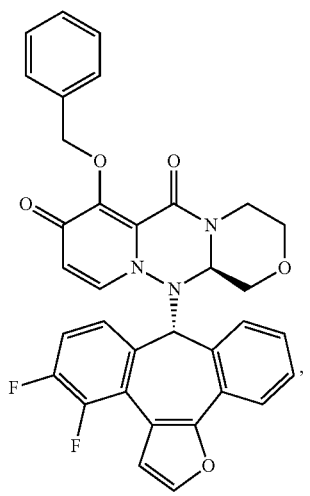
(448)
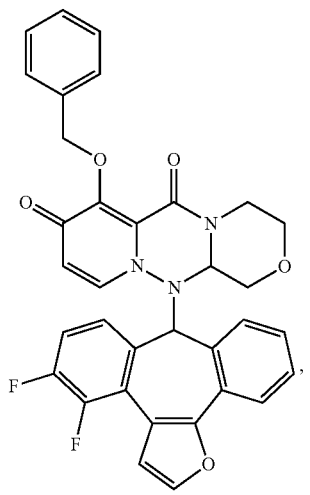
(449)
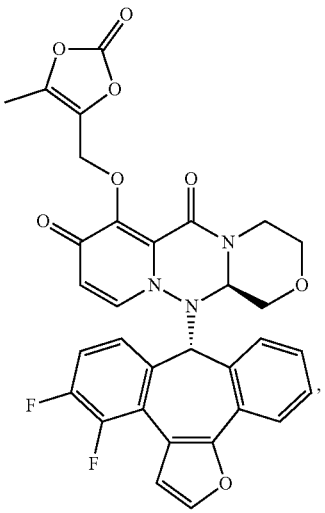

475
-continued
(450)
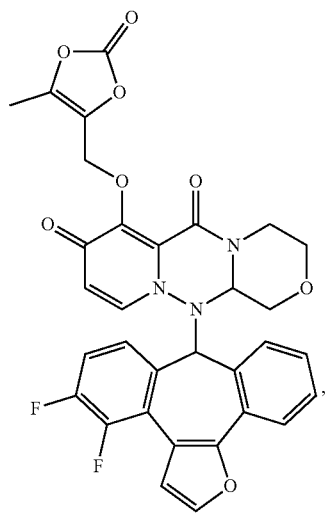
(451)
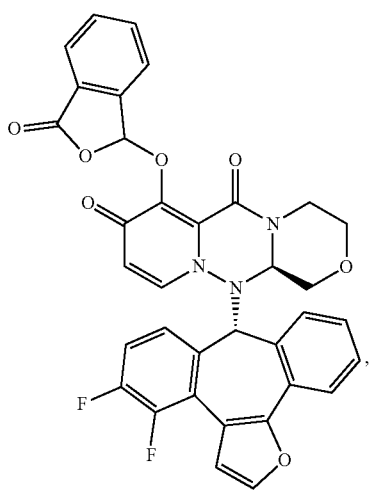
(452)
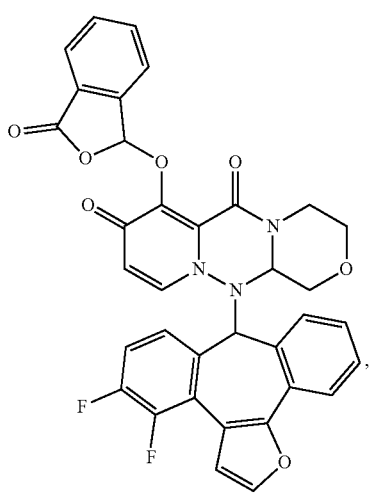
476
-continued
(453)
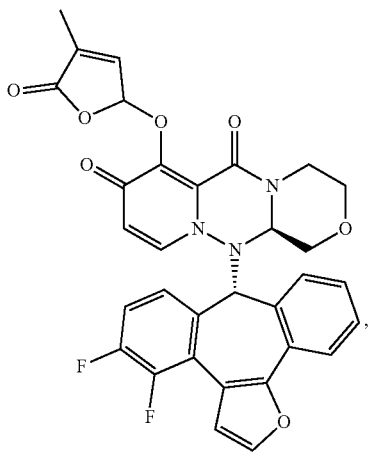
(454)
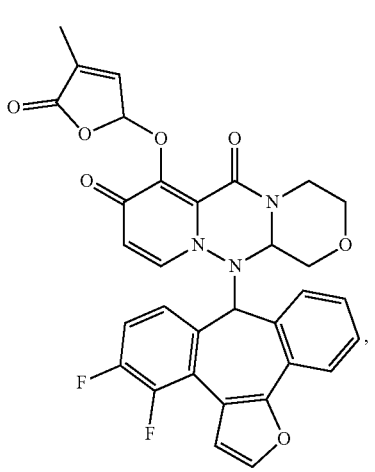
(455)
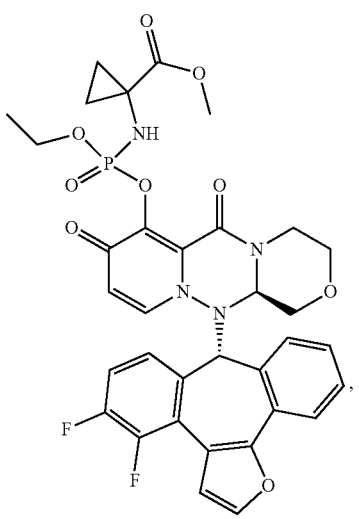

(456)
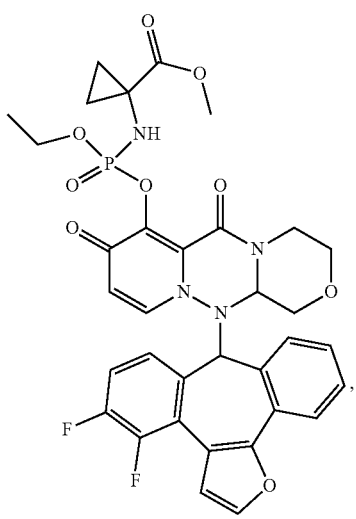
(457)
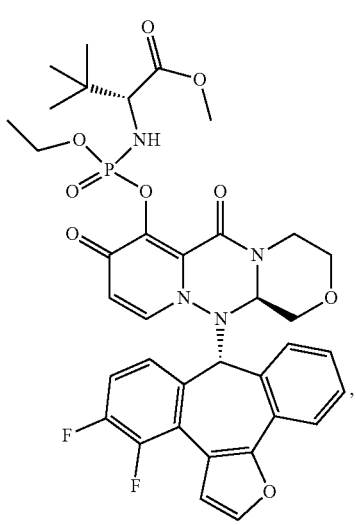
(458)
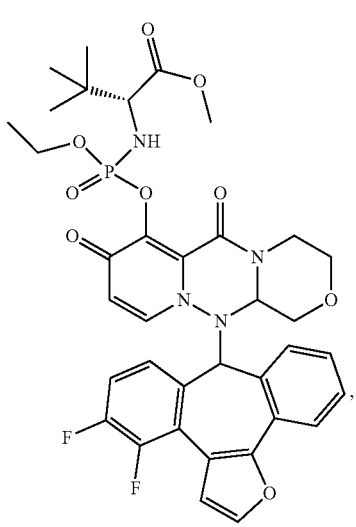
(459)
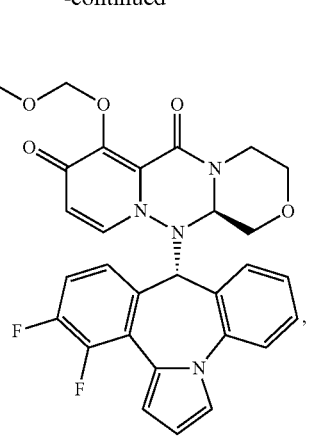
(460)
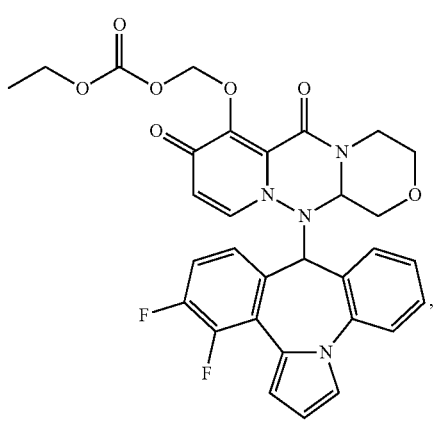
(461)
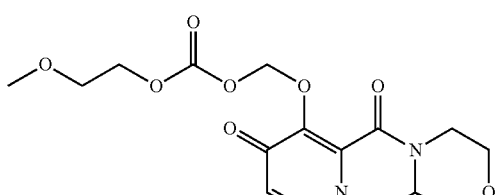
(462)
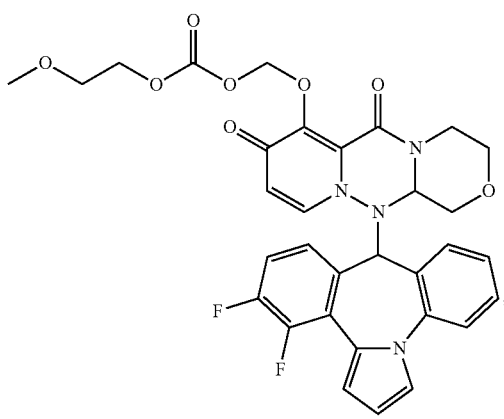

(463) 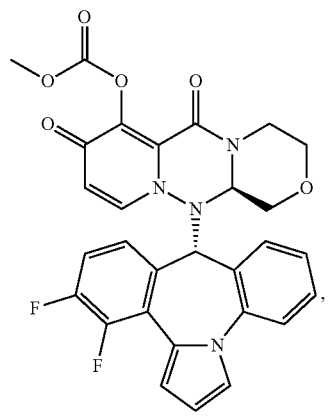
(464) 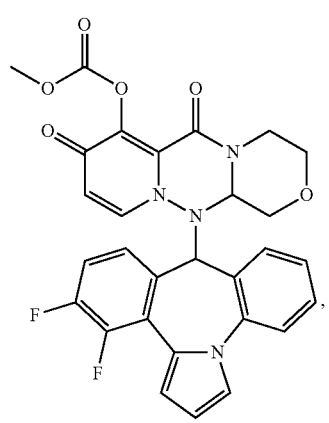
(465) 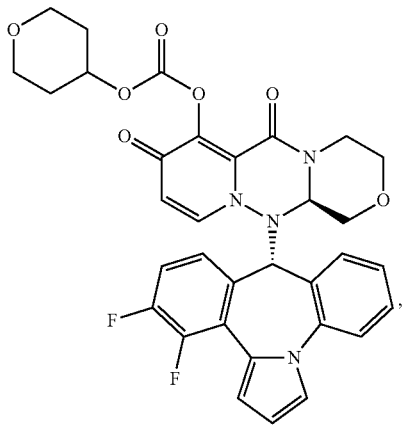
(466) 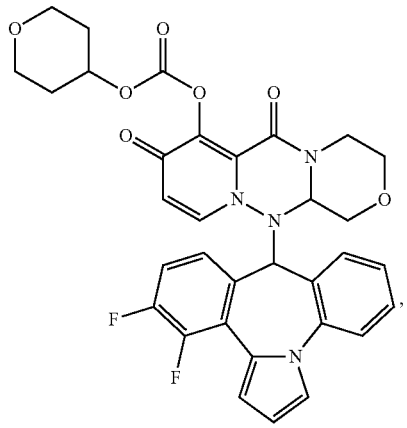
(467) 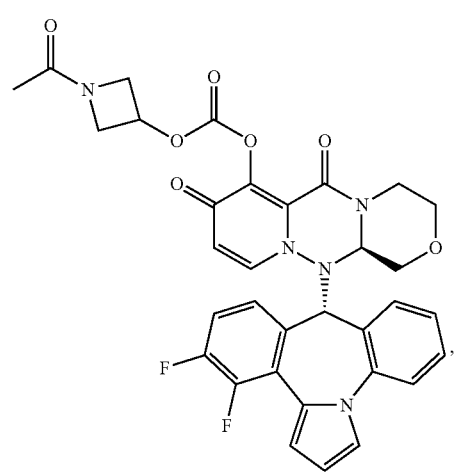
(468) 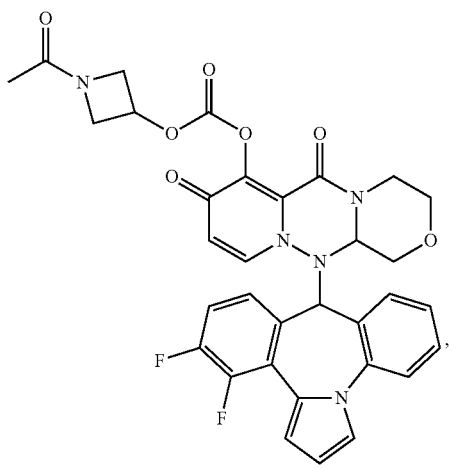

481
-continued
(469)
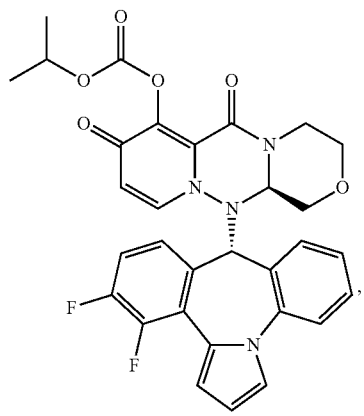
(470)
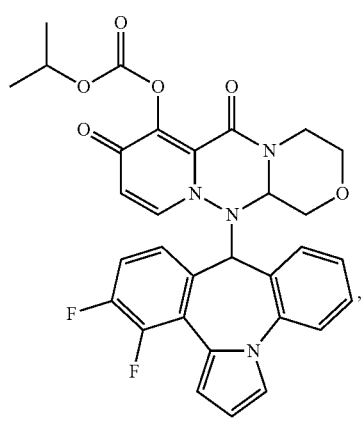
(471)
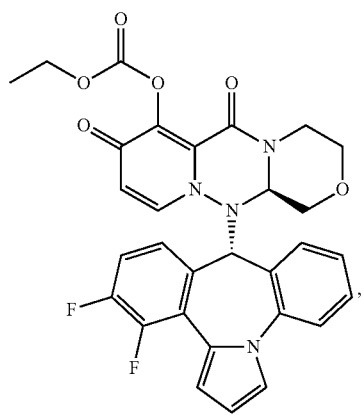
(472)
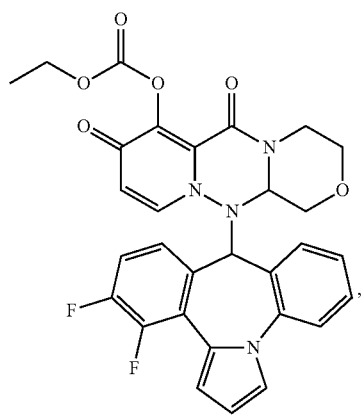
482
-continued
(473)
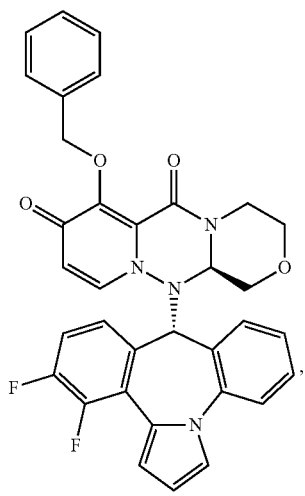
(474)
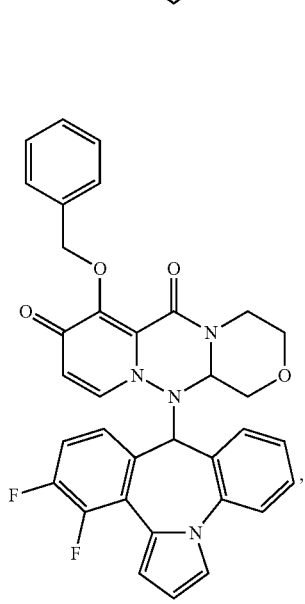
(475)
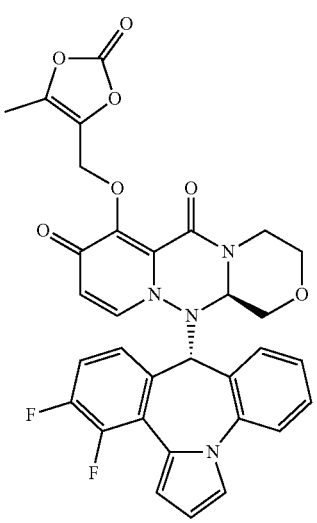

483
-continued
(476)
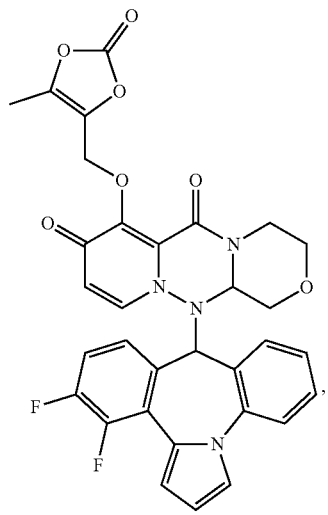
(477)
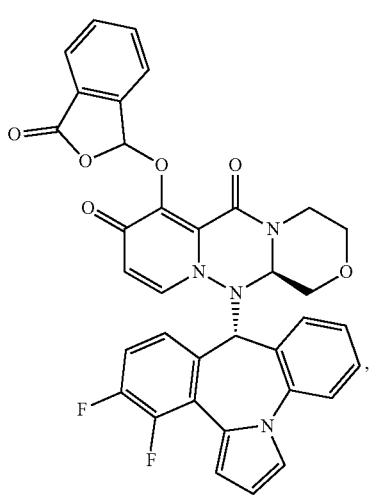
(478)
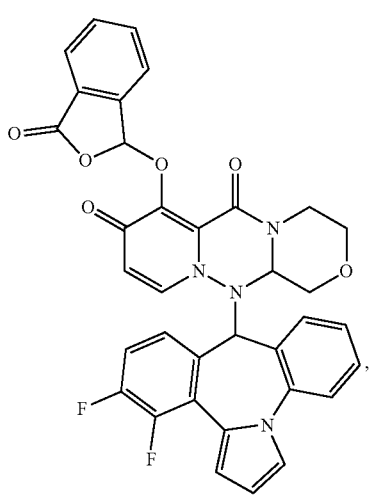
484
-continued
(479)
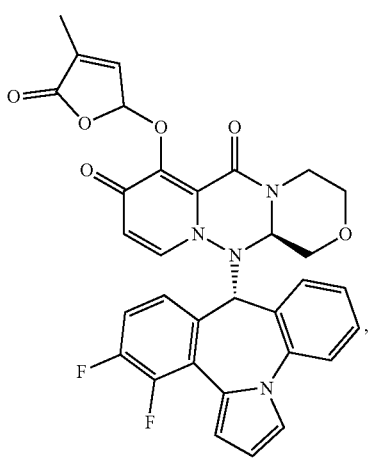
(480)
(481)
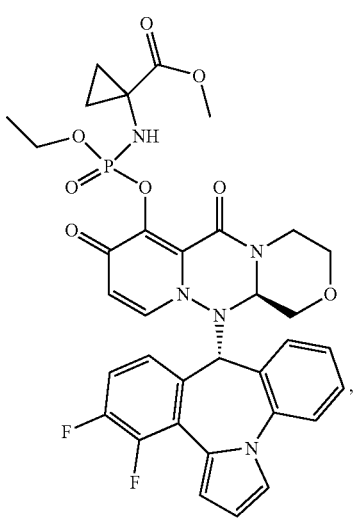

485
-continued
(482)
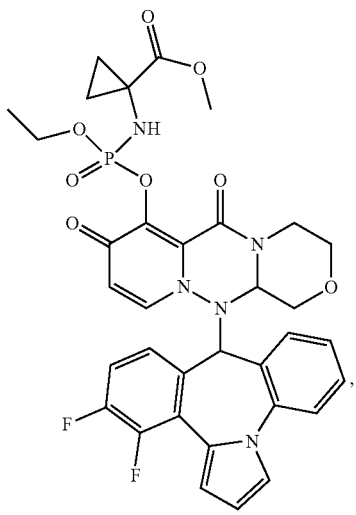
(483)
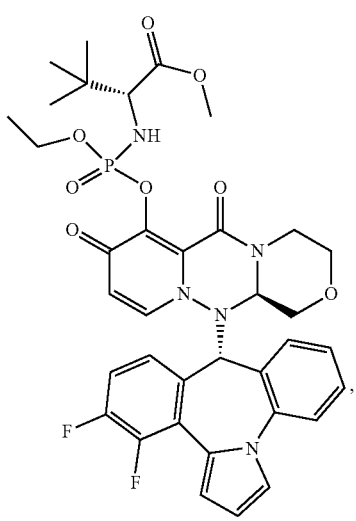
(484)
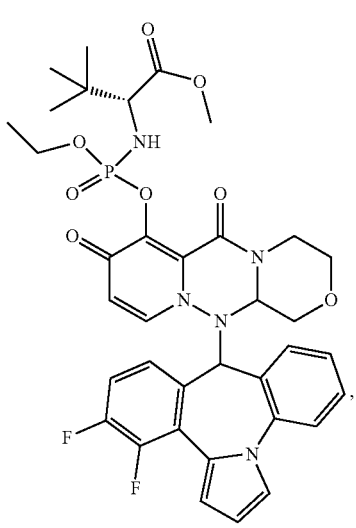
486
-continued
(485)
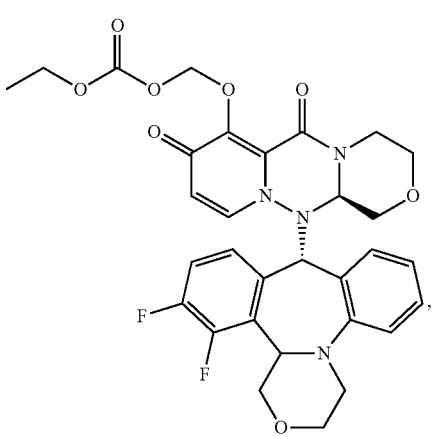
(486)
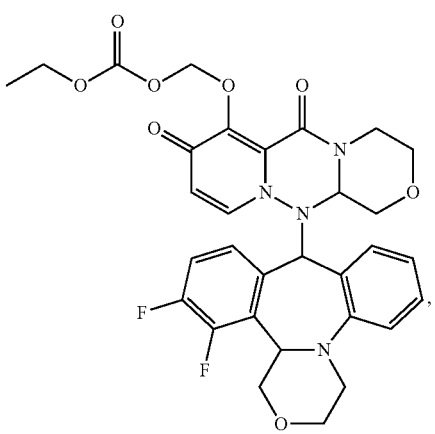
(487)
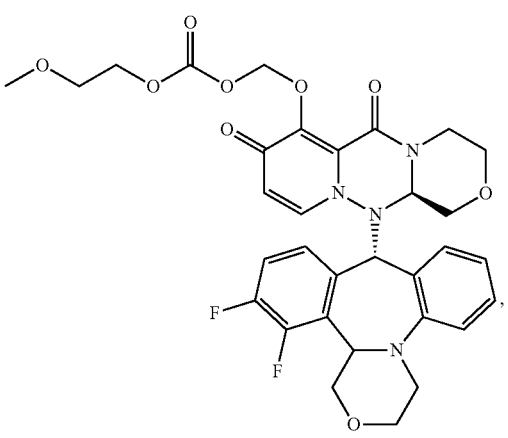

-continued
(488)
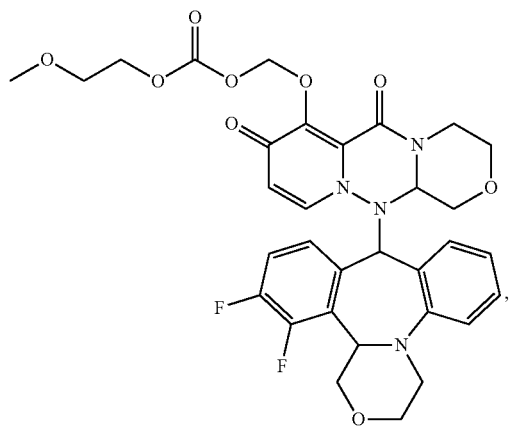
(489)
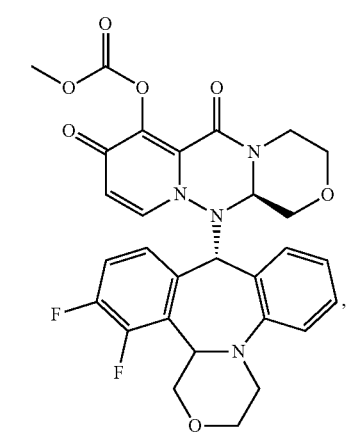
(490)
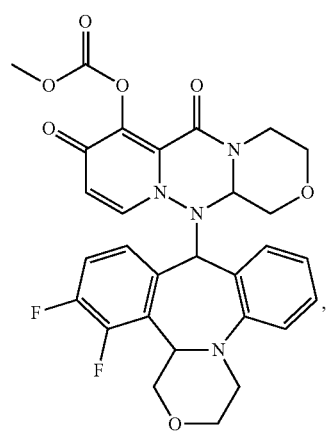
-continued
(491)
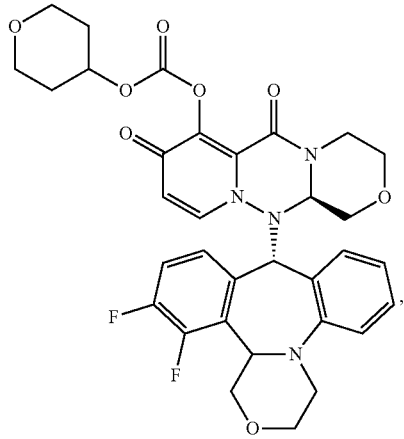
(492)
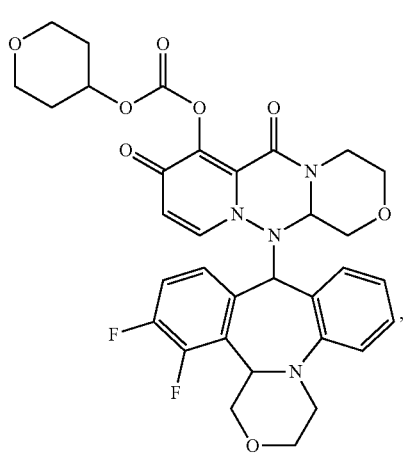
(493)
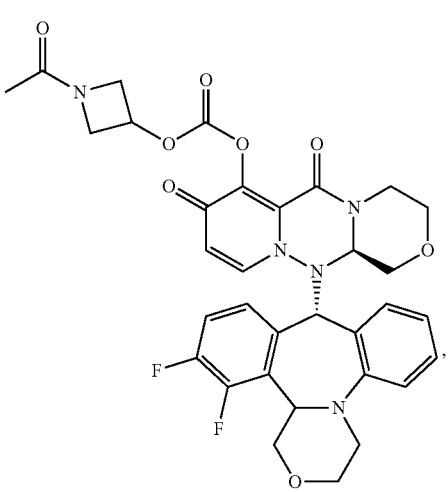

(494)
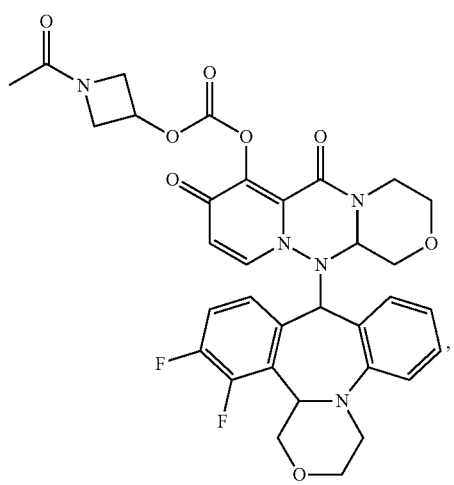
(495)
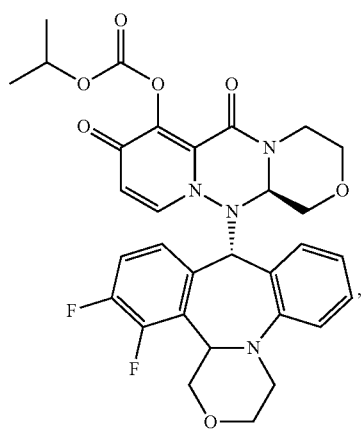
(496)
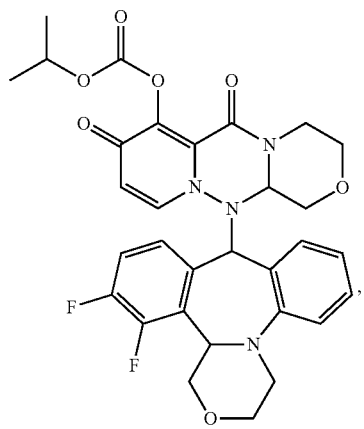
(497)
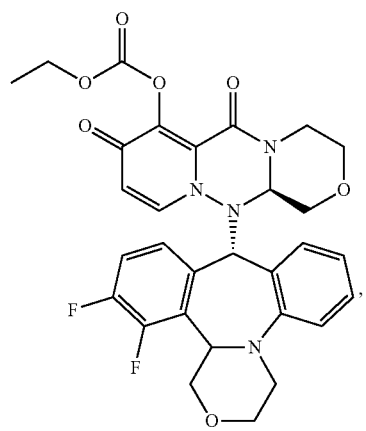
(498)
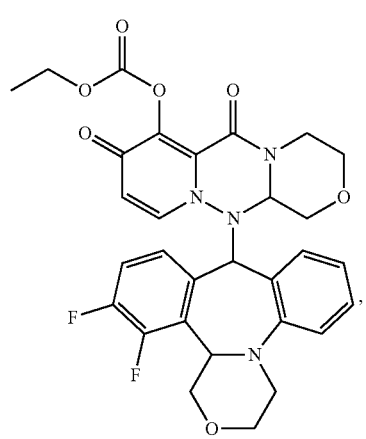
(499)
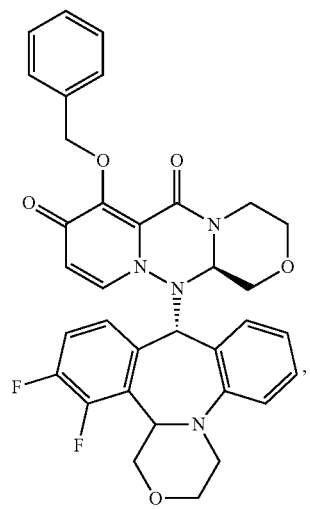

491
-continued
(500)
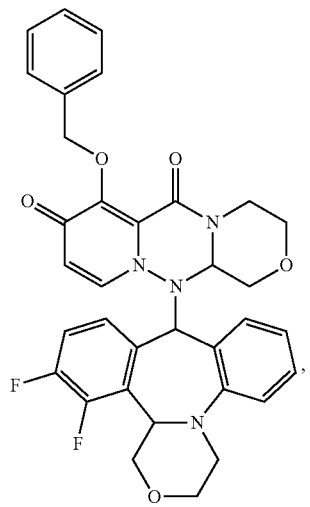
(501)
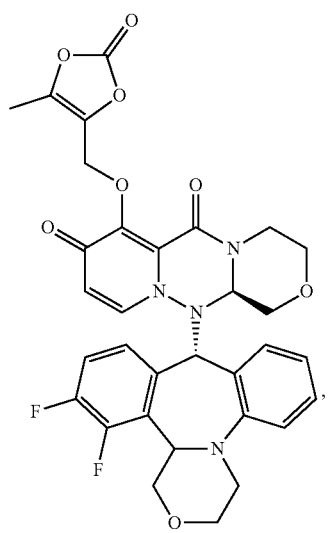
(502)
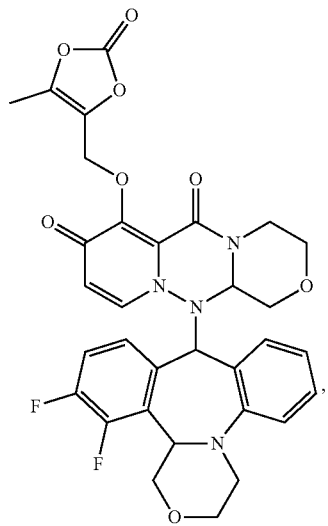
492
-continued
(503)
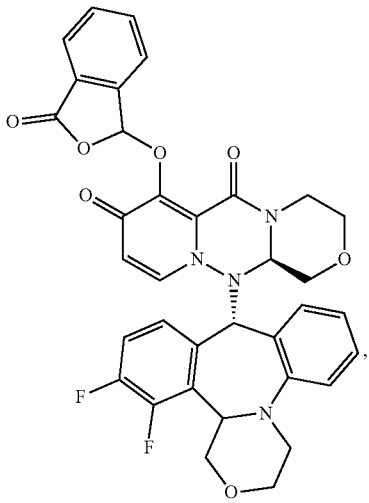
(504)
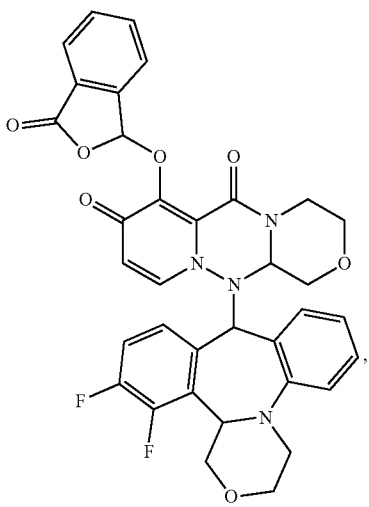
(505)
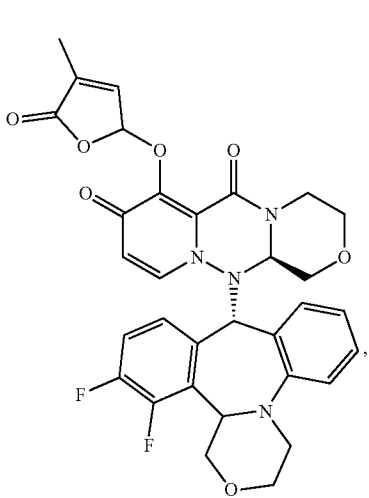

493
-continued
(506)
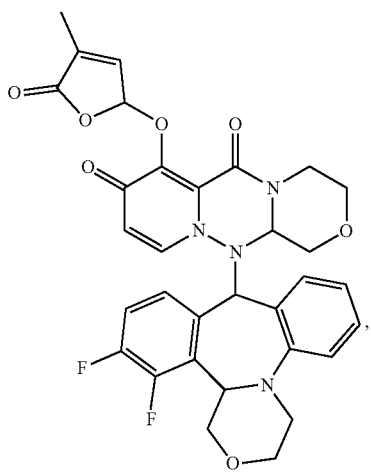
(507)
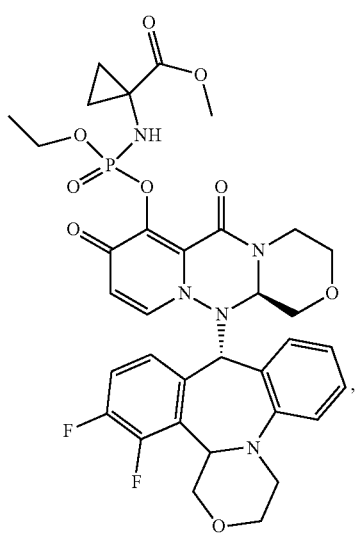
(508)
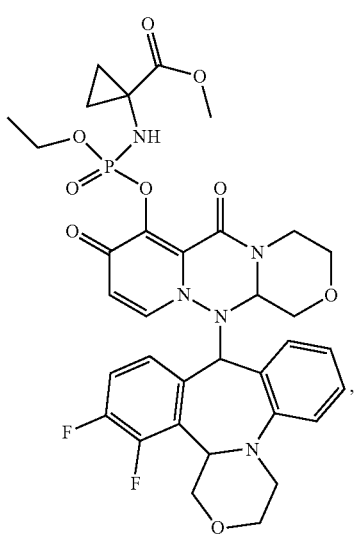
494
-continued
(509)
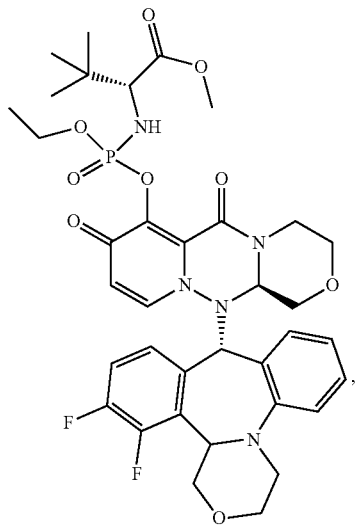
(510)
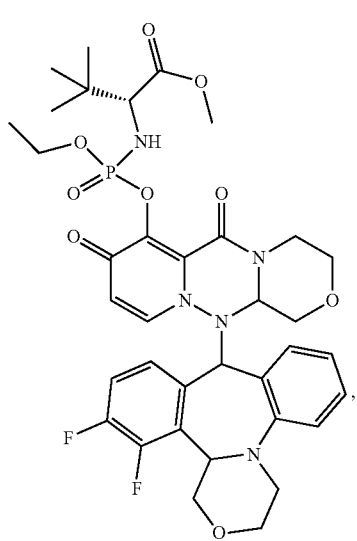
(511)
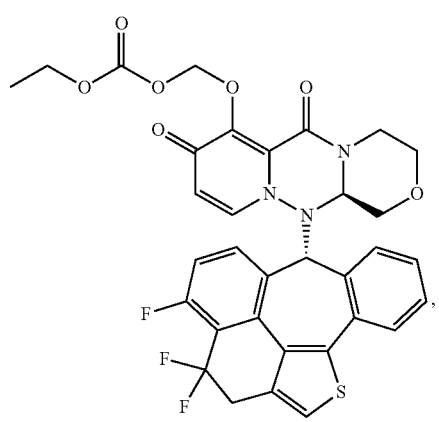

(512) 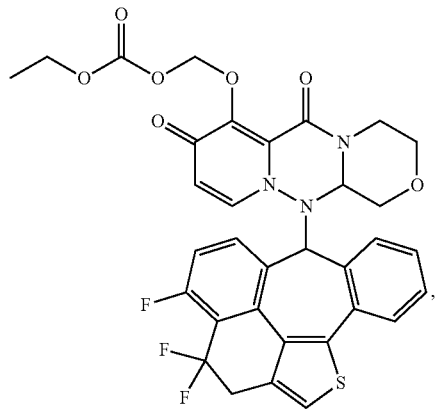
(513) 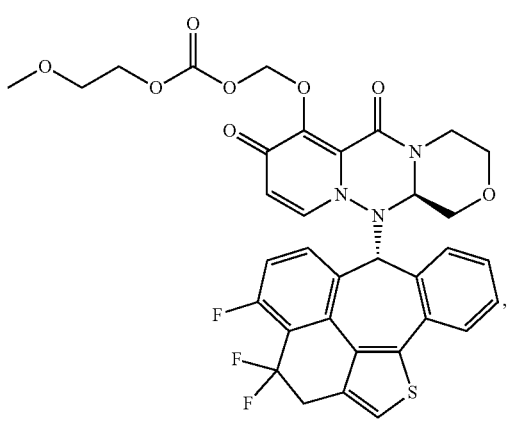
(514) 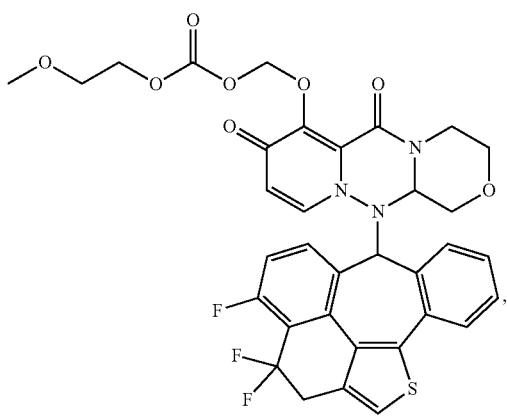
(515) 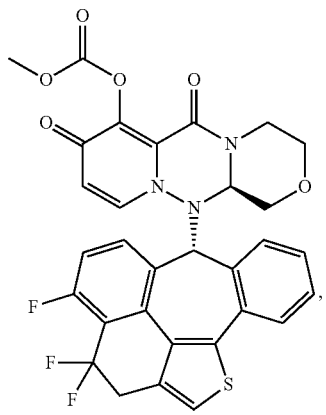
(516) 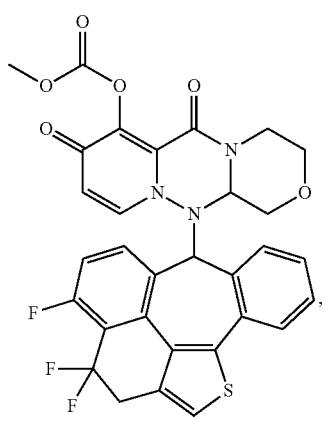
(517) 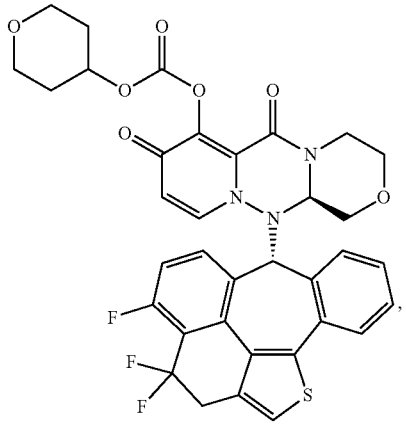

(518)
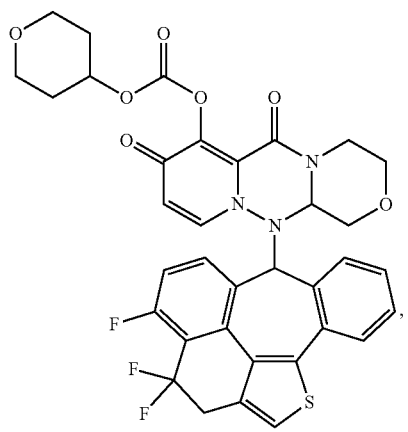
(519)
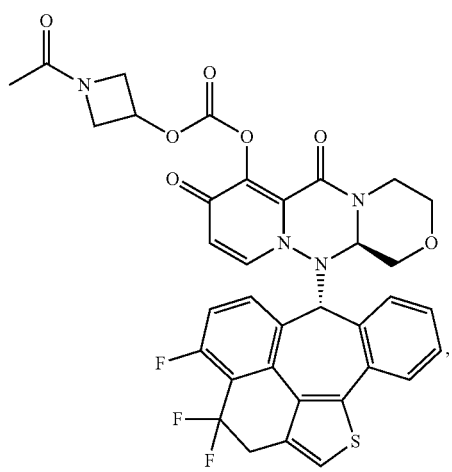
(520)
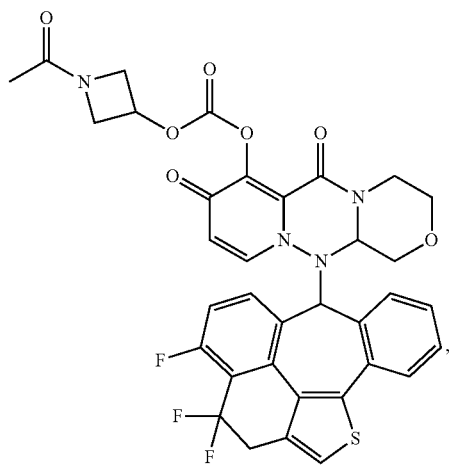
(521)
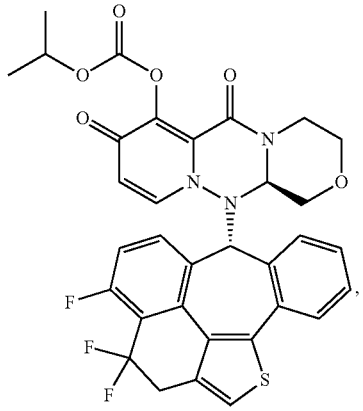
(522)
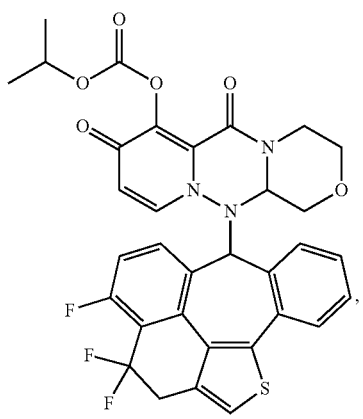
(523)
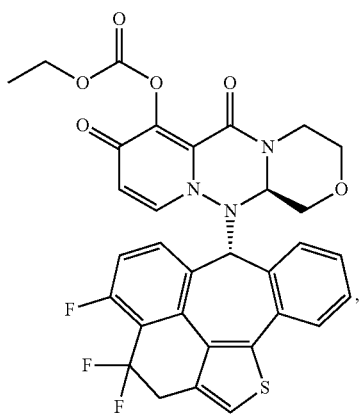
(524)
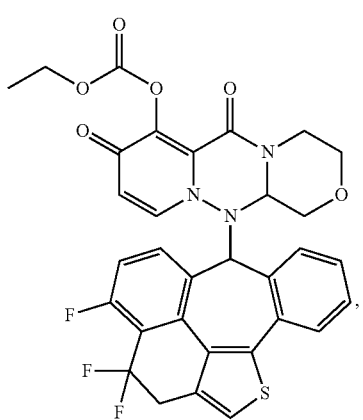

(525)
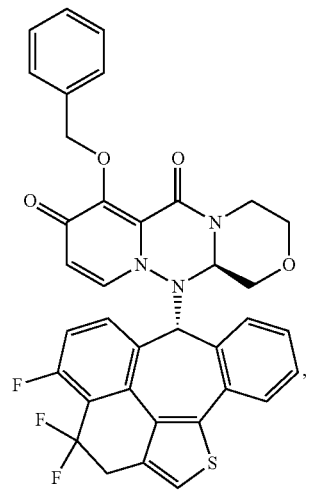
(526)
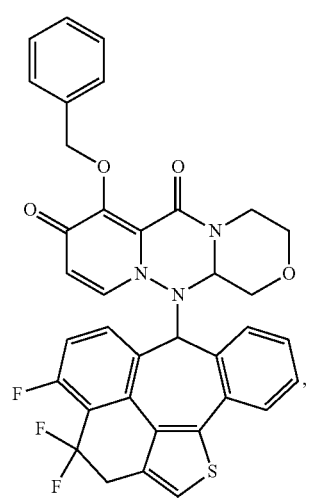
(527)
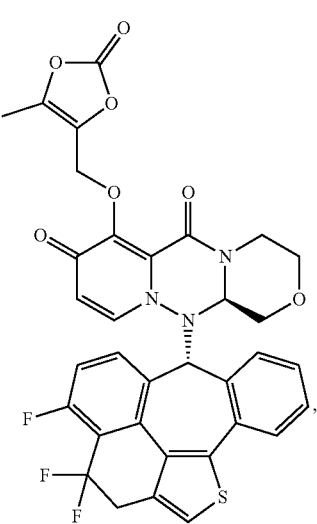
(528)
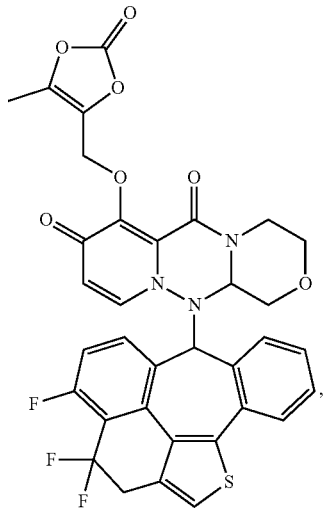
(529)
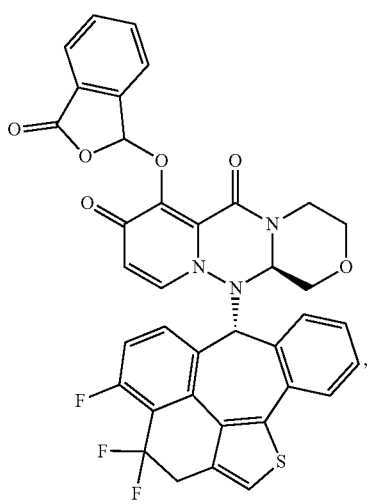
(530)
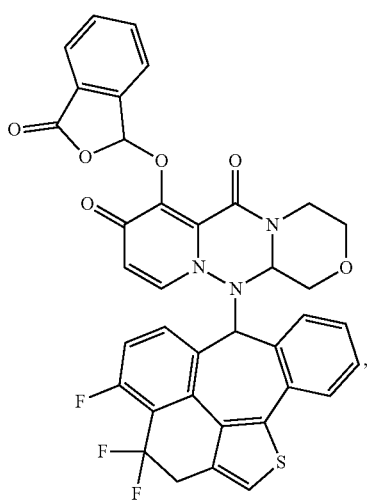

501
-continued
(531)
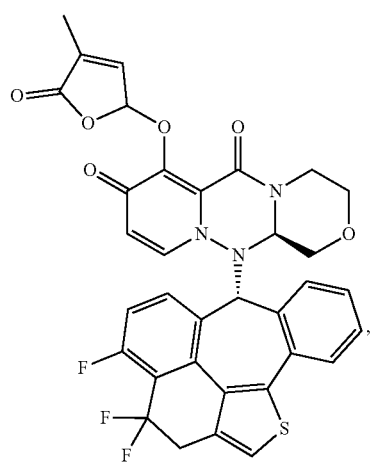
(532)
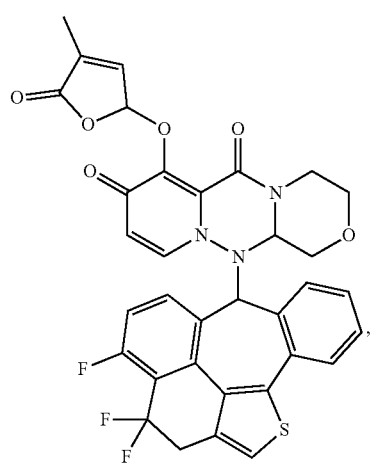
(533)
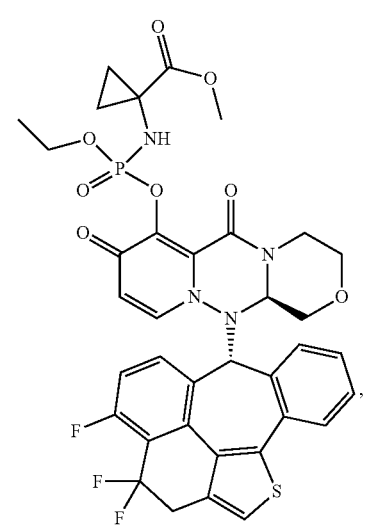
502
-continued
(534)
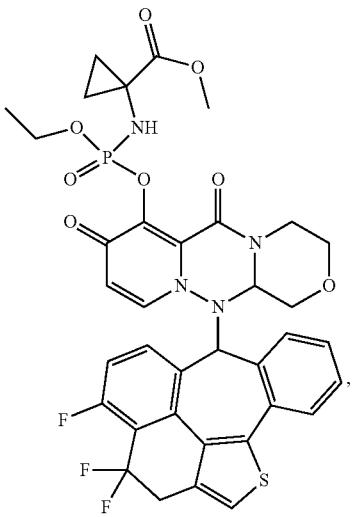
(535)
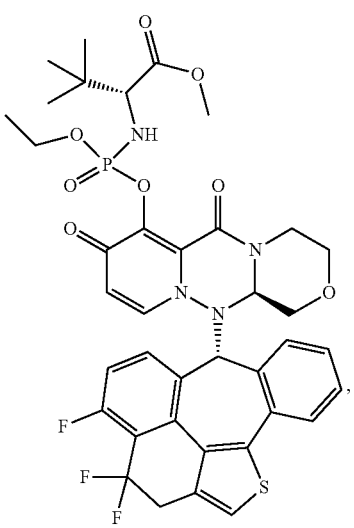
(536)
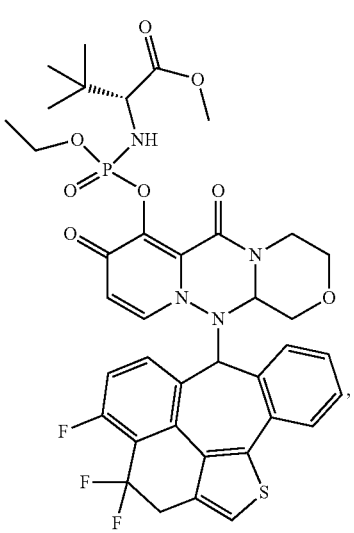

503
-continued
(537)
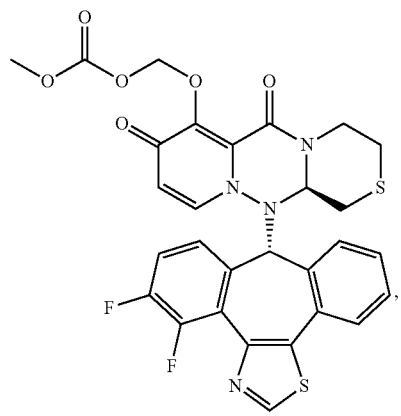
(538)
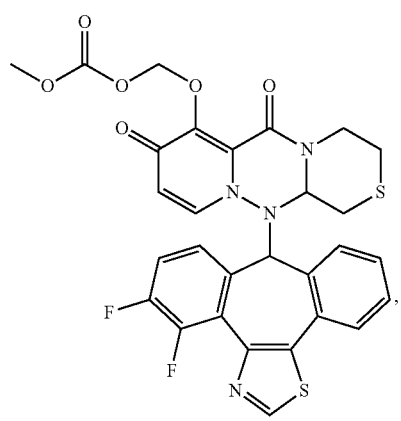
(539)
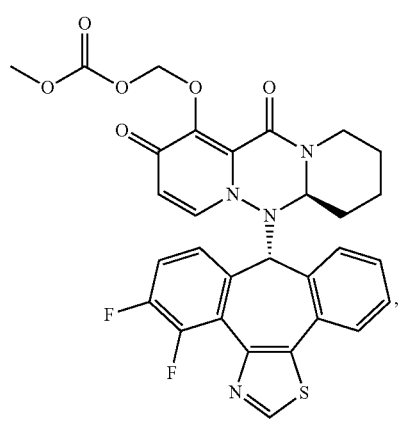
(540)
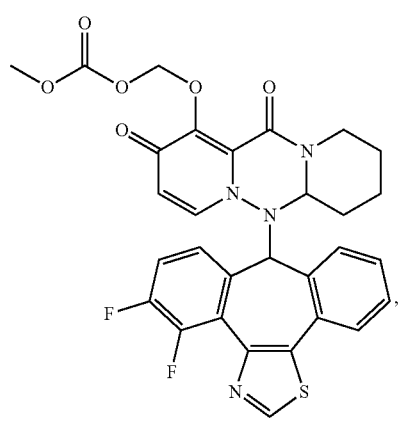
504
-continued
(541)
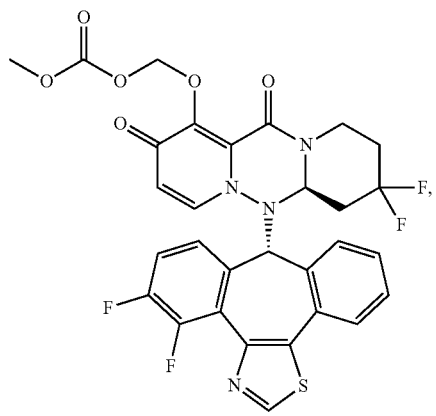
(542)
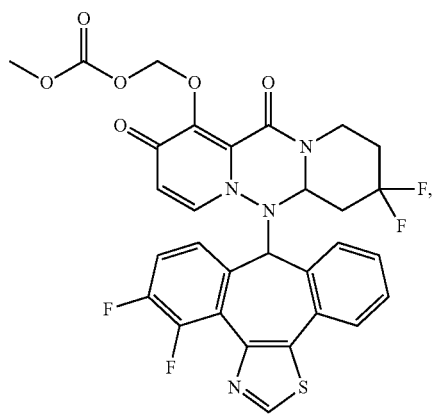
(543)
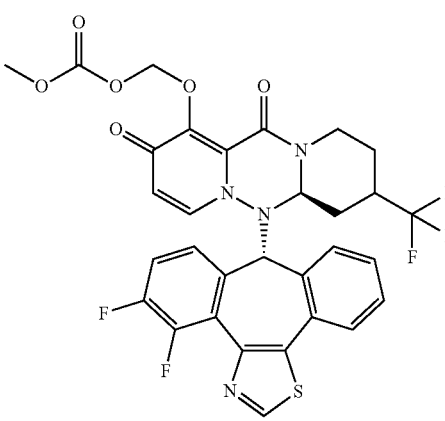
(544)
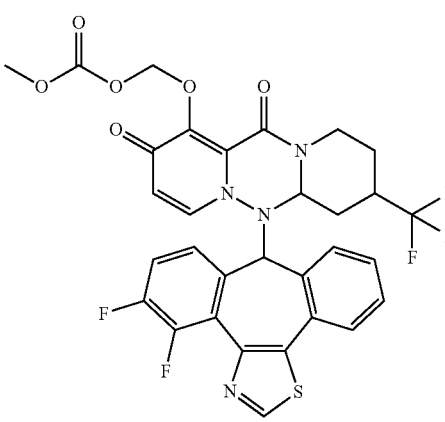

505
-continued
(545)
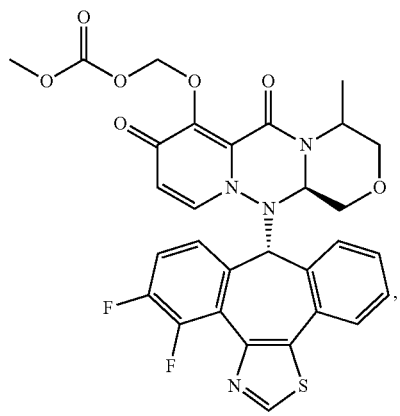
(546)
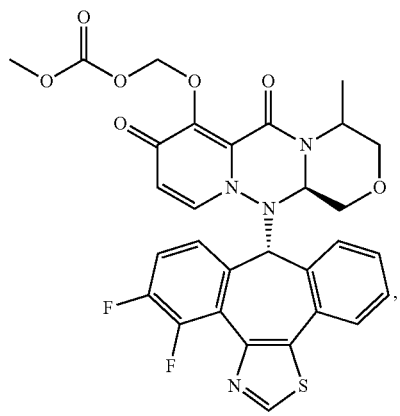
(547)
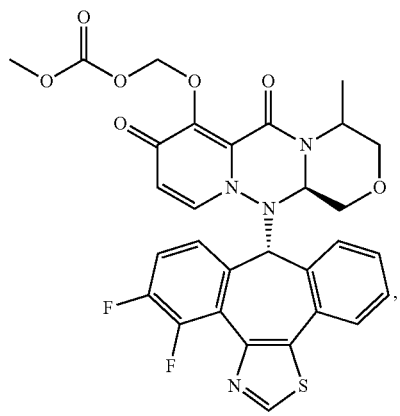
(548)
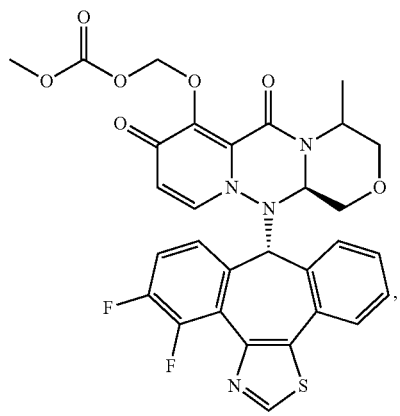
506
-continued
(549)
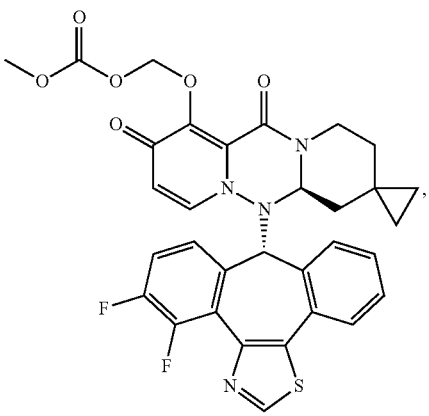
(550)
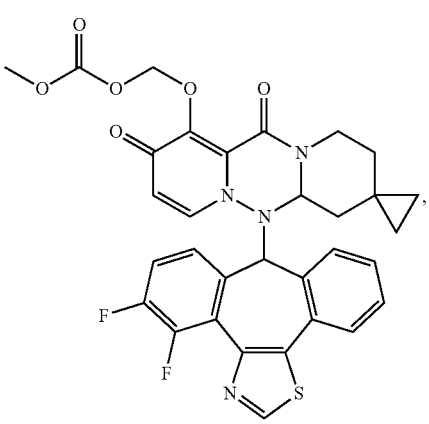
(551)
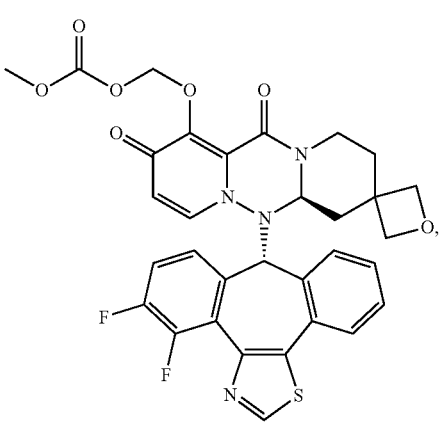
(552)
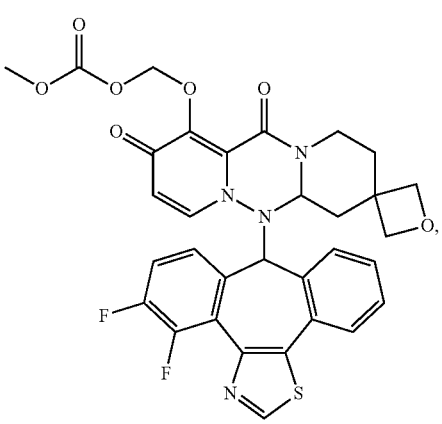

507
-continued
(553)
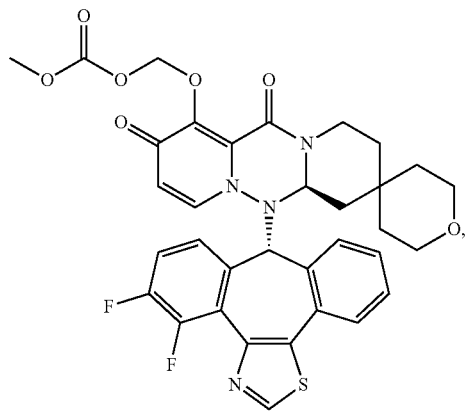
(554)
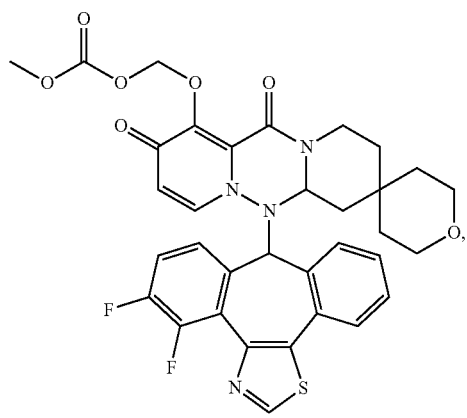
(555)
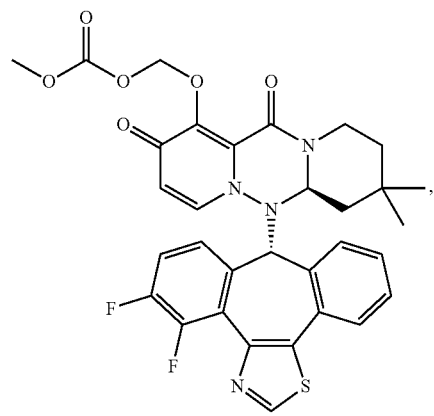
(556)
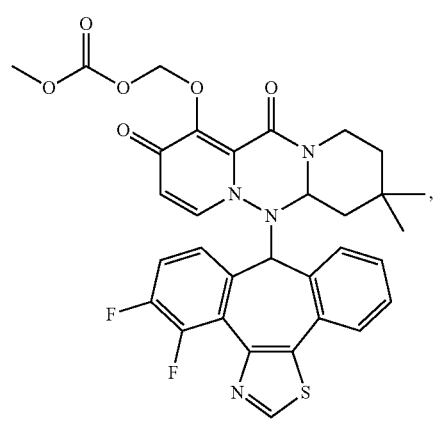
508
-continued
(557)
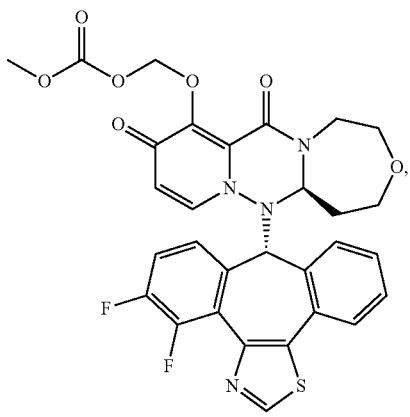
(558)
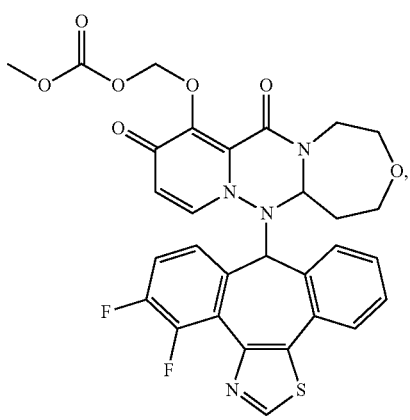
(559)
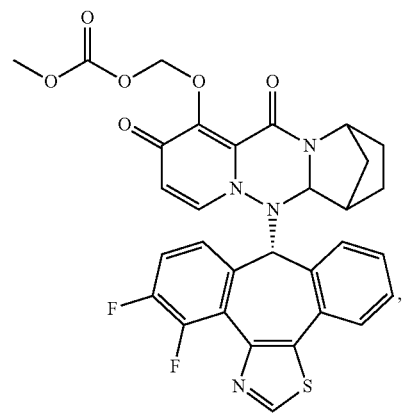
(560)
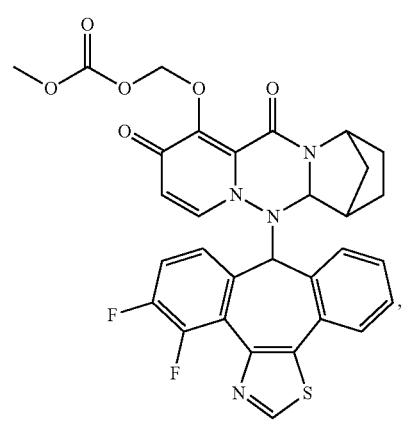

509
-continued
(561)
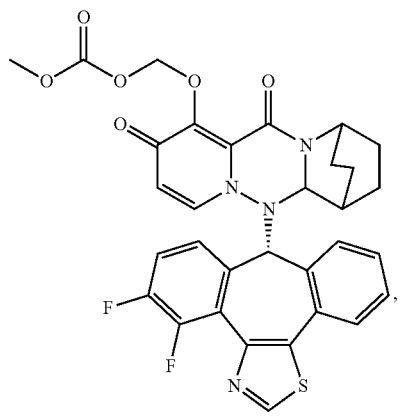
(562)
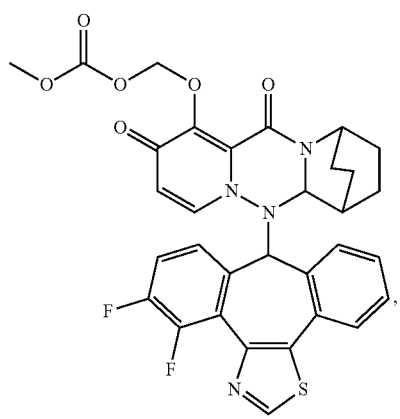
(563)
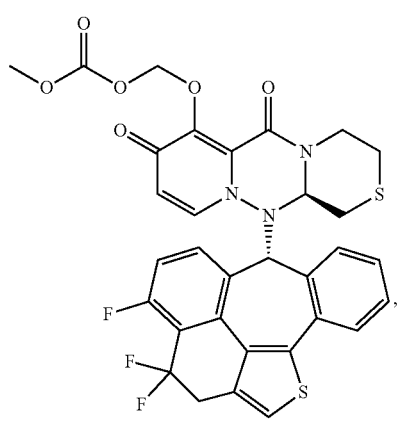
(564)
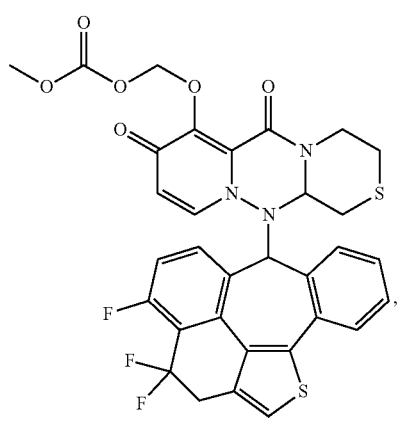
510
-continued
(565)
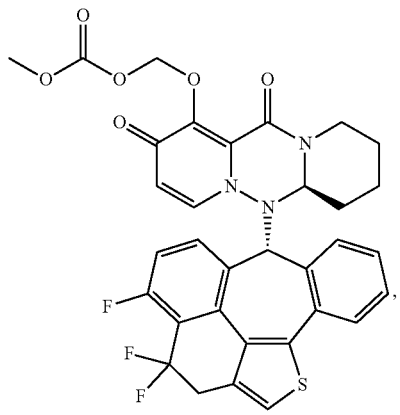
(566)
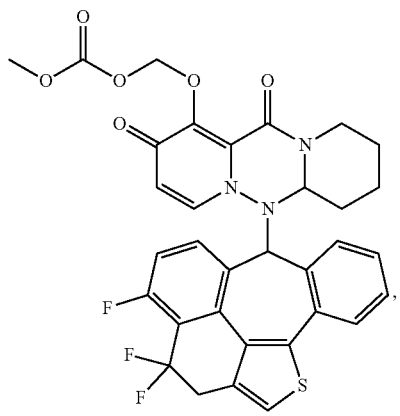
(567)
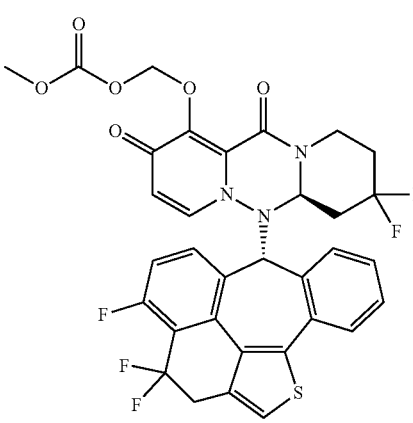
(568)
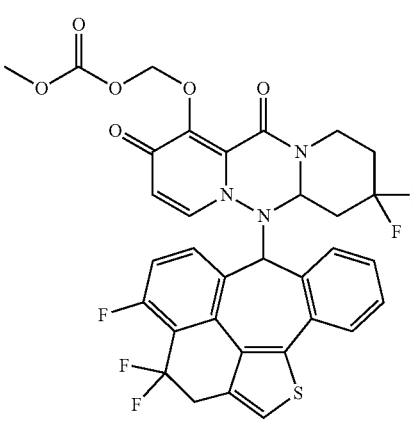

511
-continued
(569)
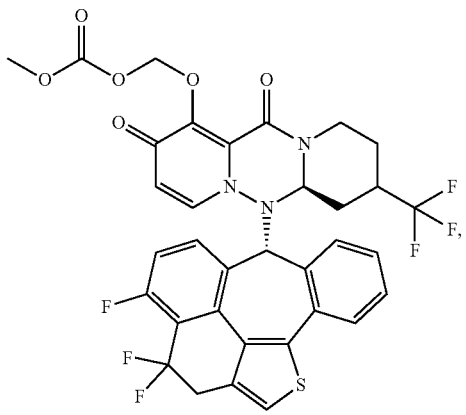
(570)
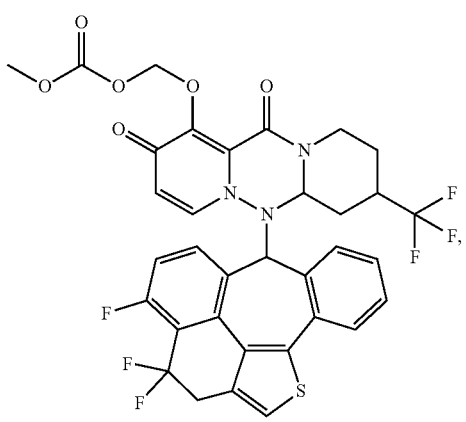
(571)
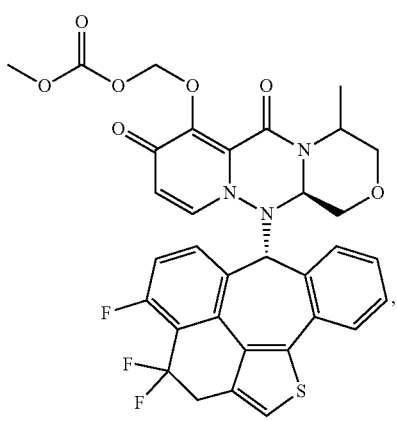
512
-continued
(572)
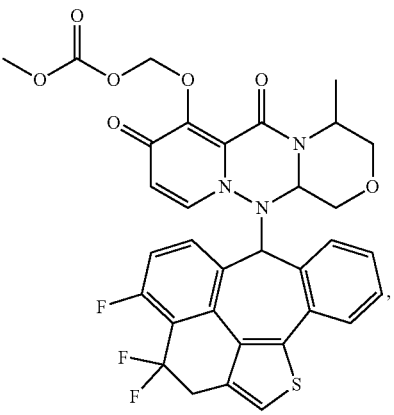
(573)
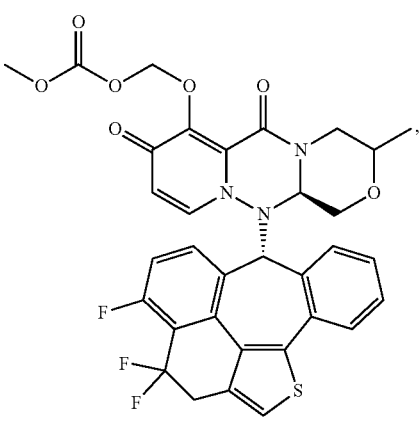
(574)
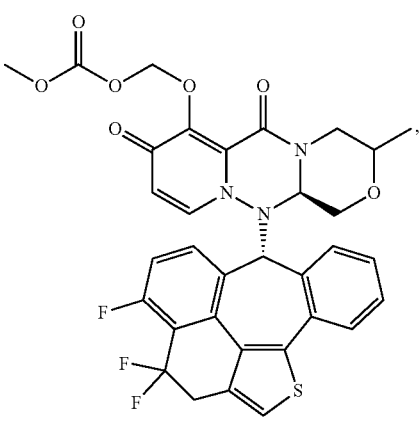
(575)
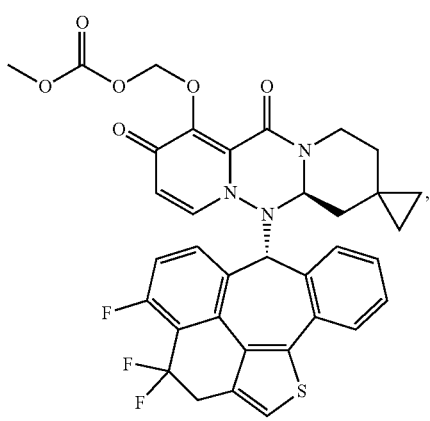

513
-continued
(576)
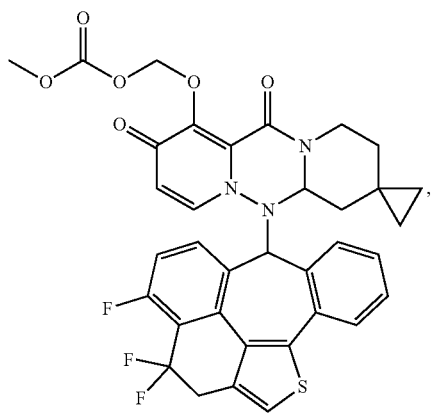
(577)
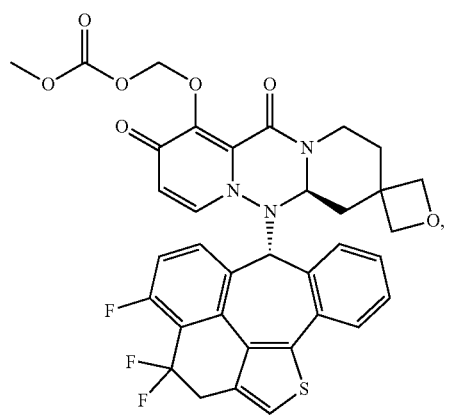
(578)
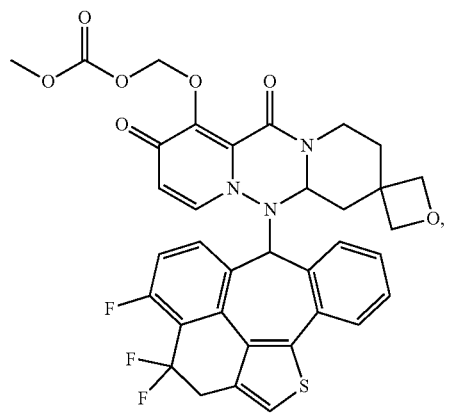
514
-continued
(579)
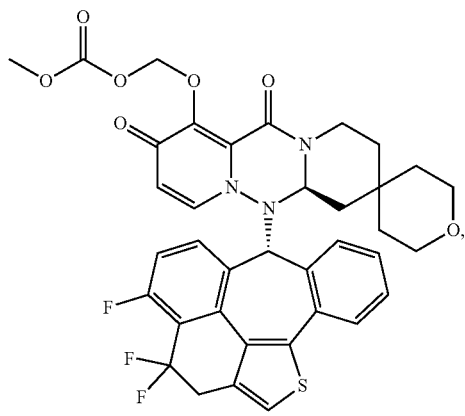
(580)
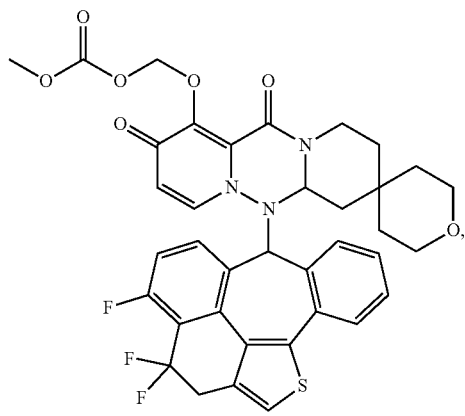
(581)
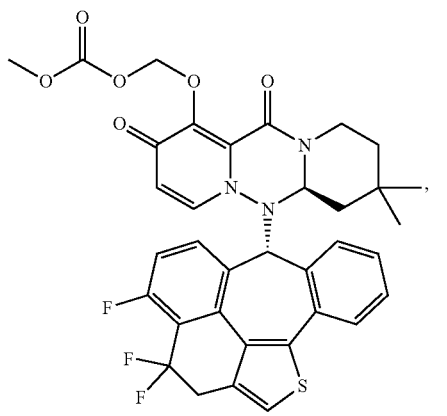

515
-continued
(582)
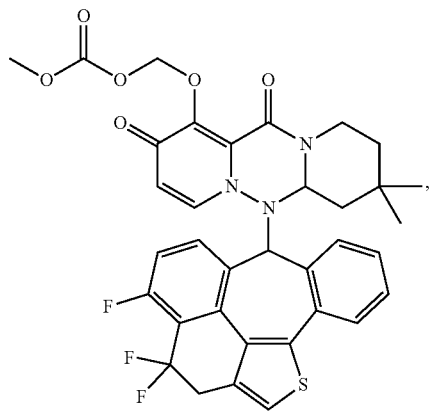
(583)
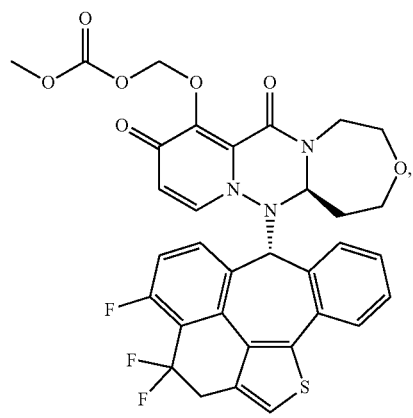
(584)
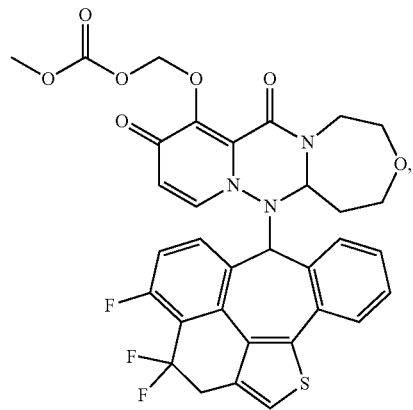
(585)
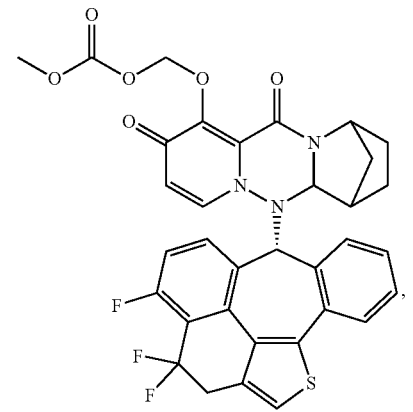
516
-continued
(586)
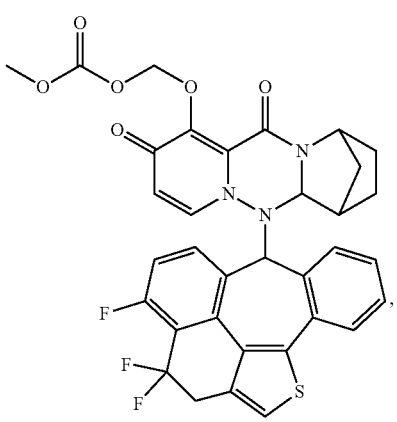
(587)
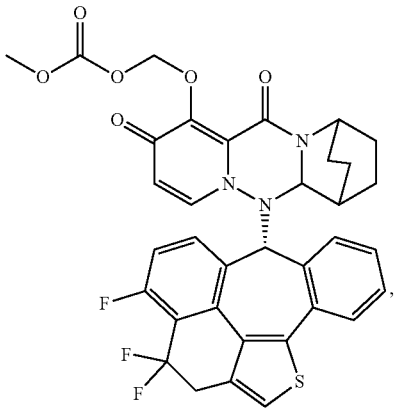
(588)
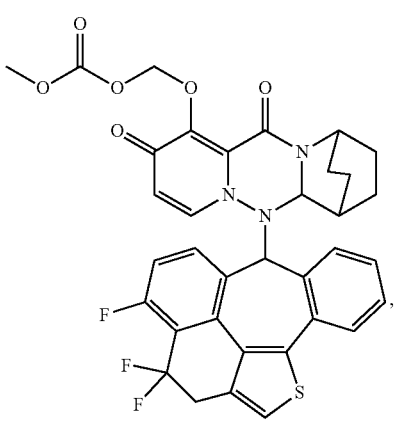
(589)
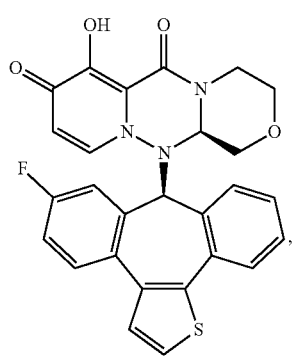

517
-continued
(590)
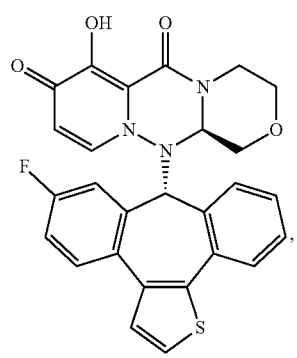
(591)
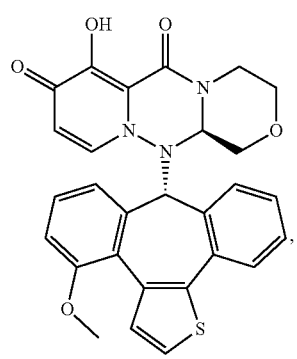
(592)
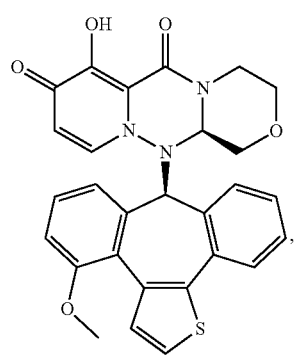
(593)
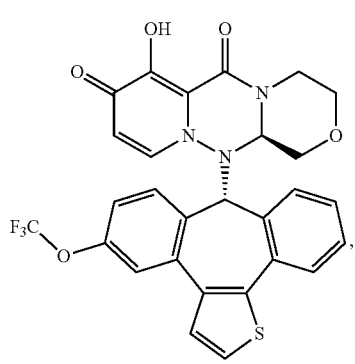
518
-continued
(594)
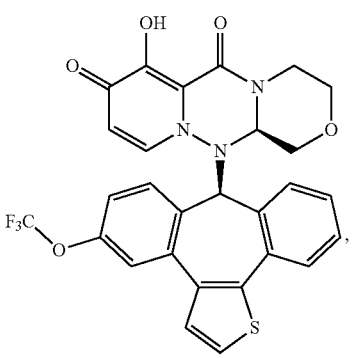
(595)
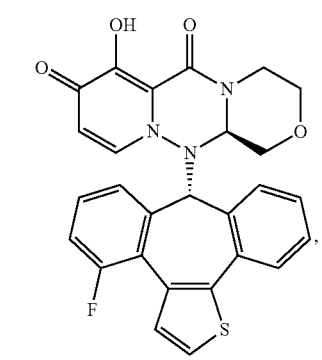
(596)
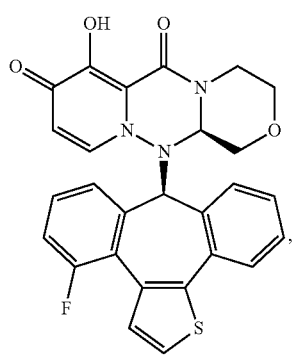
(597)
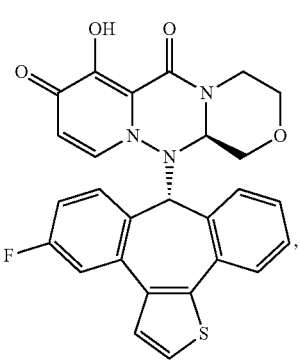

519
-continued
(598)
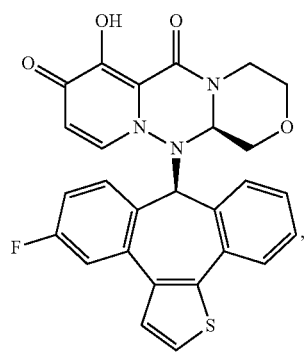
(599)
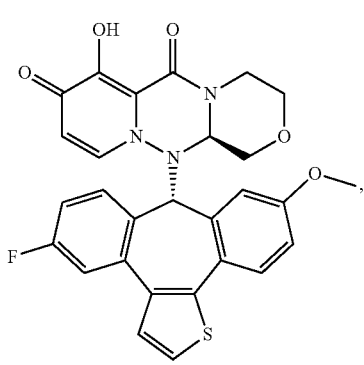
(600)
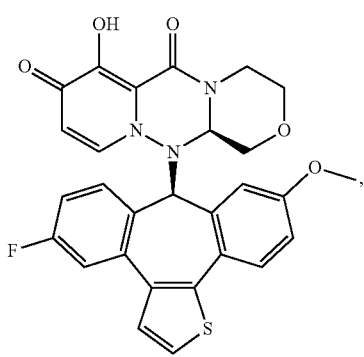
(601)
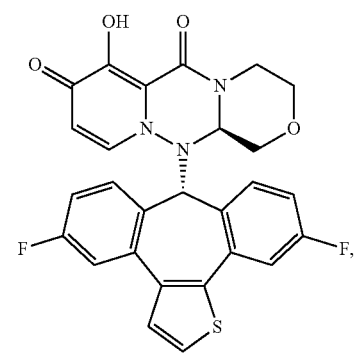
520
-continued
(602)
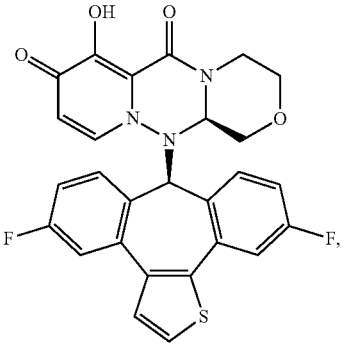
(607)
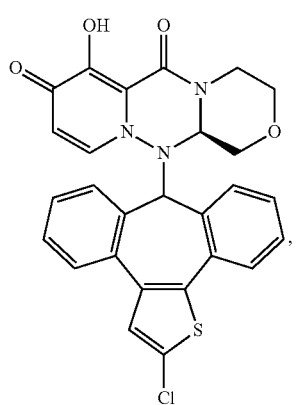
(608)
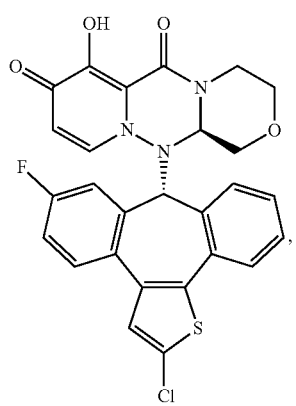
(609)
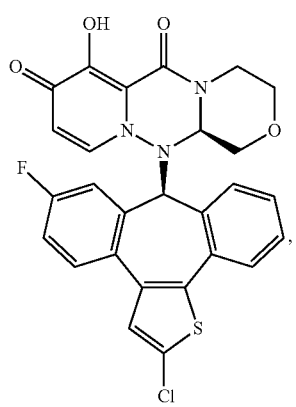

521
-continued
(610)
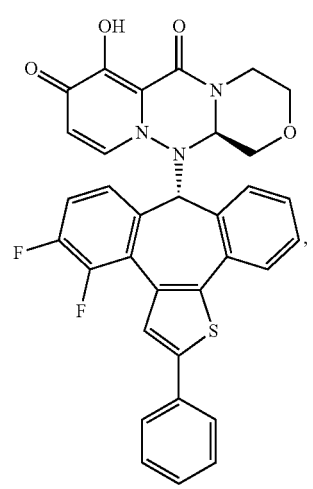
(611)
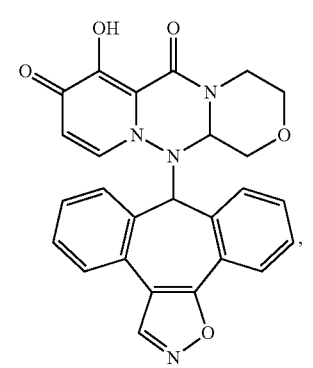
(612)
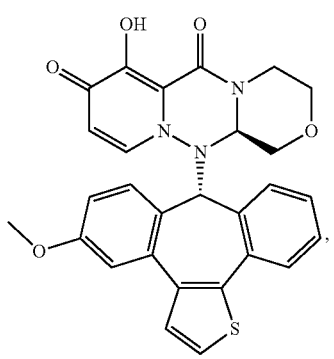
(613)
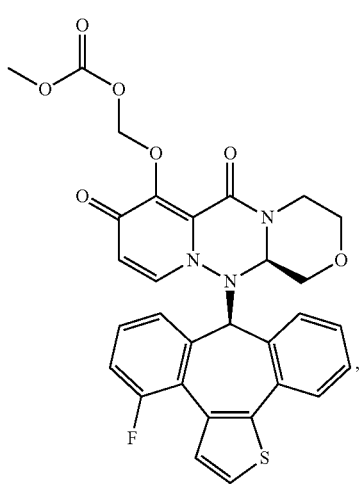
522
-continued
(614)
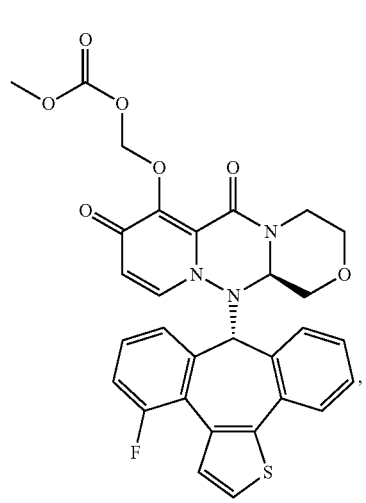
(615)
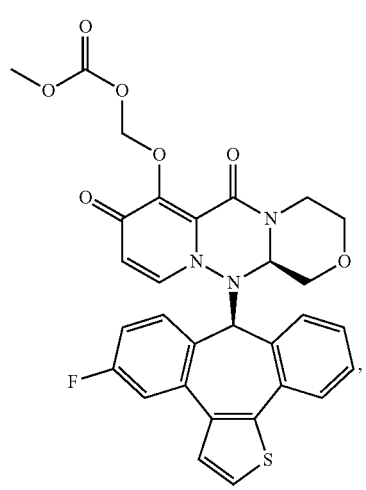
(616)
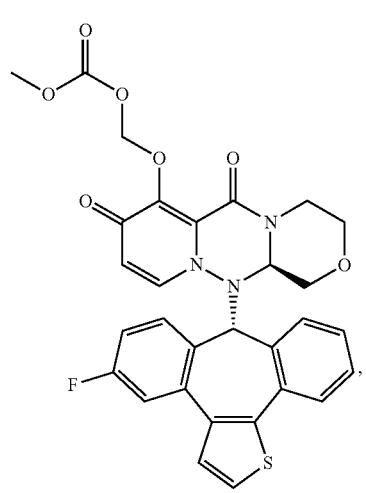

523
-continued
(617)
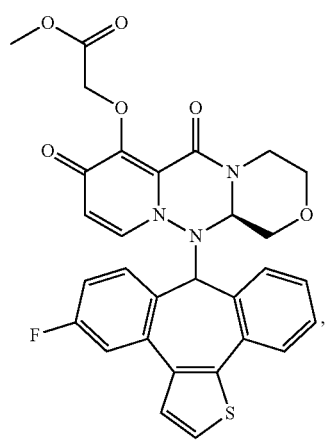
(618)
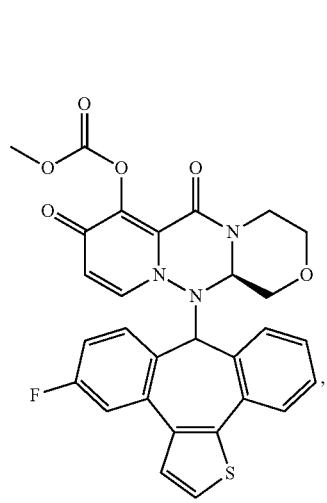
(619)
524
-continued
(620)
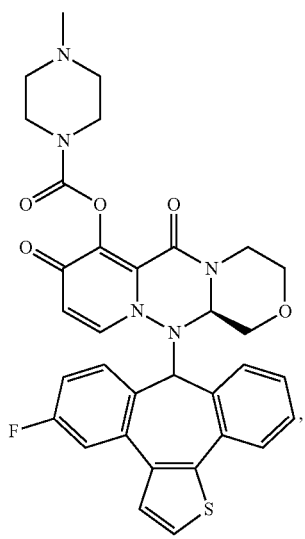
(621)
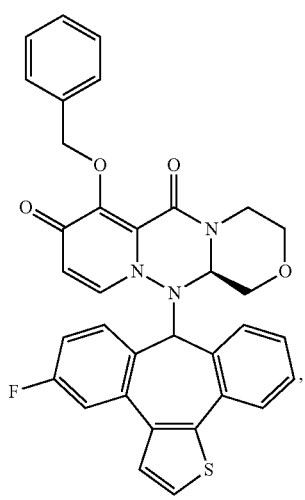
(622)
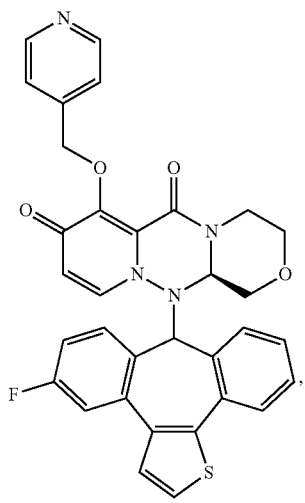

(623)
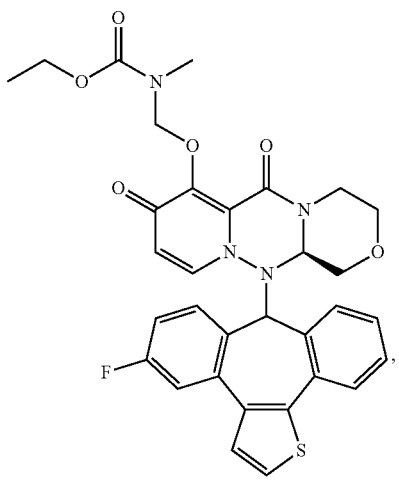
(626)
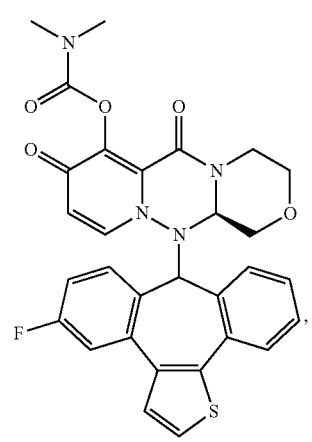
(624)
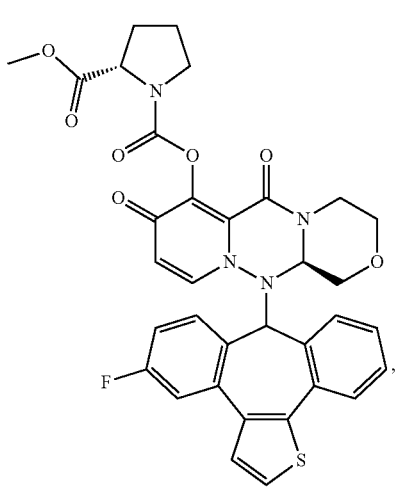
(627)
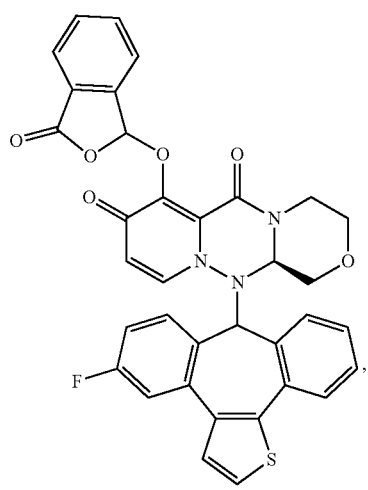
(625)
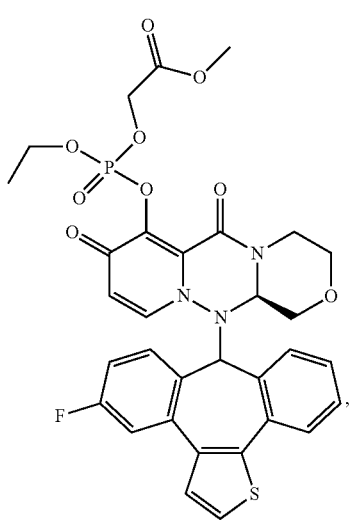
(628)
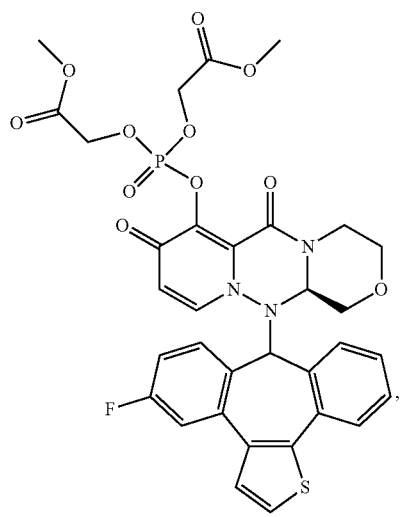

527
-continued
(629)
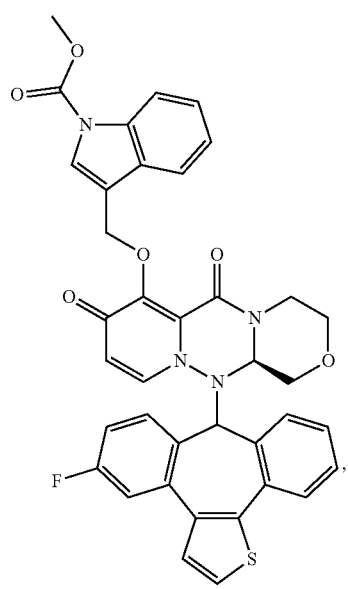
(630)
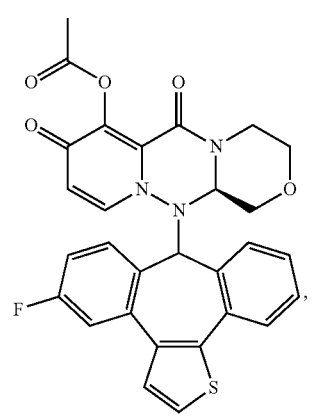
(631)
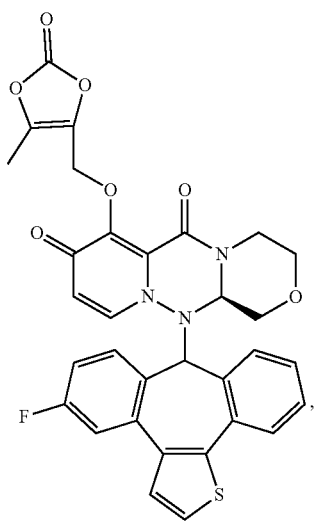
528
-continued
(632)
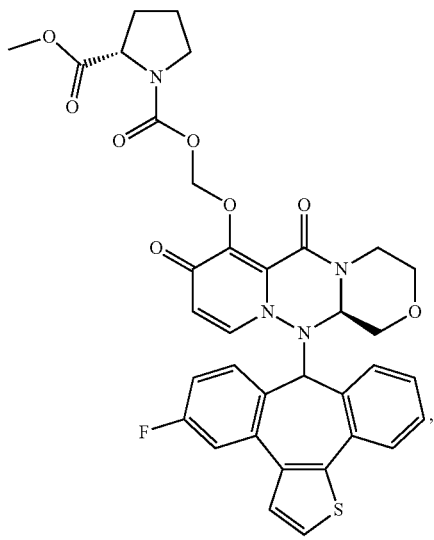
(633)
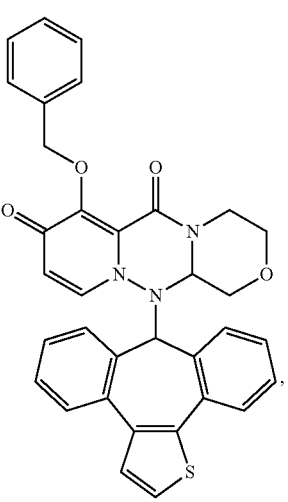
(634)
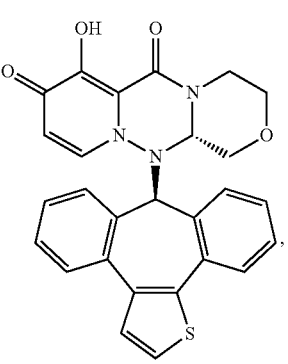

529
-continued
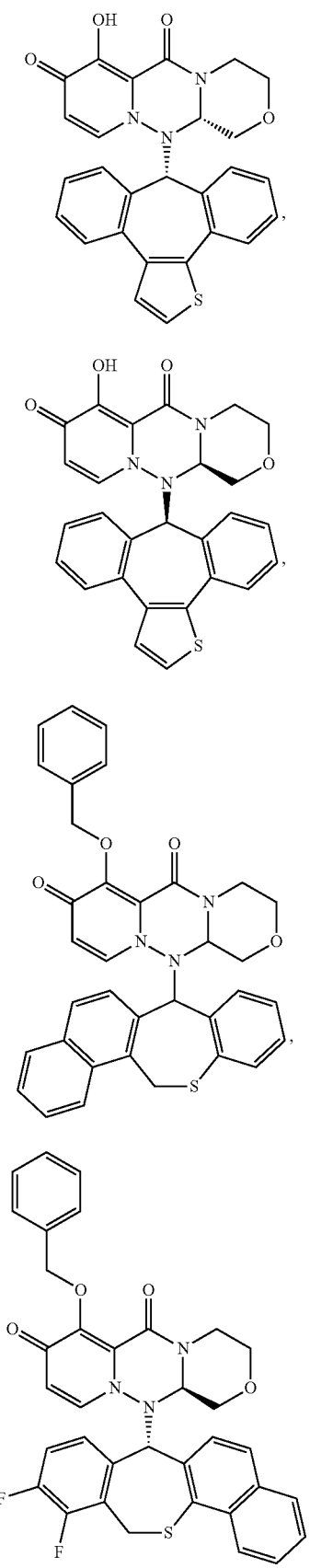
530
-continued
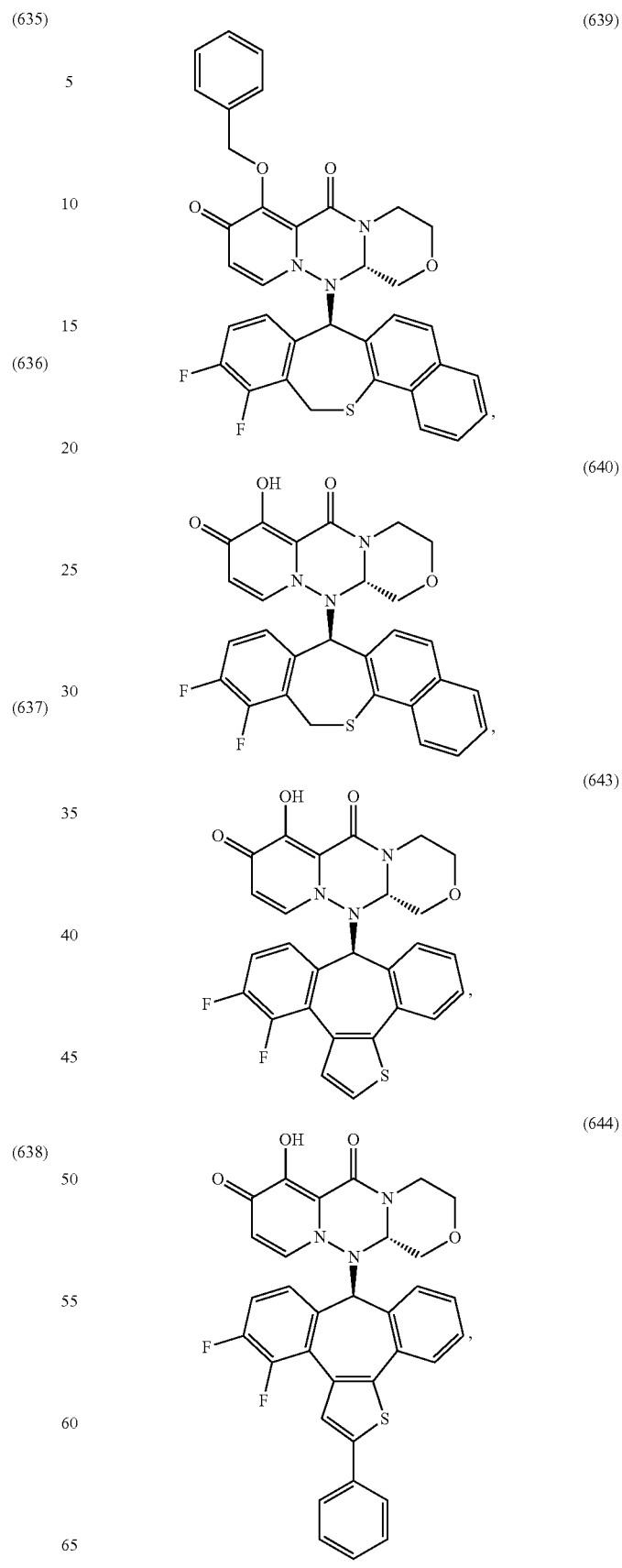

531
-continued
(645)
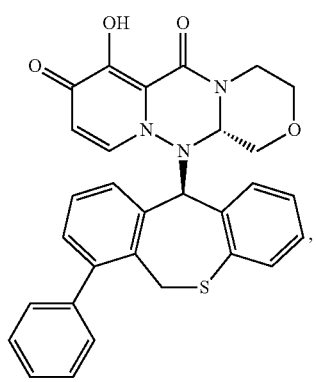
(646)
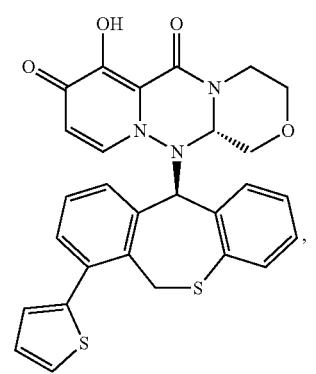
(647)
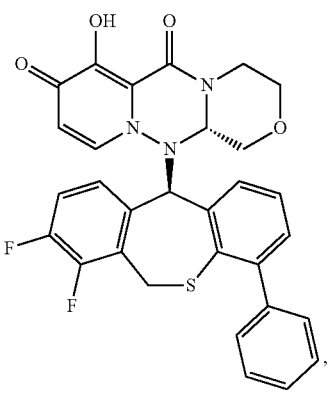
(648)
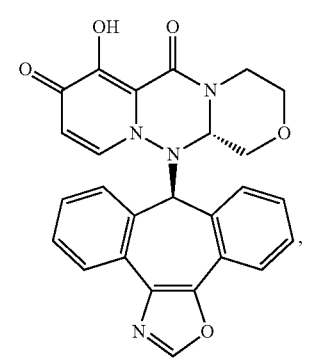
532
-continued
(649)
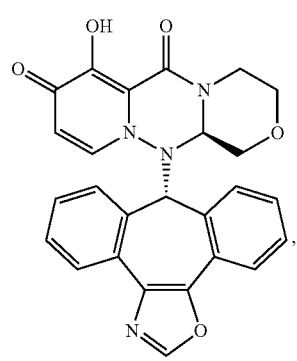
(650)
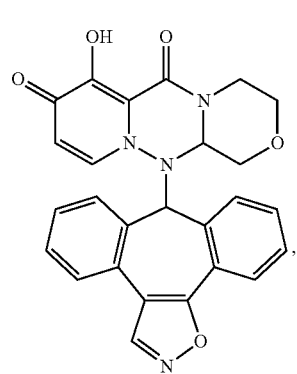
(651)
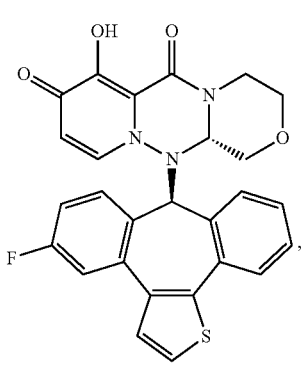
(652)
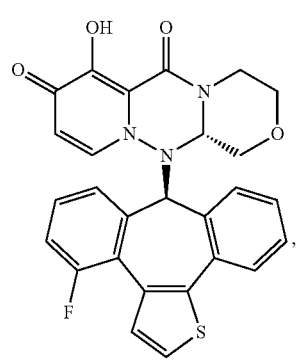

533
-continued (653)
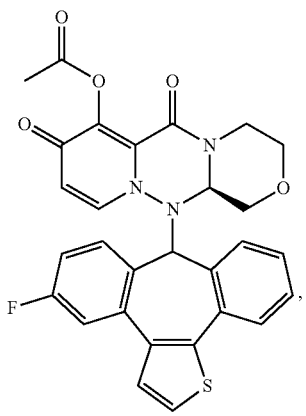

(654)
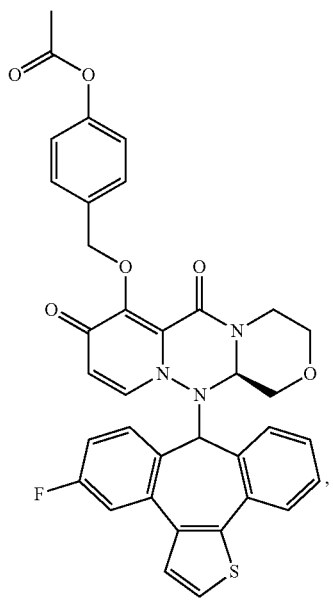

a stereoisomer of the compound, a tautomer of the compound, or a pharmaceutically acceptable salt of the compound.

16. A pharmaceutical composition comprising the compound of claim 1, and a pharmaceutically acceptable carrier, an adjuvant, a vehicle or a combination thereof.

17. The pharmaceutical composition of claim 16, further comprising one or more other therapeutic agents, wherein the other therapeutic agent is selected from at least one anti-influenza agent or vaccine; or the other therapeutic agent is amantadine, rimantadine, oseltamivir, zanamivir, Peramivir, laninamivir, laninamivir octanoate hydrate, favipiravir, arbidol, ribavirin, stachyflin, ingavirin, Fludase, CAS NO. 1422050-75-6, pimodivir, S-033188, flu vaccine or combinations thereof.

18. A method of preventing, managing, treating or lessening an influenza virus infection, comprising administering a therapeutically effective dose of the compound of claim 1 to a patient.

19. A method of preventing, managing, treating or lessening an influenza virus infection, comprising administering a therapeutically effective dose of the pharmaceutical composition of claim 16 to a patient.

20. A method of inhibiting RNA polymerase of influenza virus, comprising administering a therapeutically effective dose of the compound of claim 1 to a subject in need thereof, wherein the RNA polymerase is cap-dependent endonuclease.

21. A method of inhibiting RNA polymerase of influenza virus, comprising administering a therapeutically effective dose of the pharmaceutical composition of claim 16 to a subject in need thereof, wherein the RNA polymerase is cap-dependent endonuclease.

* * * * *